(12) United States Patent
Deschaght et al.

(10) Patent No.: US 11,919,966 B2
(45) Date of Patent: Mar. 5, 2024

(54) METHODS FOR INHIBITING TUMOR GROWTH OR TREATING CANCER BY ADMINISTERING AN IMMUNOGLOBULIN SINGLE VARIABLE DOMAIN THAT BINDS GLUCOCORTICOID-INDUCED TNFR FAMILY-RELATED RECEPTOR (GITR)

(71) Applicant: Ablynx N.V., Ghent-Zwijnaarde (BE)

(72) Inventors: Pieter Deschaght, Assebroek (BE); Sandra Li, Dilbeek (BE); Veerle Snoeck, Zingem (BE); Jan Pype, Herne (BE)

(73) Assignee: Ablynx N.V., Zwijnaarde (BE)

( * ) Notice: Subject to any disclaimer, the term of this patent is extended or adjusted under 35 U.S.C. 154(b) by 204 days.

(21) Appl. No.: 17/320,395

(22) Filed: May 14, 2021

(65) Prior Publication Data
US 2022/0411521 A1 Dec. 29, 2022

Related U.S. Application Data

(62) Division of application No. 15/769,205, filed as application No. PCT/EP2016/075558 on Oct. 24, 2016, now Pat. No. 11,059,899.

(60) Provisional application No. 62/276,352, filed on Jan. 8, 2016, provisional application No. 62/245,188, filed on Oct. 22, 2015.

(51) Int. Cl.
*C07K 16/28* (2006.01)
*A61K 39/00* (2006.01)
*A61P 35/00* (2006.01)

(52) U.S. Cl.
CPC .......... *C07K 16/2878* (2013.01); *A61P 35/00* (2018.01); *A61K 39/00* (2013.01); *A61K 2039/507* (2013.01); *C07K 2317/22* (2013.01); *C07K 2317/24* (2013.01); *C07K 2317/33* (2013.01); *C07K 2317/35* (2013.01); *C07K 2317/565* (2013.01); *C07K 2317/567* (2013.01); *C07K 2317/569* (2013.01); *C07K 2317/75* (2013.01); *C07K 2317/92* (2013.01); *C07K 2317/94* (2013.01)

(58) Field of Classification Search
CPC ............ C07K 16/2878; C07K 2317/24; C07K 2317/565; C07K 2317/75; C07K 2317/94; A61P 35/00; A61K 39/00; A61K 2039/507
See application file for complete search history.

(56) References Cited

U.S. PATENT DOCUMENTS 11,059,899 B1 7/2021 Deschaght et al.
2015/0064204 A1 3/2015 Beers et al.

FOREIGN PATENT DOCUMENTS

| JP | 2017-523771 A | 8/2017 |
|---|---|---|
| WO | WO 2006/105021 A2 | 10/2006 |
| WO | WO 2011/028683 A1 | 3/2011 |
| WO | WO 2015/031667 A2 | 3/2015 |
| WO | WO 2015/184099 A1 | 12/2015 |
| WO | WO 2015/187835 A2 | 12/2015 |
| WO | WO 2016/196792 A1 | 12/2016 |
| WO | WO 2017/015623 A2 | 1/2017 |

OTHER PUBLICATIONS

Cote AL. et al. (2011) J Immunol. 186(1):275-283. (https://doi.org/10.4049/jimmunol.1001308).*
Schaer DA, et al. (Dec. 2010) Curr Opin Investig Drugs. 11(12):1378-86.*
Chodorge et al., A series of Fas receptor agonist antibodies that demonstrate an inverse correlation between affinity and potency. Cell Death Differ. Jul. 2012;19(7):1187-95. doi: 10.1038/cdd.2011.208. Epub Jan. 20, 2012.
Cohen et al., Agonist anti-GITR monoclonal antibody induces melanoma tumor immunity in mice by altering regulatory T cell stability and intra-tumor accumulation. PLoS One. May 3, 2010;5(5):e10436. doi: 10.1371/journal.pone.0010436.
Colman et al., Effects of amino acid sequence changes on antibody-antigen interactions. Res Immunol. Jan. 1994;145(1):33-6. doi: 10.1016/s0923-2494(94)80039-1.
Paul, Fundamental Immunology—Chapter 9. Raven Press, NY. 3rd ed. 1993:292-295.
Rudikoff et al., Single amino acid substitution altering antigen-binding specificity. Proc Natl Acad Sci U S A. Mar. 1982;79(6):1979-83. doi: 10.1073/pnas.79.6.1979.
Smolarek et al., Variable fragments of heavy chain antibodies (VHHs): a new magic bullet molecule of medicine? Postepy Hig Med Dosw (Online). Jun. 14, 2012;66:348-58.
PCT/EP2016/075558, Mar. 2, 2017, International Search Report and Written Opinion.
PCT/EP2016/075558, May 3, 2018, International Preliminary Report on Patentability.
Georges et al., The Contorsbody, an antibody format for agonism: Design, structure, and function. Comput Struct Biotechnol J. May 14, 2020;18:1210-1220. doi: 10.1016/j.csbj.2020.05.007.

* cited by examiner

*Primary Examiner* — Robert S Landsman
(74) *Attorney, Agent, or Firm* — Wolf, Greenfield & Sacks, P.C.

(57) ABSTRACT

The present invention relates to immunoglobulin single variable domains that bind GITR and more in particular to polypeptides that comprise or essentially consist of one or more such immunoglobulin single variable domains; to nucleic acids encoding such polypeptides; to methods for preparing such polypeptides; to compositions and in particular to pharmaceutical compositions that comprise such polypeptides, for prophylactic, therapeutic or diagnostic purposes. In particular, the polypeptides of the present invention enhance the biological activity of GITR.

20 Claims, 27 Drawing Sheets

Figure 1A:
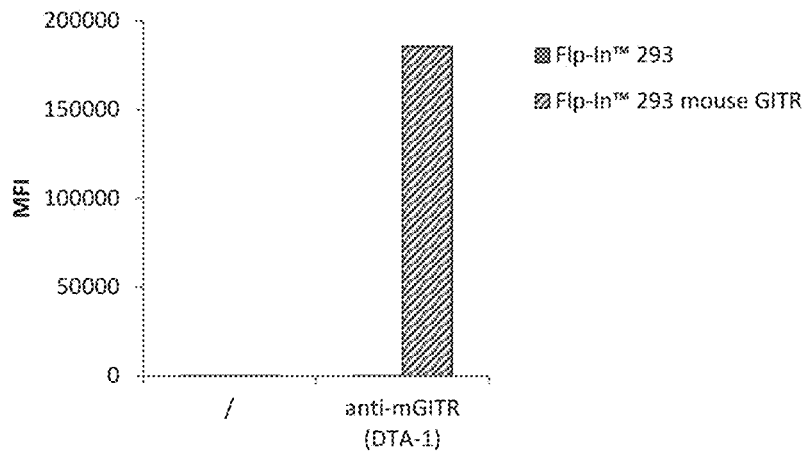

Specification includes a Sequence Listing.

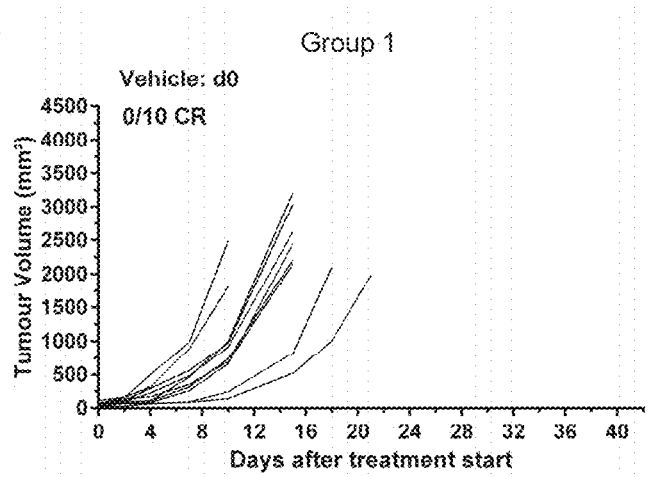
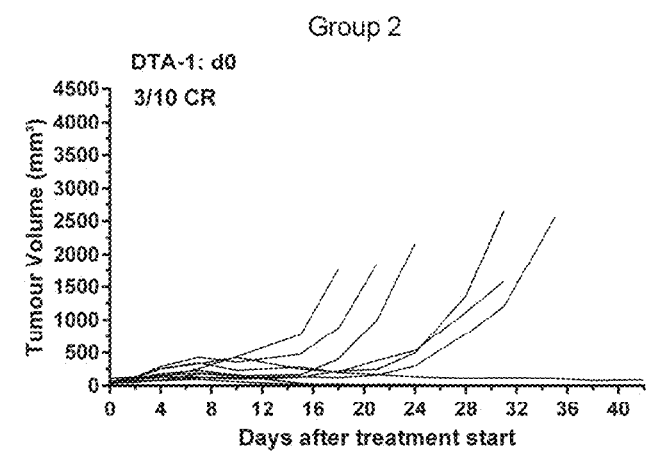
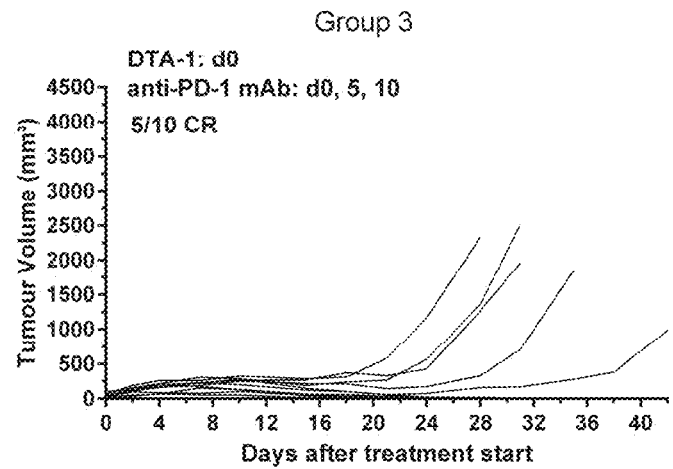

SEQUENCE LISTING

```
<160> NUMBER OF SEQ ID NOS: 292

<210> SEQ ID NO 1
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 1
```

Glu Val Gln Leu Val Glu Ser Gly Gly Gly Leu Val Gln Pro Gly Gly
1               5                   10                  15

Ser Leu Arg Leu Ser Cys Ala Ala Ser Glu Thr Ile Phe Ser Ile Asp
            20                  25                  30

Ser Met Ala Trp Tyr Arg Gln Ala Pro Gly Lys Gln Arg Glu Leu Val
        35                  40                  45

Ala Ala Ile Thr Gly Gly Gly Ser Pro Asn Tyr Ala Asp Ser Val Lys

```
                    50                  55                  60

Gly Arg Phe Thr Ile Ser Ser Asp Val Ala Lys Arg Thr Val Tyr Leu
 65                  70                  75                  80

Gln Met Asn Ser Leu Lys Pro Glu Asp Thr Ala Val Tyr Tyr Cys Asn
                     85                  90                  95

Ala Glu Gly Gln Ala Gly Trp Gly Thr Ala Leu Met Asp Tyr Trp Gly
                100                 105                 110

Lys Gly Thr Leu Val Thr Val Ser Ser
            115                 120

<210> SEQ ID NO 2
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 2

Glu Val Gln Leu Val Glu Ser Gly Gly Gly Leu Val Gln Pro Gly Gly
  1               5                  10                  15

Ser Leu Arg Leu Ser Cys Thr Ala Ser Glu Ser Ile Phe Ser Ile Asp
                 20                  25                  30

Ala Met Gly Trp His Arg Gln Ala Pro Gly Lys Gln Arg Glu Leu Val
             35                  40                  45

Ala His Ile Thr Gly Gly Gly Arg Ser Asn Tyr Ala Asp Ser Val Lys
         50                  55                  60

Gly Arg Phe Thr Ile Ser Gly Asp Ser Ala Lys Arg Thr Val Tyr Leu
 65                  70                  75                  80

Gln Met Asn Ser Leu Lys Pro Glu Asp Thr Ala Val Tyr Tyr Cys Asn
                     85                  90                  95

Ala Glu Gly Gln Ala Gly Trp Gly Thr Ala Leu Met Asp Tyr Trp Gly
                100                 105                 110

Lys Gly Thr Leu Val Thr Val Ser Ser
            115                 120

<210> SEQ ID NO 3
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 3

Glu Val Gln Leu Val Glu Ser Gly Gly Gly Leu Val Gln Pro Gly Gly
  1               5                  10                  15

Ser Leu Arg Leu Ser Cys Ala Ala Ser Glu Ser Ile Phe Ser Ile Asp
                 20                  25                  30

Ala Met Gly Trp Tyr His Gln Ala Pro Gly Lys Gln Arg Glu Leu Val
             35                  40                  45

Ala Thr Ile Thr Gly Gly Gly Ser Thr Asn Tyr Ala Asp Ser Val Lys
         50                  55                  60

Gly Arg Phe Thr Ile Ser Gly Asp Ser Ala Lys Arg Thr Val Tyr Leu
 65                  70                  75                  80

Gln Met Asp Ser Leu Lys Pro Glu Asp Thr Ala Val Tyr Tyr Cys Asn
                     85                  90                  95

Ala Glu Gly Gln Ala Gly Trp Gly Thr Ala Leu Met Asp Tyr Trp Gly
                100                 105                 110
```

```
Lys Gly Thr Leu Val Thr Val Ser Ser
        115                 120

<210> SEQ ID NO 4
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 4

Glu Val Gln Leu Val Glu Ser Gly Gly Gly Leu Val Gln Ser Gly Gly
1               5                   10                  15

Ser Leu Arg Leu Ser Cys Ala Ala Ser Glu Ser Ile Phe Ser Ile Asp
            20                  25                  30

Ala Met Gly Trp Tyr Arg Gln Ala Pro Gly Lys Gln Arg Glu Leu Val
        35                  40                  45

Ala Thr Ile Thr Gly Gly Arg Arg Asn Tyr Ala Asp Ser Val Met
    50                  55                  60

Gly Arg Phe Ser Ile Ser Gly Asp Asn Ala Lys Arg Thr Val Tyr Leu
65                  70                  75                  80

Gln Met Asn Ser Leu Lys Pro Glu Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

Lys Gly Thr Gln Val Thr Val Ser Ser
        115                 120

<210> SEQ ID NO 5
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Glu Ser Ile Phe Ser Ile Asp
            20                  25                  30

Ala Met Gly Trp His Arg Gln Ala Pro Gly Lys Gln Arg Glu Leu Val
        35                  40                  45

Ala His Ile Thr Gly Gly Arg Ser Asn Tyr Ala Asp Ser Val Lys
    50                  55                  60

Gly Arg Phe Thr Ile Ser Gly Asp Ser Ala Lys Arg Thr Val Tyr Leu
65                  70                  75                  80

Gln Met Asn Ser Leu Lys Pro Glu Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

Lys Gly Thr Gln Val Thr Val Ser Ser
        115                 120

<210> SEQ ID NO 6
<211> LENGTH: 121
<212> TYPE: PRT
<213> ORGANISM: Artificial Sequence
<220> FEATURE:
<223> OTHER INFORMATION: Nanobody Sequence
```

```
<400> SEQUENCE: 6

Glu Val Gln Leu Val Glu Ser Gly Gly Gly Leu Val Gln Pro Gly Gly
1               5                   10                  15

Ser Leu Arg Leu Ser Cys Thr Ala Ser Glu Ser Ile Phe Ser Ile Asp
            20                  25                  30

Ala Met Gly Trp His Arg Gln Ala Pro Gly Lys Gln Arg Glu Leu Val
        35                  40                  45

Ala His Ile Thr Gly Gly Arg Ser Asn Tyr Ala Asp Ser Val Lys
    50                  55                  60

Gly Arg Phe Thr Ile Ser Gly Asp Ser Ala Lys Arg Thr Val Tyr Leu
65              70                  75                  80

Gln Met Asn Ser Leu Arg Pro Glu Asp Thr Ala Val Tyr Tyr Cys Asn
            85                  90                  95

Ala Glu Gly Gln Ala Gly Trp Gly Thr Ala Leu Met Asp Tyr Trp Gly
            100                 105                 110

Lys Gly Thr Leu Val Thr Val Ser Ser
            115                 120

<210> SEQ ID NO 7
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 7

Glu Val Gln Leu Val Glu Ser Gly Gly Gly Leu Val Arg Pro Gly Gly
1               5                   10                  15

Ser Leu Arg Leu Ser Cys Ala Ala Ser Glu Ser Ile Phe Ser Ile Asp
            20                  25                  30

Ala Met Gly Trp Tyr Arg Gln Ala Pro Gly Lys Gln Arg Glu Leu Val
        35                  40                  45

Ala Thr Met Thr Gly Gly Gly Ser Thr Asn Tyr Ala Asp Ser Val Lys
    50                  55                  60

Gly Arg Phe Thr Ile Ser Ser Asp Val Ala Lys Arg Thr Val Tyr Leu
65              70                  75                  80

Gln Met Asn Ser Leu Lys Pro Glu Asp Thr Ala Val Tyr Tyr Cys Asn
            85                  90                  95

Ala Glu Gly Gln Ala Gly Trp Gly Thr Ala Leu Met Asp Tyr Trp Gly
            100                 105                 110

Lys Gly Thr Gln Val Thr Val Ser Ser
            115                 120

<210> SEQ ID NO 8
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Thr Ala Ser Glu Ser Ile Phe Ser Ile Asp
            20                  25                  30

Ala Met Gly Trp His Arg Gln Ala Pro Gly Lys Gln Arg Glu Leu Val
        35                  40                  45
```

Ala His Ile Thr Gly Gly Gly Ser Asn Tyr Ala Asp Ser Val Lys
    50              55                  60

Gly Arg Phe Thr Ile Ser Gly Asp Ser Ala Lys Arg Thr Val Tyr Leu
65                  70                  75                  80

Gln Met Asn Ser Leu Lys Pro Glu Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

Lys Gly Thr Gln Val Thr Val Ser Ser
            115                 120

<210> SEQ ID NO 9
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Glu Thr Ile Phe Ser Ile Asp
            20                  25                  30

Ser Met Ala Trp Tyr Arg Gln Ala Pro Gly Arg Gln Arg Glu Leu Val
        35                  40                  45

Ala Ala Ile Thr Gly Gly Ser Pro Asn Tyr Ala Asp Ser Val Lys
    50              55                  60

Gly Arg Phe Thr Ile Ser Asp Val Ala Lys Arg Thr Val Tyr Leu
65                  70                  75                  80

Gln Met Asn Ser Leu Lys Pro Glu Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

Lys Gly Thr Leu Val Thr Val Ser Ser
            115                 120

<210> SEQ ID NO 10
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Glu Thr Ile Phe Ser Ile Asp
            20                  25                  30

Ser Met Ala Trp Tyr Arg Gln Ala Pro Gly Lys Gln Arg Glu Leu Val
        35                  40                  45

Ala Ala Ile Thr Gly Gly Ser Pro Asn Tyr Ala Asp Ser Val Lys
    50              55                  60

Gly Arg Phe Thr Ile Ser Ser Asp Val Ala Lys Arg Thr Ala Tyr Leu
65                  70                  75                  80

Gln Met Asn Ser Leu Lys Pro Glu Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

```
Lys Gly Thr Leu Val Thr Val Ser Ser
        115                 120

<210> SEQ ID NO 11
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 11

Glu Val Gln Leu Val Glu Ser Gly Gly Gly Leu Val Arg Pro Gly Gly
1               5                   10                  15

Ser Leu Arg Leu Ser Cys Ala Ala Ser Glu Ser Ile Phe Ser Ile Asp
            20                  25                  30

Ala Met Gly Trp Tyr Arg Gln Ala Pro Gly Lys Gln Arg Glu Leu Val
        35                  40                  45

Ala Thr Met Thr Gly Gly Gly Ser Thr Asn Tyr Ala Asp Ser Val Arg
    50                  55                  60

Gly Arg Phe Thr Ile Ser Ser Asp Val Ala Lys Arg Thr Val Tyr Leu
65                  70                  75                  80

Gln Met Asn Ser Leu Lys Pro Glu Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

Lys Gly Thr Gln Val Thr Val Ser Ser
        115                 120

<210> SEQ ID NO 12
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Thr Ala Ser Glu Ser Ile Phe Ser Ile Asp
            20                  25                  30

Ala Met Gly Trp His Arg Gln Ala Pro Gly Lys Gln Arg Glu Leu Val
        35                  40                  45

Ala His Ile Thr Gly Gly Gly Arg Ser Asn Tyr Ala Asp Ser Val Lys
    50                  55                  60

Gly Arg Phe Ala Ile Ser Gly Asp Ser Ala Lys Arg Thr Val Tyr Leu
65                  70                  75                  80

Gln Met Asn Ser Leu Lys Pro Glu Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

Lys Gly Thr Gln Val Thr Val Ser Ser
        115                 120

<210> SEQ ID NO 13
<211> LENGTH: 121
<212> TYPE: PRT
<213> ORGANISM: Artificial Sequence
<220> FEATURE:
<223> OTHER INFORMATION: Nanobody Sequence
```

-continued

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Glu Ser Ile Phe Ser Ile Asp
            20                  25                  30

Ala Met Gly Trp Tyr Arg Gln Ala Pro Gly Lys Gln Arg Glu Leu Val
        35                  40                  45

Ala Thr Ile Thr Gly Gly Ser Thr Asn Tyr Ala Asp Ser Val Lys
    50                  55                  60

Gly Arg Phe Thr Ile Ser Gly Asp Ser Ala Lys Arg Thr Val Tyr Leu
65                  70                  75                  80

Gln Met Asp Ser Leu Lys Pro Glu Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

Lys Gly Thr Leu Val Thr Val Ser Ser
        115                 120

<210> SEQ ID NO 14
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 14

Glu Val Gln Leu Val Glu Ser Gly Gly Gly Leu Val Arg Pro Gly Gly
1               5                   10                  15

Ser Leu Arg Leu Pro Cys Ala Ala Ser Glu Ser Ile Phe Ser Ile Asp
            20                  25                  30

Ala Met Gly Trp Tyr Arg Gln Ala Pro Gly Lys Gln Arg Glu Leu Val
        35                  40                  45

Ala Thr Met Thr Gly Gly Ser Thr Asn Tyr Ala Asp Ser Val Lys
    50                  55                  60

Gly Arg Phe Thr Ile Ser Ser Asp Val Ala Lys Arg Thr Val Tyr Leu
65                  70                  75                  80

Gln Met Asn Ser Leu Lys Pro Glu Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

Lys Gly Thr Leu Val Thr Val Ser Ser
        115                 120

<210> SEQ ID NO 15
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 15

Glu Val Gln Leu Val Glu Ser Gly Gly Gly Leu Val Gln Ser Gly Gly
1               5                   10                  15

Ser Leu Arg Leu Ser Cys Ala Ala Ser Glu Ser Ile Phe Ser Ile Asn
            20                  25                  30

Ala Met Gly Trp Tyr Arg Gln Ala Pro Gly Lys Gln Arg Glu Leu Val
        35                  40                  45

Ala Thr Ile Thr Gly Gly Arg Arg Asn Tyr Ala Asp Ser Val Met
        50                  55                  60

Gly Arg Phe Ser Ile Ser Gly Asp Asn Ala Lys Arg Thr Val Tyr Leu
65                  70                  75                  80

Gln Met Asn Ser Leu Lys Pro Glu Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

Lys Gly Thr Gln Val Thr Val Ser Ser
            115                 120

<210> SEQ ID NO 16
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Glu Ser Ile Phe Ser Ile Asp
            20                  25                  30

Ala Met Gly Trp Tyr Arg Gln Ala Pro Gly Lys Gln Arg Glu Leu Val
        35                  40                  45

Ala Thr Ile Thr Gly Gly Ser Ser Thr Asn Tyr Ala Asp Ser Val Lys
        50                  55                  60

Gly Arg Phe Thr Ile Ser Gly Asp Asn Ala Lys Arg Thr Val Tyr Leu
65                  70                  75                  80

Gln Met Asn Ser Leu Lys Pro Glu Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

Lys Gly Thr Gln Val Thr Val Ser Ser
            115                 120

<210> SEQ ID NO 17
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Glu Ser Ile Phe Ser Ile Asp
            20                  25                  30

Ala Met Gly Trp Tyr Arg Gln Ala Pro Gly Lys Gln Arg Glu Leu Val
        35                  40                  45

Ala Thr Ile Thr Gly Gly Gly Ser Thr Asn Tyr Ala Asp Ser Val Lys
        50                  55                  60

Gly Arg Phe Thr Ile Ser Gly Asp Asn Ala Lys Arg Thr Val Tyr Leu
65                  70                  75                  80

Gln Met Asn Ser Leu Lys Pro Glu Asp Thr Ala Ala Tyr Tyr Cys Asn
                85                  90                  95

Ala Glu Gly Gln Ala Gly Trp Gly Thr Ala Leu Met Asp Tyr Trp Gly

```
                100                 105                 110
Lys Gly Thr Leu Val Thr Val Ser Ser
        115                 120

<210> SEQ ID NO 18
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Thr Ala Ser Glu Ser Ile Phe Ser Ile Asp
            20                  25                  30

Ala Met Gly Trp His Arg Gln Ala Pro Gly Lys Gln Arg Glu Leu Val
        35                  40                  45

Ala His Ile Thr Gly Gly Gly Arg Ser Asn Tyr Ala Asp Ser Val Lys
    50                  55                  60

Gly Arg Phe Thr Ile Ser Gly Asp Ser Ala Lys Arg Thr Val Tyr Leu
65                  70                  75                  80

Gln Met Asn Ser Leu Lys Pro Gly Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

Lys Gly Thr Gln Val Thr Val Ser Ser
        115                 120

<210> SEQ ID NO 19
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Glu Ser Ile Phe Ser Ile Asp
            20                  25                  30

Ala Met Gly Trp Tyr Arg Gln Ala Pro Gly Lys Gln Arg Glu Leu Val
        35                  40                  45

Ala Thr Ile Thr Gly Gly Gly Ser Thr Asn Tyr Ala Asp Ser Val Lys
    50                  55                  60

Gly Arg Phe Thr Ile Ser Gly Asp Asn Ala Lys Arg Thr Val Tyr Leu
65                  70                  75                  80

Gln Met Asn Ser Leu Lys Pro Glu Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

Lys Gly Thr Gln Val Thr Val Ser Ser
        115                 120

<210> SEQ ID NO 20
<211> LENGTH: 121
<212> TYPE: PRT
<213> ORGANISM: Artificial Sequence
<220> FEATURE:
```

<223> OTHER INFORMATION: Nanobody Sequence

<400> SEQUENCE: 20

```
Glu Val Gln Leu Val Glu Ser Gly Gly Gly Leu Val Gln Pro Gly Gly
1               5                   10                  15
Ser Leu Arg Leu Ser Cys Thr Ala Ser Glu Ser Ile Phe Ser Ile Asp
            20                  25                  30
Ala Met Gly Trp His Arg Gln Ala Pro Gly Lys Gln Arg Glu Leu Val
        35                  40                  45
Ala His Ile Thr Gly Gly Arg Pro Asn Tyr Ala Asp Ser Val Lys
    50                  55                  60
Gly Arg Phe Thr Ile Ser Gly Asp Ser Ala Lys Arg Thr Val Tyr Leu
65                  70                  75                  80
Gln Met Asn Ser Leu Lys Pro Glu Asp Thr Ala Val Tyr Tyr Cys Asn
            85                  90                  95
Ala Glu Gly Gln Ala Gly Trp Gly Thr Ala Leu Met Asp Tyr Trp Gly
        100                 105                 110
Lys Gly Thr Leu Val Thr Val Ser Ser
        115                 120
```

<210> SEQ ID NO 21
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 21

```
Glu Val Gln Leu Val Glu Ser Gly Gly Gly Leu Val Gln Pro Gly Gly
1               5                   10                  15
Ser Leu Arg Leu Ser Cys Ala Gly Ser Glu Ser Ile Phe Ser Ile Asp
            20                  25                  30
Ala Met Gly Trp Tyr Arg Gln Ala Pro Gly Lys Gln Arg Glu Leu Val
        35                  40                  45
Ala Gly Ile Ser Gly Gly Gly Arg Thr Asn Tyr Ala Asp Ser Val Lys
    50                  55                  60
Gly Arg Phe Thr Ile Ser Gly Asp Asn Ala Lys Asn Thr Val Tyr Leu
65                  70                  75                  80
Gln Met Asn Ser Leu Lys Pro Glu Asp Thr Ala Val Tyr Tyr Cys Asn
            85                  90                  95
Ala Glu Gly Gln Ala Gly Trp Gly Thr Pro Leu Met Asn Tyr Trp Gly
        100                 105                 110
Lys Gly Thr Leu Val Thr Val Ser Ser
        115                 120
```

<210> SEQ ID NO 22
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 22

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Ser Ile Phe Ser Ile Asp
            20                  25                  30
Ser Met Gly Trp Tyr Arg Gln Ala Pro Gly Lys Gln Arg Glu Leu Val
```

```
                35                  40                  45

Ala Ala Ile Thr Ser Ser Thr Asn Tyr Ala Asp Ser Val Lys Gly Arg
            50                  55                  60

Phe Thr Ile Ser Arg Asp Asn Ala Lys Asn Thr Val Tyr Leu Gln Met
 65                  70                  75                  80

Asn Ser Leu Lys Pro Glu Asp Thr Ala Val Tyr Tyr Cys Asn Leu Glu
                 85                  90                  95

Gly Gln Ala Gly Trp Gly Thr Ala Leu Ile Asn Tyr Trp Gly Lys Gly
            100                 105                 110

Thr Leu Val Thr Val Ser Ser
            115

<210> SEQ ID NO 23
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 23

Glu Val Gln Leu Val Glu Ser Gly Gly Gly Leu Val Gln Pro Gly Gly
 1               5                  10                  15

Ser Leu Arg Leu Thr Cys Ala Ala Ser Gly Ser Ile Phe Ser Ile Asp
                20                  25                  30

Ala Met Gly Trp Tyr Arg Gln Ala Pro Gly Lys Gln Arg Glu Leu Val
            35                  40                  45

Ala Ser Ile Thr Ser Thr Thr Asn Tyr Ala Glu Ser Val Lys Gly Arg
        50                  55                  60

Phe Thr Ile Ser Arg Ala Asn Ala Lys Asn Thr Val Tyr Leu Gln Met
 65                  70                  75                  80

Asn Ser Leu Lys Pro Glu Asp Thr Ala Val Tyr Tyr Cys Asn Val Lys
                85                  90                  95

Gly Gln Thr Gly Trp Gly Thr Ala Leu Met Asp Tyr Trp Gly Lys Gly
            100                 105                 110

Thr Gln Val Thr Val Ser Ser
            115

<210> SEQ ID NO 24
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 24

Glu Val Gln Leu Val Glu Ser Gly Gly Gly Leu Val Gln Pro Gly Gly
 1               5                  10                  15

Ser Leu Arg Leu Thr Cys Ala Ala Ser Gly Ser Ile Phe Ser Ile Asp
                20                  25                  30

Ala Met Gly Trp Tyr Arg Gln Ala Pro Gly Lys Gln Arg Glu Leu Val
            35                  40                  45

Ala Ser Ile Thr Ser Thr Thr Asn Tyr Ala Glu Ser Val Lys Gly Arg
        50                  55                  60

Phe Thr Ile Ser Arg Ala Asn Ala Lys Asn Thr Val Tyr Leu Gln Met
 65                  70                  75                  80

Asn Ser Leu Lys Pro Glu Asp Thr Ala Val Tyr Tyr Cys Ser Val Lys
                85                  90                  95
```

Gly Gln Thr Gly Trp Gly Thr Ala Leu Met Asp Tyr Trp Gly Lys Gly
            100                 105                 110

Thr Leu Val Thr Val Ser Ser
            115

<210> SEQ ID NO 25
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
            35                  40                  45

Ala Ala Ile Thr Ser Gly Thr Asn Tyr Ala Asp Ser Ala Lys Gly Arg
        50                  55                  60

Phe Thr Ile Ser Arg Asp His Ala Lys Asn Thr Val Tyr Leu Gln Met
65                  70                  75                  80

Asn Ser Leu Lys Pro Glu Asp Thr Ala Val Tyr Tyr Cys Asn Leu Glu
                85                  90                  95

Gly Gln Thr Gly Trp Gly Thr Ala Leu Met Asp Tyr Trp Gly Lys Gly
            100                 105                 110

Thr Leu Val Thr Val Ser Ser
            115

<210> SEQ ID NO 26
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
            35                  40                  45

Ala Ala Ile Thr Ser Gly Thr Asn Tyr Ala Asp Ser Val Lys Gly Arg
        50                  55                  60

Phe Thr Ile Ser Arg Asp His Ala Lys Asn Thr Val Tyr Leu Gln Met
65                  70                  75                  80

Asn Ser Leu Lys Pro Glu Asp Thr Ala Val Tyr Tyr Cys Asn Leu Glu
                85                  90                  95

Gly Gln Thr Gly Trp Gly Thr Ala Leu Met Asp Tyr Trp Gly Lys Gly
            100                 105                 110

Thr Gln Val Thr Val Ser Ser
            115

<210> SEQ ID NO 27
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 27

Glu Val Gln Leu Val Glu Ser Gly Gly Gly Leu Val Gln Pro Gly Gly
1               5                   10                  15

Ser Leu Arg Leu Phe Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Thr Ser Gly Thr Asn Tyr Ala Asp Ser Val Arg Gly Arg
    50                  55                  60

Phe Thr Ile Ser Arg Asp His Ala Lys Asn Thr Val Tyr Leu Gln Met
65                  70                  75                  80

Asn Ser Leu Lys Pro Glu Asp Thr Ala Val Tyr Tyr Cys Asn Leu Glu
                85                  90                  95

Gly Gln Thr Gly Trp Gly Thr Ala Leu Met Asp Tyr Trp Gly Lys Gly
            100                 105                 110

Thr Gln Val Thr Val Ser Ser
        115

<210> SEQ ID NO 28
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Thr Ser Gly Thr Asn Tyr Ala Asp Ser Val Lys Gly Arg
    50                  55                  60

Phe Thr Ile Ser Arg Asp His Ala Lys Asn Thr Val Tyr Leu Gln Met
65                  70                  75                  80

Asn Ser Leu Lys Pro Glu Asp Thr Ala Val Tyr Tyr Cys Asn Leu Glu
                85                  90                  95

Gly Gln Thr Gly Trp Gly Thr Ala Leu Met Asp Tyr Trp Gly Lys Gly
            100                 105                 110

Thr Leu Val Thr Val Ser Ser
        115

<210> SEQ ID NO 29
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ser Gly Ser Ile Phe Ser Ile Asp
            20                  25                  30

```
Ser Met Gly Trp Tyr Arg Gln Ala Pro Gly Lys Gln Arg Glu Leu Val
        35                  40                  45

Ala Ala Ile Thr Ser Arg Thr Ile Tyr Ala Asp Ser Val Lys Gly Arg
 50                  55                  60

Phe Thr Ile Ser Arg Asp Asn Ala Lys Asn Thr Val Tyr Leu Gln Met
 65                  70                  75                  80

Asn Ser Leu Lys Pro Glu Asp Thr Ala Val Tyr Tyr Cys Asn Leu Glu
                 85                  90                  95

Gly Gln Ala Gly Trp Gly Thr Ala Leu Met Asp Tyr Trp Gly Lys Gly
            100                 105                 110

Thr Leu Val Thr Val Ser Ser
        115

<210> SEQ ID NO 30
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 30

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Ser Ile Asp
             20                  25                  30

Ala Met Gly Trp Tyr Arg Gln Ala Pro Gly Lys Gln Arg Glu Leu Val
        35                  40                  45

Ala Thr Ile Thr Ser Gly Lys Asn Tyr Ala Asp Ser Val Lys Gly Arg
 50                  55                  60

Phe Thr Ile Ser Arg Asp Asn Ala Lys Asn Ala Val Tyr Leu Gln Met
 65                  70                  75                  80

Asn Ser Leu Lys Pro Glu Asp Thr Ala Val Tyr Tyr Cys Asn Leu Glu
                 85                  90                  95

Gly Gln Ala Gly Trp Gly Thr Ala Leu Met Asp Tyr Trp Gly Lys Gly
            100                 105                 110

Thr Gln Val Thr Val Ser Ser
        115

<210> SEQ ID NO 31
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 31

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Ser Ile Asp
             20                  25                  30

Ser Met Gly Trp Tyr Arg Gln Ala Pro Gly Lys Gln Arg Glu Leu Val
        35                  40                  45

Ala Ala Ile Thr Ser Ser Thr Asn Tyr Ala Asp Ser Val Lys Gly Arg
 50                  55                  60

Phe Thr Ile Ser Arg Asp Asn Ala Lys Asn Thr Val Tyr Leu Gln Thr
 65                  70                  75                  80

Asn Ser Leu Lys Pro Glu Asp Thr Ala Val Tyr Tyr Cys Asn Leu Glu
                 85                  90                  95
```

-continued

Gly Gln Ala Gly Trp Gly Thr Ala Leu Met Asp Tyr Trp Gly Lys Gly
            100                 105                 110

Thr Gln Val Thr Val Ser Ser
        115

<210> SEQ ID NO 32
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Thr Ser Ser Thr Asn Tyr Ala Asp Ser Val Lys Gly Arg
    50                  55                  60

Phe Thr Ile Ser Arg Ala Asn Ala Lys Asn Thr Val Tyr Leu Gln Met
65                  70                  75                  80

Asn Ser Leu Lys Pro Glu Asp Thr Ala Val Tyr Tyr Cys His Leu Glu
                85                  90                  95

Gly Gln Ala Gly Trp Gly Thr Ala Leu Leu Asp Tyr Trp Gly Lys Gly
            100                 105                 110

Thr Leu Val Thr Val Ser Ser
        115

<210> SEQ ID NO 33
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 33

Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Val Phe Ser Ile Asn
            20                  25                  30

Asp Met Gly Trp Phe Arg Gln Ala Pro Gly Lys Gln Arg Glu Leu Val
        35                  40                  45

Ala Asp Ile Ile Ser Arg Gly Val Thr Asn Tyr Ala Asp Ser Val Lys
    50                  55                  60

Gly Arg Phe Thr Ile Ser Gly Asp Pro Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala His Ile Ser Thr Gly Trp Gly Arg Pro His Asn Asn Tyr Trp Gly
            100                 105                 110

Gln Gly Thr Gln Val Thr Val Ser Ser
        115                 120

<210> SEQ ID NO 34
<211> LENGTH: 121
<212> TYPE: PRT

<213> ORGANISM: Artificial Sequence
<220> FEATURE:
<223> OTHER INFORMATION: Nanobody Sequence

<400> SEQUENCE: 34

Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Ile Phe Ser Ile Asp
            20                  25                  30

Ser Met Gly Trp Phe Arg Gln Ala Pro Gly Lys Gln Arg Glu Leu Val
        35                  40                  45

Ala Asp Ile Ile Ser Ala Asp Val Thr Asn Tyr Ala Asp Ser Val Lys
    50                  55                  60

Gly Arg Phe Thr Ile Ser Gly Asp His Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala His Ile Ser Thr Gly Trp Gly Arg Pro His Asn Asn Tyr Trp Gly
            100                 105                 110

Gln Gly Thr Gln Val Thr Val Ser Ser
        115                 120

<210> SEQ ID NO 35
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 35

Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Ile Phe Ser Ile Asp
            20                  25                  30

Ser Met Gly Trp Phe Arg Gln Ala Pro Gly Lys Gln Arg Glu Leu Val
        35                  40                  45

Ala Asp Ile Ile Ser Ala Asp Val Thr Asn Tyr Ala Asp Ser Val Lys
    50                  55                  60

Gly Arg Phe Thr Ile Ser Gly Asp His Ala Gln Asn Thr Val Tyr Leu
65                  70                  75                  80

Gln Met Asn Ser Leu Lys Pro Glu Asp Thr Ala Val Tyr Tyr Cys Asn
                85                  90                  95

Ala His Ile Ser Thr Gly Trp Gly Arg Pro His Asn Asn Tyr Trp Gly
            100                 105                 110

Gln Gly Thr Gln Val Thr Val Ser Ser
        115                 120

<210> SEQ ID NO 36
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 36

Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Ile Phe Ser Ile Asp
            20                  25                  30

Ser Met Gly Trp Phe Arg Gln Ala Pro Gly Lys Gln Arg Glu Leu Val
           35                  40                  45

Ala Asp Ile Ile Ser Ala Gly Val Thr Asn Tyr Ala Asp Ser Val Lys
     50                  55                  60

Gly Arg Phe Thr Ile Ser Gly Asp His Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala His Ile Ser Thr Gly Trp Gly Arg Pro His Asn Asn Tyr Trp Gly
             100                 105                 110

Gln Gly Thr Gln Val Thr Val Ser Ser
             115                 120

<210> SEQ ID NO 37
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 37

Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Ile Phe Ser Ile Asp
             20                  25                  30

Asp Met Gly Trp Phe Arg Gln Ala Pro Gly Lys Gln Arg Glu Leu Val
           35                  40                  45

Ala Asp Ile Ile Ser Ala Gly Val Thr Asn Tyr Ala Asp Ser Val Lys
     50                  55                  60

Gly Arg Phe Thr Ile Ser Gly Asp His Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala His Ile Ser Thr Gly Trp Gly Arg Pro His Asn Asn Tyr Trp Gly
             100                 105                 110

Gln Gly Thr Leu Val Thr Val Ser Ser
             115                 120

<210> SEQ ID NO 38
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 38

Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Ile Phe Ser Ile Asn
             20                  25                  30

Asp Val Gly Trp Phe Arg Gln Ala Pro Gly Lys Gln Arg Glu Leu Val
           35                  40                  45

Ala Asp Ile Ile Ser Arg Gly Val Thr Asn Tyr Ala Asp Ser Val Lys
     50                  55                  60

Gly Arg Phe Thr Ile Ser Gly Asp Pro Ala Lys Asn Thr Val Tyr Leu
 65                  70                  75                  80

Gln Met Asn Ser Leu Lys Pro Glu Asp Thr Ala Ala Tyr Tyr Cys Asn

```
                 85                  90                  95
Ala His Ile Ser Thr Gly Trp Gly Arg Pro His Asn Asn Tyr Trp Gly
            100                 105                 110

Gln Gly Thr Gln Val Thr Val Ser Ser
            115                 120

<210> SEQ ID NO 39
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 39

Glu Val Gln Leu Val Glu Ser Gly Gly Asp Leu Val Gln Pro Gly Gly
1               5                  10                  15

Pro Leu Arg Leu Ser Cys Ala Ala Ser Gly Asn Ile Phe Ser Ile Asn
            20                  25                  30

Asp Met Gly Trp Phe Arg Gln Ala Pro Gly Lys Gln Arg Glu Leu Val
        35                  40                  45

Ala Asp Ile Ile Ser Arg Gly Val Thr Asn Tyr Ala Asp Ser Val Lys
    50                  55                  60

Gly Arg Phe Thr Ile Ser Gly Asp Pro Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala His Ile Ser Thr Gly Trp Gly Arg Pro His Asn Asn Tyr Trp Gly
            100                 105                 110

Gln Gly Thr Gln Val Thr Val Ser Ser
            115                 120

<210> SEQ ID NO 40
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 40

Glu Val Gln Leu Val Glu Ser Gly Gly Asp Leu Val Gln Pro Gly Gly
1               5                  10                  15

Pro Leu Arg Leu Ser Cys Ala Ala Ser Gly Ser Ile Phe Ser Ile Asn
            20                  25                  30

Asp Met Gly Trp Phe Arg Gln Ala Pro Gly Lys Gln Arg Glu Leu Val
        35                  40                  45

Ala Asp Ile Ile Ser Arg Gly Val Thr Asn Tyr Ala Asp Ser Val Lys
    50                  55                  60

Gly Arg Phe Thr Ile Ser Gly Asp Pro Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala His Ile Ser Thr Gly Trp Gly Arg Pro His Asn Asn Tyr Trp Gly
            100                 105                 110

Gln Gly Thr Gln Val Thr Val Ser Ser
            115                 120

<210> SEQ ID NO 41
<211> LENGTH: 121
```

```
<212> TYPE: PRT
<213> ORGANISM: Artificial Sequence
<220> FEATURE:
<223> OTHER INFORMATION: Nanobody Sequence

<400> SEQUENCE: 41

Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Ile Phe Ser Ile Asn
            20                  25                  30

Asp Met Gly Trp Phe Arg Gln Ala Pro Gly Lys Gln Arg Glu Leu Val
        35                  40                  45

Ala Asp Ile Ile Ser Arg Gly Val Thr Asn Tyr Ala Asp Ser Val Lys
    50                  55                  60

Gly Arg Phe Thr Ile Ser Gly Asp Pro Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala His Ile Ser Thr Gly Trp Gly Arg Pro His Asn Asn Tyr Trp Gly
            100                 105                 110

Gln Gly Thr Gln Val Thr Val Ser Ser
        115                 120

<210> SEQ ID NO 42
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 42

Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Ile Phe Ser Ile Asn
            20                  25                  30

Asp Thr Gly Trp Phe Arg Gln Ala Pro Gly Lys Gln Arg Glu Leu Val
        35                  40                  45

Ala Asp Ile Ile Ser Arg Gly Val Thr Asn Tyr Ala Asp Ser Val Lys
    50                  55                  60

Gly Arg Phe Thr Ile Ser Gly Asp Pro Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala His Ile Ser Thr Gly Trp Gly Arg Pro His Asn Asn Tyr Trp Gly
            100                 105                 110

Gln Gly Thr Gln Val Thr Val Ser Ser
        115                 120

<210> SEQ ID NO 43
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 43

Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Ile Phe Ser Ile Asn
```

```
                    20                  25                  30
Asp Met Gly Trp Phe Arg Gln Ala Pro Gly Lys Gln Arg Glu Leu Val
            35                  40                  45
Ala Asp Ile Ile Ser Ala Gly Val Thr Asn Tyr Ala Asp Ser Val Lys
        50                  55                  60
Gly Arg Phe Thr Ile Ser Gly Asp Pro Ala Lys Asn Thr Val Tyr Leu
65                  70                  75                  80
Gln Met Asn Ser Leu Lys Pro Glu Asp Thr Ala Val Tyr Tyr Cys Asn
                85                  90                  95
Ala His Ile Ser Thr Gly Trp Gly Arg Pro His Asn Asn Tyr Trp Gly
            100                 105                 110
Gln Gly Thr Gln Val Thr Val Ser Ser
        115                 120

<210> SEQ ID NO 44
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 44

Glu Val Gln Leu Val Glu Ser Gly Gly Asp Leu Val Gln Pro Gly Gly
1               5                   10                  15
Ser Leu Arg Leu Ser Cys Ala Ala Ser Gly Ser Ile Phe Ser Ile Asn
            20                  25                  30
Asp Met Gly Trp Phe Arg Gln Ala Pro Gly Lys Gln Arg Glu Leu Val
        35                  40                  45
Ala Gly Ile Ile Ser Arg Gly Val Thr Asn Tyr Ala Asp Ser Val Lys
    50                  55                  60
Gly Arg Phe Thr Ile Ser Gly Asp Pro Ala Lys Asn Thr Val Tyr Leu
65                  70                  75                  80
Gln Met Asn Ser Leu Lys Pro Glu Asp Thr Ala Val Tyr Tyr Cys Asn
                85                  90                  95
Ala His Ile Ser Thr Gly Trp Gly Arg Pro His Asn Asn Tyr Trp Gly
            100                 105                 110
Gln Gly Thr Gln Val Thr Val Ser Ser
        115                 120

<210> SEQ ID NO 45
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 45

Glu Val Gln Leu Val Glu Ser Gly Gly Asp Leu Val Gln Pro Gly Gly
1               5                   10                  15
Ser Leu Arg Leu Ser Cys Ala Ala Ser Gly Ser Ile Phe Ser Ile Asn
            20                  25                  30
Asp Met Gly Trp Phe Arg Gln Ala Pro Gly Lys Gln Arg Glu Leu Val
        35                  40                  45
Ala Asp Ile Ile Ser Arg Gly Val Thr Asn Tyr Ala Asp Ser Val Lys
    50                  55                  60
Gly Arg Phe Thr Ile Ser Gly Asp Pro Ala Lys Asn Thr Ala Tyr Leu
65                  70                  75                  80
```

Gln Met Asn Ser Leu Lys Pro Glu Asp Thr Ala Val Tyr Tyr Cys Asn
            85                  90                  95

Ala His Ile Ser Thr Gly Trp Gly Arg Pro His Asn Asn Tyr Trp Gly
            100                 105                 110

Gln Gly Thr Gln Val Thr Val Ser Ser
        115                 120

<210> SEQ ID NO 46
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 46

Glu Val Gln Leu Val Glu Ser Gly Gly Asp Leu Val Gln Pro Gly Gly
1               5                   10                  15

Ser Leu Gly Leu Ser Cys Ala Ala Ser Gly Ser Ile Phe Ser Ile Asn
            20                  25                  30

Asp Met Gly Trp Phe Arg Gln Ala Pro Gly Lys Gln Arg Glu Leu Val
        35                  40                  45

Ala Asp Ile Ile Ser Arg Gly Val Thr Asn Tyr Ala Asp Ser Val Lys
    50                  55                  60

Gly Arg Phe Thr Ile Ser Gly Asp Pro Ala Lys Asn Thr Val Tyr Leu
65                  70                  75                  80

Gln Met Asn Ser Leu Lys Pro Glu Asp Thr Ala Val Tyr Tyr Cys Asn
            85                  90                  95

Ala His Ile Ser Thr Gly Trp Gly Arg Pro His Asn Asn Tyr Trp Gly
            100                 105                 110

Gln Gly Thr Gln Val Thr Val Ser Ser
        115                 120

<210> SEQ ID NO 47
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 47

Glu Val Gln Leu Val Glu Ser Gly Gly Asp Leu Val Arg Pro Gly Gly
1               5                   10                  15

Ser Leu Arg Leu Ser Cys Ala Ala Ser Gly Ser Ile Phe Ser Ile Asn
            20                  25                  30

Asp Met Gly Trp Phe Arg Gln Ala Pro Gly Lys Gln Arg Glu Leu Val
        35                  40                  45

Ala Asp Ile Ile Ser Arg Gly Val Thr Asn Tyr Ala Asp Ser Val Lys
    50                  55                  60

Gly Arg Phe Thr Ile Ser Gly Asp Pro Ala Lys Asn Thr Val Tyr Leu
65                  70                  75                  80

Gln Met Asn Ser Leu Lys Pro Glu Asp Thr Ala Val Tyr Tyr Cys Asn
            85                  90                  95

Ala His Ile Ser Thr Gly Trp Gly Arg Pro His Asn Asn Tyr Trp Gly
            100                 105                 110

Gln Gly Thr Gln Val Thr Val Ser Ser
        115                 120

<210> SEQ ID NO 48

```
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 48

Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Ile Phe Ser Ile Asn
            20                  25                  30

Asp Met Gly Trp Phe Arg Gln Ala Pro Gly Lys Gln Arg Glu Leu Val
        35                  40                  45

Ala Asp Ile Ile Ser Arg Gly Val Thr Asn Cys Ala Asp Ser Val Lys
    50                  55                  60

Gly Arg Phe Thr Ile Ser Gly Asp Pro Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala His Ile Ser Thr Gly Trp Gly Arg Pro His Asn Asn Tyr Trp Gly
            100                 105                 110

Gln Gly Thr Gln Val Thr Val Ser Ser
        115                 120

<210> SEQ ID NO 49
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 49

Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Ile Phe Ser Ile Asn
            20                  25                  30

Asp Met Gly Trp Leu Arg Gln Ala Pro Gly Lys Gln Arg Glu Leu Val
        35                  40                  45

Ala Asp Ile Ile Ser Arg Gly Val Thr Asn Tyr Ala Asp Ser Val Lys
    50                  55                  60

Gly Arg Phe Thr Ile Ser Gly Asp Pro Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala His Ile Ser Thr Gly Trp Gly Arg Pro His Asn Asn Tyr Trp Gly
            100                 105                 110

Gln Gly Thr Gln Val Thr Val Ser Ser
        115                 120

<210> SEQ ID NO 50
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 50

Glu Val Gln Leu Val Glu Ser Gly Gly Asp Leu Val Gln Pro Gly Gly
1               5                   10                  15
```

```
Ser Leu Arg Leu Ser Cys Ala Ala Ser Gly Ser Ile Phe Ser Ile Asn
            20                  25                  30

Asp Met Gly Trp Phe Arg Gln Ala Pro Gly Lys Gln Arg Glu Leu Val
        35                  40                  45

Ala Asp Ile Ile Ser Arg Gly Val Thr Asn Tyr Ala Asp Ser Val Arg
50                  55                  60

Gly Arg Phe Thr Ile Ser Gly Asp Pro Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala His Ile Ser Thr Gly Trp Gly Arg Pro His Asn Asn Tyr Trp Gly
            100                 105                 110

Gln Gly Thr Gln Val Thr Val Ser Ser
            115                 120

<210> SEQ ID NO 51
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Asp Met Gly Trp Phe Arg Gln Ala Pro Gly Lys Gln Arg Glu Leu Val
        35                  40                  45

Ala Asp Ile Ile Ser Arg Gly Val Thr Asn Tyr Ala Asp Ser Val Lys
50                  55                  60

Gly Arg Phe Thr Ile Ser Gly Asp Pro Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala His Ile Ser Thr Gly Trp Gly Arg Pro His Asn Asn Tyr Trp Gly
            100                 105                 110

Gln Gly Thr Gln Val Thr Val Ser Ser
            115                 120

<210> SEQ ID NO 52
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 52

Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Ile Phe Ser Ile Asn
            20                  25                  30

Asp Met Gly Trp Phe Arg Gln Ala Pro Gly Lys Gln Arg Glu Leu Val
        35                  40                  45

Ala Asp Ile Ile Ser Arg Gly Val Thr Asn Tyr Ala Asp Ser Val Lys
50                  55                  60

Gly Arg Phe Thr Val Ser Gly Asp Pro Ala Lys Asn Thr Val Tyr Leu
65                  70                  75                  80
```

Gln Met Asn Ser Leu Lys Pro Glu Asp Thr Ala Val Tyr Tyr Cys Asn
                85                  90                  95

Ala His Ile Ser Thr Gly Trp Gly Arg Pro His Asn Asn Tyr Trp Gly
            100                 105                 110

Gln Gly Thr Gln Val Thr Val Ser Ser
        115                 120

<210> SEQ ID NO 53
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 53

Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Ile Phe Ser Ile Asn
            20                  25                  30

Asp Met Gly Trp Phe Arg Gln Ala Pro Gly Lys Gln Arg Glu Leu Val
        35                  40                  45

Ala Asp Ile Ile Ser Arg Gly Val Thr Asn Tyr Ala Asp Ser Val Lys
    50                  55                  60

Gly Arg Phe Thr Ile Ser Gly Asp His Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala His Ile Ser Thr Gly Trp Gly Arg Pro His Asn Asn Tyr Trp Gly
            100                 105                 110

Gln Gly Thr Gln Val Thr Val Ser Ser
        115                 120

<210> SEQ ID NO 54
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 54

Glu Val Gln Leu Val Glu Ser Gly Gly Asp Leu Val Gln Pro Gly Gly
1               5                   10                  15

Ser Leu Arg Leu Ser Cys Ala Ser Gly Ser Ile Phe Ser Ile Asn
            20                  25                  30

Asp Met Gly Trp Phe Arg Gln Ala Pro Gly Lys Gln Arg Glu Leu Val
        35                  40                  45

Ala Asp Ile Ile Ser Arg Asp Val Thr Asn Tyr Ala Asp Ser Val Lys
    50                  55                  60

Gly Arg Phe Thr Ile Ser Gly Asp His Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala His Ile Ser Thr Gly Trp Gly Arg Pro His Asn Asn Tyr Trp Gly
            100                 105                 110

Gln Gly Thr Gln Val Thr Val Ser Ser
        115                 120

<210> SEQ ID NO 55
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 55

```
Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Ile Phe Ser Ile Asn
            20                  25                  30

Asp Met Gly Trp Phe Arg Gln Ala Pro Gly Lys Gln Arg Glu Leu Val
        35                  40                  45

Ala Asp Ile Ile Ser Arg Gly Val Thr Asn Tyr Ala Asp Ser Val Lys
    50                  55                  60

Gly Arg Phe Thr Ile Ser Gly Asp Pro Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala His Ile Ser Met Gly Trp Gly Arg Pro His Asn Asn Tyr Trp Gly
            100                 105                 110

Gln Gly Thr Leu Val Thr Val Ser Ser
        115                 120
```

<210> SEQ ID NO 56
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 56

```
Glu Val Gln Leu Val Glu Ser Gly Gly Gly Leu Val Gln Ala Gly Gly
1               5                   10                  15

Ser Leu Arg Leu Ser Cys Thr Gly Ser Arg Ser Ile Phe Ser Thr Tyr
            20                  25                  30

Ala Met Ala Trp His Arg Gln Ala Pro Gly Lys Gln Arg Glu Leu Val
        35                  40                  45

Gly Phe Ile Tyr Trp Gly Gly Thr Thr Thr Tyr Ser Asp Ser Val Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Ala Gly Val Tyr Tyr Cys Asn
                85                  90                  95

Ile Tyr Gly Ser Tyr Ala Leu Pro Trp Gly Gln Gly Thr Leu Val Thr
            100                 105                 110

Val Ser Ser
        115
```

<210> SEQ ID NO 57
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 57

```
Glu Val Gln Leu Val Glu Ser Gly Gly Gly Leu Val Gln Ala Gly Gly
1               5                   10                  15
```

-continued

```
Ser Leu Arg Leu Ser Cys Thr Gly Ser Arg Asn Ile Phe Ser Thr Tyr
            20                  25                  30

Ala Met Ala Trp His Arg Gln Ala Pro Gly Lys Gln Arg Glu Leu Val
            35                  40                  45

Gly Phe Ile Tyr Trp Gly Gly Thr Thr Ser Tyr Val Asp Ser Val Lys
 50                  55                  60

Gly Arg Phe Thr Ile Ser Arg Asp Asn Ala Lys Asn Thr Met Tyr Leu
 65                  70                  75                  80

Gln Met Asn Ser Leu Lys Pro Glu Asp Ala Ala Val Tyr Tyr Cys Asn
                 85                  90                  95

Ile Tyr Gly Ser Tyr Ala Leu Pro Trp Gly Gln Gly Thr Leu Val Thr
            100                 105                 110

Val Ser Ser
        115
```

<210> SEQ ID NO 58
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 58

```
Glu Val Gln Leu Val Glu Ser Gly Gly Gly Leu Val Gln Ala Gly Gly
 1               5                  10                  15

Ser Leu Arg Leu Ser Cys Thr Gly Ser Arg Ser Ile Phe Ser Thr Tyr
            20                  25                  30

Ala Met Ala Trp His Arg Gln Ala Pro Gly Lys Gln Arg Glu Leu Val
            35                  40                  45

Gly Phe Ile Tyr Trp Gly Gly Thr Thr Thr Tyr Ser Asp Ser Val Lys
 50                  55                  60

Gly Arg Phe Thr Ile Ser Arg Asp Asn Ala Lys Asn Thr Met Tyr Leu
 65                  70                  75                  80

Gln Met Asn Ser Leu Lys Pro Glu Asp Ala Gly Val Tyr Tyr Cys Asn
                 85                  90                  95

Ile Tyr Gly Ser Tyr Ala Leu Pro Gln Gly Gln Gly Thr Leu Val Thr
            100                 105                 110

Val Ser Ser
        115
```

<210> SEQ ID NO 59
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 59

```
Glu Val Gln Leu Val Glu Ser Gly Gly Gly Met Val Gln Ala Gly Gly
 1               5                  10                  15

Ser Leu Arg Leu Ser Cys Thr Gly Ser Arg Asn Ile Phe Ser Thr Tyr
            20                  25                  30

Ala Met Ala Trp His Arg Gln Ala Pro Gly Lys Gln Arg Glu Leu Val
            35                  40                  45

Gly Phe Ile Tyr Trp Gly Gly Thr Thr Ser Tyr Val Asp Ser Val Lys
 50                  55                  60

Gly Arg Phe Thr Ile Ser Arg Asp Asn Ala Lys Asn Thr Met Tyr Leu
```

```
                 65                  70                  75                  80
Gln Met Asn Ser Leu Lys Pro Glu Asp Ala Val Tyr Tyr Cys Asn
                85                  90                  95

Ile Tyr Gly Ser Tyr Ala Leu Pro Trp Gly Gln Gly Thr Gln Val Thr
                100                 105                 110

Val Ser Ser
        115
```

<210> SEQ ID NO 60
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 60

```
Glu Val Gln Leu Val Glu Ser Gly Gly Gly Leu Val Gln Ala Gly Gly
1               5                   10                  15

Ser Leu Arg Leu Ser Cys Thr Gly Ser Arg Ser Ile Phe Ser Thr Tyr
                20                  25                  30

Ala Met Ala Trp His Arg Gln Ala Pro Gly Lys Gln Arg Glu Leu Val
                35                  40                  45

Gly Phe Ile Tyr Trp Gly Gly Thr Thr Ser Tyr Val Asp Ser Val Lys
        50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Ala Val Tyr Tyr Cys Asn
                85                  90                  95

Ile Tyr Gly Ser Tyr Ala Leu Pro Trp Gly Gln Gly Thr Leu Val Thr
                100                 105                 110

Val Ser Ser
        115
```

<210> SEQ ID NO 61
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 61

```
Glu Val Gln Leu Val Glu Ser Gly Gly Gly Leu Val Gln Ala Gly Gly
1               5                   10                  15

Ser Leu Arg Leu Ser Cys Thr Gly Ser Arg Ser Ile Phe Ser Thr Tyr
                20                  25                  30

Ala Met Ala Trp His Arg Gln Ala Pro Gly Lys Gln Arg Glu Leu Val
                35                  40                  45

Gly Phe Ile Tyr Trp Gly Gly Thr Thr Thr Tyr Ser Asp Ser Val Lys
        50                  55                  60

Gly Arg Phe Thr Ile Ser Arg Asp Asn Ala Lys Ser Thr Met Tyr Leu
65                  70                  75                  80

Gln Met Asn Ser Leu Lys Pro Glu Asp Ala Gly Val Tyr Tyr Cys Asn
                85                  90                  95

Ile Tyr Gly Ser Tyr Ala Leu Pro Trp Gly Gln Gly Thr Leu Val Thr
                100                 105                 110

Val Ser Ser
        115
```

```
<210> SEQ ID NO 62
<211> LENGTH: 120
<212> TYPE: PRT
<213> ORGANISM: Artificial Sequence
<220> FEATURE:
<223> OTHER INFORMATION: Nanobody Sequence

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Ile Phe Ser Ile Ser
            20                  25                  30

Thr Met Gly Trp Tyr Arg Gln Ala Pro Gly Lys Gln Arg Glu Val Val
        35                  40                  45

Ala Val Thr Ser Gly Phe Ser Thr Asn Tyr Ser Ala Val Lys Gly
    50                  55                  60

Arg Phe Thr Leu Ser Arg Asp Pro Ala Lys Asn Thr Val Phe Leu Gln
65                  70                  75                  80

Met Asn Ser Leu Gln Pro Glu Asp Thr Ala Thr Tyr Tyr Cys Asn Ala
                85                  90                  95

Tyr Leu Ser Leu Ala Trp Arg Asp Pro Asp Arg Asp Tyr Trp Gly Gln
            100                 105                 110

Gly Thr Gln Val Thr Val Ser Ser
        115                 120

<210> SEQ ID NO 63
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 63

Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Ile Phe Ser Ile Asp
            20                  25                  30

Ala Met Gly Trp Tyr Arg Gln Ala Pro Gly Lys Gln Arg Glu Leu Val
        35                  40                  45

Ala Glu Ile Ser Asp His Thr Thr Tyr Gly Asp Ser Val Lys Gly Arg
    50                  55                  60

Phe Thr Ile Ser Arg Gly Asn Ala Glu Asn Thr Val Ala Leu Gln Met
65                  70                  75                  80

Asn Ser Leu Lys Pro Glu Asp Thr Gly Val Tyr Tyr Cys Asn Val His
                85                  90                  95

His Gln Arg Gly Trp Gly Thr Ser Ile Thr Val Thr Trp Gly Gln Gly
            100                 105                 110

Thr Gln Val Thr Val Ser Ser
        115

<210> SEQ ID NO 64
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 64

Glu Val Gln Leu Val Glu Ser Gly Gly Gly Leu Val Gln Ala Gly Glu
```

```
                1               5                      10                      15
             Ser Leu Arg Leu Ser Cys Ala Ala Ser Gly Ser Ile Phe Ser Ile Asp
                            20                      25                      30

Ala Met Gly Trp Tyr Arg Gln Ala Pro Gly Lys Gln Arg Glu Leu Val
                            35                      40                      45

Ala Glu Ile Ser Asp His Thr Thr Tyr Gly Asp Ser Val Lys Gly Arg
                    50                      55                      60

Phe Thr Ile Ser Arg Gly Asn Ala Glu Asn Thr Val Ala Leu Gln Met
             65                      70                      75                      80

Asn Ser Leu Lys Pro Glu Asp Thr Gly Val Tyr Tyr Cys Asn Val His
                            85                      90                      95

His Gln Arg Gly Trp Gly Thr Ser Ile Thr Val Ala Trp Gly Gln Gly
                            100                     105                     110

Thr Gln Val Thr Val Ser Ser
                    115
```

<210> SEQ ID NO 65
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 65

```
             Glu Val Gln Leu Val Glu Ser Gly Gly Gly Leu Val Gln Ala Gly Glu
             1               5                      10                      15

Ser Leu Arg Leu Ser Cys Ala Ala Ser Gly Ser Ile Phe Ser Ile Asp
                            20                      25                      30

Ala Met Gly Trp Tyr Arg Gln Ala Pro Gly Lys Gln Arg Glu Leu Val
                            35                      40                      45

Ala Glu Ile Ser Asp His Thr Thr Tyr Gly Asp Ser Met Lys Gly Arg
                    50                      55                      60

Phe Thr Ile Ser Arg Gly Asn Ala Glu Asn Thr Val Ala Leu Gln Met
             65                      70                      75                      80

Asn Ser Leu Lys Pro Glu Asp Thr Gly Val Tyr Tyr Cys Asn Val His
                            85                      90                      95

His Gln Arg Gly Trp Gly Thr Ser Ile Thr Val Thr Trp Gly Gln Gly
                            100                     105                     110

Thr Gln Val Thr Val Ser Ser
                    115
```

<210> SEQ ID NO 66
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 66

```
             Glu Val Gln Leu Val Glu Ser Gly Gly Arg Leu Val Gln Ala Gly Glu
             1               5                      10                      15

Ser Leu Arg Leu Ser Cys Ala Ala Ser Gly Ser Ile Phe Ser Ile Asp
                            20                      25                      30

Ala Met Gly Trp Tyr Arg Gln Ala Pro Gly Lys Gln Arg Glu Leu Val
                            35                      40                      45

Ala Glu Ile Ser Gly His Thr Thr Tyr Gly Asp Ser Val Lys Gly Arg
                    50                      55                      60
```

```
Phe Thr Ile Ser Arg Gly Asn Ala Glu Asn Thr Val Ala Leu Gln Met
65                  70                  75                  80

Asn Ser Leu Lys Pro Glu Asp Thr Gly Val Tyr Tyr Cys Asn Val His
                85                  90                  95

His Gln Arg Gly Trp Gly Thr Pro Ile Thr Val Thr Trp Gly Gln Gly
            100                 105                 110

Thr Gln Val Thr Val Ser Ser
            115

<210> SEQ ID NO 67
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 67

Glu Val Gln Leu Val Glu Ser Gly Gly Arg Leu Val Gln Ala Gly Glu
1               5                   10                  15

Ser Leu Arg Leu Ser Cys Ala Ala Ser Gly Ser Ile Phe Ser Ile Asp
                20                  25                  30

Ala Met Gly Trp Tyr Arg Gln Ala Pro Gly Lys Gln Arg Glu Leu Val
            35                  40                  45

Ala Glu Ile Ser Asp His Thr Thr Tyr Gly Asp Ser Val Lys Gly Arg
        50                  55                  60

Phe Thr Ile Ser Arg Gly Asn Ala Glu Asn Thr Val Ala Leu Gln Met
65                  70                  75                  80

Asn Ser Leu Lys Pro Glu Asp Thr Gly Val Tyr Tyr Cys Asn Val His
                85                  90                  95

His Gln Arg Gly Trp Gly Thr Pro Ile Thr Val Thr Trp Gly Gln Gly
            100                 105                 110

Thr Gln Val Thr Val Ser Ser
            115

<210> SEQ ID NO 68
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 68

Glu Val Gln Leu Val Glu Ser Gly Gly Gly Leu Val Arg Ala Gly Glu
1               5                   10                  15

Ser Leu Arg Leu Ser Cys Ala Ala Ser Gly Ser Ile Phe Ser Ile Asp
                20                  25                  30

Ala Met Gly Trp Tyr Arg Gln Ala Pro Gly Lys Gln Arg Glu Leu Val
            35                  40                  45

Ala Glu Ile Ser Asp His Thr Thr Tyr Gly Asp Ser Val Lys Gly Arg
        50                  55                  60

Phe Thr Ile Ser Arg Gly Asn Ala Glu Asn Thr Val Ala Leu Gln Met
65                  70                  75                  80

Asn Ser Leu Lys Pro Glu Asp Thr Gly Val Tyr Tyr Cys Asn Val His
                85                  90                  95

His Gln Arg Gly Trp Gly Thr Ser Ile Thr Val Thr Trp Gly Gln Gly
            100                 105                 110

Thr Leu Val Thr Val Ser Ser
            115
```

-continued

```
<210> SEQ ID NO 69
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 69
```

Glu Val Gln Leu Val Glu Ser Gly Gly Gly Leu Val Gln Ala Gly
1               5                   10                  15

Ser Leu Arg Leu Ser Cys Val Ala Ser Gly Ser Ile Ser Ser Ile Thr
            20                  25                  30

Ala Met Gly Trp His Arg Gln Ala Pro Gly Ala Gln Arg Glu Gly Val
        35                  40                  45

Ala Val Ile Ser Arg Ser Gly Ala Thr Met Leu Val Asp Ser Val Lys
    50                  55                  60

Gly Arg Phe Thr Ile Val Gln Asp Asn Ala Lys Asn Thr Val Tyr Leu
65                  70                  75                  80

Gln Met Asn Ser Leu Lys Val Glu Asp Thr Ala Val Tyr Gly Cys Ser
                85                  90                  95

Ala Ile Thr Gln Gly Arg Thr Tyr Trp Gly Gln Gly Thr Leu Val Thr
            100                 105                 110

Val Ser Ser
        115

```
<210> SEQ ID NO 70
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 70
```

Glu Val Gln Leu Val Glu Ser Gly Gly Gly Leu Val Gln Ala Gly
1               5                   10                  15

Ser Leu Arg Leu Ser Cys Val Ala Ser Gly Ser Ile Ser Ser Ile Thr
            20                  25                  30

Ala Met Gly Trp His Arg Gln Ala Pro Gly Ala Gln Arg Glu Gly Val
        35                  40                  45

Ala Ile Ile Ser Arg Ser Gly Ala Thr Met Leu Val Asp Ser Val Lys
    50                  55                  60

Gly Arg Phe Thr Ile Val Gln Asp Asn Ala Lys Asn Thr Val Tyr Leu
65                  70                  75                  80

Gln Met Asn Ser Leu Lys Val Glu Asp Thr Ala Val Tyr Gly Cys Ser
                85                  90                  95

Ala Ile Thr Gln Gly Arg Thr Tyr Trp Gly Gln Gly Thr Gln Val Thr
            100                 105                 110

Val Ser Ser
        115

```
<210> SEQ ID NO 71
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 71
```

```
Glu Val Gln Leu Val Glu Ser Gly Gly Gly Leu Val Gln Ala Gly Gly
1               5                   10                  15

Ser Leu Arg Leu Ser Cys Val Ala Ser Gly Ser Ile Ser Ile Thr
            20                  25                  30

Ala Met Gly Trp His Arg Gln Ala Pro Gly Ala Gln Arg Glu Gly Val
            35                  40                  45

Ala Ala Ile Ser Arg Ser Gly Ala Thr Ile Leu Ala Asp Ser Val Lys
        50                  55                  60

Gly Arg Phe Thr Ile Val Gln Asp Asn Ala Lys Asn Thr Val Tyr Leu
65                  70                  75                  80

Gln Met Asn Ser Leu Lys Val Glu Asp Thr Ala Val Tyr Gly Cys Ser
            85                  90                  95

Ala Ile Thr Gln Glu Gln Thr Tyr Trp Gly Gln Gly Thr Gln Val Thr
            100                 105                 110

Val Ser Ser
        115
```

<210> SEQ ID NO 72
<211> LENGTH: 118
<212> TYPE: PRT
<213> ORGANISM: Artificial Sequence
<220> FEATURE:
<223> OTHER INFORMATION: Nanobody Sequence

<400> SEQUENCE: 72

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Phe Ile
            20                  25                  30

Val Met Gly Trp Tyr Arg Gln Ala Pro Gly Glu Gln Arg Ala Leu Val
            35                  40                  45

Ala Thr Val Thr Ser Gly Gly Asp Thr Phe Tyr Val Asp Ser Val Lys
        50                  55                  60

Asp Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Phe Cys Tyr
            85                  90                  95

Phe Thr Lys Val Ser Pro Tyr Lys Glu Thr Thr Trp Gly Gln Gly Thr
            100                 105                 110

Leu Val Thr Val Ser Ser
        115
```

<210> SEQ ID NO 73
<211> LENGTH: 10
<212> TYPE: PRT
<213> ORGANISM: Artificial Sequence
<220> FEATURE:
<223> OTHER INFORMATION: CDR1

<400> SEQUENCE: 73

```
Glu Thr Ile Phe Ser Ile Asp Ser Met Ala
1               5                   10
```

<210> SEQ ID NO 74
<211> LENGTH: 10
<212> TYPE: PRT
<213> ORGANISM: Artificial Sequence
<220> FEATURE:
<223> OTHER INFORMATION: CDR1

```
<400> SEQUENCE: 74

Glu Ser Ile Phe Ser Ile Asp Ala Met Gly
1               5                   10

<210> SEQ ID NO 75
<211> LENGTH: 10
<212> TYPE: PRT
<213> ORGANISM: Artificial Sequence
<220> FEATURE:
<223> OTHER INFORMATION: CDR1

<400> SEQUENCE: 75

Glu Ser Ile Phe Ser Ile Asn Ala Met Gly
1               5                   10

<210> SEQ ID NO 76
<211> LENGTH: 10
<212> TYPE: PRT
<213> ORGANISM: Artificial Sequence
<220> FEATURE:
<223> OTHER INFORMATION: CDR1

<400> SEQUENCE: 76

Gly Ser Ile Phe Ser Ile Asp Ser Met Gly
1               5                   10

<210> SEQ ID NO 77
<211> LENGTH: 10
<212> TYPE: PRT
<213> ORGANISM: Artificial Sequence
<220> FEATURE:
<223> OTHER INFORMATION: CDR1

<400> SEQUENCE: 77

Gly Ser Ile Phe Ser Ile Asp Ala Met Gly
1               5                   10

<210> SEQ ID NO 78
<211> LENGTH: 10
<212> TYPE: PRT
<213> ORGANISM: Artificial Sequence
<220> FEATURE:
<223> OTHER INFORMATION: CDR1

<400> SEQUENCE: 78

Gly Ser Ile Phe Ser Ile Asn Ala Met Gly
1               5                   10

<210> SEQ ID NO 79
<211> LENGTH: 10
<212> TYPE: PRT
<213> ORGANISM: Artificial Sequence
<220> FEATURE:
<223> OTHER INFORMATION: CDR1

<400> SEQUENCE: 79

Gly Ser Val Phe Ser Ile Asn Asp Met Gly
1               5                   10

<210> SEQ ID NO 80
<211> LENGTH: 10
<212> TYPE: PRT
<213> ORGANISM: Artificial Sequence
<220> FEATURE:
<223> OTHER INFORMATION: CDR1

<400> SEQUENCE: 80
```

```
Gly Ser Ile Phe Ser Ile Asp Asp Met Gly
1               5                   10

<210> SEQ ID NO 81
<211> LENGTH: 10
<212> TYPE: PRT
<213> ORGANISM: Artificial Sequence
<220> FEATURE:
<223> OTHER INFORMATION: CDR1

<400> SEQUENCE: 81

Gly Ser Ile Phe Ser Ile Asn Asp Val Gly
1               5                   10

<210> SEQ ID NO 82
<211> LENGTH: 10
<212> TYPE: PRT
<213> ORGANISM: Artificial Sequence
<220> FEATURE:
<223> OTHER INFORMATION: CDR1

<400> SEQUENCE: 82

Gly Asn Ile Phe Ser Ile Asn Asp Met Gly
1               5                   10

<210> SEQ ID NO 83
<211> LENGTH: 10
<212> TYPE: PRT
<213> ORGANISM: Artificial Sequence
<220> FEATURE:
<223> OTHER INFORMATION: CDR1

<400> SEQUENCE: 83

Gly Ser Ile Phe Ser Ile Asn Asp Met Gly
1               5                   10

<210> SEQ ID NO 84
<211> LENGTH: 10
<212> TYPE: PRT
<213> ORGANISM: Artificial Sequence
<220> FEATURE:
<223> OTHER INFORMATION: CDR1

<400> SEQUENCE: 84

Gly Ser Ile Phe Ser Ile Asn Asp Thr Gly
1               5                   10

<210> SEQ ID NO 85
<211> LENGTH: 10
<212> TYPE: PRT
<213> ORGANISM: Artificial Sequence
<220> FEATURE:
<223> OTHER INFORMATION: CDR1

<400> SEQUENCE: 85

Arg Ser Ile Phe Ser Thr Tyr Ala Met Ala
1               5                   10

<210> SEQ ID NO 86
<211> LENGTH: 10
<212> TYPE: PRT
<213> ORGANISM: Artificial Sequence
<220> FEATURE:
<223> OTHER INFORMATION: CDR1

<400> SEQUENCE: 86
```

Arg Asn Ile Phe Ser Thr Tyr Ala Met Ala
1               5                   10

<210> SEQ ID NO 87
<211> LENGTH: 10
<212> TYPE: PRT
<213> ORGANISM: Artificial Sequence
<220> FEATURE:
<223> OTHER INFORMATION: CDR1

<400> SEQUENCE: 87

Gly Thr Ile Phe Ser Ile Ser Thr Met Gly
1               5                   10

<210> SEQ ID NO 88
<211> LENGTH: 10
<212> TYPE: PRT
<213> ORGANISM: Artificial Sequence
<220> FEATURE:
<223> OTHER INFORMATION: CDR1

<400> SEQUENCE: 88

Gly Ser Ile Ser Ser Ile Thr Ala Met Gly
1               5                   10

<210> SEQ ID NO 89
<211> LENGTH: 10
<212> TYPE: PRT
<213> ORGANISM: Artificial Sequence
<220> FEATURE:
<223> OTHER INFORMATION: CDR1

<400> SEQUENCE: 89

Gly Ser Ile Phe Ser Phe Ile Val Met Gly
1               5                   10

<210> SEQ ID NO 90
<211> LENGTH: 9
<212> TYPE: PRT
<213> ORGANISM: Artificial Sequence
<220> FEATURE:
<223> OTHER INFORMATION: CDR2

<400> SEQUENCE: 90

Ala Ile Thr Gly Gly Gly Ser Pro Asn
1               5

<210> SEQ ID NO 91
<211> LENGTH: 9
<212> TYPE: PRT
<213> ORGANISM: Artificial Sequence
<220> FEATURE:
<223> OTHER INFORMATION: CDR2

<400> SEQUENCE: 91

His Ile Thr Gly Gly Gly Arg Ser Asn
1               5

<210> SEQ ID NO 92
<211> LENGTH: 9
<212> TYPE: PRT
<213> ORGANISM: Artificial Sequence
<220> FEATURE:
<223> OTHER INFORMATION: CDR2

<400> SEQUENCE: 92

Thr Ile Thr Gly Gly Gly Ser Thr Asn

```
<210> SEQ ID NO 93
<211> LENGTH: 9
<212> TYPE: PRT
<213> ORGANISM: Artificial Sequence
<220> FEATURE:
<223> OTHER INFORMATION: CDR2

<400> SEQUENCE: 93

Thr Ile Thr Gly Gly Gly Arg Arg Asn
1               5

<210> SEQ ID NO 94
<211> LENGTH: 9
<212> TYPE: PRT
<213> ORGANISM: Artificial Sequence
<220> FEATURE:
<223> OTHER INFORMATION: CDR2

<400> SEQUENCE: 94

Thr Met Thr Gly Gly Gly Ser Thr Asn
1               5

<210> SEQ ID NO 95
<211> LENGTH: 9
<212> TYPE: PRT
<213> ORGANISM: Artificial Sequence
<220> FEATURE:
<223> OTHER INFORMATION: CDR2

<400> SEQUENCE: 95

His Ile Thr Gly Gly Gly Gly Ser Asn
1               5

<210> SEQ ID NO 96
<211> LENGTH: 9
<212> TYPE: PRT
<213> ORGANISM: Artificial Sequence
<220> FEATURE:
<223> OTHER INFORMATION: CDR2

<400> SEQUENCE: 96

Thr Ile Thr Gly Gly Ser Ser Thr Asn
1               5

<210> SEQ ID NO 97
<211> LENGTH: 9
<212> TYPE: PRT
<213> ORGANISM: Artificial Sequence
<220> FEATURE:
<223> OTHER INFORMATION: CDR2

<400> SEQUENCE: 97

His Ile Thr Gly Gly Gly Arg Pro Asn
1               5

<210> SEQ ID NO 98
<211> LENGTH: 9
<212> TYPE: PRT
<213> ORGANISM: Artificial Sequence
<220> FEATURE:
<223> OTHER INFORMATION: CDR2

<400> SEQUENCE: 98

Gly Ile Ser Gly Gly Gly Arg Thr Asn
1               5
```

<210> SEQ ID NO 99
<211> LENGTH: 9
<212> TYPE: PRT
<213> ORGANISM: Artificial Sequence
<220> FEATURE:
<223> OTHER INFORMATION: CDR2

<400> SEQUENCE: 99

Ala Ile Thr Ser Ser Thr Asn Tyr Ala
1               5

<210> SEQ ID NO 100
<211> LENGTH: 9
<212> TYPE: PRT
<213> ORGANISM: Artificial Sequence
<220> FEATURE:
<223> OTHER INFORMATION: CDR2

<400> SEQUENCE: 100

Ser Ile Thr Ser Thr Thr Asn Tyr Ala
1               5

<210> SEQ ID NO 101
<211> LENGTH: 9
<212> TYPE: PRT
<213> ORGANISM: Artificial Sequence
<220> FEATURE:
<223> OTHER INFORMATION: CDR2

<400> SEQUENCE: 101

Ala Ile Thr Ser Gly Thr Asn Tyr Ala
1               5

<210> SEQ ID NO 102
<211> LENGTH: 9
<212> TYPE: PRT
<213> ORGANISM: Artificial Sequence
<220> FEATURE:
<223> OTHER INFORMATION: CDR2

<400> SEQUENCE: 102

Ala Ile Thr Ser Arg Thr Ile Tyr Ala
1               5

<210> SEQ ID NO 103
<211> LENGTH: 9
<212> TYPE: PRT
<213> ORGANISM: Artificial Sequence
<220> FEATURE:
<223> OTHER INFORMATION: CDR2

<400> SEQUENCE: 103

Thr Ile Thr Ser Gly Lys Asn Tyr Ala
1               5

<210> SEQ ID NO 104
<211> LENGTH: 9
<212> TYPE: PRT
<213> ORGANISM: Artificial Sequence
<220> FEATURE:
<223> OTHER INFORMATION: CDR2

<400> SEQUENCE: 104

Asp Ile Ile Ser Arg Gly Val Thr Asn
1               5

<210> SEQ ID NO 105
<211> LENGTH: 9
<212> TYPE: PRT
<213> ORGANISM: Artificial Sequence
<220> FEATURE:
<223> OTHER INFORMATION: CDR2

<400> SEQUENCE: 105

Asp Ile Ile Ser Ala Asp Val Thr Asn
1               5

<210> SEQ ID NO 106
<211> LENGTH: 9
<212> TYPE: PRT
<213> ORGANISM: Artificial Sequence
<220> FEATURE:
<223> OTHER INFORMATION: CDR2

<400> SEQUENCE: 106

Asp Ile Ile Ser Ala Gly Val Thr Asn
1               5

<210> SEQ ID NO 107
<211> LENGTH: 9
<212> TYPE: PRT
<213> ORGANISM: Artificial Sequence
<220> FEATURE:
<223> OTHER INFORMATION: CDR2

<400> SEQUENCE: 107

Gly Ile Ile Ser Arg Gly Val Thr Asn
1               5

<210> SEQ ID NO 108
<211> LENGTH: 9
<212> TYPE: PRT
<213> ORGANISM: Artificial Sequence
<220> FEATURE:
<223> OTHER INFORMATION: CDR2

<400> SEQUENCE: 108

Asp Ile Ile Ser Arg Asp Val Thr Asn
1               5

<210> SEQ ID NO 109
<211> LENGTH: 9
<212> TYPE: PRT
<213> ORGANISM: Artificial Sequence
<220> FEATURE:
<223> OTHER INFORMATION: CDR2

<400> SEQUENCE: 109

Phe Ile Tyr Trp Gly Gly Thr Thr Thr
1               5

<210> SEQ ID NO 110
<211> LENGTH: 9
<212> TYPE: PRT
<213> ORGANISM: Artificial Sequence
<220> FEATURE:
<223> OTHER INFORMATION: CDR2

<400> SEQUENCE: 110

Phe Ile Tyr Trp Gly Gly Thr Thr Ser
1               5

```
<210> SEQ ID NO 111
<211> LENGTH: 9
<212> TYPE: PRT
<213> ORGANISM: Artificial Sequence
<220> FEATURE:
<223> OTHER INFORMATION: CDR2

<400> SEQUENCE: 111

Val Thr Ser Gly Phe Ser Thr Asn Tyr
1               5

<210> SEQ ID NO 112
<211> LENGTH: 9
<212> TYPE: PRT
<213> ORGANISM: Artificial Sequence
<220> FEATURE:
<223> OTHER INFORMATION: CDR2

<400> SEQUENCE: 112

Glu Ile Ser Asp His Thr Thr Tyr Gly
1               5

<210> SEQ ID NO 113
<211> LENGTH: 9
<212> TYPE: PRT
<213> ORGANISM: Artificial Sequence
<220> FEATURE:
<223> OTHER INFORMATION: CDR2

<400> SEQUENCE: 113

Glu Ile Ser Gly His Thr Thr Tyr Gly
1               5

<210> SEQ ID NO 114
<211> LENGTH: 9
<212> TYPE: PRT
<213> ORGANISM: Artificial Sequence
<220> FEATURE:
<223> OTHER INFORMATION: CDR2

<400> SEQUENCE: 114

Val Ile Ser Arg Ser Gly Ala Thr Met
1               5

<210> SEQ ID NO 115
<211> LENGTH: 9
<212> TYPE: PRT
<213> ORGANISM: Artificial Sequence
<220> FEATURE:
<223> OTHER INFORMATION: CDR2

<400> SEQUENCE: 115

Ile Ile Ser Arg Ser Gly Ala Thr Met
1               5

<210> SEQ ID NO 116
<211> LENGTH: 9
<212> TYPE: PRT
<213> ORGANISM: Artificial Sequence
<220> FEATURE:
<223> OTHER INFORMATION: CDR2

<400> SEQUENCE: 116

Ala Ile Ser Arg Ser Gly Ala Thr Ile
1               5

<210> SEQ ID NO 117
```

```
<211> LENGTH: 9
<212> TYPE: PRT
<213> ORGANISM: Artificial Sequence
<220> FEATURE:
<223> OTHER INFORMATION: CDR2

<400> SEQUENCE: 117

Thr Val Thr Ser Gly Gly Asp Thr Phe
1               5

<210> SEQ ID NO 118
<211> LENGTH: 13
<212> TYPE: PRT
<213> ORGANISM: Artificial Sequence
<220> FEATURE:
<223> OTHER INFORMATION: CDR3

<400> SEQUENCE: 118

Glu Gly Gln Ala Gly Trp Gly Thr Ala Leu Met Asp Tyr
1               5                   10

<210> SEQ ID NO 119
<211> LENGTH: 13
<212> TYPE: PRT
<213> ORGANISM: Artificial Sequence
<220> FEATURE:
<223> OTHER INFORMATION: CDR3

<400> SEQUENCE: 119

Glu Gly Gln Ala Gly Trp Gly Thr Pro Leu Met Asn Tyr
1               5                   10

<210> SEQ ID NO 120
<211> LENGTH: 13
<212> TYPE: PRT
<213> ORGANISM: Artificial Sequence
<220> FEATURE:
<223> OTHER INFORMATION: CDR3

<400> SEQUENCE: 120

Glu Gly Gln Ala Gly Trp Gly Thr Ala Leu Ile Asn Tyr
1               5                   10

<210> SEQ ID NO 121
<211> LENGTH: 13
<212> TYPE: PRT
<213> ORGANISM: Artificial Sequence
<220> FEATURE:
<223> OTHER INFORMATION: CDR3

<400> SEQUENCE: 121

Lys Gly Gln Thr Gly Trp Gly Thr Ala Leu Met Asp Tyr
1               5                   10

<210> SEQ ID NO 122
<211> LENGTH: 13
<212> TYPE: PRT
<213> ORGANISM: Artificial Sequence
<220> FEATURE:
<223> OTHER INFORMATION: CDR3

<400> SEQUENCE: 122

Glu Gly Gln Thr Gly Trp Gly Thr Ala Leu Met Asp Tyr
1               5                   10

<210> SEQ ID NO 123
<211> LENGTH: 13
```

```
<212> TYPE: PRT
<213> ORGANISM: Artificial Sequence
<220> FEATURE:
<223> OTHER INFORMATION: CDR3

<400> SEQUENCE: 123

Glu Gly Gln Ala Gly Trp Gly Thr Ala Leu Leu Asp Tyr
1               5                   10

<210> SEQ ID NO 124
<211> LENGTH: 13
<212> TYPE: PRT
<213> ORGANISM: Artificial Sequence
<220> FEATURE:
<223> OTHER INFORMATION: CDR3

<400> SEQUENCE: 124

His Ile Ser Thr Gly Trp Gly Arg Pro His Asn Asn Tyr
1               5                   10

<210> SEQ ID NO 125
<211> LENGTH: 13
<212> TYPE: PRT
<213> ORGANISM: Artificial Sequence
<220> FEATURE:
<223> OTHER INFORMATION: CDR3

<400> SEQUENCE: 125

His Ile Ser Met Gly Trp Gly Arg Pro His Asn Asn Tyr
1               5                   10

<210> SEQ ID NO 126
<211> LENGTH: 7
<212> TYPE: PRT
<213> ORGANISM: Artificial Sequence
<220> FEATURE:
<223> OTHER INFORMATION: CDR3

<400> SEQUENCE: 126

Tyr Gly Ser Tyr Ala Leu Pro
1               5

<210> SEQ ID NO 127
<211> LENGTH: 13
<212> TYPE: PRT
<213> ORGANISM: Artificial Sequence
<220> FEATURE:
<223> OTHER INFORMATION: CDR3

<400> SEQUENCE: 127

Tyr Leu Ser Leu Ala Trp Arg Asp Pro Asp Arg Asp Tyr
1               5                   10

<210> SEQ ID NO 128
<211> LENGTH: 13
<212> TYPE: PRT
<213> ORGANISM: Artificial Sequence
<220> FEATURE:
<223> OTHER INFORMATION: CDR3

<400> SEQUENCE: 128

His His Gln Arg Gly Trp Gly Thr Ser Ile Thr Val Thr
1               5                   10

<210> SEQ ID NO 129
<211> LENGTH: 13
<212> TYPE: PRT
```

<213> ORGANISM: Artificial Sequence
<220> FEATURE:
<223> OTHER INFORMATION: CDR3

<400> SEQUENCE: 129

His His Gln Arg Gly Trp Gly Thr Ser Ile Thr Val Ala
1               5                   10

<210> SEQ ID NO 130
<211> LENGTH: 13
<212> TYPE: PRT
<213> ORGANISM: Artificial Sequence
<220> FEATURE:
<223> OTHER INFORMATION: CDR3

<400> SEQUENCE: 130

His His Gln Arg Gly Trp Gly Thr Pro Ile Thr Val Thr
1               5                   10

<210> SEQ ID NO 131
<211> LENGTH: 7
<212> TYPE: PRT
<213> ORGANISM: Artificial Sequence
<220> FEATURE:
<223> OTHER INFORMATION: CDR3

<400> SEQUENCE: 131

Ile Thr Gln Gly Arg Thr Tyr
1               5

<210> SEQ ID NO 132
<211> LENGTH: 7
<212> TYPE: PRT
<213> ORGANISM: Artificial Sequence
<220> FEATURE:
<223> OTHER INFORMATION: CDR3

<400> SEQUENCE: 132

Ile Thr Gln Glu Gln Thr Tyr
1               5

<210> SEQ ID NO 133
<211> LENGTH: 10
<212> TYPE: PRT
<213> ORGANISM: Artificial Sequence
<220> FEATURE:
<223> OTHER INFORMATION: CDR3

<400> SEQUENCE: 133

Thr Lys Val Ser Pro Tyr Lys Glu Thr Thr
1               5                   10

<210> SEQ ID NO 134
<211> LENGTH: 25
<212> TYPE: PRT
<213> ORGANISM: Artificial Sequence
<220> FEATURE:
<223> OTHER INFORMATION: FW1

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 135

```
<211> LENGTH: 25
<212> TYPE: PRT
<213> ORGANISM: Artificial Sequence
<220> FEATURE:
<223> OTHER INFORMATION: FW1

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Thr Ala Ser
            20                  25

<210> SEQ ID NO 136
<211> LENGTH: 25
<212> TYPE: PRT
<213> ORGANISM: Artificial Sequence
<220> FEATURE:
<223> OTHER INFORMATION: FW1

<400> SEQUENCE: 136

Glu Val Gln Leu Val Glu Ser Gly Gly Gly Leu Val Gln Ser Gly Gly
1               5                   10                  15

Ser Leu Arg Leu Ser Cys Ala Ala Ser
            20                  25

<210> SEQ ID NO 137
<211> LENGTH: 25
<212> TYPE: PRT
<213> ORGANISM: Artificial Sequence
<220> FEATURE:
<223> OTHER INFORMATION: FW1

<400> SEQUENCE: 137

Glu Val Gln Leu Val Glu Ser Gly Gly Gly Leu Val Arg Pro Gly Gly
1               5                   10                  15

Ser Leu Arg Leu Ser Cys Ala Ala Ser
            20                  25

<210> SEQ ID NO 138
<211> LENGTH: 25
<212> TYPE: PRT
<213> ORGANISM: Artificial Sequence
<220> FEATURE:
<223> OTHER INFORMATION: FW1

<400> SEQUENCE: 138

Glu Val Gln Leu Val Glu Ser Gly Gly Gly Leu Val Arg Pro Gly Gly
1               5                   10                  15

Ser Leu Arg Leu Pro Cys Ala Ala Ser
            20                  25

<210> SEQ ID NO 139
<211> LENGTH: 25
<212> TYPE: PRT
<213> ORGANISM: Artificial Sequence
<220> FEATURE:
<223> OTHER INFORMATION: FW1

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Gly Ser
            20                  25
```

```
<210> SEQ ID NO 140
<211> LENGTH: 25
<212> TYPE: PRT
<213> ORGANISM: Artificial Sequence
<220> FEATURE:
<223> OTHER INFORMATION: FW1

<400> SEQUENCE: 140

Glu Val Gln Leu Val Glu Ser Gly Gly Gly Leu Val Gln Pro Gly Gly
1               5                   10                  15

Ser Leu Arg Leu Thr Cys Ala Ala Ser
            20                  25

<210> SEQ ID NO 141
<211> LENGTH: 25
<212> TYPE: PRT
<213> ORGANISM: Artificial Sequence
<220> FEATURE:
<223> OTHER INFORMATION: FW1

<400> SEQUENCE: 141

Glu Val Gln Leu Val Glu Ser Gly Gly Gly Leu Val Gln Pro Gly Gly
1               5                   10                  15

Ser Leu Arg Leu Phe Cys Ala Ala Ser
            20                  25

<210> SEQ ID NO 142
<211> LENGTH: 25
<212> TYPE: PRT
<213> ORGANISM: Artificial Sequence
<220> FEATURE:
<223> OTHER INFORMATION: FW1

<400> SEQUENCE: 142

Glu Val Gln Leu Val Glu Ser Gly Gly Asp Leu Val Gln Pro Gly Gly
1               5                   10                  15

Ser Leu Arg Leu Ser Cys Ala Ala Ser
            20                  25

<210> SEQ ID NO 143
<211> LENGTH: 25
<212> TYPE: PRT
<213> ORGANISM: Artificial Sequence
<220> FEATURE:
<223> OTHER INFORMATION: FW1

<400> SEQUENCE: 143

Glu Val Gln Leu Val Glu Ser Gly Gly Asp Leu Val Gln Pro Gly Gly
1               5                   10                  15

Pro Leu Arg Leu Ser Cys Ala Ala Ser
            20                  25

<210> SEQ ID NO 144
<211> LENGTH: 25
<212> TYPE: PRT
<213> ORGANISM: Artificial Sequence
<220> FEATURE:
<223> OTHER INFORMATION: FW1

<400> SEQUENCE: 144

Glu Val Gln Leu Val Glu Ser Gly Gly Asp Leu Val Gln Pro Gly Gly
1               5                   10                  15

Ser Leu Gly Leu Ser Cys Ala Ala Ser
            20                  25
```

```
<210> SEQ ID NO 145
<211> LENGTH: 25
<212> TYPE: PRT
<213> ORGANISM: Artificial Sequence
<220> FEATURE:
<223> OTHER INFORMATION: FW1

<400> SEQUENCE: 145

Glu Val Gln Leu Val Glu Ser Gly Gly Asp Leu Val Arg Pro Gly Gly
1               5                   10                  15

Ser Leu Arg Leu Ser Cys Ala Ala Ser
            20                  25

<210> SEQ ID NO 146
<211> LENGTH: 25
<212> TYPE: PRT
<213> ORGANISM: Artificial Sequence
<220> FEATURE:
<223> OTHER INFORMATION: FW1

<400> SEQUENCE: 146

Glu Val Gln Leu Val Glu Ser Gly Gly Gly Leu Val Gln Ala Gly Gly
1               5                   10                  15

Ser Leu Arg Leu Ser Cys Thr Gly Ser
            20                  25

<210> SEQ ID NO 147
<211> LENGTH: 25
<212> TYPE: PRT
<213> ORGANISM: Artificial Sequence
<220> FEATURE:
<223> OTHER INFORMATION: FW1

<400> SEQUENCE: 147

Glu Val Gln Leu Val Glu Ser Gly Gly Gly Met Val Gln Ala Gly Gly
1               5                   10                  15

Ser Leu Arg Leu Ser Cys Thr Gly Ser
            20                  25

<210> SEQ ID NO 148
<211> LENGTH: 25
<212> TYPE: PRT
<213> ORGANISM: Artificial Sequence
<220> FEATURE:
<223> OTHER INFORMATION: FW1

<400> SEQUENCE: 148

Glu Val Gln Leu Val Glu Ser Gly Gly Gly Leu Val Gln Ala Gly Glu
1               5                   10                  15

Ser Leu Arg Leu Ser Cys Ala Ala Ser
            20                  25

<210> SEQ ID NO 149
<211> LENGTH: 25
<212> TYPE: PRT
<213> ORGANISM: Artificial Sequence
<220> FEATURE:
<223> OTHER INFORMATION: FW1

<400> SEQUENCE: 149

Glu Val Gln Leu Val Glu Ser Gly Gly Arg Leu Val Gln Ala Gly Glu
1               5                   10                  15

Ser Leu Arg Leu Ser Cys Ala Ala Ser
            20                  25
```

<210> SEQ ID NO 150
<211> LENGTH: 25
<212> TYPE: PRT
<213> ORGANISM: Artificial Sequence
<220> FEATURE:
<223> OTHER INFORMATION: FW1

<400> SEQUENCE: 150

Glu Val Gln Leu Val Glu Ser Gly Gly Gly Leu Val Arg Ala Gly Glu
1               5                   10                  15

Ser Leu Arg Leu Ser Cys Ala Ala Ser
            20                  25

<210> SEQ ID NO 151
<211> LENGTH: 25
<212> TYPE: PRT
<213> ORGANISM: Artificial Sequence
<220> FEATURE:
<223> OTHER INFORMATION: FW1

<400> SEQUENCE: 151

Glu Val Gln Leu Val Glu Ser Gly Gly Gly Leu Val Gln Ala Gly Gly
1               5                   10                  15

Ser Leu Arg Leu Ser Cys Val Ala Ser
            20                  25

<210> SEQ ID NO 152
<211> LENGTH: 25
<212> TYPE: PRT
<213> ORGANISM: Artificial Sequence
<220> FEATURE:
<223> OTHER INFORMATION: FW1

<400> SEQUENCE: 152

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 153
<211> LENGTH: 14
<212> TYPE: PRT
<213> ORGANISM: Artificial Sequence
<220> FEATURE:
<223> OTHER INFORMATION: FW2

<400> SEQUENCE: 153

Trp Tyr Arg Gln Ala Pro Gly Lys Gln Arg Glu Leu Val Ala
1               5                   10

<210> SEQ ID NO 154
<211> LENGTH: 14
<212> TYPE: PRT
<213> ORGANISM: Artificial Sequence
<220> FEATURE:
<223> OTHER INFORMATION: FW2

<400> SEQUENCE: 154

Trp His Arg Gln Ala Pro Gly Lys Gln Arg Glu Leu Val Ala
1               5                   10

<210> SEQ ID NO 155
<211> LENGTH: 14
<212> TYPE: PRT

```
<213> ORGANISM: Artificial Sequence
<220> FEATURE:
<223> OTHER INFORMATION: FW2

<400> SEQUENCE: 155

Trp Tyr His Gln Ala Pro Gly Lys Gln Arg Glu Leu Val Ala
1               5                   10

<210> SEQ ID NO 156
<211> LENGTH: 14
<212> TYPE: PRT
<213> ORGANISM: Artificial Sequence
<220> FEATURE:
<223> OTHER INFORMATION: FW2

<400> SEQUENCE: 156

Trp Tyr Arg Gln Ala Pro Gly Arg Gln Arg Glu Leu Val Ala
1               5                   10

<210> SEQ ID NO 157
<211> LENGTH: 14
<212> TYPE: PRT
<213> ORGANISM: Artificial Sequence
<220> FEATURE:
<223> OTHER INFORMATION: FW2

<400> SEQUENCE: 157

Trp Phe Arg Gln Ala Pro Gly Lys Gln Arg Glu Leu Val Ala
1               5                   10

<210> SEQ ID NO 158
<211> LENGTH: 14
<212> TYPE: PRT
<213> ORGANISM: Artificial Sequence
<220> FEATURE:
<223> OTHER INFORMATION: FW2

<400> SEQUENCE: 158

Trp Leu Arg Gln Ala Pro Gly Lys Gln Arg Glu Leu Val Ala
1               5                   10

<210> SEQ ID NO 159
<211> LENGTH: 14
<212> TYPE: PRT
<213> ORGANISM: Artificial Sequence
<220> FEATURE:
<223> OTHER INFORMATION: FW2

<400> SEQUENCE: 159

Trp His Arg Gln Ala Pro Gly Lys Gln Arg Glu Leu Val Gly
1               5                   10

<210> SEQ ID NO 160
<211> LENGTH: 14
<212> TYPE: PRT
<213> ORGANISM: Artificial Sequence
<220> FEATURE:
<223> OTHER INFORMATION: FW2

<400> SEQUENCE: 160

Trp Tyr Arg Gln Ala Pro Gly Lys Gln Arg Glu Val Val Ala
1               5                   10

<210> SEQ ID NO 161
<211> LENGTH: 14
<212> TYPE: PRT
<213> ORGANISM: Artificial Sequence
```

```
<220> FEATURE:
<223> OTHER INFORMATION: FW2

<400> SEQUENCE: 161

Trp His Arg Gln Ala Pro Gly Ala Gln Arg Glu Gly Val Ala
1               5                   10

<210> SEQ ID NO 162
<211> LENGTH: 14
<212> TYPE: PRT
<213> ORGANISM: Artificial Sequence
<220> FEATURE:
<223> OTHER INFORMATION: FW2

<400> SEQUENCE: 162

Trp Tyr Arg Gln Ala Pro Gly Glu Gln Arg Ala Leu Val Ala
1               5                   10

<210> SEQ ID NO 163
<211> LENGTH: 39
<212> TYPE: PRT
<213> ORGANISM: Artificial Sequence
<220> FEATURE:
<223> OTHER INFORMATION: FW3

<400> SEQUENCE: 163

Tyr Ala Asp Ser Val Lys Gly Arg Phe Thr Ile Ser Ser Asp Val Ala
1               5                   10                  15

Lys Arg Thr Val Tyr Leu Gln Met Asn Ser Leu Lys Pro Glu Asp Thr
            20                  25                  30

Ala Val Tyr Tyr Cys Asn Ala
        35

<210> SEQ ID NO 164
<211> LENGTH: 39
<212> TYPE: PRT
<213> ORGANISM: Artificial Sequence
<220> FEATURE:
<223> OTHER INFORMATION: FW3

<400> SEQUENCE: 164

Tyr Ala Asp Ser Val Lys Gly Arg Phe Thr Ile Ser Gly Asp Ser Ala
1               5                   10                  15

Lys Arg Thr Val Tyr Leu Gln Met Asn Ser Leu Lys Pro Glu Asp Thr
            20                  25                  30

Ala Val Tyr Tyr Cys Asn Ala
        35

<210> SEQ ID NO 165
<211> LENGTH: 39
<212> TYPE: PRT
<213> ORGANISM: Artificial Sequence
<220> FEATURE:
<223> OTHER INFORMATION: FW3

<400> SEQUENCE: 165

Tyr Ala Asp Ser Val Lys Gly Arg Phe Thr Ile Ser Gly Asp Ser Ala
1               5                   10                  15

Lys Arg Thr Val Tyr Leu Gln Met Asp Ser Leu Lys Pro Glu Asp Thr
            20                  25                  30

Ala Val Tyr Tyr Cys Asn Ala
        35
```

```
<210> SEQ ID NO 166
<211> LENGTH: 39
<212> TYPE: PRT
<213> ORGANISM: Artificial Sequence
<220> FEATURE:
<223> OTHER INFORMATION: FW3

<400> SEQUENCE: 166

Tyr Ala Asp Ser Val Met Gly Arg Phe Ser Ile Ser Gly Asp Asn Ala
1               5                   10                  15

Lys Arg Thr Val Tyr Leu Gln Met Asn Ser Leu Lys Pro Glu Asp Thr
            20                  25                  30

Ala Val Tyr Tyr Cys Asn Ala
        35

<210> SEQ ID NO 167
<211> LENGTH: 39
<212> TYPE: PRT
<213> ORGANISM: Artificial Sequence
<220> FEATURE:
<223> OTHER INFORMATION: FW3

<400> SEQUENCE: 167

Tyr Ala Asp Ser Val Lys Gly Arg Phe Thr Ile Ser Gly Asp Ser Ala
1               5                   10                  15

Lys Arg Thr Val Tyr Leu Gln Met Asn Ser Leu Arg Pro Glu Asp Thr
            20                  25                  30

Ala Val Tyr Tyr Cys Asn Ala
        35

<210> SEQ ID NO 168
<211> LENGTH: 39
<212> TYPE: PRT
<213> ORGANISM: Artificial Sequence
<220> FEATURE:
<223> OTHER INFORMATION: FW3

<400> SEQUENCE: 168

Tyr Ala Asp Ser Val Lys Gly Arg Phe Thr Ile Ser Ser Asp Val Ala
1               5                   10                  15

Lys Arg Thr Ala Tyr Leu Gln Met Asn Ser Leu Lys Pro Glu Asp Thr
            20                  25                  30

Ala Val Tyr Tyr Cys Asn Ala
        35

<210> SEQ ID NO 169
<211> LENGTH: 39
<212> TYPE: PRT
<213> ORGANISM: Artificial Sequence
<220> FEATURE:
<223> OTHER INFORMATION: FW3

<400> SEQUENCE: 169

Tyr Ala Asp Ser Val Arg Gly Arg Phe Thr Ile Ser Ser Asp Val Ala
1               5                   10                  15

Lys Arg Thr Val Tyr Leu Gln Met Asn Ser Leu Lys Pro Glu Asp Thr
            20                  25                  30

Ala Val Tyr Tyr Cys Asn Ala
        35

<210> SEQ ID NO 170
<211> LENGTH: 39
<212> TYPE: PRT
```

```
<213> ORGANISM: Artificial Sequence
<220> FEATURE:
<223> OTHER INFORMATION: FW3

<400> SEQUENCE: 170

Tyr Ala Asp Ser Val Lys Gly Arg Phe Ala Ile Ser Gly Asp Ser Ala
1               5                   10                  15

Lys Arg Thr Val Tyr Leu Gln Met Asn Ser Leu Lys Pro Glu Asp Thr
            20                  25                  30

Ala Val Tyr Tyr Cys Asn Ala
        35

<210> SEQ ID NO 171
<211> LENGTH: 39
<212> TYPE: PRT
<213> ORGANISM: Artificial Sequence
<220> FEATURE:
<223> OTHER INFORMATION: FW3

<400> SEQUENCE: 171

Tyr Ala Asp Ser Val Lys Gly Arg Phe Thr Ile Ser Gly Asp Asn Ala
1               5                   10                  15

Lys Arg Thr Val Tyr Leu Gln Met Asn Ser Leu Lys Pro Glu Asp Thr
            20                  25                  30

Ala Val Tyr Tyr Cys Asn Ala
        35

<210> SEQ ID NO 172
<211> LENGTH: 39
<212> TYPE: PRT
<213> ORGANISM: Artificial Sequence
<220> FEATURE:
<223> OTHER INFORMATION: FW3

<400> SEQUENCE: 172

Tyr Ala Asp Ser Val Lys Gly Arg Phe Thr Ile Ser Gly Asp Asn Ala
1               5                   10                  15

Lys Arg Thr Val Tyr Leu Gln Met Asn Ser Leu Lys Pro Glu Asp Thr
            20                  25                  30

Ala Ala Tyr Tyr Cys Asn Ala
        35

<210> SEQ ID NO 173
<211> LENGTH: 39
<212> TYPE: PRT
<213> ORGANISM: Artificial Sequence
<220> FEATURE:
<223> OTHER INFORMATION: FW3

<400> SEQUENCE: 173

Tyr Ala Asp Ser Val Lys Gly Arg Phe Thr Ile Ser Gly Asp Ser Ala
1               5                   10                  15

Lys Arg Thr Val Tyr Leu Gln Met Asn Ser Leu Lys Pro Gly Asp Thr
            20                  25                  30

Ala Val Tyr Tyr Cys Asn Ala
        35

<210> SEQ ID NO 174
<211> LENGTH: 39
<212> TYPE: PRT
<213> ORGANISM: Artificial Sequence
<220> FEATURE:
<223> OTHER INFORMATION: FW3
```

<400> SEQUENCE: 174

Tyr Ala Asp Ser Val Lys Gly Arg Phe Thr Ile Ser Gly Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Asn Ala
        35

<210> SEQ ID NO 175
<211> LENGTH: 37
<212> TYPE: PRT
<213> ORGANISM: Artificial Sequence
<220> FEATURE:
<223> OTHER INFORMATION: FW3

<400> SEQUENCE: 175

Asp Ser Val Lys Gly Arg Phe Thr Ile Ser Arg Asp Asn Ala Lys Asn
1               5                   10                  15

Thr Val Tyr Leu Gln Met Asn Ser Leu Lys Pro Glu Asp Thr Ala Val
            20                  25                  30

Tyr Tyr Cys Asn Leu
        35

<210> SEQ ID NO 176
<211> LENGTH: 37
<212> TYPE: PRT
<213> ORGANISM: Artificial Sequence
<220> FEATURE:
<223> OTHER INFORMATION: FW3

<400> SEQUENCE: 176

Glu Ser Val Lys Gly Arg Phe Thr Ile Ser Arg Ala Asn Ala Lys Asn
1               5                   10                  15

Thr Val Tyr Leu Gln Met Asn Ser Leu Lys Pro Glu Asp Thr Ala Val
            20                  25                  30

Tyr Tyr Cys Asn Val
        35

<210> SEQ ID NO 177
<211> LENGTH: 37
<212> TYPE: PRT
<213> ORGANISM: Artificial Sequence
<220> FEATURE:
<223> OTHER INFORMATION: FW3

<400> SEQUENCE: 177

Glu Ser Val Lys Gly Arg Phe Thr Ile Ser Arg Ala Asn Ala Lys Asn
1               5                   10                  15

Thr Val Tyr Leu Gln Met Asn Ser Leu Lys Pro Glu Asp Thr Ala Val
            20                  25                  30

Tyr Tyr Cys Ser Val
        35

<210> SEQ ID NO 178
<211> LENGTH: 37
<212> TYPE: PRT
<213> ORGANISM: Artificial Sequence
<220> FEATURE:
<223> OTHER INFORMATION: FW3

<400> SEQUENCE: 178

```
Asp Ser Ala Lys Gly Arg Phe Thr Ile Ser Arg Asp His Ala Lys Asn
1               5                   10                  15

Thr Val Tyr Leu Gln Met Asn Ser Leu Lys Pro Glu Asp Thr Ala Val
            20                  25                  30

Tyr Tyr Cys Asn Leu
        35

<210> SEQ ID NO 179
<211> LENGTH: 37
<212> TYPE: PRT
<213> ORGANISM: Artificial Sequence
<220> FEATURE:
<223> OTHER INFORMATION: FW3

<400> SEQUENCE: 179

Asp Ser Val Lys Gly Arg Phe Thr Ile Ser Arg Asp His Ala Lys Asn
1               5                   10                  15

Thr Val Tyr Leu Gln Met Asn Ser Leu Lys Pro Glu Asp Thr Ala Val
            20                  25                  30

Tyr Tyr Cys Asn Leu
        35

<210> SEQ ID NO 180
<211> LENGTH: 37
<212> TYPE: PRT
<213> ORGANISM: Artificial Sequence
<220> FEATURE:
<223> OTHER INFORMATION: FW3

<400> SEQUENCE: 180

Asp Ser Val Arg Gly Arg Phe Thr Ile Ser Arg Asp His Ala Lys Asn
1               5                   10                  15

Thr Val Tyr Leu Gln Met Asn Ser Leu Lys Pro Glu Asp Thr Ala Val
            20                  25                  30

Tyr Tyr Cys Asn Leu
        35

<210> SEQ ID NO 181
<211> LENGTH: 37
<212> TYPE: PRT
<213> ORGANISM: Artificial Sequence
<220> FEATURE:
<223> OTHER INFORMATION: FW3

<400> SEQUENCE: 181

Asp Ser Val Lys Gly Arg Phe Thr Ile Ser Arg Asp Asn Ala Lys Asn
1               5                   10                  15

Ala Val Tyr Leu Gln Met Asn Ser Leu Lys Pro Glu Asp Thr Ala Val
            20                  25                  30

Tyr Tyr Cys Asn Leu
        35

<210> SEQ ID NO 182
<211> LENGTH: 37
<212> TYPE: PRT
<213> ORGANISM: Artificial Sequence
<220> FEATURE:
<223> OTHER INFORMATION: FW3

<400> SEQUENCE: 182

Asp Ser Val Lys Gly Arg Phe Thr Ile Ser Arg Asp Asn Ala Lys Asn
1               5                   10                  15
```

Thr Val Tyr Leu Gln Thr Asn Ser Leu Lys Pro Glu Asp Thr Ala Val
            20                  25                  30

Tyr Tyr Cys Asn Leu
            35

<210> SEQ ID NO 183
<211> LENGTH: 37
<212> TYPE: PRT
<213> ORGANISM: Artificial Sequence
<220> FEATURE:
<223> OTHER INFORMATION: FW3

<400> SEQUENCE: 183

Asp Ser Val Lys Gly Arg Phe Thr Ile Ser Arg Ala Asn Ala Lys Asn
1               5                   10                  15

Thr Val Tyr Leu Gln Met Asn Ser Leu Lys Pro Glu Asp Thr Ala Val
            20                  25                  30

Tyr Tyr Cys His Leu
            35

<210> SEQ ID NO 184
<211> LENGTH: 39
<212> TYPE: PRT
<213> ORGANISM: Artificial Sequence
<220> FEATURE:
<223> OTHER INFORMATION: FW3

<400> SEQUENCE: 184

Tyr Ala Asp Ser Val Lys Gly Arg Phe Thr Ile Ser Gly Asp Pro Ala
1               5                   10                  15

Lys Asn Thr Val Tyr Leu Gln Met Asn Ser Leu Lys Pro Glu Asp Thr
            20                  25                  30

Ala Val Tyr Tyr Cys Asn Ala
            35

<210> SEQ ID NO 185
<211> LENGTH: 39
<212> TYPE: PRT
<213> ORGANISM: Artificial Sequence
<220> FEATURE:
<223> OTHER INFORMATION: FW3

<400> SEQUENCE: 185

Tyr Ala Asp Ser Val Lys Gly Arg Phe Thr Ile Ser Gly Asp His Ala
1               5                   10                  15

Lys Asn Thr Val Tyr Leu Gln Met Asn Ser Leu Lys Pro Glu Asp Thr
            20                  25                  30

Ala Val Tyr Tyr Cys Asn Ala
            35

<210> SEQ ID NO 186
<211> LENGTH: 39
<212> TYPE: PRT
<213> ORGANISM: Artificial Sequence
<220> FEATURE:
<223> OTHER INFORMATION: FW3

<400> SEQUENCE: 186

Tyr Ala Asp Ser Val Lys Gly Arg Phe Thr Ile Ser Gly Asp His Ala
1               5                   10                  15

Gln Asn Thr Val Tyr Leu Gln Met Asn Ser Leu Lys Pro Glu Asp Thr
            20                  25                  30

Ala Val Tyr Tyr Cys Asn Ala
        35

<210> SEQ ID NO 187
<211> LENGTH: 39
<212> TYPE: PRT
<213> ORGANISM: Artificial Sequence
<220> FEATURE:
<223> OTHER INFORMATION: FW3

<400> SEQUENCE: 187

Tyr Ala Asp Ser Val Lys Gly Arg Phe Thr Ile Ser Gly Asp Pro Ala
1               5                   10                  15

Lys Asn Thr Val Tyr Leu Gln Met Asn Ser Leu Lys Pro Glu Asp Thr
            20                  25                  30

Ala Ala Tyr Tyr Cys Asn Ala
        35

<210> SEQ ID NO 188
<211> LENGTH: 39
<212> TYPE: PRT
<213> ORGANISM: Artificial Sequence
<220> FEATURE:
<223> OTHER INFORMATION: FW3

<400> SEQUENCE: 188

Tyr Ala Asp Ser Val Lys Gly Arg Phe Thr Ile Ser Gly Asp Pro Ala
1               5                   10                  15

Lys Asn Thr Ala Tyr Leu Gln Met Asn Ser Leu Lys Pro Glu Asp Thr
            20                  25                  30

Ala Val Tyr Tyr Cys Asn Ala
        35

<210> SEQ ID NO 189
<211> LENGTH: 39
<212> TYPE: PRT
<213> ORGANISM: Artificial Sequence
<220> FEATURE:
<223> OTHER INFORMATION: FW3

<400> SEQUENCE: 189

Cys Ala Asp Ser Val Lys Gly Arg Phe Thr Ile Ser Gly Asp Pro Ala
1               5                   10                  15

Lys Asn Thr Val Tyr Leu Gln Met Asn Ser Leu Lys Pro Glu Asp Thr
            20                  25                  30

Ala Val Tyr Tyr Cys Asn Ala
        35

<210> SEQ ID NO 190
<211> LENGTH: 39
<212> TYPE: PRT
<213> ORGANISM: Artificial Sequence
<220> FEATURE:
<223> OTHER INFORMATION: FW3

<400> SEQUENCE: 190

Tyr Ala Asp Ser Val Arg Gly Arg Phe Thr Ile Ser Gly Asp Pro Ala
1               5                   10                  15

Lys Asn Thr Val Tyr Leu Gln Met Asn Ser Leu Lys Pro Glu Asp Thr
            20                  25                  30

Ala Val Tyr Tyr Cys Asn Ala
        35

-continued

```
<210> SEQ ID NO 191
<211> LENGTH: 39
<212> TYPE: PRT
<213> ORGANISM: Artificial Sequence
<220> FEATURE:
<223> OTHER INFORMATION: FW3

<400> SEQUENCE: 191

Tyr Ala Asp Ser Val Lys Gly Arg Phe Thr Val Ser Gly Asp Pro Ala
1               5                   10                  15

Lys Asn Thr Val Tyr Leu Gln Met Asn Ser Leu Lys Pro Glu Asp Thr
            20                  25                  30

Ala Val Tyr Tyr Cys Asn Ala
        35

<210> SEQ ID NO 192
<211> LENGTH: 39
<212> TYPE: PRT
<213> ORGANISM: Artificial Sequence
<220> FEATURE:
<223> OTHER INFORMATION: FW3

<400> SEQUENCE: 192

Tyr Ser Asp Ser Val Lys Gly Arg Phe Thr Ile Ser Arg Asp Asn Ala
1               5                   10                  15

Lys Asn Thr Met Tyr Leu Gln Met Asn Ser Leu Lys Pro Glu Asp Ala
            20                  25                  30

Gly Val Tyr Tyr Cys Asn Ile
        35

<210> SEQ ID NO 193
<211> LENGTH: 39
<212> TYPE: PRT
<213> ORGANISM: Artificial Sequence
<220> FEATURE:
<223> OTHER INFORMATION: FW3

<400> SEQUENCE: 193

Tyr Val Asp Ser Val Lys Gly Arg Phe Thr Ile Ser Arg Asp Asn Ala
1               5                   10                  15

Lys Asn Thr Met Tyr Leu Gln Met Asn Ser Leu Lys Pro Glu Asp Ala
            20                  25                  30

Ala Val Tyr Tyr Cys Asn Ile
        35

<210> SEQ ID NO 194
<211> LENGTH: 39
<212> TYPE: PRT
<213> ORGANISM: Artificial Sequence
<220> FEATURE:
<223> OTHER INFORMATION: FW3

<400> SEQUENCE: 194

Tyr Ser Asp Ser Val Lys Gly Arg Phe Thr Ile Ser Arg Asp Asn Ala
1               5                   10                  15

Lys Ser Thr Met Tyr Leu Gln Met Asn Ser Leu Lys Pro Glu Asp Ala
            20                  25                  30

Gly Val Tyr Tyr Cys Asn Ile
        35

<210> SEQ ID NO 195
<211> LENGTH: 38
```

```
<212> TYPE: PRT
<213> ORGANISM: Artificial Sequence
<220> FEATURE:
<223> OTHER INFORMATION: FW3

<400> SEQUENCE: 195

Ser Ser Ala Val Lys Gly Arg Phe Thr Leu Ser Arg Asp Pro Ala Lys
1               5                   10                  15

Asn Thr Val Phe Leu Gln Met Asn Ser Leu Gln Pro Glu Asp Thr Ala
                20                  25                  30

Thr Tyr Tyr Cys Asn Ala
            35

<210> SEQ ID NO 196
<211> LENGTH: 37
<212> TYPE: PRT
<213> ORGANISM: Artificial Sequence
<220> FEATURE:
<223> OTHER INFORMATION: FW3

<400> SEQUENCE: 196

Asp Ser Val Lys Gly Arg Phe Thr Ile Ser Arg Gly Asn Ala Glu Asn
1               5                   10                  15

Thr Val Ala Leu Gln Met Asn Ser Leu Lys Pro Glu Asp Thr Gly Val
                20                  25                  30

Tyr Tyr Cys Asn Val
            35

<210> SEQ ID NO 197
<211> LENGTH: 37
<212> TYPE: PRT
<213> ORGANISM: Artificial Sequence
<220> FEATURE:
<223> OTHER INFORMATION: FW3

<400> SEQUENCE: 197

Asp Ser Met Lys Gly Arg Phe Thr Ile Ser Arg Gly Asn Ala Glu Asn
1               5                   10                  15

Thr Val Ala Leu Gln Met Asn Ser Leu Lys Pro Glu Asp Thr Gly Val
                20                  25                  30

Tyr Tyr Cys Asn Val
            35

<210> SEQ ID NO 198
<211> LENGTH: 39
<212> TYPE: PRT
<213> ORGANISM: Artificial Sequence
<220> FEATURE:
<223> OTHER INFORMATION: FW3

<400> SEQUENCE: 198

Leu Val Asp Ser Val Lys Gly Arg Phe Thr Ile Val Gln Asp Asn Ala
1               5                   10                  15

Lys Asn Thr Val Tyr Leu Gln Met Asn Ser Leu Lys Val Glu Asp Thr
                20                  25                  30

Ala Val Tyr Gly Cys Ser Ala
            35

<210> SEQ ID NO 199
<211> LENGTH: 39
<212> TYPE: PRT
<213> ORGANISM: Artificial Sequence
<220> FEATURE:
```

```
<223> OTHER INFORMATION: FW3

<400> SEQUENCE: 199

Leu Ala Asp Ser Val Lys Gly Arg Phe Thr Ile Val Gln Asp Asn Ala
1               5                   10                  15

Lys Asn Thr Val Tyr Leu Gln Met Asn Ser Leu Lys Val Glu Asp Thr
            20                  25                  30

Ala Val Tyr Gly Cys Ser Ala
        35

<210> SEQ ID NO 200
<211> LENGTH: 39
<212> TYPE: PRT
<213> ORGANISM: Artificial Sequence
<220> FEATURE:
<223> OTHER INFORMATION: FW3

<400> SEQUENCE: 200

Tyr Val Asp Ser Val Lys Asp Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Phe Cys Tyr Phe
        35

<210> SEQ ID NO 201
<211> LENGTH: 11
<212> TYPE: PRT
<213> ORGANISM: Artificial Sequence
<220> FEATURE:
<223> OTHER INFORMATION: FW4

<400> SEQUENCE: 201

Trp Gly Lys Gly Thr Leu Val Thr Val Ser Ser
1               5                   10

<210> SEQ ID NO 202
<211> LENGTH: 11
<212> TYPE: PRT
<213> ORGANISM: Artificial Sequence
<220> FEATURE:
<223> OTHER INFORMATION: FW4

<400> SEQUENCE: 202

Trp Gly Lys Gly Thr Gln Val Thr Val Ser Ser
1               5                   10

<210> SEQ ID NO 203
<211> LENGTH: 11
<212> TYPE: PRT
<213> ORGANISM: Artificial Sequence
<220> FEATURE:
<223> OTHER INFORMATION: FW4

<400> SEQUENCE: 203

Trp Gly Gln Gly Thr Gln Val Thr Val Ser Ser
1               5                   10

<210> SEQ ID NO 204
<211> LENGTH: 11
<212> TYPE: PRT
<213> ORGANISM: Artificial Sequence
<220> FEATURE:
<223> OTHER INFORMATION: FW4
```

-continued

<400> SEQUENCE: 204

Trp Gly Gln Gly Thr Leu Val Thr Val Ser Ser
1               5                   10

<210> SEQ ID NO 205
<211> LENGTH: 11
<212> TYPE: PRT
<213> ORGANISM: Artificial Sequence
<220> FEATURE:
<223> OTHER INFORMATION: FW4

<400> SEQUENCE: 205

Gln Gly Gln Gly Thr Leu Val Thr Val Ser Ser
1               5                   10

<210> SEQ ID NO 206
<211> LENGTH: 423
<212> TYPE: PRT
<213> ORGANISM: Artificial Sequence
<220> FEATURE:
<223> OTHER INFORMATION: Nanobody Sequence

<400> SEQUENCE: 206

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asp
            20                  25                  30

Ser Met Gly Trp Tyr Arg Gln Ala Pro Gly Lys Gln Arg Glu Leu Val
        35                  40                  45

Ala Ala Ile Thr Ser Ser Thr Asn Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Asn Ser Leu Lys Pro Glu Asp Thr Ala Val Tyr Tyr Cys Asn Leu Glu
                85                  90                  95

Gly Gln Ala Gly Trp Gly Thr Ala Leu Ile Asn Tyr Trp Gly Lys Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Leu Val Gln Pro Gly Gly Ser Leu Arg Leu Ser Cys
                165                 170                 175

Ala Ala Ser Gly Ser Ile Phe Ser Ile Asp Ser Met Gly Trp Tyr Arg
            180                 185                 190

Gln Ala Pro Gly Lys Gln Arg Glu Leu Val Ala Ala Ile Thr Ser Ser
        195                 200                 205

Thr Asn Tyr Ala Asp Ser Val Lys Gly Arg Phe Thr Ile Ser Arg Asp
    210                 215                 220

Asn Ala Lys Asn Thr Val Tyr Leu Gln Met Asn Ser Leu Lys Pro Glu
225                 230                 235                 240

Asp Thr Ala Val Tyr Tyr Cys Asn Leu Glu Gly Gln Ala Gly Trp Gly
                245                 250                 255

Thr Ala Leu Ile Asn Tyr Trp Gly Lys Gly Thr Leu Val Thr Val Ser
            260                 265                 270

```
Ser Gly Gly Gly Ser Gly Gly Gly Ser Gly Gly Gly Ser
            275                 280                 285
Gly Gly Gly Gly Ser Gly Gly Gly Ser Gly Gly Gly Ser Gly
            290                 295                 300
Gly Gly Gly Ser Glu Val Gln Leu Val Glu Ser Gly Gly Leu Val
305                 310                 315                 320
Gln Pro Gly Asn Ser Leu Arg Leu Ser Cys Ala Ala Ser Gly Phe Thr
                325                 330                 335
Phe Ser Ser Phe Gly Met Ser Trp Val Arg Gln Ala Pro Gly Lys Gly
            340                 345                 350
Leu Glu Trp Val Ser Ser Ile Ser Gly Ser Gly Ser Asp Thr Leu Tyr
        355                 360                 365
Ala Asp Ser Val Lys Gly Arg Phe Thr Ile Ser Arg Asp Asn Ala Lys
370                 375                 380
Thr Thr Leu Tyr Leu Gln Met Asn Ser Leu Arg Pro Glu Asp Thr Ala
385                 390                 395                 400
Val Tyr Tyr Cys Thr Ile Gly Gly Ser Leu Ser Arg Ser Ser Gln Gly
                405                 410                 415
Thr Leu Val Thr Val Ser Ser
            420
```

<210> SEQ ID NO 207
<211> LENGTH: 427
<212> TYPE: PRT
<213> ORGANISM: Artificial Sequence
<220> FEATURE:
<223> OTHER INFORMATION: Nanobody Sequence

<400> SEQUENCE: 207

```
Glu Val Gln Leu Val Glu Ser Gly Gly Gly Leu Val Gln Pro Gly Gly
1               5                   10                  15
Ser Leu Arg Leu Ser Cys Ala Ala Ser Glu Thr Ile Phe Ser Ile Asp
            20                  25                  30
Ser Met Ala Trp Tyr Arg Gln Ala Pro Gly Lys Gln Arg Glu Leu Val
        35                  40                  45
Ala Ala Ile Thr Gly Gly Ser Pro Asn Tyr Ala Asp Ser Val Lys
50                  55                  60
Gly Arg Phe Thr Ile Ser Ser Asp Val Ala Lys Arg Thr Val Tyr Leu
65                  70                  75                  80
Gln Met Asn Ser Leu Lys Pro Glu Asp Thr Ala Val Tyr Tyr Cys Asn
                85                  90                  95
Ala Glu Gly Gln Ala Gly Trp Gly Thr Ala Leu Met Asp Tyr Trp Gly
            100                 105                 110
Lys Gly Thr Leu Val Thr Val Ser Ser Gly Gly Gly Ser Gly Gly
        115                 120                 125
Gly Gly Ser Gly Gly Gly Ser Gly Gly Gly Ser Gly Gly Gly
    130                 135                 140
Gly Ser Gly Gly Gly Ser Gly Gly Gly Ser Glu Val Gln Leu
145                 150                 155                 160
Val Glu Ser Gly Gly Gly Leu Val Gln Pro Gly Gly Ser Leu Arg Leu
                165                 170                 175
Ser Cys Ala Ala Ser Glu Thr Ile Phe Ser Ile Asp Ser Met Ala Trp
            180                 185                 190
Tyr Arg Gln Ala Pro Gly Lys Gln Arg Glu Leu Val Ala Ala Ile Thr
        195                 200                 205
```

Gly Gly Gly Ser Pro Asn Tyr Ala Asp Ser Val Lys Gly Arg Phe Thr
            210                 215                 220

Ile Ser Ser Asp Val Ala Lys Arg Thr Val Tyr Leu Gln Met Asn Ser
225                 230                 235                 240

Leu Lys Pro Glu Asp Thr Ala Val Tyr Tyr Cys Asn Ala Glu Gly Gln
                245                 250                 255

Ala Gly Trp Gly Thr Ala Leu Met Asp Tyr Trp Gly Lys Gly Thr Leu
            260                 265                 270

Val Thr Val Ser Ser Gly Gly Gly Ser Gly Gly Gly Ser Gly
            275                 280                 285

Gly Gly Ser Gly Gly Gly Ser Gly Gly Gly Ser Gly Gly
        290                 295                 300

Gly Gly Ser Gly Gly Gly Ser Glu Val Gln Leu Val Glu Ser Gly
305                 310                 315                 320

Gly Gly Leu Val Gln Pro Gly Asn Ser Leu Arg Leu Ser Cys Ala Ala
                325                 330                 335

Ser Gly Phe Thr Phe Ser Ser Phe Gly Met Ser Trp Val Arg Gln Ala
            340                 345                 350

Pro Gly Lys Gly Leu Glu Trp Val Ser Ser Ile Ser Gly Ser Gly Ser
            355                 360                 365

Asp Thr Leu Tyr Ala Asp Ser Val Lys Gly Arg Phe Thr Ile Ser Arg
370                 375                 380

Asp Asn Ala Lys Thr Thr Leu Tyr Leu Gln Met Asn Ser Leu Arg Pro
385                 390                 395                 400

Glu Asp Thr Ala Val Tyr Tyr Cys Thr Ile Gly Gly Ser Leu Ser Arg
                405                 410                 415

Ser Ser Gln Gly Thr Leu Val Thr Val Ser Ser
            420                 425

<210> SEQ ID NO 208
<211> LENGTH: 415
<212> TYPE: PRT
<213> ORGANISM: Artificial Sequence
<220> FEATURE:
<223> OTHER INFORMATION: Nanobody Sequence

<400> SEQUENCE: 208

Glu Val Gln Leu Val Glu Ser Gly Gly Leu Val Gln Ala Gly Gly
1               5                   10                  15

Ser Leu Arg Leu Ser Cys Val Ala Ser Gly Ser Ile Ser Ile Thr
            20                  25                  30

Ala Met Gly Trp His Arg Gln Ala Pro Gly Ala Gln Arg Glu Gly Val
            35                  40                  45

Ala Val Ile Ser Arg Ser Gly Ala Thr Met Leu Val Asp Ser Val Lys
50                  55                  60

Gly Arg Phe Thr Ile Val Gln Asp Asn Ala Lys Asn Thr Val Tyr Leu
65                  70                  75                  80

Gln Met Asn Ser Leu Lys Val Glu Asp Thr Ala Val Tyr Gly Cys Ser
                85                  90                  95

Ala Ile Thr Gln Gly Arg Thr Tyr Trp Gly Gln Gly Thr Leu Val Thr
            100                 105                 110

Val Ser Ser Gly Gly Gly Gly Ser Gly Gly Gly Ser Gly Gly Gly
            115                 120                 125

Gly Ser Gly Gly Gly Gly Ser Gly Gly Gly Gly Ser Gly Gly Gly Gly
130                 135                 140

```
Ser Gly Gly Gly Gly Ser Glu Val Gln Leu Val Glu Ser Gly Gly Gly
145                 150                 155                 160

Leu Val Gln Ala Gly Gly Ser Leu Arg Leu Ser Cys Val Ala Ser Gly
            165                 170                 175

Ser Ile Ser Ser Ile Thr Ala Met Gly Trp His Arg Gln Ala Pro Gly
            180                 185                 190

Ala Gln Arg Glu Gly Val Ala Val Ile Ser Arg Ser Gly Ala Thr Met
            195                 200                 205

Leu Val Asp Ser Val Lys Gly Arg Phe Thr Ile Val Gln Asp Asn Ala
            210                 215                 220

Lys Asn Thr Val Tyr Leu Gln Met Asn Ser Leu Lys Val Glu Asp Thr
225                 230                 235                 240

Ala Val Tyr Gly Cys Ser Ala Ile Thr Gln Gly Arg Thr Tyr Trp Gly
            245                 250                 255

Gln Gly Thr Leu Val Thr Val Ser Ser Gly Gly Gly Ser Gly Gly
            260                 265                 270

Gly Gly Ser Gly Gly Gly Ser Gly Gly Gly Ser Gly Gly Gly
            275                 280                 285

Gly Ser Gly Gly Gly Ser Gly Gly Gly Ser Glu Val Gln Leu
            290                 295                 300

Val Glu Ser Gly Gly Gly Leu Val Gln Pro Gly Asn Ser Leu Arg Leu
305                 310                 315                 320

Ser Cys Ala Ala Ser Gly Phe Thr Phe Ser Ser Phe Gly Met Ser Trp
            325                 330                 335

Val Arg Gln Ala Pro Gly Lys Gly Leu Glu Trp Val Ser Ser Ile Ser
            340                 345                 350

Gly Ser Gly Ser Asp Thr Leu Tyr Ala Asp Ser Val Lys Gly Arg Phe
            355                 360                 365

Thr Ile Ser Arg Asp Asn Ala Lys Thr Thr Leu Tyr Leu Gln Met Asn
            370                 375                 380

Ser Leu Arg Pro Glu Asp Thr Ala Val Tyr Tyr Cys Thr Ile Gly Gly
385                 390                 395                 400

Ser Leu Ser Arg Ser Ser Gln Gly Thr Leu Val Thr Val Ser Ser
            405                 410                 415

<210> SEQ ID NO 209
<211> LENGTH: 577
<212> TYPE: PRT
<213> ORGANISM: Artificial Sequence
<220> FEATURE:
<223> OTHER INFORMATION: Nanobody Sequence

<400> SEQUENCE: 209

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asp
            20                  25                  30

Ser Met Gly Trp Tyr Arg Gln Ala Pro Gly Lys Gln Arg Glu Leu Val
            35                  40                  45

Ala Ala Ile Thr Ser Ser Thr Asn Tyr Ala Asp Ser Val Lys Gly Arg
        50                  55                  60

Phe Thr Ile Ser Arg Asp Asn Ala Lys Asn Thr Val Tyr Leu Gln Met
65                  70                  75                  80

Asn Ser Leu Lys Pro Glu Asp Thr Ala Val Tyr Tyr Cys Asn Leu Glu
            85                  90                  95
```

Gly Gln Ala Gly Trp Gly Thr Ala Leu Ile Asn Tyr Trp Gly Lys Gly
                100                 105                 110

Thr Leu Val Thr Val Ser Ser Gly Gly Gly Ser Gly Gly Gly Gly
            115                 120                 125

Ser Gly Gly Gly Ser Gly Gly Gly Ser Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Leu Val Gln Pro Gly Gly Ser Leu Arg Leu Ser Cys
                165                 170                 175

Ala Ala Ser Gly Ser Ile Phe Ser Ile Asp Ser Met Gly Trp Tyr Arg
            180                 185                 190

Gln Ala Pro Gly Lys Gln Arg Glu Leu Val Ala Ala Ile Thr Ser Ser
            195                 200                 205

Thr Asn Tyr Ala Asp Ser Val Lys Gly Arg Phe Thr Ile Ser Arg Asp
            210                 215                 220

Asn Ala Lys Asn Thr Val Tyr Leu Gln Met Asn Ser Leu Lys Pro Glu
225                 230                 235                 240

Asp Thr Ala Val Tyr Tyr Cys Asn Leu Glu Gly Gln Ala Gly Trp Gly
                245                 250                 255

Thr Ala Leu Ile Asn Tyr Trp Gly Lys Gly Thr Leu Val Thr Val Ser
            260                 265                 270

Ser Gly Gly Gly Gly Ser Gly Gly Gly Ser Gly Gly Gly Gly Ser
    275                 280                 285

Gly Gly Gly Gly Ser Gly Gly Gly Ser Gly Gly Gly Gly Ser Gly
    290                 295                 300

Gly Gly Gly Ser Glu Val Gln Leu Val Glu Ser Gly Gly Gly Leu Val
305                 310                 315                 320

Gln Pro Gly Gly Ser Leu Arg Leu Ser Cys Ala Ala Ser Gly Ser Ile
            325                 330                 335

Phe Ser Ile Asp Ser Met Gly Trp Tyr Arg Gln Ala Pro Gly Lys Gln
            340                 345                 350

Arg Glu Leu Val Ala Ala Ile Thr Ser Ser Thr Asn Tyr Ala Asp Ser
            355                 360                 365

Val Lys Gly Arg Phe Thr Ile Ser Arg Asp Asn Ala Lys Asn Thr Val
            370                 375                 380

Tyr Leu Gln Met Asn Ser Leu Lys Pro Glu Asp Thr Ala Val Tyr Tyr
385                 390                 395                 400

Cys Asn Leu Glu Gly Gln Ala Gly Trp Gly Thr Ala Leu Ile Asn Tyr
                405                 410                 415

Trp Gly Lys Gly Thr Leu Val Thr Val Ser Ser Gly Gly Gly Gly Ser
            420                 425                 430

Gly Gly Gly Gly Ser Gly Gly Gly Ser Gly Gly Gly Gly Ser Gly
    435                 440                 445

Gly Gly Gly Ser Gly Gly Gly Ser Gly Gly Gly Gly Ser Glu Val
    450                 455                 460

Gln Leu Val Glu Ser Gly Gly Gly Leu Val Gln Pro Gly Asn Ser Leu
465                 470                 475                 480

Arg Leu Ser Cys Ala Ala Ser Gly Phe Thr Phe Ser Ser Phe Gly Met
            485                 490                 495

Ser Trp Val Arg Gln Ala Pro Gly Lys Gly Leu Glu Trp Val Ser Ser
            500                 505                 510

Ile Ser Gly Ser Gly Ser Asp Thr Leu Tyr Ala Asp Ser Val Lys Gly

```
            515                 520                 525
Arg Phe Thr Ile Ser Arg Asp Asn Ala Lys Thr Thr Leu Tyr Leu Gln
    530                 535                 540

Met Asn Ser Leu Arg Pro Glu Asp Thr Ala Val Tyr Tyr Cys Thr Ile
545                 550                 555                 560

Gly Gly Ser Leu Ser Arg Ser Gln Gly Thr Leu Val Thr Val Ser
                565                 570                 575

Ser

<210> SEQ ID NO 210
<211> LENGTH: 565
<212> TYPE: PRT
<213> ORGANISM: Artificial Sequence
<220> FEATURE:
<223> OTHER INFORMATION: Nanobody Sequence

<400> SEQUENCE: 210

Glu Val Gln Leu Val Glu Ser Gly Gly Gly Leu Val Gln Ala Gly Gly
1               5                   10                  15

Ser Leu Arg Leu Ser Cys Val Ala Ser Gly Ser Ile Ser Ser Ile Thr
            20                  25                  30

Ala Met Gly Trp His Arg Gln Ala Pro Gly Ala Gln Arg Glu Gly Val
        35                  40                  45

Ala Val Ile Ser Arg Ser Gly Ala Thr Met Leu Val Asp Ser Val Lys
    50                  55                  60

Gly Arg Phe Thr Ile Val Gln Asp Asn Ala Lys Asn Thr Val Tyr Leu
65                  70                  75                  80

Gln Met Asn Ser Leu Lys Val Glu Asp Thr Ala Val Tyr Gly Cys Ser
                85                  90                  95

Ala Ile Thr Gln Gly Arg Thr Tyr Trp Gly Gln Gly Thr Leu Val Thr
            100                 105                 110

Val Ser Ser Gly Gly Gly Gly Ser Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Ala Gly Gly Ser Leu Arg Leu Ser Cys Val Ala Ser Gly
                165                 170                 175

Ser Ile Ser Ser Ile Thr Ala Met Gly Trp His Arg Gln Ala Pro Gly
            180                 185                 190

Ala Gln Arg Glu Gly Val Ala Val Ile Ser Arg Ser Gly Ala Thr Met
        195                 200                 205

Leu Val Asp Ser Val Lys Gly Arg Phe Thr Ile Val Gln Asp Asn Ala
    210                 215                 220

Lys Asn Thr Val Tyr Leu Gln Met Asn Ser Leu Lys Val Glu Asp Thr
225                 230                 235                 240

Ala Val Tyr Gly Cys Ser Ala Ile Thr Gln Gly Arg Thr Tyr Trp Gly
                245                 250                 255

Gln Gly Thr Leu Val Thr Val Ser Ser Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Gly Gly Gly Gly Ser Gly Gly Gly Gly Ser Glu Val Gln Leu
    290                 295                 300
```

-continued

Val Glu Ser Gly Gly Gly Leu Val Gln Ala Gly Ser Leu Arg Leu
305                 310                 315                 320

Ser Cys Val Ala Ser Gly Ser Ile Ser Ile Thr Ala Met Gly Trp
            325                 330                 335

His Arg Gln Ala Pro Gly Ala Gln Arg Glu Gly Val Ala Val Ile Ser
            340                 345                 350

Arg Ser Gly Ala Thr Met Leu Val Asp Ser Val Lys Gly Arg Phe Thr
            355                 360                 365

Ile Val Gln Asp Asn Ala Lys Asn Thr Val Tyr Leu Gln Met Asn Ser
370                 375                 380

Leu Lys Val Glu Asp Thr Ala Val Tyr Gly Cys Ser Ala Ile Thr Gln
385                 390                 395                 400

Gly Arg Thr Tyr Trp Gly Gln Gly Thr Leu Val Thr Val Ser Ser Gly
            405                 410                 415

Gly Gly Gly Ser Gly Gly Gly Gly Ser Gly Gly Gly Ser Gly Gly
            420                 425                 430

Gly Gly Ser Gly Gly Gly Gly Ser Gly Gly Gly Gly Ser Gly Gly Gly
            435                 440                 445

Gly Ser Glu Val Gln Leu Val Glu Ser Gly Gly Gly Leu Val Gln Pro
450                 455                 460

Gly Asn Ser Leu Arg Leu Ser Cys Ala Ala Ser Gly Phe Thr Phe Ser
465                 470                 475                 480

Ser Phe Gly Met Ser Trp Val Arg Gln Ala Pro Gly Lys Gly Leu Glu
            485                 490                 495

Trp Val Ser Ser Ile Ser Gly Ser Gly Ser Asp Thr Leu Tyr Ala Asp
            500                 505                 510

Ser Val Lys Gly Arg Phe Thr Ile Ser Arg Asp Asn Ala Lys Thr Thr
            515                 520                 525

Leu Tyr Leu Gln Met Asn Ser Leu Arg Pro Glu Asp Thr Ala Val Tyr
530                 535                 540

Tyr Cys Thr Ile Gly Gly Ser Leu Ser Arg Ser Ser Gln Gly Thr Leu
545                 550                 555                 560

Val Thr Val Ser Ser
            565

<210> SEQ ID NO 211
<211> LENGTH: 577
<212> TYPE: PRT
<213> ORGANISM: Artificial Sequence
<220> FEATURE:
<223> OTHER INFORMATION: Nanobody Sequence

<400> SEQUENCE: 211

Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Ile Phe Ser Ile Asp
            20                  25                  30

Ala Met Gly Trp Tyr Arg Gln Ala Pro Gly Lys Gln Arg Glu Leu Val
            35                  40                  45

Ala Glu Ile Ser Asp His Thr Thr Tyr Gly Asp Ser Val Lys Gly Arg
        50                  55                  60

Phe Thr Ile Ser Arg Gly Asn Ala Glu Asn Thr Val Ala Leu Gln Met
65                  70                  75                  80

Asn Ser Leu Lys Pro Glu Asp Thr Gly Val Tyr Tyr Cys Asn Val His
                85                  90                  95

```
His Gln Arg Gly Trp Gly Thr Ser Ile Thr Val Thr Trp Gly Gln Gly
                100                 105                 110

Thr Leu Val Thr Val Ser Ser Gly Gly Gly Gly Ser Gly Gly Gly Gly
                115                 120                 125

Ser Gly Gly Gly Ser Gly Gly Gly Gly Ser Gly Gly Gly Gly Ser
            130                 135                 140

Gly Gly Gly Gly Ser Gly Gly Gly Ser Glu Val Gln Leu Val Glu
145                 150                 155                 160

Ser Gly Gly Gly Leu Val Gln Ala Gly Glu Ser Leu Arg Leu Ser Cys
                165                 170                 175

Ala Ala Ser Gly Ser Ile Phe Ser Ile Asp Ala Met Gly Trp Tyr Arg
                180                 185                 190

Gln Ala Pro Gly Lys Gln Arg Glu Leu Val Ala Glu Ile Ser Asp His
                195                 200                 205

Thr Thr Tyr Gly Asp Ser Val Lys Gly Arg Phe Thr Ile Ser Arg Gly
                210                 215                 220

Asn Ala Glu Asn Thr Val Ala Leu Gln Met Asn Ser Leu Lys Pro Glu
225                 230                 235                 240

Asp Thr Gly Val Tyr Tyr Cys Asn Val His His Gln Arg Gly Trp Gly
                245                 250                 255

Thr Ser Ile Thr Val Thr Trp Gly Gln Gly Thr Leu Val Thr Val Ser
                260                 265                 270

Ser Gly Gly Gly Gly Ser Gly Gly Gly Gly Ser Gly Gly Gly Gly Ser
            275                 280                 285

Gly Gly Gly Ser Gly Gly Gly Ser Gly Gly Gly Ser Gly
            290                 295                 300

Gly Gly Ser Glu Val Gln Leu Val Glu Ser Gly Gly Gly Leu Val
305                 310                 315                 320

Gln Ala Gly Glu Ser Leu Arg Leu Ser Cys Ala Ala Ser Gly Ser Ile
                325                 330                 335

Phe Ser Ile Asp Ala Met Gly Trp Tyr Arg Gln Ala Pro Gly Lys Gln
                340                 345                 350

Arg Glu Leu Val Ala Glu Ile Ser Asp His Thr Thr Tyr Gly Asp Ser
                355                 360                 365

Val Lys Gly Arg Phe Thr Ile Ser Arg Gly Asn Ala Glu Asn Thr Val
                370                 375                 380

Ala Leu Gln Met Asn Ser Leu Lys Pro Glu Asp Thr Gly Val Tyr Tyr
385                 390                 395                 400

Cys Asn Val His His Gln Arg Gly Trp Gly Thr Ser Ile Thr Val Thr
                405                 410                 415

Trp Gly Gln Gly Thr Leu Val Thr Val Ser Ser Gly Gly Gly Gly Ser
                420                 425                 430

Gly Gly Gly Gly Ser Gly Gly Gly Ser Gly Gly Gly Gly Ser Gly
            435                 440                 445

Gly Gly Gly Ser Gly Gly Gly Ser Gly Gly Gly Ser Glu Val
                450                 455                 460

Gln Leu Val Glu Ser Gly Gly Gly Leu Val Gln Pro Gly Asn Ser Leu
465                 470                 475                 480

Arg Leu Ser Cys Ala Ala Ser Gly Phe Thr Phe Ser Ser Phe Gly Met
                485                 490                 495

Ser Trp Val Arg Gln Ala Pro Gly Lys Gly Leu Glu Trp Val Ser Ser
                500                 505                 510
```

```
Ile Ser Gly Ser Gly Ser Asp Thr Leu Tyr Ala Asp Ser Val Lys Gly
            515                 520                 525

Arg Phe Thr Ile Ser Arg Asp Asn Ala Lys Thr Thr Leu Tyr Leu Gln
        530                 535                 540

Met Asn Ser Leu Arg Pro Glu Asp Thr Ala Val Tyr Tyr Cys Thr Ile
545                 550                 555                 560

Gly Gly Ser Leu Ser Arg Ser Ser Gln Gly Thr Leu Val Thr Val Ser
                565                 570                 575

Ser

<210> SEQ ID NO 212
<211> LENGTH: 583
<212> TYPE: PRT
<213> ORGANISM: Artificial Sequence
<220> FEATURE:
<223> OTHER INFORMATION: Nanobody Sequence

<400> SEQUENCE: 212

Glu Val Gln Leu Val Glu Ser Gly Gly Gly Leu Val Gln Pro Gly Gly
1               5                   10                  15

Ser Leu Arg Leu Ser Cys Ala Ala Ser Glu Thr Ile Phe Ser Ile Asp
            20                  25                  30

Ser Met Ala Trp Tyr Arg Gln Ala Pro Gly Lys Gln Arg Glu Leu Val
        35                  40                  45

Ala Ala Ile Thr Gly Gly Ser Pro Asn Tyr Ala Asp Ser Val Lys
    50                  55                  60

Gly Arg Phe Thr Ile Ser Ser Asp Val Ala Lys Arg Thr Val Tyr Leu
65                  70                  75                  80

Gln Met Asn Ser Leu Lys Pro Glu Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

Lys Gly Thr Leu Val Thr Val Ser Ser Gly Gly Gly Ser Gly Gly
            115                 120                 125

Gly Gly Ser Gly Gly Gly Ser Gly Gly Gly Ser Gly Gly Gly
        130                 135                 140

Gly Ser Gly Gly Gly Ser Gly Gly Gly Ser Glu Val Gln Leu
145                 150                 155                 160

Val Glu Ser Gly Gly Leu Val Gln Pro Gly Gly Ser Leu Arg Leu
                165                 170                 175

Ser Cys Ala Ala Ser Glu Thr Ile Phe Ser Ile Asp Ser Met Ala Trp
            180                 185                 190

Tyr Arg Gln Ala Pro Gly Lys Gln Arg Glu Leu Val Ala Ala Ile Thr
        195                 200                 205

Gly Gly Gly Ser Pro Asn Tyr Ala Asp Ser Val Lys Gly Arg Phe Thr
    210                 215                 220

Ile Ser Ser Asp Val Ala Lys Arg Thr Val Tyr Leu Gln Met Asn Ser
225                 230                 235                 240

Leu Lys Pro Glu Asp Thr Ala Val Tyr Tyr Cys Asn Ala Glu Gly Gln
                245                 250                 255

Ala Gly Trp Gly Thr Ala Leu Met Asp Tyr Trp Gly Lys Gly Thr Leu
            260                 265                 270

Val Thr Val Ser Ser Gly Gly Gly Gly Ser Gly Gly Gly Ser Gly
        275                 280                 285

Gly Gly Ser Gly Gly Gly Gly Ser Gly Gly Gly Gly Ser Gly Gly
```

```
                290                 295                 300
Gly Gly Ser Gly Gly Gly Ser Glu Val Gln Leu Val Glu Ser Gly
305                 310                 315                 320

Gly Gly Leu Val Gln Pro Gly Gly Ser Leu Arg Leu Ser Cys Ala Ala
                325                 330                 335

Ser Glu Thr Ile Phe Ser Ile Asp Ser Met Ala Trp Tyr Arg Gln Ala
                340                 345                 350

Pro Gly Lys Gln Arg Glu Leu Val Ala Ala Ile Thr Gly Gly Ser
                355                 360                 365

Pro Asn Tyr Ala Asp Ser Val Lys Gly Arg Phe Thr Ile Ser Ser Asp
370                 375                 380

Val Ala Lys Arg Thr Val Tyr Leu Gln Met Asn Ser Leu Lys Pro Glu
385                 390                 395                 400

Asp Thr Ala Val Tyr Tyr Cys Asn Ala Glu Gly Gln Ala Gly Trp Gly
                405                 410                 415

Thr Ala Leu Met Asp Tyr Trp Gly Lys Gly Thr Leu Val Thr Val Ser
                420                 425                 430

Ser Gly Gly Gly Gly Ser Gly Gly Gly Ser Gly Gly Gly Gly Ser
                435                 440                 445

Gly Gly Gly Ser Gly Gly Gly Ser Gly Gly Gly Ser Gly
                450                 455                 460

Gly Gly Ser Glu Val Gln Leu Val Glu Ser Gly Gly Gly Leu Val
465                 470                 475                 480

Gln Pro Gly Asn Ser Leu Arg Leu Ser Cys Ala Ala Ser Gly Phe Thr
                485                 490                 495

Phe Ser Ser Phe Gly Met Ser Trp Val Arg Gln Ala Pro Gly Lys Gly
                500                 505                 510

Leu Glu Trp Val Ser Ser Ile Ser Gly Ser Gly Ser Asp Thr Leu Tyr
                515                 520                 525

Ala Asp Ser Val Lys Gly Arg Phe Thr Ile Ser Arg Asp Asn Ala Lys
                530                 535                 540

Thr Thr Leu Tyr Leu Gln Met Asn Ser Leu Arg Pro Glu Asp Thr Ala
545                 550                 555                 560

Val Tyr Tyr Cys Thr Ile Gly Gly Ser Leu Ser Arg Ser Ser Gln Gly
                565                 570                 575

Thr Leu Val Thr Val Ser Ser
            580

<210> SEQ ID NO 213
<211> LENGTH: 565
<212> TYPE: PRT
<213> ORGANISM: Artificial Sequence
<220> FEATURE:
<223> OTHER INFORMATION: Nanobody Sequence

<400> SEQUENCE: 213

Glu Val Gln Leu Val Glu Ser Gly Gly Gly Leu Val Gln Ala Gly Gly
1               5                   10                  15

Ser Leu Arg Leu Ser Cys Thr Gly Ser Arg Ser Ile Phe Ser Thr Tyr
                20                  25                  30

Ala Met Ala Trp His Arg Gln Ala Pro Gly Lys Gln Arg Glu Leu Val
                35                  40                  45

Gly Phe Ile Tyr Trp Gly Gly Thr Thr Thr Tyr Ser Asp Ser Val Lys
                50                  55                  60

Gly Arg Phe Thr Ile Ser Arg Asp Asn Ala Lys Asn Thr Met Tyr Leu
```

```
                65                  70                  75                  80
Gln Met Asn Ser Leu Lys Pro Glu Asp Ala Gly Val Tyr Tyr Cys Asn
                    85                  90                  95
Ile Tyr Gly Ser Tyr Ala Leu Pro Trp Gly Gln Gly Thr Leu Val Thr
                    100                 105                 110
Val Ser Ser Gly Gly Gly Gly Ser Gly Gly Gly Gly Ser Gly Gly Gly
                    115                 120                 125
Gly Ser Gly Gly Gly Gly Ser Gly Gly Gly Gly Ser Gly Gly Gly Gly
        130                 135                 140
Ser Gly Gly Gly Ser Glu Val Gln Leu Val Glu Ser Gly Gly Gly
145                 150                 155                 160
Leu Val Gln Ala Gly Gly Ser Leu Arg Leu Ser Cys Thr Gly Ser Arg
                    165                 170                 175
Ser Ile Phe Ser Thr Tyr Ala Met Ala Trp His Arg Gln Ala Pro Gly
                    180                 185                 190
Lys Gln Arg Glu Leu Val Gly Phe Ile Tyr Trp Gly Gly Thr Thr Thr
                    195                 200                 205
Tyr Ser Asp Ser Val Lys Gly Arg Phe Thr Ile Ser Arg Asp Asn Ala
                    210                 215                 220
Lys Asn Thr Met Tyr Leu Gln Met Asn Ser Leu Lys Pro Glu Asp Ala
225                 230                 235                 240
Gly Val Tyr Tyr Cys Asn Ile Tyr Gly Ser Tyr Ala Leu Pro Trp Gly
                    245                 250                 255
Gln Gly Thr Leu Val Thr Val Ser Ser Gly Gly Gly Gly Ser Gly Gly
                    260                 265                 270
Gly Gly Ser Gly Gly Gly Gly Ser Gly Gly Gly Gly Ser Gly Gly Gly
        275                 280                 285
Gly Ser Gly Gly Gly Gly Ser Gly Gly Gly Gly Ser Glu Val Gln Leu
        290                 295                 300
Val Glu Ser Gly Gly Gly Leu Val Gln Ala Gly Gly Ser Leu Arg Leu
305                 310                 315                 320
Ser Cys Thr Gly Ser Arg Ser Ile Phe Ser Thr Tyr Ala Met Ala Trp
                    325                 330                 335
His Arg Gln Ala Pro Gly Lys Gln Arg Glu Leu Val Gly Phe Ile Tyr
                    340                 345                 350
Trp Gly Gly Thr Thr Thr Tyr Ser Asp Ser Val Lys Gly Arg Phe Thr
                    355                 360                 365
Ile Ser Arg Asp Asn Ala Lys Asn Thr Met Tyr Leu Gln Met Asn Ser
        370                 375                 380
Leu Lys Pro Glu Asp Ala Gly Val Tyr Tyr Cys Asn Ile Tyr Gly Ser
385                 390                 395                 400
Tyr Ala Leu Pro Trp Gly Gln Gly Thr Leu Val Thr Val Ser Ser Gly
                    405                 410                 415
Gly Gly Ser Gly Gly Gly Gly Ser Gly Gly Gly Gly Ser Gly Gly Gly
                    420                 425                 430
Gly Ser Gly Gly Gly Gly Ser Gly Gly Gly Gly Ser Gly Gly Gly Gly
        435                 440                 445
Gly Ser Glu Val Gln Leu Val Glu Ser Gly Gly Gly Leu Val Gln Pro
        450                 455                 460
Gly Asn Ser Leu Arg Leu Ser Cys Ala Ala Ser Gly Phe Thr Phe Ser
465                 470                 475                 480
Ser Phe Gly Met Ser Trp Val Arg Gln Ala Pro Gly Lys Gly Leu Glu
                    485                 490                 495
```

```
Trp Val Ser Ser Ile Ser Gly Ser Gly Ser Asp Thr Leu Tyr Ala Asp
            500                 505                 510

Ser Val Lys Gly Arg Phe Thr Ile Ser Arg Asp Asn Ala Lys Thr Thr
            515                 520                 525

Leu Tyr Leu Gln Met Asn Ser Leu Arg Pro Glu Asp Thr Ala Val Tyr
            530                 535                 540

Tyr Cys Thr Ile Gly Gly Ser Leu Ser Arg Ser Ser Gln Gly Thr Leu
545                 550                 555                 560

Val Thr Val Ser Ser
                565

<210> SEQ ID NO 214
<211> LENGTH: 583
<212> TYPE: PRT
<213> ORGANISM: Artificial Sequence
<220> FEATURE:
<223> OTHER INFORMATION: Nanobody Sequence

<400> SEQUENCE: 214

Glu Val Gln Leu Val Glu Ser Gly Gly Asp Leu Val Gln Pro Gly Gly
1               5                   10                  15

Ser Leu Arg Leu Ser Cys Ala Ala Ser Gly Ser Val Phe Ser Ile Asn
            20                  25                  30

Asp Met Gly Trp Phe Arg Gln Ala Pro Gly Lys Gln Arg Glu Leu Val
            35                  40                  45

Ala Asp Ile Ile Ser Arg Gly Val Thr Asn Tyr Ala Asp Ser Val Lys
        50                  55                  60

Gly Arg Phe Thr Ile Ser Gly Asp Pro Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala His Ile Ser Thr Gly Trp Gly Arg Pro His Asn Asn Tyr Trp Gly
            100                 105                 110

Gln Gly Thr Leu Val Thr Val Ser Ser Gly Gly Gly Gly Ser Gly Gly
            115                 120                 125

Gly Gly Ser Gly Gly Gly Ser Gly Gly Gly Ser Gly Gly Gly
            130                 135                 140

Gly Ser Gly Gly Gly Ser Gly Gly Gly Ser Glu Val Gln Leu
145                 150                 155                 160

Val Glu Ser Gly Gly Asp Leu Val Gln Pro Gly Gly Ser Leu Arg Leu
            165                 170                 175

Ser Cys Ala Ala Ser Gly Ser Val Phe Ser Ile Asn Asp Met Gly Trp
            180                 185                 190

Phe Arg Gln Ala Pro Gly Lys Gln Arg Glu Leu Val Ala Asp Ile Ile
            195                 200                 205

Ser Arg Gly Val Thr Asn Tyr Ala Asp Ser Val Lys Gly Arg Phe Thr
            210                 215                 220

Ile Ser Gly Asp Pro Ala Lys Asn Thr Val Tyr Leu Gln Met Asn Ser
225                 230                 235                 240

Leu Lys Pro Glu Asp Thr Ala Val Tyr Tyr Cys Asn Ala His Ile Ser
                245                 250                 255

Thr Gly Trp Gly Arg Pro His Asn Asn Tyr Trp Gly Gln Gly Thr Leu
            260                 265                 270

Val Thr Val Ser Ser Gly Gly Gly Gly Ser Gly Gly Gly Gly Ser Gly
            275                 280                 285
```

Gly Gly Gly Ser Gly Gly Gly Ser Gly Gly Gly Ser Gly Gly
            290                 295                 300

Gly Gly Ser Gly Gly Gly Ser Glu Val Gln Leu Val Glu Ser Gly
305                 310                 315                 320

Gly Asp Leu Val Gln Pro Gly Ser Leu Arg Leu Ser Cys Ala Ala
                325                 330                 335

Ser Gly Ser Val Phe Ser Ile Asn Asp Met Gly Trp Phe Arg Gln Ala
                340                 345                 350

Pro Gly Lys Gln Arg Glu Leu Val Ala Asp Ile Ile Ser Arg Gly Val
                355                 360                 365

Thr Asn Tyr Ala Asp Ser Val Lys Gly Arg Phe Thr Ile Ser Gly Asp
370                 375                 380

Pro Ala Lys Asn Thr Val Tyr Leu Gln Met Asn Ser Leu Lys Pro Glu
385                 390                 395                 400

Asp Thr Ala Val Tyr Tyr Cys Asn Ala His Ile Ser Thr Gly Trp Gly
                405                 410                 415

Arg Pro His Asn Asn Tyr Trp Gly Gln Gly Thr Leu Val Thr Val Ser
                420                 425                 430

Ser Gly Gly Gly Gly Ser Gly Gly Gly Ser Gly Gly Gly Gly Ser
            435                 440                 445

Gly Gly Gly Ser Gly Gly Gly Ser Gly Gly Gly Ser Gly
450                 455                 460

Gly Gly Gly Ser Glu Val Gln Leu Val Glu Ser Gly Gly Leu Val
465                 470                 475                 480

Gln Pro Gly Asn Ser Leu Arg Leu Ser Cys Ala Ala Ser Gly Phe Thr
                485                 490                 495

Phe Ser Ser Phe Gly Met Ser Trp Val Arg Gln Ala Pro Gly Lys Gly
            500                 505                 510

Leu Glu Trp Val Ser Ser Ile Ser Gly Ser Gly Ser Asp Thr Leu Tyr
            515                 520                 525

Ala Asp Ser Val Lys Gly Arg Phe Thr Ile Ser Arg Asp Asn Ala Lys
            530                 535                 540

Thr Thr Leu Tyr Leu Gln Met Asn Ser Leu Arg Pro Glu Asp Thr Ala
545                 550                 555                 560

Val Tyr Tyr Cys Thr Ile Gly Gly Ser Leu Ser Arg Ser Ser Gln Gly
                565                 570                 575

Thr Leu Val Thr Val Ser Ser
            580

<210> SEQ ID NO 215
<211> LENGTH: 580
<212> TYPE: PRT
<213> ORGANISM: Artificial Sequence
<220> FEATURE:
<223> OTHER INFORMATION: Nanobody Sequence

<400> SEQUENCE: 215

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Ile Phe Ser Ile Ser
                20                  25                  30

Thr Met Gly Trp Tyr Arg Gln Ala Pro Gly Lys Gln Arg Glu Val Val
            35                  40                  45

Ala Val Thr Ser Gly Phe Ser Thr Asn Tyr Ser Ser Ala Val Lys Gly
            50                  55                  60

-continued

```
Arg Phe Thr Leu Ser Arg Asp Pro Ala Lys Asn Thr Val Phe Leu Gln
65                  70                  75                  80

Met Asn Ser Leu Gln Pro Glu Asp Thr Ala Thr Tyr Tyr Cys Asn Ala
                85                  90                  95

Tyr Leu Ser Leu Ala Trp Arg Asp Pro Asp Arg Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Thr Ile Phe Ser Ile Ser Thr Met Gly Trp Tyr
            180                 185                 190

Arg Gln Ala Pro Gly Lys Gln Arg Glu Val Val Ala Val Thr Ser Gly
        195                 200                 205

Phe Ser Thr Asn Tyr Ser Ser Ala Val Lys Gly Arg Phe Thr Leu Ser
    210                 215                 220

Arg Asp Pro Ala Lys Asn Thr Val Phe Leu Gln Met Asn Ser Leu Gln
225                 230                 235                 240

Pro Glu Asp Thr Ala Thr Tyr Tyr Cys Asn Ala Tyr Leu Ser Leu Ala
                245                 250                 255

Trp Arg Asp Pro Asp Arg Asp Tyr Trp Gly Gln Gly Thr Leu Val Thr
            260                 265                 270

Val Ser Ser Gly Gly Gly Gly Ser Gly Gly Gly Gly Ser Gly Gly Gly
        275                 280                 285

Gly Ser Gly Gly Gly Gly Ser Gly Gly Gly Gly Ser Gly Gly Gly Gly
    290                 295                 300

Ser Gly Gly Gly Gly Ser Glu Val Gln Leu Val Glu Ser Gly Gly Gly
305                 310                 315                 320

Leu Val Gln Pro Gly Gly Ser Leu Arg Leu Ser Cys Ala Ala Ser Gly
                325                 330                 335

Thr Ile Phe Ser Ile Ser Thr Met Gly Trp Tyr Arg Gln Ala Pro Gly
            340                 345                 350

Lys Gln Arg Glu Val Val Ala Val Thr Ser Gly Phe Ser Thr Asn Tyr
        355                 360                 365

Ser Ser Ala Val Lys Gly Arg Phe Thr Leu Ser Arg Asp Pro Ala Lys
    370                 375                 380

Asn Thr Val Phe Leu Gln Met Asn Ser Leu Gln Pro Glu Asp Thr Ala
385                 390                 395                 400

Thr Tyr Tyr Cys Asn Ala Tyr Leu Ser Leu Ala Trp Arg Asp Pro Asp
                405                 410                 415

Arg Asp Tyr Trp Gly Gln Gly Thr Leu Val Thr Val Ser Ser Gly Gly
            420                 425                 430

Gly Gly Ser Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Glu Val Gln Leu Val Glu Ser Gly Gly Gly Leu Val Gln Pro Gly
465                 470                 475                 480
```

Asn Ser Leu Arg Leu Ser Cys Ala Ala Ser Gly Phe Thr Phe Ser Ser
            485                 490                 495

Phe Gly Met Ser Trp Val Arg Gln Ala Pro Lys Gly Leu Glu Trp
            500                 505                 510

Val Ser Ser Ile Ser Gly Ser Gly Ser Asp Thr Leu Tyr Ala Asp Ser
            515                 520                 525

Val Lys Gly Arg Phe Thr Ile Ser Arg Asp Asn Ala Lys Thr Thr Leu
530                 535                 540

Tyr Leu Gln Met Asn Ser Leu Arg Pro Glu Asp Thr Ala Val Tyr Tyr
545                 550                 555                 560

Cys Thr Ile Gly Gly Ser Leu Ser Arg Ser Gln Gly Thr Leu Val
            565                 570                 575

Thr Val Ser Ser
            580

<210> SEQ ID NO 216
<211> LENGTH: 375
<212> TYPE: PRT
<213> ORGANISM: Artificial Sequence
<220> FEATURE:
<223> OTHER INFORMATION: Nanobody Sequence

<400> SEQUENCE: 216

Glu Val Gln Leu Val Glu Ser Gly Gly Gly Leu Val Gln Pro Gly Gly
1               5                   10                  15

Ser Leu Arg Leu Ser Cys Ala Ala Ser Glu Thr Ile Phe Ser Ile Asp
            20                  25                  30

Ser Met Ala Trp Tyr Arg Gln Ala Pro Gly Lys Gln Arg Glu Leu Val
            35                  40                  45

Ala Ala Ile Thr Gly Gly Ser Pro Asn Tyr Ala Asp Ser Val Lys
50                  55                  60

Gly Arg Phe Thr Ile Ser Ser Asp Val Ala Lys Arg Thr Val Tyr Leu
65                  70                  75                  80

Gln Met Asn Ser Leu Lys Pro Glu Asp Thr Ala Val Tyr Tyr Cys Asn
            85                  90                  95

Ala Glu Gly Gln Ala Gly Trp Gly Thr Ala Leu Met Asp Tyr Trp Gly
            100                 105                 110

Lys Gly Thr Leu Val Thr Val Ser Ser Gly Gly Gly Gly Ser Gly Gly
            115                 120                 125

Gly Ser Glu Val Gln Leu Val Glu Ser Gly Gly Gly Leu Val Gln Pro
130                 135                 140

Gly Gly Ser Leu Arg Leu Ser Cys Ala Ala Ser Glu Thr Ile Phe Ser
145                 150                 155                 160

Ile Asp Ser Met Ala Trp Tyr Arg Gln Ala Pro Gly Lys Gln Arg Glu
            165                 170                 175

Leu Val Ala Ala Ile Thr Gly Gly Ser Pro Asn Tyr Ala Asp Ser
            180                 185                 190

Val Lys Gly Arg Phe Thr Ile Ser Ser Asp Val Ala Lys Arg Thr Val
            195                 200                 205

Tyr Leu Gln Met Asn Ser Leu Lys Pro Glu Asp Thr Ala Val Tyr Tyr
            210                 215                 220

Cys Asn Ala Glu Gly Gln Ala Gly Trp Gly Thr Ala Leu Met Asp Tyr
225                 230                 235                 240

Trp Gly Lys Gly Thr Leu Val Thr Val Ser Ser Gly Gly Gly Gly Ser
            245                 250                 255

```
Gly Gly Gly Ser Glu Val Gln Leu Val Ser Gly Gly Leu Val
            260                 265                 270

Gln Pro Gly Asn Ser Leu Arg Leu Ser Cys Ala Ala Ser Gly Phe Thr
            275                 280                 285

Phe Ser Ser Phe Gly Met Ser Trp Val Arg Gln Ala Pro Gly Lys Gly
            290                 295                 300

Leu Glu Trp Val Ser Ser Ile Ser Gly Ser Gly Ser Asp Thr Leu Tyr
305                 310                 315                 320

Ala Asp Ser Val Lys Gly Arg Phe Thr Ile Ser Arg Asp Asn Ala Lys
                325                 330                 335

Thr Thr Leu Tyr Leu Gln Met Asn Ser Leu Arg Pro Glu Asp Thr Ala
            340                 345                 350

Val Tyr Tyr Cys Thr Ile Gly Gly Ser Leu Ser Arg Ser Ser Gln Gly
            355                 360                 365

Thr Leu Val Thr Val Ser Ser
            370                 375

<210> SEQ ID NO 217
<211> LENGTH: 427
<212> TYPE: PRT
<213> ORGANISM: Artificial Sequence
<220> FEATURE:
<223> OTHER INFORMATION: Nanobody Sequence

<400> SEQUENCE: 217

Glu Val Gln Leu Val Glu Ser Gly Gly Gly Leu Val Gln Pro Gly Gly
1               5                   10                  15

Ser Leu Arg Leu Ser Cys Ala Ala Ser Glu Thr Ile Phe Ser Ile Asp
            20                  25                  30

Ser Met Ala Trp Tyr Arg Gln Ala Pro Gly Lys Gln Arg Glu Leu Val
        35                  40                  45

Ala Ala Ile Thr Gly Gly Gly Ser Pro Asn Tyr Ala Asp Ser Val Lys
    50                  55                  60

Gly Arg Phe Thr Ile Ser Ser Asp Val Ala Lys Arg Thr Val Tyr Leu
65                  70                  75                  80

Gln Met Asn Ser Leu Lys Pro Glu Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

Lys Gly Thr Leu Val Thr Val Ser Ser Gly Gly Gly Ser Gly Gly Gly
        115                 120                 125

Gly Gly Ser Gly Gly Gly Ser Gly Gly Gly Ser Gly Gly Gly
    130                 135                 140

Gly Ser Gly Gly Gly Ser Gly Gly Gly Ser Glu Val Gln Leu
145                 150                 155                 160

Val Glu Ser Gly Gly Gly Leu Val Gln Pro Gly Gly Ser Leu Arg Leu
                165                 170                 175

Ser Cys Ala Ala Ser Glu Thr Ile Phe Ser Ile Asp Ser Met Ala Trp
            180                 185                 190

Tyr Arg Gln Ala Pro Gly Lys Gln Arg Glu Leu Val Ala Ala Ile Thr
        195                 200                 205

Gly Gly Gly Ser Pro Asn Tyr Ala Asp Ser Val Lys Gly Arg Phe Thr
    210                 215                 220

Ile Ser Ser Asp Val Ala Lys Arg Thr Val Tyr Leu Gln Met Asn Ser
225                 230                 235                 240
```

```
Leu Lys Pro Glu Asp Thr Ala Val Tyr Tyr Cys Asn Ala Glu Gly Gln
                245                 250                 255

Ala Gly Trp Gly Thr Ala Leu Met Asp Tyr Trp Gly Lys Gly Thr Leu
        260                 265                 270

Val Thr Val Ser Ser Gly Gly Gly Ser Gly Gly Gly Ser Gly
    275                 280                 285

Gly Gly Gly Ser Gly Gly Gly Ser Gly Gly Gly Ser Gly Gly
    290                 295                 300

Gly Gly Ser Gly Gly Gly Ser Glu Val Gln Leu Val Glu Ser Gly
305                 310                 315                 320

Gly Gly Leu Val Gln Pro Gly Asn Ser Leu Arg Leu Ser Cys Ala Ala
                325                 330                 335

Ser Gly Phe Thr Phe Ser Ser Phe Gly Met Ser Trp Val Arg Gln Ala
                340                 345                 350

Pro Gly Lys Gly Leu Glu Trp Val Ser Ser Ile Ser Gly Ser Gly Ser
                355                 360                 365

Asp Thr Leu Tyr Ala Asp Ser Val Lys Gly Arg Phe Thr Ile Ser Arg
    370                 375                 380

Asp Asn Ala Lys Thr Thr Leu Tyr Leu Gln Met Asn Ser Leu Arg Pro
385                 390                 395                 400

Glu Asp Thr Ala Val Tyr Tyr Cys Thr Ile Gly Gly Ser Leu Ser Arg
                405                 410                 415

Ser Ser Gln Gly Thr Leu Val Thr Val Ser Ser
                420                 425

<210> SEQ ID NO 218
<211> LENGTH: 505
<212> TYPE: PRT
<213> ORGANISM: Artificial Sequence
<220> FEATURE:
<223> OTHER INFORMATION: Nanobody Sequence

<400> SEQUENCE: 218

Glu Val Gln Leu Val Glu Ser Gly Gly Gly Leu Val Gln Pro Gly Gly
1               5                   10                  15

Ser Leu Arg Leu Ser Cys Ala Ala Ser Glu Thr Ile Phe Ser Ile Asp
            20                  25                  30

Ser Met Ala Trp Tyr Arg Gln Ala Pro Gly Lys Gln Arg Glu Leu Val
        35                  40                  45

Ala Ala Ile Thr Gly Gly Ser Pro Asn Tyr Ala Asp Ser Val Lys
    50                  55                  60

Gly Arg Phe Thr Ile Ser Ser Asp Val Ala Lys Arg Thr Val Tyr Leu
65                  70                  75                  80

Gln Met Asn Ser Leu Lys Pro Glu Asp Thr Ala Val Tyr Tyr Cys Asn
                85                  90                  95

Ala Glu Gly Gln Ala Gly Trp Gly Thr Ala Leu Met Asp Tyr Trp Gly
            100                 105                 110

Lys Gly Thr Leu Val Thr Val Ser Ser Gly Gly Gly Ser Gly Gly
        115                 120                 125

Gly Ser Glu Val Gln Leu Val Glu Ser Gly Gly Leu Val Gln Pro
    130                 135                 140

Gly Gly Ser Leu Arg Leu Ser Cys Ala Ala Ser Glu Thr Ile Phe Ser
145                 150                 155                 160

Ile Asp Ser Met Ala Trp Tyr Arg Gln Ala Pro Gly Lys Gln Arg Glu
                165                 170                 175
```

Leu Val Ala Ala Ile Thr Gly Gly Ser Pro Asn Tyr Ala Asp Ser
            180                 185                 190

Val Lys Gly Arg Phe Thr Ile Ser Ser Asp Val Ala Lys Arg Thr Val
        195                 200                 205

Tyr Leu Gln Met Asn Ser Leu Lys Pro Glu Asp Thr Ala Val Tyr Tyr
    210                 215                 220

Cys Asn Ala Glu Gly Gln Ala Gly Trp Gly Thr Ala Leu Met Asp Tyr
225                 230                 235                 240

Trp Gly Lys Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
                260                 265                 270

Gln Pro Gly Gly Ser Leu Arg Leu Ser Cys Ala Ala Ser Glu Thr Ile
            275                 280                 285

Phe Ser Ile Asp Ser Met Ala Trp Tyr Arg Gln Ala Pro Gly Lys Gln
        290                 295                 300

Arg Glu Leu Val Ala Ala Ile Thr Gly Gly Ser Pro Asn Tyr Ala
305                 310                 315                 320

Asp Ser Val Lys Gly Arg Phe Thr Ile Ser Ser Asp Val Ala Lys Arg
                325                 330                 335

Thr Val Tyr Leu Gln Met Asn Ser Leu Lys Pro Glu Asp Thr Ala Val
                340                 345                 350

Tyr Tyr Cys Asn Ala Glu Gly Gln Ala Gly Trp Gly Thr Ala Leu Met
            355                 360                 365

Asp Tyr Trp Gly Lys Gly Thr Leu Val Thr Val Ser Ser Gly Gly Gly
        370                 375                 380

Gly Ser Gly Gly Gly Ser Glu Val Gln Leu Val Glu Ser Gly Gly Gly
385                 390                 395                 400

Leu Val Gln Pro Gly Asn Ser Leu Arg Leu Ser Cys Ala Ala Ser Gly
                405                 410                 415

Phe Thr Phe Ser Ser Phe Gly Met Ser Trp Val Arg Gln Ala Pro Gly
            420                 425                 430

Lys Gly Leu Glu Trp Val Ser Ser Ile Ser Gly Ser Gly Ser Asp Thr
        435                 440                 445

Leu Tyr Ala Asp Ser Val Lys Gly Arg Phe Thr Ile Ser Arg Asp Asn
450                 455                 460

Ala Lys Thr Thr Leu Tyr Leu Gln Met Asn Ser Leu Arg Pro Glu Asp
465                 470                 475                 480

Thr Ala Val Tyr Tyr Cys Thr Ile Gly Gly Ser Leu Ser Arg Ser Ser
                485                 490                 495

Gln Gly Thr Leu Val Thr Val Ser Ser
                500                 505

<210> SEQ ID NO 219
<211> LENGTH: 365
<212> TYPE: PRT
<213> ORGANISM: Artificial Sequence
<220> FEATURE:
<223> OTHER INFORMATION: Nanobody Sequence

<400> SEQUENCE: 219

Glu Val Gln Leu Val Glu Ser Gly Gly Gly Leu Val Gln Pro Gly Gly
1               5                   10                  15

Ser Leu Arg Leu Ser Cys Ala Ser Gly Ser Ile Phe Ser Ile Asp
            20                  25                  30

Ser Met Gly Trp Tyr Arg Gln Ala Pro Gly Lys Gln Arg Glu Leu Val
                35                  40                  45

Ala Ala Ile Thr Ser Ser Thr Asn Tyr Ala Asp Ser Val Lys Gly Arg
 50                  55                  60

Phe Thr Ile Ser Arg Asp Asn Ala Lys Asn Thr Val Tyr Leu Gln Met
 65                  70                  75                  80

Asn Ser Leu Lys Pro Glu Asp Thr Ala Val Tyr Tyr Cys Asn Leu Glu
                85                  90                  95

Gly Gln Ala Gly Trp Gly Thr Ala Leu Ile Asn Tyr Trp Gly Lys Gly
                100                 105                 110

Thr Leu Val Thr Val Ser Ser Ala Ala Ala Glu Val Gln Leu Val Glu
                115                 120                 125

Ser Gly Gly Gly Leu Val Gln Pro Gly Gly Ser Leu Arg Leu Ser Cys
                130                 135                 140

Ala Ala Ser Gly Ser Ile Phe Ser Ile Asp Ser Met Gly Trp Tyr Arg
145                 150                 155                 160

Gln Ala Pro Gly Lys Gln Arg Glu Leu Val Ala Ala Ile Thr Ser Ser
                165                 170                 175

Thr Asn Tyr Ala Asp Ser Val Lys Gly Arg Phe Thr Ile Ser Arg Asp
                180                 185                 190

Asn Ala Lys Asn Thr Val Tyr Leu Gln Met Asn Ser Leu Lys Pro Glu
                195                 200                 205

Asp Thr Ala Val Tyr Tyr Cys Asn Leu Glu Gly Gln Ala Gly Trp Gly
                210                 215                 220

Thr Ala Leu Ile Asn Tyr Trp Gly Lys Gly Thr Leu Val Thr Val Ser
225                 230                 235                 240

Ser Gly Gly Gly Gly Ser Gly Gly Ser Glu Val Gln Leu Val Glu
                245                 250                 255

Ser Gly Gly Gly Leu Val Gln Pro Gly Asn Ser Leu Arg Leu Ser Cys
                260                 265                 270

Ala Ala Ser Gly Phe Thr Phe Ser Ser Phe Gly Met Ser Trp Val Arg
                275                 280                 285

Gln Ala Pro Gly Lys Gly Leu Glu Trp Val Ser Ser Ile Ser Gly Ser
                290                 295                 300

Gly Ser Asp Thr Leu Tyr Ala Asp Ser Val Lys Gly Arg Phe Thr Ile
305                 310                 315                 320

Ser Arg Asp Asn Ala Lys Thr Thr Leu Tyr Leu Gln Met Asn Ser Leu
                325                 330                 335

Arg Pro Glu Asp Thr Ala Val Tyr Tyr Cys Thr Ile Gly Gly Ser Leu
                340                 345                 350

Ser Arg Ser Ser Gln Gly Thr Leu Val Thr Val Ser Ser
                355                 360                 365

<210> SEQ ID NO 220
<211> LENGTH: 359
<212> TYPE: PRT
<213> ORGANISM: Artificial Sequence
<220> FEATURE:
<223> OTHER INFORMATION: Nanobody Sequence

<400> SEQUENCE: 220

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asp
                20                  25                  30

Ser Met Gly Trp Tyr Arg Gln Ala Pro Gly Lys Gln Arg Glu Leu Val
        35                  40                  45

Ala Ala Ile Thr Ser Ser Thr Asn Tyr Ala Asp Ser Val Lys Gly Arg
 50                  55                  60

Phe Thr Ile Ser Arg Asp Asn Ala Lys Asn Thr Val Tyr Leu Gln Met
 65                  70                  75                  80

Asn Ser Leu Lys Pro Glu Asp Thr Ala Val Tyr Tyr Cys Asn Leu Glu
                85                  90                  95

Gly Gln Ala Gly Trp Gly Thr Ala Leu Ile Asn Tyr Trp Gly Lys Gly
            100                 105                 110

Thr Leu Val Thr Val Ser Ser Ala Ala Glu Val Gln Leu Val Glu
        115                 120                 125

Ser Gly Gly Gly Leu Val Gln Pro Gly Gly Ser Leu Arg Leu Ser Cys
130                 135                 140

Ala Ala Ser Gly Ser Ile Phe Ser Ile Asp Ser Met Gly Trp Tyr Arg
145                 150                 155                 160

Gln Ala Pro Gly Lys Gln Arg Glu Leu Val Ala Ala Ile Thr Ser Ser
                165                 170                 175

Thr Asn Tyr Ala Asp Ser Val Lys Gly Arg Phe Thr Ile Ser Arg Asp
            180                 185                 190

Asn Ala Lys Asn Thr Val Tyr Leu Gln Met Asn Ser Leu Lys Pro Glu
        195                 200                 205

Asp Thr Ala Val Tyr Tyr Cys Asn Leu Glu Gly Gln Ala Gly Trp Gly
    210                 215                 220

Thr Ala Leu Ile Asn Tyr Trp Gly Lys Gly Thr Leu Val Thr Val Ser
225                 230                 235                 240

Ser Ala Ala Ala Glu Val Gln Leu Val Glu Ser Gly Gly Gly Leu Val
                245                 250                 255

Gln Pro Gly Asn Ser Leu Arg Leu Ser Cys Ala Ala Ser Gly Phe Thr
            260                 265                 270

Phe Ser Ser Phe Gly Met Ser Trp Val Arg Gln Ala Pro Gly Lys Gly
        275                 280                 285

Leu Glu Trp Val Ser Ser Ile Ser Gly Ser Gly Ser Asp Thr Leu Tyr
    290                 295                 300

Ala Asp Ser Val Lys Gly Arg Phe Thr Ile Ser Arg Asp Asn Ala Lys
305                 310                 315                 320

Thr Thr Leu Tyr Leu Gln Met Asn Ser Leu Arg Pro Glu Asp Thr Ala
                325                 330                 335

Val Tyr Tyr Cys Thr Ile Gly Gly Ser Leu Ser Arg Ser Ser Gln Gly
            340                 345                 350

Thr Leu Val Thr Val Ser Ser
        355

<210> SEQ ID NO 221
<211> LENGTH: 371
<212> TYPE: PRT
<213> ORGANISM: Artificial Sequence
<220> FEATURE:
<223> OTHER INFORMATION: Nanobody Sequence

<400> SEQUENCE: 221

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asp
            20                  25                  30

```
Ser Met Gly Trp Tyr Arg Gln Ala Pro Gly Lys Gln Arg Glu Leu Val
         35                  40                  45

Ala Ala Ile Thr Ser Ser Thr Asn Tyr Ala Asp Ser Val Lys Gly Arg
 50                  55                  60

Phe Thr Ile Ser Arg Asp Asn Ala Lys Asn Thr Val Tyr Leu Gln Met
 65                  70                  75                  80

Asn Ser Leu Lys Pro Glu Asp Thr Ala Val Tyr Tyr Cys Asn Leu Glu
                 85                  90                  95

Gly Gln Ala Gly Trp Gly Thr Ala Leu Ile Asn Tyr Trp Gly Lys Gly
                100                 105                 110

Thr Leu Val Thr Val Ser Ser Gly Gly Gly Ser Gly Gly Gly Ser
        115                 120                 125

Glu Val Gln Leu Val Glu Ser Gly Gly Gly Leu Val Gln Pro Gly Gly
        130                 135                 140

Ser Leu Arg Leu Ser Cys Ala Ala Ser Gly Ser Ile Phe Ser Ile Asp
145                 150                 155                 160

Ser Met Gly Trp Tyr Arg Gln Ala Pro Gly Lys Gln Arg Glu Leu Val
                165                 170                 175

Ala Ala Ile Thr Ser Ser Thr Asn Tyr Ala Asp Ser Val Lys Gly Arg
                180                 185                 190

Phe Thr Ile Ser Arg Asp Asn Ala Lys Asn Thr Val Tyr Leu Gln Met
                195                 200                 205

Asn Ser Leu Lys Pro Glu Asp Thr Ala Val Tyr Tyr Cys Asn Leu Glu
                210                 215                 220

Gly Gln Ala Gly Trp Gly Thr Ala Leu Ile Asn Tyr Trp Gly Lys Gly
225                 230                 235                 240

Thr Leu Val Thr Val Ser Ser Gly Gly Gly Ser Gly Gly Gly Ser
                245                 250                 255

Glu Val Gln Leu Val Glu Ser Gly Gly Gly Leu Val Gln Pro Gly Asn
                260                 265                 270

Ser Leu Arg Leu Ser Cys Ala Ala Ser Gly Phe Thr Phe Ser Ser Phe
                275                 280                 285

Gly Met Ser Trp Val Arg Gln Ala Pro Gly Lys Gly Leu Glu Trp Val
                290                 295                 300

Ser Ser Ile Ser Gly Ser Gly Ser Asp Thr Leu Tyr Ala Asp Ser Val
305                 310                 315                 320

Lys Gly Arg Phe Thr Ile Ser Arg Asp Asn Ala Lys Thr Thr Leu Tyr
                325                 330                 335

Leu Gln Met Asn Ser Leu Arg Pro Glu Asp Thr Ala Val Tyr Tyr Cys
                340                 345                 350

Thr Ile Gly Gly Ser Leu Ser Arg Ser Ser Gln Gly Thr Leu Val Thr
                355                 360                 365

Val Ser Ser
    370

<210> SEQ ID NO 222
<211> LENGTH: 499
<212> TYPE: PRT
<213> ORGANISM: Artificial Sequence
<220> FEATURE:
<223> OTHER INFORMATION: Nanobody Sequence

<400> SEQUENCE: 222

Glu Val Gln Leu Val Glu Ser Gly Gly Gly Leu Val Gln Pro Gly Gly
 1               5                  10                  15
```

Ser Leu Arg Leu Ser Cys Ala Ala Ser Gly Ser Ile Phe Ser Ile Asp
             20                  25                  30

Ser Met Gly Trp Tyr Arg Gln Ala Pro Gly Lys Gln Arg Glu Leu Val
         35                  40                  45

Ala Ala Ile Thr Ser Ser Thr Asn Tyr Ala Asp Ser Val Lys Gly Arg
     50                  55                  60

Phe Thr Ile Ser Arg Asp Asn Ala Lys Asn Thr Val Tyr Leu Gln Met
65                  70                  75                  80

Asn Ser Leu Lys Pro Glu Asp Thr Ala Val Tyr Tyr Cys Asn Leu Glu
                 85                  90                  95

Gly Gln Ala Gly Trp Gly Thr Ala Leu Ile Asn Tyr Trp Gly Lys Gly
             100                 105                 110

Thr Leu Val Thr Val Ser Ser Gly Gly Gly Ser Gly Gly Gly Ser
         115                 120                 125

Glu Val Gln Leu Val Glu Ser Gly Gly Gly Leu Val Gln Pro Gly Gly
     130                 135                 140

Ser Leu Arg Leu Ser Cys Ala Ala Ser Gly Ser Ile Phe Ser Ile Asp
145                 150                 155                 160

Ser Met Gly Trp Tyr Arg Gln Ala Pro Gly Lys Gln Arg Glu Leu Val
                 165                 170                 175

Ala Ala Ile Thr Ser Ser Thr Asn Tyr Ala Asp Ser Val Lys Gly Arg
             180                 185                 190

Phe Thr Ile Ser Arg Asp Asn Ala Lys Asn Thr Val Tyr Leu Gln Met
         195                 200                 205

Asn Ser Leu Lys Pro Glu Asp Thr Ala Val Tyr Tyr Cys Asn Leu Glu
     210                 215                 220

Gly Gln Ala Gly Trp Gly Thr Ala Leu Ile Asn Tyr Trp Gly Lys Gly
225                 230                 235                 240

Thr Leu Val Thr Val Ser Ser Gly Gly Gly Ser Gly Gly Gly Ser
                 245                 250                 255

Glu Val Gln Leu Val Glu Ser Gly Gly Gly Leu Val Gln Pro Gly Gly
             260                 265                 270

Ser Leu Arg Leu Ser Cys Ala Ala Ser Gly Ser Ile Phe Ser Ile Asp
         275                 280                 285

Ser Met Gly Trp Tyr Arg Gln Ala Pro Gly Lys Gln Arg Glu Leu Val
     290                 295                 300

Ala Ala Ile Thr Ser Ser Thr Asn Tyr Ala Asp Ser Val Lys Gly Arg
305                 310                 315                 320

Phe Thr Ile Ser Arg Asp Asn Ala Lys Asn Thr Val Tyr Leu Gln Met
                 325                 330                 335

Asn Ser Leu Lys Pro Glu Asp Thr Ala Val Tyr Tyr Cys Asn Leu Glu
             340                 345                 350

Gly Gln Ala Gly Trp Gly Thr Ala Leu Ile Asn Tyr Trp Gly Lys Gly
         355                 360                 365

Thr Leu Val Thr Val Ser Ser Gly Gly Gly Ser Gly Gly Gly Ser
     370                 375                 380

Glu Val Gln Leu Val Glu Ser Gly Gly Gly Leu Val Gln Pro Gly Asn
385                 390                 395                 400

Ser Leu Arg Leu Ser Cys Ala Ala Ser Gly Phe Thr Phe Ser Ser Phe
                 405                 410                 415

Gly Met Ser Trp Val Arg Gln Ala Pro Gly Lys Gly Leu Glu Trp Val
             420                 425                 430

Ser Ser Ile Ser Gly Ser Gly Ser Asp Thr Leu Tyr Ala Asp Ser Val

```
            435                 440                 445
Lys Gly Arg Phe Thr Ile Ser Arg Asp Asn Ala Lys Thr Thr Leu Tyr
        450                 455                 460

Leu Gln Met Asn Ser Leu Arg Pro Glu Asp Thr Ala Val Tyr Tyr Cys
465                 470                 475                 480

Thr Ile Gly Gly Ser Leu Ser Arg Ser Gln Gly Thr Leu Val Thr
                485                 490                 495

Val Ser Ser

<210> SEQ ID NO 223
<211> LENGTH: 481
<212> TYPE: PRT
<213> ORGANISM: Artificial Sequence
<220> FEATURE:
<223> OTHER INFORMATION: Nanobody Sequence

<400> SEQUENCE: 223

Glu Val Gln Leu Val Glu Ser Gly Gly Leu Val Gln Pro Gly Gly
1               5                   10                  15

Ser Leu Arg Leu Ser Cys Ala Ala Ser Gly Ser Ile Phe Ser Ile Asp
                20                  25                  30

Ser Met Gly Trp Tyr Arg Gln Ala Pro Gly Lys Gln Arg Glu Leu Val
            35                  40                  45

Ala Ala Ile Thr Ser Ser Thr Asn Tyr Ala Asp Ser Val Lys Gly Arg
50                  55                  60

Phe Thr Ile Ser Arg Asp Asn Ala Lys Asn Thr Val Tyr Leu Gln Met
65                  70                  75                  80

Asn Ser Leu Lys Pro Glu Asp Thr Ala Val Tyr Tyr Cys Asn Leu Glu
                85                  90                  95

Gly Gln Ala Gly Trp Gly Thr Ala Leu Ile Asn Tyr Trp Gly Lys Gly
            100                 105                 110

Thr Leu Val Thr Val Ser Ser Ala Ala Ala Glu Val Gln Leu Val Glu
        115                 120                 125

Ser Gly Gly Gly Leu Val Gln Pro Gly Gly Ser Leu Arg Leu Ser Cys
130                 135                 140

Ala Ala Ser Gly Ser Ile Phe Ser Ile Asp Ser Met Gly Trp Tyr Arg
145                 150                 155                 160

Gln Ala Pro Gly Lys Gln Arg Glu Leu Val Ala Ala Ile Thr Ser Ser
                165                 170                 175

Thr Asn Tyr Ala Asp Ser Val Lys Gly Arg Phe Thr Ile Ser Arg Asp
            180                 185                 190

Asn Ala Lys Asn Thr Val Tyr Leu Gln Met Asn Ser Leu Lys Pro Glu
        195                 200                 205

Asp Thr Ala Val Tyr Tyr Cys Asn Leu Glu Gly Gln Ala Gly Trp Gly
210                 215                 220

Thr Ala Leu Ile Asn Tyr Trp Gly Lys Gly Thr Leu Val Thr Val Ser
225                 230                 235                 240

Ser Ala Ala Ala Glu Val Gln Leu Val Glu Ser Gly Gly Gly Leu Val
                245                 250                 255

Gln Pro Gly Gly Ser Leu Arg Leu Ser Cys Ala Ala Ser Gly Ser Ile
            260                 265                 270

Phe Ser Ile Asp Ser Met Gly Trp Tyr Arg Gln Ala Pro Gly Lys Gln
        275                 280                 285

Arg Glu Leu Val Ala Ala Ile Thr Ser Ser Thr Asn Tyr Ala Asp Ser
290                 295                 300
```

```
Val Lys Gly Arg Phe Thr Ile Ser Arg Asp Asn Ala Lys Asn Thr Val
305                 310                 315                 320

Tyr Leu Gln Met Asn Ser Leu Lys Pro Glu Asp Thr Ala Val Tyr Tyr
                325                 330                 335

Cys Asn Leu Glu Gly Gln Ala Gly Trp Gly Thr Ala Leu Ile Asn Tyr
            340                 345                 350

Trp Gly Lys Gly Thr Leu Val Thr Val Ser Ser Ala Ala Glu Val
        355                 360                 365

Gln Leu Val Glu Ser Gly Gly Leu Val Gln Pro Gly Asn Ser Leu
370                 375                 380

Arg Leu Ser Cys Ala Ala Ser Gly Phe Thr Phe Ser Ser Phe Gly Met
385                 390                 395                 400

Ser Trp Val Arg Gln Ala Pro Gly Lys Gly Leu Glu Trp Val Ser Ser
                405                 410                 415

Ile Ser Gly Ser Gly Ser Asp Thr Leu Tyr Ala Asp Ser Val Lys Gly
            420                 425                 430

Arg Phe Thr Ile Ser Arg Asp Asn Ala Lys Thr Thr Leu Tyr Leu Gln
        435                 440                 445

Met Asn Ser Leu Arg Pro Glu Asp Thr Ala Val Tyr Tyr Cys Thr Ile
    450                 455                 460

Gly Gly Ser Leu Ser Arg Ser Ser Gln Gly Thr Leu Val Thr Val Ser
465                 470                 475                 480

Ser
```

<210> SEQ ID NO 224
<211> LENGTH: 421
<212> TYPE: PRT
<213> ORGANISM: Artificial Sequence
<220> FEATURE:
<223> OTHER INFORMATION: Nanobody Sequence

<400> SEQUENCE: 224

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Phe Ile
                20                  25                  30

Val Met Gly Trp Tyr Arg Gln Ala Pro Gly Glu Gln Arg Ala Leu Val
            35                  40                  45

Ala Thr Val Thr Ser Gly Gly Asp Thr Phe Tyr Val Asp Ser Val Lys
        50                  55                  60

Asp Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Phe Cys Tyr
                85                  90                  95

Phe Thr Lys Val Ser Pro Tyr Lys Glu Thr Thr Trp Gly Gln Gly Thr
                100                 105                 110

Leu Val Thr Val Ser Ser Gly Gly Gly Gly Ser Gly Gly Gly Gly Ser
            115                 120                 125

Gly Gly Gly Gly Ser Gly Gly Gly Ser Gly Gly Gly Gly Ser Gly
        130                 135                 140

Gly Gly Gly Ser Gly Gly Gly Ser Glu Val Gln Leu Val Glu Ser
145                 150                 155                 160

Gly Gly Gly Leu Val Gln Ala Gly Gly Ser Leu Arg Leu Ser Cys Ala
                165                 170                 175
```

Ala Ser Gly Ser Ile Phe Ser Phe Ile Val Met Gly Trp Tyr Arg Gln
            180                 185                 190

Ala Pro Gly Glu Gln Arg Ala Leu Val Ala Thr Val Thr Ser Gly Gly
        195                 200                 205

Asp Thr Phe Tyr Val Asp Ser Val Lys Asp Arg Phe Thr Ile Ser Arg
    210                 215                 220

Asp Asn Ala Lys Asn Thr Val Tyr Leu Gln Met Asn Ser Leu Lys Pro
225                 230                 235                 240

Glu Asp Thr Ala Val Tyr Phe Cys Tyr Phe Thr Lys Val Ser Pro Tyr
                245                 250                 255

Lys Glu Thr Thr Trp Gly Gln Gly Thr Leu Val Thr Val Ser Ser Gly
            260                 265                 270

Gly Gly Gly Ser Gly Gly Gly Ser Gly Gly Gly Ser Gly Gly
            275                 280                 285

Gly Gly Ser Gly Gly Gly Ser Gly Gly Gly Ser Gly Gly Gly
        290                 295                 300

Gly Ser Glu Val Gln Leu Val Glu Ser Gly Gly Gly Leu Val Gln Pro
305                 310                 315                 320

Gly Asn Ser Leu Arg Leu Ser Cys Ala Ala Ser Gly Phe Thr Phe Ser
                325                 330                 335

Ser Phe Gly Met Ser Trp Val Arg Gln Ala Pro Gly Lys Gly Leu Glu
            340                 345                 350

Trp Val Ser Ser Ile Ser Gly Ser Gly Ser Asp Thr Leu Tyr Ala Asp
        355                 360                 365

Ser Val Lys Gly Arg Phe Thr Ile Ser Arg Asp Asn Ala Lys Thr Thr
370                 375                 380

Leu Tyr Leu Gln Met Asn Ser Leu Arg Pro Glu Asp Thr Ala Val Tyr
385                 390                 395                 400

Tyr Cys Thr Ile Gly Gly Ser Leu Ser Arg Ser Ser Gln Gly Thr Leu
                405                 410                 415

Val Thr Val Ser Ser
            420

<210> SEQ ID NO 225
<211> LENGTH: 574
<212> TYPE: PRT
<213> ORGANISM: Artificial Sequence
<220> FEATURE:
<223> OTHER INFORMATION: Nanobody Sequence

<400> SEQUENCE: 225

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Phe Ile
            20                  25                  30

Val Met Gly Trp Tyr Arg Gln Ala Pro Gly Glu Gln Arg Ala Leu Val
        35                  40                  45

Ala Thr Val Thr Ser Gly Gly Asp Thr Phe Tyr Val Asp Ser Val Lys
    50                  55                  60

Asp Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Phe Cys Tyr
                85                  90                  95

Phe Thr Lys Val Ser Pro Tyr Lys Glu Thr Thr Trp Gly Gln Gly Thr
            100                 105                 110

-continued

```
Leu Val Thr Val Ser Ser Gly Gly Gly Gly Ser Gly Gly Gly Ser
            115                 120                 125
Gly Gly Gly Gly Ser Gly Gly Gly Ser Gly Gly Gly Ser Gly
        130                 135                 140
Gly Gly Gly Ser Gly Gly Gly Ser Glu Val Gln Leu Val Glu Ser
145                 150                 155                 160
Gly Gly Gly Leu Val Gln Ala Gly Gly Ser Leu Arg Leu Ser Cys Ala
                165                 170                 175
Ala Ser Gly Ser Ile Phe Ser Phe Ile Val Met Gly Trp Tyr Arg Gln
            180                 185                 190
Ala Pro Gly Glu Gln Arg Ala Leu Val Ala Thr Val Thr Ser Gly Gly
        195                 200                 205
Asp Thr Phe Tyr Val Asp Ser Val Lys Asp Arg Phe Thr Ile Ser Arg
    210                 215                 220
Asp Asn Ala Lys Asn Thr Val Tyr Leu Gln Met Asn Ser Leu Lys Pro
225                 230                 235                 240
Glu Asp Thr Ala Val Tyr Phe Cys Tyr Phe Thr Lys Val Ser Pro Tyr
                245                 250                 255
Lys Glu Thr Thr Trp Gly Gln Gly Thr Leu Val Thr Val Ser Ser Gly
            260                 265                 270
Gly Gly Gly Ser Gly Gly Gly Ser Gly Gly Gly Ser Gly Gly
        275                 280                 285
Gly Gly Ser Gly Gly Gly Ser Gly Gly Gly Ser Gly Gly Gly
    290                 295                 300
Gly Ser Glu Val Gln Leu Val Glu Ser Gly Gly Leu Val Gln Ala
305                 310                 315                 320
Gly Gly Ser Leu Arg Leu Ser Cys Ala Ala Ser Gly Ser Ile Phe Ser
                325                 330                 335
Phe Ile Val Met Gly Trp Tyr Arg Gln Ala Pro Gly Glu Gln Arg Ala
            340                 345                 350
Leu Val Ala Thr Val Thr Ser Gly Gly Asp Thr Phe Tyr Val Asp Ser
        355                 360                 365
Val Lys Asp Arg Phe Thr Ile Ser Arg Asp Asn Ala Lys Asn Thr Val
    370                 375                 380
Tyr Leu Gln Met Asn Ser Leu Lys Pro Glu Asp Thr Ala Val Tyr Phe
385                 390                 395                 400
Cys Tyr Phe Thr Lys Val Ser Pro Tyr Lys Glu Thr Thr Trp Gly Gln
                405                 410                 415
Gly Thr Leu Val Thr Val Ser Ser Gly Gly Gly Ser Gly Gly Gly
            420                 425                 430
Gly Ser Gly Gly Gly Ser Gly Gly Gly Ser Gly Gly Gly
        435                 440                 445
Ser Gly Gly Gly Ser Gly Gly Gly Ser Glu Val Gln Leu Val
    450                 455                 460
Glu Ser Gly Gly Gly Leu Val Gln Pro Gly Asn Ser Leu Arg Leu Ser
465                 470                 475                 480
Cys Ala Ala Ser Gly Phe Thr Phe Ser Ser Phe Gly Met Ser Trp Val
                485                 490                 495
Arg Gln Ala Pro Gly Lys Gly Leu Glu Trp Val Ser Ser Ile Ser Gly
            500                 505                 510
Ser Gly Ser Asp Thr Leu Tyr Ala Asp Ser Val Lys Gly Arg Phe Thr
        515                 520                 525
Ile Ser Arg Asp Asn Ala Lys Thr Thr Leu Tyr Leu Gln Met Asn Ser
```

```
                530              535              540
Leu Arg Pro Glu Asp Thr Ala Val Tyr Tyr Cys Thr Ile Gly Gly Ser
545              550              555              560

Leu Ser Arg Ser Ser Gln Gly Thr Leu Val Thr Val Ser Ser
            565              570

<210> SEQ ID NO 226
<211> LENGTH: 369
<212> TYPE: PRT
<213> ORGANISM: Artificial Sequence
<220> FEATURE:
<223> OTHER INFORMATION: Nanobody Sequence

<400> SEQUENCE: 226

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Phe Ile
            20                  25                  30

Val Met Gly Trp Tyr Arg Gln Ala Pro Gly Glu Gln Arg Ala Leu Val
        35                  40                  45

Ala Thr Val Thr Ser Gly Gly Asp Thr Phe Tyr Val Asp Ser Val Lys
50                  55                  60

Asp Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Phe Cys Tyr
                85                  90                  95

Phe Thr Lys Val Ser Pro Tyr Lys Glu Thr Thr Trp Gly Gln Gly Thr
            100                 105                 110

Leu Val Thr Val Ser Ser Gly Gly Gly Gly Ser Gly Gly Gly Ser Glu
        115                 120                 125

Val Gln Leu Val Glu Ser Gly Gly Gly Leu Val Gln Ala Gly Gly Ser
    130                 135                 140

Leu Arg Leu Ser Cys Ala Ala Ser Gly Ser Ile Phe Ser Phe Ile Val
145                 150                 155                 160

Met Gly Trp Tyr Arg Gln Ala Pro Gly Glu Gln Arg Ala Leu Val Ala
                165                 170                 175

Thr Val Thr Ser Gly Gly Asp Thr Phe Tyr Val Asp Ser Val Lys Asp
            180                 185                 190

Arg Phe Thr Ile Ser Arg Asp Asn Ala Lys Asn Thr Val Tyr Leu Gln
        195                 200                 205

Met Asn Ser Leu Lys Pro Glu Asp Thr Ala Val Tyr Phe Cys Tyr Phe
    210                 215                 220

Thr Lys Val Ser Pro Tyr Lys Glu Thr Thr Trp Gly Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Asn Ser Leu
            260                 265                 270

Arg Leu Ser Cys Ala Ala Ser Gly Phe Thr Phe Ser Ser Phe Gly Met
        275                 280                 285

Ser Trp Val Arg Gln Ala Pro Gly Lys Gly Leu Glu Trp Val Ser Ser
    290                 295                 300

Ile Ser Gly Ser Gly Ser Asp Thr Leu Tyr Ala Asp Ser Val Lys Gly
305                 310                 315                 320

Arg Phe Thr Ile Ser Arg Asp Asn Ala Lys Thr Thr Leu Tyr Leu Gln
```

```
                            325                 330                 335
Met Asn Ser Leu Arg Pro Glu Asp Thr Ala Val Tyr Tyr Cys Thr Ile
                    340                 345                 350
Gly Gly Ser Leu Ser Arg Ser Ser Gln Gly Thr Leu Val Thr Val Ser
                355                 360                 365
Ser

<210> SEQ ID NO 227
<211> LENGTH: 496
<212> TYPE: PRT
<213> ORGANISM: Artificial Sequence
<220> FEATURE:
<223> OTHER INFORMATION: Nanobody Sequence

<400> SEQUENCE: 227

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Phe Ile
                20                  25                  30

Val Met Gly Trp Tyr Arg Gln Ala Pro Gly Glu Gln Arg Ala Leu Val
            35                  40                  45

Ala Thr Val Thr Ser Gly Gly Asp Thr Phe Tyr Val Asp Ser Val Lys
        50                  55                  60

Asp Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Phe Cys Tyr
                85                  90                  95

Phe Thr Lys Val Ser Pro Tyr Lys Glu Thr Thr Trp Gly Gln Gly Thr
            100                 105                 110

Leu Val Thr Val Ser Ser Gly Gly Gly Ser Gly Gly Gly Ser Glu
        115                 120                 125

Val Gln Leu Val Glu Ser Gly Gly Gly Leu Val Gln Ala Gly Gly Ser
    130                 135                 140

Leu Arg Leu Ser Cys Ala Ala Ser Gly Ser Ile Phe Ser Phe Ile Val
145                 150                 155                 160

Met Gly Trp Tyr Arg Gln Ala Pro Gly Glu Gln Arg Ala Leu Val Ala
                165                 170                 175

Thr Val Thr Ser Gly Gly Asp Thr Phe Tyr Val Asp Ser Val Lys Asp
            180                 185                 190

Arg Phe Thr Ile Ser Arg Asp Asn Ala Lys Asn Thr Val Tyr Leu Gln
        195                 200                 205

Met Asn Ser Leu Lys Pro Glu Asp Thr Ala Val Tyr Phe Cys Tyr Phe
    210                 215                 220

Thr Lys Val Ser Pro Tyr Lys Glu Thr Thr Trp Gly Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Ala Gly Gly Ser Leu
            260                 265                 270

Arg Leu Ser Cys Ala Ala Ser Gly Ser Ile Phe Ser Phe Ile Val Met
        275                 280                 285

Gly Trp Tyr Arg Gln Ala Pro Gly Glu Gln Arg Ala Leu Val Ala Thr
    290                 295                 300

Val Thr Ser Gly Gly Asp Thr Phe Tyr Val Asp Ser Val Lys Asp Arg
305                 310                 315                 320
```

Phe Thr Ile Ser Arg Asp Asn Ala Lys Asn Thr Val Tyr Leu Gln Met
            325                 330                 335

Asn Ser Leu Lys Pro Glu Asp Thr Ala Val Tyr Phe Cys Tyr Phe Thr
            340                 345                 350

Lys Val Ser Pro Tyr Lys Glu Thr Thr Trp Gly Gln Gly Thr Leu Val
            355                 360                 365

Thr Val Ser Ser Gly Gly Gly Ser Gly Gly Ser Glu Val Gln
370                 375                 380

Leu Val Glu Ser Gly Gly Gly Leu Val Gln Pro Gly Asn Ser Leu Arg
385                 390                 395                 400

Leu Ser Cys Ala Ala Ser Gly Phe Thr Phe Ser Ser Phe Gly Met Ser
            405                 410                 415

Trp Val Arg Gln Ala Pro Gly Lys Gly Leu Glu Trp Val Ser Ser Ile
            420                 425                 430

Ser Gly Ser Gly Ser Asp Thr Leu Tyr Ala Asp Ser Val Lys Gly Arg
            435                 440                 445

Phe Thr Ile Ser Arg Asp Asn Ala Lys Thr Thr Leu Tyr Leu Gln Met
            450                 455                 460

Asn Ser Leu Arg Pro Glu Asp Thr Ala Val Tyr Tyr Cys Thr Ile Gly
465                 470                 475                 480

Gly Ser Leu Ser Arg Ser Ser Gln Gly Thr Leu Val Thr Val Ser Ser
            485                 490                 495

<210> SEQ ID NO 228
<211> LENGTH: 619
<212> TYPE: PRT
<213> ORGANISM: Artificial Sequence
<220> FEATURE:
<223> OTHER INFORMATION: Nanobody Sequence

<400> SEQUENCE: 228

Glu Val Gln Leu Val Glu Ser Gly Gly Ser Val Gln Ala Gly Gly
1               5                   10                  15

Ser Leu Arg Leu Ser Cys Ala Ala Ser Gly Tyr Thr Ile Gly Pro Tyr
            20                  25                  30

Cys Met Gly Trp Phe Arg Gln Ala Pro Gly Lys Glu Arg Glu Gly Val
            35                  40                  45

Ala Ala Ile Asn Met Gly Gly Ile Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Leu Met Asn Ser Leu Glu Pro Glu Asp Thr Ala Ile Tyr Tyr Cys
            85                  90                  95

Ala Ala Asp Ser Thr Ile Tyr Ala Ser Tyr Tyr Glu Cys Gly His Gly
            100                 105                 110

Leu Ser Thr Gly Gly Tyr Gly Tyr Asp Ser Trp Gly Gln Gly Thr Leu
            115                 120                 125

Val Thr Val Ser Ser Gly Gly Gly Gly Ser Gly Gly Gly Gly Ser Gly
            130                 135                 140

Gly Gly Gly Ser Gly Gly Gly Gly Ser Gly Gly Gly Gly Ser Gly Gly
145                 150                 155                 160

Gly Gly Ser Gly Gly Gly Gly Ser Glu Val Gln Leu Val Glu Ser Gly
            165                 170                 175

Gly Gly Ser Val Gln Ala Gly Gly Ser Leu Arg Leu Ser Cys Ala Ala
            180                 185                 190

```
Ser Gly Tyr Thr Ile Gly Pro Tyr Cys Met Gly Trp Phe Arg Gln Ala
        195                 200                 205

Pro Gly Lys Glu Arg Glu Gly Val Ala Ala Ile Asn Met Gly Gly Gly
        210                 215                 220

Ile Thr Tyr Tyr Ala Asp Ser Val Lys Gly Arg Phe Thr Ile Ser Gln
225                 230                 235                 240

Asp Asn Ala Lys Asn Thr Val Tyr Leu Leu Met Asn Ser Leu Glu Pro
                245                 250                 255

Glu Asp Thr Ala Ile Tyr Tyr Cys Ala Ala Asp Ser Thr Ile Tyr Ala
            260                 265                 270

Ser Tyr Tyr Glu Cys Gly His Gly Leu Ser Thr Gly Gly Tyr Gly Tyr
        275                 280                 285

Asp Ser Trp Gly Gln Gly Thr Leu Val Thr Val Ser Ser Gly Gly Gly
        290                 295                 300

Gly Ser Gly Gly Gly Ser Gly Gly Gly Ser Gly Gly Gly Gly Gly Gly
305                 310                 315                 320

Ser Gly Gly Gly Gly Ser Gly Gly Gly Ser Gly Gly Gly Ser
        325                 330                 335

Glu Val Gln Leu Val Glu Ser Gly Gly Ser Val Ala Gly Gly
            340                 345                 350

Ser Leu Arg Leu Ser Cys Ala Ala Ser Gly Tyr Thr Ile Gly Pro Tyr
        355                 360                 365

Cys Met Gly Trp Phe Arg Gln Ala Pro Gly Lys Glu Arg Glu Gly Val
        370                 375                 380

Ala Ala Ile Asn Met Gly Gly Gly Ile Thr Tyr Tyr Ala Asp Ser Val
385                 390                 395                 400

Lys Gly Arg Phe Thr Ile Ser Gln Asp Asn Ala Lys Asn Thr Val Tyr
                405                 410                 415

Leu Leu Met Asn Ser Leu Glu Pro Glu Asp Thr Ala Ile Tyr Tyr Cys
            420                 425                 430

Ala Ala Asp Ser Thr Ile Tyr Ala Ser Tyr Tyr Glu Cys Gly His Gly
        435                 440                 445

Leu Ser Thr Gly Gly Tyr Gly Tyr Asp Ser Trp Gly Gln Gly Thr Leu
        450                 455                 460

Val Thr Val Ser Ser Gly Gly Gly Gly Ser Gly Gly Gly Gly Ser Gly
465                 470                 475                 480

Gly Gly Ser Gly Gly Gly Gly Ser Gly Gly Gly Ser Gly Gly
            485                 490                 495

Gly Gly Ser Gly Gly Gly Ser Glu Val Gln Leu Val Glu Ser Gly
            500                 505                 510

Gly Gly Leu Val Gln Pro Gly Asn Ser Leu Arg Leu Ser Cys Ala Ala
        515                 520                 525

Ser Gly Phe Thr Phe Ser Ser Phe Gly Met Ser Trp Val Arg Gln Ala
        530                 535                 540

Pro Gly Lys Gly Leu Glu Trp Val Ser Ser Ile Ser Gly Ser Gly Ser
545                 550                 555                 560

Asp Thr Leu Tyr Ala Asp Ser Val Lys Gly Arg Phe Thr Ile Ser Arg
                565                 570                 575

Asp Asn Ala Lys Thr Thr Leu Tyr Leu Gln Met Asn Ser Leu Arg Pro
            580                 585                 590

Glu Asp Thr Ala Val Tyr Tyr Cys Thr Ile Gly Gly Ser Leu Ser Arg
        595                 600                 605
```

```
Ser Ser Gln Gly Thr Leu Val Thr Val Ser Ser
    610                 615

<210> SEQ ID NO 229
<211> LENGTH: 248
<212> TYPE: PRT
<213> ORGANISM: Artificial Sequence
<220> FEATURE:
<223> OTHER INFORMATION: Nanobody Chimera Sequence

<400> SEQUENCE: 229

Met Ser Val Pro Thr Gln Val Leu Gly Leu Leu Leu Leu Trp Leu Thr
1               5                   10                  15

Asp Ala Arg Cys Glu Val Gln Leu Val Glu Ser Gly Gly Gly Leu Val
            20                  25                  30

Gln Pro Gly Gly Ser Leu Arg Leu Ser Cys Ala Ala Ser Glu Thr Ile
        35                  40                  45

Phe Ser Ile Asp Ser Met Ala Trp Tyr Arg Gln Ala Pro Gly Lys Gln
    50                  55                  60

Arg Glu Leu Val Ala Ala Ile Thr Gly Gly Gly Ser Pro Asn Tyr Ala
65                  70                  75                  80

Asp Ser Val Lys Gly Arg Phe Thr Ile Ser Ser Asp Val Ala Lys Arg
                85                  90                  95

Thr Val Tyr Leu Gln Met Asn Ser Leu Lys Pro Glu Asp Thr Ala Val
            100                 105                 110

Tyr Tyr Cys Asn Ala Glu Gly Gln Ala Gly Trp Gly Thr Ala Leu Met
        115                 120                 125

Asp Tyr Trp Gly Lys Gly Thr Leu Val Thr Val Ser Ser Arg Thr Val
    130                 135                 140

Ala Ala Pro Ser Val Phe Ile Phe Pro Pro Ser Asp Glu Gln Leu Lys
145                 150                 155                 160

Ser Gly Thr Ala Ser Val Val Cys Leu Leu Asn Asn Phe Tyr Pro Arg
                165                 170                 175

Glu Ala Lys Val Gln Trp Lys Val Asp Asn Ala Leu Gln Ser Gly Asn
            180                 185                 190

Ser Gln Glu Ser Val Thr Glu Gln Asp Ser Lys Asp Ser Thr Tyr Ser
        195                 200                 205

Leu Ser Ser Thr Leu Thr Leu Ser Lys Ala Asp Tyr Glu Lys His Lys
    210                 215                 220

Val Tyr Ala Cys Glu Val Thr His Gln Gly Leu Ser Ser Pro Val Thr
225                 230                 235                 240

Lys Ser Phe Asn Arg Gly Glu Cys
                245

<210> SEQ ID NO 230
<211> LENGTH: 470
<212> TYPE: PRT
<213> ORGANISM: Artificial Sequence
<220> FEATURE:
<223> OTHER INFORMATION: Nanobody Chimera Sequence

<400> SEQUENCE: 230

Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Glu Thr Ile Phe
        35                  40                  45
```

Ser Ile Asp Ser Met Ala Trp Tyr Arg Gln Ala Pro Gly Lys Gln Arg
 50                  55                  60

Glu Leu Val Ala Ala Ile Thr Gly Gly Ser Pro Asn Tyr Ala Asp
 65                  70                  75                  80

Ser Val Lys Gly Arg Phe Thr Ile Ser Ser Asp Val Ala Lys Arg Thr
                 85                  90                  95

Val Tyr Leu Gln Met Asn Ser Leu Lys Pro Glu Asp Thr Ala Val Tyr
                100                 105                 110

Tyr Cys Asn Ala Glu Gly Gln Ala Gly Trp Gly Thr Ala Leu Met Asp
            115                 120                 125

Tyr Trp Gly Lys Gly Thr Leu Val Thr Val Ser Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

```
Ser Leu Ser Pro Gly Lys
465                 470

<210> SEQ ID NO 231
<211> LENGTH: 241
<212> TYPE: PRT
<213> ORGANISM: Homo sapiens

<400> SEQUENCE: 231

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val

<210> SEQ ID NO 232
<211> LENGTH: 228
<212> TYPE: PRT
<213> ORGANISM: Mus musculus

<400> SEQUENCE: 232

Met Gly Ala Trp Ala Met Leu Tyr Gly Val Ser Met Leu Cys Val Leu
1               5                   10                  15

Asp Leu Gly Gln Pro Ser Val Val Glu Glu Pro Gly Cys Gly Pro Gly
            20                  25                  30

Lys Val Gln Asn Gly Ser Gly Asn Thr Arg Cys Cys Ser Leu Tyr
        35                  40                  45

Ala Pro Gly Lys Glu Asp Cys Pro Lys Glu Arg Cys Ile Cys Val Thr
    50                  55                  60

Pro Glu Tyr His Cys Gly Asp Pro Gln Cys Lys Ile Cys Lys His Tyr
```

```
              65                  70                  75                  80
        Pro Cys Gln Pro Gly Gln Arg Val Glu Ser Gln Gly Asp Ile Val Phe
                         85                  90                  95

Gly Phe Arg Cys Val Ala Cys Ala Met Gly Thr Phe Ser Ala Gly Arg
                        100                 105                 110

Asp Gly His Cys Arg Leu Trp Thr Asn Cys Ser Gln Phe Gly Phe Leu
                        115                 120                 125

Thr Met Phe Pro Gly Asn Lys Thr His Asn Ala Val Cys Ile Pro Glu
                130                 135                 140

Pro Leu Pro Thr Glu Gln Tyr Gly His Leu Thr Val Ile Phe Leu Val
        145                 150                 155                 160

Met Ala Ala Cys Ile Phe Phe Leu Thr Thr Val Gln Leu Gly Leu His
                        165                 170                 175

Ile Trp Gln Leu Arg Arg Gln His Met Cys Pro Arg Glu Thr Gln Pro
                        180                 185                 190

Phe Ala Glu Val Gln Leu Ser Ala Glu Asp Ala Cys Ser Phe Gln Phe
                        195                 200                 205

Pro Glu Glu Glu Arg Gly Glu Gln Thr Glu Glu Lys Cys His Leu Gly
                        210                 215                 220

Gly Arg Trp Pro
        225

<210> SEQ ID NO 233
<211> LENGTH: 235
<212> TYPE: PRT
<213> ORGANISM: Macaca fascicularis

<400> SEQUENCE: 233

Met Cys Ala Cys Gly Thr Leu Cys Cys Leu Ala Leu Leu Cys Ala Ala
        1               5                   10                  15

Ser Leu Gly Gln Arg Pro Thr Gly Gly Pro Gly Cys Gly Pro Gly Arg
                        20                  25                  30

Leu Leu Leu Gly Thr Gly Lys Asp Ala Arg Cys Cys Arg Val His Pro
                        35                  40                  45

Thr Arg Cys Cys Arg Asp Tyr Gln Ser Glu Glu Cys Cys Ser Glu Trp
                50                  55                  60

Asp Cys Val Cys Val Gln Pro Glu Phe His Cys Gly Asn Pro Cys Cys
        65                  70                  75                  80

Thr Thr Cys Gln His His Pro Cys Pro Ser Gly Gln Gly Val Gln Pro
                        85                  90                  95

Gln Gly Lys Phe Ser Phe Gly Phe Arg Cys Val Asp Cys Ala Leu Gly
                        100                 105                 110

Thr Phe Ser Arg Gly His Asp Gly His Cys Lys Pro Trp Thr Asp Cys
                        115                 120                 125

Thr Gln Phe Gly Phe Leu Thr Val Phe Pro Gly Asn Lys Thr His Asn
                130                 135                 140

Ala Val Cys Val Pro Gly Ser Pro Ala Glu Pro Pro Gly Trp Leu
        145                 150                 155                 160

Thr Ile Val Leu Leu Ala Val Ala Ala Cys Val Leu Leu Thr Ser
                        165                 170                 175

Ala Gln Leu Gly Leu His Ile Trp Gln Leu Gly Ser Gln Pro Thr Gly
                        180                 185                 190

Pro Arg Glu Thr Gln Leu Leu Leu Glu Val Pro Pro Ser Thr Glu Asp
                        195                 200                 205
```

```
Ala Ser Ser Cys Gln Phe Pro Glu Glu Arg Gly Glu Arg Leu Ala
        210                 215                 220
Glu Glu Lys Gly Arg Leu Gly Asp Leu Trp Val
225                 230                 235

<210> SEQ ID NO 234
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 234

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 235
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 235

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 236
<211> LENGTH: 116
<212> TYPE: PRT
<213> ORGANISM: Artificial Sequence
```

<220> FEATURE:
<223> OTHER INFORMATION: Nanobody Sequence

<400> SEQUENCE: 236

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
            115

<210> SEQ ID NO 237
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 237

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
            115

<210> SEQ ID NO 238
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 238

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
                100                 105                 110

Val Ser Ser
        115

<210> SEQ ID NO 239
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 239

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
                100                 105                 110

Val Ser Ser Ala
        115

<210> SEQ ID NO 240
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 240

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 241
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 241

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 242
<211> LENGTH: 117
<212> TYPE: PRT
<213> ORGANISM: Artificial Sequence
<220> FEATURE:
<223> OTHER INFORMATION: Nanobody Sequence

<400> SEQUENCE: 242

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala
        115

<210> SEQ ID NO 243
<211> LENGTH: 118
<212> TYPE: PRT

<213> ORGANISM: Artificial Sequence
<220> FEATURE:
<223> OTHER INFORMATION: Nanobody Sequence

<400> SEQUENCE: 243

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala Ala
        115

<210> SEQ ID NO 244
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 244

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly
        115

<210> SEQ ID NO 245
<211> LENGTH: 117
<212> TYPE: PRT
<213> ORGANISM: Artificial Sequence
<220> FEATURE:
<223> OTHER INFORMATION: Nanobody Sequence

<400> SEQUENCE: 245

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

```
Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly
            115

<210> SEQ ID NO 246
<211> LENGTH: 118
<212> TYPE: PRT
<213> ORGANISM: Artificial Sequence
<220> FEATURE:
<223> OTHER INFORMATION: Nanobody Sequence

<400> SEQUENCE: 246

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly
            115

<210> SEQ ID NO 247
<211> LENGTH: 3
<212> TYPE: PRT
<213> ORGANISM: Artificial Sequence
<220> FEATURE:
<223> OTHER INFORMATION: Linker

<400> SEQUENCE: 247

Ala Ala Ala
1

<210> SEQ ID NO 248
<211> LENGTH: 5
<212> TYPE: PRT
<213> ORGANISM: Artificial Sequence
<220> FEATURE:
<223> OTHER INFORMATION: Linker

<400> SEQUENCE: 248

Gly Gly Gly Gly Ser
1               5
```

<210> SEQ ID NO 249
<211> LENGTH: 7
<212> TYPE: PRT
<213> ORGANISM: Artificial Sequence
<220> FEATURE:
<223> OTHER INFORMATION: Linker

<400> SEQUENCE: 249

Ser Gly Gly Ser Gly Gly Ser
1               5

<210> SEQ ID NO 250
<211> LENGTH: 9
<212> TYPE: PRT
<213> ORGANISM: Artificial Sequence
<220> FEATURE:
<223> OTHER INFORMATION: Linker

<400> SEQUENCE: 250

Gly Gly Gly Gly Cys Gly Gly Gly Ser
1               5

<210> SEQ ID NO 251
<211> LENGTH: 9
<212> TYPE: PRT
<213> ORGANISM: Artificial Sequence
<220> FEATURE:
<223> OTHER INFORMATION: Linker

<400> SEQUENCE: 251

Gly Gly Gly Gly Ser Gly Gly Gly Ser
1               5

<210> SEQ ID NO 252
<211> LENGTH: 10
<212> TYPE: PRT
<213> ORGANISM: Artificial Sequence
<220> FEATURE:
<223> OTHER INFORMATION: Linker

<400> SEQUENCE: 252

Gly Gly Gly Gly Ser Gly Gly Gly Gly Ser
1               5                   10

<210> SEQ ID NO 253
<211> LENGTH: 15
<212> TYPE: PRT
<213> ORGANISM: Artificial Sequence
<220> FEATURE:
<223> OTHER INFORMATION: Linker

<400> SEQUENCE: 253

Gly Gly Gly Gly Ser Gly Gly Gly Gly Ser Gly Gly Gly Gly Ser
1               5                   10                  15

<210> SEQ ID NO 254
<211> LENGTH: 18
<212> TYPE: PRT
<213> ORGANISM: Artificial Sequence
<220> FEATURE:
<223> OTHER INFORMATION: Linker

<400> SEQUENCE: 254

Gly Gly Gly Gly Ser Gly Gly Gly Ser Gly Gly Gly Gly Gly
1               5                   10                  15

Gly Ser

<210> SEQ ID NO 255
<211> LENGTH: 20
<212> TYPE: PRT
<213> ORGANISM: Artificial Sequence
<220> FEATURE:
<223> OTHER INFORMATION: Linker

<400> SEQUENCE: 255

Gly Gly Gly Gly Ser Gly Gly Gly Ser Gly Gly Gly Gly Ser Gly
1               5                   10                  15

Gly Gly Gly Ser
            20

<210> SEQ ID NO 256
<211> LENGTH: 25
<212> TYPE: PRT
<213> ORGANISM: Artificial Sequence
<220> FEATURE:
<223> OTHER INFORMATION: Linker

<400> SEQUENCE: 256

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 257
<211> LENGTH: 30
<212> TYPE: PRT
<213> ORGANISM: Artificial Sequence
<220> FEATURE:
<223> OTHER INFORMATION: Linker

<400> SEQUENCE: 257

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 258
<211> LENGTH: 35
<212> TYPE: PRT
<213> ORGANISM: Artificial Sequence
<220> FEATURE:
<223> OTHER INFORMATION: Linker

<400> SEQUENCE: 258

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 259
<211> LENGTH: 40
<212> TYPE: PRT
<213> ORGANISM: Artificial Sequence
<220> FEATURE:
<223> OTHER INFORMATION: Linker

<400> SEQUENCE: 259

Gly Gly Gly Gly Ser Gly Gly Gly Gly Ser Gly Gly Gly Gly Ser Gly

```
1               5                   10                  15
Gly Gly Gly Ser Gly Gly Gly Ser Gly Gly Gly Ser Gly Gly
            20                  25                  30

Gly Gly Ser Gly Gly Gly Gly Ser
        35                  40
```

<210> SEQ ID NO 260
<211> LENGTH: 15
<212> TYPE: PRT
<213> ORGANISM: Artificial Sequence
<220> FEATURE:
<223> OTHER INFORMATION: Linker

<400> SEQUENCE: 260

```
Glu Pro Lys Ser Cys Asp Lys Thr His Thr Cys Pro Pro Cys Pro
1               5                   10                  15
```

<210> SEQ ID NO 261
<211> LENGTH: 24
<212> TYPE: PRT
<213> ORGANISM: Artificial Sequence
<220> FEATURE:
<223> OTHER INFORMATION: Linker

<400> SEQUENCE: 261

```
Gly Gly Gly Gly Ser Gly Gly Gly Ser Glu Pro Lys Ser Cys Asp Lys
1               5                   10                  15

Thr His Thr Cys Pro Pro Cys Pro
            20
```

<210> SEQ ID NO 262
<211> LENGTH: 12
<212> TYPE: PRT
<213> ORGANISM: Artificial Sequence
<220> FEATURE:
<223> OTHER INFORMATION: Linker

<400> SEQUENCE: 262

```
Glu Pro Lys Thr Pro Lys Pro Gln Pro Ala Ala Ala
1               5                   10
```

<210> SEQ ID NO 263
<211> LENGTH: 62
<212> TYPE: PRT
<213> ORGANISM: Artificial Sequence
<220> FEATURE:
<223> OTHER INFORMATION: Linker

<400> SEQUENCE: 263

```
Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60
```

<210> SEQ ID NO 264
<211> LENGTH: 115
<212> TYPE: PRT
<213> ORGANISM: Artificial Sequence
<220> FEATURE:
<223> OTHER INFORMATION: Nanobody

<400> SEQUENCE: 264

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 265
<211> LENGTH: 116
<212> TYPE: PRT
<213> ORGANISM: Artificial Sequence
<220> FEATURE:
<223> OTHER INFORMATION: Nanobody

<400> SEQUENCE: 265

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 266
<211> LENGTH: 245
<212> TYPE: PRT
<213> ORGANISM: Artificial Sequence
<220> FEATURE:
<223> OTHER INFORMATION: Nanobody Chimera Sequence

<400> SEQUENCE: 266

Met Ser Val Pro Thr Gln Val Leu Gly Leu Leu Leu Leu Trp Leu Thr
1               5                   10                  15

Asp Ala Arg Cys Glu Val Gln Leu Val Glu Ser Gly Gly Gly Leu Val
            20                  25                  30

Gln Pro Gly Gly Ser Leu Arg Leu Ser Cys Ala Ala Ser Glu Thr Ile
        35                  40                  45

```
Phe Ser Ile Asp Ser Met Ala Trp Tyr Arg Gln Ala Pro Gly Lys Gln
     50                  55                  60

Arg Glu Leu Val Ala Ala Ile Thr Gly Gly Gly Ser Pro Asn Tyr Ala
 65                  70                  75                  80

Asp Ser Val Lys Gly Arg Phe Thr Ile Ser Ser Asp Val Ala Lys Arg
                 85                  90                  95

Thr Val Tyr Leu Gln Met Asn Ser Leu Lys Pro Glu Asp Thr Ala Val
            100                 105                 110

Tyr Tyr Cys Asn Ala Glu Gly Gln Ala Gly Trp Gly Thr Ala Leu Met
        115                 120                 125

Asp Tyr Trp Gly Lys Gly Thr Leu Val Thr Val Ser Ser Gln Pro Lys
    130                 135                 140

Ser Thr Pro Gln Leu Thr Val Phe Pro Pro Ser Thr Glu Glu Leu Gln
145                 150                 155                 160

Gly Asn Lys Ala Thr Leu Val Cys Leu Ile Ser Asp Phe Tyr Pro Ser
                165                 170                 175

Asp Val Glu Val Ala Trp Lys Ala Asn Gly Ala Pro Ile Ser Gln Gly
            180                 185                 190

Val Asp Thr Ala Asn Pro Thr Lys Gln Gly Asn Lys Tyr Ile Ala Ser
        195                 200                 205

Ser Phe Leu Arg Leu Thr Ala Glu Gln Trp Arg Ser Arg Asn Ser Phe
    210                 215                 220

Thr Cys Gln Val Thr His Glu Gly Asn Thr Val Glu Lys Ser Leu Ser
225                 230                 235                 240

Pro Ala Glu Cys Val
                245

<210> SEQ ID NO 267
<211> LENGTH: 473
<212> TYPE: PRT
<213> ORGANISM: Artificial Sequence
<220> FEATURE:
<223> OTHER INFORMATION: Nanobody Chimera Sequence

<400> SEQUENCE: 267

Met Glu Trp Ser Trp Val Phe Leu Phe Phe Leu Ser Val Thr Thr Gly
 1               5                  10                  15

Val His Ser Glu Val Gln Leu Val Glu Ser Gly Gly Gly Leu Val Gln
             20                  25                  30

Pro Gly Gly Ser Leu Arg Leu Ser Cys Ala Ala Ser Glu Thr Ile Phe
         35                  40                  45

Ser Ile Asp Ser Met Ala Trp Tyr Arg Gln Ala Pro Gly Lys Gln Arg
     50                  55                  60

Glu Leu Val Ala Ala Ile Thr Gly Gly Gly Ser Pro Asn Tyr Ala Asp
 65                  70                  75                  80

Ser Val Lys Gly Arg Phe Thr Ile Ser Ser Asp Val Ala Lys Arg Thr
                 85                  90                  95

Val Tyr Leu Gln Met Asn Ser Leu Lys Pro Glu Asp Thr Ala Val Tyr
            100                 105                 110

Tyr Cys Asn Ala Glu Gly Gln Ala Gly Trp Gly Thr Ala Leu Met Asp
        115                 120                 125

Tyr Trp Gly Lys Gly Thr Leu Val Thr Val Ser Ser Ala Gln Thr Thr
    130                 135                 140

Ala Pro Ser Val Tyr Pro Leu Ala Pro Gly Cys Gly Asp Thr Thr Ser
145                 150                 155                 160
```

```
Ser Thr Val Thr Leu Gly Cys Leu Val Lys Gly Tyr Phe Pro Glu Pro
            165                 170                 175

Val Thr Val Thr Trp Asn Ser Gly Ala Leu Ser Ser Asp Val His Thr
            180                 185                 190

Phe Pro Ala Val Leu Gln Ser Gly Leu Tyr Thr Leu Thr Ser Ser Val
            195                 200                 205

Thr Ser Ser Thr Trp Pro Ser Gln Thr Val Thr Cys Asn Val Ala His
            210                 215                 220

Pro Ala Ser Ser Thr Lys Val Asp Lys Val Glu Arg Arg Asn Gly
225                 230                 235                 240

Gly Ile Gly His Lys Cys Pro Thr Cys Pro Thr Cys His Lys Cys Pro
                245                 250                 255

Val Pro Glu Leu Leu Gly Gly Pro Ser Val Phe Ile Phe Pro Pro Lys
            260                 265                 270

Pro Lys Asp Ile Leu Leu Ile Ser Gln Asn Ala Lys Val Thr Cys Val
            275                 280                 285

Val Val Asp Val Ser Glu Glu Glu Pro Asp Val Gln Phe Ser Trp Phe
            290                 295                 300

Val Asn Asn Val Glu Val His Thr Ala Gln Thr Gln Pro Arg Glu Glu
305                 310                 315                 320

Gln Tyr Asn Ser Thr Phe Arg Val Val Ser Ala Leu Pro Ile Gln His
                325                 330                 335

Gln Asp Trp Met Ser Gly Lys Glu Phe Lys Cys Lys Val Asn Asn Lys
            340                 345                 350

Ala Leu Pro Ser Pro Ile Glu Lys Thr Ile Ser Lys Pro Lys Gly Leu
            355                 360                 365

Val Arg Lys Pro Gln Val Tyr Val Met Gly Pro Pro Thr Glu Gln Leu
            370                 375                 380

Thr Glu Gln Thr Val Ser Leu Thr Cys Leu Thr Ser Gly Phe Leu Pro
385                 390                 395                 400

Asn Asp Ile Gly Val Glu Trp Thr Ser Asn Gly His Ile Glu Lys Asn
                405                 410                 415

Tyr Lys Asn Thr Glu Pro Val Met Asp Ser Asp Gly Ser Phe Phe Met
            420                 425                 430

Tyr Ser Lys Leu Asn Val Glu Arg Ser Arg Trp Asp Ser Arg Ala Pro
            435                 440                 445

Phe Val Cys Ser Val Val His Glu Gly Leu His Asn His His Val Glu
            450                 455                 460

Lys Ser Ile Ser Arg Pro Pro Gly Lys
465                 470

<210> SEQ ID NO 268
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 268

Glu Val Gln Leu Val Glu Ser Gly Gly Gly Val Gln Pro Gly Gly
1               5                   10                  15

Ser Leu Arg Leu Ser Cys Thr Gly Ser Arg Ser Ile Phe Ser Thr Tyr
            20                  25                  30

Ala Met Ala Trp His Arg Gln Ala Pro Gly Lys Gln Arg Glu Leu Val
            35                  40                  45
```

Gly Phe Ile Tyr Trp Gly Gly Thr Thr Thr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Pro Glu Asp Thr Ala Leu Tyr Tyr Cys Asn
                85                  90                  95

Ile Tyr Gly Ser Tyr Ala Leu Pro Trp Gly Gln Gly Thr Leu Val Thr
                100                 105                 110

Val Ser Ser
        115

<210> SEQ ID NO 269
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 269

Glu Val Gln Leu Val Glu Ser Gly Gly Gly Val Val Gln Pro Gly Gly
1               5                   10                  15

Ser Leu Arg Leu Ser Cys Ala Ala Ser Gly Ser Ile Phe Ser Ile Asp
                20                  25                  30

Ser Met Gly Trp Tyr Arg Gln Ala Pro Gly Lys Gln Arg Glu Leu Val
            35                  40                  45

Ala Ala Ile Thr Ser Ser Thr Asn Tyr Ala Asp Ser Val Lys Gly Arg
        50                  55                  60

Phe Thr Ile Ser Arg Asp Asn Ser Lys Asn Thr Val Tyr Leu Gln Met
65                  70                  75                  80

Asn Ser Leu Arg Pro Glu Asp Thr Ala Leu Tyr Tyr Cys Asn Leu Glu
                85                  90                  95

Gly Gln Ala Gly Trp Gly Thr Ala Leu Ile Asn Tyr Trp Gly Gln Gly
                100                 105                 110

Thr Leu Val Thr Val Ser Ser
        115

<210> SEQ ID NO 270
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 270

Glu Val Gln Leu Val Glu Ser Gly Gly Gly Val Val Gln Pro Gly Gly
1               5                   10                  15

Ser Leu Arg Leu Ser Cys Ala Ala Ser Gly Ser Val Phe Ser Ile Asn
                20                  25                  30

Asp Met Gly Trp Phe Arg Gln Ala Pro Gly Lys Gln Arg Glu Leu Val
            35                  40                  45

Ala Asp Ile Ile Ser Arg Gly Val Thr Asn Tyr Ala Asp Ser Val Lys
        50                  55                  60

Gly Arg Phe Thr Ile Ser Gly Asp Pro Ser Lys Asn Thr Val Tyr Leu
65                  70                  75                  80

Gln Met Asn Ser Leu Arg Pro Glu Asp Thr Ala Leu Tyr Tyr Cys Asn
                85                  90                  95

Ala His Ile Ser Thr Gly Trp Gly Arg Pro His Asn Asn Tyr Trp Gly

Gln Gly Thr Leu Val Thr Val Ser Ser
         115                 120

<210> SEQ ID NO 271
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 271

Glu Val Gln Leu Val Glu Ser Gly Gly Gly Val Val Gln Pro Gly Gly
1               5                   10                  15

Ser Leu Arg Leu Ser Cys Ala Ala Ser Glu Thr Ile Phe Ser Ile Asp
            20                  25                  30

Ser Met Ala Trp Tyr Arg Gln Ala Pro Gly Lys Gln Arg Glu Leu Val
        35                  40                  45

Ala Ala Ile Thr Gly Gly Gly Ser Pro Asn Tyr Ala Asp Ser Val Lys
    50                  55                  60

Gly Arg Phe Thr Ile Ser Ser Asp Val Ser Lys Arg Thr Val Tyr Leu
65                  70                  75                  80

Gln Met Asn Ser Leu Arg Pro Glu Asp Thr Ala Leu Tyr Tyr Cys Asn
                85                  90                  95

Ala Glu Gly Gln Ala Gly Trp Gly Thr Ala Leu Met Asp Tyr Trp Gly
            100                 105                 110

Gln Gly Thr Leu Val Thr Val Ser Ser
         115                 120

<210> SEQ ID NO 272
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 272

Glu Val Gln Leu Val Glu Ser Gly Gly Gly Val Val Gln Pro Gly Gly
1               5                   10                  15

Ser Leu Arg Leu Ser Cys Ala Ala Ser Glu Thr Ile Phe Ser Ile Asp
            20                  25                  30

Ser Met Ala Trp Tyr Arg Gln Ala Pro Gly Lys Gln Arg Glu Leu Val
        35                  40                  45

Ala Ala Ile Thr Gly Gly Gly Ser Pro Asn Tyr Ala Asp Ser Val Lys
    50                  55                  60

Gly Arg Phe Thr Ile Ser Ser Asp Val Ser Lys Arg Thr Val Tyr Leu
65                  70                  75                  80

Gln Met Asn Ser Leu Arg Pro Glu Asp Thr Ala Leu Tyr Tyr Cys Asn
                85                  90                  95

Ala Glu Gly Gln Ala Gly Trp Gly Thr Ala Leu Leu Asp Tyr Trp Gly
            100                 105                 110

Gln Gly Thr Leu Val Thr Val Ser Ser
         115                 120

<210> SEQ ID NO 273
<211> LENGTH: 121
<212> TYPE: PRT
<213> ORGANISM: Artificial Sequence
<220> FEATURE:

<223> OTHER INFORMATION: Nanobody Sequence

<400> SEQUENCE: 273

Glu Val Gln Leu Val Glu Ser Gly Gly Gly Val Val Gln Pro Gly Gly
1               5                   10                  15

Ser Leu Arg Leu Ser Cys Ala Ala Ser Glu Thr Ile Phe Ser Ile Asp
            20                  25                  30

Ser Met Ala Trp Tyr Arg Gln Ala Pro Gly Lys Gln Arg Glu Leu Val
        35                  40                  45

Ala Ala Ile Thr Gly Gly Gly Ser Pro Asn Tyr Ala Asp Ser Val Lys
    50                  55                  60

Gly Arg Phe Thr Ile Ser Ser Asp Val Ser Lys Arg Thr Val Tyr Leu
65                  70                  75                  80

Gln Met Asn Ser Leu Arg Pro Glu Asp Thr Ala Leu Tyr Tyr Cys Asn
                85                  90                  95

Ala Glu Gly Gln Ala Gly Trp Gly Thr Ala Leu Lys Asp Tyr Trp Gly
            100                 105                 110

Gln Gly Thr Leu Val Thr Val Ser Ser
        115                 120

<210> SEQ ID NO 274
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 274

Glu Val Gln Leu Val Glu Ser Gly Gly Gly Val Val Gln Pro Gly Gly
1               5                   10                  15

Ser Leu Arg Leu Ser Cys Ala Ala Ser Glu Thr Ile Phe Ser Ile Asp
            20                  25                  30

Ser Met Ala Trp Tyr Arg Gln Ala Pro Gly Lys Gln Arg Glu Leu Val
        35                  40                  45

Ala Ala Ile Thr Gly Gly Gly Ser Pro Asn Tyr Ala Asp Ser Val Lys
    50                  55                  60

Gly Arg Phe Thr Ile Ser Ser Asp Val Ser Lys Arg Thr Val Tyr Leu
65                  70                  75                  80

Gln Met Asn Ser Leu Arg Pro Glu Asp Thr Ala Leu Tyr Tyr Cys Asn
                85                  90                  95

Ala Glu Gly Gln Ala Gly Trp Gly Thr Ala Leu Arg Asp Tyr Trp Gly
            100                 105                 110

Gln Gly Thr Leu Val Thr Val Ser Ser
        115                 120

<210> SEQ ID NO 275
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 275

Glu Val Gln Leu Val Glu Ser Gly Gly Gly Val Val Gln Pro Gly Gly
1               5                   10                  15

Ser Leu Arg Leu Ser Cys Ala Ala Ser Glu Thr Ile Phe Ser Ile Asp
            20                  25                  30

Ser Met Ala Trp Tyr Arg Gln Ala Pro Gly Lys Gln Arg Glu Leu Val

```
                35                  40                  45
Ala Ala Ile Thr Gly Gly Ser Pro Asn Tyr Ala Asp Ser Val Lys
        50                  55                  60

Gly Arg Phe Thr Ile Ser Ser Asp Val Ser Lys Arg Thr Val Tyr Leu
65                  70                  75                  80

Gln Met Asn Ser Leu Arg Pro Glu Asp Thr Ala Leu Tyr Tyr Cys Asn
                85                  90                  95

Ala Glu Gly Gln Ala Gly Trp Gly Thr Ala Leu Gln Ala Tyr Trp Gly
            100                 105                 110

Gln Gly Thr Leu Val Thr Val Ser Ser
            115                 120
```

<210> SEQ ID NO 276
<211> LENGTH: 25
<212> TYPE: PRT
<213> ORGANISM: Artificial Sequence
<220> FEATURE:
<223> OTHER INFORMATION: FR1

<400> SEQUENCE: 276

```
Glu Val Gln Leu Val Glu Ser Gly Gly Gly Val Val Gln Pro Gly Gly
1               5                   10                  15

Ser Leu Arg Leu Ser Cys Thr Gly Ser
            20                  25
```

<210> SEQ ID NO 277
<211> LENGTH: 39
<212> TYPE: PRT
<213> ORGANISM: Artificial Sequence
<220> FEATURE:
<223> OTHER INFORMATION: FR3

<400> SEQUENCE: 277

```
Tyr Ala Asp Ser Val Lys Gly Arg Phe Thr Ile Ser Arg Asp Asn Ser
1               5                   10                  15

Lys Asn Thr Leu Tyr Leu Gln Met Asn Ser Leu Arg Pro Glu Asp Thr
            20                  25                  30

Ala Leu Tyr Tyr Cys Asn Ile
        35
```

<210> SEQ ID NO 278
<211> LENGTH: 25
<212> TYPE: PRT
<213> ORGANISM: Artificial Sequence
<220> FEATURE:
<223> OTHER INFORMATION: FR1

<400> SEQUENCE: 278

```
Glu Val Gln Leu Val Glu Ser Gly Gly Gly Val Val Gln Pro Gly Gly
1               5                   10                  15

Ser Leu Arg Leu Ser Cys Ala Ala Ser
            20                  25
```

<210> SEQ ID NO 279
<211> LENGTH: 39
<212> TYPE: PRT
<213> ORGANISM: Artificial Sequence
<220> FEATURE:
<223> OTHER INFORMATION: FR3

<400> SEQUENCE: 279

```
Tyr Ala Asp Ser Val Lys Gly Arg Phe Thr Ile Ser Arg Asp Asn Ser
1               5                   10                  15
```

```
                 1               5                   10                  15
Lys Asn Thr Val Tyr Leu Gln Met Asn Ser Leu Arg Pro Glu Asp Thr
                20                  25                  30
Ala Leu Tyr Tyr Cys Asn Leu
        35

<210> SEQ ID NO 280
<211> LENGTH: 39
<212> TYPE: PRT
<213> ORGANISM: Artificial Sequence
<220> FEATURE:
<223> OTHER INFORMATION: FR3

<400> SEQUENCE: 280

Tyr Ala Asp Ser Val Lys Gly Arg Phe Thr Ile Ser Gly Asp Pro Ser
1               5                   10                  15
Lys Asn Thr Val Tyr Leu Gln Met Asn Ser Leu Arg Pro Glu Asp Thr
                20                  25                  30
Ala Leu Tyr Tyr Cys Asn Ala
        35

<210> SEQ ID NO 281
<211> LENGTH: 39
<212> TYPE: PRT
<213> ORGANISM: Artificial Sequence
<220> FEATURE:
<223> OTHER INFORMATION: FR3

<400> SEQUENCE: 281

Tyr Ala Asp Ser Val Lys Gly Arg Phe Thr Ile Ser Ser Asp Val Ser
1               5                   10                  15
Lys Arg Thr Val Tyr Leu Gln Met Asn Ser Leu Arg Pro Glu Asp Thr
                20                  25                  30
Ala Leu Tyr Tyr Cys Asn Ala
        35

<210> SEQ ID NO 282
<211> LENGTH: 13
<212> TYPE: PRT
<213> ORGANISM: Artificial Sequence
<220> FEATURE:
<223> OTHER INFORMATION: CDR3

<400> SEQUENCE: 282

Glu Gly Gln Ala Gly Trp Gly Thr Ala Leu Lys Asp Tyr
1               5                   10

<210> SEQ ID NO 283
<211> LENGTH: 13
<212> TYPE: PRT
<213> ORGANISM: Artificial Sequence
<220> FEATURE:
<223> OTHER INFORMATION: CDR3

<400> SEQUENCE: 283

Glu Gly Gln Ala Gly Trp Gly Thr Ala Leu Arg Asp Tyr
1               5                   10

<210> SEQ ID NO 284
<211> LENGTH: 13
<212> TYPE: PRT
<213> ORGANISM: Artificial Sequence
<220> FEATURE:
<223> OTHER INFORMATION: CDR3
```

<400> SEQUENCE: 284

Glu Gly Gln Ala Gly Trp Gly Thr Ala Leu Gln Asp Tyr
1               5                   10

<210> SEQ ID NO 285
<211> LENGTH: 532
<212> TYPE: PRT
<213> ORGANISM: Artificial Sequence
<220> FEATURE:
<223> OTHER INFORMATION: Nanobody Sequence

<400> SEQUENCE: 285

Asp Val Gln Leu Val Glu Ser Gly Gly Gly Val Gln Pro Gly Gly
1               5                   10                  15

Ser Leu Arg Leu Ser Cys Ala Ala Ser Glu Thr Ile Phe Ser Ile Asp
            20                  25                  30

Ser Met Ala Trp Tyr Arg Gln Ala Pro Gly Lys Gln Arg Glu Leu Val
        35                  40                  45

Ala Ala Ile Thr Gly Gly Ser Pro Asn Tyr Ala Asp Ser Val Lys
    50                  55                  60

Gly Arg Phe Thr Ile Ser Ser Asp Val Ser Lys Arg Thr Val Tyr Leu
65                  70                  75                  80

Gln Met Asn Ser Leu Arg Pro Glu Asp Thr Ala Leu Tyr Tyr Cys Asn
                85                  90                  95

Ala Glu Gly Gln Ala Gly Trp Gly Thr Ala Leu Leu Asp Tyr Trp Gly
            100                 105                 110

Gln Gly Thr Leu Val Thr Val Ser Ser Gly Gly Gly Ser Gly Gly
        115                 120                 125

Gly Ser Glu Val Gln Leu Val Glu Ser Gly Gly Gly Val Val Gln Pro
    130                 135                 140

Gly Gly Ser Leu Arg Leu Ser Cys Ala Ala Ser Glu Thr Ile Phe Ser
145                 150                 155                 160

Ile Asp Ser Met Ala Trp Tyr Arg Gln Ala Pro Gly Lys Gln Arg Glu
                165                 170                 175

Leu Val Ala Ala Ile Thr Gly Gly Ser Pro Asn Tyr Ala Asp Ser
            180                 185                 190

Val Lys Gly Arg Phe Thr Ile Ser Ser Asp Val Ser Lys Arg Thr Val
        195                 200                 205

Tyr Leu Gln Met Asn Ser Leu Arg Pro Glu Asp Thr Ala Leu Tyr Tyr
    210                 215                 220

Cys Asn Ala Glu Gly Gln Ala Gly Trp Gly Thr Ala Leu Leu Asp Tyr
225                 230                 235                 240

Trp Gly Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Val Val
            260                 265                 270

Gln Pro Gly Gly Ser Leu Arg Leu Ser Cys Ala Ala Ser Glu Thr Ile
        275                 280                 285

Phe Ser Ile Asp Ser Met Ala Trp Tyr Arg Gln Ala Pro Gly Lys Gln
    290                 295                 300

Arg Glu Leu Val Ala Ala Ile Thr Gly Gly Ser Pro Asn Tyr Ala
305                 310                 315                 320

Asp Ser Val Lys Gly Arg Phe Thr Ile Ser Ser Asp Val Ser Lys Arg
                325                 330                 335

```
Thr Val Tyr Leu Gln Met Asn Ser Leu Arg Pro Glu Asp Thr Ala Leu
                340                 345                 350

Tyr Tyr Cys Asn Ala Glu Gly Gln Ala Gly Trp Gly Thr Ala Leu Leu
            355                 360                 365

Asp Tyr Trp Gly Gln Gly Thr Leu Val Thr Val Ser Ser Gly Gly Gly
    370                 375                 380

Gly Ser Gly Gly Gly Ser Gly Gly Gly Ser Gly Gly Gly
385                 390                 395                 400

Ser Gly Gly Gly Ser Gly Gly Gly Ser Gly Gly Gly Ser
                405                 410                 415

Glu Val Gln Leu Val Glu Ser Gly Gly Val Val Gln Pro Gly Gly
            420                 425                 430

Ser Leu Arg Leu Ser Cys Ala Ala Ser Gly Phe Thr Phe Arg Ser Phe
        435                 440                 445

Gly Met Ser Trp Val Arg Gln Ala Pro Gly Lys Gly Pro Glu Trp Val
        450                 455                 460

Ser Ser Ile Ser Gly Ser Gly Ser Asp Thr Leu Tyr Ala Asp Ser Val
465                 470                 475                 480

Lys Gly Arg Phe Thr Ile Ser Arg Asp Asn Ser Lys Asn Thr Leu Tyr
                485                 490                 495

Leu Gln Met Asn Ser Leu Arg Pro Glu Asp Thr Ala Leu Tyr Tyr Cys
            500                 505                 510

Thr Ile Gly Gly Ser Leu Ser Arg Ser Ser Gln Gly Thr Leu Val Thr
        515                 520                 525

Val Ser Ser Ala
    530

<210> SEQ ID NO 286
<211> LENGTH: 526
<212> TYPE: PRT
<213> ORGANISM: Artificial Sequence
<220> FEATURE:
<223> OTHER INFORMATION: Nanobody Sequence

<400> SEQUENCE: 286

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Phe Ser Ile Asp
            20                  25                  30

Ser Met Gly Trp Tyr Arg Gln Ala Pro Gly Lys Gln Arg Glu Leu Val
        35                  40                  45

Ala Ala Ile Thr Ser Ser Thr Asn Tyr Ala Asp Ser Val Lys Gly Arg
    50                  55                  60

Phe Thr Ile Ser Arg Asp Asn Ser Lys Asn Thr Val Tyr Leu Gln Met
65                  70                  75                  80

Asn Ser Leu Arg Pro Glu Asp Thr Ala Leu Tyr Tyr Cys Asn Leu Glu
            85                  90                  95

Gly Gln Ala Gly Trp Gly Thr Ala Leu Ile Asn Tyr Trp Gly Gln Gly
        100                 105                 110

Thr Leu Val Thr Val Ser Ser Gly Gly Gly Ser Gly Gly Gly Ser
        115                 120                 125

Glu Val Gln Leu Val Glu Ser Gly Gly Gly Val Val Gln Pro Gly Gly
        130                 135                 140

Ser Leu Arg Leu Ser Cys Ala Ala Ser Gly Ser Ile Phe Ser Ile Asp
145                 150                 155                 160
```

Ser Met Gly Trp Tyr Arg Gln Ala Pro Gly Lys Gln Arg Glu Leu Val
            165                 170                 175

Ala Ala Ile Thr Ser Ser Thr Asn Tyr Ala Asp Ser Val Lys Gly Arg
            180                 185                 190

Phe Thr Ile Ser Arg Asp Asn Ser Lys Asn Thr Val Tyr Leu Gln Met
            195                 200                 205

Asn Ser Leu Arg Pro Glu Asp Thr Ala Leu Tyr Tyr Cys Asn Leu Glu
            210                 215                 220

Gly Gln Ala Gly Trp Gly Thr Ala Leu Ile Asn Tyr Trp Gly Gln Gly
225                 230                 235                 240

Thr Leu Val Thr Val Ser Ser Gly Gly Gly Ser Gly Gly Gly Ser
            245                 250                 255

Glu Val Gln Leu Val Glu Ser Gly Gly Gly Val Val Gln Pro Gly Gly
            260                 265                 270

Ser Leu Arg Leu Ser Cys Ala Ala Ser Gly Ser Ile Phe Ser Ile Asp
            275                 280                 285

Ser Met Gly Trp Tyr Arg Gln Ala Pro Gly Lys Gln Arg Glu Leu Val
            290                 295                 300

Ala Ala Ile Thr Ser Ser Thr Asn Tyr Ala Asp Ser Val Lys Gly Arg
305                 310                 315                 320

Phe Thr Ile Ser Arg Asp Asn Ser Lys Asn Thr Val Tyr Leu Gln Met
            325                 330                 335

Asn Ser Leu Arg Pro Glu Asp Thr Ala Leu Tyr Tyr Cys Asn Leu Glu
            340                 345                 350

Gly Gln Ala Gly Trp Gly Thr Ala Leu Ile Asn Tyr Trp Gly Gln Gly
            355                 360                 365

Thr Leu Val Thr Val Ser Ser Gly Gly Gly Gly Ser Gly Gly Gly Gly
            370                 375                 380

Ser Gly Gly Gly Gly Ser Gly Gly Gly Ser Gly Gly Gly Gly Ser
385                 390                 395                 400

Gly Gly Gly Gly Ser Gly Gly Gly Ser Glu Val Gln Leu Val Glu
            405                 410                 415

Ser Gly Gly Gly Val Val Gln Pro Gly Gly Ser Leu Arg Leu Ser Cys
            420                 425                 430

Ala Ala Ser Gly Phe Thr Phe Arg Ser Phe Gly Met Ser Trp Val Arg
            435                 440                 445

Gln Ala Pro Gly Lys Gly Pro Glu Trp Val Ser Ser Ile Ser Gly Ser
            450                 455                 460

Gly Ser Asp Thr Leu Tyr Ala Asp Ser Val Lys Gly Arg Phe Thr Ile
465                 470                 475                 480

Ser Arg Asp Asn Ser Lys Asn Thr Leu Tyr Leu Gln Met Asn Ser Leu
            485                 490                 495

Arg Pro Glu Asp Thr Ala Leu Tyr Tyr Cys Thr Ile Gly Gly Ser Leu
            500                 505                 510

Ser Arg Ser Ser Gln Gly Thr Leu Val Thr Val Ser Ser Ala
            515                 520                 525

<210> SEQ ID NO 287
<211> LENGTH: 662
<212> TYPE: PRT
<213> ORGANISM: Artificial Sequence
<220> FEATURE:
<223> OTHER INFORMATION: Nanobody Sequence

<400> SEQUENCE: 287

```
Asp Val Gln Leu Val Glu Ser Gly Gly Val Gln Pro Gly Gly
  1               5                  10                 15

Ser Leu Arg Leu Ser Cys Ala Ala Ser Glu Thr Ile Phe Ser Ile Asp
             20                  25                  30

Ser Met Ala Trp Tyr Arg Gln Ala Pro Gly Lys Gln Arg Glu Leu Val
         35                  40                  45

Ala Ala Ile Thr Gly Gly Ser Pro Asn Tyr Ala Asp Ser Val Lys
 50                  55                  60

Gly Arg Phe Thr Ile Ser Ser Asp Val Ser Arg Thr Val Tyr Leu
 65                  70                  75                  80

Gln Met Asn Ser Leu Arg Pro Glu Asp Thr Ala Leu Tyr Tyr Cys Asn
             85                  90                  95

Ala Glu Gly Gln Ala Gly Trp Gly Thr Ala Leu Leu Asp Tyr Trp Gly
            100                 105                 110

Gln Gly Thr Leu Val Thr Val Ser Gly Gly Gly Ser Gly Gly
            115                 120                 125

Gly Ser Glu Val Gln Leu Val Glu Ser Gly Gly Val Val Gln Pro
            130                 135                 140

Gly Gly Ser Leu Arg Leu Ser Cys Ala Ala Ser Glu Thr Ile Phe Ser
145                 150                 155                 160

Ile Asp Ser Met Ala Trp Tyr Arg Gln Ala Pro Gly Lys Gln Arg Glu
            165                 170                 175

Leu Val Ala Ala Ile Thr Gly Gly Ser Pro Asn Tyr Ala Asp Ser
            180                 185                 190

Val Lys Gly Arg Phe Thr Ile Ser Ser Asp Val Ser Lys Arg Thr Val
            195                 200                 205

Tyr Leu Gln Met Asn Ser Leu Arg Pro Glu Asp Thr Ala Leu Tyr Tyr
            210                 215                 220

Cys Asn Ala Glu Gly Gln Ala Gly Trp Gly Thr Ala Leu Leu Asp Tyr
225                 230                 235                 240

Trp Gly Gln Gly Thr Leu Val Thr Val Ser Ser Gly Gly Gly Ser
            245                 250                 255

Gly Gly Gly Ser Glu Val Gln Leu Val Glu Ser Gly Gly Val Val
            260                 265                 270

Gln Pro Gly Gly Ser Leu Arg Leu Ser Cys Ala Ala Ser Glu Thr Ile
            275                 280                 285

Phe Ser Ile Asp Ser Met Ala Trp Tyr Arg Gln Ala Pro Gly Lys Gln
            290                 295                 300

Arg Glu Leu Val Ala Ala Ile Thr Gly Gly Ser Pro Asn Tyr Ala
305                 310                 315                 320

Asp Ser Val Lys Gly Arg Phe Thr Ile Ser Ser Asp Val Ser Lys Arg
            325                 330                 335

Thr Val Tyr Leu Gln Met Asn Ser Leu Arg Pro Glu Asp Thr Ala Leu
            340                 345                 350

Tyr Tyr Cys Asn Ala Glu Gly Gln Ala Gly Trp Gly Thr Ala Leu Leu
            355                 360                 365

Asp Tyr Trp Gly Gln Gly Thr Leu Val Thr Val Ser Ser Gly Gly Gly
            370                 375                 380

Gly Ser Gly Gly Gly Ser Glu Val Gln Leu Val Glu Ser Gly Gly
385                 390                 395                 400

Val Val Gln Pro Gly Gly Ser Leu Arg Leu Ser Cys Ala Ala Ser Glu
            405                 410                 415

Thr Ile Phe Ser Ile Asp Ser Met Ala Trp Tyr Arg Gln Ala Pro Gly
```

```
                420                 425                 430
Lys Gln Arg Glu Leu Val Ala Ala Ile Thr Gly Gly Gly Ser Pro Asn
            435                 440                 445

Tyr Ala Asp Ser Val Lys Gly Arg Phe Thr Ile Ser Ser Asp Val Ser
        450                 455                 460

Lys Arg Thr Val Tyr Leu Gln Met Asn Ser Leu Arg Pro Glu Asp Thr
465                 470                 475                 480

Ala Leu Tyr Tyr Cys Asn Ala Glu Gly Gln Ala Gly Trp Gly Thr Ala
            485                 490                 495

Leu Leu Asp Tyr Trp Gly Gln Gly Thr Leu Val Thr Val Ser Ser Gly
        500                 505                 510

Gly Gly Gly Ser Gly Gly Gly Ser Gly Gly Gly Ser Gly Gly
            515                 520                 525

Gly Gly Ser Gly Gly Gly Ser Gly Gly Gly Ser Gly Gly Gly
        530                 535                 540

Gly Ser Glu Val Gln Leu Val Glu Ser Gly Gly Val Val Gln Pro
545                 550                 555                 560

Gly Gly Ser Leu Arg Leu Ser Cys Ala Ala Ser Gly Phe Thr Phe Arg
            565                 570                 575

Ser Phe Gly Met Ser Trp Val Arg Gln Ala Pro Gly Lys Gly Pro Glu
        580                 585                 590

Trp Val Ser Ser Ile Ser Gly Ser Gly Ser Asp Thr Leu Tyr Ala Asp
            595                 600                 605

Ser Val Lys Gly Arg Phe Thr Ile Ser Arg Asp Asn Ser Lys Asn Thr
        610                 615                 620

Leu Tyr Leu Gln Met Asn Ser Leu Arg Pro Glu Asp Thr Ala Leu Tyr
625                 630                 635                 640

Tyr Cys Thr Ile Gly Gly Ser Leu Ser Arg Ser Ser Gln Gly Thr Leu
            645                 650                 655

Val Thr Val Ser Ser Ala
            660

<210> SEQ ID NO 288
<211> LENGTH: 792
<212> TYPE: PRT
<213> ORGANISM: Artificial Sequence
<220> FEATURE:
<223> OTHER INFORMATION: Nanobody Sequence

<400> SEQUENCE: 288

Asp Val Gln Leu Val Glu Ser Gly Gly Gly Val Val Gln Pro Gly Gly
1               5                   10                  15

Ser Leu Arg Leu Ser Cys Ala Ala Ser Glu Thr Ile Phe Ser Ile Asp
            20                  25                  30

Ser Met Ala Trp Tyr Arg Gln Ala Pro Gly Lys Gln Arg Glu Leu Val
        35                  40                  45

Ala Ala Ile Thr Gly Gly Gly Ser Pro Asn Tyr Ala Asp Ser Val Lys
    50                  55                  60

Gly Arg Phe Thr Ile Ser Ser Asp Val Ser Lys Arg Thr Val Tyr Leu
65                  70                  75                  80

Gln Met Asn Ser Leu Arg Pro Glu Asp Thr Ala Leu Tyr Tyr Cys Asn
            85                  90                  95

Ala Glu Gly Gln Ala Gly Trp Gly Thr Ala Leu Leu Asp Tyr Trp Gly
        100                 105                 110

Gln Gly Thr Leu Val Thr Val Ser Ser Gly Gly Gly Gly Ser Gly Gly
```

```
                115                 120                 125
Gly Ser Glu Val Gln Leu Val Glu Ser Gly Gly Val Val Gln Pro
    130                 135                 140
Gly Gly Ser Leu Arg Leu Ser Cys Ala Ala Ser Glu Thr Ile Phe Ser
145                 150                 155                 160
Ile Asp Ser Met Ala Trp Tyr Arg Gln Ala Pro Gly Lys Gln Arg Glu
                165                 170                 175
Leu Val Ala Ala Ile Thr Gly Gly Ser Pro Asn Tyr Ala Asp Ser
                180                 185                 190
Val Lys Gly Arg Phe Thr Ile Ser Ser Asp Val Ser Lys Arg Thr Val
                195                 200                 205
Tyr Leu Gln Met Asn Ser Leu Arg Pro Glu Asp Thr Ala Leu Tyr Tyr
    210                 215                 220
Cys Asn Ala Glu Gly Gln Ala Gly Trp Gly Thr Ala Leu Leu Asp Tyr
225                 230                 235                 240
Trp Gly Gln Gly Thr Leu Val Thr Val Ser Ser Gly Gly Gly Gly Ser
                245                 250                 255
Gly Gly Gly Ser Glu Val Gln Leu Val Glu Ser Gly Gly Val Val
                260                 265                 270
Gln Pro Gly Gly Ser Leu Arg Leu Ser Cys Ala Ala Ser Glu Thr Ile
    275                 280                 285
Phe Ser Ile Asp Ser Met Ala Trp Tyr Arg Gln Ala Pro Gly Lys Gln
    290                 295                 300
Arg Glu Leu Val Ala Ala Ile Thr Gly Gly Ser Pro Asn Tyr Ala
305                 310                 315                 320
Asp Ser Val Lys Gly Arg Phe Thr Ile Ser Ser Asp Val Ser Lys Arg
                325                 330                 335
Thr Val Tyr Leu Gln Met Asn Ser Leu Arg Pro Glu Asp Thr Ala Leu
                340                 345                 350
Tyr Tyr Cys Asn Ala Glu Gly Gln Ala Gly Trp Gly Thr Ala Leu Leu
    355                 360                 365
Asp Tyr Trp Gly Gln Gly Thr Leu Val Thr Val Ser Ser Gly Gly Gly
    370                 375                 380
Gly Ser Gly Gly Gly Ser Glu Val Gln Leu Val Glu Ser Gly Gly Gly
385                 390                 395                 400
Val Val Gln Pro Gly Gly Ser Leu Arg Leu Ser Cys Ala Ala Ser Glu
                405                 410                 415
Thr Ile Phe Ser Ile Asp Ser Met Ala Trp Tyr Arg Gln Ala Pro Gly
                420                 425                 430
Lys Gln Arg Glu Leu Val Ala Ala Ile Thr Gly Gly Ser Pro Asn
    435                 440                 445
Tyr Ala Asp Ser Val Lys Gly Arg Phe Thr Ile Ser Ser Asp Val Ser
    450                 455                 460
Lys Arg Thr Val Tyr Leu Gln Met Asn Ser Leu Arg Pro Glu Asp Thr
465                 470                 475                 480
Ala Leu Tyr Tyr Cys Asn Ala Glu Gly Gln Ala Gly Trp Gly Thr Ala
                485                 490                 495
Leu Leu Asp Tyr Trp Gly Gln Gly Thr Leu Val Thr Val Ser Ser Gly
                500                 505                 510
Gly Gly Gly Ser Gly Gly Gly Ser Glu Val Gln Leu Val Glu Ser Gly
    515                 520                 525
Gly Gly Val Val Gln Pro Gly Gly Ser Leu Arg Leu Ser Cys Ala Ala
    530                 535                 540
```

```
Ser Glu Thr Ile Phe Ser Ile Asp Ser Met Ala Trp Tyr Arg Gln Ala
545                 550                 555                 560

Pro Gly Lys Gln Arg Glu Leu Val Ala Ala Ile Thr Gly Gly Gly Ser
            565                 570                 575

Pro Asn Tyr Ala Asp Ser Val Lys Gly Arg Phe Thr Ile Ser Ser Asp
            580                 585                 590

Val Ser Lys Arg Thr Val Tyr Leu Gln Met Asn Ser Leu Arg Pro Glu
        595                 600                 605

Asp Thr Ala Leu Tyr Tyr Cys Asn Ala Glu Gly Gln Ala Gly Trp Gly
    610                 615                 620

Thr Ala Leu Leu Asp Tyr Trp Gly Gln Gly Thr Leu Val Thr Val Ser
625                 630                 635                 640

Ser Gly Gly Gly Gly Ser Gly Gly Gly Ser Gly Gly Gly Gly Gly Ser
                645                 650                 655

Gly Gly Gly Gly Ser Gly Gly Gly Ser Gly Gly Gly Ser Gly
            660                 665                 670

Gly Gly Gly Ser Glu Val Gln Leu Val Glu Ser Gly Gly Gly Val Val
            675                 680                 685

Gln Pro Gly Gly Ser Leu Arg Leu Ser Cys Ala Ala Ser Gly Phe Thr
    690                 695                 700

Phe Arg Ser Phe Gly Met Ser Trp Val Arg Gln Ala Pro Gly Lys Gly
705                 710                 715                 720

Pro Glu Trp Val Ser Ser Ile Ser Gly Ser Gly Ser Asp Thr Leu Tyr
                725                 730                 735

Ala Asp Ser Val Lys Gly Arg Phe Thr Ile Ser Arg Asp Asn Ser Lys
            740                 745                 750

Asn Thr Leu Tyr Leu Gln Met Asn Ser Leu Arg Pro Glu Asp Thr Ala
        755                 760                 765

Leu Tyr Tyr Cys Thr Ile Gly Gly Ser Leu Ser Arg Ser Ser Gln Gly
    770                 775                 780

Thr Leu Val Thr Val Ser Ser Ala
785                 790
```

<210> SEQ ID NO 289
<211> LENGTH: 654
<212> TYPE: PRT
<213> ORGANISM: Artificial Sequence
<220> FEATURE:
<223> OTHER INFORMATION: Nanobody Sequence

<400> SEQUENCE: 289

```
Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Phe Ser Ile Asp
            20                  25                  30

Ser Met Gly Trp Tyr Arg Gln Ala Pro Gly Lys Gln Arg Glu Leu Val
        35                  40                  45

Ala Ala Ile Thr Ser Ser Thr Asn Tyr Ala Asp Ser Val Lys Gly Arg
    50                  55                  60

Phe Thr Ile Ser Arg Asp Asn Ser Lys Asn Thr Val Tyr Leu Gln Met
65                  70                  75                  80

Asn Ser Leu Arg Pro Glu Asp Thr Ala Leu Tyr Tyr Cys Asn Leu Glu
                85                  90                  95

Gly Gln Ala Gly Trp Gly Thr Ala Leu Ile Asn Tyr Trp Gly Gln Gly
            100                 105                 110
```

```
Thr Leu Val Thr Val Ser Ser Gly Gly Gly Ser Gly Gly Gly Ser
            115                 120                 125

Glu Val Gln Leu Val Glu Ser Gly Gly Val Val Gln Pro Gly Gly
        130                 135                 140

Ser Leu Arg Leu Ser Cys Ala Ala Ser Gly Ser Ile Phe Ser Ile Asp
145                 150                 155                 160

Ser Met Gly Trp Tyr Arg Gln Ala Pro Gly Lys Gln Arg Glu Leu Val
                165                 170                 175

Ala Ala Ile Thr Ser Ser Thr Asn Tyr Ala Asp Ser Val Lys Gly Arg
            180                 185                 190

Phe Thr Ile Ser Arg Asp Asn Ser Lys Asn Thr Val Tyr Leu Gln Met
        195                 200                 205

Asn Ser Leu Arg Pro Glu Asp Thr Ala Leu Tyr Tyr Cys Asn Leu Glu
    210                 215                 220

Gly Gln Ala Gly Trp Gly Thr Ala Leu Ile Asn Tyr Trp Gly Gln Gly
225                 230                 235                 240

Thr Leu Val Thr Val Ser Ser Gly Gly Gly Ser Gly Gly Gly Ser
            245                 250                 255

Glu Val Gln Leu Val Glu Ser Gly Gly Val Val Gln Pro Gly Gly
        260                 265                 270

Ser Leu Arg Leu Ser Cys Ala Ala Ser Gly Ser Ile Phe Ser Ile Asp
            275                 280                 285

Ser Met Gly Trp Tyr Arg Gln Ala Pro Gly Lys Gln Arg Glu Leu Val
                290                 295                 300

Ala Ala Ile Thr Ser Ser Thr Asn Tyr Ala Asp Ser Val Lys Gly Arg
305                 310                 315                 320

Phe Thr Ile Ser Arg Asp Asn Ser Lys Asn Thr Val Tyr Leu Gln Met
                325                 330                 335

Asn Ser Leu Arg Pro Glu Asp Thr Ala Leu Tyr Tyr Cys Asn Leu Glu
            340                 345                 350

Gly Gln Ala Gly Trp Gly Thr Ala Leu Ile Asn Tyr Trp Gly Gln Gly
        355                 360                 365

Thr Leu Val Thr Val Ser Ser Gly Gly Gly Ser Gly Gly Gly Ser
    370                 375                 380

Glu Val Gln Leu Val Glu Ser Gly Gly Val Val Gln Pro Gly Gly
385                 390                 395                 400

Ser Leu Arg Leu Ser Cys Ala Ala Ser Gly Ser Ile Phe Ser Ile Asp
                405                 410                 415

Ser Met Gly Trp Tyr Arg Gln Ala Pro Gly Lys Gln Arg Glu Leu Val
            420                 425                 430

Ala Ala Ile Thr Ser Ser Thr Asn Tyr Ala Asp Ser Val Lys Gly Arg
        435                 440                 445

Phe Thr Ile Ser Arg Asp Asn Ser Lys Asn Thr Val Tyr Leu Gln Met
    450                 455                 460

Asn Ser Leu Arg Pro Glu Asp Thr Ala Leu Tyr Tyr Cys Asn Leu Glu
465                 470                 475                 480

Gly Gln Ala Gly Trp Gly Thr Ala Leu Ile Asn Tyr Trp Gly Gln Gly
                485                 490                 495

Thr Leu Val Thr Val Ser Ser Gly Gly Gly Ser Gly Gly Gly Gly
            500                 505                 510

Ser Gly Gly Gly Ser Gly Gly Gly Ser Gly Gly Gly Ser
        515                 520                 525
```

```
Gly Gly Gly Gly Ser Gly Gly Gly Ser Glu Val Gln Leu Val Glu
            530             535                 540

Ser Gly Gly Val Val Gln Pro Gly Gly Ser Leu Arg Leu Ser Cys
545             550                 555                 560

Ala Ala Ser Gly Phe Thr Phe Arg Ser Phe Gly Met Ser Trp Val Arg
                565             570                 575

Gln Ala Pro Gly Lys Gly Pro Glu Trp Val Ser Ser Ile Ser Gly Ser
                580             585                 590

Gly Ser Asp Thr Leu Tyr Ala Asp Ser Val Lys Gly Arg Phe Thr Ile
        595             600                 605

Ser Arg Asp Asn Ser Lys Asn Thr Leu Tyr Leu Gln Met Asn Ser Leu
        610             615                 620

Arg Pro Glu Asp Thr Ala Leu Tyr Tyr Cys Thr Ile Gly Gly Ser Leu
625             630                 635                 640

Ser Arg Ser Ser Gln Gly Thr Leu Val Thr Val Ser Ser Ala
                645             650
```

<210> SEQ ID NO 290
<211> LENGTH: 782
<212> TYPE: PRT
<213> ORGANISM: Artificial Sequence
<220> FEATURE:
<223> OTHER INFORMATION: Nanobody Sequence

<400> SEQUENCE: 290

```
Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Phe Ser Ile Asp
            20                  25                  30

Ser Met Gly Trp Tyr Arg Gln Ala Pro Gly Lys Gln Arg Glu Leu Val
        35                  40                  45

Ala Ala Ile Thr Ser Ser Thr Asn Tyr Ala Asp Ser Val Lys Gly Arg
    50                  55                  60

Phe Thr Ile Ser Arg Asp Asn Ser Lys Asn Thr Val Tyr Leu Gln Met
65                  70                  75                  80

Asn Ser Leu Arg Pro Glu Asp Thr Ala Leu Tyr Tyr Cys Asn Leu Glu
            85                  90                  95

Gly Gln Ala Gly Trp Gly Thr Leu Ile Asn Tyr Trp Gly Gln Gly
        100                 105                 110

Thr Leu Val Thr Val Ser Ser Gly Gly Gly Ser Gly Gly Gly Ser
    115                 120                 125

Glu Val Gln Leu Val Glu Ser Gly Gly Gly Val Val Gln Pro Gly Gly
    130                 135                 140

Ser Leu Arg Leu Ser Cys Ala Ala Ser Gly Ser Ile Phe Ser Ile Asp
145                 150                 155                 160

Ser Met Gly Trp Tyr Arg Gln Ala Pro Gly Lys Gln Arg Glu Leu Val
                165                 170                 175

Ala Ala Ile Thr Ser Ser Thr Asn Tyr Ala Asp Ser Val Lys Gly Arg
            180                 185                 190

Phe Thr Ile Ser Arg Asp Asn Ser Lys Asn Thr Val Tyr Leu Gln Met
        195                 200                 205

Asn Ser Leu Arg Pro Glu Asp Thr Ala Leu Tyr Tyr Cys Asn Leu Glu
    210                 215                 220

Gly Gln Ala Gly Trp Gly Thr Leu Ile Asn Tyr Trp Gly Gln Gly
225                 230                 235                 240
```

-continued

```
Thr Leu Val Thr Val Ser Ser Gly Gly Gly Ser Gly Gly Gly Ser
            245                 250                 255

Glu Val Gln Leu Val Glu Ser Gly Gly Gly Val Val Gln Pro Gly Gly
            260                 265                 270

Ser Leu Arg Leu Ser Cys Ala Ala Ser Gly Ser Ile Phe Ser Ile Asp
            275                 280                 285

Ser Met Gly Trp Tyr Arg Gln Ala Pro Gly Lys Gln Arg Glu Leu Val
            290                 295                 300

Ala Ala Ile Thr Ser Ser Thr Asn Tyr Ala Asp Ser Val Lys Gly Arg
305                 310                 315                 320

Phe Thr Ile Ser Arg Asp Asn Ser Lys Asn Thr Val Tyr Leu Gln Met
            325                 330                 335

Asn Ser Leu Arg Pro Glu Asp Thr Ala Leu Tyr Tyr Cys Asn Leu Glu
            340                 345                 350

Gly Gln Ala Gly Trp Gly Thr Ala Leu Ile Asn Tyr Trp Gly Gln Gly
            355                 360                 365

Thr Leu Val Thr Val Ser Ser Gly Gly Gly Gly Ser Gly Gly Gly Ser
            370                 375                 380

Glu Val Gln Leu Val Glu Ser Gly Gly Gly Val Val Gln Pro Gly Gly
385                 390                 395                 400

Ser Leu Arg Leu Ser Cys Ala Ala Ser Gly Ser Ile Phe Ser Ile Asp
            405                 410                 415

Ser Met Gly Trp Tyr Arg Gln Ala Pro Gly Lys Gln Arg Glu Leu Val
            420                 425                 430

Ala Ala Ile Thr Ser Ser Thr Asn Tyr Ala Asp Ser Val Lys Gly Arg
            435                 440                 445

Phe Thr Ile Ser Arg Asp Asn Ser Lys Asn Thr Val Tyr Leu Gln Met
450                 455                 460

Asn Ser Leu Arg Pro Glu Asp Thr Ala Leu Tyr Tyr Cys Asn Leu Glu
465                 470                 475                 480

Gly Gln Ala Gly Trp Gly Thr Ala Leu Ile Asn Tyr Trp Gly Gln Gly
            485                 490                 495

Thr Leu Val Thr Val Ser Ser Gly Gly Gly Gly Ser Gly Gly Gly Ser
            500                 505                 510

Glu Val Gln Leu Val Glu Ser Gly Gly Gly Val Val Gln Pro Gly Gly
            515                 520                 525

Ser Leu Arg Leu Ser Cys Ala Ala Ser Gly Ser Ile Phe Ser Ile Asp
            530                 535                 540

Ser Met Gly Trp Tyr Arg Gln Ala Pro Gly Lys Gln Arg Glu Leu Val
545                 550                 555                 560

Ala Ala Ile Thr Ser Ser Thr Asn Tyr Ala Asp Ser Val Lys Gly Arg
            565                 570                 575

Phe Thr Ile Ser Arg Asp Asn Ser Lys Asn Thr Val Tyr Leu Gln Met
            580                 585                 590

Asn Ser Leu Arg Pro Glu Asp Thr Ala Leu Tyr Tyr Cys Asn Leu Glu
            595                 600                 605

Gly Gln Ala Gly Trp Gly Thr Ala Leu Ile Asn Tyr Trp Gly Gln Gly
            610                 615                 620

Thr Leu Val Thr Val Ser Ser Gly Gly Gly Ser Gly Gly Gly Gly
625                 630                 635                 640

Ser Gly Gly Gly Ser Gly Gly Gly Gly Ser Gly Gly Gly Ser
            645                 650                 655

Gly Gly Gly Gly Ser Gly Gly Gly Gly Ser Glu Val Gln Leu Val Glu
```

Ser Gly Gly Gly Val Gln Pro Gly Gly Ser Leu Arg Leu Ser Cys
        660             665                 670

Ala Ala Ser Gly Phe Thr Phe Arg Ser Phe Gly Met Ser Trp Val Arg
675                 680                 685

Gln Ala Pro Gly Lys Gly Pro Glu Trp Val Ser Ser Ile Ser Gly Ser
690                 695                 700

Gly Ser Asp Thr Leu Tyr Ala Asp Ser Val Lys Gly Arg Phe Thr Ile
705                 710                 715                 720

Ser Arg Asp Asn Ser Lys Asn Thr Leu Tyr Leu Gln Met Asn Ser Leu
            725                 730                 735

Arg Pro Glu Asp Thr Ala Leu Tyr Tyr Cys Thr Ile Gly Gly Ser Leu
        740                 745                 750

755                 760                 765

Ser Arg Ser Ser Gln Gly Thr Leu Val Thr Val Ser Ser Ala
        770                 775                 780

<210> SEQ ID NO 291
<211> LENGTH: 248
<212> TYPE: PRT
<213> ORGANISM: Artificial Sequence
<220> FEATURE:
<223> OTHER INFORMATION: Nanobody Chimera Sequence

<400> SEQUENCE: 291

Met Ser Val Pro Thr Gln Val Leu Gly Leu Leu Leu Leu Trp Leu Thr
1               5                   10                  15

Asp Ala Arg Cys Glu Val Gln Leu Val Glu Ser Gly Gly Gly Val Val
            20                  25                  30

Gln Pro Gly Gly Ser Leu Arg Leu Ser Cys Ala Ala Ser Glu Thr Ile
        35                  40                  45

Phe Ser Ile Asp Ser Met Ala Trp Tyr Arg Gln Ala Pro Gly Lys Gln
50                  55                  60

Arg Glu Leu Val Ala Ala Ile Thr Gly Gly Ser Pro Asn Tyr Ala
65                  70                  75                  80

Asp Ser Val Lys Gly Arg Phe Thr Ile Ser Ser Asp Val Ser Lys Arg
            85                  90                  95

Thr Val Tyr Leu Gln Met Asn Ser Leu Arg Pro Glu Asp Thr Ala Leu
            100                 105                 110

Tyr Tyr Cys Asn Ala Glu Gly Gln Ala Gly Trp Gly Thr Ala Leu Leu
            115                 120                 125

Asp Tyr Trp Gly Gln Gly Thr Leu Val Thr Val Ser Ser Arg Thr Val
130                 135                 140

Ala Ala Pro Ser Val Phe Ile Phe Pro Pro Ser Asp Glu Gln Leu Lys
145                 150                 155                 160

Ser Gly Thr Ala Ser Val Val Cys Leu Leu Asn Asn Phe Tyr Pro Arg
            165                 170                 175

Glu Ala Lys Val Gln Trp Lys Val Asp Asn Ala Leu Gln Ser Gly Asn
            180                 185                 190

Ser Gln Glu Ser Val Thr Glu Gln Asp Ser Lys Asp Ser Thr Tyr Ser
            195                 200                 205

Leu Ser Ser Thr Leu Thr Leu Ser Lys Ala Asp Tyr Glu Lys His Lys
            210                 215                 220

Val Tyr Ala Cys Glu Val Thr His Gln Gly Leu Ser Ser Pro Val Thr
225                 230                 235                 240

Lys Ser Phe Asn Arg Gly Glu Cys

-continued

245

<210> SEQ ID NO 292
<211> LENGTH: 470
<212> TYPE: PRT
<213> ORGANISM: Artificial Sequence
<220> FEATURE:
<223> OTHER INFORMATION: Nanobody Chimera Sequence

<400> SEQUENCE: 292

```
Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Val Val Gln
            20                  25                  30

Pro Gly Gly Ser Leu Arg Leu Ser Cys Ala Ala Ser Glu Thr Ile Phe
        35                  40                  45

Ser Ile Asp Ser Met Ala Trp Tyr Arg Gln Ala Pro Gly Lys Gln Arg
    50                  55                  60

Glu Leu Val Ala Ala Ile Thr Gly Gly Gly Ser Pro Asn Tyr Ala Asp
65                  70                  75                  80

Ser Val Lys Gly Arg Phe Thr Ile Ser Ser Asp Val Ser Lys Arg Thr
                85                  90                  95

Val Tyr Leu Gln Met Asn Ser Leu Arg Pro Glu Asp Thr Ala Leu Tyr
            100                 105                 110

Tyr Cys Asn Ala Glu Gly Gln Ala Gly Trp Gly Thr Ala Leu Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
```

```
                355                 360                 365
Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465             470
```

METHODS FOR INHIBITING TUMOR GROWTH OR TREATING CANCER BY ADMINISTERING AN IMMUNOGLOBULIN SINGLE VARIABLE DOMAIN THAT BINDS GLUCOCORTICOID-INDUCED TNFR FAMILY-RELATED RECEPTOR (GITR)

RELATED APPLICATIONS

This Application is divisional of U.S. application Ser. No. 15/769,205 (now U.S. Pat. No. 11,059,899), filed Apr. 18, 2018, which is a national stage filing under 35 U.S.C. 371 of International Patent Application Serial No. PCT/EP2016/075558, filed Oct. 24, 2016, and claims the benefit under 35 U.S.C. § 119(e) of U.S. Provisional Application Ser. No. 62/276,352, filed Jan. 8, 2016, and U.S. Provisional Application Ser. No. 62/245,188, filed Oct. 22, 2015, the contents of each of which is incorporated by reference herein in its entirety for all purposes.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on May 12, 2021, is named A084870182US03-SEQ-JRV, and is 309,640 bytes in size.

FIELD OF THE INVENTION

The present invention relates to immunoglobulin single variable domains that bind GITR and more in particular to polypeptides, that comprise or essentially consist of one or more such immunoglobulin single variable domains (also referred to herein as "ISVD(s) of the invention", and "polypeptides of the invention", respectively).

The invention also relates to nucleic acids encoding such polypeptides (also referred to herein as "nucleic acid(s) of the invention"); to methods for preparing such polypeptides; to host cells expressing or capable of expressing such polypeptides; to compositions, and in particular to pharmaceutical compositions, that comprise such polypeptides, nucleic acids and/or host cells; and to uses of polypeptides, nucleic acids, host cells and/or compositions, in particular for prophylactic and/or therapeutic purposes, such as the prophylactic and/or therapeutic purposes mentioned herein.

Other aspects, embodiments, advantages and applications of the invention will become clear from the further description herein.

BACKGROUND ART

Cancer takes an enormous human toll around the world. It is nowadays the world's leading cause of death, followed by heart disease and stroke. Cancers figure among the leading causes of morbidity and mortality worldwide, with approximately 14 million new cases and 8.2 million cancer related deaths in 2012. The number of new cases is expected to rise by about 70% over the next 2 decades (source: WHO Cancer). The total economic impact of premature death and disability from cancer worldwide was about $900 billion in 2008, representing 1.5% of the world's gross domestic product.

Chemotherapy has been a mainstay in cancer treatment for many years now. Despite some success, the cure rate with chemotherapy remains unsatisfactory, and severe side effects from these treatments are a concern. Improved therapies combatting cancer are eagerly awaited.

Considerable effort has recently been invested in cancer immunotherapy as a new treatment modality to eliminate cancer. Cancer immunotherapy attempts to stimulate the immune system to reject and destroy tumors.

The generation and maintenance of immune responses are controlled by both co-stimulatory and co-inhibitory signaling through T cell co-receptors. Immune activation is regulated by two major families of co-receptors expressed by T cells: the immunoglobulin-like (Ig) superfamily and the TNFR superfamily. The glucocorticoid-induced Tumor Necrosis Factor receptor-related protein (GITR) is a co-stimulatory member of the latter family. Human GITR exists as a trimer and signaling involves the recruitment of three receptor ectodomains by trimeric GITR ligand (GITRL), resulting in a 3:3 receptor:ligand complex formation [Chattopadhyay et al. *PNAS* (2007) 104:19452-19457]. A substantial level of GITR is constitutively expressed on $CD4^+$ $CD25^+$ regulatory T cells (Tregs) and plays a key role in the peripheral tolerance that is mediated by these cells. GITR is also expressed at low levels on CD4+ and CD8+ T cells (T effector cells) and its expression is enhanced rapidly after activation [Nocentini et al. *Br. J. Pharmacol.* (2012) 165: 2089-2099]. Additionally, expression of GITR has also been identified on dendritic cells, natural killer (NK) cells, B cells, macrophages and monocytes. Its ligand GITRL (TNFSF18) is expressed on the surface of various antigen presenting cells (such as dendritic cells, B-cells and macrophages) and on endothelial cells, triggering co-stimulation and leucocyte adhesion and transmigration, respectively [Schaer et al *J Immunother Cancer* (2014) 2: 1-9; Lacal et al, *J. Pharmacol. Exp. Ther.* (2013) 347: 164-172].

GITR activation has been implicated in a wide range of immune functions, involving both effector and regulatory T cells, and thus participating in the development of immune responses against tumors and infectious agents. In particular, preclinical evidence has been accumulating to indicate that GITR activation has effective anti-tumor properties. To date, agonistic monoclonal antibodies against GITR have been shown to promote anti-tumor immunity [Turk et al., *J. Exp. Med.* (2004) 200:771-782; Ko et al., *J. Exp. Med.* (2005) 202:885-891; Ramirez-Montagut et al., *J. Immunol.* (2006) 176:6434-6442; Zhou et al., *J. Immunol.* (2007) 179:7365-7375; Cohen et al., *PLoS One* (2010) 5:e10436; Coe et al., *Cancer Immunol. Immunother.* (2010) 59:1367-1377; Zhou et al., *J. Immunother.* (2010) 33:789-797; Cote et al., *J. Immunol.* (2011) 186:275-283], to augment anti-tumor immunity in combination with vaccines against cancer antigens [Cohen et al., *Cancer Res.* (2006) 66:4904-4912, Ko et al., *Cancer Res.* (2007) 67:7477-7486, Hoffman et al., *J. Immunother.* (2010) 33:136-145, Boczkowski et al., *Cancer Gene Ther.* (2009) 16:900-911], to synergize with other immune-modulatory therapies [Ko et al., *J. Exp. Med.* (2005) 202:885-891, Houot et al., *Blood* (2009) 113:3546-3552, Mitsui, et al. *Clin. Can. Res.* (2010) 16:2781-2791], to enhance rejection of tumors expressing mutated self [Duan et al., *Cancer Res.* (2009) 69:3545-3553] and to enhance adoptive cell therapy [Liu et al., *Mol Ther.* (2009) 17:1274-81, Imai et al., *Can. Sci.* (2009) 100:1317-25]. Furthermore, targeting GITR in vivo has also produced some notable results in treating infectious diseases. During Friend virus infection in mice, treatment with agonist antibody to GITR reverses the effect of natural Treg cells, leading to enhanced Th1 and CD8+ T cell responses, reduction of viral load and pathology and restoration of CD8+ T cell mediated antitumor responses [He et al., *J. Virol.* (2004) 78:11641-11647].

Similarly, treatment of mice with agonist antibody to GITR diminishes herpetic keratitis [Suvas et al., *J. Virol.* (2005) (18):11935-11942].

Several mechanisms appear to contribute to GITR-mediated therapeutic effects. GITR activation in vivo for example, has been shown to impair expression of FoxP3 in intramural regulatory T cells (Treg), resulting in a loss of Treg lineage stability with subsequent reduced suppression of effector T cells (Teff) [Schaer et al *Cancer Immunol. Res.* (2013) 1: 320-331]. Furthermore, GITR modulation is supporting Teff activity by inducing T cell proliferation and effector functions and by promoting T cell survival [Mahoney et al *Nat Rev Drug Discov.* (2015) 14:561-84].

Although GITR seems to be an attractive target for cancer immunotherapy, it remains unclear whether anti-GITR agonistic antibodies depend on their Fc function for anti-tumor effects. Ponte et al. demonstrated that FcR-mediated cross-linking of anti-GITR antibodies, is not required for enhancement of humoral and cellular immunity [Ponte et al *Immunol.* (2010) 130, 231-242]. Furthermore, Ponte showed that an Fc-disabled anti-GITR monoclonal antibody was effective in an in vitro lung tumor model as monotherapy and in combination with chemotherapeutic drugs enhanced anti-tumor immunity against established tumors in a s.c. tumor model (Ponte et al. *Keystone symposia*, April 2011). In contrast, Bulliard et al. found that activating FcγRs were essential for anti-tumor activities of anti-GITR antibodies [Bulliard et al *J Exp Med.* (2013) 210: 1685-1693].

Efficacious immunotherapies should inhibit Treg and simultaneously activate Teff, tipping the balance towards immuno-activation. However, while the results obtained to date establish GITR as a useful target for immunotherapy, it remains unclear which particular features of GITR agonists are especially advantageous for therapeutic purposes. As such, there is a need in the art for further insight into the specific functional properties that make GITR agonists therapeutically effective, as well as for improved therapeutic GITR agonists which are more effective in treating cancer and other conditions, such as infectious diseases.

SUMMARY OF THE INVENTION

The present invention provides GITR agonists with particular functional properties which are linked with improved and desirable therapeutic and/or pharmacological properties, in addition to other advantageous properties (such as, for example, improved ease of preparation, good stability, and/or reduced costs of goods), compared to the prior art amino acid sequences and antibodies.

Based on extensive screening, characterization and combinatory strategies, the present inventors surprisingly observed that polypeptides comprising immunoglobulin single variable domains binding GITR showed improved properties for modulating GITR activity compared to the GITR agonizing molecules described in the prior art. More specifically, the present inventors surprisingly observed that the polypeptides of the present invention exhibited higher efficacies at equipotent or even lower $EC_{50}$ values as compared to the prior art antibodies. This is clinically very important as the effectiveness of a drug depends on its maximal efficacy.

Accordingly, the present invention relates to a polypeptide comprising at least one immunoglobulin single variable domain (ISVD) that specifically binds glucocorticoid-induced TNFR family-related receptor (GITR) with an $EC_{50}$ value of less than 200 pM, and wherein the binding of said ISVD to said GITR enhances an immune response.

In particular, the polypeptides that can bind GITR, and in particular human GITR (SEQ ID NO: 231), are characterised by a biological potency, suitably measured and/or expressed as an $EC_{50}$ value, as further described and defined herein, for instance, such as by a NF-κB luciferase reporter assay or a T-cell activation assay.

In one aspect, the polypeptides of the present invention are such that they bind (human) GITR with an $EC_{50}$ of 200 pM or less, such as less than 190, 180, 170, 160, 150, 140, 130, 120, 110, 100 or even less, such as less than 90, 80, 70, 60, 50, 45, 40, 35, 30, 25, 20, 18, 16, 15, 14 or even less, such as less than 12 pM, as determined in a NF-κB luciferase reporter assay.

In another aspect, the polypeptides of the present invention are such that they bind (human) GITR with an $EC_{50}$ of 200 pM or less, such as less than 190, 180, 170, 160, 150, 140, 130, 120, 110, 100 or even less, such as less than 90, 80, 70, 60, 50, 40 or even less, such as less than 30 pM, as determined in a T-cell activation assay.

It will be appreciated that binding of polypeptides of the invention to (human) GITR may result in enhancing the proliferation or activation of T cells, B cells or natural killer cells as described herein.

It will further be appreciated that binding of the polypeptides of the invention to (human) GITR may result in inhibiting tumor cell growth, such as described herein.

The efficacy of the polypeptides of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person, and for example include the assays and animal models used in the experimental part below and in the prior art cited herein.

Some preferred technical values for binding, enhancing an immune response, inhibiting tumor cell growth or other in vivo and/or in vitro potency of the polypeptides of the invention to (human) GITR will become clear from the further description and examples herein.

In one aspect the present invention provides a polypeptide as described herein, wherein said polypeptide has the structure FR1-CDR1-FR2-CDR2-FR3-CDR3-FR4, in which CDR1, CDR2 and CDR3 are as defined herein, and FR1, FR2, FR3 and FR4 are framework sequences. Accordingly, the present invention relates to polypeptides that (essentially) consist of 4 framework regions (FR1 to FR4, respectively) and 3 complementarity determining regions (CDR1 to CDR3, respectively), in which:

(i) CDR1 is chosen from the group consisting of:
  (a) SEQ ID NOs: 73-88; and
  (b) amino acid sequences that have 4, 3, 2, or 1 amino acid(s) difference with the amino acid sequences of SEQ ID NOs: 73-88; and/or (ii) CDR2 is chosen from the group consisting of:
  (c) SEQ ID NOs: 90-116; and
  (d) amino acid sequences that have 4, 3, 2, or 1 amino acid(s) difference with the amino acid sequences of SEQ ID NOs: 90-116; and/or (iii) CDR3 is chosen from the group consisting of:
  (e) SEQ ID NOs: 118-132 and 282-284; and
  (f) amino acid sequences that have 4, 3, 2, or 1 amino acid(s) difference with the amino acid sequences of SEQ ID NOs: 118-132 and 282-284.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 73-75; and
    (b) amino acid sequences that have 4, 3, 2, or 1 amino acid(s) difference with the amino acid sequence of SEQ ID NO: 73; and/or
  (ii) CDR2 is chosen from the group consisting of:
    (c) SEQ ID NOs: 90-98; and
    (d) amino acid sequences that have 4, 3, 2, or 1 amino acid(s) difference with the amino acid sequence of SEQ ID NO: 90; and/or
  (iii) CDR3 is chosen from the group consisting of:
    (e) SEQ ID NOs: 118-119, 123 and 282-284; and
    (f) amino acid sequences that have 2, or 1 amino acid(s) difference with the amino acid sequence of SEQ ID NO: 118.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which:
  (i) CDR1 is chosen from the group consisting of:
    (a) SEQ ID NO: 73; and
    (b) amino acid sequences that have 4, 3, 2, or 1 amino acid difference(s) with SEQ ID NO: 73, wherein
      at position 2 the T has been changed into S;
      at position 7 the D has been changed into N;
      at position 8 the S has been changed into A; and/or
      at position 10 the A has been changed into G;
  and/or
  (ii) CDR2 is chosen from the group consisting of:
    (c) SEQ ID NO: 90; and
    (d) amino acid sequences that have 4, 3, 2, or 1 amino acid difference(s) with SEQ ID NO: 90, wherein
      at position 1 the A has been changed into H, T, or G;
      at position 2 the I has been changed into M;
      at position 3 the T has been changed into S;
      at position 6 the G has been changed into S;
      at position 7 the S has been changed into R, or G; and/or
      at position 8 the P has been changed into S, T, or R
  and/or
  (iii) CDR3 is chosen from the group consisting of:
    (e) SEQ ID NO: 118; and
    (f) amino acid sequences that have 2, or 1 amino acid difference(s) with SEQ ID NO: 118, wherein
      at position 9 the A has been changed into P;
      at position 11 the M has been changed into L, K, R, or Q; and/or
      at position 12 the D has been changed into N.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which:
  i) CDR1 is represented by SEQ ID NO: 73, CDR2 is represented by SEQ ID NO: 90, and CDR3 is represented by SEQ ID NO: 118; or
  ii) CDR1 is represented by SEQ ID NO: 73, CDR2 is represented by SEQ ID NO: 90, and CDR3 is represented by SEQ ID NO: 123.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 76-78; and
    (b) amino acid sequences that have 2, or 1 amino acid(s) difference with the amino acid sequence of SEQ ID NO: 76; and/or
  (ii) CDR2 is chosen from the group consisting of:
    (c) SEQ ID NOs: 99-103; and
    (d) amino acid sequences that have 3, 2, or 1 amino acid(s) difference with the amino acid sequence of SEQ ID NO: 99; and/or
  (iii) CDR3 is chosen from the group consisting of:
    (e) SEQ ID NOs: 120-123; and
    (f) amino acid sequences that have 4, 3, 2, or 1 amino acid(s) difference with the amino acid sequence of SEQ ID NO: 120.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which:
  (i) CDR1 is chosen from the group consisting of:
    (a) SEQ ID NO: 76; and
    (b) amino acid sequences that have 2, or 1 amino acid difference(s) with SEQ ID NO: 76, wherein
      at position 7 the D has been changed into N; and/or
      at position 8 the S has been changed into A;
  and/or
  (ii) CDR2 is chosen from the group consisting of:
    (c) SEQ ID NO: 99; and
    (d) amino acid sequences that have 3, 2, or 1 amino acid difference(s) with SEQ ID NO: 99, wherein
      at position 1 the A has been changed into S, or T;
      at position 5 the S has been changed into T, G, or R;
      at position 6 the T has been changed into K; and/or
      at position 7 the N has been changed into I;
  and/or
  (iii) CDR3 is chosen from the group consisting of:
    (e) SEQ ID NO: 120; and
    (f) amino acid sequences that have 4, 3, 2, or 1 amino acid difference(s) with SEQ ID NO: 120, wherein
      at position 1 the E has been changed into K;
      at position 4 the A has been changed into T;
      at position 11 the I has been changed into M, or L; and/or
      at position 12 the N has been changed into D.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which: CDR1 is represented by SEQ ID NO: 76, CDR2 is represented by SEQ ID NO: 99, and CDR3 is represented by SEQ ID NO: 120.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 79-84; and
    (b) amino acid sequences that have 3, 2, or 1 amino acid(s) difference with the amino acid sequence of SEQ ID NO: 79; and/or
  (ii) CDR2 is chosen from the group consisting of:
    (c) SEQ ID NOs: 104-108; and
    (d) amino acid sequences that have 2, or 1 amino acid(s) difference with the amino acid sequence of SEQ ID NO: 104; and/or (iii) CDR3 is chosen from the group consisting of:
(e) SEQ ID NOs: 124-125; and
(f) amino acid sequences that have 1 amino acid difference with the amino acid sequence of SEQID NO:124.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which:
(i) CDR1 is chosen from the group consisting of:
(a) SEQ ID NO: 79; and
(b) amino acid sequences that have 3, 2, or 1 amino acid difference(s) with SEQ ID NO: 79, wherein
at position 2 the S has been changed into N;
at position 3 the V has been changed into I;
at position 7 the N has been changed into D;
at position 8 the D has been changed into S; and/or
at position 9 the M has been changed into V, or T;
and/or
(ii) CDR2 is chosen from the group consisting of:
(c) SEQ ID NO: 104; and
(d) amino acid sequences that have 2, or 1 amino acid difference(s) with SEQ ID NO: 104, wherein
at position 1 the D has been changed into G;
at position 5 the R has been changed into A; and/or
at position 6 the G has been changed into D;
and/or
(iii) CDR3 is chosen from the group consisting of:
(e) SEQ ID NO: 124; and
(f) amino acid sequences that have 1 amino acid difference with SEQ ID NO: 124, wherein
at position 4 the T has been changed into M.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which: CDR1 is represented by SEQ ID NO: 79, CDR2 is represented by SEQ ID NO: 104, and CDR3 is represented by SEQ ID NO: 124.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which:
(i) CDR1 is chosen from the group consisting of:
(a) SEQ ID NOs: 85-86; and
(b) amino acid sequences that have 1 amino acid difference with the amino acid sequence of SEQ ID NO: 85; and/or
(ii) CDR2 is chosen from the group consisting of:
(c) SEQ ID NOs: 109-110; and
(d) amino acid sequences that have 1 amino acid difference with the amino acid sequence of SEQ ID NO: 109; and/or
(iii) CDR3 is SEQ ID NO: 126.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which:
(i) CDR1 is chosen from the group consisting of:
(a) SEQ ID NO: 85; and
(b) amino acid sequences that have 1 amino acid difference with SEQ ID NO: 85, wherein
at position 2 the S has been changed into N;
and/or
(ii) CDR2 is chosen from the group consisting of:
(c) SEQ ID NO: 109; and
(d) amino acid sequences that have 1 amino acid difference with SEQ ID NO: 109, wherein
at position 9 the T has been changed into S;
and/or
(iii) CDR3 is SEQ ID NO: 126.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which: CDR1 is represented by SEQ ID NO: 85, CDR2 is represented by SEQ ID NO: 109, and CDR3 is represented by SEQ ID NO: 126.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which: CDR1 is represented by SEQ ID NO: 87, CDR2 is represented by SEQ ID NO: 111, and CDR3 is represented by SEQ ID NO: 127.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which:
(i) CDR1 is SEQ ID NO: 77; and/or
(ii) CDR2 is chosen from the group consisting of:
(c) SEQ ID NOs: 112-113; and
(d) amino acid sequences that have 1 amino acid difference with the amino acid sequence of SEQ ID NO: 112; and/or
(iii) CDR3 is chosen from the group consisting of:
(e) SEQ ID NOs: 128-130; and
(f) amino acid sequences that have 1 amino acid difference with the amino acid sequence of SEQ ID NO: 128.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which:
(i) CDR1 is SEQ ID NO: 77; and/or
(ii) CDR2 is chosen from the group consisting of:
(a) SEQ ID NO: 112; and
(b) amino acid sequences that have 1 amino acid difference with SEQ ID NO: 112, wherein
at position 4 the D has been changed into G;
and/or
(iii) CDR3 is chosen from the group consisting of:
(c) SEQ ID NO: 128; and
(d) amino acid sequences that have 1 amino acid difference with SEQ ID NO: 128, wherein
at position 9 the S has been changed into P; and/or
at position 13 the T has been changed into A.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which: CDR1 is represented by SEQ ID NO: 77, CDR2 is represented by SEQ ID NO: 112, and CDR3 is represented by SEQ ID NO: 128.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which:

(i) CDR1 is SEQ ID NO: 88; and/or
(ii) CDR2 is chosen from the group consisting of:
   (c) SEQ ID NOs: 114-116; and
   (d) amino acid sequences that have 2, or 1 amino acid(s) difference with the amino acid sequence of SEQ ID NO: 114; and/or
(iii) CDR3 is chosen from the group consisting of:
   (e) SEQ ID NOs: 131-132; and
   (f) amino acid sequences that have 2, or 1 amino acid(s) difference with the amino acid sequence of SEQ ID NO: 131.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which:
(i) CDR1 is SEQ ID NO: 88; and/or
(ii) CDR2 is chosen from the group consisting of:
   (a) SEQ ID NO: 114; and
   (b) amino acid sequences that have 2, or 1 amino acid(s) difference with SEQ ID NO: 114, wherein
      at position 1 the V has been changed into I, or A; and/or
      at position 9 the M has been changed into I;
and/or
(iii) CDR3 is chosen from the group consisting of:
   (c) SEQ ID NO: 131; and
   (d) amino acid sequences that have 2, or 1 amino acid(s) difference with SEQ ID NO: 131, wherein
      at position 4 the G has been changed into E; and/or
      at position 5 the R has been changed into Q.

In a further aspect the present invention provides a polypeptide as described herein, wherein said polypeptide (essentially) consist of 4 framework regions (FR1 to FR4, respectively) and 3 complementarity determining regions (CDR1 to CDR3, respectively), in which: CDR1 is represented by SEQ ID NO: 88, CDR2 is represented by SEQ ID NO: 114, and CDR3 is represented by SEQ ID NO: 131.

In a preferred aspect, the at least one ISVD is chosen from the group of ISVDs, wherein:
CDR1 is SEQ ID NO: 73, CDR2 is SEQ ID NO: 90; and CDR3 is SEQ ID NO: 118;
CDR1 is SEQ ID NO: 74, CDR2 is SEQ ID NO: 91; and CDR3 is SEQ ID NO: 118;
CDR1 is SEQ ID NO: 74, CDR2 is SEQ ID NO: 92; and CDR3 is SEQ ID NO: 118;
CDR1 is SEQ ID NO: 74, CDR2 is SEQ ID NO: 93; and CDR3 is SEQ ID NO: 118;
CDR1 is SEQ ID NO: 74, CDR2 is SEQ ID NO: 94; and CDR3 is SEQ ID NO: 118;
CDR1 is SEQ ID NO: 74, CDR2 is SEQ ID NO: 95; and CDR3 is SEQ ID NO: 118;
CDR1 is SEQ ID NO: 75, CDR2 is SEQ ID NO: 93; and CDR3 is SEQ ID NO: 118;
CDR1 is SEQ ID NO: 74, CDR2 is SEQ ID NO: 96; and CDR3 is SEQ ID NO: 118;
CDR1 is SEQ ID NO: 74, CDR2 is SEQ ID NO: 97; and CDR3 is SEQ ID NO: 118;
CDR1 is SEQ ID NO: 74, CDR2 is SEQ ID NO: 98; and CDR3 is SEQ ID NO: 119;
CDR1 is SEQ ID NO: 73, CDR2 is SEQ ID NO: 90; and CDR3 is SEQ ID NO: 123;
CDR1 is SEQ ID NO: 73, CDR2 is SEQ ID NO: 90; and CDR3 is SEQ ID NO: 282;
CDR1 is SEQ ID NO: 73, CDR2 is SEQ ID NO: 90; and CDR3 is SEQ ID NO: 283;
CDR1 is SEQ ID NO: 73, CDR2 is SEQ ID NO: 90; and CDR3 is SEQ ID NO: 284;
CDR1 is SEQ ID NO: 76, CDR2 is SEQ ID NO: 99; and CDR3 is SEQ ID NO: 120;
CDR1 is SEQ ID NO: 77, CDR2 is SEQ ID NO: 100; and CDR3 is SEQ ID NO: 121;
CDR1 is SEQ ID NO: 78, CDR2 is SEQ ID NO: 101; and CDR3 is SEQ ID NO: 122;
CDR1 is SEQ ID NO: 76, CDR2 is SEQ ID NO: 102; and CDR3 is SEQ ID NO: 118;
CDR1 is SEQ ID NO: 77, CDR2 is SEQ ID NO: 103; and CDR3 is SEQ ID NO: 118;
CDR1 is SEQ ID NO: 76, CDR2 is SEQ ID NO: 99; and CDR3 is SEQ ID NO: 118;
CDR1 is SEQ ID NO: 78, CDR2 is SEQ ID NO: 99; and CDR3 is SEQ ID NO: 123;
CDR1 is SEQ ID NO: 79, CDR2 is SEQ ID NO: 104; and CDR3 is SEQ ID NO: 124;
CDR1 is SEQ ID NO: 76, CDR2 is SEQ ID NO: 105; and CDR3 is SEQ ID NO: 124;
CDR1 is SEQ ID NO: 76, CDR2 is SEQ ID NO: 106; and CDR3 is SEQ ID NO: 124;
CDR1 is SEQ ID NO: 80, CDR2 is SEQ ID NO: 106; and CDR3 is SEQ ID NO: 124;
CDR1 is SEQ ID NO: 81, CDR2 is SEQ ID NO: 104; and CDR3 is SEQ ID NO: 124;
CDR1 is SEQ ID NO: 82, CDR2 is SEQ ID NO: 104; and CDR3 is SEQ ID NO: 124;
CDR1 is SEQ ID NO: 83, CDR2 is SEQ ID NO: 104; and CDR3 is SEQ ID NO: 124;
CDR1 is SEQ ID NO: 84, CDR2 is SEQ ID NO: 104; and CDR3 is SEQ ID NO: 124;
CDR1 is SEQ ID NO: 83, CDR2 is SEQ ID NO: 106; and CDR3 is SEQ ID NO: 124;
CDR1 is SEQ ID NO: 83, CDR2 is SEQ ID NO: 107; and CDR3 is SEQ ID NO: 124;
CDR1 is SEQ ID NO: 83, CDR2 is SEQ ID NO: 108; and CDR3 is SEQ ID NO: 124;
CDR1 is SEQ ID NO: 83, CDR2 is SEQ ID NO: 104; and CDR3 is SEQ ID NO: 125;
CDR1 is SEQ ID NO: 85, CDR2 is SEQ ID NO: 109; and CDR3 is SEQ ID NO: 126;
CDR1 is SEQ ID NO: 86, CDR2 is SEQ ID NO: 110; and CDR3 is SEQ ID NO: 126;
CDR1 is SEQ ID NO: 85, CDR2 is SEQ ID NO: 110; and CDR3 is SEQ ID NO: 126;
CDR1 is SEQ ID NO: 87, CDR2 is SEQ ID NO: 111; and CDR3 is SEQ ID NO: 127;
CDR1 is SEQ ID NO: 77, CDR2 is SEQ ID NO: 112; and CDR3 is SEQ ID NO: 128;
CDR1 is SEQ ID NO: 77, CDR2 is SEQ ID NO: 112; and CDR3 is SEQ ID NO: 129;
CDR1 is SEQ ID NO: 77, CDR2 is SEQ ID NO: 113; and CDR3 is SEQ ID NO: 130;
CDR1 is SEQ ID NO: 77, CDR2 is SEQ ID NO: 112; and CDR3 is SEQ ID NO: 130;
CDR1 is SEQ ID NO: 88, CDR2 is SEQ ID NO: 114; and CDR3 is SEQ ID NO: 131;
CDR1 is SEQ ID NO: 88, CDR2 is SEQ ID NO: 115; and CDR3 is SEQ ID NO: 131; and
CDR1 is SEQ ID NO: 88, CDR2 is SEQ ID NO: 116; and CDR3 is SEQ ID NO: 132.

The polypeptides of the invention may (essentially) consist of an immunoglobulin single variable domain selected from a light chain variable domain sequence (e.g., a $V_L$-sequence) and from a heavy chain variable domain sequence (e.g., a $V_H$-sequence). The polypeptides of the invention may (essentially) consist of an immunoglobulin single variable domain selected from a heavy chain variable domain sequence that is derived from a conventional four-chain antibody and from a heavy chain variable domain sequence that is derived from heavy chain antibody. The polypeptides of the invention may (essentially) consist of an immunoglobulin single variable domain selected from a domain antibody (or an amino acid that is suitable for use as a domain antibody), a single domain antibody (or an amino acid that is suitable for use as a single domain antibody), a "dAb" (or an amino acid that is suitable for use as a dAb), a Nanobody®, a VHH sequence, a camelized VH sequence, or a VHH sequence that has been obtained by affinity maturation. In a preferred aspect, the polypeptide of the invention (essentially) consists of a partially or fully humanized Nanobody®, such as a partially or fully humanized VHH.

Preferred polypeptides of the invention are selected from any of SEQ ID NOs: 1-71 and 268-275 or polypeptides that have a sequence identity of more than 80%, preferably more than 90%, more preferably more than 95%, such as 96%, 97%, 98%, 99% or more sequence identity (as defined herein) with any of SEQ ID NOs: 1-71 and 268-275.

The polypeptide provided by the invention (also referred to as "polypeptide of the invention") is preferably in essentially isolated form (as defined herein), which may comprise, or (essentially) consist of one or more ISVDs and which may optionally further comprise one or more further immunoglobulins (all optionally linked via one or more suitable linkers).

More particularly, the present invention provides multivalent polypeptides comprising, or (essentially) consisting of at least two, at least three, at least four or at least five ISVDs that can bind GITR, wherein said at least two, said at least three, said at least four, or said at least five ISVDs can be the same or different and wherein said at least two, said at least three, said at least four or said at least five ISVDs are directly linked to each other or linked to each other via a linker.

Without being limiting, suitable linkers may be selected from the group of linkers with SEQ ID NOs: 247-263, of which shorter linker lengths are preferred. Some particularly preferred linkers comprise between 1 and 20 amino acid residues, such as between 2 and 10 amino acid residues, such as 2, 3, 4, 5, 6, 7, 8 or 9 amino acid residues. In particular linker 9GS (SEQ ID NO: 251) or linker 3A (SEQ ID NO: 247) are especially preferred.

In another aspect, the invention relates to a compound or construct (also referred to herein as a "compound of the invention" or "construct of the invention", respectively) that comprises or (essentially) consists of one or more polypeptides of the invention (or suitable fragments thereof), and optionally further comprises one or more other groups, residues, moieties or binding units, optionally linked via one or more peptidic linkers. As will become clear to the skilled person from the further disclosure herein, such further groups, residues, moieties or binding units may or may not provide further functionality to the polypeptides of the invention (and/or to the compound, construct or compositions in which it is present) and may or may not modify the properties of the polypeptide of the invention.

In one specific aspect of the invention, a compound of the invention or a construct of the invention may have an increased half-life, compared to the corresponding polypeptide of the invention. Some preferred, but non-limiting examples of such compounds or constructs will become clear to the skilled person based on the further disclosure herein, and for example comprise polypeptides of the invention that have been chemically modified to increase the half-life thereof (for example, by means of pegylation); polypeptides of the invention that comprise at least one additional binding site for binding to a serum protein (such as serum albumin); or polypeptides of the invention that comprise at least one polypeptide of the invention that is linked to at least one moiety that increases the half-life of the polypeptide of the invention.

Examples of polypeptides of the invention that comprise such half-life extending moieties will become clear to the skilled person based on the further disclosure herein; and for example include, without limitation, polypeptides in which the one or more polypeptides of the invention are suitable linked to one or more serum proteins or fragments thereof (such as (human) serum albumin or suitable fragments thereof) or to one or more binding units that can bind to serum proteins (such as, for example, domain antibodies, amino acids that are suitable for use as a domain antibody, single domain antibodies, amino acids that are suitable for use as a single domain antibody, "dAb"'s, amino acids that are suitable for use as a dAb, Nanobodies®, VHH sequences, humanized VHH sequences, or camelized VH sequences that can bind to serum albumin (such as human serum albumin) or a serum immunoglobulin (such as IgG); reference is made to the further description and references mentioned herein); polypeptides in which a polypeptide of the invention is linked to an Fc portion (such as a human Fc) or a suitable part or fragment thereof; or polypeptides in which the one or more polypeptides of the invention are suitable linked to one or more small proteins or peptides that can bind to serum proteins (such as, without limitation, the proteins and peptides described in WO 91/01743, WO 01/45746, WO 02/076489).

In one aspect, the compound or construct according to the invention that provides the polypeptide with increased half-life is chosen from the group consisting of an antibody constant region or fragments thereof, wherein the antibody constant region or fragments thereof are derived from human IgG, such as IgG1, IgG2, IgG3 or IgG4. In particular, such antibody constant region comprises a CH1 heavy chain domain, a CH2 heavy chain domain, a CH3 heavy chain domain and/or a CL light chain domain.

In one specific aspect of the invention, a compound or construct of the invention comprises
   i) a monovalent polypeptide of the invention, wherein said monovalent polypeptide is linked to a CH1 heavy chain domain, which is followed by a CH2 heavy chain domain and a CH3 heavy chain domain respectively; and/or
   ii) a monovalent polypeptide of the invention, wherein said monovalent polypeptide is linked to a CL light chain domain (such as Cκ or Cλ).

Preferred heavy chain and/or light chain domains of the invention are of the IgG type and comprise an amino acid sequence set forth in one of SEQ ID NO: 229, SEQ ID NO: 230, SEQ ID NO: 266, SEQ ID NO: 267, SEQ ID NO: 291 and SEQ ID NO: 292 or an amino acid sequence that has a sequence identity of more than 80%, preferably more than 90%, more preferably more than 95%, such as 96%, 97%, 98%, 99% or more sequence identity (as defined herein) with any of SEQ ID NOs: 229-230, SEQ ID NOs: 266-267 and SEQ ID NOs: 291-292.

Generally, the compounds or constructs of the invention with increased half-life preferably have a half-life that is at least 1.5 times, preferably at least 2 times, such as at least 5 times, for example at least 10 times or more than 20 times, greater than the half-life of the corresponding polypeptide of the invention per se.

In a preferred, but non-limiting aspect, such compounds or constructs of the invention have a serum half-life that is increased with more than 1 hour, preferably more than 2 hours, more preferably more than 6 hours, such as more than 12 hours, or even more than 24, 48 or 72 hours, compared to the corresponding polypeptide of the invention per se.

In another preferred, but non-limiting aspect, such compounds or constructs of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In a preferred aspect, the invention relates to a compound or construct as defined above, which is selected from any of SEQ ID NOs: 206-223 and 285-290 or compounds or constructs that have a sequence identity of more than 80%, preferably more than 90%, more preferably more than 95%, such as 96%, 97%, 98%, 99% or more sequence identity (as defined herein) with any of SEQ ID NOs: 206-223 and 285-290 (see Table A-11).

The invention also relates to nucleic acids or nucleotide sequences that encode a polypeptide, a compound and/or construct of the invention. Such a nucleic acid will also be referred to herein as "nucleic acid(s) of the invention" and may for example be in the form of a genetic construct, as further described herein. Accordingly, the present invention also relates to a nucleic acid or nucleotide sequence that is in the form of a genetic construct.

Nucleic acids encoding a polypeptide, a compound and/or construct of the invention can be linked to obtain a nucleic acid encoding a multivalent polypeptide of the invention. Accordingly, the present invention also relates to the use of a nucleic acid or nucleotide sequence that encodes a polypeptide, a compound and/or construct of the invention for the preparation of a genetic construct that encodes a multivalent polypeptide of the invention.

The invention further relates to a host or host cell that expresses (or that under suitable circumstances is capable of expressing) a polypeptide, a compound and/or construct of the invention; and/or that contains a nucleic acid of the invention. Some preferred but non-limiting examples of such hosts or host cells will become clear from the further description herein.

The invention further relates to a composition containing or comprising at least one polypeptide, compound and/or construct of the invention and/or at least one nucleic acid of the invention, and optionally one or more further components of such compositions known per se, i.e. depending on the intended use of the composition. Such a composition may for example be a pharmaceutical composition (as described herein) or a veterinary composition. Some preferred but non-limiting examples of such compositions will become clear from the further description herein.

The invention further relates to methods for preparing polypeptides, compounds and/or constructs, nucleic acids, host cells, and composition described herein. The method for producing a polypeptide, compound and/or construct, nucleic acid, host cell, and composition of the invention may comprise the following steps:
a) expressing, in a suitable host cell or host organism or in another suitable expression system, a nucleic acid or nucleotide sequence of the invention, or a genetic construct of the invention; optionally followed by:
b) isolating and/or purifying the polypeptide, compound and/or construct of the invention thus obtained.

The invention further relates to applications and uses of the polypeptides, compound and/or constructs, nucleic acids, host cells, and compositions described herein, as well as to methods for the prevention and/or treatment of GITR associated diseases, disorders or conditions. Some preferred but non-limiting applications and uses will become clear from the further description herein.

The polypeptides, compounds and/or constructs and compositions of the present invention can be used for enhancing an immune response.

In particular, the polypeptides, compounds and/or constructs and compositions of the present invention can be used for enhancing the proliferation or activation of T cells, B cells or natural killer cells.

The polypeptides, compounds and/or constructs and compositions of the present invention can be used for inhibiting tumor growth.

The polypeptides, compounds and/or constructs and compositions of the present invention can be used for prevention and/or treatment of T cell, B cell or natural killer cell mediated diseases.

The polypeptides, compounds and/or constructs and compositions of the present invention can be used for prevention and/or treatment of infectious diseases. Infections can be broadly classified as bacterial, fungal, viral, or parasitic based on the category of infectious organism or agent involved. Accordingly, the polypeptides, compounds and/or constructs and compositions of the present invention can be used for prevention and/or treatment of bacterial, fungal, viral or parasitic infectious diseases.

The polypeptides, compounds and/or constructs and compositions of the present invention can be used for prevention and/or treatment of cancer. Exemplary cancers whose growth can be inhibited using the polypeptides, compounds and/or constructs and compositions of the present invention include cancers typically responsive to immunotherapy. Non-limiting examples of preferred cancers for treatment include squamous cell cancer, small-cell lung cancer, non-small cell lung cancer, melanoma, kidney cancer such as renal cell carcinoma and Wilms' tumors, glioblastoma, glioma, prostate cancer, testicular cancer, gastrointestinal cancer, pancreatic cancer, biliary tract cancer, cervical cancer, ovarian cancer, liver cancer, bladder cancer, breast cancer, colon cancer, colorectal cancer, small bowel or appendix cancer, uterine or endometrial cancer, multiple myeloma, salivary gland carcinoma, adrenal gland cancer, osteosarcoma, chondrosarcoma, nasopharyngeal carcinoma, basal cell carcinoma, vulval cancer, thyroid cancer, testicular cancer, esophageal cancer, head and neck cancer, leukemia, lymphomas, merkel cell cancer and other hematologic malignancies.

As such, the polypeptides, compounds and/or constructs and compositions of the present invention can be used for the prevention and/or treatment of cancer, wherein the cancer is selected from squamous cell cancer, small-cell lung cancer, non-small cell lung cancer, melanoma, kidney cancer such as renal cell carcinoma and Wilms' tumors, glioblastoma, glioma, prostate cancer, testicular cancer, gastrointestinal cancer, pancreatic cancer, biliary tract cancer, cervical cancer, ovarian cancer, liver cancer, bladder cancer, breast cancer, colon cancer, colorectal cancer, small bowel or appendix cancer, uterine or endometrial cancer, multiple myeloma, salivary gland carcinoma, adrenal gland cancer, osteosarcoma, chondrosarcoma, nasopharyngeal carcinoma, basal cell carcinoma, vulval cancer, thyroid cancer, testicular cancer, esophageal cancer, head and neck cancer, leukemia, lymphomas, merkel cell cancer and other hematologic malignancies.

The methods for enhancing an immune response, in particular enhancing proliferation or activation of T cells, B cells or natural killer cells and the method for inhibiting tumor growth that are described herein can be used to treat and prevent a wide variety of GITR associated diseases, disorders or conditions. For example, in one aspect, the present invention provides a method for prevention and/or treatment of T cell, B cell or natural killer cell associated diseases comprising the step of administering to a subject in need thereof, a pharmaceutically active amount of at least one polypeptide, compound and/or construct and composition as described herein.

In another aspect, the present invention provides a method for prevention and/or treatment of bacterial, fungal, viral or parasitic infectious diseases comprising the step of administering to a subject in need thereof, a pharmaceutically active amount of at least one polypeptide, compound and/or construct and composition as described herein.

In yet another aspect, the present invention provides a method for prevention and/or treatment of cancer comprising the step of administering to a subject in need thereof, a pharmaceutically active amount of at least one polypeptide, compound and/or construct and composition as described herein. In particular, the present invention provides a method for prevention and/or treatment of cancer, wherein the cancer is selected from squamous cell cancer, small-cell lung cancer, non-small cell lung cancer, melanoma, kidney cancer such as renal cell carcinoma and Wilms' tumors, glioblastoma, glioma, prostate cancer, testicular cancer, gastrointestinal cancer, pancreatic cancer, biliary tract cancer, cervical cancer, ovarian cancer, liver cancer, bladder cancer, breast cancer, colon cancer, colorectal cancer, small bowel or appendix cancer, uterine or endometrial cancer, multiple myeloma, salivary gland carcinoma, adrenal gland cancer, osteosarcoma, chondrosarcoma, nasopharyngeal carcinoma, basal cell carcinoma, vulval cancer, thyroid cancer, testicular cancer, esophageal cancer, head and neck cancer, leukemia, lymphomas, merkel cell cancer and other hematologic malignancies.

It will be further appreciated that the methods and compositions described herein can be used in combination with other agents or therapeutic modalities. In one aspect, the methods and compositions described herein are administered in combination with chemotherapy, radiation therapy, cancer vaccines or one or more additional therapeutic agents, or a combination of any of the foregoing. Exemplary therapeutic agents that can be administered in combination with the methods and compositions of the invention include PD-1, PD-L1, PD-L2, CTLA-4, 4-1 BB (CD137), 4-1BB ligand, OX40, OX40 ligand, CD27, TNFRSF25, TL1A, CD40, CD40 ligand, LIGHT, LTA, HVEM, BTLA, CD160, CEACAM-1, CEACAM-5, LAIR1, 2B4, TGFR, LAG-3, TIM-3, Siglecs, ICOS (CD278), ICOS ligand, B7-H3, B7-H4, B7-1, B7-2, VISTA, HHLA2, TMIGD2, BTNL2, CD244, CD48, CD2, CDS, TIGIT, PVR family members, KIRs, ILTs, LIRs, NKG2D, NKG2A, MICA, MICB, CSF1R, IDO, TGFβ, Adenosine, ICAM-1, ICAM-2, ICAM-3, LFA-1 (CD11a/CD18), LFA-2, LFA-3, BAFFR, NKG2C, SLAMF7, NKp80, CD83 ligand, CD24, CD39, CD30, CD70, CD73, CD7, CXCR4, CXCL12, Phosphatidylserine, SIRPA, CD47, VEGF and Neuropilin.

The invention further relates to the use of a polypeptide, compound and/or construct of the invention or composition of the invention for the manufacture of a pharmaceutical composition for enhancing an immune response. In particular, the invention relates to the use of a polypeptide, compound and/or construct of the invention or composition of the invention for the manufacture of a pharmaceutical composition for enhancing proliferation or activation of T cells, B cells or natural killer cells.

The invention also relates to the use of a polypeptide, compound and/or construct of the invention or composition of the invention for the manufacture of a pharmaceutical composition for inhibiting tumor growth.

The invention also relates to the use of a polypeptide, compound and/or construct of the invention or composition of the invention for the manufacture of a pharmaceutical composition for prevention and/or treatment of at least one GITR associated diseases, disorders or conditions. Some preferred but non-limiting diseases, disorders or conditions will become clear from the further description herein.

In particular, the invention relates to the use of a polypeptide, compound and/or construct of the invention or composition of the invention for the manufacture of a pharmaceutical composition for prevention and/or treatment of T cell, B cell or natural killer cell mediated diseases.

The invention also relates to the use of a polypeptide, compound and/or construct of the invention or composition of the invention for the manufacture of a pharmaceutical composition for prevention and/or treatment of bacterial, fungal, viral or parasitic infectious diseases.

The invention also relates to the use of a polypeptide, compound and/or construct of the invention or composition of the invention for the manufacture of a pharmaceutical composition for prevention and/or treatment of cancer, wherein the cancer is selected from squamous cell cancer, small-cell lung cancer, non-small cell lung cancer, melanoma, kidney cancer such as renal cell carcinoma and Wilms' tumors, glioblastoma, glioma, prostate cancer, testicular cancer, gastrointestinal cancer, pancreatic cancer, biliary tract cancer, cervical cancer, ovarian cancer, liver cancer, bladder cancer, breast cancer, colon cancer, colorectal cancer, small bowel or appendix cancer, uterine or endometrial cancer, multiple myeloma, salivary gland carcinoma, adrenal gland cancer, osteosarcoma, chondrosarcoma, nasopharyngeal carcinoma, basal cell carcinoma, vulval cancer, thyroid cancer, testicular cancer, esophageal cancer, head and neck cancer, leukemia, lymphomas, merkel cell cancer and other hematologic malignancies.

Other aspects, advantages, applications and uses of the polypeptides and compositions will become clear from the further disclosure herein. Several documents are cited throughout the text of this specification. Each of the documents cited herein (including all patents, patent applications, scientific publications, manufacturer's specifications, instructions, etc.), whether supra or infra, are hereby incorporated by reference in their entirety.

FIGURE LEGENDS

Figure 1B:
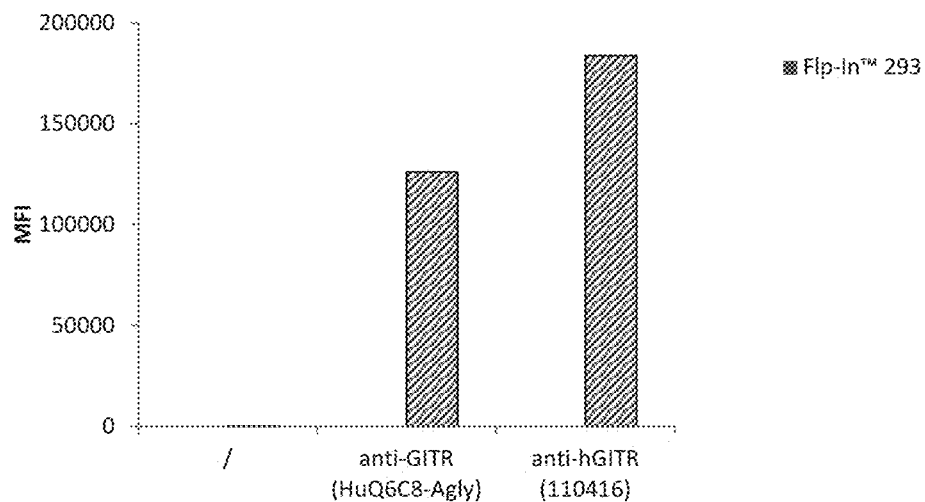
Figure 1C:
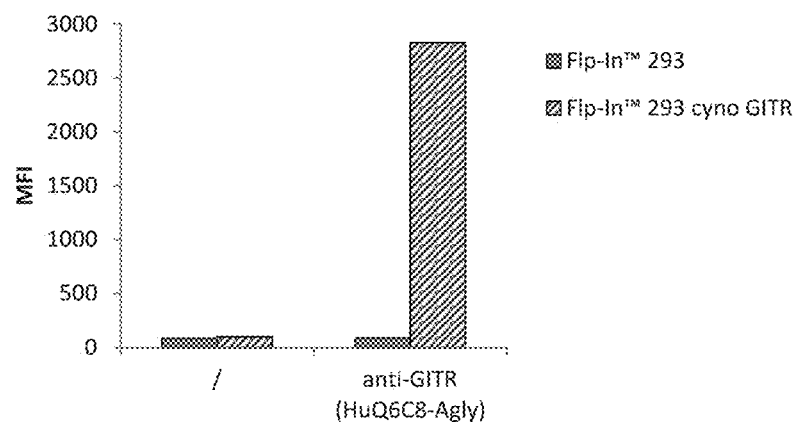
Figure 1D:
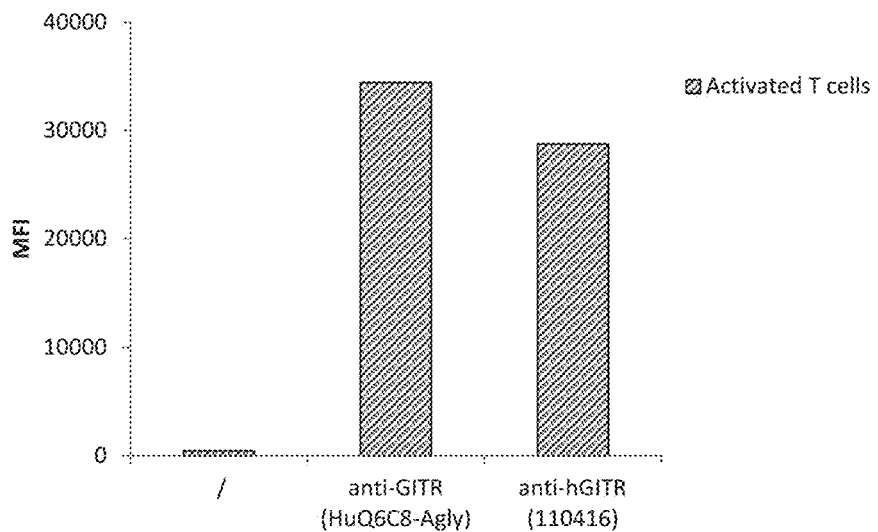

FIGS. 1A-1D: Quality control of the Flp-In™-293 cells stably transfected with mouse GITR (FIG. 1A), human GITR (FIG. 1B) or cyno GITR (FIG. 1C) and of activated T cells (FIG. 1D). The MFI value (mean fluorescence intensity) is plotted for each cell line. Detection with secondary antibody only (i.e. without the anti-GITR antibody) is indicated with "/".

Figure 2A:
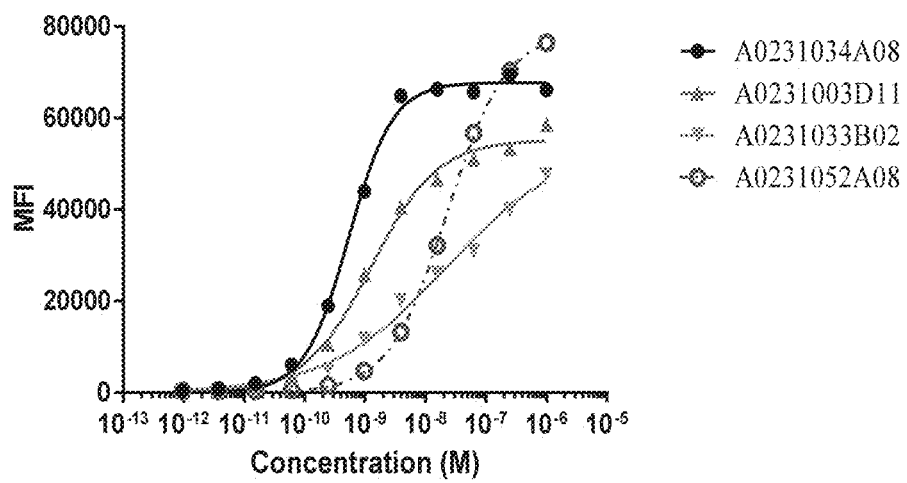
Figure 2B:
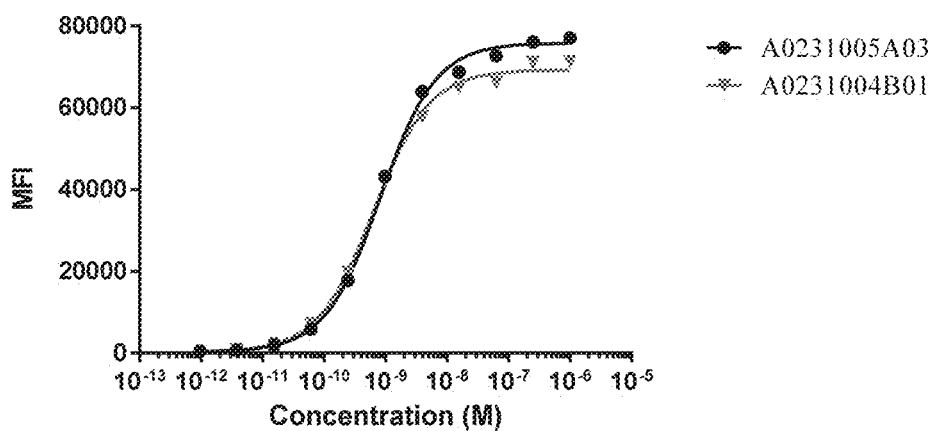

FIGS. 2A-2B: Dose dependent binding of monovalent anti-GITR Nanobodies® to human GITR expressed on activated human T cells (FIG. 2A-FIG. 2B). The MFI value (mean fluorescence intensity) is plotted against the concentration of the Nanobody®.

Figure 3:
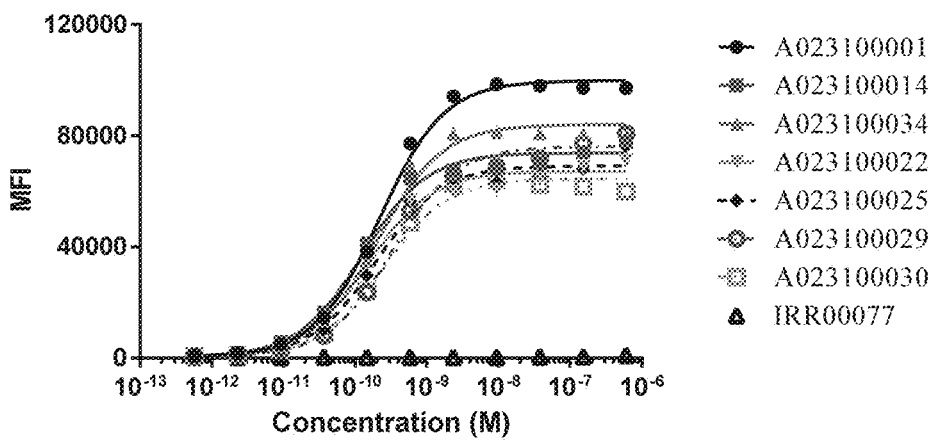
Figure 4A:
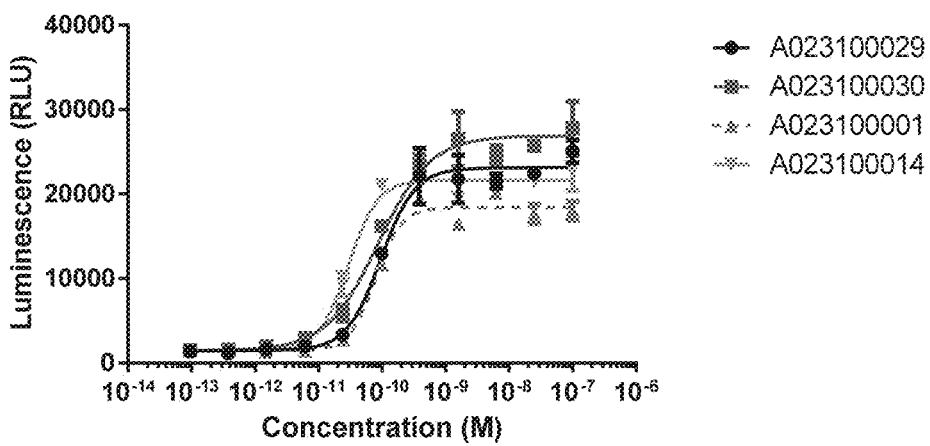
Figure 4B:
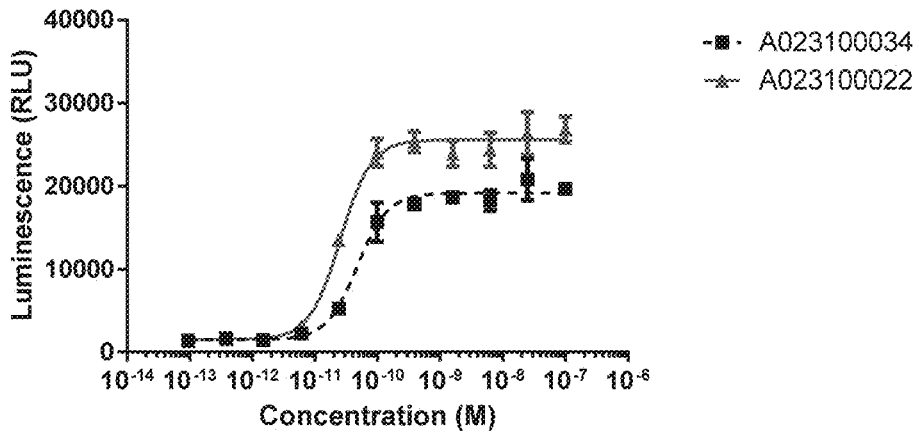
Figure 4C:
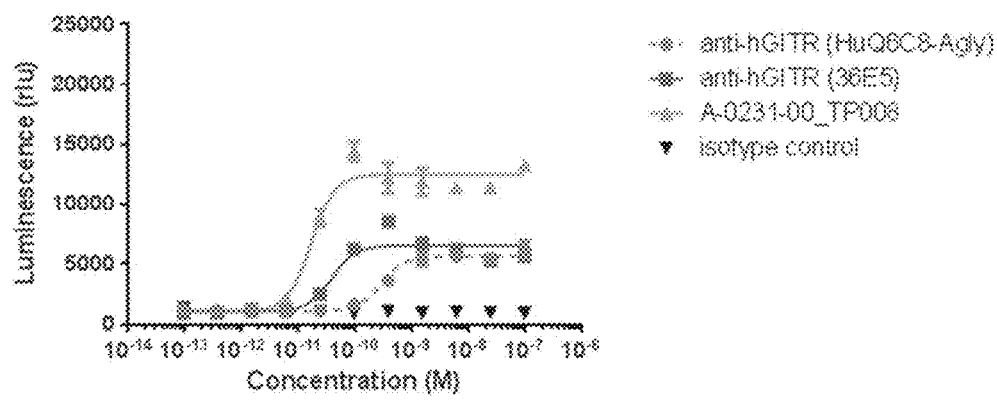
Figure 4D:
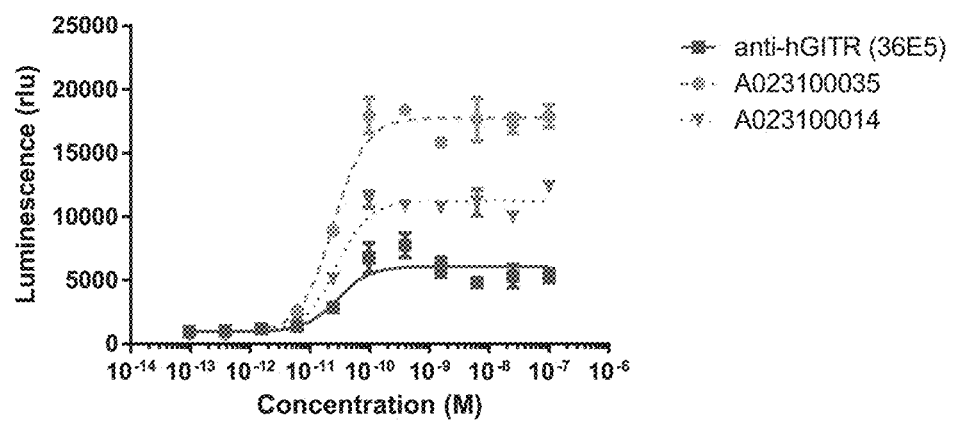

FIG. 3: Dose dependent binding of multivalent anti-GITR Nanobodies® and an irrelevant Nanobody® (IRR00077) to HEK293_NFkB-Nluc2P human GITR cells. The MFI value (mean fluorescence intensity) is plotted against the concentration of the Nanobody®.

FIGS. 4A-4D: GITR activation in GloResponse™ NF-κB-Nluc2P HEK293 luciferase reporter cells expressing human GITR. Activation is assessed by measuring luminescence. The RLU value (Relative Light Units) is plotted against the concentration of the Nanobody®.

FIGS. 5A-5F: Effect of GITR activation on T cell activation. On each plate, a range of concentrations of one Nanobody® construct and human GITR-ligand (hGITRL) (R&D Systems 6987-GL-025/CF) were tested. Each graph represents that data retrieved from one plate. Activation is measured by monitoring the IFN-γ expression.

FIGS. 6A-6D: Effect of the linker length of the Nanobody® constructs assessed in the GloResponse™ NF-κB-Nluc2P HEK293 luciferase reporter cells expressing human GITR (FIG. 6A-FIG. 6D). In constructs A023100032 and A023100035 are the A0231005A03 Nanobodies® (Family 7) linked by a 9GS linker. In constructs A023100034 and A023100022 are the A0231005A03 Nanobodies® linked by a 35GS linker. In constructs A023100045, A023100082 and A023100085 are the A0231004B01 Nanobodies® (Family 26) linked by a 3A linker. In constructs A023100083 and A023100084 are the A0231004B01 Nanobodies® linked by a 9GS linker. In construct A023100014 is the A0231004B01 Nanobody® linked by a 35GS linker.

Figure 7:
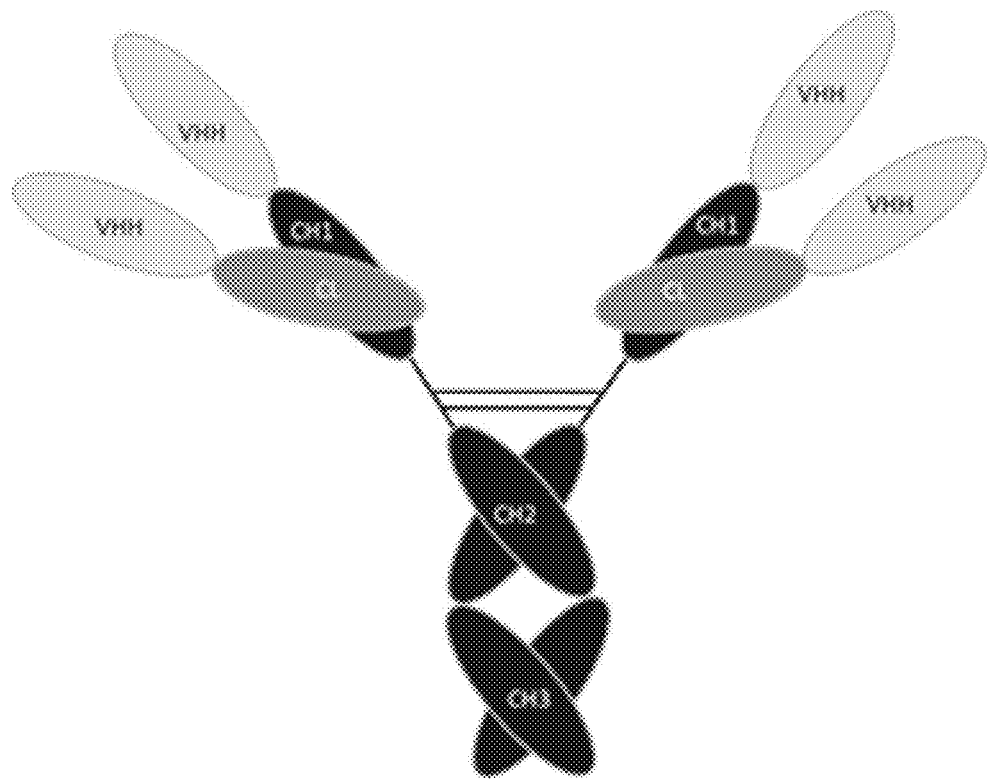

FIG. 7: Schematic representation of a Nanobody®-human IgG1 chimera.

Figure 8A:
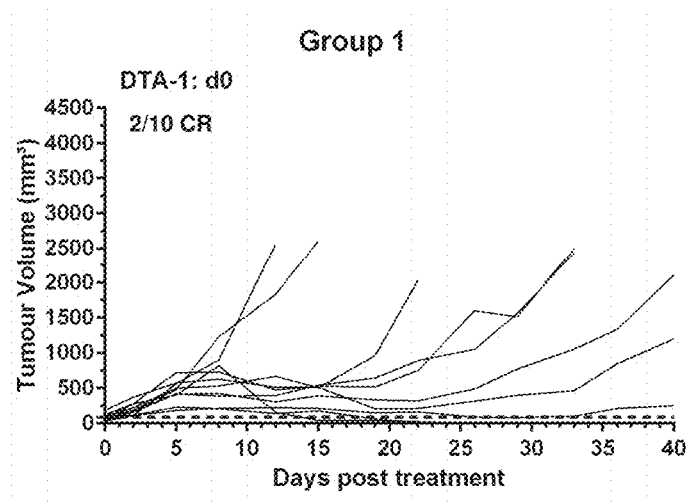
Figure 8B:
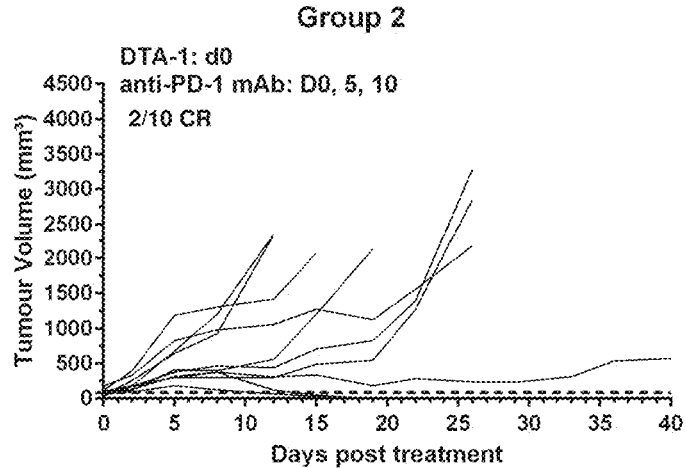
Figure 8C:
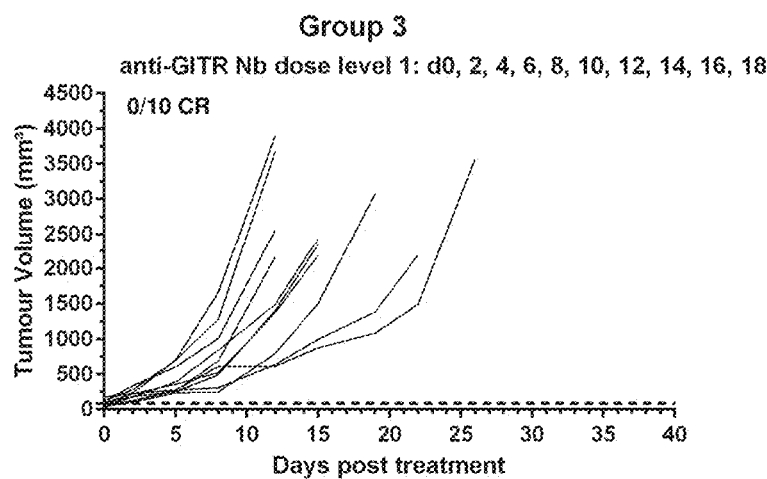
Figure 8D:
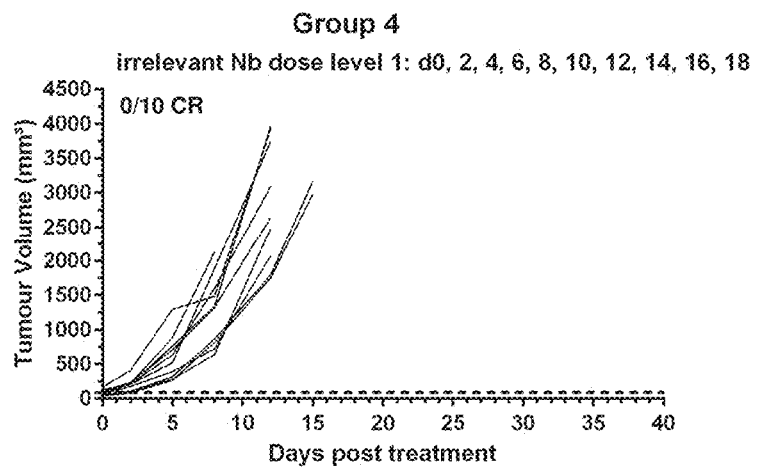
Figure 8E:
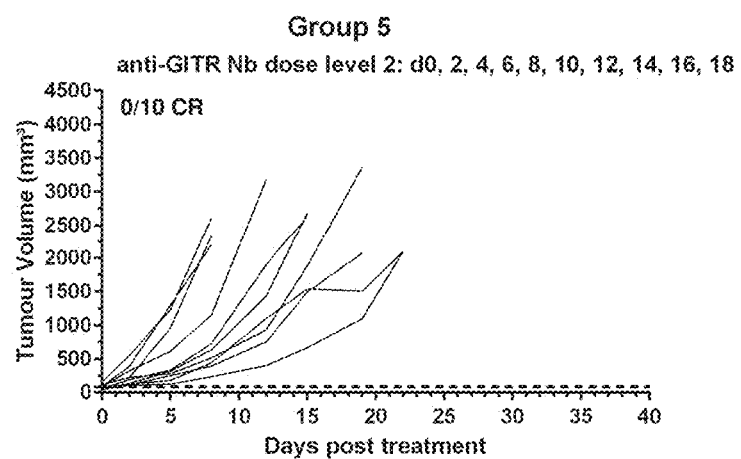
Figure 8F:
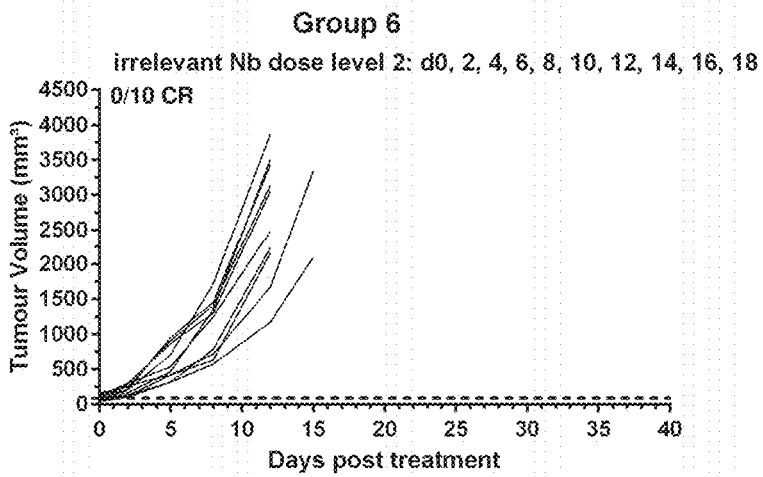
Figure 8G:
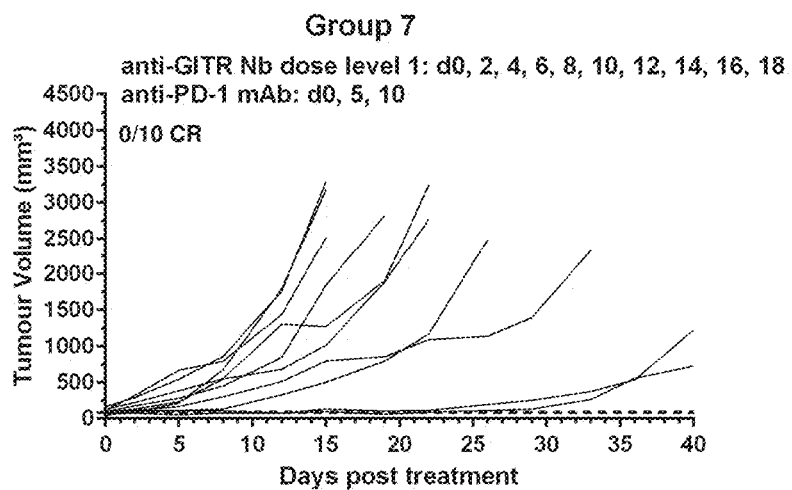
Figure 8H:
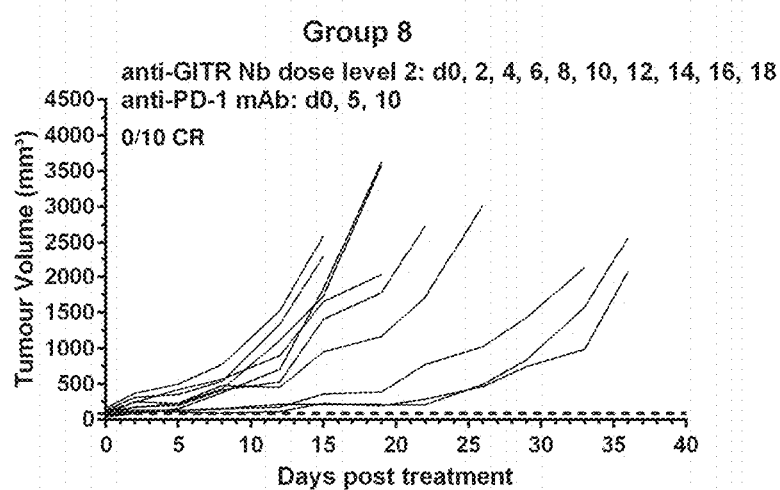
Figure 8I:
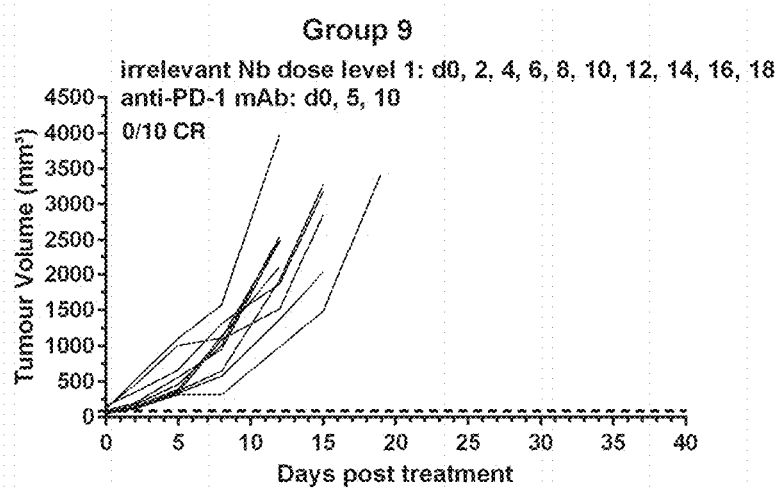
Figure 8J:
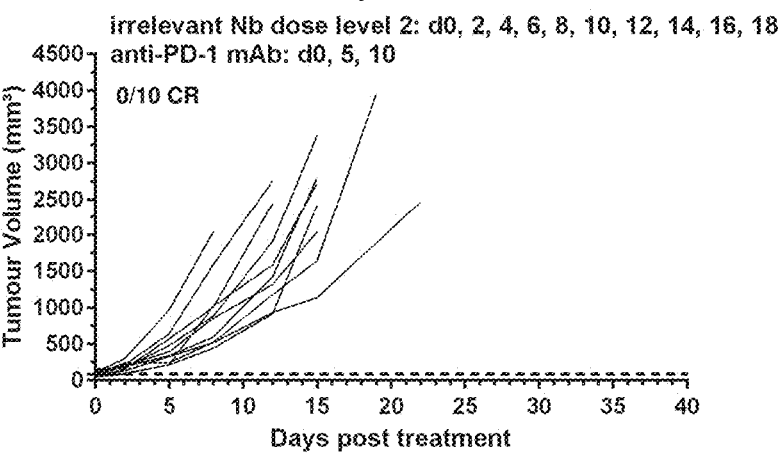
Figure 8K:
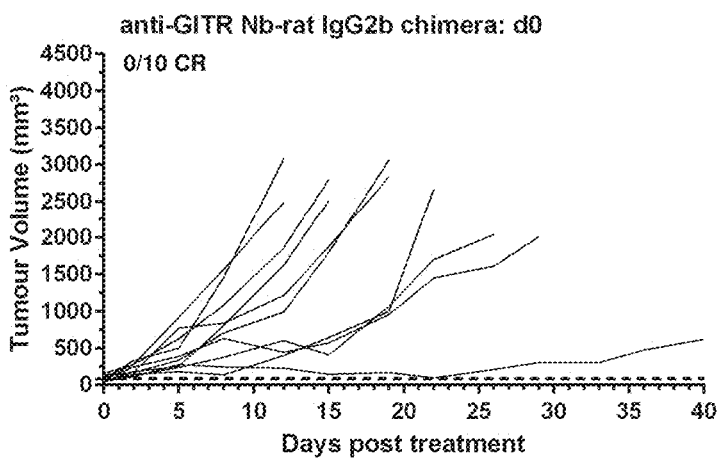
Figure 8L:
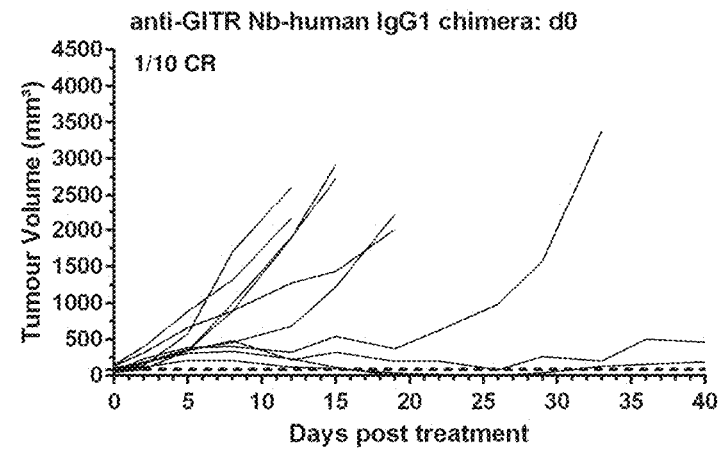
Figure 8M:
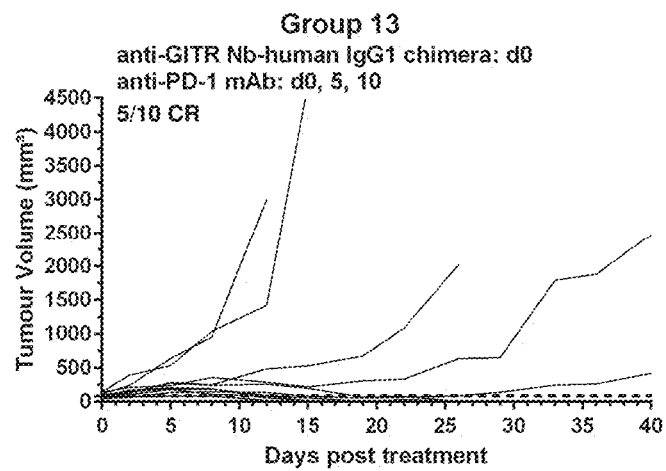
Figure 8N:
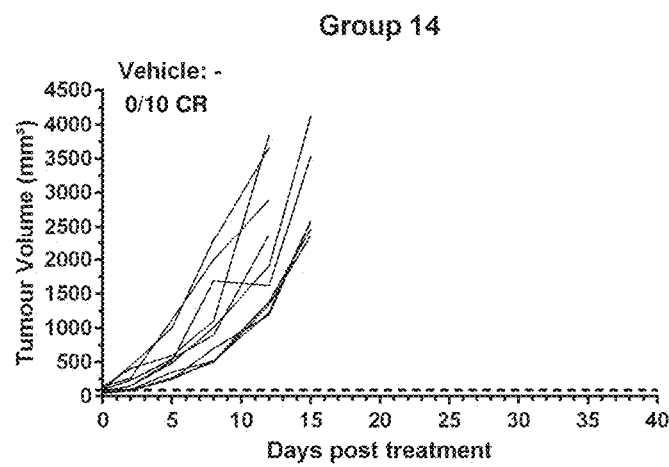
Figure 9A:
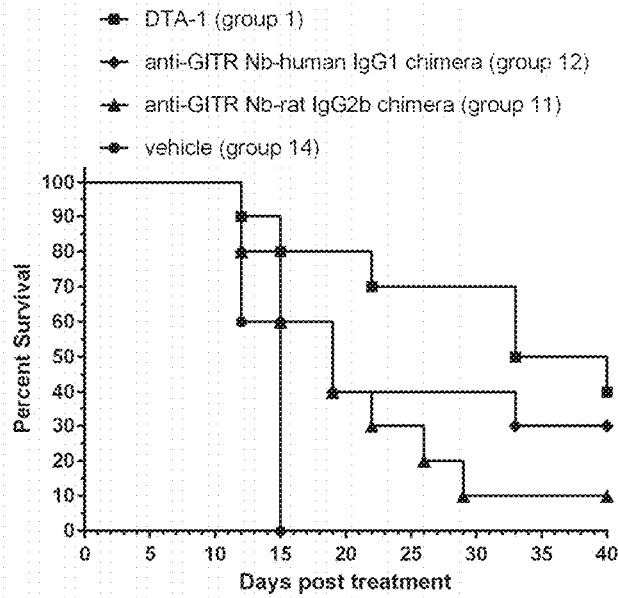
Figure 9B:
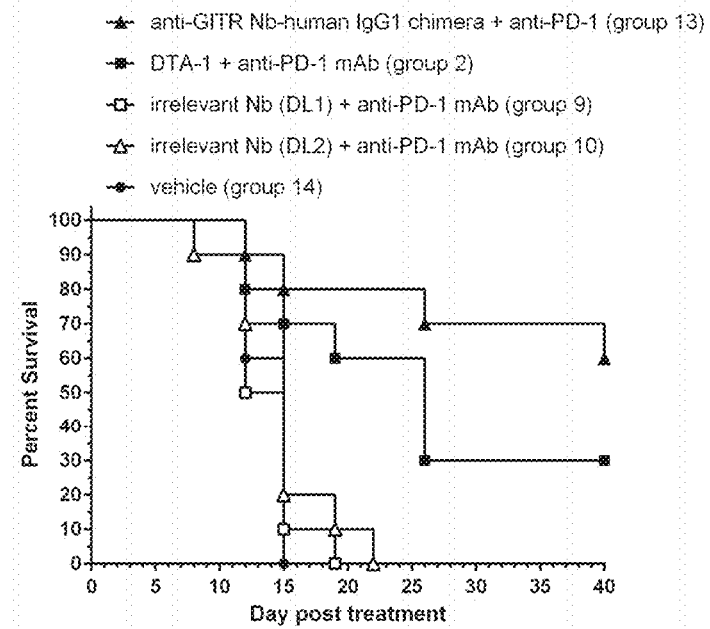
Figure 9C:
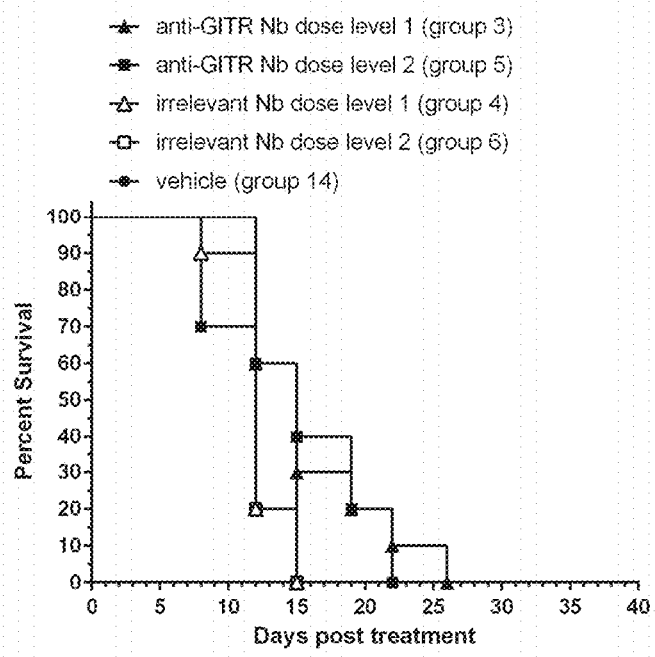
Figure 9D:
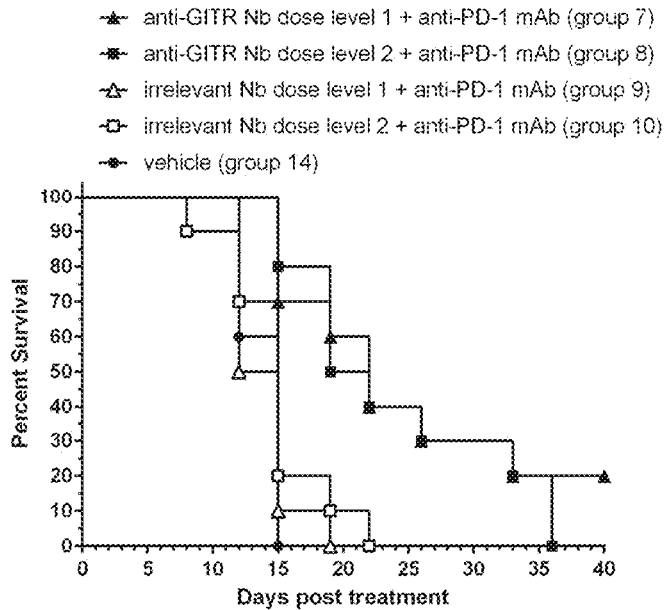

FIGS. 8A-8N: Effect of different tested compounds, alone or in combination with anti-PD-1 mAb, on anti-tumor activity measured by changes in the tumor volume in groups of mice treated with DTA-1 (FIG. 8A); DTA-1+anti-PD-1 mAb (FIG. 8B); anti-GITR NB dose level 1 (FIG. 8C); irrelevant NB dose level 1 (FIG. 8D); anti-GITR NB dose level 2 (FIG. 8E); irrelevant NB dose level 2 (FIG. 8F); anti-GITR NB dose level 1+anti-PD-1 mAb (FIG. 8G); anti-GITR NB dose level 2+anti-PD-1 mAb (FIG. 8H); irrelevant NB dose level 1+anti-PD-1 mAb (FIG. 8I); irrelevant NB dose level 2+anti-PD-1 mAb (FIG. 8J); anti-GITR Nb-rat IgG2b chimera (FIG. 8K); anti-GITR Nb-human IgG1 chimera (FIG. 8L); anti-GITR Nb-human IgG1 chimera+anti-PD-1 mAb (FIG. 8M) and vehicle (FIG. 8N). CR denotes complete regression.

FIGS. 9A-9D: Effect of different tested compounds, alone or in combination with anti-PD-1 mAb, on survival during the course of treatment.

Figure 10A:
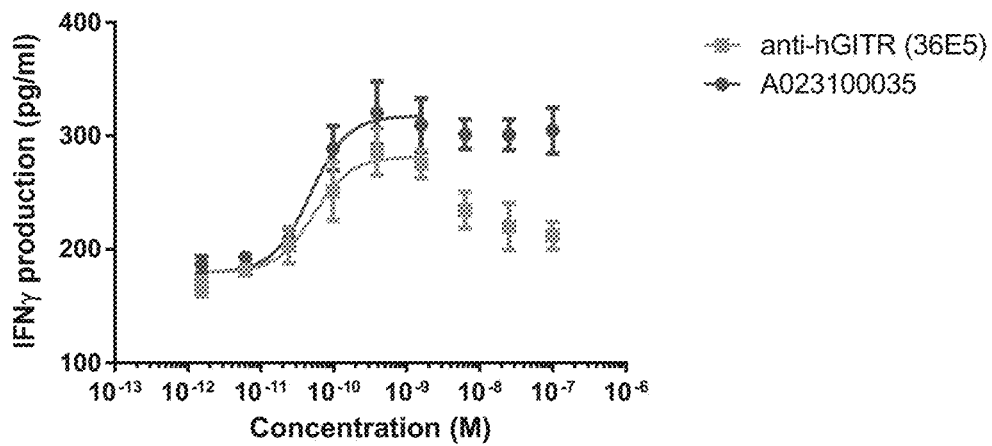
Figure 10B:
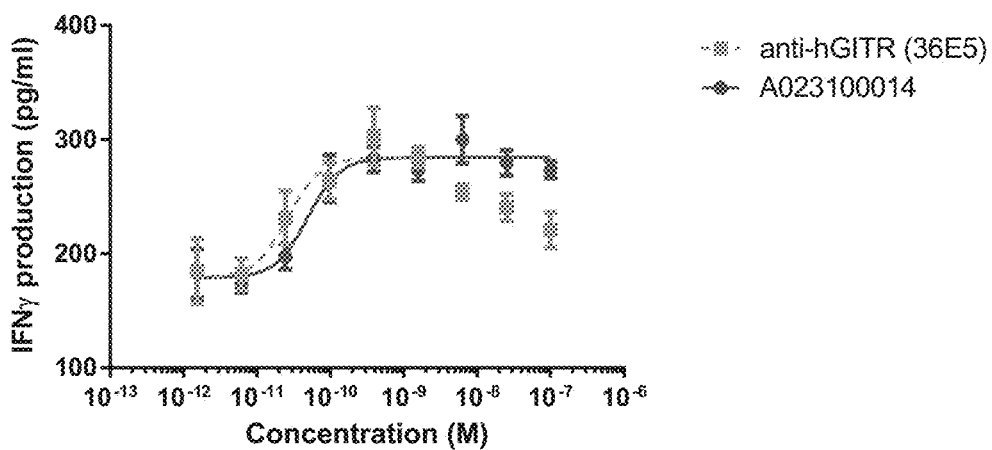
Figure 10C:
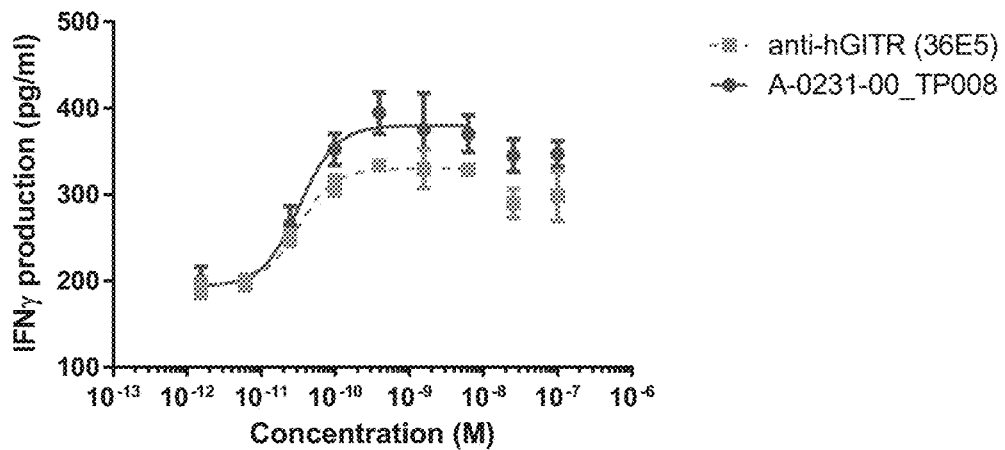

FIGS. 10A-10C: In vitro benchmarking of the anti-GITR Nanobodies® as assessed in the T cell activation assay. On each plate, a range of concentrations of one Nanobody® construct and the clinical stage 36E5 mAb were tested. Each graph represents that data retrieved from one plate. Activation is measured by monitoring the IFN-γ expression.

Figure 11:
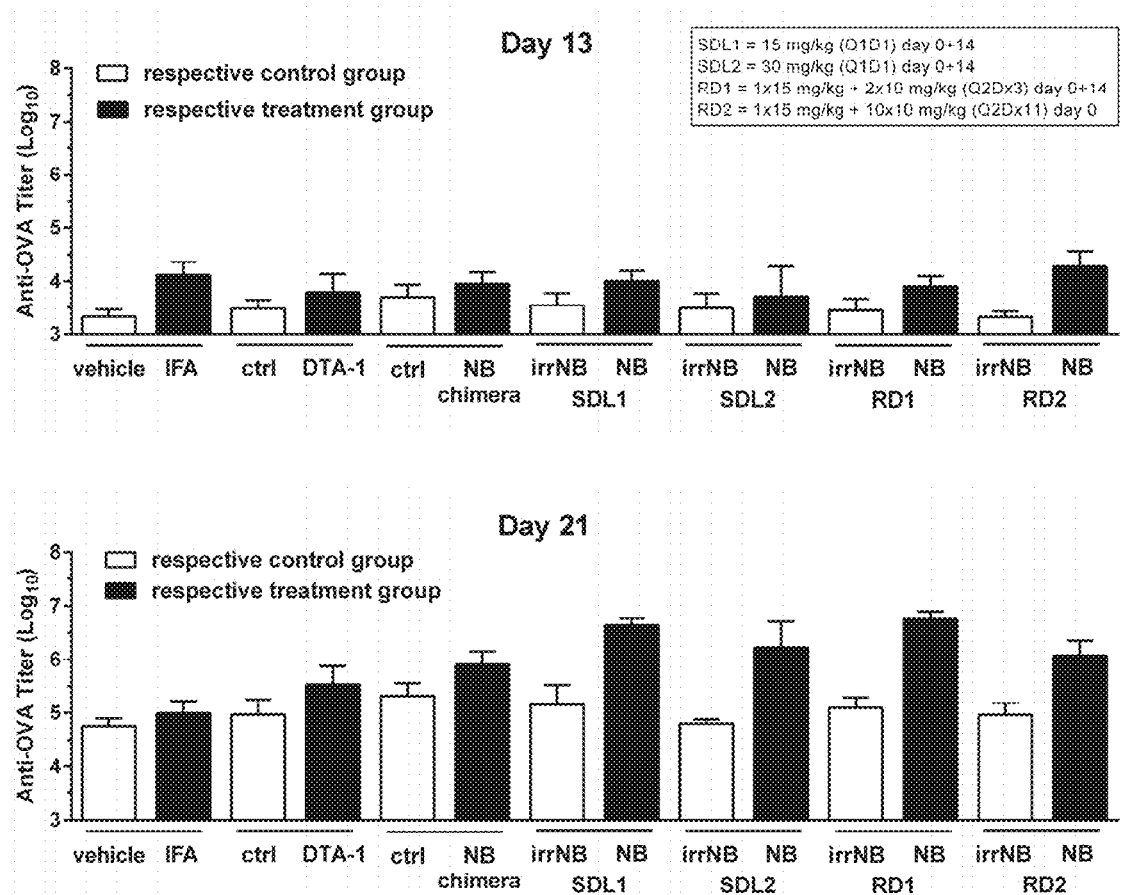
Figure 12A:
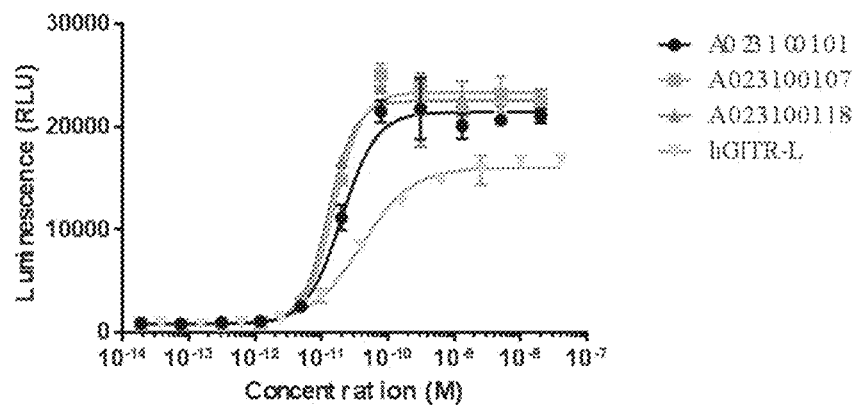
Figure 12B:
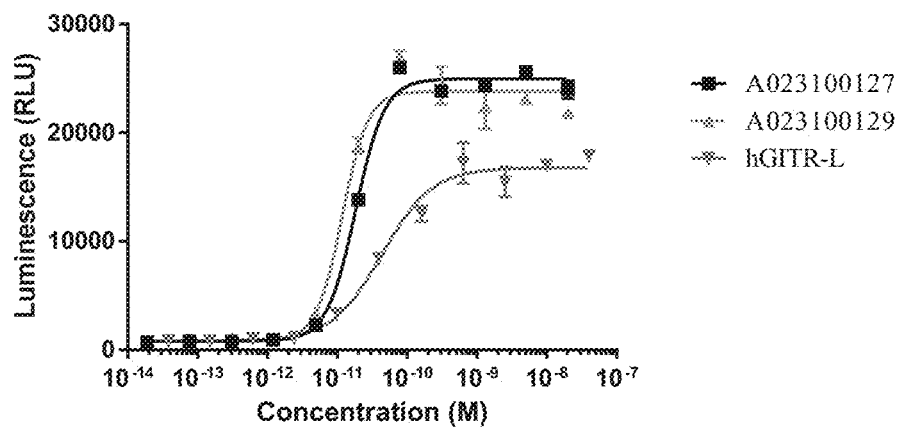
Figure 12C:
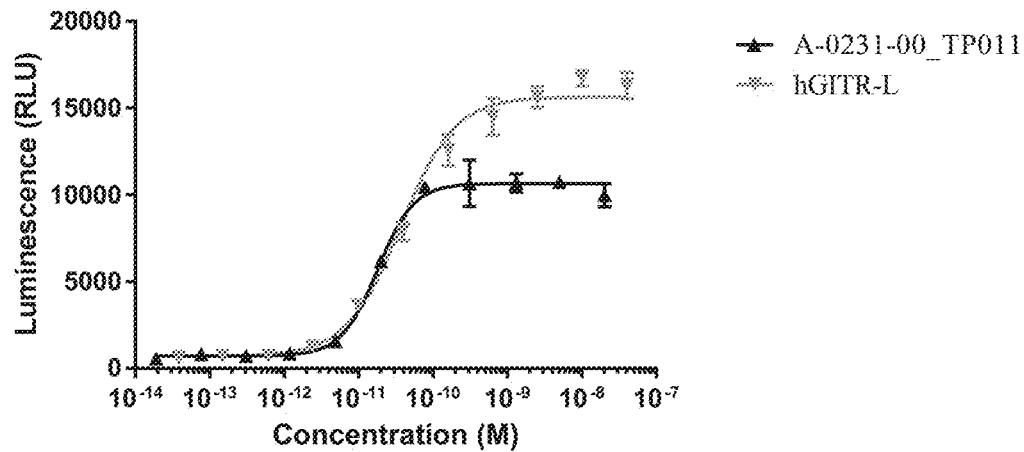
Figure 12D:
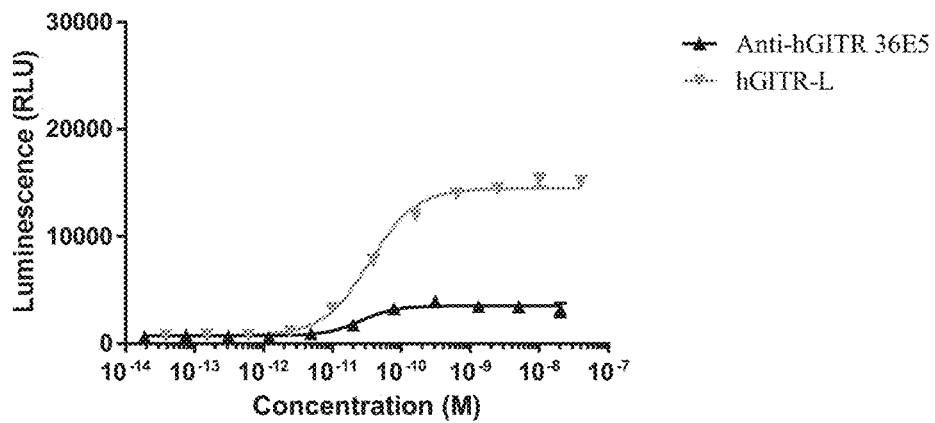
Figure 13A:
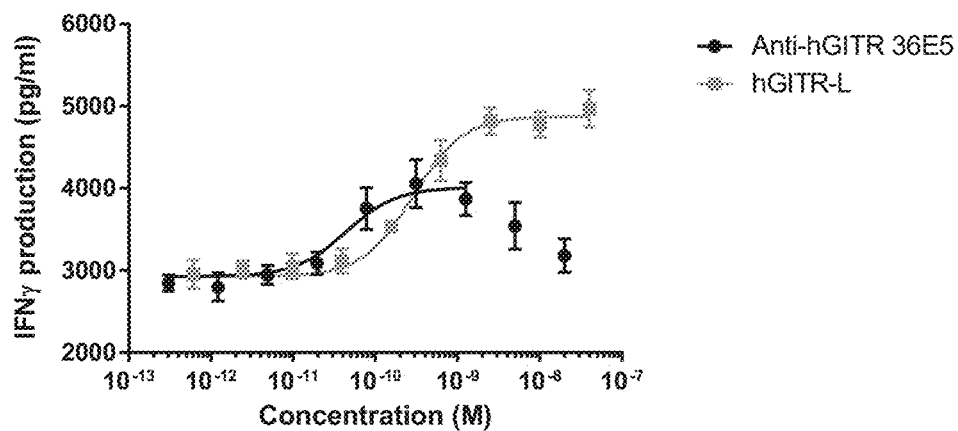
Figure 13B:
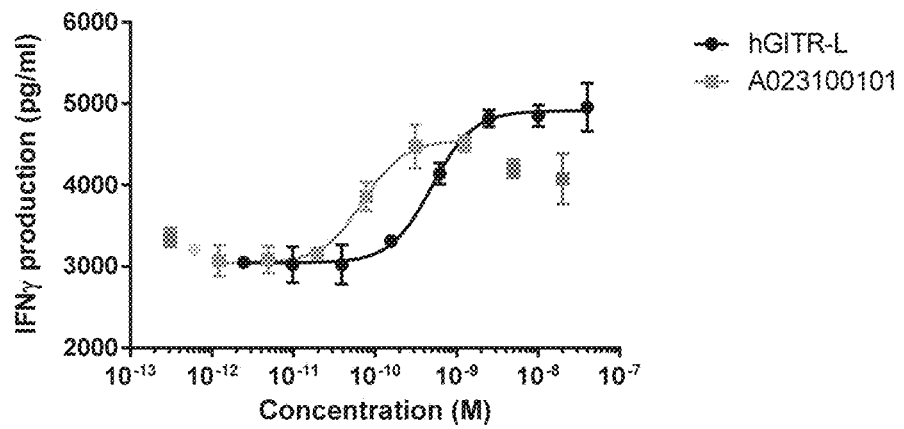
Figure 13C:
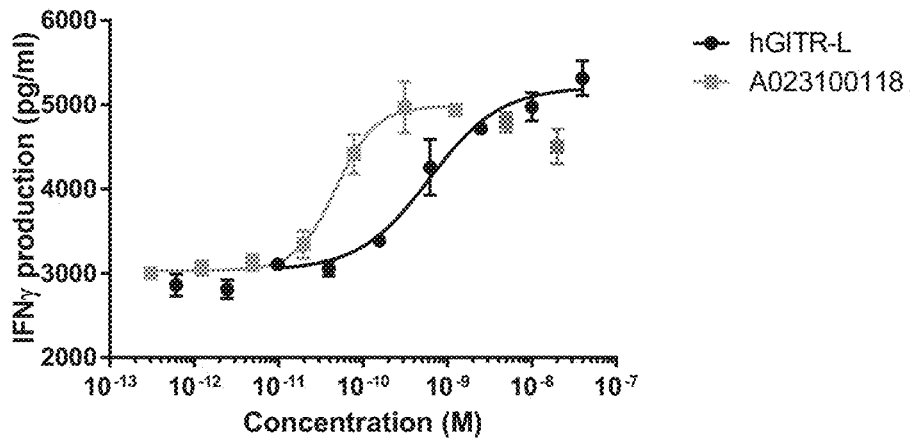
Figure 13D:
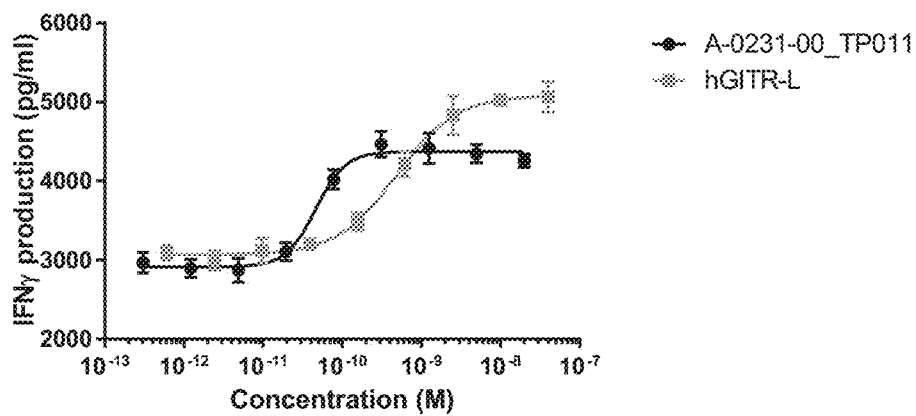
Figure 13E:
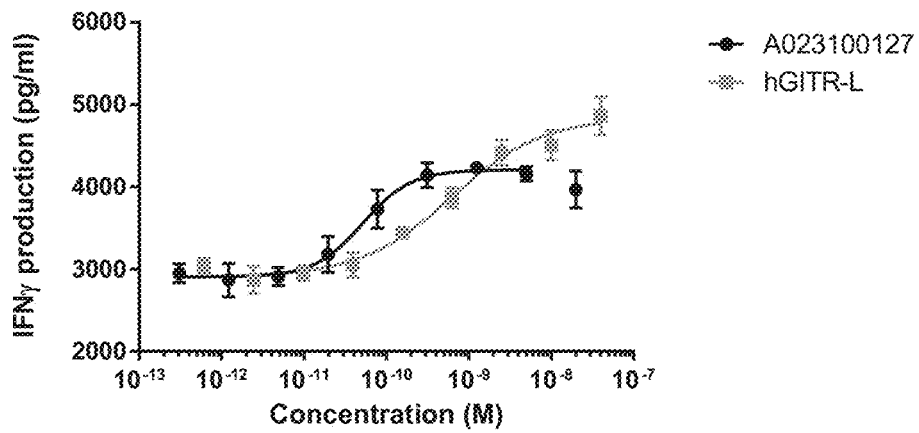
Figure 13F:
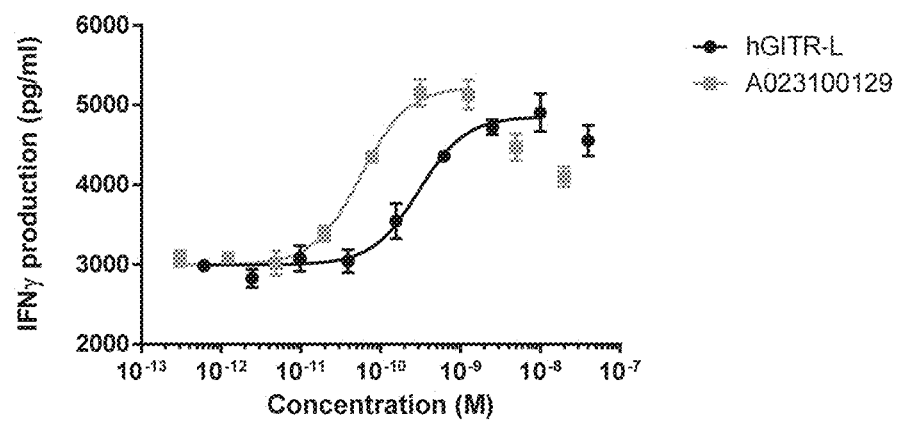
Figure 13G:
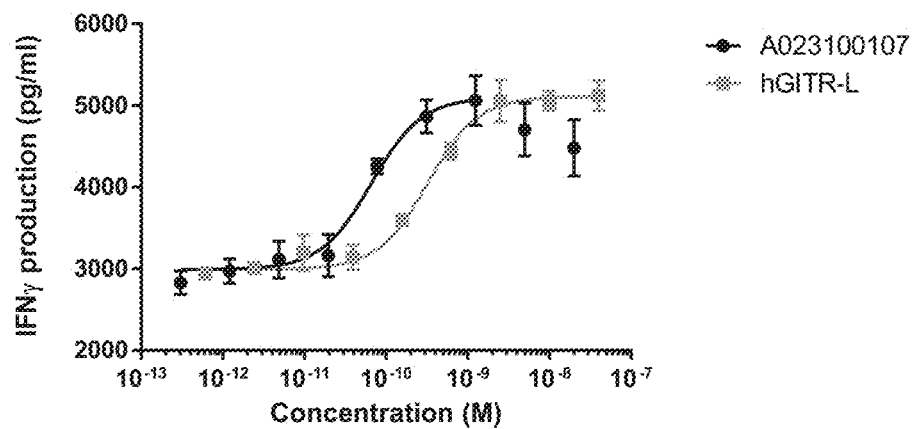

FIG. 11: Adjuvant effect of anti-GITR multivalent Nanobody® A023100035 and anti-GITR Nanobody®-huIgG1 chimera (A-0231-00 TP008) measured as anti-OVA total IgG titres on days 13 and day 21 after OVA prime and day 14 boost immunization. SDL1: single dose level 1 (on day 0 and day 14); SDL2: single dose level 2 (on day 0 and day 14); RD1: repeated dosing regimen 1 (3 injections with 1 injection every 2 days starting on day 0 and day 14, Q2Dx3); RD2: repeated dosing regimen 2 (11 injections with 1 injection every 2 days, Q2Dx11).

FIGS. 12A-12D: GITR activation by multivalent sequence optimized Nanobodies® in GloResponse™ NF-κB-Nluc2P HEK293 luciferase reporter cells expressing human GITR. Activation is assessed by measuring luminescence. The RLU value (Relative Light Units) is plotted against the concentration of the Nanobody®.

FIGS. 13A-13G: Effect of GITR activation by multivalent sequence optimized Nanobodies® on T cell activation. On each plate, a range of concentrations of one Nanobody® construct and human GITR-ligand (hGITRL) (R&D Systems 6987-GL-025/CF) were tested. Each graph represents that data retrieved from one plate. Activation is measured by monitoring the IFN-γ expression.

Figure 14D:
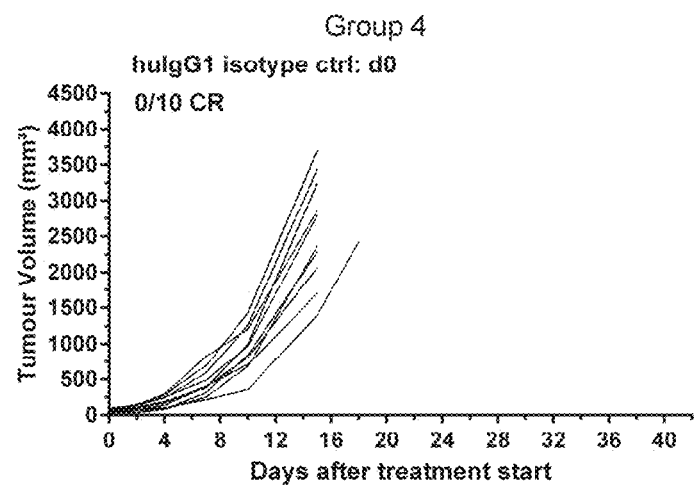
Figure 14E:
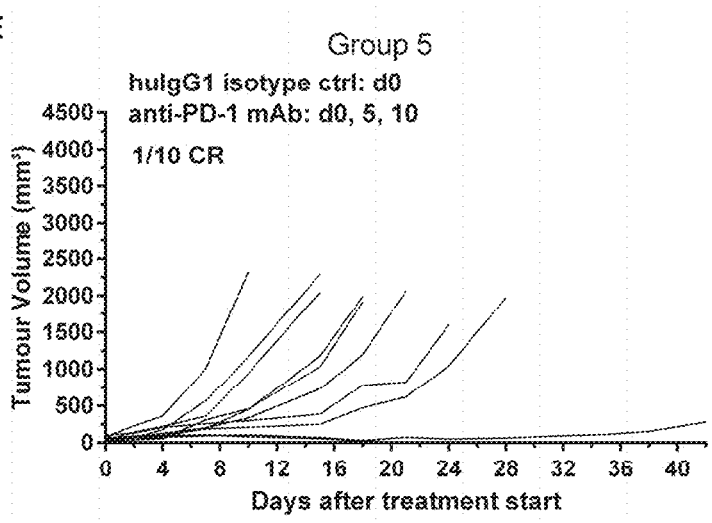
Figure 14F:
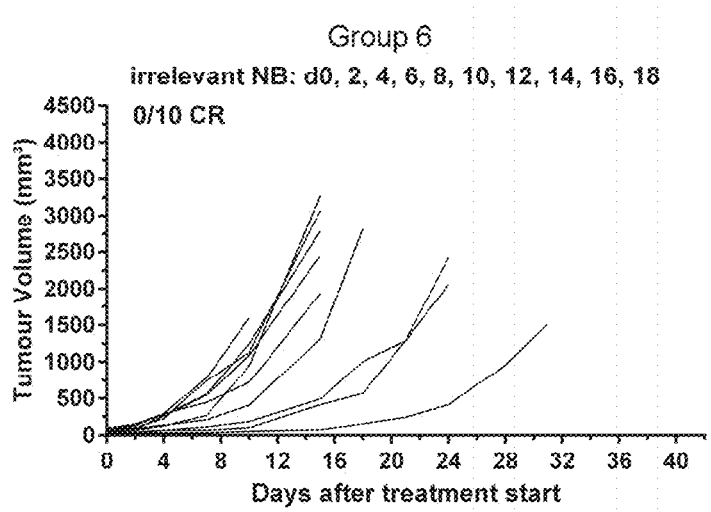
Figure 14G:
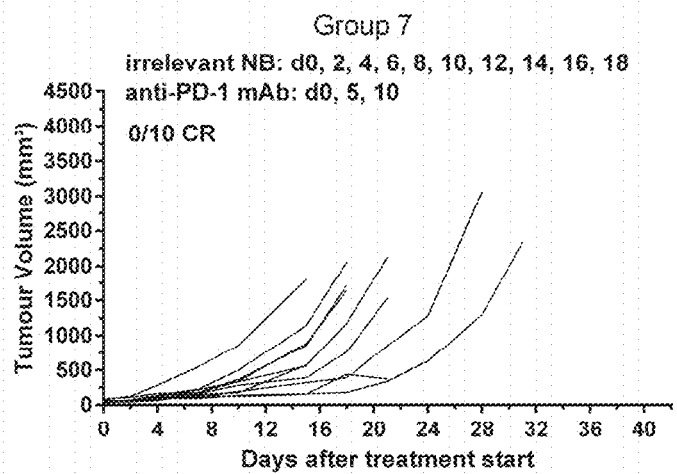
Figure 14H:
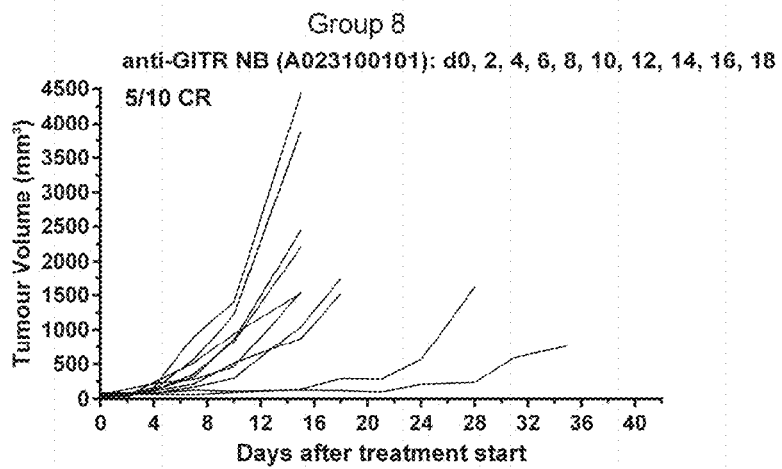
Figure 14I:
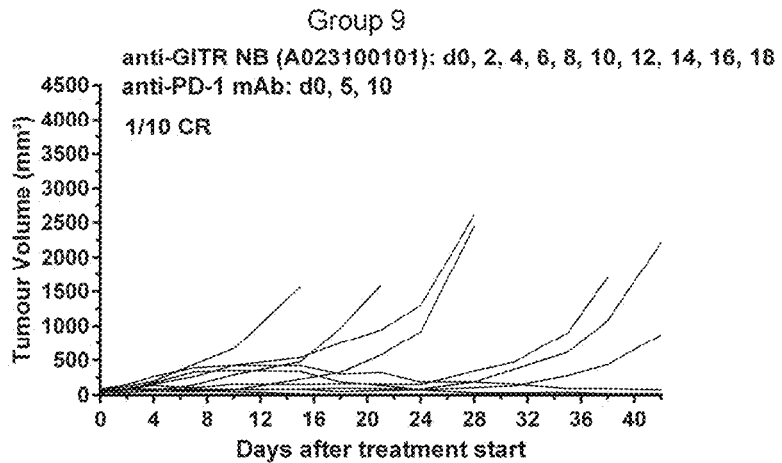
Figure 14J:
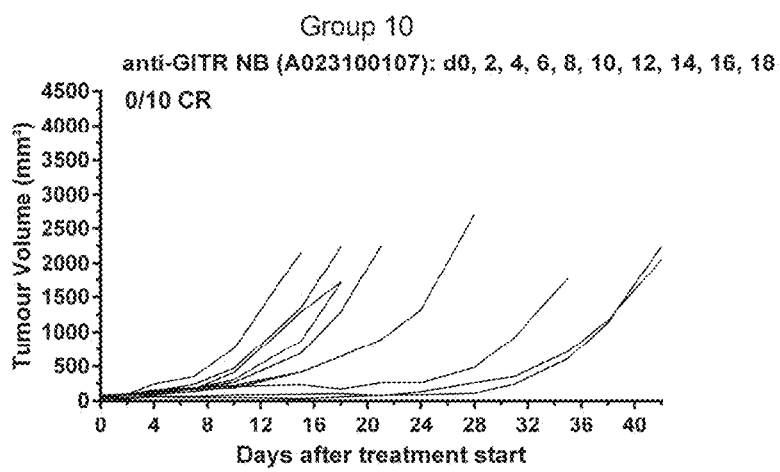
Figure 14K:
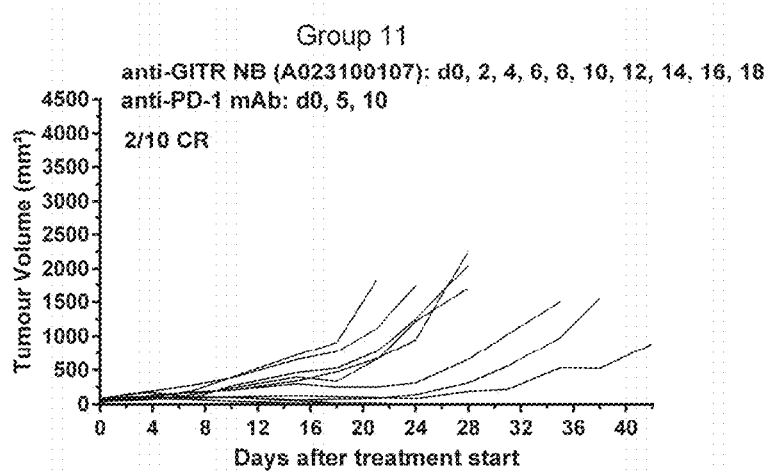
Figure 14L:
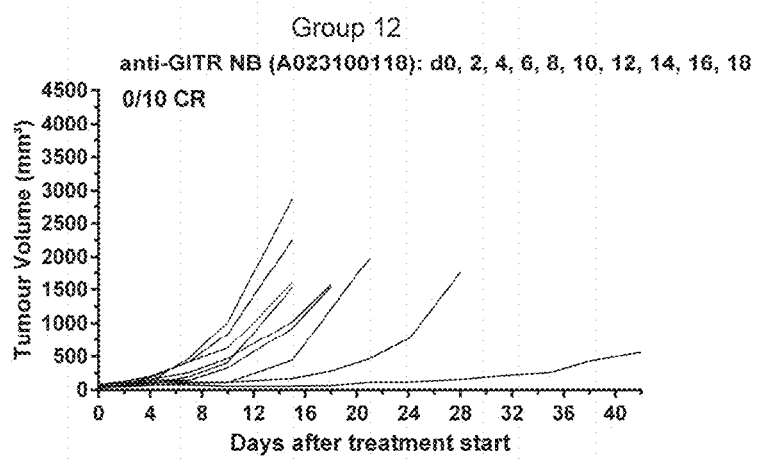
Figure 14M:
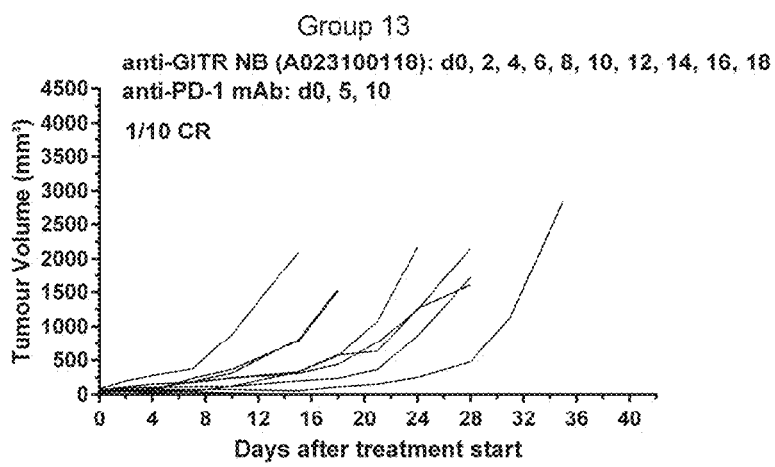
Figure 14N:
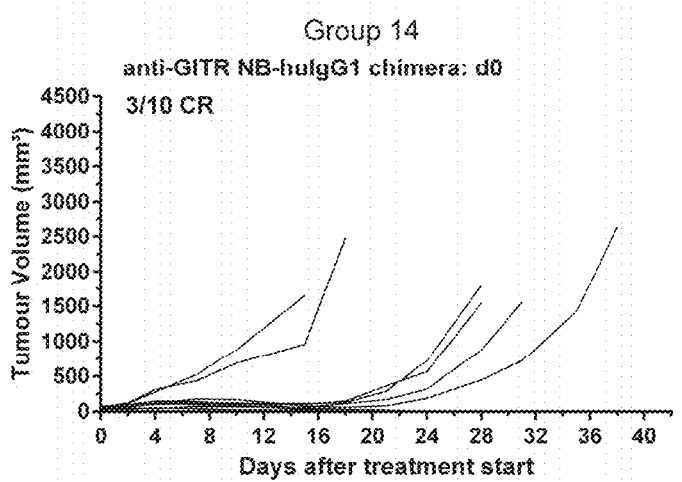
Figure 14O:
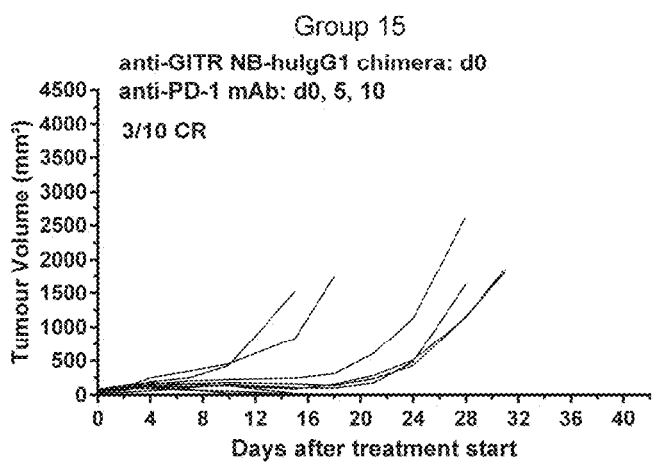

FIGS. 14A-14O: Effect of different tested compounds, alone or in combination with anti-PD-1 mAb, on anti-tumor activity measured by changes in the tumor volume over time in groups of mice treated with vehicle (FIG. 14A); DTA-1 (FIG. 14B); DTA-1+anti-PD-1 mAb (FIG. 14C); huIgG1 isotype control (FIG. 14D); huIgG1 isotype control+anti-PD-1 (FIG. 14E); irrelevant NB (FIG. 14F); irrelevant NB+anti-PD-1 mAb (FIG. 14G); anti-GITR NB A023100101 (FIG. 14H); anti-GITR NB A023100101+anti-PD-1 mAb (FIG. 14I); anti-GITR NB A023100107 (FIG. 14J); anti-GITR NB A023100107+anti-PD-1 mAb (FIG. 14K); anti-GITR NB A023100118 (FIG. 14L); anti-GITR NB A023100118+anti-PD-1 mAb (FIG. 14M); anti-GITR Nanobody®-huIgG1 chimera (FIG. 14N); anti-GITR Nanobody®-huIgG1 chimera+anti-PD-1 mAb (FIG. 14O). CR denotes complete regression.

Figure 15A:
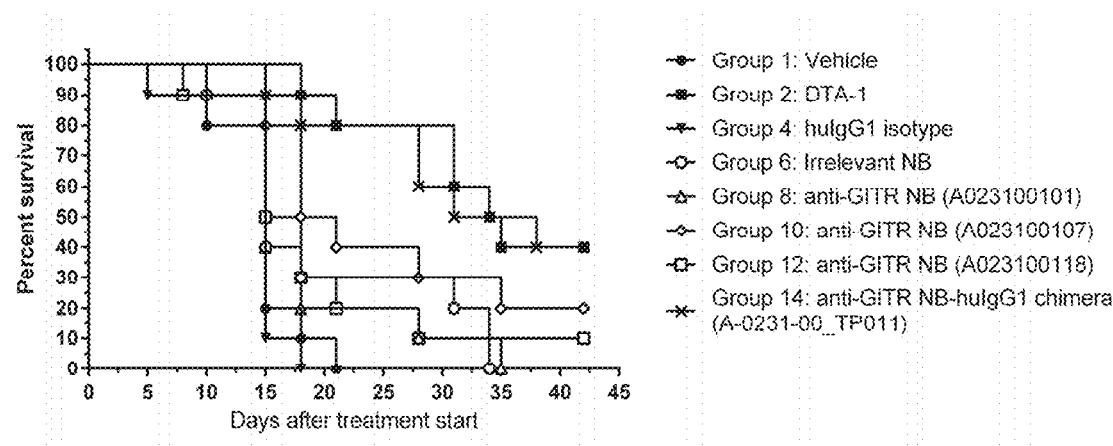
Figure 15B:
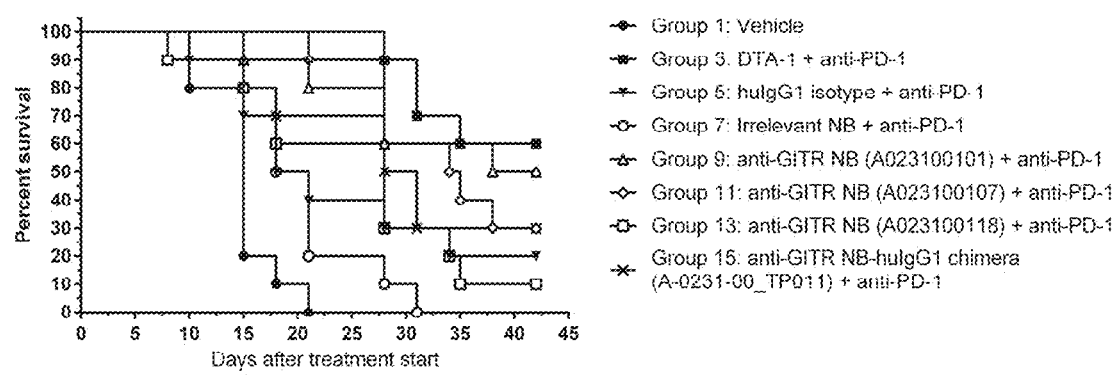

FIGS. 15A-15B: Effect of different tested compounds, alone or in combination with anti-PD-1 mAb, on survival during the course of treatment.

DETAILED DESCRIPTION

Definitions

Unless indicated or defined otherwise, all terms used have their usual meaning in the art, which will be clear to the skilled person. Reference is for example made to the standard handbooks, such as Sambrook et al. (Molecular Cloning: A Laboratory Manual (2nd.Ed.) Vols. 1-3, Cold Spring Harbor Laboratory Press, 1989), F. Ausubel et al. (Current protocols in molecular biology, Green Publishing and Wiley Interscience, New York, 1987), Lewin (Genes II, John Wiley & Sons, New York, N.Y., 1985), Old et al. (Principles of Gene Manipulation: An Introduction to Genetic Engineering (2nd edition) University of California Press, Berkeley, C A, 1981); Roitt et al. (Immunology (6th. Ed.) Mosby/Elsevier, Edinburgh, 2001), Roitt et al. (Roitt's Essential Immunology ($10^{th}$ Ed.) Blackwell Publishing, U K, 2001), and Janeway et al. (Immunobiology (6th Ed.) Garland Science Publishing/Churchill Livingstone, New York, 2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as for example the following reviews Presta (Adv. Drug Deliv. Rev. 58 (5-6): 640-56, 2006), Levin and Weiss (Mol. Biosyst. 2(1): 49-57, 2006), Irving et al. (J. Immunol. Methods 248(1-2): 31-45, 2001), Schmitz et al. (Placenta 21 Suppl. A: S106-12, 2000), Gonzales et al. (Tumour Biol. 26(1): 31-43, 2005), which describe techniques for protein engineering, such as affinity maturation and other techniques for improving the specificity and other desired properties of proteins such as immunoglobulins.

The term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

Amino acid residues will be indicated according to the standard three-letter or one-letter amino acid code. Reference is made to Table A-2 on page 48 of WO 08/020079.

A nucleic acid or amino acid is considered to be "(in) (essentially) isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or amino acid is considered "(essentially) isolated" when it has been purified at least 2-fold, in particular at least 10-fold, more in particular at least 100-fold, and up to 1000-fold or more. A nucleic acid or amino acid that is "in (essentially) isolated form" is preferably essentially homogeneous, as determined using a suitable technique, such as a suitable chromatographical technique, such as polyacrylamide-gel electrophoresis.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain, this may mean that said immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence).

By "essentially consist of" is meant that the immunoglobulin single variable domain used in the method of the invention either is exactly the same as the polypeptide of the invention or corresponds to the polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the immunoglobulin single variable domain.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as NCBI Blast v2.0, using standard settings. Some other techniques, computer algorithms and settings for determining the degree of sequence identity are for example described in WO 04/037999, EP 0967284, EP 1085089, WO 00/55318, WO 00/78972, WO 98/49185 and GB 2357768. Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein. Alternatively, the degree of sequence identity between two amino acid sequences may be calculated using a known computer algorithm, such as those mentioned above for determining the degree of sequence identity for nucleotide sequences, again using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB 2357768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, lie, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into lie or into Val; Lys into Arg, into Gln or into Glu; Met into Leu, into Tyr or into lie; Phe into Met, into Leu or into Tyr; Ser into Thr; Thr into Ser; Trp into Tyr; Tyr into Trp; and/or Phe into Val, into lie or into Leu.

Any amino acid substitutions applied to the polypeptides described herein may also be based on 5 the analysis of the frequencies of amino acid variations between homologous proteins of different species developed by Schulz et al. ("Principles of Protein Structure", Springer-Verlag, 1978), on the analyses of structure forming potentials developed by Chou and Fasman (Biochemistry 13: 211, 1974; Adv. Enzymol., 47: 45-149, 1978), and on the analysis of hydrophobicity patterns in proteins developed by Eisenberg et al. (Proc. Natl. Acad Sci. USA 81: 140-144, 1984), Kyte and Doolittle (J. Molec. Biol. 157: 105-132, 1981), and Goldman et al. (Ann. Rev. Biophys. Chem. 15: 321-353, 1986), all incorporated herein in their entirety by reference. Information on the primary, secondary and tertiary structure of Nanobodies® is given in the description herein and in the general background art cited above. Also, for this purpose, the crystal structure of a $V_{HH}$ domain from a llama is for example given by Desmyter et al. (Nature Structural Biology, 3: 803, 1996), Spinelli et al. (Natural Structural Biology, 3: 752-757, 1996) and Decanniere et al. (Structure, 7 (4): 361, 1999). Further information about some of the amino acid residues that in conventional $V_H$ domains form the $V_H/V_L$ interface and potential camelizing substitutions on these positions can be found in the prior art cited above.

Amino acid sequences and nucleic acid sequences are said to be "exactly the same" if they have 100% sequence identity (as defined herein) over their entire length.

When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences.

The "amino acid difference" can be any one, two, three or maximal four substitutions, deletions or insertions, or any combination thereof, that either improve the properties of the polypeptide of the invention or that at least do not detract too much from the desired properties or from the balance or combination of desired properties of the polypeptide of the invention. In this respect, the resulting polypeptide of the invention should at least bind GITR with the same, about the same, or a higher affinity compared to the polypeptide comprising the one or more CDR sequences without the one, two, three or maximal four substitutions, deletions or insertions, said affinity as e.g. measured by surface plasmon resonance (SPR).

For example, and depending on the host organism used to express the polypeptide of the invention, such deletions and/or substitutions may be designed in such a way that one or more sites for post-translational modification (such as one or more glycosylation sites) are removed, as will be within the ability of the person skilled in the art.

A "Nanobody® family", "VHH family" or "family" as used in the present specification refers to a group of Nanobodies® and/or VHH sequences that have identical lengths (i.e. they have the same number of amino acids within their sequence) and of which the amino acid sequence between position 8 and position 106 (according to Kabat numbering) has an amino acid sequence identity of 89% or more.

The terms "epitope" and "antigenic determinant", which can be used interchangeably, refer to the part of a macromolecule, such as a polypeptide or protein that is recognized by antigen-binding molecules, such as immunoglobulins, conventional antibodies, immunoglobulin single variable domains and/or polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as an immunoglobulin, a conventional antibody, an immunoglobulin single variable domain and/or a polypeptide of the invention) that recognizes the epitope is called a "paratope".

A polypeptide (such as an immunoglobulin, an antibody, an immunoglobulin single variable domain, a polypeptide of the invention, or generally an antigen binding molecule or a fragment thereof) that can "bind to" or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g., "anti"-GITR).

The term "specificity" has the meaning given to it in paragraph n) on pages 53-56 of WO 08/020079; and as mentioned therein refers to the number of different types of antigens or antigenic determinants to which a particular antigen-binding molecule or antigen-binding protein (such as an immunoglobulin single variable domain and/or a polypeptide of the invention) can bind. The specificity of an antigen-binding protein can be determined based on affinity and/or avidity, as described on pages 53-56 of WO 08/020079 (incorporated herein by reference), which also describes some preferred techniques for measuring binding between an antigen-binding molecule (such as an immunoglobulin single variable domain and/or polypeptide of the invention) and the pertinent antigen. Typically, antigen-binding proteins (such as the immunoglobulin single variable domains and/or polypeptides of the invention) will bind to their antigen with a dissociation constant ($K_D$) of $10^5$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ $M^{-1}$) is generally considered to indicate non-specific binding. Preferably, a monovalent polypeptide of the invention will bind to the desired antigen with an affinity less than 500 nM, preferably less than 200 nM, more preferably less than 10 nM, such as e.g., between 10 and 5 nM or less. Specific binding of an antigen-binding protein to an antigen or antigenic determinant can be determined in any suitable manner known per se, including, for example, Scatchard analysis and/or competitive binding assays, such as radio-immunoassays (RIA), enzyme immunoassays (EIA) and sandwich competition assays, and the different variants thereof known in the art; as well as the other techniques mentioned herein. As will be clear to the skilled person, and as described on pages 53-56 of WO 08/020079, the dissociation constant may be the actual or apparent dissociation constant. Methods for determining the dissociation constant will be clear to the skilled person, and for example include the techniques mentioned on pages 53-56 of WO 08/020079.

An immunoglobulin single variable domain and/or polypeptide is said to be "specific for" a first target or antigen compared to a second target or antigen when it binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times or more better than the affinity with which the immunoglobulin single variable domain and/or polypeptide binds to the second target or antigen. For example, the immunoglobulin single variable domain and/or polypeptide may bind to the first target or antigen with a $K_D$ value that is at least 10 times less, such as at least 100 times less, and preferably at least 1000 times less or even less than that, than the $K_D$ with which said immunoglobulin single variable domain and/or polypeptide binds to the second target or antigen. Preferably, when an immunoglobulin single variable domain and/or polypeptide is "specific for" a first target or antigen compared to a second target or antigen, it is directed against (as defined herein) said first target or antigen, but not directed against said second target or antigen.

The terms "(cross)-block", "(cross)-blocked", "(cross)-blocking", "competitive binding", "(cross)-compete", "(cross)-competing" and "(cross)-competition" are used interchangeably herein to mean the ability of an immunoglobulin, antibody, immunoglobulin single variable domain, polypeptide or other binding agent to interfere with the binding of other immunoglobulins, antibodies, immunoglobulin single variable domains, polypeptides or binding agents to a given target. The extent to which an immunoglobulin, antibody, immunoglobulin single variable domain, polypeptide or other binding agent is able to interfere with the binding of another to the target, and therefore whether it can be said to cross-block according to the invention, can be determined using competition binding assays. Particularly suitable quantitative cross-blocking assays are described in the Examples and include e.g. a fluorescence-activated cell sorting (FACS) binding assay with GITR expressed on cells. The extent of (cross)-blocking can be measured by the (reduced) channel fluorescence.

The following generally describes a suitable FACS assay for determining whether an immunoglobulin, antibody, immunoglobulin single variable domain, polypeptide or other binding agent cross-blocks or is capable of cross-blocking according to the invention. It will be appreciated that the assay can be used with any of the immunoglobulins, antibodies, immunoglobulin single variable domains, polypeptides or other binding agents described herein. The FACS instrument (e.g. FACS Canto; Becton Dickinson) is operated in line with the manufacturer's recommendations.

To evaluate the "(cross)-blocking" or "(cross)-competition" between two binding agents (such as e.g. two immunoglobulin single variable domains and/or Nanobodies®) for binding GITR, a FACS competition experiment can be performed using cells (such as e.g. Flp-In™-293 cells) overexpressing human GITR and the parental cells as background cell line. Different detection reagents can be used including e.g. monoclonal ANTI-FLAG® M2 antibody (Sigma-Aldrich, cat #F1804), monoclonal anti-C-myc antibody (Sigma-Aldrich, cat #WH0004609M2), monoclonal ANTI-HIS TAG antibody (Sigma-Aldrich, cat #SAB1305538), each labeled differently. A wide range of fluorophores can be used as labels in flow cytometry (such as e.g PE (R-Phycoerythrin), 7-aminoactinomycin D (7-AAD), Acridine Orange, various forms of Alexa Fluor, Allophycocyanin (APC), AmCyan, Aminocoumarin, APC Cy5, APC Cy7, APC-H7, APC/Alexa Fluor 750, AsRed2, Azami-Green, Azurite, B ODIPY FL C5-ceramide, BCECF-AM, Bis-oxonol DiBAC2(3), BODIPY-FL, Calcein, Calcein AM, Caroxy-H2DCFDA, Cascade Blue, Cascade Yellow, Cell Tracker Green, Cerulean, CFSE, Chromomycin A3, CM-H2DCFDA, Cy2, Cy3, Cy3.5, Cy3B, Cy5, Cy5.5, Cy7, CyPet, DAF-FM DAF-FM diacetate, DAPI, DCFH (2'7'Dichorodihydrofluorescein), DHR, Dihydrocalcein AM, Dihydrorhoadamine, Dihydrothidium, DiLC1(5), DiOC6(3), DiOC7(3), dKeima-Red, DRAQ5, Dronpa-Green, various forms of DsRed dTomato, various forms of DyLight, E. coli BioParticles AF488, E2-Crimson, E2-Orange, EBFP2, ECFP, various forms of eFluor, EGFP, EGFP*, Emerald, eqFP650, eqFP670, ER-Tracker Blue-White DPX, Ethidium Bromide, Express2, EYFP, Fc OxyBurst Green, Fc Oxy-Burst Green 123, FITC, Fluo-3, Fluo-4, Fluorescein, Fura-2, Fura-Red, GFPuv, H2DCFDA, HcRed1, Hoechst Blue (33258), Hoechst Red (33342), Hydroxycoumarin, HyPer, Indo-1, Indo-1 Blue (Low Ca2+), Indo-1 Violet (High Ca2+), iRFP, J-Red, JC-1, JC-9, Katushka (TurboFP635), Katushka2 Kusabira-Orange, LDS 751, Lissamine Rhodamine B, various forms of Live/Dead, Lucifer yellow, Lucifer Yellow CH, Lyso Tracker Blue, Lyso Tracker Green, Lyso Tracker Red, mAmertrine, Marina Blue, mBanana, mCFP, mCherry, mCitrine, Methoxycoumarin, mHoney-Dew, Midoriishi-Cyan, Mithramycin, Mito Tracker Deep Red, Mito Tracker Green, Mito Tracker Orange, Mito Tracker Red, MitoFluor Green, mKate (TagFP635), mKate2, mKeima, mKeima-Red, mKO, mKOk, mNeptune, Monochlorobimane, mOrange, mOrange2, mRaspberry, mPlum, mRFP1, mStrawberry, mTangerine, mTarquoise, mTFP1, mTFP1 (Teal), NBD, OxyBurst Green H2DCFDA, OxyBurst Green H2HFF BSA, Pacific Blue, PE (R-Phycoerythrin), PE Cy5, PE Cy5.5, PE Cy7, PE Texas Red, PE-Cy5 conjugates, PE-Cy7 conjugates, PerCP (Peridinin chlorphyll protein), PerCP Cy5.5, PhiYFP, PhiYFP-m, Propidium Iodide (PI), various forms of Qdot, Red 613, RFP Tomato, Rhod-2, S65A, S65C, S65L, S65T, Singlet Oxygen Sensor Green, Sirius, SNARF, Superfolder GFP, SYTOX Blue, SYTOX Green, SYTOX Orange, T-Sapphire, TagBFP, TagCFP, TagGFP, TagRFP, TagRFP657, TagYFP, tdTomato, Texas Red, Thiazole Orange, TMRE, TMRM, Topaz, TOTO-1, TO-PRO-1, TRITC, TRITC TruRed, TurboFP602, TurboFP635, TurboGFP, TurboRFP, TurboYFP, Venus, Vybrant CycleDye Violet, Wild Type GFP, X-Rhodamin, Y66F, Y66H, Y66W, YOYO-1, YPet, ZsGreen1, ZsYellow1, Zymosan A BioParticles AF488 (see more at: thefcn.org/flow-fluorochromes). Fluorophores, or simply "fluors", are typically attached to the antibody (e.g. the immunoglobulin single variable domains, such as Nanobodies®) that recognizes GITR or to the antibody that is used as detection reagent. Various conjugated antibodies are available, such as (without being limiting) for example antibodies conjugated to Alexa Fluor®, DyLight®, Rhodamine, PE, FITC, and Cy3. Each fluorophore has a characteristic peak excitation and emission wavelength. The combination of labels which can be used will depend on the wavelength of the lamp(s) or laser(s) used to excite the fluorophore and on the detectors available.

To evaluate the competition between two test binding agents (termed A and B) for binding to GITR, a dilution series of cold (without any label) binding agent A is added to (e.g. 200 000) cells together with the labeled binding agent B*. The concentration of binding agent B* in the test mix should be high enough to readily saturate the binding sites on GITR expressed on the cells. The concentration of binding agent B* that saturates the binding sites for that binding agent on GITR expressed on the cells can be determined with a titration series of binding agent B* on the GITR cells and determination of the $EC_{50}$ value for binding. In order to work at saturating concentration, binding agent B* can be used at 100× the $EC_{50}$ concentration.

After incubation of the cells with the mixture of binding agent A and binding agent B* and cells wash, read out can be performed on a FACS. First a gate is set on the intact cells as determined from the scatter profile and the total amount of channel fluorescence is recorded.

A separate solution of binding agent B* is also prepared. Binding agent B* in this solutions should be in the same buffer and at the same concentration as in the test mix (with binding agent A and B*). This separate solution is also added to the cells. After incubation and cells wash, read out can be performed on a FACS. First a gate is set on the intact cells as determined from the scatter profile and the total amount of channel fluorescence is recorded.

A reduction of fluorescence for the cells incubated with the mixture of binding agent A and B* compared to the fluorescence for the cells incubated with the separate solution of binding agent B* indicates that binding agent A (cross)-blocks binding by binding agent B* for binding to GITR expressed on the cells.

A cross-blocking immunoglobulin, antibody, immunoglobulin single variable domain, polypeptide or other binding agent according to the invention is one which will bind to the GITR in the above FACS cross-blocking assay such that during the assay and in the presence of a second immunoglobulin, antibody, immunoglobulin single variable domain, polypeptide or other binding agent the recorded fluorescence is between 80% and 0.1% (e.g. 80% to 4%) of the maximum fluorescence (measured for the separate labelled immunoglobulin, antibody, immunoglobulin single variable domain, polypeptide or other binding agent), specifically between 75% and 0.1% (e.g. 75% to 4%) of the maximum fluorescence, and more specifically between 70% and 0.1% (e.g. 70% to 4%) of maximum fluorescence (as just defined above).

The competition between two test binding agents (termed A* and B*) for binding to GITR can also be evaluated by adding both binding agents, each labeled with a different fluorophore, to the GITR expressing cells. After incubation and cells wash, read out can be performed on a FACS. A gate is set for each fluorophore and the total amount of channel fluorescence is recorded. Reduction and/or absence of fluorescence of one of the fluorophore indicate (cross)-blocking by the binding agents for binding to GITR expressed on the cells.

Other methods for determining whether an immunoglobulin, antibody, immunoglobulin single variable domain, polypeptide or other binding agent directed against a target (cross)-blocks, is capable of (cross)-blocking, competitively binds or is (cross)-competitive as defined herein are described e.g. in Xiao-Chi Jia et al. (Journal of Immunological Methods 288: 91-98, 2004), Miller et al. (Journal of Immunological Methods 365: 118-125, 2011) and/or the methods described herein (see e.g. Example 7).

An amino acid sequence is said to be "cross-reactive" for two different antigens or antigenic determinants (such as e.g., serum albumin from two different species of mammal, such as e.g., human serum albumin and cyno serum albumin, such as e.g., GITR from different species of mammal, such as e.g., human GITR, cyno GITR and rat GITR) if it is specific for (as defined herein) these different antigens or antigenic determinants.

The term "glucocorticoid-induced TNF receptor", hereinafter referred to as "GITR" is also known as Tumor Necrosis Receptor Superfamily 18 (TNFRSF18), Activation-Inducible TNFR Family Receptor (AITR), TEASR, CD357 and 312C2. GITR is constitutively expressed in all T cell subtypes and mostly in regulatory T cells (Treg), is up-regulated in $CD4^+CD25^-$ and $CD8^+CD25^-$ effector cells following TCR stimulation and cell activation (Nocentini et al. 2007, Eur J Immunol. 37:1165-1169). GITR acts as a costimulatory molecule in effector T cell activation and regulates Treg cell suppressor activity (Esparza et al. 2005, J Immunol. 174:7869-7874).

In the context of the present invention, "enhancing" or "to enhance" generally means increasing, potentiating or stimulating the activity of GITR, as measured using a suitable in vitro, cellular or in vivo assay (such as those mentioned herein). In particular, increasing or enhancing the activity of GITR, as measured using a suitable in vitro, cellular or in vivo assay (such as those mentioned herein), by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, such as 100%, compared to the activity of GITR in the same assay under the same conditions but without the presence of the polypeptide of the invention.

A "synergistic effect" of two compounds is one in which the effect of the combination of the two agents is greater than the sum of their individual effects and is preferably statistically different from the controls and the single drugs.

As used herein, the term "T cell, B cell or natural killer cell mediated disease" refers to any disease mediated by T cells (including effector T cells (e.g., $CD8^+$ cells) and helper T cells (e.g., $CD4^+$ cells)), B cells or natural killer cells.

A "GITR associated disease, disorder or condition" refers to disease or symptom associated with the disease that is treatable by inducing, stimulating, or enhancing GITR activity, e.g. via the use of an agonist GITR polypeptide as described herein. Exemplary GITR associated diseases, disorders or conditions include, but are not limited to, cancer and infectious diseases.

As used herein, an "agonist" refers to a compound that partially or fully increases, enhances, induces or stimulates one or more biological activities of a corresponding target (e.g., GITR) in vitro or in vivo. Examples of such biological activities of GITR include promoting CD4+ and CD8+ T cell survival, proliferation, NF-κB signaling, interleukin-2 production and effector functions and abrogate Treg cell suppressive effects or the generation of Treg cells. As will be clear to the skilled person, such an increase in biological activity may be determined in any suitable manner and/or using any suitable (in vitro, cellular or in vivo) assay known per se, such as the assays described herein or in the prior art cited herein. In particular, the biological activity may be increased, by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, such as 100%, compared to the biological activity in the same assay under the same conditions but without the presence of the polypeptide of the invention.

Full agonists are capable of maximal receptor stimulation (functional response), i.e. they elicit substantially the same level of full response as the endogenous ligand of the receptor (E=Emax=100%). Here, the term "substantially the same", means that the efficacy of a test compound ranges from 70% to 150%, more preferably from 80% to 140%, such as 90% to 120% compared to the maximal efficacy of said endogenous ligand measured in the same experimental setup and set at a 100%.

Partial agonists are unable to elicit maximal activity of the receptor, even at saturating concentrations. In other words, the maximum magnitude of the functional response produced by a full agonist of a target molecule (e.g., GITR) cannot be produced by a partial agonist of the same target molecule, even by increasing the dosage of the partial agonist. The terms "enhancing an immune response" and "inducing an immune response" are used interchangeably herein and refer to a process that results in the activation, stimulation or proliferation of one or more cellular response(s) of either T cells, B cells and/or natural killer (NK) cells. The polypeptides of the invention are capable of inducing proliferation or activation of T cells, B cells or natural killer cells. Suitable assays to measure T cell, B cell and natural killer cell activation are known in the art described herein, for instance as described in Buillard et al. 2013, J. Exp. Med. Vol. 210, 9: 1685-1693; Zhou et al. October 2010, J. Immunother. Vol. 33, No 8; and Hanabuchi 2006, Blood, Vol. 107, No 9: 3617-3623, respectively, or as exemplified in the examples below.

As used herein, the term "inhibits tumor cell growth" is intended to include any measurable decrease in the proliferation of tumor cells in vitro or tumor growth in vivo, e.g., decrease by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, such as 100%.

As used herein, the term "potency" is a measure of an agent, such as a polypeptide, ISVD or Nanobody®, its biological activity. Potency of an agent can be determined by any suitable method known in the art, such as for instance as described in the experimental section. Cell culture based potency assays are often the preferred format for determining biological activity since they measure the physiological response elicited by the agent and can generate results within a relatively short period of time. Various types of cell based assays, based on the mechanism of action of the product, can be used, including but not limited to proliferation assays, cytotoxicity assays, cell killing assays, reporter gene assays (e.g. NF-κB luciferase reporter assay), T cell activation assay, cell surface receptor binding assays and assays to measure expression of known markers of activation or cytokine secretion, all well known in the art.

In contrast, the "efficacy" of the polypeptide of the invention measures the maximum strength of the effect itself, at saturating polypeptide concentrations. Efficacy indicates the maximum response achievable from the polypeptide of the invention. It refers to the ability of a polypeptide to produce the desired (therapeutic) effect. The efficacy of a polypeptide of the invention can be evaluated using in vivo models, such as the OVA immunization model or the syngeneic CT-26 colon carcinoma model (for instance as set out in the Examples section).

The "half-life" of a polypeptide of the invention can generally be defined as described in paragraph o) on page 57 of WO 08/020079 and as mentioned therein refers to the time taken for the serum concentration of the polypeptide to be reduced by 50%, in vivo, for example due to degradation of the polypeptide and/or clearance or sequestration of the polypeptide by natural mechanisms. The in vivo half-life of a polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t½-alpha, t½-beta and the area under the curve (AUC). Reference is for example made to the standard handbooks, such as Kenneth et al (Chemical Stability of Pharmaceuticals: A Handbook for Pharmacists, John Wiley & Sons Inc, 1986) and M Gibaldi and D Perron ("Pharmacokinetics", Marcel Dekker, 2nd Rev. Edition, 1982). The terms "increase in half-life" or "increased half-life" are also as defined in paragraph o) on page 57 of WO 08/020079 and in particular refer to an increase in the t½-beta, either with or without an increase in the t½-alpha and/or the AUC or both.

Unless indicated otherwise, the terms "immunoglobulin" and "immunoglobulin sequence"-whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively).

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

The term "immunoglobulin single variable domain", interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associated) immunoglobulin domains such as light and heavy chain variable domains, i.e., by a VH-VL pair of immunoglobulin domains, which jointly bind to an epitope of the respective antigen.

In contrast, immunoglobulin single variable domains are capable of specifically binding to an epitope of the antigen without pairing with an additional immunoglobulin variable domain. The binding site of an immunoglobulin single variable domain is formed by a single VH/VHH or VL domain. Hence, the antigen binding site of an immunoglobulin single variable domain is formed by no more than three CDRs.

As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

In one embodiment of the invention, the immunoglobulin single variable domains are heavy chain variable domain sequences (e.g., a VH-sequence); more specifically, the immunoglobulin single variable domains can be heavy chain variable domain sequences that are derived from a conventional four-chain antibody or heavy chain variable domain sequences that are derived from a heavy chain antibody.

For example, the immunoglobulin single variable domain may be a (single) domain antibody (or an amino acid that is suitable for use as a (single) domain antibody), a "dAb" or dAb (or an amino acid that is suitable for use as a dAb) or a Nanobody® (as defined herein, and including but not limited to a VHH); other single variable domains, or any suitable fragment of any one thereof.

In particular, the immunoglobulin single variable domain may be a Nanobody® (as defined herein) or a suitable fragment thereof. [Note: Nanobody®, Nanobodies® and Nanoclone® are registered trademarks of Ablynx N.V.] For a general description of Nanobodies®, reference is made to the further description below, as well as to the prior art cited herein, such as e.g. described in WO 08/020079 (page 16).

"VHH domains", also known as VHHs, $V_HH$ domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al. Nature 363: 446-448, 1993). The term "VHH domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). For a further description of VHH's and Nanobodies®, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies® (in particular VHH sequences and partially humanized Nanobodies®) can in particular be characterized by the presence of one or more "Hallmark residues" in one or more of the framework sequences. A further description of the Nanobodies®, including humanization and/or camelization of Nanobodies®, as well as other modifications, parts or fragments, derivatives or "Nanobody® fusions", multivalent constructs (including some non-limiting examples of linker sequences) and different modifications to increase the half-life of the Nanobodies® and their preparations can be found e.g. in WO 08/101985 and WO 08/142164. For a further general description of Nanobodies®, reference is made to the prior art cited herein, such as e.g., described in WO 08/020079 (page 16).

"Domain antibodies", also known as "Dab"s, "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans.

It should also be noted that, although less preferred in the context of the present invention because they are not of mammalian origin, single variable domains can be derived from certain species of shark (for example, the so-called "IgNAR domains", see for example WO 05/18629).

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g., described in Davies and Riechmann (FEBS 339: 285-290, 1994; Biotechnol. 13: 475-479, 1995; Prot. Eng. 9: 531-537, 1996) and Riechmann and Muyldermans (J. Immunol. Methods 231: 25-38, 1999).

The amino acid residues of a VHH domain are numbered according to the general numbering for $V_H$ domains given by Kabat et al. ("Sequence of proteins of immunological interest", US Public Health Services, NIH Bethesda, MD, Publication No. 91), as applied to VHH domains from Camelids, as shown e.g., in FIG. 2 of Riechmann and Muyldermans (J. Immunol. Methods 231: 25-38, 1999). Alternative methods for numbering the amino acid residues of $V_H$ domains, which methods can also be applied in an analogous manner to VHH domains, are known in the art. However, in the present description, claims and figures, the numbering according to Kabat applied to VHH domains as described above will be followed, unless indicated otherwise.

It should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

Determination of CDR regions may also be done according to different methods. In the CDR determination according to Kabat, FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113.

In the present application, however, CDR sequences were determined according to Kontermann and Dübel (Eds., Antibody Engineering, vol 2, Springer Verlag Heidelberg Berlin, Martin, Chapter 3, pp. 33-51, 2010). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113 (according to Kabat numbering).

Immunoglobulin single variable domains such as Domain antibodies and Nanobodies® (including VHH domains) can be subjected to humanization. In particular, humanized immunoglobulin single variable domains, such as Nanobodies® (including VHH domains) may be immunoglobulin single variable domains that are as generally defined for in the previous paragraphs, but in which at least one amino acid residue is present (and in particular, at least one framework residue) that is and/or that corresponds to a humanizing substitution (as defined herein). Potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) an immunoglobulin single variable domain, such as a Nanobody® (including VHH domains) may be partially humanized or fully humanized.

Immunoglobulin single variable domains such as Domain antibodies and Nanobodies® (including VHH domains and humanized VHH domains), can also be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al. (Biotechnology 10:779-783, 1992), Barbas, et al. (Proc. Nat. Acad. Sci, USA 91: 3809-3813, 1994), Shier et al. (Gene 169: 147-155, 1995), Yelton et al. (Immunol. 155: 1994-2004, 1995), Jackson et al. (J. Immunol. 154: 3310-9, 1995), Hawkins et al. (J. Mol. Biol. 226: 889 896, 1992), Johnson and Hawkins (Affinity maturation of antibodies using phage display, Oxford University Press, 1996).

The process of designing/selecting and/or preparing a polypeptide, starting from an immunoglobulin single variable domain such as a Domain antibody or a Nanobody®, is also referred to herein as "formatting" said immunoglobulin single variable domain; and an immunoglobulin single variable domain that is made part of a polypeptide is said to be "formatted" or to be "in the format of" said polypeptide. Examples of ways in which an immunoglobulin single variable domain can be formatted and examples of such formats will be clear to the skilled person based on the disclosure herein; and such formatted immunoglobulin single variable domain form a further aspect of the invention.

For example, and without limitation, one or more immunoglobulin single variable domains may be used as a "binding unit", "binding domain" or "building block" (these terms are used interchangeable) for the preparation of a polypeptide, which may optionally contain one or more further immunoglobulin single variable domains that can serve as a binding unit (i.e., against the same or another epitope on GITR and/or against one or more other antigens, proteins or targets than GITR).

Monovalent polypeptides comprise or essentially consist of only one binding unit (such as e.g., immunoglobulin single variable domains). Polypeptides that comprise two or more binding units (such as e.g., immunoglobulin single variable domains) will also be referred to herein as "multivalent" polypeptides, and the binding units/immunoglobulin single variable domains present in such polypeptides will also be referred to herein as being in a "multivalent format". For example a "bivalent" polypeptide may comprise two immunoglobulin single variable domains, optionally linked via a linker sequence, whereas a "trivalent" polypeptide may comprise three immunoglobulin single variable domains, optionally linked via two linker sequences; whereas a "tetravalent" polypeptide may comprise four immunoglobulin single variable domains, optionally linked via three linker sequences; whereas a "pentavalent" polypeptide may comprise five immunoglobulin single variable domains, optionally linked via four linker sequences; whereas a "hexavalent" polypeptide may comprise six immunoglobulin single variable domains, optionally linked via five linker sequences, etc.

In a multivalent polypeptide, the two or more immunoglobulin single variable domains may be the same or different, and may be directed against the same antigen or antigenic determinant (for example against the same part(s) or epitope(s) or against different parts or epitopes) or may alternatively be directed against different antigens or antigenic determinants; or any suitable combination thereof. Polypeptides that contain at least two binding units (such as e.g., immunoglobulin single variable domains) in which at least one binding unit is directed against a first antigen (i.e., GITR) and at least one binding unit is directed against a second antigen (i.e., different from GITR) will also be referred to as "multispecific" polypeptides, and the binding units (such as e.g., immunoglobulin single variable domains) present in such polypeptides will also be referred to herein as being in a "multispecific format". Thus, for example, a "bispecific" polypeptide of the invention is a polypeptide that comprises at least one immunoglobulin single variable domain directed against a first antigen (i.e., GITR) and at least one further immunoglobulin single variable domain directed against a second antigen (i.e., different from GITR), whereas a "trispecific" polypeptide of the invention is a polypeptide that comprises at least one immunoglobulin single variable domain directed against a first antigen (i.e., GITR), at least one further immunoglobulin single variable domain directed against a second antigen (i.e., different from GITR) and at least one further immunoglobulin single variable domain directed against a third antigen (i.e., different from both GITR and the second antigen); etc.

"Multiparatopic polypeptides", such as e.g., "biparatopic polypeptides" or "triparatopic polypeptides", comprise or essentially consist of two or more binding units that each have a different paratope (as will be further described herein).

GITR Agonists

The present invention provides polypeptides (also referred to herein as "polypeptides of the invention") that have specificity for and/or that bind GITR, preferably human GITR. GITR also known as TNFRSF18, AITR, CD357, TEASR or 312C2, is a protein that, in humans, is encoded by the TNFRSF18 gene, which maps on chromosome 1, at 1p36.3 according to Entrez Gene. The polypeptides of the invention preferably bind to human GITR (SEQ ID NO: 231).

The polypeptides provided by the present invention are GITR agonists and can thus induce, increase, stimulate or enhance GITR signaling. Activating the GITR biological pathway modulates T cell activation and enhances immune responses. Accordingly, the polypeptides provided by the present invention can be used in a variety of immunotherapeutic applications, such as in the treatment of a variety of cancers, immune disorders and infectious diseases, as will be further defined herein.

Based on extensive screening, characterization and combinatory strategies, the present inventors surprisingly observed that polypeptides comprising immunoglobulin single variable domains binding GITR showed improved properties for modulating GITR activity compared to the GITR agonizing molecules described in the prior art. More specifically, the present inventors surprisingly observed that the polypeptides of the present invention exhibited higher efficacies at equipotent or even lower $EC_{50}$ values as compared to the prior art antibodies. This is clinically very important as the effectiveness of a drug depends on its maximal efficacy.

Accordingly, the present invention provides GITR agonists with particular functional properties which are linked with improved and desirable therapeutic and/or pharmacological properties, in addition to other advantageous properties (such as, for example, improved ease of preparation, good stability, and/or reduced costs of goods), compared to the prior art amino acid sequences and antibodies.

Binding of the polypeptides of the invention to GITR can be measured in binding assays. Typical assays include (without being limiting) assays in which GITR is exposed on a cell surface (such as e.g. Flp-In™-293 cells or GloResponse™ NF-κB-Nluc2P HEK293 cells). A preferred assay for measuring binding of the polypeptides of the invention to GITR is a FACS assay, such as e.g. the FACS assay as described in the examples, wherein binding of the polypeptides of the invention to GITR expressed on Flp-In™-293 cells and/or activated T cells is determined. Some preferred $EC_{50}$ values for binding of the polypeptides of the invention to GITR will become clear from the further description and examples herein.

In such FACS binding assay, the polypeptides of the present invention may have $EC_{50}$ values in binding human GITR of $10^{-8}$ M or lower, more preferably of $10^{-9}$ M or lower, or even of $10^{-10}$ M or lower, such as $10^{-11}$ M. For example, in such FACS binding assay, the polypeptides of the present invention may have $EC_{50}$ values in binding human GITR between $10^{-11}$ M and $10^{-8}$ M, such as between $10^{-9}$ M and $10^{-8}$ M, between $10^{-10}$ M and $10^{-9}$ M or between $10^{-11}$ M and $10^{-10}$ M.

The polypeptides of the invention bind GITR and can modulate (i.e. increase, enhance, stimulate or potentiate) the activity of GITR. More particularly, the polypeptides of the present invention may enhance an immune response.

Accordingly, in one aspect, the present invention relates to a polypeptide that specifically binds GITR with an $EC_{50}$ of less than 200 pM, and wherein the binding of said polypeptide to said GITR enhances an immune response. More particularly, the polypeptides of the present invention enhance proliferation or activation of T cells, B cells or natural killer cells.

Proliferation or activation of T cell, B cells or natural killer cells can be determined by a variety of assays, including but not limited to proliferation assays, cytotoxicity assays, cell killing assays, reporter gene assays (e.g. NF-κB luciferase reporter assay), T cell activation assay, cell surface receptor binding assays and assays to measure expression of known markers of activation or cytokine secretion, which are all well known in the art.

For example, any one of several conventional assays for monitoring cytokine production (such as IFN-γ and interleukins) as a measure of immune cells activation can be used. For example, for tracking T cell activation, interleukin-2 can be employed as a marker, which can be assayed as described in Proc. Natl. Acad. Sci. USA. 86:1333 (1989).

One can also employ immunofluorescence and flow cytometry to monitor cytokine production on a cellular basis, and to monitor cell surface markers that reflect cellular activation states. A host of such markers are known, detecting antibodies are broadly commercially available, and the markers are well known in the art.

A common assay for T cell proliferation entails measuring tritiated thymidine incorporation. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

Some preferred $EC_{50}$ values for activating GITR by the polypeptides of the invention will become clear from the further description and examples herein.

In some embodiments, the polypeptides of the invention enhance IFN-gamma production in a T-cell activation assay with activated CD4+ T cells stimulated with anti-CD3 antibody OKT3, as described in Example 10. In this T cell activation assay, the polypeptides of the present invention have $EC_{50}$ values for enhancing IFN-gamma production of $10^{-7}$ M or lower, preferably of $10^{-8}$ M or lower, more preferably of $10^{-9}$ M or lower, $10^{-10}$ M or lower, or even of $10^{-11}$ M or lower. More particularly, in this T-cell activation assay, the polypeptides of the present invention enhance IFN-gamma production with $EC_{50}$ values of 200 pM or less, such as less than 190, 180, 170, 160, 150, 140, 130, 120, 110, 100 or even less, such as less than 90, 80, 70, 60, 50, 40 or even less, such as less than 30 pM.

Accordingly, the present invention relates to a polypeptide that specifically binds to GITR, and wherein the binding of said polypeptide to said GITR enhances IFN-gamma production in T cells with an $EC_{50}$ of 200 pM or less, such as less than 190, 180, 170, 160, 150, 140, 130, 120, 110, 100 or even less, such as less than 90, 80, 70, 60, 50, 40 or even less, such as less than 30 pM, as measured in a T-cell activation assay with activated CD4+ T cells stimulated with anti-CD3 antibody OKT3 (as described in Example 10).

In some embodiments, the polypeptides of the invention enhance the activity of nuclear factor-kappa B (NF-κB) in a NF-κB luciferase reporter assay, as described in Example 9 and 18. NF-κB luciferase reporter assays have been described in Buillard et al. 2013, J. Exp. Med. Vol. 210, 9: 1685-1693. Some preferred $EC_{50}$ values for activating GITR by the polypeptides of the invention will become clear from the further description and examples herein.

NF-κB plays a key role in inflammation, immune response and cell proliferation. This assay is specifically designed to monitor the activity of NF-κB regulated signal transduction pathways in cultured cells. In this NF-κB luciferase reporter assay, the polypeptides of the present invention enhance NF-κB activity as measured by luminescence after addition of Nano-Glo™ Reagent (Promega #N1120) with $EC_{50}$ values of $10^{-7}$ M or lower, preferably of $10^{-8}$ M or lower, more preferably of $10_{-9}$ M or lower, $10^{-10}$ M or lower, or even of $10^{-11}$ M or lower. More particularly, in this NF-κB luciferase reporter assay, the polypeptides of the present invention enhance NF-κB activity with $EC_{50}$ values of 200 pM or less, such as less than 190, 180, 170, 160, 150, 140, 130, 120, 110, 100 or even less, such as less than 90, 80, 70, 60, 50, 40, 35, 30, 25, 20, 18, 16, 15, 14 or even less, such as less than 12 pM.

Accordingly, the present invention relates to a polypeptide that specifically binds to GITR, and wherein the binding of said polypeptide to said GITR enhances NF-κB activity with an $EC_{50}$ of 200 pM or less, such as less than 190, 180, 170, 160, 150, 140, 130, 120, 110, 100 or even less, such as less than 90, 80, 70, 60, 50, 40, 35, 30, 25, 20, 18, 16, 15, 14 or even less, such as less than 12 pM, as measured in a NF-κB luciferase reporter assay (as described in Example 9 and 18).

Therapeutic effects of the polypeptides of the invention can further be evaluated in in vivo models, such as e.g. in mice, rats, pigs and/or primates. The CT26 model in BALB/c mice provides a syngeneic in vivo test system, which is frequently used for developing and testing immunotherapeutic concepts (Fearon et al. Cancer Res. 48: 2975-2980, 1988). For example, in the syngeneic CT-26 colon carcinoma model as described in Examples 13, 14 and 21, the polypeptides of the invention may inhibit tumor cell growth. In some embodiments, the polypeptides of the invention inhibit tumor cell growth, inhibit or prevent an increase in tumor weight or volume, and/or cause a decrease in tumor weight or volume by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, such as 100%.

Accordingly, the present invention relates to a polypeptide that specifically binds to GITR, and wherein the binding of said polypeptide to said GITR inhibits tumor cell growth, in a syngeneic CT-26 colon carcinoma model (as described in Examples 13, 14 and 21).

Monovalent Polypeptides of the Invention

The present invention provides stretches of amino acid residues (SEQ ID NOs: 73-88, SEQ ID NOs: 90-116, and SEQ ID NOs: 118-132 and 282-284; Table A-10) that are particularly suited for binding GITR. In particular, the invention provides stretches of amino acid residues which bind GITR and wherein the binding of said stretches to said GITR enhances an immune response (as described above). These stretches of amino acid residues may be present in, and/or may be incorporated into, a polypeptide of the invention, in particular in such a way that they form (part of) the antigen binding site of the polypeptide of the invention. These stretches of amino acid residues have been generated as CDR sequences of heavy chain antibodies or V$_{HH}$ sequences that were raised against GITR. These stretches of amino acid residues are also referred to herein as "CDR sequence(s) of the invention" (i.e., as "CDR1 sequence(s) of the invention", "CDR2 sequence(s) of the invention" and "CDR3 sequence(s) of the invention", respectively).

It should however be noted that the invention in its broadest sense is not limited to a specific structural role or function that these stretches of amino acid residues may have in a polypeptide of the invention, as long as these stretches of amino acid residues allow the polypeptide of the invention to bind to GITR with a certain affinity and potency (as defined herein). Thus, generally, the invention in its broadest sense provides monovalent polypeptides (also referred to herein as "monovalent polypeptide(s) of the invention") that are capable of binding to GITR with a certain specified affinity, avidity, efficacy and/or potency and that comprises one or more CDR sequences as described herein and, in particular a suitable combination of two or more such CDR sequences, that are suitably linked to each other via one or more further amino acid sequences, such that the entire polypeptide forms a binding domain and/or binding unit that is capable of binding to GITR. It should however also be noted that the presence of only one such CDR sequence in a monovalent polypeptide of the invention may by itself already be sufficient to provide the monovalent polypeptide of the invention the capacity of binding to GITR; reference is for example made to the so-called "Expedite fragments" described in WO 03/050531.

In a specific, but non-limiting aspect, the monovalent polypeptide of the invention, may comprise at least one stretch of amino acid residues that is chosen from the group consisting of:
 (i) CDR1 sequences:
   (a) SEQ ID NOs: 73-88; and
   (b) amino acid sequences that have 4, 3, 2, or 1 amino acid(s) difference with the amino acid sequences of SEQ ID NOs: 73-88; and/or
 (ii) CDR2 sequences:
   (c) SEQ ID NOs: 90-116; and
   (d) amino acid sequences that have 4, 3, 2, or 1 amino acid(s) difference with the amino acid sequences of SEQ ID NOs: 90-116; and/or
 (iii) CDR3 sequences:
   (e) SEQ ID NOs: 118-132 and 282-284; and
   (f) amino acid sequences that have 4, 3, 2, or 1 amino acid(s) difference with the amino acid sequences of SEQ ID NOs: 118-132 and 282-284.

In a further aspect, the monovalent polypeptide of the invention, may comprise at least one stretch of amino acid residues that is chosen from the group consisting of:
 (i) CDR1 sequences:
   (a) SEQ ID NOs: 73-75; and
   (b) amino acid sequences that have 4, 3, 2, or 1 amino acid(s) difference with the amino acid sequence of SEQ ID NO: 73; and/or
 (ii) CDR2 sequences:
   (c) SEQ ID NOs: 90-98; and
   (d) amino acid sequences that have 4, 3, 2, or 1 amino acid(s) difference with the amino acid sequence of SEQ ID NO: 90; and/or
 (iii) CDR3 sequences:
   (e) SEQ ID NOs: 118-119, 123 and 282-284; and
   (f) amino acid sequences that have 2, or 1 amino acid(s) difference with the amino acid sequence of SEQ ID NO: 118.

In a further aspect, the monovalent polypeptide of the invention, may comprise at least one stretch of amino acid residues that is chosen from the group consisting of:
 (i) CDR1 sequences:
   (a) SEQ ID NO: 73; and
   (b) amino acid sequences that have 4, 3, 2, or 1 amino acid difference(s) with SEQ ID NO: 73, wherein
     at position 2 the T has been changed into S;
     at position 7 the D has been changed into N;
     at position 8 the S has been changed into A; and/or
     at position 10 the A has been changed into G;
 and/or
 (ii) CDR2 sequences:
   (c) SEQ ID NO: 90; and
   (d) amino acid sequences that have 4, 3, 2, or 1 amino acid difference(s) with SEQ ID NO: 90, wherein
     at position 1 the A has been changed into H, T, or G;
     at position 2 the I has been changed into M;
     at position 3 the T has been changed into S;
     at position 6 the G has been changed into S;
     at position 7 the S has been changed into R, or G; and/or
     at position 8 the P has been changed into S, T, or R
 and/or
 (iii) CDR3 sequences:
   (e) SEQ ID NO: 118; and
   (f) amino acid sequences that have 2, or 1 amino acid difference(s) with SEQ ID NO: 118, wherein
     at position 9 the A has been changed into P;
     at position 11 the M has been changed into L, K, R, or Q; and/or
     at position 12 the D has been changed into N.

In a further aspect, the monovalent polypeptide of the invention, may comprise at least one stretch of amino acid residues that is chosen from the group consisting of:
 (i) CDR1 sequence SEQ ID NO: 73; and/or
 (ii) CDR2 sequence SEQ ID NO: 90; and/or
 (iii) CDR3 sequence SEQ ID NO: 118, or
 (i) CDR1 sequence SEQ ID NO: 73; and/or
 (ii) CDR2 sequence SEQ ID NO: 90; and/or
 (iii) CDR3 sequence SEQ ID NO: 123.

In a further aspect, the monovalent polypeptide of the invention, may comprise at least one stretch of amino acid residues that is chosen from the group consisting of:
 (i) CDR1 sequences:
   (a) SEQ ID NOs: 76-78; and
   (b) amino acid sequences that have 2, or 1 amino acid(s) difference with the amino acid sequence of SEQ ID NO: 76; and/or
 (ii) CDR2 sequences:
   (c) SEQ ID NOs: 99-103; and
   (d) amino acid sequences that have 3, 2, or 1 amino acid(s) difference with the amino acid sequence of SEQ ID NO: 99; and/or
 (iii) CDR3 sequences:
   (e) SEQ ID NOs: 120-123; and
   (f) amino acid sequences that have 4, 3, 2, or 1 amino acid(s) difference with the amino acid sequence of SEQ ID NO: 120.

In a further aspect, the monovalent polypeptide of the invention, may comprise at least one stretch of amino acid residues that is chosen from the group consisting of:
(i) CDR1 sequences:
(a) SEQ ID NO: 76; and
(b) amino acid sequences that have 2, or 1 amino acid difference(s) with SEQ ID NO: 76, wherein
at position 7 the D has been changed into N; and/or
at position 8 the S has been changed into A;
and/or
(ii) CDR2 sequences:
(c) SEQ ID NO: 99; and
(d) amino acid sequences that have 3, 2, or 1 amino acid difference(s) with SEQ ID NO: 99, wherein
at position 1 the A has been changed into S, or T;
at position 5 the S has been changed into T, G, or R;
at position 6 the T has been changed into K; and/or
at position 7 the N has been changed into I;
and/or
(iii) CDR3 sequences:
(e) SEQ ID NO: 120; and
(f) amino acid sequences that have 4, 3, 2, or 1 amino acid difference(s) with SEQ ID NO: 120, wherein
at position 1 the E has been changed into K;
at position 4 the A has been changed into T;
at position 11 the I has been changed into M, or L; and/or
at position 12 the N has been changed into D.

In a further aspect, the monovalent polypeptide of the invention, may comprise at least one stretch of amino acid residues that is chosen from the group consisting of:
(i) CDR1 sequence SEQ ID NO: 76; and/or
(ii) CDR2 sequence SEQ ID NO: 99; and/or
(iii) CDR3 sequence SEQ ID NO: 120.

In a further aspect, the monovalent polypeptide of the invention, may comprise at least one stretch of amino acid residues that is chosen from the group consisting of:
(i) CDR1 sequences:
(a) SEQ ID NOs: 79-84; and
(b) amino acid sequences that have 3, 2, or 1 amino acid(s) difference with the amino acid sequence of SEQ ID NO: 79; and/or
(ii) CDR2 sequences:
(c) SEQ ID NOs: 104-108; and
(d) amino acid sequences that have 2, or 1 amino acid(s) difference with the amino acid sequence of SEQ ID NO: 104; and/or
(iii) CDR3 sequences:
(e) SEQ ID NOs: 124-125; and
(f) amino acid sequences that have 1 amino acid difference with the amino acid sequence of SEQ ID NO: 124.

In a further aspect, the monovalent polypeptide of the invention, may comprise at least one stretch of amino acid residues that is chosen from the group consisting of:
(i) CDR1 sequences:
(a) SEQ ID NO: 79; and
(b) amino acid sequences that have 3, 2, or 1 amino acid difference(s) with SEQ ID NO: 79, wherein
at position 2 the S has been changed into N;
at position 3 the V has been changed into I;
at position 7 the N has been changed into D;
at position 8 the D has been changed into S; and/or
at position 9 the M has been changed into V, or T;
and/or
(ii) CDR2 sequences:
(c) SEQ ID NO: 104; and
(d) amino acid sequences that have 2, or 1 amino acid difference(s) with SEQ ID NO: 104, wherein
at position 1 the D has been changed into G;
at position 5 the R has been changed into A; and/or
at position 6 the G has been changed into D;
and/or
(iii) CDR3 sequences:
(e) SEQ ID NO: 124; and
(f) amino acid sequences that have 1 amino acid difference with SEQ ID NO: 124, wherein
at position 4 the T has been changed into M.

In a further aspect, the monovalent polypeptide of the invention, may comprise at least one stretch of amino acid residues that is chosen from the group consisting of:
(i) CDR1 sequence SEQ ID NO: 79; and/or
(ii) CDR2 sequence SEQ ID NO: 104; and/or
(iii) CDR3 sequence SEQ ID NO: 124.

In a further aspect, the monovalent polypeptide of the invention, may comprise at least one stretch of amino acid residues that is chosen from the group consisting of:
(i) CDR1 sequences:
(a) SEQ ID NOs: 85-86; and
(b) amino acid sequences that have 1 amino acid difference with the amino acid sequence of SEQ ID NO: 85; and/or
(ii) CDR2 sequences:
(c) SEQ ID NOs: 109-110; and
(d) amino acid sequences that have 1 amino acid difference with the amino acid sequence of SEQ ID NO: 109; and/or
(iii) CDR3 sequence SEQ ID NO: 126.

In a further aspect, the monovalent polypeptide of the invention, may comprise at least one stretch of amino acid residues that is chosen from the group consisting of:
(i) CDR1 sequences:
(a) SEQ ID NO: 85; and
(b) amino acid sequences that have 1 amino acid difference with SEQ ID NO: 85, wherein
at position 2 the S has been changed into N;
and/or
(ii) CDR2 sequences:
(c) SEQ ID NO: 109; and
(d) amino acid sequences that have 1 amino acid difference with SEQ ID NO: 109, wherein
at position 9 the T has been changed into S;
and/or
(iii) CDR3 sequence SEQ ID NO: 126.

In a further aspect, the monovalent polypeptide of the invention, may comprise at least one stretch of amino acid residues that is chosen from the group consisting of:
(i) CDR1 sequence SEQ ID NO: 85; and/or
(ii) CDR2 sequence SEQ ID NO: 109; and/or
(iii) CDR3 sequence SEQ ID NO: 126.

In a further aspect, the monovalent polypeptide of the invention, may comprise at least one stretch of amino acid residues that is chosen from the group consisting of:
(i) CDR1 sequence SEQ ID NO: 87; and/or
(ii) CDR2 sequence SEQ ID NO: 111; and/or
(iii) CDR3 sequence SEQ ID NO: 127.

In a further aspect, the monovalent polypeptide of the invention, may comprise at least one stretch of amino acid residues that is chosen from the group consisting of:
(i) CDR1 sequence SEQ ID NO: 77; and/or
(ii) CDR2 sequence:
  (a) SEQ ID NOs: 112-113; and
  (b) amino acid sequences that have 1 amino acid difference with the amino acid sequence of SEQ ID NO: 112; and/or
(iii) CDR3 sequence:
  (c) SEQ ID NOs: 128-130; and
  (d) amino acid sequences that have 1 amino acid difference with the amino acid sequence of SEQ ID NO: 128.

In a further aspect, the monovalent polypeptide of the invention, may comprise at least one stretch of amino acid residues that is chosen from the group consisting of:
(i) CDR1 sequence SEQ ID NO: 77; and/or
(ii) CDR2 sequences:
  (a) SEQ ID NO: 112; and
  (b) amino acid sequences that have 1 amino acid difference with SEQ ID NO: 112, wherein
    at position 4 the D has been changed into G; and/or
(iii) CDR3 sequences:
  (c) SEQ ID NO: 128; and
  (d) amino acid sequences that have 1 amino acid difference with SEQ ID NO: 128, wherein
    at position 9 the S has been changed into P; and/or
    at position 13 the T has been changed into A.

In a further aspect, the monovalent polypeptide of the invention, may comprise at least one stretch of amino acid residues that is chosen from the group consisting of:
(i) CDR1 sequence SEQ ID NO: 77; and/or
(ii) CDR2 sequence SEQ ID NO: 112; and/or
(iii) CDR3 sequence SEQ ID NO: 128.

In a further aspect, the monovalent polypeptide of the invention, may comprise at least one stretch of amino acid residues that is chosen from the group consisting of:
(i) CDR1 sequence SEQ ID NO: 88; and/or
(ii) CDR2 sequences:
  (a) SEQ ID NOs: 114-116; and
  (b) amino acid sequences that have 2, or 1 amino acid(s) difference with the amino acid sequence of SEQ ID NO: 114; and/or
(iii) CDR3 sequences:
  (c) SEQ ID NOs: 131-132; and
  (d) amino acid sequences that have 2, or 1 amino acid(s) difference with the amino acid sequence of SEQ ID NO: 131.

In a further aspect, the monovalent polypeptide of the invention, may comprise at least one stretch of amino acid residues that is chosen from the group consisting of:
(i) CDR1 sequence SEQ ID NO: 88; and/or
(ii) CDR2 sequences:
  (a) SEQ ID NO: 114; and
  (b) amino acid sequences that have 2, or 1 amino acid(s) difference with SEQ ID NO: 114, wherein
    at position 1 the V has been changed into I, or A; and/or
    at position 9 the M has been changed into I;
and/or
(iii) CDR3 sequences:
  (c) SEQ ID NO: 131; and
  (d) amino acid sequences that have 2, or 1 amino acid(s) difference with SEQ ID NO: 131, wherein
    at position 4 the G has been changed into E; and/or
    at position 5 the R has been changed into Q.

In a further aspect, the monovalent polypeptide of the invention, may comprise at least one stretch of amino acid residues that is chosen from the group consisting of:
(i) CDR1 sequence SEQ ID NO: 88; and/or
(ii) CDR2 sequence SEQ ID NO: 114; and/or
(iii) CDR3 sequence SEQ ID NO: 131.

In particular, a monovalent polypeptide of the invention may be a monovalent polypeptide that comprises one antigen binding site, wherein said antigen binding site comprises at least one stretch of amino acid residues that is chosen from the group consisting of the CDR1 sequences, CDR2 sequences and CDR3 sequences as described above (or any suitable combination thereof). In a preferred aspect, however, the monovalent polypeptide of the invention comprises more than one, such as two or more stretches of amino acid residues chosen from the group consisting of the CDR1 sequences of the invention, the CDR2 sequences of the invention and/or the CDR3 sequences of the invention.

Preferably, the monovalent polypeptide of the invention comprises three stretches of amino acid residues chosen from the group consisting of the CDR1 sequences of the invention, the CDR2 sequences of the invention and the CDR3 sequences of the invention, respectively. The combinations of CDR's that are mentioned herein as being preferred for the monovalent polypeptides of the invention are listed in Table A-10.

It should be further noted that the invention is not limited as to the origin of the monovalent polypeptide of the invention (or of the nucleic acid of the invention used to express it), nor as to the way that the monovalent polypeptide or nucleic acid of the invention is (or has been) generated or obtained. Thus, the monovalent polypeptides of the invention may be naturally occurring monovalent polypeptides (from any suitable species) or synthetic or semi-synthetic monovalent polypeptides.

Furthermore, it will also be clear to the skilled person that it is possible to "graft" one or more of the CDR's mentioned above onto other "scaffolds", including but not limited to human scaffolds or non-immunoglobulin scaffolds. Suitable scaffolds and techniques for such CDR grafting will be clear to the skilled person and are well known in the art, see for example U.S. Pat. No. 7,180,370, WO 01/27160, EP 0605522, EP 0460167, U.S. Pat. No. 7,054,297, Nicaise et al. (Protein Science 13: 1882-1891, 2004), Ewert et al. (Methods 34: 184-199, 2004), Kettleborough et al. (Protein Eng. 4: 773-783, 1991), O'Brien and Jones (Methods Mol. Biol. 207: 81-100, 2003), Skerra (J. Mol. Recognit. 13: 167-187, 2000) and Saerens et al. (J. Mol. Biol. 352: 597-607, 2005) and the further references cited therein. For example, techniques known per se for grafting mouse or rat CDR's onto human frameworks and scaffolds can be used in an analogous manner to provide chimeric proteins comprising one or more of the CDR sequences defined herein for the monovalent polypeptides of the invention and one or more human framework regions or sequences. Suitable scaffolds for presenting amino acid sequences will be clear to the skilled person, and for example comprise, without limitation, the binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al. Nat. Biotech., 23: 1257, 2005), and binding moieties based on DNA or RNA including but not limited to DNA or RNA aptamers (Ulrich et al. Comb. Chem. High Throughput Screen 9: 619-32, 2006).

In said monovalent polypeptides of the invention, the CDR's may be linked to further amino acid sequences and/or may be linked to each other via amino acid sequences, in which said amino acid sequences are preferably framework sequences or are amino acid sequences that act as framework sequences, or together form a scaffold for presenting the CDR's.

According to a preferred, but non-limiting embodiment, the monovalent polypeptides of the invention comprise at least three CDR sequences linked to at least two framework sequences, in which preferably at least one of the three CDR sequences is a CDR3 sequence, with the other two CDR sequences being CDR1 or CDR2 sequences, and preferably being one CDR1 sequence and one CDR2 sequence. According to one specifically preferred, but non-limiting embodiment, the monovalent polypeptides of the invention have the structure FR1-CDR1-FR2-CDR2-FR3-CDR3-FR4, in which CDR1, CDR2 and CDR3 are as defined herein for the monovalent polypeptides of the invention, and FR1, FR2, FR3 and FR4 are framework sequences. In such a monovalent polypeptide of the invention, the framework sequences may be any suitable framework sequence, and examples of suitable framework sequences will be clear to the skilled person, for example on the basis of the standard handbooks and the further disclosure and prior art mentioned herein.

Accordingly, a monovalent polypeptide of the present invention essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NOs: 73-88; and
  (b) amino acid sequences that have 4, 3, 2, or 1 amino acid(s) difference with the amino acid sequences of SEQ ID NOs: 73-88; and/or
(ii) CDR2 is chosen from the group consisting of:
  (c) SEQ ID NOs: 90-116; and
  (d) amino acid sequences that have 4, 3, 2, or 1 amino acid(s) difference with the amino acid sequences of SEQ ID NOs: 90-116; and/or
(iii) CDR3 is chosen from the group consisting of:
  (e) SEQ ID NOs: 118-132 and 282-284; and
  (f) amino acid sequences that have 4, 3, 2, or 1 amino acid(s) difference with the amino acid sequences of SEQ ID NOs: 118-132 and 282-284.

Further preferred CDR sequences are depicted in Table A-10.

Sequence analysis of the resulting binders further resulted in the identification of 8 distinct families, i.e. Family 7, Family 26, Family 82, Family 109, Family 85, Family 38, Family 110 and Family 108. Corresponding alignments are provided in Table A-1, Table A-2, Table A-3, Table A-4, Table A-5, Table A-6, Table A-7 and Table A-8, respectively. Classification into different families was based on sequence similarities and differences in the CDRs. Family 7 comprises 21 clones (SEQ ID NOs: 1-21), Family 26 comprises 11 clones (SEQ ID NOs: 22-32), Family 82 comprises 23 clones (SEQ ID NOs: 33-55), Family 109 comprises 6 clones (SEQ ID NOs: 56-61), Families 85 and 108 are each represented by only 1 clone (SEQ ID NO: 62 and SEQ ID NO: 72, respectively), Family 38 comprises 6 clones (SEQ ID NOs: 63-68) and Family 110 comprises 3 clones (SEQ ID NOs: 69-71). Representatives of all families were isolated based on high affinity binding to GITR and human T cell activation (Example 5). In general Family 7, Family 26 and Family 109 representatives demonstrated the best $EC_{50}$ values.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NOs: 73-75; and
  (b) amino acid sequences that have 4, 3, 2, or 1 amino acid(s) difference with the amino acid sequence of SEQ ID NO: 73; and/or
(ii) CDR2 is chosen from the group consisting of:
  (c) SEQ ID NOs: 90-98; and
  (d) amino acid sequences that have 4, 3, 2, or 1 amino acid(s) difference with the amino acid sequence of SEQ ID NO: 90; and/or
(iii) CDR3 is chosen from the group consisting of:
  (e) SEQ ID NOs: 118-119, 123 and 282-284; and
  (f) amino acid sequences that have 2, or 1 amino acid(s) difference with the amino acid sequence of SEQ ID NO: 118.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which:
(i) CDR1 is chosen from the group consisting of:
  (a) SEQ ID NO: 73; and
  (b) amino acid sequences that have 4, 3, 2, or 1 amino acid difference(s) with SEQ ID NO: 73, wherein
    at position 2 the T has been changed into S;
    at position 7 the D has been changed into N;
    at position 8 the S has been changed into A; and/or
    at position 10 the A has been changed into G;
and/or
(ii) CDR2 is chosen from the group consisting of:
  (c) SEQ ID NO: 90; and
  (d) amino acid sequences that have 4, 3, 2, or 1 amino acid difference(s) with SEQ ID NO: 90, wherein
    at position 1 the A has been changed into H, T, or G;
    at position 2 the I has been changed into M;
    at position 3 the T has been changed into S;
    at position 6 the G has been changed into S;
    at position 7 the S has been changed into R, or G; and/or
    at position 8 the P has been changed into S, T, or R
and/or
(iii) CDR3 is chosen from the group consisting of:
  (e) SEQ ID NO: 118; and
  (f) amino acid sequences that have 2, or 1 amino acid difference(s) with SEQ ID NO: 118, wherein
    at position 9 the A has been changed into P;
    at position 11 the M has been changed into L, K, R, or Q; and/or
    at position 12 the D has been changed into N.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which:
- i) CDR1 is represented by SEQ ID NO: 73, CDR2 is represented by SEQ ID NO: 90, and CDR3 is represented by SEQ ID NO: 118; or
- ii) CDR1 is represented by SEQ ID NO: 73, CDR2 is represented by SEQ ID NO: 90, and CDR3 is represented by SEQ ID NO: 123.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which:
- (i) CDR1 is chosen from the group consisting of:
  - (a) SEQ ID NOs: 76-78; and
  - (b) amino acid sequences that have 2, or 1 amino acid(s) difference with the amino acid sequence of SEQ ID NO: 76; and/or
- (ii) CDR2 is chosen from the group consisting of:
  - (c) SEQ ID NOs: 99-103; and
  - (d) amino acid sequences that have 3, 2, or 1 amino acid(s) difference with the amino acid sequence of SEQ ID NO: 99; and/or
- (iii) CDR3 is chosen from the group consisting of:
  - (e) SEQ ID NOs: 120-123; and
  - (f) amino acid sequences that have 4, 3, 2, or 1 amino acid(s) difference with the amino acid sequence of SEQ ID NO: 120.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which:
- (i) CDR1 is chosen from the group consisting of:
  - (a) SEQ ID NO: 76; and
  - (b) amino acid sequences that have 2, or 1 amino acid difference(s) with SEQ ID NO: 76, wherein
    - at position 7 the D has been changed into N; and/or
    - at position 8 the S has been changed into A;

and/or
- (ii) CDR2 is chosen from the group consisting of:
  - (c) SEQ ID NO: 99; and
  - (d) amino acid sequences that have 3, 2, or 1 amino acid difference(s) with SEQ ID NO: 99, wherein
    - at position 1 the A has been changed into S, or T;
    - at position 5 the S has been changed into T, G, or R;
    - at position 6 the T has been changed into K; and/or
    - at position 7 the N has been changed into I;

and/or
- (iii) CDR3 is chosen from the group consisting of:
  - (e) SEQ ID NO: 120; and
  - (f) amino acid sequences that have 4, 3, 2, or 1 amino acid difference(s) with SEQ ID NO: 120, wherein
    - at position 1 the E has been changed into K;
    - at position 4 the A has been changed into T;
    - at position 11 the I has been changed into M, or L; and/or
    - at position 12 the N has been changed into D.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which: CDR1 is represented by SEQ ID NO: 76, CDR2 is represented by SEQ ID NO: 99, and CDR3 is represented by SEQ ID NO: 120.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which:
- (i) CDR1 is chosen from the group consisting of:
  - (a) SEQ ID NOs: 79-84; and
  - (b) amino acid sequences that have 3, 2, or 1 amino acid(s) difference with the amino acid sequence of SEQ ID NO: 79; and/or
- (ii) CDR2 is chosen from the group consisting of:
  - (c) SEQ ID NOs: 104-108; and
  - (d) amino acid sequences that have 2, or 1 amino acid(s) difference with the amino acid sequence of SEQ ID NO: 104; and/or
- (iii) CDR3 is chosen from the group consisting of:
  - (e) SEQ ID NOs: 124-125; and
  - (f) amino acid sequences that have 1 amino acid difference with the amino acid sequence of SEQ ID NO: 124.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which:
- (i) CDR1 is chosen from the group consisting of:
  - (a) SEQ ID NO: 79; and
  - (b) amino acid sequences that have 3, 2, or 1 amino acid difference(s) with SEQ ID NO: 79, wherein
    - at position 2 the S has been changed into N;
    - at position 3 the V has been changed into I;
    - at position 7 the N has been changed into D;
    - at position 8 the D has been changed into S; and/or
    - at position 9 the M has been changed into V, or T;

and/or
- (ii) CDR2 is chosen from the group consisting of:
  - (c) SEQ ID NO: 104; and
  - (d) amino acid sequences that have 2, or 1 amino acid difference(s) with SEQ ID NO: 104, wherein
    - at position 1 the D has been changed into G;
    - at position 5 the R has been changed into A; and/or
    - at position 6 the G has been changed into D;

and/or
- (iii) CDR3 is chosen from the group consisting of:
  - (e) SEQ ID NO: 124; and
  - (f) amino acid sequences that have 1 amino acid difference with SEQ ID NO: 124, wherein
    - at position 4 the T has been changed into M.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which: CDR1 is represented by SEQ ID NO: 79, CDR2 is represented by SEQ ID NO: 104, and CDR3 is represented by SEQ ID NO: 124.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which:
- (i) CDR1 is chosen from the group consisting of:
  - (a) SEQ ID NOs: 85-86; and
  - (b) amino acid sequences that have 1 amino acid difference with the amino acid sequence of SEQ ID NO: 85; and/or
- (ii) CDR2 is chosen from the group consisting of:
  - (c) SEQ ID NOs: 109-110; and
  - (d) amino acid sequences that have 1 amino acid difference with the amino acid sequence of SEQ ID NO: 109; and/or
- (iii) CDR3 is SEQ ID NO: 126.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which:
- (i) CDR1 is chosen from the group consisting of:
  - (a) SEQ ID NO: 85; and
  - (b) amino acid sequences that have 1 amino acid difference with SEQ ID NO: 85, wherein
    at position 2 the S has been changed into N; and/or
- (ii) CDR2 is chosen from the group consisting of:
  - (c) SEQ ID NO: 109; and
  - (d) amino acid sequences that have 1 amino acid difference with SEQ ID NO: 109, wherein
    at position 9 the T has been changed into S; and/or
- (iii) CDR3 is SEQ ID NO: 126.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which: CDR1 is represented by SEQ ID NO: 85, CDR2 is represented by SEQ ID NO: 109, and CDR3 is represented by SEQ ID NO: 126.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which: CDR1 is represented by SEQ ID NO: 87, CDR2 is represented by SEQ ID NO: 111, and CDR3 is represented by SEQ ID NO: 127.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which:
- (i) CDR1 is SEQ ID NO: 77; and/or
- (ii) CDR2 is chosen from the group consisting of:
  - (a) SEQ ID NOs: 112-113; and
  - (b) amino acid sequences that have 1 amino acid difference with the amino acid sequence of SEQ ID NO: 112; and/or
- (iii) CDR3 is chosen from the group consisting of:
  - (c) SEQ ID NOs: 128-130; and
  - (d) amino acid sequences that have 1 amino acid difference with the amino acid sequence of SEQ ID NO: 128.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which:
- (i) CDR1 is SEQ ID NO: 77; and/or
- (ii) CDR2 is chosen from the group consisting of:
  - (a) SEQ ID NO: 112; and
  - (b) amino acid sequences that have 1 amino acid difference with SEQ ID NO: 112, wherein
    at position 4 the D has been changed into G; and/or
- (iii) CDR3 is chosen from the group consisting of:
  - (c) SEQ ID NO: 128; and
  - (d) amino acid sequences that have 1 amino acid difference with SEQ ID NO: 128, wherein
    at position 9 the S has been changed into P; and/or
    at position 13 the T has been changed into A.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which: CDR1 is represented by SEQ ID NO: 77, CDR2 is represented by SEQ ID NO: 112, and CDR3 is represented by SEQ ID NO: 128.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which:
- (i) CDR1 is SEQ ID NO: 88; and/or
- (ii) CDR2 is chosen from the group consisting of:
  - (c) SEQ ID NOs: 114-116; and
  - (d) amino acid sequences that have 2, or 1 amino acid(s) difference with the amino acid sequence of SEQ ID NO: 114; and/or
- (iii) CDR3 is chosen from the group consisting of:
  - (e) SEQ ID NOs: 131-132; and
  - (f) amino acid sequences that have 2, or 1 amino acid(s) difference with the amino acid sequence of SEQ ID NO: 131.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which:
- (i) CDR1 is SEQ ID NO: 88; and/or
- (ii) CDR2 is chosen from the group consisting of:
  - (a) SEQ ID NO: 114; and (b) amino acid sequences that have 2, or 1 amino acid(s) difference with SEQ ID NO: 114, wherein
at position 1 the V has been changed into I, or A; and/or
at position 9 the M has been changed into I;
and/or
(iii) CDR3 is chosen from the group consisting of:
(c) SEQ ID NO: 131; and
(d) amino acid sequences that have 2, or 1 amino acid(s) difference with SEQ ID NO: 131, wherein
at position 4 the G has been changed into E; and/or
at position 5 the R has been changed into Q.

According to a preferred but non-limiting aspect, the present invention relates to a monovalent polypeptide as described herein, wherein said at least one immunoglobulin single variable domain essentially consists of 4 framework regions (FR1 to FR4, respectively) and 3 complementarity determining regions (CDR1 to CDR3, respectively), in which: CDR1 is represented by SEQ ID NO: 88, CDR2 is represented by SEQ ID NO: 114, and CDR3 is represented by SEQ ID NO: 131.

According to a preferred but non-limiting aspect, the present invention relates to a monovalent polypeptide as described herein, wherein said at least one immunoglobulin single variable domain is chosen from the group of ISVDs, wherein:

CDR1 is SEQ ID NO: 73, CDR2 is SEQ ID NO: 90; and CDR3 is SEQ ID NO: 118;
CDR1 is SEQ ID NO: 74, CDR2 is SEQ ID NO: 91; and CDR3 is SEQ ID NO: 118;
CDR1 is SEQ ID NO: 74, CDR2 is SEQ ID NO: 92; and CDR3 is SEQ ID NO: 118;
CDR1 is SEQ ID NO: 74, CDR2 is SEQ ID NO: 93; and CDR3 is SEQ ID NO: 118;
CDR1 is SEQ ID NO: 74, CDR2 is SEQ ID NO: 94; and CDR3 is SEQ ID NO: 118;
CDR1 is SEQ ID NO: 74, CDR2 is SEQ ID NO: 95; and CDR3 is SEQ ID NO: 118;
CDR1 is SEQ ID NO: 75, CDR2 is SEQ ID NO: 93; and CDR3 is SEQ ID NO: 118;
CDR1 is SEQ ID NO: 74, CDR2 is SEQ ID NO: 96; and CDR3 is SEQ ID NO: 118;
CDR1 is SEQ ID NO: 74, CDR2 is SEQ ID NO: 97; and CDR3 is SEQ ID NO: 118;
CDR1 is SEQ ID NO: 74, CDR2 is SEQ ID NO: 98; and CDR3 is SEQ ID NO: 119;
CDR1 is SEQ ID NO: 73, CDR2 is SEQ ID NO: 90; and CDR3 is SEQ ID NO: 123;
CDR1 is SEQ ID NO: 73, CDR2 is SEQ ID NO: 90; and CDR3 is SEQ ID NO: 282;
CDR1 is SEQ ID NO: 73, CDR2 is SEQ ID NO: 90; and CDR3 is SEQ ID NO: 283;
CDR1 is SEQ ID NO: 73, CDR2 is SEQ ID NO: 90; and CDR3 is SEQ ID NO: 284;
CDR1 is SEQ ID NO: 76, CDR2 is SEQ ID NO: 99; and CDR3 is SEQ ID NO: 120;
CDR1 is SEQ ID NO: 77, CDR2 is SEQ ID NO: 100; and CDR3 is SEQ ID NO: 121;
CDR1 is SEQ ID NO: 78, CDR2 is SEQ ID NO: 101; and CDR3 is SEQ ID NO: 122;
CDR1 is SEQ ID NO: 76, CDR2 is SEQ ID NO: 102; and CDR3 is SEQ ID NO: 118;
CDR1 is SEQ ID NO: 77, CDR2 is SEQ ID NO: 103; and CDR3 is SEQ ID NO: 118;
CDR1 is SEQ ID NO: 76, CDR2 is SEQ ID NO: 99; and CDR3 is SEQ ID NO: 118;
CDR1 is SEQ ID NO: 78, CDR2 is SEQ ID NO: 99; and CDR3 is SEQ ID NO: 123;
CDR1 is SEQ ID NO: 79, CDR2 is SEQ ID NO: 104; and CDR3 is SEQ ID NO: 124;
CDR1 is SEQ ID NO: 76, CDR2 is SEQ ID NO: 105; and CDR3 is SEQ ID NO: 124;
CDR1 is SEQ ID NO: 76, CDR2 is SEQ ID NO: 106; and CDR3 is SEQ ID NO: 124;
CDR1 is SEQ ID NO: 80, CDR2 is SEQ ID NO: 106; and CDR3 is SEQ ID NO: 124;
CDR1 is SEQ ID NO: 81, CDR2 is SEQ ID NO: 104; and CDR3 is SEQ ID NO: 124;
CDR1 is SEQ ID NO: 82, CDR2 is SEQ ID NO: 104; and CDR3 is SEQ ID NO: 124;
CDR1 is SEQ ID NO: 83, CDR2 is SEQ ID NO: 104; and CDR3 is SEQ ID NO: 124;
CDR1 is SEQ ID NO: 84, CDR2 is SEQ ID NO: 104; and CDR3 is SEQ ID NO: 124;
CDR1 is SEQ ID NO: 83, CDR2 is SEQ ID NO: 106; and CDR3 is SEQ ID NO: 124;
CDR1 is SEQ ID NO: 83, CDR2 is SEQ ID NO: 107; and CDR3 is SEQ ID NO: 124;
CDR1 is SEQ ID NO: 83, CDR2 is SEQ ID NO: 108; and CDR3 is SEQ ID NO: 124;
CDR1 is SEQ ID NO: 83, CDR2 is SEQ ID NO: 104; and CDR3 is SEQ ID NO: 125;
CDR1 is SEQ ID NO: 85, CDR2 is SEQ ID NO: 109; and CDR3 is SEQ ID NO: 126;
CDR1 is SEQ ID NO: 86, CDR2 is SEQ ID NO: 110; and CDR3 is SEQ ID NO: 126;
CDR1 is SEQ ID NO: 85, CDR2 is SEQ ID NO: 110; and CDR3 is SEQ ID NO: 126;
CDR1 is SEQ ID NO: 87, CDR2 is SEQ ID NO: 111; and CDR3 is SEQ ID NO: 127;
CDR1 is SEQ ID NO: 77, CDR2 is SEQ ID NO: 112; and CDR3 is SEQ ID NO: 128;
CDR1 is SEQ ID NO: 77, CDR2 is SEQ ID NO: 112; and CDR3 is SEQ ID NO: 129;
CDR1 is SEQ ID NO: 77, CDR2 is SEQ ID NO: 113; and CDR3 is SEQ ID NO: 130;
CDR1 is SEQ ID NO: 77, CDR2 is SEQ ID NO: 112; and CDR3 is SEQ ID NO: 130;
CDR1 is SEQ ID NO: 88, CDR2 is SEQ ID NO: 114; and CDR3 is SEQ ID NO: 131;
CDR1 is SEQ ID NO: 88, CDR2 is SEQ ID NO: 115; and CDR3 is SEQ ID NO: 131; and
CDR1 is SEQ ID NO: 88, CDR2 is SEQ ID NO: 116; and CDR3 is SEQ ID NO: 132.

Representative polypeptides of the present invention having the CDRs described above are shown in Table A-10.

In one aspect, the monovalent polypeptide has the same number of amino acids within its sequence compared to any one of SEQ ID NOs: 1-21. In another aspect, the monovalent polypeptide has an amino acid sequence between position 8 and position 106 (according to Kabat numbering) that has 89% or more sequence identity compared to any one of SEQ ID NOs: 1-21. Preferably, the monovalent polypeptide has the same number of amino acids within its sequence compared to any one of SEQ ID NOs: 1-21 and the monovalent polypeptide has an amino acid sequence between position 8 and position 106 (according to Kabat numbering) that has 89% or more sequence identity compared to any one of SEQ ID NOs: 1-21. In another preferred aspect, the monovalent polypeptide belongs to Family 7, such as e.g. a monovalent polypeptide selected from any one of SEQ ID NOs: 1-21.

In one aspect, the monovalent polypeptide has the same number of amino acids within its sequence compared to any one of SEQ ID NOs: 22-32. In another aspect, the monovalent polypeptide has an amino acid sequence between position 8 and position 106 (according to Kabat numbering) that has 89% or more sequence identity compared to any one of SEQ ID NOs: 22-32. Preferably, the monovalent polypeptide has the same number of amino acids within its sequence compared to any one of SEQ ID NOs: 22-32 and the monovalent polypeptide has an amino acid sequence between position 8 and position 106 (according to Kabat numbering) that has 89% or more sequence identity compared to any one of SEQ ID NOs: 22-32. In another preferred aspect, the monovalent polypeptide belongs to Family 26, such as e.g. a monovalent polypeptide selected from any one of SEQ ID NOs: 22-32.

In one aspect, the monovalent polypeptide has the same number of amino acids within its sequence compared to any one of SEQ ID NOs: 33-55. In another aspect, the monovalent polypeptide has an amino acid sequence between position 8 and position 106 (according to Kabat numbering) that has 89% or more sequence identity compared to any one of SEQ ID NOs: 33-55. Preferably, the monovalent polypeptide has the same number of amino acids within its sequence compared to any one of SEQ ID NOs: 33-55 and the monovalent polypeptide has an amino acid sequence between position 8 and position 106 (according to Kabat numbering) that has 89% or more sequence identity compared to any one of SEQ ID NOs: 33-55. In another preferred aspect, the monovalent polypeptide belongs to Family 82, such as e.g. a monovalent polypeptide selected from any one of SEQ ID NOs: 33-55.

In one aspect, the monovalent polypeptide has the same number of amino acids within its sequence compared to any one of SEQ ID NOs: 56-61. In another aspect, the monovalent polypeptide has an amino acid sequence between position 8 and position 106 (according to Kabat numbering) that has 89% or more sequence identity compared to any one of SEQ ID NOs: 56-61. Preferably, the monovalent polypeptide has the same number of amino acids within its sequence compared to any one of SEQ ID NOs: 56-61 and the monovalent polypeptide has an amino acid sequence between position 8 and position 106 (according to Kabat numbering) that has 89% or more sequence identity compared to any one of SEQ ID NOs: 56-61. In another preferred aspect, the monovalent polypeptide belongs to Family 109, such as e.g. a monovalent polypeptide selected from any one of SEQ ID NOs: 56-61.

In one aspect, the monovalent polypeptide has the same number of amino acids within its sequence compared to any one of SEQ ID NOs: 63-68. In another aspect, the monovalent polypeptide has an amino acid sequence between position 8 and position 106 (according to Kabat numbering) that has 89% or more sequence identity compared to any one of SEQ ID NOs: 63-68. Preferably, the monovalent polypeptide has the same number of amino acids within its sequence compared to any one of SEQ ID NOs: 63-68 and the monovalent polypeptide has an amino acid sequence between position 8 and position 106 (according to Kabat numbering) that has 89% or more sequence identity compared to any one of SEQ ID NOs: 63-68. In another preferred aspect, the monovalent polypeptide belongs to Family 38, such as e.g. a monovalent polypeptide selected from any one of SEQ ID NOs: 63-68.

In one aspect, the monovalent polypeptide has the same number of amino acids within its sequence compared to any one of SEQ ID NOs: 69-71. In another aspect, the monovalent polypeptide has an amino acid sequence between position 8 and position 106 (according to Kabat numbering) that has 89% or more sequence identity compared to any one of SEQ ID NOs: 69-71. Preferably, the monovalent polypeptide has the same number of amino acids within its sequence compared to any one of SEQ ID NOs: 69-71 and the monovalent polypeptide has an amino acid sequence between position 8 and position 106 (according to Kabat numbering) that has 89% or more sequence identity compared to any one of SEQ ID NOs: 69-71. In another preferred aspect, the monovalent polypeptide belongs to Family 110, such as e.g. a monovalent polypeptide selected from any one of SEQ ID NOs: 69-71.

Monovalent polypeptides comprising one or more of the above specified stretches of amino acid residues may modulate (i.e. increase, enhance, stimulate or potentiate) the activity of GITR. More particularly, the monovalent polypeptides of the present invention may enhance an immune response. As such, these polypeptides of the invention may enhance proliferation or activation of T cells, B cells or natural killer cells.

Proliferation or activation of T cell, B cells or natural killer cells can be determined by a variety of assays, including but not limited to proliferation assays, cytotoxicity assays, cell killing assays, reporter gene assays (e.g. NF-κB luciferase reporter assay), T cell activation assay, cell surface receptor binding assays and assays to measure expression of known markers of activation or cytokine secretion, which are all well known in the art.

For example, any one of several conventional assays for monitoring cytokine production (such as IFN-γ and interleukins) as a measure of immune cells activation can be used. For example, for tracking T cell activation, interleukin-2 can be employed as a marker, which can be assayed as described in Proc. Natl. Acad. Sci. USA. 86:1333 (1989).

One can also employ immunofluorescence and flow cytometry to monitor cytokine production on a cellular basis, and to monitor cell surface markers that reflect cellular activation states. A host of such markers are known, detecting antibodies are broadly commercially available, and the markers are well known in the art.

A common assay for T cell proliferation entails measuring tritiated thymidine incorporation. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

Binding of the monovalent polypeptides of the invention to GITR can be measured in binding assays. Typical assays include (without being limiting) assays in which GITR is exposed on a cell surface (such as e.g. Flp-In™-293 cells or GloResponse™ NF-κB-Nluc2P HEK293 cells). A preferred assay for measuring binding of the polypeptides of the invention to GITR is a FACS assay, such as e.g. the FACS assay as described in the examples, wherein binding of the polypeptides of the invention to GITR expressed on Flp-In™-293 cells and/or activated T cells is determined. Some preferred $EC_{50}$ values for binding of the polypeptides of the invention to GITR will become clear from the further description and examples herein.

In such FACS binding assay, the monovalent polypeptides of the present invention may have $EC_{50}$ values in binding human GITR of $10^{-8}$ M or lower, more preferably of $10^{-9}$ M or lower, or even of $10^{-10}$ M or lower. For example, in such FACS binding assay, the monovalent polypeptides of the present invention may have $EC_{50}$ values in binding human GITR between $10^{-10}$ M and $10^{-8}$ M, such as between $10^{-9}$ M and $10^{-8}$ M or between $10^{-10}$ M and $10^{-9}$ M.

The invention also relates to a monovalent polypeptide which has at least 80% amino acid identity (or sequence identity as defined herein), preferably at least 85% amino acid identity, more preferably at least 90% amino acid identity, such as 95%, 96%, 97%, 98%, 99% amino acid identity or more or even (essentially) 100% amino acid identity with at least one of the amino acid sequences of SEQ ID NOs: 1-71.

In one specific, but non-limiting aspect, the monovalent polypeptide of the invention may be a monovalent polypeptide that comprises an immunoglobulin fold or a monovalent polypeptide that, under suitable conditions (such as physiological conditions) is capable of forming an immunoglobulin fold (i.e., by folding). Reference is inter alia made to the review by Halaby et al. (J. Protein Eng. 12: 563-71, 1999). Preferably, when properly folded so as to form an immunoglobulin fold, the stretches of amino acid residues may be capable of properly forming the antigen binding site for binding GITR. Accordingly, in a preferred aspect the monovalent polypeptide of the invention is an immunoglobulin, such as e.g. an immunoglobulin single variable domain.

Accordingly, the framework sequences are preferably (a suitable combination of) immunoglobulin framework sequences or framework sequences that have been derived from immunoglobulin framework sequences (for example, by sequence optimization such as humanization or camelization). For example, the framework sequences may be framework sequences derived from an immunoglobulin single variable domain such as a light chain variable domain (e.g., a $V_L$-sequence) and/or from a heavy chain variable domain (e.g., a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

The framework sequences may preferably be such that the monovalent polypeptide of the invention is an immunoglobulin single variable domain such as a Domain antibody (or an amino acid sequence that is suitable for use as a domain antibody); a single domain antibody (or an amino acid that is suitable for use as a single domain antibody); a "dAb" (or an amino acid that is suitable for use as a dAb); a Nanobody®; a $V_{HH}$ sequence; a humanized $V_{HH}$ sequence; a camelized $V_H$ sequence; or a $V_{HH}$ sequence that has been obtained by affinity maturation. Again, suitable framework sequences will be clear to the skilled person, for example on the basis of the standard handbooks and the further disclosure and prior art mentioned herein.

In particular, the framework sequences present in the monovalent polypeptides of the invention may contain one or more of Hallmark residues (as defined in WO 08/020079 (Tables A-3 to A-8)), such that the monovalent polypeptide of the invention is a Nanobody®. Some preferred, but non-limiting examples of (suitable combinations of) such framework sequences will become clear from the further disclosure herein (see e.g., Table A-10). Generally, Nanobodies® (in particular $V_{HH}$ sequences and partially humanized Nanobodies®) can in particular be characterized by the presence of one or more "Hallmark residues" in one or more of the framework sequences (as e.g., further described in WO 08/020079, page 61, line 24 to page 98, line 3).

More in particular, the invention provides polypeptides comprising at least one immunoglobulin single variable domain that is an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and which:

i) have at least 80%, more preferably 90%, even more preferably 95% amino acid identity with at least one of the amino acid sequences of SEQ ID NOs: 1-71 (see Table A-9), in which for the purposes of determining the degree of amino acid identity, the amino acid residues that form the CDR sequences are disregarded. In this respect, reference is also made to Table A-10, which lists the framework 1 sequences (SEQ ID NOs: 134-152), framework 2 sequences (SEQ ID NOs: 153-162), framework 3 sequences (SEQ ID NOs: 163-200) and framework 4 sequences (SEQ ID NOs: 201-205) of the immunoglobulin single variable domains of SEQ ID NOs: 1-71 (see Table A-9); or ii) combinations of framework sequences as depicted in Table A-10;

and in which:

iii) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020079.

The present invention also provides a number of sequence optimized immunoglobulin single variable domains.

In particular, sequence optimized immunoglobulin single variable domains may be amino acid sequences that are as generally defined for immunoglobulin single variable domains in the previous paragraphs, but in which at least one amino acid residue is present (and in particular, in at least one of the framework residues) that is and/or that corresponds to a humanizing substitution (as defined herein). Some preferred, but non-limiting humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring VHH sequence with the corresponding framework sequence of one or more closely related human VH sequences, after which one or more of the potentially useful humanizing substitutions (or combinations thereof) thus determined can be introduced into said VHH sequence (in any manner known per se, as further described herein) and the resulting humanized VHH sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) an immunoglobulin single variable domains may be partially humanized or fully humanized.

The present invention also provides a number of sequence optimized immunoglobulin single variable domains that may show improved expression and/or increased stability upon storage during stability studies. The amino acid sequences of the present invention may show reduced pyroglutamate post-translational modification of the N-terminus and hence have increased product stability. In addition, the amino acid sequences of the present invention may show other improved properties such as e.g. less immunogenicity, improved binding characteristics (suitably measured and/or expressed as a KD-value (actual or apparent), a KA-value (actual or apparent), a kon-rate and/or a koff-rate, or alternatively as an $IC_{50}$ value, as further described herein) for GITR, improved affinity and/or improved avidity for GITR and/or improved efficacy and/or potency for agonizing GITR, compared to their corresponding parental amino acid sequences.

Some particularly preferred sequence optimized immunoglobulin single variable domains of the invention are sequence optimized variants of the immunoglobulin single variable domains of SEQ ID NOs: 1-71; the amino acid sequences of SEQ ID NOs: 268-275 are some especially preferred examples.

Thus, some other preferred immunoglobulin single variable domains of the invention are Nanobodies® which can bind (as further defined herein) to GITR and which:
  i) are a sequence optimized variant of one of the immunoglobulin single variable domains of SEQ ID NOs: 1-71; and/or
  ii) have at least 80% amino acid identity with at least one of the immunoglobulin single variable domains of SEQ ID NOs: 1-71 and/or at least one of the immunoglobulin single variable domains of SEQ ID NOs: 268-275 (see Table A-9), in which for the purposes of determining the degree of amino acid identity, the amino acid residues that form the CDR sequences are disregarded; In this respect, reference is also made to Table A-10, which lists the framework 1 sequences (SEQ ID NOs: 134-152, 276 and 278), framework 2 sequences (SEQ ID NOs: 153-162), framework 3 sequences (SEQ ID NOs: 163-200, 277 and 279-281) and framework 4 sequences (SEQ ID NOs: 201-205) of the immunoglobulin single variable domains of SEQ ID NOs: 1-71 and 268-275 (see Table A-9); or
  iii) combinations of framework sequences as depicted in Table A-10; and in which:
  iv) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020079.

The immunoglobulins (and in particular immunoglobulin single variable domains) of the invention may also contain the specific mutations/amino acid residues described in the following co-pending US provisional applications, all entitled "Improved immunoglobulin variable domains": U.S. 61/994,552 filed May 16, 2014; U.S. 61/014,015 filed Jun. 18, 2014; U.S. 62/040,167 filed Aug. 21, 2014; and U.S. 62/047,560, filed Sep. 8, 2014 (all assigned to Ablynx N.V.) as well as the International application WO 2015/173325 which was based on these provisional applications and which was published on Nov. 19, 2015.

In particular, the immunoglobulins (and in particular immunoglobulin single variable domains) of the invention may suitably contain (i) a K or Q at position 112; or (ii) a K or Q at position 110 in combination with a V at position 11; or (iii) a T at position 89; or (iv) an L on position 89 with a K or Q at position 110; or (v) a V at position 11 and an L at position 89; or any suitable combination of (i) to (v).

As also described in said co-pending US provisional applications, when the immunoglobulins of the invention contain the mutations according to one of (i) to (v) above (or a suitable combination thereof):
  the amino acid residue at position 11 is preferably chosen from L, V or K (and is most preferably V); and
  the amino acid residue at position 14 is preferably suitably chosen from A or P; and
  the amino acid residue at position 41 is preferably suitably chosen from A or P; and
  the amino acid residue at position 89 is preferably suitably chosen from T, V or L; and
  the amino acid residue at position 108 is preferably suitably chosen from Q or L; and
  the amino acid residue at position 110 is preferably suitably chosen from T, K or Q; and
  the amino acid residue at position 112 is preferably suitably chosen from S, K or Q.

As mentioned in said co-pending US provisional applications, said mutations are effective in preventing or reducing binding of so-called "pre-existing antibodies" to the immunoglobulins and compounds of the invention. For this purpose, the immunoglobulins of the invention may also contain (optionally in combination with said mutations) a C-terminal extension (X)n (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I)), for which reference is again made to said US provisional applications as well as to WO 12/175741. In particular, an immunoglobulin of the invention may contain such a C-terminal extension when it forms the C-terminal end of a protein, polypeptide or other compound or construct comprising the same (again, as further described in said US provisional applications as well as WO 12/175741).

Some specifically preferred, but non-limiting examples of immunoglobulins of the invention that contain such mutations and/or such a C-terminal extension are given in SEQ ID NOs: 268-275 and 285-290.

In a preferred aspect, the present invention provides an immunoglobulin or monovalent polypeptide that is selected from any of SEQ ID NOs: 1-71 and 268-275.

The present invention also relates to monovalent polypeptides and/or immunoglobulin single variable domains directed against GITR, that cross-blocks the binding to GITR of at least one of the immunoglobulins with SEQ ID NOs: 1-71 and 268-275 and/or that are cross-blocked from binding to GITR by at least one of the immunoglobulins with SEQ ID NOs: 1-71 and 268-275.

The invention further relates to monovalent polypeptides and/or immunoglobulin single variable domains directed against GITR that bind the same epitope as is bound by the monovalent polypeptides of the present invention, more particularly by the monovalent polypeptides with SEQ ID NOs: 1-71 and 268-275.

In a particular aspect, the invention relates to monovalent polypeptides and/or immunoglobulin single variable domains directed against GITR that bind the same epitope as is bound by the monovalent polypeptides of the present invention that belong to Family 7, Family 26, Family 82, Family 85 and Family 38, more particularly by the monovalent polypeptides with SEQ ID NOs: 1-55, 62-68 and 269-275.

In another particular aspect, the invention relates to monovalent polypeptides and/or immunoglobulin single variable domains directed against GITR that bind the same epitope as is bound by the monovalent polypeptides of the present invention that belong to Family 109 and Family 110, more particularly by the monovalent polypeptides with SEQ ID NOs: 56-61, 69-71 and 268.

Again, such monovalent polypeptides may be an immunoglobulin, such as an immunoglobulin single variable domain, derived in any suitable manner and from any suitable source, and may for example be naturally occurring $V_{HH}$ sequences (i.e., from a suitable species of Camelid) or synthetic or semi-synthetic amino acid sequences, including but not limited to "humanized" (as defined herein) Nanobodies® or VHH sequences, "camelized" (as defined herein) immunoglobulin sequences (and in particular camelized heavy chain variable domain sequences), as well as Nanobodies® that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when an immunoglobulin comprises a $V_{HH}$ sequence, said immunoglobulin may be suitably humanized, as further described herein, so as to provide one or more further (partially or fully) humanized immunoglobulins of the invention. Similarly, when an immunoglobulin comprises a synthetic or semi-synthetic sequence (such as a partially humanized sequence), said immunoglobulin may optionally be further suitably humanized, again as described herein, again so as to provide one or more further (partially or fully) humanized immunoglobulins of the invention.

These monovalent polypeptides of the invention, and in particular the immunoglobulins comprising the CDR sequences of the invention are particularly suited for use as building block or binding unit for the preparation of multivalent polypeptides.

Accordingly, the monovalent polypeptides of the invention that bind GITR can be in essentially isolated form (as defined herein), or they may form part of a protein or polypeptide, which may comprise or essentially consist of one or more monovalent polypeptides that bind GITR and which may optionally further comprise one or more further amino acid sequences (all optionally linked via one or more suitable linkers). The present invention also relates to a protein or polypeptide that comprises or essentially consists of one or more monovalent polypeptides of the invention (or suitable fragments thereof).

The one or more monovalent polypeptides of the invention are thus used as a binding unit or building block in such a protein or polypeptide, so as to provide a monovalent, multivalent or multiparatopic polypeptide of the invention, respectively, all as described herein. The present invention thus also relates to a polypeptide which is a monovalent construct comprising or essentially consisting of one monovalent polypeptide of the invention. The present invention thus also relates to a polypeptide which is a multivalent polypeptide, such as e.g., a bivalent, trivalent, tetravalent, pentavalent or hexavalent polypeptide comprising or essentially consisting of two or more monovalent polypeptides of the invention (for multivalent and multispecific polypeptides containing one or more VHH domains and their preparation, reference is also made to Conrath et al. (J. Biol. Chem. 276: 7346-7350, 2001), as well as to for example WO 96/34103, WO 99/23221 and WO 2010/115998).

Multivalent Polypeptides of the Invention

The invention further relates to a multivalent polypeptide (also referred to herein as a "multivalent polypeptide(s) of the invention") that comprises or (essentially) consists of at least one immunoglobulin single variable domain (or suitable fragments thereof) directed against GITR, preferably human GITR, and one additional immunoglobulin single variable domain.

In a preferred aspect, the multivalent polypeptide of the invention comprises or essentially consists of two or more immunoglobulin single variable domains directed against GITR. The two or more immunoglobulin single variable domains may optionally be linked via one or more peptidic linkers.

In the multivalent polypeptide of the invention, the two or more immunoglobulin single variable domains or Nanobodies® may be the same or different, and may be directed against the same antigen or antigenic determinant (for example against the same part(s) or epitope(s) or against different parts or epitopes) or may alternatively be directed against different antigens or antigenic determinants; or any suitable combination thereof. For example, a bivalent polypeptide of the invention may comprise (a) two identical immunoglobulin single variable domains or Nanobodies®; (b) a first immunoglobulin single variable domain or Nanobody® directed against a first antigenic determinant of a protein or antigen and a second immunoglobulin single variable domain or Nanobody® directed against the same antigenic determinant of said protein or antigen which is different from the first immunoglobulin single variable domain or Nanobody®; (c) a first immunoglobulin single variable domain or Nanobody® directed against a first antigenic determinant of a protein or antigen and a second immunoglobulin single variable domain or Nanobody® directed against another antigenic determinant of said protein or antigen, different from said first antigenic determinant; or (d) a first immunoglobulin single variable domain or Nanobody® directed against a first protein or antigen and a second immunoglobulin single variable domain or Nanobody® directed against a second protein or antigen (i.e. different from said first protein or antigen). Similarly, a trivalent polypeptide of the invention may, for example and without being limited thereto. comprise (a) three identical immunoglobulin single variable domains or Nanobodies®; (b) two identical immunoglobulin single variable domains or Nanobodies® against a first antigenic determinant of a protein or antigen and a third immunoglobulin single variable domain or Nanobody® directed against a different antigenic determinant of the same protein or antigen; (c) two identical immunoglobulin single variable domains or Nanobodies® against a first antigenic determinant of a protein or antigen and a third immunoglobulin single variable domain or Nanobody® directed against a second protein or antigen different from said first protein or antigen; (d) a first immunoglobulin single variable domain or Nanobody® directed against a first antigenic determinant of a first protein or antigen, a second immunoglobulin single variable domain or Nanobody® directed against a second antigenic determinant of said first protein or antigen, different from said first antigenic determinant and a third immunoglobulin single variable domain or Nanobody® directed against a second protein or antigen different from said first protein or antigen; or (e) a first immunoglobulin single variable domain or Nanobody® directed against a first protein or antigen, a second immunoglobulin single variable domain or Nanobody® directed against a second protein or antigen different from said first protein or antigen, and a third immunoglobulin single variable domain or Nanobody® directed against a third protein or antigen different from said first and second protein or antigen.

Polypeptides of the invention that contain at least two immunoglobulin single variable domains and/or Nanobodies®, in which at least one immunoglobulin single variable domain or Nanobody® is directed against a first antigen (i.e. against GITR) and at least one immunoglobulin single variable domain or Nanobody® is directed against a second antigen (i.e. different from GITR), will also be referred to as "multispecific" polypeptides of the invention, and the immunoglobulin single variable domains or Nanobodies® present in such polypeptides will also be referred to herein as being in a "multispecific format". Thus, for example, a "bispecific" polypeptide of the invention is a polypeptide that comprises at least one immunoglobulin single variable domain or Nanobody® directed against a first antigen (i.e. GITR) and at least one further immunoglobulin single variable domain or Nanobody® directed against a second antigen (i.e. different from GITR), whereas a "trispecific" polypeptide of the invention is a polypeptide that comprises at least one immunoglobulin single variable domain or Nanobody® directed against a first antigen (i.e. GITR), at least one further immunoglobulin single variable domain or Nanobody® directed against a second antigen (i.e. different from GITR) and at least one further immunoglobulin single variable domain or Nanobody® directed against a third antigen (i.e. different from both GITR, and the second antigen); etc.

Accordingly, in one aspect, in its simplest form, the multivalent polypeptide of the invention is a bivalent polypeptide of the invention comprising a first immunoglobulin single variable domain or Nanobody® directed against GITR, and an identical second immunoglobulin single variable domain or Nanobody® directed against GITR, wherein said first and second immunoglobulin single variable domain or Nanobody® may optionally be linked via a linker sequence (as defined herein); in its simplest form a multivalent polypeptide of the invention may be a trivalent polypeptide of the invention, comprising a first immunoglobulin single variable domain or Nanobody® directed against GITR, an identical second immunoglobulin single variable domain or Nanobody® directed against GITR and an identical third immunoglobulin single variable domain or Nanobody® directed against GITR, in which said first, second and third immunoglobulin single variable domain or Nanobody® may optionally be linked via one or more, and in particular two, linker sequences.

In another aspect, the multivalent polypeptide of the invention may be a bispecific polypeptide of the invention, comprising a first immunoglobulin single variable domain or Nanobody® directed against GITR, and a second immunoglobulin single variable domain or Nanobody® directed against a second antigen, in which said first and second immunoglobulin single variable domain or Nanobody® may optionally be linked via a linker sequence (as defined herein); whereas a multivalent polypeptide of the invention may also be a trispecific polypeptide of the invention, comprising a first immunoglobulin single variable domain or Nanobody® directed against GITR, a second immunoglobulin single variable domain or Nanobody® directed against a second antigen and a third immunoglobulin single variable domain or Nanobody® directed against a third antigen, in which said first, second and third immunoglobulin single variable domain or Nanobody® may optionally be linked via one or more, and in particular two, linker sequences.

In a preferred aspect, the polypeptide of the invention is a trivalent, bispecific polypeptide. A trivalent, bispecific polypeptide of the invention in its simplest form may be a trivalent polypeptide of the invention (as defined herein), comprising two identical immunoglobulin single variable domains or Nanobodies® against GITR and a third immunoglobulin single variable domain or Nanobody® directed against another antigen (e.g. serum albumin), in which said first, second and third immunoglobulin single variable domain or Nanobody® may optionally be linked via one or more, and in particular two, linker sequences. Particularly preferred trivalent, bispecific polypeptides in accordance with the invention are those shown in the Examples described herein and in Table A-11.

In another preferred aspect, the polypeptide of the invention is a tetravalent, bispecific polypeptide. A tetravalent, bispecific polypeptide of the invention in its simplest form may be a tetravalent polypeptide of the invention (as defined herein), comprising three identical immunoglobulin single variable domains or Nanobodies® against GITR and a fourth immunoglobulin single variable domain or Nanobody® directed against another antigen (e.g. serum albumin), in which said first, second, third and fourth immunoglobulin single variable domain or Nanobody® may optionally be linked via one or more, and in particular three, linker sequences. Particularly preferred tetravalent, bispecific polypeptides in accordance with the invention are those shown in the Examples described herein and in Table A-11.

In another preferred aspect, the polypeptide of the invention is a pentavalent, bispecific polypeptide. A pentavalent, bispecific polypeptide of the invention in its simplest form may be a pentavalent polypeptide of the invention (as defined herein), comprising four identical immunoglobulin single variable domains or Nanobodies® against GITR and a fifth immunoglobulin single variable domain or Nanobody® directed against another antigen (e.g. serum albumin), in which said first, second, third, fourth and fifth immunoglobulin single variable domain or Nanobody® may optionally be linked via one or more, and in particular four, linker sequences.

In another preferred aspect, the polypeptide of the invention is a hexavalent, bispecific polypeptide. A hexavalent, bispecific polypeptide of the invention in its simplest form may be a hexavalent polypeptide of the invention (as defined herein), comprising five identical immunoglobulin single variable domains or Nanobodies® against GITR and a sixth immunoglobulin single variable domain or Nanobody® directed against another antigen (e.g. serum albumin), in which said first, second, third, fourth, fifth and sixth immunoglobulin single variable domain or Nanobody® may optionally be linked via one or more, and in particular five, linker sequences.

In a further aspect, the polypeptide of the invention is a multiparatopic polypeptide (also referred to herein as "multiparatopic polypeptide(s) of the invention"), such as e.g., (a) "biparatopic polypeptide(s) of the invention" or "triparatopic polypeptide(s) of the invention". The term "multiparatopic" (antigen-) binding molecule or "multiparatopic" polypeptide as used herein shall mean a polypeptide comprising at least two (i.e. two or more) immunoglobulin single variable domains, wherein a "first" immunoglobulin single variable domain is directed against GITR and a "second" immunoglobulin single variable domain is directed against GITR, and wherein these "first" and "second" immunoglobulin single variable domains have a different paratope. Accordingly, the multiparatopic polypeptide comprises or consists of two or more immunoglobulin single variable domains that are directed against GITR, wherein at least one "first" immunoglobulin single variable domain is directed against a first epitope on GITR and at least one "second" immunoglobulin single variable domain is directed against a second epitope on GITR different from the first epitope on GITR.

In a further aspect, the polypeptide of the invention is a biparatopic polypeptide. The term "biparatopic" (antigen-)

binding molecule or "biparatopic" polypeptide as used herein shall mean a polypeptide comprising a "first" immunoglobulin single variable domain directed against GITR and a "second" immunoglobulin single variable domain directed against GITR, wherein these "first" and "second" immunoglobulin single variable domains have a different paratope. Accordingly, the biparatopic polypeptide comprises or consists of two or more immunoglobulin single variable domains that are directed against GITR, wherein a "first" immunoglobulin single variable domain is directed against a first epitope on GITR and a "second" immunoglobulin single variable domain is directed against a second epitope on GITR different from the first epitope on GITR.

In another further aspect, the polypeptide of the invention is a triparatopic polypeptide. The term "triparatopic" (antigen-)binding molecule or "triparatopic" polypeptide as used herein shall mean a polypeptide comprising a "first" immunoglobulin single variable domain directed against GITR, a "second" immunoglobulin single variable domain directed against GITR and a "third" immunoglobulin single variable domain directed against GITR, wherein these "first", "second" and "third" immunoglobulin single variable domains have a different paratope. Accordingly, the triparatopic polypeptide comprises or consists of three or more immunoglobulin single variable domains that are directed against GITR, wherein a "first" immunoglobulin single variable domain is directed against a first epitope on GITR, a "second" immunoglobulin single variable domain is directed against a second epitope on GITR different from the first epitope on GITR, and a "third" immunoglobulin single variable domain is directed against a third epitope on GITR different from the first and second epitope on GITR.

The two or more (such as two, three, four, five or six) immunoglobulin single variable domains present in the multivalent polypeptide of the invention may consist of a light chain variable domain sequence (e.g., a $V_L$-sequence) or of a heavy chain variable domain sequence (e.g., a $V_H$-sequence); they may consist of a heavy chain variable domain sequence that is derived from a conventional four-chain antibody or of a heavy chain variable domain sequence that is derived from a heavy chain antibody. In a preferred aspect, they consist of a Domain antibody (or an amino acid that is suitable for use as a domain antibody), of a single domain antibody (or an amino acid that is suitable for use as a single domain antibody), of a "dAb" (or an amino acid that is suitable for use as a dAb), of a Nanobody® (including but not limited to $V_{HH}$), of a humanized $V_{HH}$ sequence, of a camelized $V_H$ sequence; or of a $V_{HH}$ sequence that has been obtained by affinity maturation. The two or more immunoglobulin single variable domains may consist of a partially or fully humanized Nanobody® or a partially or fully humanized VHH. In a preferred aspect of the invention, the immunoglobulin single variable domains encompassed in the multivalent polypeptide of the invention are one or more monovalent polypeptides of the invention, as defined herein.

Binding of the multivalent polypeptides of the invention to GITR can be measured in binding assays. Typical assays include (without being limiting) assays in which GITR is exposed on a cell surface (such as e.g. Flp-In™-293 cells or GloResponse™ NF-κB-Nluc2P HEK293 cells). A preferred assay for measuring binding of the multivalent polypeptides of the invention to GITR is a FACS assay, such as e.g. the FACS assay as described in the examples, wherein binding of the multivalent polypeptides of the invention to GITR expressed on Flp-In™-293 cells and/or activated T cells is determined. Some preferred $EC_{50}$ values for binding of the polypeptides of the invention to GITR will become clear from the further description and examples herein.

In such FACS binding assay, the multivalent polypeptides of the present invention may have $EC_{50}$ values in binding human GITR of $10^{-8}$ M or lower, more preferably of $10^{-9}$ M or lower, or even of $10^{-10}$ M or lower, such as $10^{-11}$ M. For example, in such FACS binding assay, the multivalent polypeptides of the present invention may have $EC_{50}$ values in binding human GITR between $10^{-11}$ M and $10^{-8}$ M, such as between $10^{-11}$ M and $10^{-10}$ M, between $10^{-10}$ M and $10^{-9}$ M or between $10^{-11}$ M and $10^{-10}$ M. More particularly, multivalent polypeptides of the present invention that comprise 2 or more monovalent polypeptides belonging to Families 7, 26, 82, 85 and 109 may have $EC_{50}$ values in binding human GITR between $10^{-11}$ M and $10^{-9}$ M, such as between $10^{-11}$ M and $10^{-10}$ M.

The multivalent polypeptides of the invention bind GITR and can modulate (i.e. increase, enhance, stimulate or potentiate) the activity of GITR. More particularly, the polypeptides of the present invention may enhance an immune response, such as enhance proliferation or activation of T cells, B cells or natural killer cells.

Proliferation or activation of T cell, B cells or natural killer cells can be determined by a variety of assays, including but not limited to proliferation assays, cytotoxicity assays, cell killing assays, reporter gene assays (e.g. NF-κB luciferase reporter assay), T cell activation assay, cell surface receptor binding assays and assays to measure expression of known markers of activation or cytokine secretion, which are all well known in the art.

For example, any one of several conventional assays for monitoring cytokine production (e.g., IFN-γ, TNF-α, IL-6, IL-2, IL-4 and IL-10) as a measure of immune cells activation can be used. For example, for tracking T cell activation, interleukin-2 can be employed as a marker, which can be assayed as described in Proc. Natl. Acad. Sci. USA. 86:1333 (1989).

One can also employ immunofluorescence and flow cytometry to monitor cytokine production on a cellular basis, and to monitor cell surface markers that reflect cellular activation states. A host of such markers are known, detecting antibodies are broadly commercially available, and the markers are well known in the art.

A common assay for T cell proliferation entails measuring tritiated thymidine incorporation. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

Some preferred $EC_{50}$ values for activating GITR by the multivalent polypeptides of the invention will become clear from the further description and examples herein.

In some embodiments, the multivalent polypeptides of the invention enhance IFN-gamma production in a T-cell activation assay with activated CD4+ T cells stimulated with anti-CD3 antibody OKT3, as described in Example 10. In this T cell activation assay, the multivalent polypeptides of the present invention have $EC_{50}$ values for enhancing IFN-gamma production of $10^{-7}$ M or lower, preferably of $10^{-8}$ M or lower, more preferably of $10^{-9}$ M or lower, $10^{-10}$ M or lower, or even of $10^{-11}$ M or lower. More particularly, multivalent polypeptides of the present invention that comprise 2 or more monovalent polypeptides belonging to Families 7, 26 and 109 may have $EC_{50}$ values for enhancing IFN-gamma production between $10^{-11}$ M and $10^{-9}$ M, such as between $10^{-11}$ M and $10^{-10}$ M. Preferably, in this T-cell activation assay, the multivalent polypeptides of the present invention enhance IFN-gamma production with $EC_{50}$ values of 200 pM or less, such as less than 190, 180, 170, 160, 150, 140, 130, 120, 110, 100 or even less, such as less than 90, 80, 70, 60, 50, 40 or even less, such as less than 30 pM.

In some embodiments, the multivalent polypeptides of the invention enhance the activity of nuclear factor-kappa B (NF-κB) in a NF-κB luciferase reporter assay, as described in Example 9. NF-κB luciferase reporter assays have been described in Buillard et al. 2013, *J. Exp. Med.* Vol. 210, 9: 1685-1693. Some preferred $EC_{50}$ values for activating GITR by the polypeptides of the invention will become clear from the further description and examples herein.

NF-κB plays a key role in inflammation, immune response and cell proliferation. This assay is specifically designed to monitor the activity of NF-κB regulated signal transduction pathways in cultured cells. In this NF-κB luciferase reporter assay, the multivalent polypeptides of the present invention enhance NF-κB activity as measured by luminescence after addition of Nano-Glo™ Reagent (Promega #N1120) with $EC_{50}$ values of $10^{-7}$ M or lower, preferably of $10^{-8}$ M or lower, more preferably of $10^{-9}$ M or lower, $10^{-10}$ M or lower, or even of $10^{-11}$ M or lower. More particularly, multivalent polypeptides of the present invention that comprise 2 or more monovalent polypeptides belonging to Families 7, 26, 38, 82, 85 and 109 may have $EC_{50}$ values for enhancing NF-κB activity between $10^{-11}$ M and $10^{-9}$ M, such as between $10^{-11}$ M and $10^{-10}$ M. Preferably, in this NF-κB luciferase reporter assay, the multivalent polypeptides of the present invention enhance NF-κB activity with $EC_{50}$ values of 200 pM or less, such as less than 190, 180, 170, 160, 150, 140, 130, 120, 110, 100 or even less, such as less than 90, 80, 70, 60, 50, 40, 35, 30, 25, 20, 18, 16, 15, 14 or even less, such as less than 12 pM.

Therapeutic effects of the multivalent polypeptides of the invention can further be evaluated in in vivo models, such as e.g. in mice, rats, pigs and/or primates. The CT26 model in BALB/c mice provides a syngeneic in vivo test system, which is frequently used for developing and testing immunotherapeutic concepts (Fearon et al. Cancer Res. 48: 2975-2980, 1988). For example, in the syngeneic CT-26 colon carcinoma model as described in Examples 13, 14 and 21, the multivalent polypeptides of the invention may inhibit tumor cell growth. In some embodiments, the multivalent polypeptides of the invention inhibit tumor cell growth, inhibit or prevent an increase in tumor weight or volume, and/or cause a decrease in tumor weight or volume by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, such as 100%.

Compounds, Constructs and/or Polypeptides of the Invention

The monovalent polypeptide of the invention and the multivalent polypeptide of the invention, may or may not further comprise one or more other groups, residues, moieties or binding units (these monovalent polypeptides as well as multivalent polypeptides (with or without additional groups, residues, moieties or binding units) are all referred to as "compound(s) of the invention", "construct(s) of the invention" and/or "polypeptide(s) of the invention"). If present, such further groups, residues, moieties or binding units may or may not provide further functionality to the immunoglobulin single variable domain (and/or to the polypeptide in which it is present) and may or may not modify the properties of the immunoglobulin single variable domain.

For example, such further groups, residues, moieties or binding units may be one or more additional amino acid sequences, such that the polypeptide is a (fusion) protein or (fusion) polypeptide. In a preferred but non-limiting aspect, said one or more other groups, residues, moieties or binding units are immunoglobulins. Even more preferably, said one or more other groups, residues, moieties or binding units are immunoglobulin single variable domains chosen from the group consisting of Domain antibodies, amino acids that are suitable for use as a domain antibody, single domain antibodies, amino acids that are suitable for use as a single domain antibody, "dAb" 's, amino acids that are suitable for use as a dAb, Nanobodies® (such as e.g. VHH, humanized VHH or camelized VH sequences).

As described above, additional binding units, such as immunoglobulin single variable domains having different antigen specificity can be linked to form multispecific polypeptides. By combining immunoglobulin single variable domains of two or more specificities, bispecific, trispecific etc. constructs can be formed. For example, a polypeptide according to the invention may comprise one, two, three, four, five or more immunoglobulin single variable domains directed against GITR and one immunoglobulin single variable domain against another target. Such constructs and modifications thereof, which the skilled person can readily envisage, are all encompassed by the term "compound of the invention, construct of the invention and/or polypeptide of the invention" as used herein.

In the compounds, constructs and/or polypeptides described above, the one, two, three, four, five, six, or more immunoglobulin single variable domains and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting polypeptide is a fusion (protein) or fusion (polypeptide).

The one or more further groups, residues, moieties or binding units may be any suitable and/or desired amino acid sequences. The further amino acid sequences may or may not change, alter or otherwise influence the (biological) properties of the polypeptide of the invention, and may or may not add further functionality to the polypeptide of the invention. Preferably, the further amino acid sequence is such that it confers one or more desired properties or functionalities to the polypeptide of the invention.

Examples of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson (Nature Biotechnology 23: 1126-1136, 2005).

For example, such an amino acid sequence may or may not be an amino acid sequence that increases the half-life, the solubility, or the absorption, reduces the immunogenicity or the toxicity, eliminates or attenuates undesirable side effects, and/or confers other advantageous properties to and/or reduces the undesired properties of the compound, construct and/or polypeptide of the invention, compared to polypeptide of the invention per se. Some non-limiting examples of such amino acid sequences are serum proteins, such as human serum albumin (see for example WO 00/27435) or haptenic molecules (for example haptens that are recognized by circulating antibodies, see for example WO 98/22141).

In one specific aspect of the invention, a compound or construct is prepared that has an increased half-life, compared to the corresponding polypeptide of the invention. Examples of polypeptides of the invention that comprise such half-life extending moieties for example include, without limitation, polypeptides in which the immunoglobulin single variable domains are suitable linked to one or more serum proteins or fragments thereof (such as (human) serum albumin or suitable fragments thereof) or to one or more binding units that can bind to serum proteins (such as, for example, Domain antibodies, amino acids that are suitable for use as a domain antibody, single domain antibodies, amino acids that are suitable for use as a single domain antibody, "dAb" 's, amino acids that are suitable for use as a dAb, Nanobodies®, VHH sequences, humanized VHH sequences or camelized VH sequences) that can bind to serum proteins (such as serum albumin (such as human serum albumin)), serum immunoglobulins (such as IgG), transferrin or one of the other serum proteins listed in WO 04/003019; polypeptides in which the immunoglobulin single variable domain is linked to an Fc portion (such as a human Fc), an antibody constant region (such as an antibody constant region from an IgG) or a suitable part or fragment thereof; or polypeptides in which the one or more immunoglobulin single variable domains are suitably linked to one or more small proteins or peptides that can bind to serum proteins (such as, without limitation, the proteins and peptides described in WO 91/01743, WO 01/45746 or WO 02/076489). Reference is also made to the dAb's described in WO 03/002609 and WO 04/003019 and to Harmsen et al. (*Vaccine* 23: 4926-42, 2005); to EP 0368684, as well as to WO 08/028977, WO 08/043821, WO 08/043822 by Ablynx N.V. and WO 08/068280.

According to a specific, but non-limiting aspect of the invention, the polypeptides of the invention may contain, besides the one or more immunoglobulin single variable domains and/or monovalent polypeptides of the invention against GITR, at least one immunoglobulin single variable domain against human serum albumin. These immunoglobulin single variable domains against human serum albumin may be as generally described in the applications by Ablynx N.V. cited above (see for example WO 04/062551). Some particularly preferred Nanobodies® that provide for increased half-life and that can be used in the polypeptides of the invention include the Nanobodies® ALB-1 to ALB-10 disclosed in WO 06/122787 (see Tables II and III) of which ALB-8 (SEQ ID NO: 62 in WO 06/122787) is particularly preferred, as well as the Nanobodies® disclosed in WO 2012/175400 (SEQ ID NOs: 1-11 of WO 2012/175400), the Nanobody® with SEQ ID NO: 109 disclosed in the U.S. provisional application No. 62/047,560 entitled "Improved immunoglobulin single variable domains" (date of filing: Sep. 8, 2014; assignee: Ablynx N.V.), and the Nanobodies® disclosed in the U.S. provisional application No. 62/256,841 entitled "Improved serum albumin binders" (date of filing: Nov. 18, 2015; assignee: Ablynx N.V.) of which Alb92 and Alb223 are particularly preferred (SEQ ID NO: 10 and SEQ ID NO: 63 in U.S. 62/256,841, respectively).

In a particularly preferred but non-limiting aspect of the invention, the invention provides a polypeptide of the invention comprising at least one immunoglobulin single variable domain (ISVD); and further comprising one or more (preferably one) serum albumin binding immunoglobulin single variable domain as described herein, e.g. the serum albumin binding immunoglobulin single variable domain of Alb11, Alb23, Alb129, Alb132, Alb8, Alb11 (S112K)-A, Alb82, Alb82-A, Alb82-AA, Alb82-AAA, Alb82-G, Alb82-GG, Alb82-GGG, Alb92 or Alb223 (see Table A-14).

Accordingly, the polypeptide of the invention may, for example, be a tetravalent, bispecific polypeptide, comprising three immunoglobulin single variable domains, preferably monovalent polypeptides of the invention against GITR and a fourth immunoglobulin single variable domain directed against (human) serum albumin, in which said first, second, third and fourth immunoglobulin single variable domain may optionally be linked via one or more, and in particular three, linker sequences.

According to another aspect, one or more polypeptides of the invention may be linked (optionally via a suitable linker or hinge region) to one or more constant domains (for example, 2 or 3 constant domains that can be used as part of/to form an Fc portion), to an Fc portion, to an antibody constant region of an IgG type and/or to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more $C_H2$ and/or $C_H3$ domains of an antibody, such as from a heavy chain antibody (as described herein) and more preferably from a conventional human 4-chain antibody; and/or may form (part of) a Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid $V_{HH}$ domain or a humanized derivative thereof (i.e. a Nanobody®), in which the Camelidae $C_H2$ and/or $C_H3$ domain have been replaced by human $C_H2$ and $C_H3$ domains, so as to provide an immunoglobulin that consists of 2 heavy chains each comprising a Nanobody® and human $C_H2$ and $C_H3$ domains (but no $C_H$i domain), which immunoglobulin has the effector function provided by the $C_H2$ and $C_H3$ domains and which immunoglobulin can function without the presence of any light chains. In a more preferred aspect of the invention, the one or more further amino acid sequences may comprise one or more $C_H1$, $C_H2$, $C_H3$ and/or $C_L$ domains of an antibody or fragments thereof, preferably from a conventional 4-chain antibody; and/or may form (part of) a human antibody constant region, for example from IgG (e.g. from IgG1, IgG2, IgG3 or IgG4), from IgE or from another human Ig such as IgA, IgD or IgM, so as to provide a compound or construct (such as a Nanobody®-IgG chimera) that consists of i) 2 heavy chains each comprising a Nanobody® and human $C_H1$, $C_H2$ and $C_H3$ heavy chain domains, wherein the $C_H1$ heavy chain domain is directly linked to the C-terminal part of the Nanobody® and ii) 2 light chains each comprising a Nanobody® and human $C_L$ light chain domains (such as Cκ or Cλ), wherein the $C_L$ light chain domain is directly linked to the C-terminal part of the Nanobody® (see FIG. 7). More particular, such compounds or constructs are of the IgG type and comprise an amino acid sequence set forth in one of SEQ ID NO: 229, 230, 291 and SEQ ID NO: 292 or an amino acid sequence that has a sequence identity of more than 80%, preferably more than 90%, more preferably more than 95%, such as 96%, 97%, 98%, 99% or more sequence identity (as defined herein) with any of SEQ ID NOs: 229-230 and 291-292.

Other amino acid sequences that can be suitably linked to the polypeptides of the invention so as to provide an effector function will be clear to the skilled person, and may be chosen on the basis of the desired effector function(s). Reference is for example made to WO 04/058820, WO 99/42077, WO 02/056910 and WO 05/017148, as well as the review by Holliger and Hudson, supra; and to WO 09/068628. Coupling of a polypeptide of the invention to an Fc portion or an antibody constant region may also lead to an increased half-life, compared to the corresponding polypeptide of the invention.

Other suitable constructs comprising one or more polypeptides of the invention and one or more constant domains with increased half-life in vivo will be clear to the skilled person, and may for example comprise polypeptides linked to a $C_H3$ domain, optionally via a linker sequence. Generally, any fusion protein or derivatives with increased half-life will preferably have a molecular weight of more than 50 kD, the cut-off value for renal absorption.

In another specific, but non-limiting, aspect, the polypeptides of the invention may be linked (optionally via a suitable linker or hinge region) to naturally occurring, synthetic or semi-synthetic constant domains (or analogs, variants, mutants, parts or fragments thereof) that have a reduced (or essentially no) tendency to self-associate into dimers (i.e. compared to constant domains that naturally occur in conventional 4-chain antibodies). Such monomeric (i.e. not self-associating) Fc chain variants, or fragments thereof, will be clear to the skilled person. For example, Helm et al. (J. Biol. Chem. 271: 7494, 1996), describe monomeric Fc chain variants that can be used in the polypeptide chains of the invention.

Also, such monomeric Fc chain variants are preferably such that they are still capable of binding to the complement or the relevant Fc receptor(s) (depending on the Fc portion from which they are derived), and/or such that they still have some or all of the effector functions of the Fc portion from which they are derived (or at a reduced level still suitable for the intended use). Alternatively, in such a polypeptide chain of the invention, the monomeric Fc chain may be used to confer increased half-life upon the polypeptide chain, in which case the monomeric Fc chain may also have no or essentially no effector functions.

Generally, the polypeptides of the invention with increased half-life preferably have a half-life that is at least 1.5 times, preferably at least 2 times, such as at least 5 times, for example at least 10 times or more than 20 times, greater than the half-life of the corresponding immunoglobulin single variable domain or polypeptide of the invention per se.

Generally, the polypeptides of the invention with increased half-life preferably have a half-life that is increased with more than 1 hour, preferably more than 2 hours, more preferably more than 6 hours, such as more than 12 hours, or even more than 24, 48 or 72 hours, compared to the half-life of the corresponding immunoglobulin single variable domain or polypeptide of the invention per se.

In another preferred, but non-limiting aspect, such polypeptides of the invention exhibit a serum half-life in human of at least about 12 hours, preferably at least 24 hours, more preferably at least 48 hours, even more preferably at least 72 hours or more. For example, polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

The further amino acid residues may or may not change, alter or otherwise influence other (biological) properties of the polypeptide of the invention and may or may not add further functionality to the polypeptide of the invention. For example, such amino acid residues:

a) can comprise an N-terminal Met residue, for example as result of expression in a heterologous host cell or host organism.

b) may form a signal sequence or leader sequence that directs secretion of the polypeptide from a host cell upon synthesis (for example to provide a pre-, pro- or prepro-form of the polypeptide of the invention, depending on the host cell used to express the polypeptide of the invention). Suitable secretory leader peptides will be clear to the skilled person, and may be as further described herein. Usually, such a leader sequence will be linked to the N-terminus of the polypeptide, although the invention in its broadest sense is not limited thereto;

c) may form a "tag", for example an amino acid sequence or residue that allows or facilitates the purification of the polypeptide, for example using affinity techniques directed against said sequence or residue. Thereafter, said sequence or residue may be removed (e.g. by chemical or enzymatical cleavage) to provide the polypeptide (for this purpose, the tag may optionally be linked to the amino acid sequence or polypeptide sequence via a cleavable linker sequence or contain a cleavable motif). Some preferred, but non-limiting examples of such residues are multiple histidine residues, glutathione residues and a myc-tag such as AAAEQKLISEEDLNGAA;

d) may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the polypeptides of the invention.

The multivalent polypeptides of the invention can generally be prepared by a method which comprises at least the step of suitably linking the immunoglobulin single variable domain and/or monovalent polypeptide of the invention to one or more further immunoglobulin single variable domains and/or monovalent polypeptides of the invention, optionally via the one or more suitable linkers, so as to provide the multivalent polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

A method for preparing multivalent polypeptides of the invention may comprise at least the steps of linking two or more immunoglobulin single variable domains and/or monovalent polypeptides of the invention and for example one or more linkers together in a suitable manner. The immunoglobulin single variable domains and/or monovalent polypeptides of the invention (and linkers) can be coupled by any method known in the art and as further described herein. Preferred techniques include the linking of the nucleic acid sequences that encode the immunoglobulin single variable domains and/or monovalent polypeptides of the invention (and linkers) to prepare a genetic construct that expresses the multivalent polypeptide. Techniques for linking amino acids or nucleic acids will be clear to the skilled person, and reference is again made to the standard handbooks, such as Sambrook et al. and Ausubel et al., mentioned above, as well as the Examples below.

Accordingly, the present invention also relates to the use of an immunoglobulin single variable domain and/or monovalent polypeptide of the invention in preparing a multivalent polypeptide of the invention. The method for the preparation of a multivalent polypeptide will comprise the linking of an immunoglobulin single variable domain and/or monovalent polypeptide of the invention to at least one further immunoglobulin single variable domain and/or monovalent polypeptide of the invention, optionally via one or more linkers. The immunoglobulin single variable domain and/or monovalent polypeptide of the invention is then used as a binding domain or binding unit in providing and/or preparing the multivalent polypeptide comprising two (e.g., in a bivalent polypeptide), three (e.g., in a trivalent polypeptide), four (e.g., in a tetravalent polypeptide), five (e.g., in a pentavalent polypeptide), six (e.g., in a hexavalent polypeptide) or more (e.g., in a multivalent polypeptide) binding units. In this respect, the immunoglobulin singe variable domain and/or the monovalent polypeptide of the invention may be used as a binding domain or binding unit in providing and/or preparing a multivalent, such as bivalent, trivalent, tetravalent, pentavalent or hexavalent polypeptide of the invention comprising two, three, four, five, six or more binding units.

Accordingly, the present invention also relates to the use of an immunoglobulin single variable domain and/or particularly, a monovalent polypeptide of the invention (as described herein) in preparing a multivalent polypeptide. The method for the preparation of the multivalent polypeptide will comprise the linking of the immunoglobulin single variable domain and/or monovalent polypeptide of the invention to at least one further immunoglobulin single variable domain and/or monovalent polypeptide of the invention, optionally via one or more linkers.

Suitable spacers or linkers for use in multivalent polypeptides of the invention will be clear to the skilled person, and may generally be any linker or spacer used in the art to link amino acid sequences. Preferably, said linker or spacer is suitable for use in constructing polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each immunoglobulin single variable domain by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_x ser_y)_z$, such as (for example $(gly_4 ser)_3$ or $(gly_3 ser_2)_3$, as described in WO 99/42077, hinge-like regions such as the hinge regions of naturally occurring heavy chain antibodies or similar sequences (such as described in WO 94/04678).

Some other particularly preferred linkers are mentioned in Table A-15, of which GS9 (SEQ ID NO: 251) is particularly preferred.

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for GITR, or for one or more of the other antigens. Based on the disclosure herein, the skilled person will be able to determine the optimal linker(s) for use in a specific polypeptide of the invention, optionally after some limited routine experiments.

It is also within the scope of the invention that the linker(s) used confer one or more other favourable properties or functionality to the polypeptides of the invention, and/or provide one or more sites for the formation of derivatives and/or for the attachment of functional groups (e.g., as described herein for the derivatives of the polypeptides of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

Usually, for ease of expression and production, a polypeptide of the invention will be a linear polypeptide. However, the invention in its broadest sense is not limited thereto. For example, when a polypeptide of the invention comprises three of more amino acid sequences or Nanobodies®, it is possible to link them by use of a linker with three or more "arms", which each "arm" being linked to an amino acid sequence or Nanobody®, so as to provide a "star-shaped" construct. It is also possible, although usually less preferred to use circular constructs.

Also encompassed in the present invention are compounds, constructs and/or polypeptides that comprise an immunoglobulin or polypeptide of the invention and further comprising tags or other functional moieties, e.g., toxins, labels, radiochemicals, etc.

Alternatively, the additional groups, residues, moieties or binding units may for example be chemical groups, residues, moieties, which may or may not by themselves be biologically and/or pharmacologically active. For example, and without limitation, such groups may be linked to the one or more immunoglobulin single variable domains or monovalent polypeptides of the invention so as to provide a "derivative" of the polypeptide of the invention.

Accordingly, the invention in its broadest sense also comprises compounds, constructs and/or polypeptides that are derivatives of the polypeptides of the invention. Such derivatives can generally be obtained by modification, and in particular by chemical and/or biological (e.g., enzymatical) modification, of the polypeptides of the invention and/or of one or more of the amino acid residues that form polypeptide of the invention.

Examples of such modifications, as well as examples of amino acid residues within the polypeptide sequences that can be modified in such a manner (i.e. either on the protein backbone but preferably on a side chain), methods and techniques that can be used to introduce such modifications and the potential uses and advantages of such modifications will be clear to the skilled person (see also Zangi et al., Nat Biotechnol 31(10):898-907, 2013).

For example, such a modification may involve the introduction (e.g., by covalent linking or in any other suitable manner) of one or more functional groups, residues or moieties into or onto the polypeptide of the invention, and in particular of one or more functional groups, residues or moieties that confer one or more desired properties or functionalities to the polypeptide of the invention. Examples of such functional groups will be clear to the skilled person.

For example, such modification may comprise the introduction (e.g., by covalent binding or in any other suitable manner) of one or more functional groups that increase the half-life, the solubility and/or the absorption of the polypeptide of the invention, that reduce the immunogenicity and/or the toxicity of the polypeptide of the invention, that eliminate or attenuate any undesirable side effects of the polypeptide of the invention, and/or that confer other advantageous properties to and/or reduce the undesired properties of the polypeptide of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington (Pharmaceutical Sciences, 16th ed., Mack Publishing Co., Easton, PA, 1980). Such functional groups may for example be linked directly (for example covalently) to a polypeptide of the invention, or optionally via a suitable linker or spacer, as will again be clear to the skilled person.

One specific example is a derivative polypeptide of the invention wherein the polypeptide of the invention has been chemically modified to increase the half-life thereof (for example, by means of pegylation). This is one of the most widely used techniques for increasing the half-life and/or reducing the immunogenicity of pharmaceutical proteins and comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman (Nat. Biotechnol. 54: 531-545, 2002), Veronese and Harris (Adv. Drug Deliv. Rev. 54: 453-456, 2003), Harris and Chess (Nat. Rev. Drug. Discov. 2: 214-221, 2003) and WO 04/060965. Various reagents for pegylation of proteins are also commercially available, for example from Nektar Therapeutics, USA.

Preferably, site-directed pegylation is used, in particular via a cysteine-residue (see for example Yang et al. (Protein Engineering 16: 761-770, 2003). For example, for this purpose, PEG may be attached to a cysteine residue that naturally occurs in a polypeptide of the invention, a polypeptide of the invention may be modified so as to suitably introduce one or more cysteine residues for attachment of PEG, or an amino acid sequence comprising one or more cysteine residues for attachment of PEG may be fused to the N- and/or C-terminus of a polypeptide of the invention, all using techniques of protein engineering known per se to the skilled person.

Preferably, for the polypeptides of the invention, a PEG is used with a molecular weight of more than 5000 Dalton, such as more than 10,000 and less than 200,000, such as less than 100,000; for example in the range of 20,000-80,000 Dalton.

Another, usually less preferred modification comprises N-linked or O-linked glycosylation, usually as part of co-translational and/or post-translational modification, depending on the host cell used for expressing the polypeptide of the invention.

Yet another modification may comprise the introduction of one or more detectable labels or other signal-generating groups or moieties, depending on the intended use of the labelled polypeptide of the invention. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals such as $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radioisotopes (such as $^3$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metals chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{152}$Dy, $^{52}$Cr, and $^{56}$Fe)), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, β-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the polypeptide of the invention to another protein, polypeptide or chemical compound that is bound to the other half of the binding pair, i.e. through formation of the binding pair. For example, a polypeptide of the invention may be conjugated to biotin, and linked to another protein, polypeptide, compound or carrier conjugated to avidin or streptavidin. For example, such a conjugated polypeptide of the invention may be used as a reporter, for example in a diagnostic system where a detectable signal-producing agent is conjugated to avidin or streptavidin. Such binding pairs may for example also be used to bind the polypeptide of the invention to a carrier, including carriers suitable for pharmaceutical purposes. One non-limiting example are the liposomal formulations described by Cao and Suresh (Journal of Drug Targeting 8: 257, 2000). Such binding pairs may also be used to link a therapeutically active agent to the polypeptide of the invention.

Other potential chemical and enzymatical modifications will be clear to the skilled person. Such modifications may also be introduced for research purposes (e.g. to study function-activity relationships). Reference is for example made to Lundblad and Bradshaw (Biotechnol. Appl. Biochem. 26: 143-151, 1997).

Preferably, the compounds, constructs, polypeptides and/or derivatives are such that they bind to GITR, with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein (i.e. as defined for the polypeptides of the invention). Such derivatives will usually also have a GITR efficacy and/or potency as defined herein.

Such compounds, constructs and/or polypeptides of the invention and derivatives thereof may also be in essentially isolated form (as defined herein).

The invention further relates to methods for preparing the compounds, constructs, polypeptides, nucleic acids, host cells, and compositions described herein.

The polypeptides and nucleic acids of the invention can be prepared in a manner known per se, as will be clear to the skilled person from the further description herein. For example, the polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the polypeptides and nucleic acids include the methods and techniques described herein.

The method for producing a polypeptide of the invention may comprise the following steps:
the expression, in a suitable host cell or host organism (also referred to herein as a "host of the invention") or in another suitable expression system of a nucleic acid that encodes said polypeptide of the invention (also referred to herein as a "nucleic acid of the invention"), optionally followed by:
isolating and/or purifying the polypeptide of the invention thus obtained.
In particular, such a method may comprise the steps of:
cultivating and/or maintaining a host of the invention under conditions that are such that said host of the invention expresses and/or produces at least one polypeptide of the invention;
optionally followed by:
isolating and/or purifying the polypeptide of the invention thus obtained.
Accordingly, the present invention also relates to a nucleic acid or nucleotide sequence that encodes a polypeptide of the invention (also referred to as "nucleic acid of the invention"). A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one embodiment of the invention, the nucleic acid of the invention is in essentially isolated form, as defined herein. The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the polypeptides of the invention given herein, and/or can be isolated from a suitable natural source. Also, as will be clear to the skilled person, to prepare a nucleic acid of the invention, also several nucleotide sequences, such as at least two nucleic acids encoding an immunoglobulin single variable domain or a monovalent polypeptide of the invention and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned above, as well as to the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting embodiment, a genetic construct of the invention comprises
- a) at least one nucleic acid of the invention; operably connected to
- b) one or more regulatory elements, such as a promoter and optionally a suitable terminator; and optionally also
- c) one or more further elements of genetic constructs known per se;

in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used; the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required.

Preferably, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence—e.g., a coding sequence—to which it is operably linked (as defined herein).

Some particularly preferred promoters include, but are not limited to, promoters known per se for the expression in the host cells mentioned herein; and in particular promoters for the expression in the bacterial cells, such as those mentioned herein and/or those used in the Examples.

A selection marker should be such that it allows—i.e., under appropriate selection conditions—host cells and/or host organisms that have been (successfully) transformed with the nucleotide sequence of the invention to be distinguished from host cells/organisms that have not been (successfully) transformed. Some preferred, but non-limiting examples of such markers are genes that provide resistance against antibiotics (such as kanamycin or ampicillin), genes that provide for temperature resistance, or genes that allow the host cell or host organism to be maintained in the absence of certain factors, compounds and/or (food) components in the medium that are essential for survival of the non-transformed cells or organisms.

A leader sequence should be such that—in the intended host cell or host organism—it allows for the desired post-translational modifications and/or such that it directs the transcribed mRNA to a desired part or organelle of a cell. A leader sequence may also allow for secretion of the expression product from said cell. As such, the leader sequence may be any pro-, pre-, or prepro-sequence operable in the host cell or host organism. Leader sequences may not be required for expression in a bacterial cell. For example, leader sequences known per se for the expression and production of antibodies and antibody fragments (including but not limited to single domain antibodies and ScFv fragments) may be used in an essentially analogous manner.

An expression marker or reporter gene should be such that—in the host cell or host organism—it allows for detection of the expression of (a gene or nucleotide sequence present on) the genetic construct. An expression marker may optionally also allow for the localisation of the expressed product, e.g., in a specific part or organelle of a cell and/or in (a) specific cell(s), tissue(s), organ(s) or part(s) of a multicellular organism. Such reporter genes may also be expressed as a protein fusion with the amino acid sequence or polypeptide of the invention. Some preferred, but non-limiting examples include fluorescent proteins such as GFP.

Some preferred, but non-limiting examples of suitable promoters, terminator and further elements include those that can be used for the expression in the host cells mentioned herein; and in particular those that are suitable for expression in bacterial cells, such as those mentioned herein and/or those used in the Examples below. For some (further) non-limiting examples of the promoters, selection markers, leader sequences, expression markers and further elements that may be present/used in the genetic constructs of the invention—such as terminators, transcriptional and/or translational enhancers and/or integration factors—reference is made to the general handbooks such as Sambrook et al. and Ausubel et al. mentioned above, as well as to the examples that are given in WO 95/07463, WO 96/23810, WO 95/07463, WO 95/21191, WO 97/11094, WO 97/42320, WO 98/06737, WO 98/21355, U.S. Pat. Nos. 7,207,410, 5,693,492 and EP 1085089. Other examples will be clear to the skilled person. Reference is also made to the general background art cited above and the further references cited herein.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleotide sequence of the invention in a suitable (expression) vector known per se. Some preferred, but non-limiting examples of suitable expression vectors are those used in the Examples below, as well as those mentioned herein.

The nucleic acids of the invention and/or the genetic constructs of the invention may be used to transform a host cell or host organism, i.e., for expression and/or production of the polypeptide of the invention. Suitable hosts or host cells will be clear to the skilled person, and may for example be any suitable fungal, prokaryotic or eukaryotic cell or cell line or any suitable fungal, prokaryotic or (non-human) eukaryotic organism, for example:

- a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis*;
- a fungal cell, including but not limited to cells from species of *Trichoderma*, for example from *Trichoderma reesei*; of *Neurospora*, for example from *Neurospora crassa*; of *Sordaria*, for example from *Sordaria macrospora*; of *Aspergillus*, for example from *Aspergillus niger* or from *Aspergillus sojae*; or from other filamentous fungi;
- a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for example of *Arxula adeninivorans*; of *Yarrowia*, for example of *Yarrowia lipolytica*;
- an amphibian cell or cell line, such as *Xenopus* oocytes;
- an insect-derived cell or cell line, such as cells/cell lines derived from lepidoptera, including but not limited to *Spodoptera* SF9 and Sf21 cells or cells/cell lines derived from *Drosophila*, such as Schneider and Kc cells;
- a plant or plant cell, for example in tobacco plants; and/or
- a mammalian cell or cell line, for example a cell or cell line derived from a human, a cell or a cell line from mammals including but not limited to CHO-cells (for example CHO-K1 cells), BHK-cells and human cells or cell lines such as HeLa, COS, Caki and HEK293H cells;

as well as all other host cells or (non-human) hosts known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al. (Res Immunol. 149: 589-99, 1998); Riechmann and Muyldermans (1999), supra; van der Linden (J. Biotechnol. 80: 261-70, 2000); Joosten et al. (Microb. Cell Fact. 2: 1, 2003); Joosten et al. (Appl. Microbiol. Biotechnol. 66: 384-92, 2005); and the further references cited therein.

The polypeptides of the invention may also be expressed as so-called "intrabodies", as for example described in WO 94/02610, WO 95/22618 and U.S. Pat. No. 7,004,940; WO 03/014960; in Cattaneo and Biocca ("Intracellular Antibodies: Development and Applications" Landes and Springer-Verlag, 1997); and in Kontermann (Methods 34: 163-170, 2004).

The polypeptides of the invention can for example also be produced in the milk of transgenic mammals, for example in the milk of rabbits, cows, goats or sheep (see for example U.S. Pat. Nos. 6,741,957, 6,304,489 and 6,849,992 for general techniques for introducing transgenes into mammals), in plants or parts of plants including but not limited to their leaves, flowers, fruits, seed, roots or tubers (for example in tobacco, maize, soybean or alfalfa) or in for example pupae of the silkworm *Bombix mori*.

Furthermore, the polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

Preferably, in the invention, an (in vivo or in vitro) expression system, such as a bacterial expression system, is used that provides the polypeptides of the invention in a form that is suitable for pharmaceutical use, and such expression systems will again be clear to the skilled person. As also will be clear to the skilled person, polypeptides of the invention suitable for pharmaceutical use can be prepared using techniques for peptide synthesis.

For production on industrial scale, preferred heterologous hosts for the (industrial) production of immunoglobulin single variable domains or immunoglobulin single variable domain-containing polypeptide therapeutics include strains of *E. coli*, *Pichia pastoris*, *S. cerevisiae* that are suitable for large scale expression/production/fermentation, and in particular for large scale pharmaceutical expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of an immunoglobulin single variable domain-containing recombinant protein for which glycosylation is desired or required would necessitate the use of mammalian expression hosts that have the ability to glycosylate the expressed protein. In this respect, it will be clear to the skilled person that the glycosylation pattern obtained (i.e., the kind, number and position of residues attached) will depend on the cell or cell line that is used for the expression. Preferably, either a human cell or cell line is used (i.e., leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired polypeptide to be obtained.

Thus, according to one non-limiting embodiment of the invention, the polypeptide of the invention is glycosylated. According to another non-limiting embodiment of the invention, the polypeptide of the invention is non-glycosylated.

According to one preferred, but non-limiting embodiment of the invention, the polypeptide of the invention is produced in a bacterial cell, in particular a bacterial cell suitable for large scale pharmaceutical production, such as cells of the strains mentioned above.

According to another preferred, but non-limiting embodiment of the invention, the polypeptide of the invention is produced in a yeast cell, in particular a yeast cell suitable for large scale pharmaceutical production, such as cells of the species mentioned above.

According to yet another preferred, but non-limiting embodiment of the invention, the polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

When expression in a host cell is used to produce the polypeptides of the invention, the polypeptides of the invention can be produced either intracellularly (e.g., in the cytosol, in the periplasma or in inclusion bodies) and then isolated from the host cells and optionally further purified; or can be produced extracellularly (e.g., in the medium in which the host cells are cultured) and then isolated from the culture medium and optionally further purified. When eukaryotic host cells are used, extracellular production is usually preferred since this considerably facilitates the further isolation and downstream processing of the polypeptides obtained. Bacterial cells such as the strains of E. coli mentioned above normally do not secrete proteins extracellularly, except for a few classes of proteins such as toxins and hemolysin, and secretory production in E. coli refers to the translocation of proteins across the inner membrane to the periplasmic space. Periplasmic production provides several advantages over cytosolic production. For example, the N-terminal amino acid sequence of the secreted product can be identical to the natural gene product after cleavage of the secretion signal sequence by a specific signal peptidase. Also, there appears to be much less protease activity in the periplasm than in the cytoplasm. In addition, protein purification is simpler due to fewer contaminating proteins in the periplasm. Another advantage is that correct disulfide bonds may form because the periplasm provides a more oxidative environment than the cytoplasm. Proteins overexpressed in E. coli are often found in insoluble aggregates, so-called inclusion bodies. These inclusion bodies may be located in the cytosol or in the periplasm; the recovery of biologically active proteins from these inclusion bodies requires a denaturation/refolding process. Many recombinant proteins, including therapeutic proteins, are recovered from inclusion bodies. Alternatively, as will be clear to the skilled person, recombinant strains of bacteria that have been genetically modified so as to secrete a desired protein, and in particular a polypeptide of the invention, can be used.

Thus, according to one non-limiting embodiment of the invention, the polypeptide of the invention is a polypeptide that has been produced intracellularly and that has been isolated from the host cell, and in particular from a bacterial cell or from an inclusion body in a bacterial cell. According to another non-limiting embodiment of the invention, the polypeptide of the invention is a polypeptide that has been produced extracellularly, and that has been isolated from the medium in which the host cell is cultivated.

Some preferred, but non-limiting promoters for use with these host cells include:

for expression in E. coli: lac promoter (and derivatives thereof such as the lacUV5 promoter); arabinose promoter; left- (PL) and rightward (PR) promoter of phage lambda; promoter of the trp operon; hybrid lac/trp promoters (tac and trc); T7-promoter (more specifically that of T7-phage gene 10) and other T-phage promoters; promoter of the Tn10 tetracycline resistance gene; engineered variants of the above promoters that include one or more copies of an extraneous regulatory operator sequence;

for expression in S. cerevisiae: constitutive: ADH1 (alcohol dehydrogenase 1), ENO (enolase), CYC1 (cytochrome c iso-1), GAPDH (glyceraldehydes-3-phosphate dehydrogenase), PGK1 (phosphoglycerate kinase), PYK1 (pyruvate kinase); regulated: GAL1, 10,7 (galactose metabolic enzymes), ADH2 (alcohol dehydrogenase 2), PHO5 (acid phosphatase), CUP1 (copper metallothionein); heterologous: CaMV (cauliflower mosaic virus 35S promoter);

for expression in Pichia pastoris: the AOX1 promoter (alcohol oxidase 1);

for expression in mammalian cells: human cytomegalovirus (hCMV) immediate early enhancer/promoter; human cytomegalovirus (hCMV) immediate early promoter variant that contains two tetracycline operator sequences such that the promoter can be regulated by the Tet repressor; Herpes Simplex Virus thymidine kinase (TK) promoter; Rous Sarcoma Virus long terminal repeat (RSV LTR) enhancer/promoter; elongation factor 1α (hEF-1α) promoter from human, chimpanzee, mouse or rat; the SV40 early promoter; HIV-1 long terminal repeat promoter; β-actin promoter;

Some preferred, but non-limiting vectors for use with these host cells include:

vectors for expression in mammalian cells: pMAMneo (Clontech), pcDNA3 (Invitrogen), pMC1neo (Stratagene), pSG5 (Stratagene), EBO-pSV2-neo (ATCC 37593), pBPV-1 (8-2) (ATCC 37110), pdBPV-MMT-neo (342-12) (ATCC 37224), pRSVgpt (ATCC37199), pRSVneo (ATCC37198), pSV2-dhfr (ATCC 37146), pUCTag (ATCC 37460) and 1ZD35 (ATCC 37565), as well as viral-based expression systems, such as those based on adenovirus;

vectors for expression in bacterial cells: pET vectors (Novagen) and pQE vectors (Qiagen);

vectors for expression in yeast or other fungal cells: pYES2 (Invitrogen) and Pichia expression vectors (Invitrogen);

vectors for expression in insect cells: pBlueBacII (Invitrogen) and other baculovirus vectors vectors for expression in plants or plant cells: for example vectors based on cauliflower mosaic virus or tobacco mosaic virus, suitable strains of Agrobacterium, or Ti-plasmid based vectors.

Some preferred, but non-limiting secretory sequences for use with these host cells include:

for use in bacterial cells such as E. coli: PelB, Bla, OmpA, OmpC, OmpF, OmpT, StII, PhoA, PhoE, MalE, Lpp, LamB, and the like; TAT signal peptide, hemolysin C-terminal secretion signal;

for use in yeast: α-mating factor prepro-sequence, phosphatase (phol), invertase (Suc), etc.;

for use in mammalian cells: indigenous signal in case the target protein is of eukaryotic origin;

murine Ig κ-chain V-J2-C signal peptide; etc.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the polypeptide of the invention, e.g., using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g., under suitable conditions), a polypeptide of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the polypeptides of the invention, the transformed host cell or transformed host organism may generally be kept, maintained and/or cultured under conditions such that the (desired) polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g., when the nucleotide sequences of the invention are under the control of an inducible promoter); all of which may be selected by the skilled person. Again, under such conditions, the polypeptides of the invention may be expressed in a constitutive manner, in a transient manner, or only when suitably induced.

It will also be clear to the skilled person that the polypeptide of the invention may (first) be generated in an immature form (as mentioned above), which may then be subjected to post-translational modification, depending on the host cell/host organism used. Also, the polypeptide of the invention may be glycosylated, again depending on the host cell/host organism used.

The polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g., using a specific, cleavable amino acid sequence fused with the polypeptide of the invention) and/or preparative immunological techniques (i.e. using antibodies against the polypeptide to be isolated).

Compositions of the Invention

Generally, for pharmaceutical use, the polypeptides, compounds, and/or constructs of the invention may be formulated as a pharmaceutical preparation or composition comprising at least one polypeptide, compound, and/or construct of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc, wherein the parenteral administration is preferred. Such suitable administration forms—which may be solid, semi-solid or liquid, depending on the manner of administration—as well as methods and carriers for use in the preparation thereof, will be clear to the skilled person, and are further described herein. Such a pharmaceutical preparation or composition will generally be referred to herein as a "pharmaceutical composition". A pharmaceutical preparation or composition for use in a non-human organism will generally be referred to herein as a "veterinary composition".

Thus, in a further aspect, the invention relates to a pharmaceutical composition that contains at least one polypeptide of the invention, at least one compound of the invention, at least one construct of the invention or at least one nucleic acid of the invention and at least one suitable carrier, diluent or excipient (i.e., suitable for pharmaceutical use), and optionally one or more further active substances. In a particular aspect, the invention relates to a pharmaceutical composition that contains at least one of SEQ ID NOs: 1-71, 206-223, 229-230, 266-275 and 285-292, and at least one suitable carrier, diluent or excipient (i.e., suitable for pharmaceutical use), and optionally one or more further active substances.

Generally, the polypeptides, compounds and/or constructs of the invention can be formulated and administered in any suitable manner known per se. Reference is for example made to the general background art cited above (and in particular to WO 04/041862, WO 04/041863, WO 04/041865, WO 04/041867 and WO 08/020079) as well as to the standard handbooks, such as Remington's Pharmaceutical Sciences, 18$^{th}$ Ed., Mack Publishing Company, USA (1990), Remington, the Science and Practice of Pharmacy, 21st Edition, Lippincott Williams and Wilkins (2005); or the Handbook of Therapeutic Antibodies (S. Dubel, Ed.), Wiley, Weinheim, 2007 (see for example pages 252-255).

The polypeptides, compounds and/or constructs of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (e.g. intravenous, intraperitoneal, subcutaneous, intramuscular, intraluminal, intra-arterial or intrathecal administration) or for topical (i.e., transdermal or intradermal) administration.

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020079. Usually, aqueous solutions or suspensions will be preferred.

The polypeptides, compounds and/or constructs of the invention can also be administered using methods of delivery known from gene therapy, see, e.g., U.S. Pat. No. 5,399,346, which is incorporated by reference for its gene therapy delivery methods. Using a gene therapy method of delivery, primary cells transfected with the gene encoding a polypeptide, compound and/or construct of the invention can additionally be transfected with tissue specific promoters to target specific organs, tissue, grafts, tumors, or cells and can additionally be transfected with signal and stabilization sequences for subcellularly localized expression.

Thus, the polypeptides, compounds and/or constructs of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the polypeptides, compounds and/or constructs of the invention may be combined with one or more excipients and used in the form of ingestible tablets, buccal tablets, troches, capsules, elixirs, suspensions, syrups, wafers, and the like. Such compositions and preparations should contain at least 0.1% of the polypeptide, compound and/or construct of the invention. Their percentage in the compositions and preparations may, of course, be varied and may conveniently be between about 2 to about 60% of the weight of a given unit dosage form. The amount of the polypeptide, compound and/or construct of the invention in such therapeutically useful compositions is such that an effective dosage level will be obtained.

The tablets, troches, pills, capsules, and the like may also contain binders, excipients, disintegrating agents, lubricants and sweetening or flavoring agents, for example those mentioned on pages 143-144 of WO 08/020079. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the polypeptides, compounds and/or constructs of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the polypeptides, compounds and/or constructs of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The polypeptides, compounds and/or constructs of the invention may also be administered intravenously or intraperitoneally by infusion or injection. Particular examples are as further described on pages 144 and 145 of WO 08/020079 or in PCT/EP2010/062975 (entire document).

For topical administration, the polypeptides, compounds and/or constructs of the invention may be applied in pure form, i.e., when they are liquids. However, it will generally be desirable to administer them to the skin as compositions or formulations, in combination with a dermatologic acceptable carrier, which may be a solid or a liquid. Particular examples are as further described on page 145 of WO 08/020079.

Useful dosages of the polypeptides, compounds and/or constructs of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the polypeptides, compounds and/or constructs of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the polypeptides, compounds and/or constructs of the invention required for use in treatment will vary not only with the particular polypeptide, compound and/or construct selected but also with the route of administration, the nature of the condition being treated and the age and condition of the patient and will be ultimately at the discretion of the attendant physician or clinician. Also the dosage of the polypeptides, compounds and/or constructs of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. The dosage can also be adjusted by the individual physician in the event of any complication.

Uses of the Polypeptides, Compounds and/or Constructs of the Invention

The invention further relates to applications and uses of the polypeptides, compounds and/or constructs, nucleic acids, host cells and compositions described herein, as well as to methods for the prevention and/or treatment of GITR associated diseases, disorders or conditions, such as various cancers and infectious diseases. Some preferred but non-limiting applications and uses will become clear from the further description herein.

The polypeptide, compound and/or construct of the invention can generally be used to enhance an immune response. In particular, the polypeptide, compound and/or construct of the invention can enhance the proliferation or activation of T cells, B cells or natural killer cells by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, such as 100% compared to the activation status of T cells, B cells or natural killer cells in the absence of the polypeptide, compound and/or construct of the invention, as determined by a suitable assay, such as those described herein.

In another aspect, the polypeptide, compound and/or construct of the invention can inhibit tumor growth, induce tumor regression, increase progression-free survival and/or extend overall survival in an individual that has a tumor by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, such as 100% compared to the tumor, progression-free survival and/or overall survival in that individual in the absence of the polypeptide, compound and/or construct of the invention, as determined by a suitable assay, such as those described herein.

In a further aspect, the invention relates to a method for the prevention and/or treatment of at least one GITR associated disease, disorder or condition, said method comprising administering, to a subject in need thereof, a pharmaceutically active amount of a polypeptide of the invention, of a compound of the invention, of a construct of the invention and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases, disorders and conditions mentioned herein.

The invention relates to a method for the prevention and/or treatment of at least one disease, disorder or condition that is associated with GITR, with its biological or pharmacological activity, and/or with the biological pathways or signaling in which GITR is involved, said method comprising administering, to a subject in need thereof, a pharmaceutically active amount of a polypeptide of the invention, of a compound of the invention, of a construct of the invention and/or of a pharmaceutical composition comprising the same. In particular, said pharmaceutically effective amount may be an amount that is sufficient to stimulate, enhance or agonize GITR, its biological or pharmacological activity, and/or the biological pathways or signaling in which GITR is involved; and/or an amount that provides a level of the polypeptide of the invention, of the compound of the invention, and/or of the construct of the invention in the circulation that is sufficient to stimulate, enhance or agonize GITR, its biological or pharmacological activity, and/or the biological pathways or signaling in which GITR is involved.

The invention also relates to a method for the prevention and/or treatment of at least one disease, disorder and/or condition that can be prevented and/or treated by administering of a polypeptide of the invention, of a compound of the invention and/or of a construct of the invention to a patient, said method comprising administering, to a subject in need thereof, a pharmaceutically active amount of a polypeptide of the invention, of a compound of the invention, of a construct of the invention and/or of a pharmaceutical composition comprising the same.

More in particular, the invention relates to a method for the prevention and/or treatment of at least one disease, disorder and/or condition chosen from the group consisting of the diseases, disorders and conditions listed herein, said method comprising administering, to a subject in need thereof, a pharmaceutically active amount of a polypeptide of the invention, of a compound of the invention, of a construct of the invention and/or of a pharmaceutical composition comprising the same.

The invention also relates to a method for enhancing an immune response.

The invention also relates to a method for enhancing proliferation or activation of T cells, B cells or natural killer cells.

The invention also relates to a method for inhibiting tumor growth.

The invention also relates to a method for prevention and/or treatment of T cell, B cell or natural killer cell mediated diseases, said method comprising administering, to a subject in need thereof, a pharmaceutically active amount of a polypeptide of the invention, of a compound of the invention, of a construct of the invention and/or of a pharmaceutical composition comprising the same.

More in particular, the invention also relates to a method for enhancing proliferation or activation of T cells, B cells or natural killer cells, said method comprising administering, to a subject in need thereof, a pharmaceutically active amount of a polypeptide of the invention, of a compound of the invention, of a construct of the invention and/or of a pharmaceutical composition comprising the same.

The invention also relates to a method for inhibiting tumor growth, said method comprising administering, to a subject in need thereof, a pharmaceutically active amount of a polypeptide of the invention, of a compound of the invention, of a construct of the invention and/or of a pharmaceutical composition comprising the same.

The invention also relates to a method for prevention and/or treatment of bacterial, fungal, viral or parasitic infectious diseases, said method comprising administering, to a subject in need thereof, a pharmaceutically active amount of a polypeptide of the invention, of a compound of the invention, of a construct of the invention and/or of a pharmaceutical composition comprising the same.

The invention also relates to a method for prevention and/or treatment of cancer, said method comprising administering, to a subject in need thereof, a pharmaceutically active amount of a polypeptide of the invention, of a compound of the invention, of a construct of the invention and/or of a pharmaceutical composition comprising the same.

More in particular, the invention also relates to a method for enhancing proliferation or activation of T cells, B cells or natural killer cells, said method comprising administering a pharmaceutically active amount of at least one of SEQ ID NOs: 1-71, 206-223, 229-230, 266-275 and 285-292, and/or of a pharmaceutical composition comprising the same.

The invention also relates to a method for inhibiting tumor growth, said method comprising administering a pharmaceutically active amount of at least one of SEQ ID NOs: 1-71, 206-223, 229-230, 266-275 and 285-292, and/or of a pharmaceutical composition comprising the same.

The invention also relates to a method for prevention and/or treatment of T cell, B cell or natural killer mediated diseases, said method comprising administering a pharmaceutically active amount of at least one of SEQ ID NOs: 1-71, 206-223, 229-230, 266-275 and 285-, and/or of a pharmaceutical composition comprising the same.

The invention also relates to a method for prevention and/or treatment of bacterial, fungal, viral or parasitic infectious diseases, said method comprising administering a pharmaceutically active amount of at least one of SEQ ID NOs: 1-71, 206-223, 229-230, 266-275 and 285-292, and/or of a pharmaceutical composition comprising the same.

Infections can be broadly classified as bacterial, fungal, viral, or parasitic based on the category of infectious organism or agent involved. Examples of bacteria, fungi, viruses and parasites which cause infection are well known in the art.

Some preferred, but non-limiting examples of pathogenic bacteria causing infections treatable by the method of the invention include syphilis, chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria.

Some preferred, but non-limiting examples of pathogenic viruses causing infections treatable by the method of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, arboviral encephalitis virus, and ebolaviruses (e.g., BDBV, EBOV, RESTV, SUDV and TAFV).

Some preferred, but non-limiting examples of pathogenic fungi causing infections treatable by the method of the invention include Candida (albicans, krusei, glabrata, tropicalis, etc.), Cryptococcus neoformans, Aspergillus (fumigatus, niger, etc.), Genus Mucorales (mucor, absidia, rhizophus), Sporothrix schenkii, Blastomyces dermatitidis, Paracoccidioides brasiliensis, Coccidioides immitis and Histoplasma capsulatum.

Some preferred, but non-limiting examples of pathogenic parasites causing infections treatable by the method of the invention include Entamoeba histolytica, Balantidium coli, Naegleriafowleri, Acanthamoeba sp., Giardia lambia, Cryptosporidium sp., Pneumocystis carinii, Plasmodium vivax, Babesia microti, Trypanosoma brucei, Trypanosoma cruzi, Leishmania donovani, Toxoplasma gondi, and Nippostrongylus brasiliensis. Accordingly, the present invention relates to a method for the prevention and/or treatment of infectious diseases with these bacterial, fungal, viral, or parasitic agents.

The invention also relates to a method for prevention and/or treatment of cancer, said method comprising administering a pharmaceutically active amount of at least one of SEQ ID NOs: 1-71, 206-223, 229-230, 266-275 and 285-292, and/or of a pharmaceutical composition comprising the same.

In particular, the present invention relates to a method for the prevention and/or treatment of squamous cell cancer, small-cell lung cancer, non-small cell lung cancer, melanoma, kidney cancer such as renal cell carcinoma and Wilms' tumors, glioblastoma, glioma, prostate cancer, testicular cancer, gastrointestinal cancer, pancreatic cancer, biliary tract cancer, cervical cancer, ovarian cancer, liver cancer, bladder cancer, breast cancer, colon cancer, colorectal cancer, small bowel or appendix cancer, uterine or endometrial cancer, multiple myeloma, salivary gland carcinoma, adrenal gland cancer, osteosarcoma, chondrosarcoma, nasopharyngeal carcinoma, basal cell carcinoma, vulval cancer, thyroid cancer, testicular cancer, esophageal cancer, head and neck cancer, leukemia, lymphomas, merkel cell cancer and other hematologic malignancies.

In another particular aspect, the present invention relates to a method for the prevention and/or treatment of squamous cell cancer, small-cell lung cancer, non-small cell lung cancer, melanoma, kidney cancer such as renal cell carcinoma and Wilms' tumors, glioblastoma, glioma, prostate cancer, testicular cancer, gastrointestinal cancer, pancreatic cancer, biliary tract cancer, cervical cancer, ovarian cancer, liver cancer, bladder cancer, breast cancer, colon cancer, colorectal cancer, small bowel or appendix cancer, uterine or endometrial cancer, multiple myeloma, salivary gland carcinoma, adrenal gland cancer, osteosarcoma, chondrosarcoma, nasopharyngeal carcinoma, basal cell carcinoma, vulval cancer, thyroid cancer, testicular cancer, esophageal cancer, head and neck cancer, leukemia, lymphomas, merkel cell cancer and other hematologic malignancies, said method comprising administering a pharmaceutically active amount of at least one of SEQ ID NOs: 1-72, 206-223, 229-230, 266-275 and 285-292, and/or of a pharmaceutical composition comprising the same.

In a further aspect, the invention relates to a method for immunotherapy, which method comprises administering, to a subject suffering from or at risk of the diseases and disorders mentioned herein, a pharmaceutically active amount of a polypeptide of the invention, of a compound of the invention, of a construct of the invention and/or of a pharmaceutical composition comprising the same.

In the above methods, the polypeptides, compounds and/or constructs of the invention and/or the compositions comprising the same can be administered in any suitable manner, depending on the specific pharmaceutical formulation or composition to be used. Thus, the polypeptides, compounds and/or constructs of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease, disorder or condition to be prevented or treated and other factors well known to the clinician.

The polypeptides, compounds and/or constructs of the invention and/or the compositions comprising the same are administered according to a regime of treatment that is suitable for preventing and/or treating the disease, disorder or condition to be prevented or treated. The clinician will generally be able to determine a suitable treatment regimen, depending on factors such as the disease, disorder or condition to be prevented or treated, the severity of the disease to be treated and/or the severity of the symptoms thereof, the specific polypeptides, compounds and/or constructs of the invention to be used, the specific route of administration and pharmaceutical formulation or composition to be used, the age, gender, weight, diet, general condition of the patient, and similar factors well known to the clinician.

Generally, the treatment regimen will comprise the administration of one or more polypeptides, compounds and/or constructs of the invention, or of one or more compositions comprising the same, in one or more pharmaceutically effective amounts or doses. The specific amount (s) or doses to be administered can be determined by the clinician, again based on the factors cited above.

Generally, depending on the specific disease, disorder or condition to be treated, the potency of the specific polypeptide, compound and/or construct of the invention to be used, the specific route of administration and the specific pharmaceutical formulation or composition used, the clinician will be able to determine a suitable daily dose.

Usually, in the above method, a polypeptide, compound and/or construct of the invention will be used. It is however within the scope of the invention to use two or more polypeptides, compounds and/or constructs of the invention in combination.

The polypeptides, compounds and/or constructs of the invention may be used in combination with one or more further pharmaceutically active compounds or principles, i.e., as a combined treatment regimen, which may or may not lead to a synergistic effect.

Again, the clinician will be able to select such further compounds or principles, as well as a suitable combined treatment regimen, based on the factors cited above and his expert judgment.

In particular, the polypeptides, compounds and/or constructs of the invention may be used in combination with other pharmaceutically active compounds or principles that are or can be used for the prevention and/or treatment of the diseases, disorders and conditions cited herein, as a result of which a synergistic effect may or may not be obtained. Examples of such compounds and principles, as well as routes, methods and pharmaceutical formulations or compositions for administering them will be clear to the clinician.

More particular, the polypeptides, compounds and/or constructs of the invention may be co-administered with chemotherapy, radiation therapy, cancer vaccines and/or one or more additional therapeutic agents. Methods for co-administration or treatment with other such agents or therapeutic modalities are well known in the art, see, e.g. Hardman, et al. (eds.) (2001) Goodman and Gilman's The Pharmacological Basis of Therapeutics, 10th ed., McGraw-Hill, New York, NY; Poole and Peterson (eds.) (2001) Pharmacotherapeutics for Advanced Practice: A Practical Approach, Lippincott, Williams & Wilkins, Phila., PA; Chabner and Longo (eds.) (2001) Cancer Chemotherapy and Biotherapy, Lippincott, Williams & Wilkins, Phila., PA.

For example, in one embodiment, the polypeptides, compounds and/or constructs of the invention are administered in combination with one or more additional therapeutic agents. Such agents can include for instance, PD-1, PD-L1, PD-L2, CTLA-4, 4-1 BB (CD137), 4-1BB ligand, OX40, OX40 ligand, CD27, TNFRSF25, TL1A, CD40, CD40 ligand, LIGHT, LTA, HVEM, BTLA, CD160, CEACAM-1, CEACAM-5, LAIR1, 2B4, TGFR, LAG-3, TIM-3, Siglecs, ICOS (CD278), ICOS ligand, B7-H3, B7-H4, B7-1, B7-2, VISTA, HHLA2, TMIGD2, BTNL2, CD244, CD48, CD2, CDS, TIGIT, PVR family members, KIRs, ILTs, LIRs, NKG2D, NKG2A, MICA, MICB, CSF1R, IDO, TGFβ, Adenosine, ICAM-1, ICAM-2, ICAM-3, LFA-1 (CD11a/CD18), LFA-2, LFA-3, BAFFR, NKG2C, SLAMF7, NKp80, CD83 ligand, CD24, CD39, CD30, CD70, CD73, CD7, CXCR4, CXCL12, Phosphatidylserine, SIRPA, CD47, VEGF and Neuropilin.

In another embodiment, the polypeptides, compounds and/or constructs of the invention are administered in combination with an anti-PD-1 antibody or an antigen-binding fragment thereof, wherein the anti-PD-1 antibody or antigen-binding fragment thereof is administered simultaneously with the polypeptides, compounds and/or constructs of the invention, or prior to or subsequently to the administration of the polypeptides, compounds and/or constructs of the invention. As shown in Examples 14 and 21, the administration of the polypeptides, compounds and/or constructs of the invention in combination with an anti-PD-1 antibody to mice had a synergistic effect in inhibiting tumor growth.

In another embodiment, the polypeptides, compounds and/or constructs of the invention are administered in combination with an anti-CTLA-4 antibody or an antigen-binding fragment thereof, wherein the anti-CTLA-4 antibody or antigen-binding fragment thereof is administered simultaneously with the polypeptides, compounds and/or constructs of the invention, or prior to or subsequently to the administration of the polypeptides, compounds and/or constructs of the invention.

In another embodiment, the polypeptides, compounds and/or constructs of the invention are administered in combination with an anti-PD-L1 antibody or an antigen-binding fragment thereof wherein the anti-PD-L1 antibody or antigen-binding fragment thereof is administered simultaneously with the polypeptides, compounds and/or constructs of the invention, or prior to or subsequently to the administration of the polypeptides, compounds and/or constructs of the invention.

In yet other embodiments, the polypeptides, compounds and/or constructs of the invention are administered in combination with an anti-PD-1 antibody (or antigen-binding fragments thereof) and 5-FU.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease, disorder or condition involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of a polypeptide, compound and/or construct of the invention for the manufacture of a pharmaceutical composition for prevention and/or treatment of at least one disease, disorder and condition associated with GITR; and/or for use in one or more of the methods of treatment mentioned herein.

The invention also relates to the use of a polypeptide, compound and/or construct of the invention, for the manufacture of a pharmaceutical composition for prevention and/or treatment of at least one of the diseases, disorders and conditions associated with GITR and/or with the signaling pathways and/or the biological functions and responses in which GITR are involved; and/or in one or more of the methods described herein.

The invention also relates to the use of a polypeptide, compound and/or construct of the invention for the manufacture of a pharmaceutical composition for the prevention and/or treatment of at least one disease or disorder that can be prevented and/or treated by stimulating, enhancing or agonizing GITR, its biological or pharmacological activity, and/or the biological pathways or signaling in which GITR is involved.

The invention also relates to the use of a polypeptide, compound and/or construct of the invention for the manufacture of a pharmaceutical composition for the prevention and/or treatment of at least one disease, disorder or condition that can be prevented and/or treated by administering a polypeptide, compound and/or construct of the invention to a patient.

More in particular, the invention relates to the use of a polypeptide, compound and/or construct of the invention for the manufacture of a pharmaceutical composition for enhancing an immune response The invention also relates to the use of a polypeptide, compound and/or construct of the invention for the manufacture of a pharmaceutical composition for enhancing proliferation or activation of T cells, B cells or natural killer cells.

The invention also relates to the use of a polypeptide, compound and/or construct of the invention for the manufacture of a pharmaceutical composition for inhibiting tumor growth.

The invention also relates to the use of a polypeptide, compound and/or construct of the invention for the manufacture of a pharmaceutical composition for prevention and/or treatment of T cell, B cell or natural killer cell mediated diseases.

The invention also relates to the use of a polypeptide, compound and/or construct of the invention for the manufacture of a pharmaceutical composition for prevention and/or treatment of bacterial, fungal, viral or parasitic infectious diseases.

The invention also relates to the use of a polypeptide, compound and/or construct of the invention for the manufacture of a pharmaceutical composition for prevention and/or treatment of cancer.

More in particular, the invention relates to the use of a polypeptide, compound and/or construct of the invention for the manufacture of a pharmaceutical composition for the prevention and/or treatment of squamous cell cancer, small-cell lung cancer, non-small cell lung cancer, melanoma, kidney cancer such as renal cell carcinoma and Wilms' tumors, glioblastoma, glioma, prostate cancer, testicular cancer, gastrointestinal cancer, pancreatic cancer, biliary tract cancer, cervical cancer, ovarian cancer, liver cancer, bladder cancer, breast cancer, colon cancer, colorectal cancer, small bowel or appendix cancer, uterine or endometrial cancer, multiple myeloma, salivary gland carcinoma, adrenal gland cancer, osteosarcoma, chondrosarcoma, nasopharyngeal carcinoma, basal cell carcinoma, vulval cancer, thyroid cancer, testicular cancer, esophageal cancer, head and neck cancer, leukemia, lymphomas, merkel cell cancer and other hematologic malignancies.

The invention further relates to a polypeptide, compound and/or construct of the invention or a pharmaceutical composition comprising the same for use in the prevention and/or treatment of at least one GITR related disease, disorder and/or condition.

The invention further relates to a polypeptide, compound and/or construct of the invention or a pharmaceutical composition comprising the same for use in the prevention and/or treatment of at least one disease, disorder and/or condition associated with GITR, with its biological or pharmacological activity, and/or with the biological pathways or signaling in which GITR is involved.

The invention further relates to a polypeptide, compound and/or construct of the invention or a pharmaceutical composition comprising the same for use in the prevention and/or treatment of at least one disease, disorder and/or condition that can be prevented and/or treated by stimulating, enhancing or agonizing GITR, its biological or pharmacological activity, and/or the biological pathways or signaling in which GITR is involved.

The invention also relates to a polypeptide, compound and/or construct of the invention or a pharmaceutical composition comprising the same for use in the prevention and/or treatment of at least one disease, disorder and/or condition that can be prevented and/or treated by administering of a polypeptide, compound and/or construct of the invention to a patient. More in particular, the invention also relates to a polypeptide, compound and/or construct of the invention or pharmaceutical compositions comprising the same for use in enhancing an immune response.

The invention also relates to a polypeptide, compound and/or construct of the invention or a pharmaceutical composition comprising the same for use in enhancing proliferation or activation of T cells, B cells or natural killer cells.

The invention also relates to a polypeptide, compound and/or construct of the invention or a pharmaceutical composition comprising the same for use in inhibiting tumor growth.

The invention also relates to a polypeptide, compound and/or construct of the invention or a pharmaceutical composition comprising the same for use in prevention and/or treatment of T cell, B cell or natural killer cell mediated diseases.

The invention also relates to a polypeptide, compound and/or construct of the invention or a pharmaceutical composition comprising the same for use in prevention and/or treatment of bacterial, fungal, viral or parasitic infectious diseases.

The invention also relates to a polypeptide, compound and/or construct of the invention or a pharmaceutical composition comprising the same for use in prevention and/or treatment of cancer.

More in particular, the invention relates to a polypeptide, compound and/or construct of the invention or a pharmaceutical composition comprising the same for use in the prevention and/or treatment of squamous cell cancer, small-cell lung cancer, non-small cell lung cancer, melanoma, kidney cancer such as renal cell carcinoma and Wilms' tumors, glioblastoma, glioma, prostate cancer, testicular cancer, gastrointestinal cancer, pancreatic cancer, biliary tract cancer, cervical cancer, ovarian cancer, liver cancer, bladder cancer, breast cancer, colon cancer, colorectal cancer, small bowel or appendix cancer, uterine or endometrial cancer, multiple myeloma, salivary gland carcinoma, adrenal gland cancer, osteosarcoma, chondrosarcoma, nasopharyngeal carcinoma, basal cell carcinoma, vulval cancer, thyroid cancer, testicular cancer, esophageal cancer, head and neck cancer, leukemia, lymphomas, merkel cell cancer and other hematologic malignancies.

The subject to be treated may be any warm-blooded animal, but is in particular a mammal, and more in particular a human being. In veterinary applications, the subject to be treated includes any animal raised for commercial purposes or kept as a pet. As will be clear to the skilled person, the subject to be treated will in particular be a person suffering from, or at risk of, the diseases, disorders and conditions mentioned herein.

Again, in such a pharmaceutical composition, the one or more polypeptides, compounds and/or constructs of the invention, or nucleotide encoding the same, and/or a pharmaceutical composition comprising the same, may also be suitably combined with one or more other active principles, such as those mentioned herein.

The invention also relates to a composition (such as, without limitation, a pharmaceutical composition or preparation as further described herein) for use, either in vitro (e.g. in an in vitro or cellular assay) or in vivo (e.g. in an a single cell or multi-cellular organism, and in particular in a mammal, and more in particular in a human being, such as in a human being that is at risk of or suffers from a disease, disorder or condition of the invention.

The polypeptides, compounds and/or constructs of the present invention inhibit tumor cell growth, in a syngeneic CT-26 colon carcinoma model. Based on their mode of action, the polypeptides, compounds and/or constructs of the present invention may be useful in the treatment of other GITR associated diseases, including but not limited to various types of cancer and infectious diseases.

It is to be understood that reference to treatment includes both treatment of established symptoms and prophylactic treatment, unless explicitly stated otherwise.

The invention will now be further described by means of the following non-limiting preferred examples and figures.

The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1: Creation of GITR Expression Cell Lines and Recombinant Cyno GITR and Cyno GITR-Fc 1.1 GITR Expressing Cell Lines Stable Flp-In™-293 cells (Life technologies R750-07) and GloResponse™ NF-κB-Nluc2P HEK293 (Promega CS188801) cell lines with recombinant overexpression of human GITR, cynomologus GITR and mouse GITR were generated. For this, the coding sequences of GITR were cloned in a pcDNA3.1-derived vector, downstream of a CMV promotor. The sequences for human GITR and mouse GITR were retrieved from UniprotKB (humanGITR: Q9Y5U5 [SEQ ID NO: 231], mouseGITR: O35714 [SEQ ID NO: 232]). The sequence for the cynomolgus GITR was retrieved from the NCBI database (XP_005545180, SEQ ID NO: 233). Cell surface expression of human GITR was confirmed using the humanized IgG1 anti-human GITR antibody (HuQ6C8-Agly, see WO06105021) and mouse IgG1 anti-human GITR Clone #110416 (R&D Systems MAB689), cyno GITR expression with HuQ6C8-Agly and mouse GITR expression was confirmed using rat IgG2b anti-mouse GITR clone DTA-1 (eBioscience #16-5874) (FIG. 1A-C).

1.2 Recombinant Cyno GITR and Cyno GITR-Fc

The extracellular domain of cyno GITR was extended either with a HIS tag or with human IgG1 Fc and the respective cDNA sequences were cloned into a mammalian expression vector. The resulting plasmids were transfected into HEK.EBNA cells and proteins were purified from the harvested cell supernatant respectively by IMAC and Protein A chromatography followed by a desalting step to PBS buffer.

Example 2: Immunization of Llamas with Human GITR, Cloning of the Heavy Chain-Only Antibody Fragment Repertoires and Preparation of Phage 2.1 Immunization After approval of the Ethical Committee (Ablynx NV, Belgium—EC2012 #2), 6 camelids were immunized with a CMV-promoter based DNA vector encoding human GITR. Additionally, one camelid was immunized with recombinant mouse GITR-Fc (R&D Systems, 524-GR-050).

2.2 Cloning of the Heavy Chain-Only Antibody Fragment Repertoires and Preparation of Phages.

Per animal, blood samples were collected after the injection of one type of immunization antigen. From these blood samples, PBMC were prepared using Ficoll-Hypaque according to the manufacturer's instructions (Amersham Biosciences, Piscataway, NJ, USA). For each immunized llama, libraries were constructed by pooling the total RNA isolated from samples originating from a certain subset of the immunization schedule, i.e. after one type of immunization antigen. In short, the PCR-amplified VHH repertoire was cloned via specific restriction sites into a vector designed to facilitate phage display of the VHH library. The vector was derived from pUC119. In frame with the VHH coding sequence, the vector encodes a C-terminal 3×FLAG and HIS6 tag. Phages were prepared according to standard protocols (see for example WO 04/041865, WO 04/041863, WO 04/062551, WO 05/044858 and other prior art and applications filed by Ablynx N.V. cited herein).

Example 3: Selection of GITR Specific VHHs Via Phage Display

VHH repertoires obtained from all llamas and cloned as phage library were used in different selection strategies, applying a multiplicity of selection conditions. Variables included: i) the presentation form of GITR (on different backgrounds), ii) alternation of species source (human/cynomolgus/mouse GITR), iii) the antigen concentration, iv) the number of selection rounds, v) shielding of specific GITR epitopes. In brief, cells (see Example 1) or the soluble antigen (human GITR-Fc (Enzo Life Sciences, ALX-522-061-C050), cyno GITR (in-house), cyno GITR-Fc (in-house), mouse GITR (R&D Systems, 524-GR-050) were incubated for 1h-2h with the phage libraries followed by extensive washing; bound phages were eluted with trypsin (1 mg/mL) for 15 minutes and then the protease activity was immediately neutralized by applying 0.8 mM protease inhibitor ABSF. As control, selections with parental cell line or without antigen were performed in parallel.

Phage outputs were used to infect *E. coli* for analysis of individual VHH clones. Periplasmic extracts were prepared according to standard protocols (see for example WO 03/035694, WO 04/041865, WO 04/041863, WO 04/062551 and other prior art and applications filed by Ablynx N.V. cited herein).

Example 4: Construction of Nanobody®—IgG Chimeras 4.1 Construction of Nanobody®-Human IgG1 Chimeras Nanobody®-human IgG1 chimeras were composed of two heavy chains and two light chains. The heavy chain comprised an anti-GITR Nanobody® fused to human IgG1 constant domains CH1-CH3. The light chain consisted of the same anti-GITR Nanobody® fused to the constant domain of the human light chain CL (kappa). A schematic representation of a Nanobody®-human IgG1 chimera is depicted in FIG. 7.

The respective cDNA sequences were cloned in a mammalian expression vector in two separate expression cassettes. The resulting plasmids were transfected into HEK.EBNA cells and proteins were purified from the harvested cell supernatant by Protein A chromatography and desalting to PBS buffer.

4.2 Construction of Nanobody®-Rat IgG2b Chimeras

Nanobody®-rat IgG2b chimeras were composed of two heavy chains and two light chains. The heavy chain comprised an anti-GITR Nanobody® fused to rat IgG2b constant domains CH1-CH3. The light chain consisted of the same anti-GITR Nanobody® fused to the constant domain of the rat light chain CL (lambda).

The respective cDNA sequences were cloned in a mammalian expression vector in two separate expression cassettes. The resulting plasmids were transfected into HEK.EBNA cells and proteins were purified from the harvested cell supernatant by Protein A chromatography and desalting to PBS buffer.

Example 5: Screening 5.1 Screening for GITR Binding Nanobodies® in a Binding ELISA Periplasmic extracts were screened in a binding ELISA on human GITR (Enzo Life Sciences, ALX-522-061-C050) and cynomolgus GITR (in-house). To this end, a microtiter plate was coated with human or cynomolgus GITR (0.5 μg/ml), overnight incubated at 4° C. Plates were blocked for one hour at room temperature with 75 μl 1% casein in PBS. The plates were washed with PBS-Tween. The periplasmic extracts (1/5 or 1/8000 diluted in PBS with 0.1% casein+ 0.05% Tween) were incubated for at least 1 hour at RT. Plates were washed six times with PBS-Tween, after which binding of VHH was detected with anti-FLAG-HRP (Sigma-Aldrich, A8592) mAb 1/5000 in PBS with 0.1% casein+ 0.05% Tween20. Staining was performed with the substrate esTMB (SDT reagents) and the signals were measured after 15 minutes at 450 nm.

Nanobodies® which scored positive in the binding ELISA were sequenced. The sequence analysis resulted in the identification of 8 distinct families, i.e. Family 7, Family 26, Family 82, Family 109, Family 85, Family 38, Family 110 and Family 108. Corresponding alignments are provided in Table A-1, Table A-2, Table A-3, Table A-4, Table A-5, Table A-6, Table A-7 and Table A-8, respectively. The classification into different families was based on sequence similarities and differences in the CDRs. The sequence variability against a representative of each family is depicted in the tables below.

For Family 7, the amino acid sequence of the CDRs of clone A0231005A03 was used as a reference, against which the CDRs of all other Family 7 clones were compared. The sequence variability against A0231005A03 is shown below.

| | A0231005A03 CDR1 Kabat numbering | | | | | | | | | |
|---|---|---|---|---|---|---|---|---|---|---|
| | 26 | 27 | 28 | 29 | 30 | 31 | 32 | 33 | 34 | 35 |
| | | | | | absolute numbering | | | | | |
| | 1 | 2* | 3 | 4 | 5 | 6 | 7 | 8 | 9 | 10 |
| wildtype sequence | E | T | I | F | S | I | D | S | M | A |
| variations | | S | | | | | | | A | G |
| variations | | S | | | | | | N | A | G |

*in case position 2 is an S, then position 8 is also A, and position 10 is also G

| | A0231005A03 CDR2 Kabat numbering | | | | | | | | |
|---|---|---|---|---|---|---|---|---|---|
| | 50 | 51 | 52 | 53 | 54 | 55 | 56 | 57 | 58 |
| | | | | absolute numbering | | | | | |
| | 1 | 2 | 3 | 4 | 5 | 6 | 7 | 8 | 9 |
| wildtype sequence | A | I | T | G | G | G | S | P | N |
| variations | H | | | | | | R | S | |
| variations | T | | | | | | | T | |
| variations | T | | | | | | R | R | |
| variations | T | M | | | | | | T | |
| variations | H | | | | | | G | S | |
| variations | T | | | | | S | | T | |
| variations | H | | | | | | R | | |
| variations | G | | S | | | | R | T | |

| | A0231005A03 CDR3 Kabat numbering | | | | | | | | | | | | |
|---|---|---|---|---|---|---|---|---|---|---|---|---|---|
| | 95 | 96 | 97 | 98 | 99 | 100 | 100a | 100b | 100c | 100d | 100e | 101 | 102 |
| | | | | | | | absolute numbering | | | | | | |
| | 1 | 2 | 3 | 4 | 5 | 6 | 7 | 8 | 9 | 10 | 11 | 12 | 13 |
| wildtype sequence | E | G | Q | A | G | W | G | T | A | L | M | D | Y |
| variations | | | | | | | | | P | | | N | |
| variations | | | | | | | | | | | L* | | |
| variations | | | | | | | | | | | K* | | |

-continued

A0231005A03 CDR3 Kabat numbering

| | 95 | 96 | 97 | 98 | 99 | 100 | 100a | 100b | 100c | 100d | 100e | 101 | 102 |
|---|---|---|---|---|---|---|---|---|---|---|---|---|---|
| | | | | | | | | absolute numbering | | | | | |
| | 1 | 2 | 3 | 4 | 5 | 6 | 7 | 8 | 9 | 10 | 11 | 12 | 13 |
| variations | | | | | | | | | | | R* | | |
| variations | | | | | | | | | | | Q* | | |

*variations were introduced to replace Methionine in order to avoid oxidation of this residue For Family 26, the amino acid sequence of the CDRs of clone A0231004B01 was used as a reference, against which the CDRs of all other Family 26 clones were compared. The sequence variability against A0231004B01 is shown below.

For Family 82, the amino acid sequence of the CDRs of clone A0231034A08 was used as a reference, against which the CDRs of all other Family 82 clones were compared. The sequence variability against A0231034A08 is shown below.

A0231004B01 CDR1 Kabat numbering

| | 26 | 27 | 28 | 29 | 30 | 31 | 32 | 33 | 34 | 35 |
|---|---|---|---|---|---|---|---|---|---|---|
| | | | | | absolute numbering | | | | | |
| | 1 | 2 | 3 | 4 | 5 | 6 | 7 | 8 | 9 | 10 |
| wildtype sequence | G | S | I | F | S | I | D | S | M | G |
| variations | | | | | | | | A | | |
| variations | | | | | | | N | A | | |

A0231034A08 CDR1 Kabat numbering

| | 26 | 27 | 28 | 29 | 30 | 31 | 32 | 33 | 34 | 35 |
|---|---|---|---|---|---|---|---|---|---|---|
| | | | | | absolute numbering | | | | | |
| | 1 | 2 | 3 | 4 | 5 | 6 | 7 | 8 | 9 | 10 |
| wildtype sequence | G | S | V | F | S | I | N | D | M | G |
| variations | | | | | | I | | D | S | |
| variations | | | | | | I | | D | | |
| variations | | | | | | I | | | | V |
| variations | | | | N | | I | | | | |
| variations | | | | | | I | | | | |
| variations | | | | | | I | | | T | |

A0231004B01 CDR2 Kabat numbering

| | 50 | 51 | 52 | 53 | 56 | 57 | 58 |
|---|---|---|---|---|---|---|---|
| | | | | absolute numbering | | | |
| | 1 | 2 | 3 | 4 | 5 | 6 | 7 |
| wildtype sequence | A | I | T | S | S | T | N |
| variations | S | | | | T | | |
| variations | | | | | G | | |
| variations | | | | | R | | I |
| variations | T | | | | G | K | |

A0231034A08 CDR2 Kabat numbering

| | 50 | 51 | 52 | 53 | 54 | 55 | 56 | 57 | 58 |
|---|---|---|---|---|---|---|---|---|---|
| | | | | | absolute numbering | | | | |
| | 1 | 2 | 3 | 4 | 5 | 6 | 7 | 8 | 9 |
| wildtype sequence | D | I | I | S | R | G | V | T | N |
| variations | | | | | A | D | | | |

A0231004B01 CDR3 Kabat numbering

| | 95 | 96 | 97 | 98 | 99 | 100 | 100a | 100b | 100c | 100d | 100e | 101 | 102 |
|---|---|---|---|---|---|---|---|---|---|---|---|---|---|
| | | | | | | | absolute numbering | | | | | | |
| | 1 | 2 | 3 | 4 | 5 | 6 | 7 | 8 | 9 | 10 | 11 | 12 | 13 |
| wildtype sequence | E | G | Q | A | G | W | G | T | A | L | I | N | Y |
| variations | K | | | T | | | | | | | M | D | |
| variations | | | | T | | | | | | | M | D | |
| variations | | | | | | | | | | | M | D | |
| variations | | | | | | | | | | | L | D | |

A0231034A08 CDR2 Kabat numbering

| Kabat | 50 | 51 | 52 | 53 | 54 | 55 | 56 | 57 | 58 |
|---|---|---|---|---|---|---|---|---|---|
| absolute | 1 | 2 | 3 | 4 | 5 | 6 | 7 | 8 | 9 |
| variations | | | | | A | | | | |
| variations | G | | | | | | | | |
| variations | | | | | | | D | | |

A0231034A08 CDR3 Kabat numbering

| Kabat | 95 | 96 | 97 | 98 | 99 | 100 | 100a | 100b | 100c | 100d | 100e | 101 | 102 |
|---|---|---|---|---|---|---|---|---|---|---|---|---|---|
| absolute | 1 | 2 | 3 | 4 | 5 | 6 | 7 | 8 | 9 | 10 | 11 | 12 | 13 |
| wildtype sequence | H | I | S | T | G | W | G | R | P | H | N | N | Y |
| variations | | | | M | | | | | | | | | |

For Family 109, the amino acid sequence of the CDRs of clone A0231052E08 was used as a reference, against which the CDRs of all other Family 109 clones were compared. The sequence variability against A0231052E08 is shown below.

A0231052E08 CDR1 Kabat numbering

| Kabat | 26 | 27 | 28 | 29 | 30 | 31 | 32 | 33 | 34 | 35 |
|---|---|---|---|---|---|---|---|---|---|---|
| absolute | 1 | 2 | 3 | 4 | 5 | 6 | 7 | 8 | 9 | 10 |
| wildtype sequence | R | S | I | F | S | T | Y | A | M | A |
| variations | | N | | | | | | | | |

A0231052E08 CDR2 Kabat numbering

| Kabat | 50 | 51 | 52 | 53 | 54 | 55 | 56 | 57 | 58 |
|---|---|---|---|---|---|---|---|---|---|
| absolute | 1 | 2 | 3 | 4 | 5 | 6 | 7 | 8 | 9 |
| wildtype sequence | F | I | Y | W | G | G | T | T | T |
| variations | | | | | | | | | S |

A0231052E08 CDR3 Kabat numbering

| Kabat | 95 | 96 | 97 | 98 | 99 | 101 | 102 |
|---|---|---|---|---|---|---|---|
| absolute | 1 | 2 | 3 | 4 | 5 | 6 | 7 |
| wildtype sequence | Y | G | S | Y | A | L | P |

For Family 85, the amino acid sequence of the CDRs of clone A02310331302 is depicted in the tables below.

A0231033B02 CDR1 Kabat numbering

| Kabat | 26 | 27 | 28 | 29 | 30 | 31 | 32 | 33 | 34 | 35 |
|---|---|---|---|---|---|---|---|---|---|---|
| absolute | 1 | 2 | 3 | 4 | 5 | 6 | 7 | 8 | 9 | 10 |
| wildtype sequence | G | T | I | F | S | I | S | T | M | G |

A0231033B02 CDR2 Kabat numbering

| Kabat | 50 | 52 | 53 | 54 | 55 | 56 | 57 | 58 |
|---|---|---|---|---|---|---|---|---|
| absolute | 1 | 2 | 3 | 4 | 5 | 6 | 7 | 8 |
| wildtype sequence | V | T | S | G | F | S | T | N |

| A0231033B02 CDR3 Kabat numbering | | | | | | | | | | | | |
|---|---|---|---|---|---|---|---|---|---|---|---|---|
| 95 | 96 | 97 | 98 | 99 | 100 | 100a | 100b | 100c | 100d | 100e | 101 | 102 |
| | | | | | | absolute numbering | | | | | | |
| 1 | 2 | 3 | 4 | 5 | 6 | 7 | 8 | 9 | 10 | 11 | 12 | 13 |
| wildtype sequence Y | L | S | L | A | W | R | D | P | D | R | D | Y |

For Family 38, the amino acid sequence of the CDRs of clone A0231003D11 was used as a reference, against which the CDRs of all other Family 38 clones were compared. The sequence variability against A0231003D11 is depicted in the tables below.

| A0231003D11 CDR1 Kabat numbering | | | | | | | | | |
|---|---|---|---|---|---|---|---|---|---|
| 26 | 27 | 28 | 29 | 30 | 31 | 32 | 33 | 34 | 35 |
| | | | | absolute numbering | | | | | |
| 1 | 2 | 3 | 4 | 5 | 6 | 7 | 8 | 9 | 10 |
| wildtype sequence G | S | I | F | S | I | D | A | M | G |

| A0231003D11 CDR2 Kabat numbering | | | | | | |
|---|---|---|---|---|---|---|
| 50 | 51 | 52 | 54 | 55 | 56 | 57 |
| | | | absolute numbering | | | |
| 1 | 2 | 3 | 4 | 5 | 6 | 7 |
| wildtype sequence E | I | S | D | H | T | T |
| variations | | | G | | | |

| A0231003D11 CDR3 Kabat numbering | | | | | | | | | | | | |
|---|---|---|---|---|---|---|---|---|---|---|---|---|
| 95 | 96 | 97 | 98 | 99 | 100 | 100a | 100b | 100c | 100d | 100e | 101 | 102 |
| | | | | | | absolute numbering | | | | | | |
| 1 | 2 | 3 | 4 | 5 | 6 | 7 | 8 | 9 | 10 | 11 | 12 | 13 |
| wildtype sequence H | H | Q | R | G | W | G | T | S | I | T | V | T |
| variations | | | | | | | | | | | | A |
| variations | | | | | | | | P | | | | |

For Family 110, the amino acid sequence of the CDRs of clone A0231052A08 was used as a reference, against which the CDRs of all other Family 110 clones were compared. The sequence variability against A0231052A08 is depicted in the tables below.

A0231052A08 CDR1 Kabat numbering

| | | | | | | | | | |
|---|---|---|---|---|---|---|---|---|---|
| 26 | 27 | 28 | 29 | 30 | 31 | 32 | 33 | 34 | 35 |
| | | | | absolute numbering | | | | | |
| 1 | 2 | 3 | 4 | 5 | 6 | 7 | 8 | 9 | 10 |
| wildtype sequence G | S | I | S | S | I | T | A | M | G |

A0231052A08 CDR2 Kabat numbering

| | | | | | | | | |
|---|---|---|---|---|---|---|---|---|
| 50 | 51 | 52 | 53 | 54 | 55 | 56 | 57 | 58 |
| | | | | absolute numbering | | | | |
| 1 | 2 | 3 | 4 | 5 | 6 | 7 | 8 | 9 |
| wildtype sequence | V | I | S | R | S | G | A | T | M |
| variations | | I | | | | | | | |
| variations | | A | | | | | | | I |

A0231052A08 CDR3 Kabat numbering

| | | | | | | |
|---|---|---|---|---|---|---|
| 95 | 96 | 97 | 98 | 99 | 101 | 102 |
| | | | absolute numbering | | | |
| 1 | 2 | 3 | 4 | 5 | 6 | 7 |
| wildtype sequence | I | T | Q | G | R | T | Y |
| variations | | | | E | Q | | |

For Family 108, the amino acid sequence of the CDRs of clone A0231051E01 is depicted in the tables below.

A0231051E01 CDR1 Kabat numbering

| | | | | | | | | | |
|---|---|---|---|---|---|---|---|---|---|
| 26 | 27 | 28 | 29 | 30 | 31 | 32 | 33 | 34 | 35 |
| | | | | absolute numbering | | | | | |
| 1 | 2 | 3 | 4 | 5 | 6 | 7 | 8 | 9 | 10 |
| wildtype sequence G | S | I | F | S | F | I | V | M | G |

A0231051E01 CDR2 Kabat numbering

| | | | | | | | | |
|---|---|---|---|---|---|---|---|---|
| 50 | 51 | 52 | 53 | 54 | 55 | 56 | 57 | 58 |
| | | | | absolute numbering | | | | |
| 1 | 2 | 3 | 4 | 5 | 6 | 7 | 8 | 9 |
| wildtype sequence | T | V | T | S | G | G | D | T | F |

A0231051E01 CDR3 Kabat numbering

| | | | | | | | | | |
|---|---|---|---|---|---|---|---|---|---|
| 95 | 96 | 97 | 98 | 99 | 100 | 100a | 100b | 101 | 102 |
| | | | | absolute numbering | | | | | |
| 1 | 2 | 3 | 4 | 5 | 6 | 7 | 8 | 9 | 10 |
| wildtype sequence | T | K | V | S | P | Y | K | E | T | T |

5.2 Purification of Monovalent Nanobodies®

Representative Nanobodies® were selected and expressed in *E. coli* TG1 as triple Flag, HIS6-tagged proteins. Expression was induced by addition of 1 mM IPTG and allowed to continue for 4 hours at 37° C. After spinning the cell cultures, periplasmic extracts were prepared by freeze-thawing and resuspension of the pellets in D-PBS. The periplasmic extracts were filtered (0.20 μm) and imidazole was added to a final concentration of 20 mM. The Nanobodies® in these periplasmic extracts were purified via IMAC and desalted via Zebaspin (Fisher Scientific).

Example 6: Kinetic Analysis of Monovalent Anti-GITR Nanobodies®

Affinity was determined on the Proteon XPR36. Briefly, after human GITR-Fc (Enzo Life Sciences, ALX-522-061-C050) was immobilized on a GLC chip via amine coupling, a range of 6 concentrations of different monovalent Nanobodies® (representing each family) were injected. The $K_D$ values were determined by using the calculated association rate and dissociation rate constants (Table 1) (ProteOn Manager 3.1.0, Version 3.1.0.6 (2011)).

TABLE 1

$K_D$ values of monovalent anti-GITR Nanobodies ®

| | antigen: human GITR-Fc | | |
|---|---|---|---|
| | Ka 1/Ms | kd 1/s | $K_D$ M |
| A0231034A08 (Family 82) | 2.7E+05 | 6.7E−04 | 2.5E−09 |
| A0231004B01 (Family 26) | 1.1E+06 | 2.7E−03 | 2.6E−09 |
| A0231005A03 (Family 7) | 6.8E+05 | 2.3E−03 | 3.4E−09 |
| A0231003D11 (Family 38) | 6.3E+05 | 2.9E−03 | 4.6E−09 |
| A0231033B02 (Family 85) | 4.9E+05 | 8.0E−03 | 1.6E−08 |

TABLE 1-continued

K_D values of monovalent anti-GITR Nanobodies ®

|  | antigen: human GITR-Fc | | |
|---|---|---|---|
|  | Ka 1/Ms | kd 1/s | K_D M |
| A0231052A08 (Family 110) | 4.1E+04 | 9.7E−04 | 2.4E−08 |
| A0231051E01 (Family 108) | 1.9E+05 | 1.5E−02 | 7.8E−08 |
| A0231052E08 (Family 109) | 7.5E+05 | 9.0E−02 | 1.2E−07 |

Example 7: Binding of Anti-GITR Nanobodies® to GITR Expressed on Flp-In™-293 Cells and Activated T Cells Binding of purified monovalent anti-GITR Nanobodies® to human GITR expressed on activated T cells was evaluated in flow cytometry. For this purpose, PBMCs from healthy donors were cultured with Dynabeads® Human T-Activator CD3/CD28 (Gibco—Life Technologies #11131D) for 7 days in a ½ bead/cell ratio. After activation, a cell population was obtained consisting out of >98% T cells. These T cells were highly activated (CD25high, CD45RO+ T cells) and showed a good expression of GITR (FIG. 1D).

Dilution series of Nanobodies® starting from 1 pM were applied to the cells. Nanobodies® were allowed to associate for 30 minutes at 4° C. in FACS buffer (PBS supplemented with 10% FBS and 0.05% azide). Cells were washed by centrifugation and probed with anti-FLAG antibodies (Sigma F1804) for 30 minutes at 4° C., to detect bound Nanobody®. Detection was done with Goat anti-Mouse IgG-PE (Jackson ImmunoResearch #115-116-071) for 30 minutes at 4° C. Cells were washed and incubated with TOPRO3 to stain for dead cells which were subsequently removed during the gating procedure. The cells were then analysed via a BD FACSArray. The results are shown in FIGS. 2A-2B.

The $EC_{50}$ values obtained from the dose response curve are represented in Table 2.

TABLE 2

$EC_{50}$ (M) values of anti-GITR monovalent Nanobodies ® to activated T cells as determined in flow cytometry

|  | activated human T cells | | |
|---|---|---|---|
| ID | $EC_{50}$ (M) | 95% LCI | 95% UCI |
| A0231005A03 (Family 7) | 7.9E−10 | 6.7E−10 | 9.2E−10 |
| A0231004B01 (Family 26) | 6.1E−10 | 5.2E−10 | 7.1E−10 |
| A0231034A08 (Family 82) | 5.4E−10 | 4.8E−10 | 6.1E−10 |
| A0231052E08 (Family 109) | >1.0E−7 | / | / |
| A0231033B02 (Family 85) | 2.1E−8 | 9.6E−9 | 4.7E−8 |
| A0231003D11 (Family 38) | 1.3E−9 | 1.0E−9 | 1.6E−9 |
| A0231052A08 (Family 110) | 2.3E−8 | 1.9E−8 | 2.7E8 |
| A0231051E01 (Family 108) | >1.0E−7 | / | / |

Example 8: Generation and Binding of Multivalent Constructs 8.1 Construction of Multivalent Nanobody® Constructs In order to increase potency and/or efficacy, multivalent molecules were constructed by genetic engineering. Multiple Nanobodies® were genetically linked together with 3A, 9GS or 35GS linkers. All multivalent GITR Nanobody® constructs carried a C-terminal Albumin binding Nanobody® and were subsequently expressed in Pichia pastoris according to standard conditions. Constructs with a FLAG3-HIS6 tag were purified using IMAC, while the tagless construct were purified via protein A binding. Different multivalent GITR constructs were made as listed in Table A-11.

8.2 Binding of Multivalent Anti-GITR Nanobodies® to Human GITR Expressed on NFkB-Nluc2P HEK293 Cells as Determined by FACS.

Binding of the multivalent constructs to human GITR was determined by FACS. Briefly, Nanobodies® were allowed to associate for 30 minutes at 4° C. in FACS buffer (PBS supplemented with 10% FBS and 0.05% azide). Cells were washed by centrifugation and probed with an in-house anti-ALB11 antibody for 30 minutes at 4° C., to detect bound Nanobody®. Detection was done with Goat anti-Mouse IgG-PE (Jackson ImmunoResearch #115-116-071) for 30 minutes at 4° C. Cells were washed and incubated with TOPRO3 to stain for dead cells, which were subsequently removed during the gating procedure. The cells were then analysed via a BD FACSArray. Binding curves are shown in FIG. 3. The $EC_{50}$ values obtained from the dose response curve are depicted in Table 3.

TABLE 3

$EC_{50}$ (M) values of anti-GITR multivalent Nanobodies ®, Nanobody ®-human IgG1 chimera A-0231-00_TP008 and reference compounds for binding to HEK293_NFkB-Nluc2P human GITR cells as determined in flow cytometry

| Construct ID | HEK293_NFkB-Nluc2P human GITR |
|---|---|
| A023100001 (Family 26) | 2.17E−10 |
| A023100014 (Family 26) | 1.26E−10 |
| A023100022 (Family 7) | 1.51E−10 |
| A023100025 (Family 109) | 1.97E−10 |
| A023100029 (Family 82) | 3.26E−10 |
| A023100030 (Family 85) | 2.46E−10 |
| A023100034 (Family 7) | 2.04E−10 |
| A-0231-00_TP008 (Family 7) | 6.75E−11 |
| Reference compounds | |
| HuQ6C8-Agly (see WO06105021) | 4.00E−10 |
| 36E5 (see U.S. Pat. No. 8,709,424) | 1.96E−10 |

Example 9: Activation of GITR by Anti-GITR Nanobodies® Assessed in a NF-κB Luciferase Reporter Assay The functionality of the purified multivalent Nanobodies® was assessed in a NF-κB luciferase reporter assay. To this end, the GloResponse™ NF-κB-Nluc2P HEK293 (Promega CS188801) cell line was stably transfected with human GITR. To evaluate the activation capacity of anti-GITR Nanobodies®, the GITR expressing cells were seeded at 10,000 cells/well in white, tissue culture-treated 96-well plates (Costar #3917). Serial dilutions of anti-GITR Nanobodies® were added and allowed to interact for 5 hours in a 37° C. incubator at 5% $CO_2$. NF-κB activity was assessed by measuring luminescence after addition of Nano-Glo™ Reagent (Promega #N1120). Results shown in Table 4A illustrate the effect of anti-GITR Nanobodies® and HuQ6C8-Agly on a pool of cells with a heterogeneous GITR expression. Results shown in Table 4B-C illustrate the effect of anti-GITR Nanobodies®, HuQ6C8-Agly and 36E5 on single cell clones. Illustrative activation curves are shown in FIG. 4A-D.

TABLE 4A $EC_{50}$ (M) and efficacy values (human GITR ligand = 100%) of anti-GITR multivalent Nanobodies ® and reference compound

| Construct ID | HEK293_NFkB-Nluc2P human GITR $EC_{50}$ (M) | HEK293_NFkB-Nluc2P human GITR Efficacy (%) |
|---|---|---|
| A023100003 (Family 7) | 1.0E−10 | 101 |
| A023100015 (Family 110) | 1.8E−10 | 105 |
| A023100020 (Family 108) | 4.5E−10 | 105 |
| A023100021 (Family 38) Reference compound | 2.6E−11 | 116 |
| HuQ6C8-Agly | 2.2E−10 | 51 |

TABLE 4B $EC_{50}$ (M) and efficacy values (human GITR ligand = 100%) of anti-GITR multivalent Nanobodies ®, Nanobody ®-human IgG1 chimera A-0231-00_TP008 and reference compounds

| Construct ID | HEK293 human GITR NF-KB luc reporter $EC_{50}$ (M) | HEK293 human GITR NF-KB luc reporter Efficacy (%) |
|---|---|---|
| A023100001 (Family 26) | 7.82E−11 | 60 |
| A023100014 (Family 26) | 2.96E−11 | 72 |
| A023100022 (Family 7) | 2.46E−11 | 85 |
| A023100025 (Family 109) | 3.17E−11 | 76 |
| A023100029 (Family 82) | 9.53E−11 | 77 |
| A023100030 (Family 85) | 8.72E−11 | 90 |
| A023100032 (Family 7) | 2.63E−11 | 108 |
| A023100034 (Family 7) | 5.60E−11 | 62 |
| A023100035 (Family 7) | 1.55E−11 | 112 |
| A-0231-00_TP008 (Family 7) Reference compound | 1.52E−11 | 86.8 |
| HuQ6C8-Agly | 3.93E−10 | 30.4 |
| 36E5 | 3.94E−11 | ND |

TABLE 4C $EC_{50}$ (M) and efficacy values (human GITR ligand = 100%) of anti-GITR multivalent Nanobodies ®

| Construct ID | HEK293 human GITR NF-KB luc reporter $EC_{50}$ (M) | HEK293 human GITR NF-KB luc reporter Efficacy (%) |
|---|---|---|
| A-0231-00_TP008 (Family 7) | 1.89E−11 | 87 |
| A023100035 (Family 7) Reference compound | 3.66E−11 | 129 |
| 36E5 | 3.26E−11 | 37 |

Example 10: Human T Cell Activation Capacity of Anti-GITR Nanobodies®

Functionality of purified multivalent monospecific anti-GITR Nanobodies® was evaluated in a human T cell activation assay. Human CD4+ T cells were isolated from Buffy Coats from healthy donors using CD4+ T Cell Isolation Kit (Miltenyi Biotec #130-096-533) and cultured in RPM1-1640 (Life Technologies—Gibco #72400) supplemented with 10% FBS and 1% P/S. The isolated CD4+ T cells were subsequently activated for 10 days with Dynabeads® Human T-Activator CD3/CD28 (Life Technologies—Gibco #11131D) at a 1/5 bead/cell ratio and 4 additional days at a 1/1 ratio. The activation status was evaluated by flow cytometry by measuring CD25 expression (anti-CD25-PE—BD Bioscience #557138), CD45RA expression (anti-CD45RA-APC—BD Bioscience #550855) and CD45RO expression (anti-CD45RO-PE—BD Bioscience #555493). GITR expression was confirmed by detection with mouse anti-human GITR Clone 110416 (R&D Systems #MAB689).

To evaluate the activation capacity of anti-GITR Nanobodies® the activated CD4+ T cells were cultured in RPMI-1640 supplemented with 10% Human AB serum and 1% P/S. Cells were added to plates coated with anti-CD3 clone OKT3 (eBioscience #16-0037-85) at 125 ng/ml (IFN-γ production) or 8 ng/ml (proliferation) in presence or absence of anti-GITR Nanobodies®. IFN-γ production was measured by ELISA after 3 days incubation in a 37° C. incubator at 5% $CO_2$. For proliferation measurement cells were incubated for 3 days and pulsed with $^3$H-thymidine 18 hours before the cells were harvested and counted.

Figure 5A:
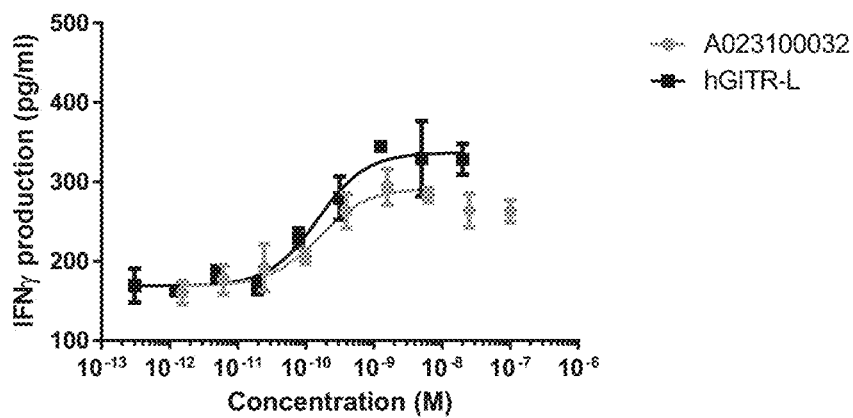
Figure 5B:
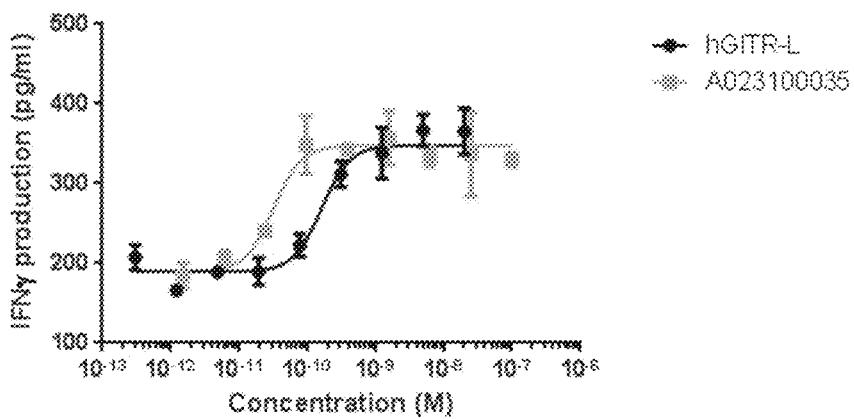
Figure 5C:
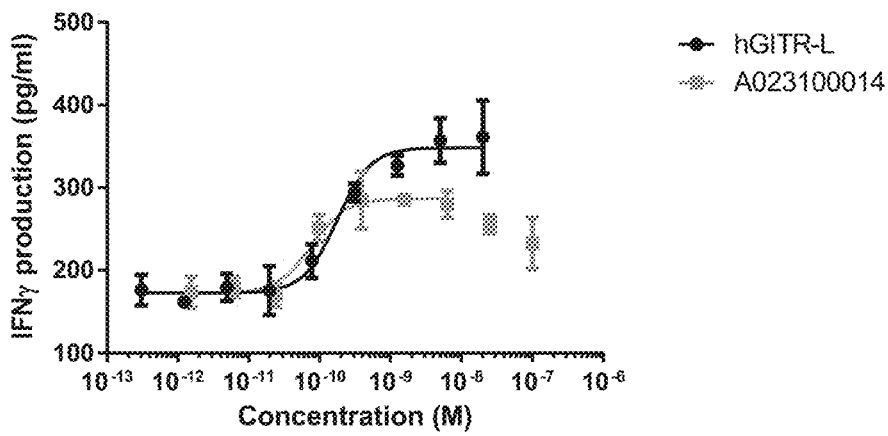
Figure 5D:
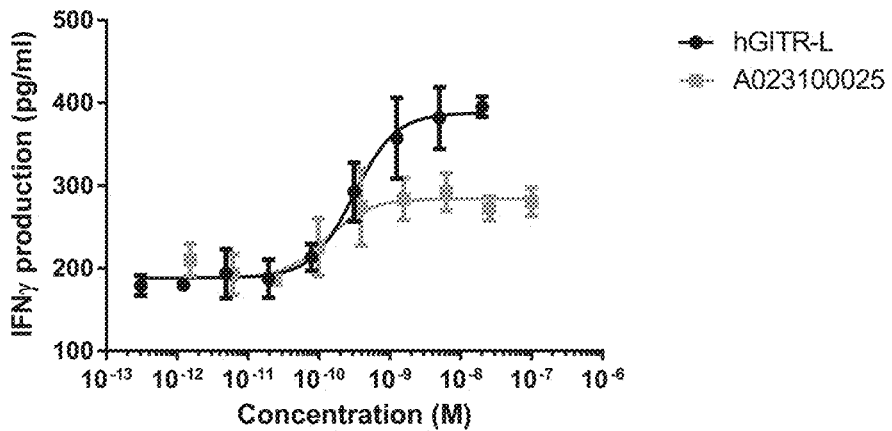
Figure 5E:
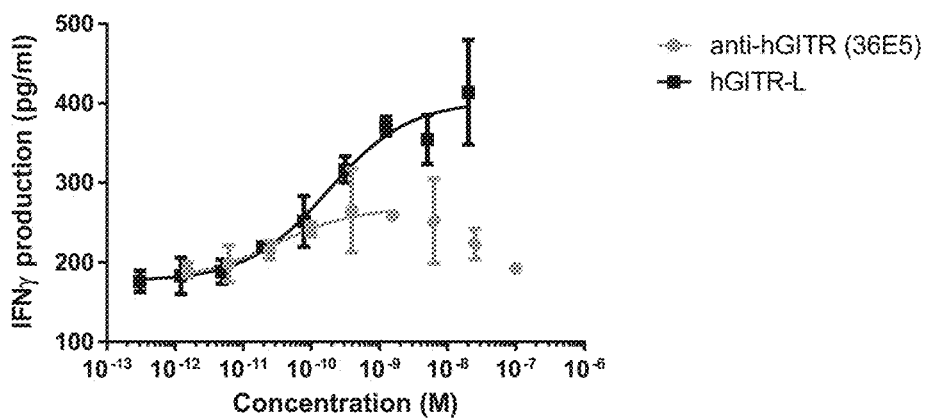
Figure 5F:
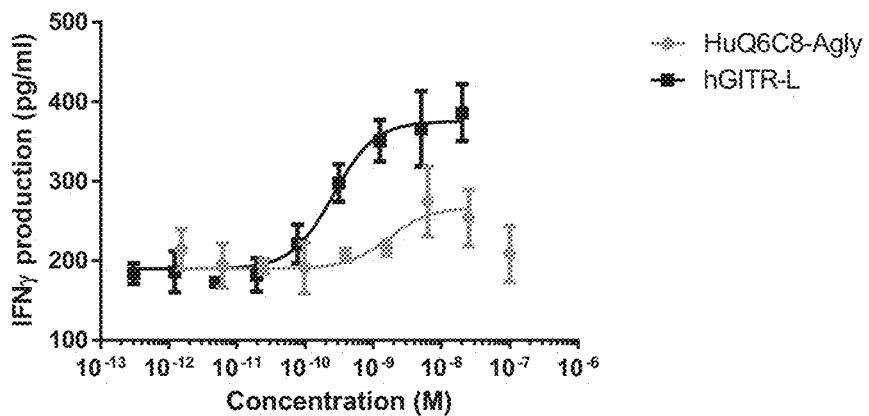
Figure 6A:
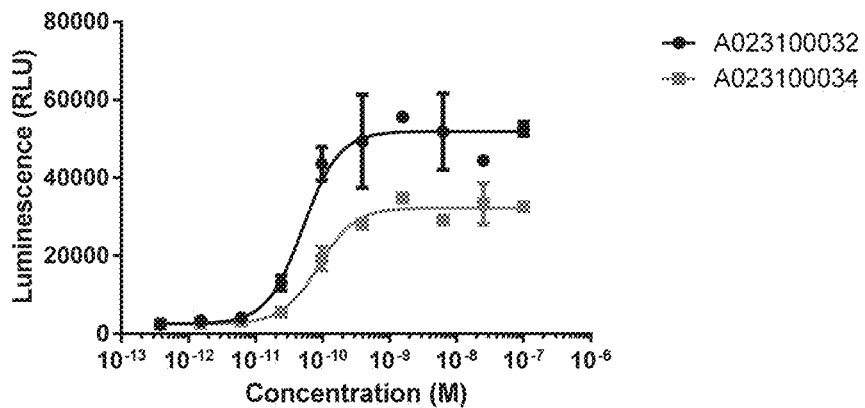
Figure 6B:
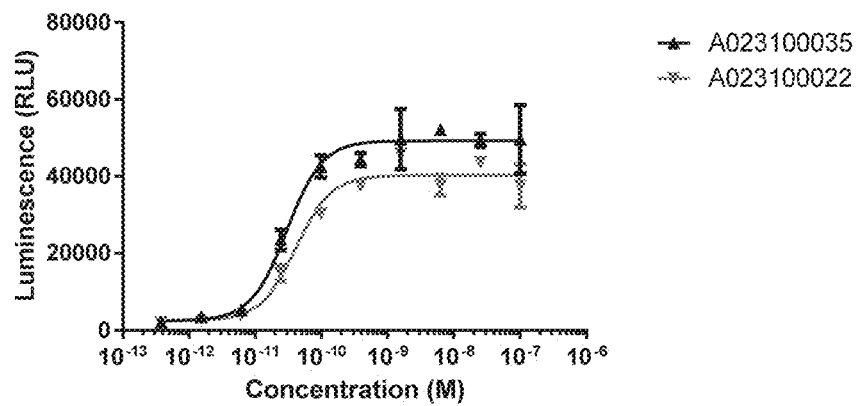
Figure 6C:
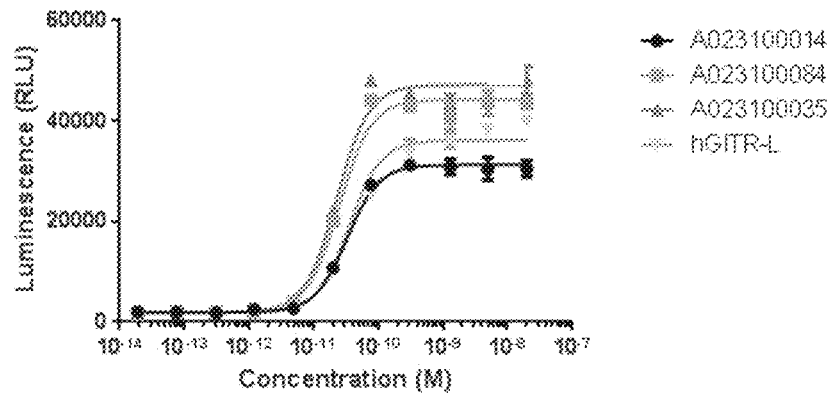
Figure 6D:
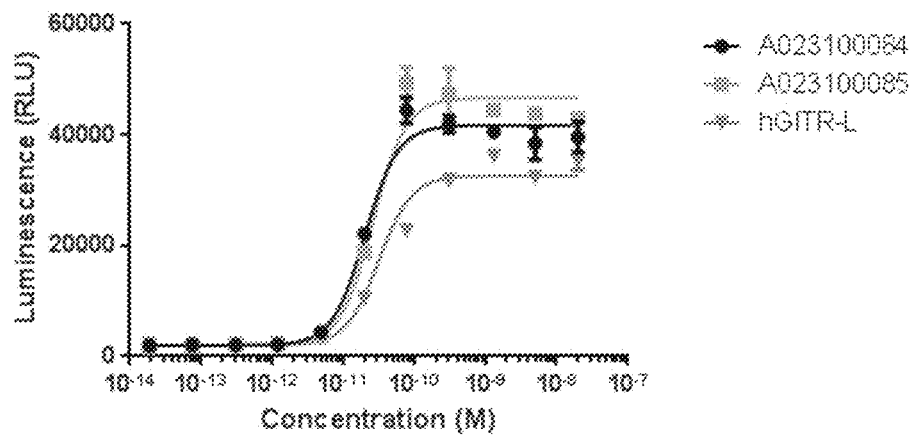

The effect of multivalent anti-GITR Nanobodies® on the IFN-γ production is exemplified in FIGS. 5A-D. Nanobody® A023100035, a tetravalent Nanobody® (Family 7) with 9GS linker between the individual building blocks, acts as a full agonist, displaying substantially the same efficacy as the natural ligand (defined as Emax) throughout the tested concentration range. FIGS. 5E and 5F show the data obtained for the reference compounds 36E5 and HuQ6C8-Agly, respectively. These antibodies acts as a partial agonist displaying a lower maximal efficacy, that even further decreases with increasing concentrations.

Table 5 shows the effect on IFN-γ production of multivalent anti-GITR Nanobodies® and anti-GITR antibodies in comparison to the natural ligand. $EC_{50}$ values reflect the potency of the Nanobodies®. The maximal efficacy as percentage of the Emax (=maximal response induced by the natural ligand) is also presented. Nanobody® A023100035 clearly shows an efficacy comparable to the natural ligand, which was set at 100%.

TABLE 5

EC$_{50}$ values (M) and the maximal efficacy values (human GITR ligand = 100%) of anti-GITR multivalent Nanobody® constructs and reference compounds (IFN-γ read-out).

| Construct ID | EC$_{50}$ (M) | Maximal efficacy (%) |
|---|---|---|
| A023100032 (Family 7) | 1.52E−10 | 74.1 |
| A023100035 (Family 7) | 4.10E−11 | 105.9 |
| A023100014 (Family 26) | 7.67E−11 | 64.2 |
| A023100025 (Family 109) | 1.30E−10 | 52.1 |
| Reference compound | | |
| 36E5 | 2.94E−11 | 39.1 |
| HuQ6C8-Agly | 1.67E−09 | 45.6 |

Example 11: Linker Length Multivalent Nanobody® Constructs

The impact of the linker length was evaluated in the human GITR NF-κB luciferase reporter assay, as described in Example 9. Nanobody® constructs with a 9GS linker showed a higher efficacy than Nanobody® constructs with a 35GS linker (see Table 6A). This was confirmed using different Nanobody® constructs (see Table 6B). In addition it was shown that Nanobody® constructs with a 3A linker have comparable efficacies to the 9GS linked constructs.

The effect of multivalent anti-GITR Nanobody® constructs with a different linker length on the NF-κB activity is also exemplified in FIGS. 6A-D. Unexpectedly, the inventors additionally showed that shortening the length of the linker can even further improve the functional properties of the GITR Nanobody® constructs.

TABLE 6A

EC$_{50}$ (M) and maximal efficacy values (human GITR ligand = 100%) of anti-GITR multivalent Nanobodies®

| Construct ID | EC$_{50}$ (M) | Maximal efficacy (%) |
|---|---|---|
| A023100012 (Family 108) (A0231051E01-35GS-A0231051E01-35GS-ALB11) | 1.72E−09 | 18.2 |
| A023100031 (Family 108) (A0231051E01-9GS-A0231051E01-9GS-ALB11) | 2.69E−09 | 51.7 |
| A023100020 (Family 108) (A0231051E01-35GS-A0231051E01-35GS-A0231051E01-35GS-ALB11) | 1.53E−09 | 85.4 |
| A023100036 (Family 108) (A0231051E01-9GS-A0231051E01-9GS-A0231051E01-9GS-ALB11) | 5.41E−10 | 89.9 |
| A023100034 (Family 7) (A0231005A03-35GS-A0231005A03-35GS-ALB11) | 8.74E−11 | 83.0 |
| A023100032 (Family 7) (A0231005A03-9GS-A0231005A03-9GS-ALB11) | 5.11E−11 | 137.9 |
| A023100022 (Family 7) (A0231005A03-35GS-A0231005A03-35GS-A0231005A03-35GS-ALB11) | 4.11E−11 | 105.5 |
| A023100035 (Family 7) (A0231005A03-9GS-A0231005A03-9GS-A0231005A03-9GS-ALB11) | 2.99E−11 | 130.5 |

TABLE 6B

EC$_{50}$ (M) and maximal efficacy values (human GITR ligand = 100%) of anti-GITR multivalent Nanobodies®

| Construct ID | EC$_{50}$ (M) | Maximal efficacy (%) |
|---|---|---|
| A023100083 (Family 26) A0231004B01-9GS-A0231004B01-9GS-ALB11 | 3.16E−11 | 126 |
| A023100045 (Family 26) A0231004B01-3A-A0231004B01-9GS-ALB11 | 2.99E−11 | 133 |
| A023100082 (Family 26) A0231004B01-3A-A0231004B01-3A-ALB11 | 3.13E−11 | 136 |
| A023100014 (Family 26) A0231004B01-35GS-A0231004B01-35GS-A0231004B01-35GS-ALB11 | 3.30E−11 | 86 |
| A023100084 (Family 26) A0231004B01-9GS-A0231004B01-9GS-A0231004B01-9GS-ALB11 | 2.27E−11 | 127 |
| A023100085 (Family 26) A0231004B01-3A-A0231004B01-3A-A0231004B01-3A-ALB11 | 2.63E−11 | 146 |
| A023100035 (Family 7) (A0231005A03-9GS-A0231005A03-9GS-A0231005A03-9GS-ALB11) | 2.30E−11 | 132 |
| Reference compound | | |
| 36E5 | 2.25E−11 | 33 |

Example 12: In Vivo Proof-of-Concept in an OVA Immunization Model

In the OVA immunization model, BALB/c mice were immunized on day zero (D0) by subcutaneous (s.c.) administration of 100 µg ovalbumin in saline or adjuvant followed by a boost with the same s.c. dose in saline or adjuvant on D14. Mice that receive OVA in adjuvant are administered OVA in a 1:1 mixture with alum or Incomplete Freund's adjuvant (IFA).

The adjuvant effect of anti-GITR Nanobody® and anti-GITR Nanobody®-ratIgG2b chimera on the humoral immune response to OVA is evaluated, reflecting the immune-enhancing effect of the anti-GITR Nanobody® and anti-GITR Nanobody®-ratIgG2b chimera To assess the effect of anti-GITR and anti-GITR Nanobody®-ratIgG2b chimera on the humoral response to OVA, the anti-GITR Nanobody® or irrelevant control Nanobody® is administered intraperitoneally at the primary (D0) or boost (D14) immunisation for 3 consecutive days with a 1×15 mg/kg loading dose on the first dosing day and a maintenance dose of 2×10 mg/kg on the next two dosing days. Anti-GITR Nanobody®-ratIgG2b chimera is administered intraperitoneally at D0 or D14 for 3 consecutive days at 25 mg/kg. Anti-OVA serum titres are determined by ELISA on D-7, D13 and D21. The OVA mixed with Alum or IFA is included for comparison. Significant increase of total anti-OVA IgG levels in anti-GITR Nanobody® and anti-GITR Nanobody®-ratIgG2b chimera treated animals are expected compared to untreated and irrelevant control animals.

Example 13: In Vivo Proof-of-Concept in a Syngeneic CT-26 Colon Carcinoma Model Tumour efficacy of anti-GITR Nanobody® and anti-GITR Nanobody®-ratIgG2b chimera is demonstrated in a syngeneic CT-26 colon carcinoma model.

In this model, BALB/c mice are inoculated with BALB/c-derived colorectal carcinoma cells (CT26 cells).

On day 0 (D0) tumours are induced by subcutaneous injection of 1×10$^6$ of CT26 cells in 200 μL of RPMI 1640 into the right flank of BALB/c mice. When tumors reach a mean volume of 50-100 mm$^3$ animals are treated according to the treatment regimen presented in Table 7.

In vivo efficacy of the anti-GITR Nanobody® and anti-GITR Nanobody®-ratIgG2b chimera on tumour growth is evaluated and compared to the irrelevant control Nanobody®. Mice are treated with the anti-GITR Nanobody® or anti-GITR Nanobody®-ratIgG2b chimera either in monotherapy or in combination therapy with anti-PD-1 antibody (Ab) or anti-PD-1 Ab+5-fluoro-uracil (5FU). Mice treated with anti-CTLA-4 Ab are included as positive control group. Efficacy of anti-GITR Nanobody® and anti-GITR Nanobody®-ratIgG2b chimera is further compared to DTA-1 as monotherapy or in combination therapy with anti-PD-1 antibody.

The viability, behavior and body weights are recorded. The length and width of the tumour is measured twice a week with calipers and tumour volume is estimated by the formula:

$$\text{Tumor volume} = \frac{\text{width}^2 \times \text{length}}{2}$$

Significant anti-tumour activity with GITR targeting Nanobody® or Nanobody®-ratIgG2b chimera reflect a markedly delay in onset of tumour development or complete tumour rejection.

A re-challenge with CT26 cells is done to evaluate establishment of anti-tumor memory in BALB/c mice that have rejected subcutaneous CT26 tumors.

On day 49 (D49, i.e. 49 days after the first SC injection of CT26 cells), 1×10$^6$ of CT26 cells are injected subcuta-

TABLE 7

Treatment regimen

| Group | No animals | Treatment | Dose | Adm. Route | Treatment schedule |
|---|---|---|---|---|---|
| 1 | 10 | Vehicle | — | IP | Q1Dx1 |
| 2 | 10 | Anti-CTLA-4 | 10 mg/kg | IP | TWx2* |
| 3 | 10 | DTA-1 | 25 mg/kg | IP | Q1Dx1 |
| 4 | 10 | DTA-1 | 25 mg/kg | IP | Q1Dx1 |
|   |    | Anti-PD-1 | 10 mg/kg | IP | Q5Dx3 |
| 5 | 10 | Anti-GITR NB | 1 × 15 mg/kg loading dose | IP | Q2Dx10 |
|   |    |              | 9 × 10 mg/kg maintenance dose |   |   |
| 6 | 10 | Irrelevant NB | 1 × 15 mg/kg loading dose | IP | Q2Dx10 |
|   |    |               | 9 × 10 mg/kg maintenance dose |   |   |
| 7 | 10 | Anti-GITR NB | 1 × 15 mg/kg loading dose | IP | Q2Dx10 |
|   |    |              | 9 × 10 mg/kg maintenance dose |   |   |
|   |    | Anti-PD-1 | 10 mg/kg | IP | Q5Dx3 |
| 8 | 10 | Irrelevant NB | 1 × 15 mg/kg loading dose | IP | Q2Dx10 |
|   |    |               | 9 × 10 mg/kg maintenance dose |   |   |
|   |    | Anti-PD-1 | 10 mg/kg | IP | Q5Dx3 |
| 9 | 10 | Anti-GITR NB | 1 × 15 mg/kg loading dose | IP | Q2Dx10 |
|   |    |              | 2 × 2.5 mg/kg maintenance dose |   |   |
|   |    | Anti-PD-1 | 10 mg/kg | IP | Q5Dx3 |
|   |    | 5-FU | 25 mg/kg | IV | Q7Dx3 |
| 10 | 10 | Irrelevant NB | 1 × 15 mg/kg loading dose | IP | Q2Dx10 |
|   |    |               | 2 × 2.5 mg/kg maintenance dose |   |   |
|   |    | Anti-PD-1 | 10 mg/kg | IP | Q5Dx3 |
|   |    | 5-FU | 25 mg/kg | IV | Q7Dx3 |
| 11 | 10 | Anti-GITR NB-ratIgG2b chimera | 25 mg/kg | IP | Q1Dx1 |
| 12 | 10 | Anti-GITR NB-ratIgG2b chimera | 1 × 25 mg/kg loading dose | IP | Q2Dx10 |
|   |    |                                | 9 × 10 mg/kg maintenance dose |   |   |
| 13 | 10 | Anti-GITR NB-ratIgG2b chimera | 25 mg/kg | IP | Q1Dx1 |
|   |    | Anti-PD-1 | 10 mg/kg | IP | Q5Dx3 |
| 14 | 10 | Anti-GITR NB-ratIgG2b chimera | 1 × 25 mg/kg loading dose | IP | Q2Dx10 |
|   |    |                                | 9 × 10 mg/kg maintenance dose |   |   |
|   |    | Anti-PD-1 | 10 mg/kg | IP | Q5Dx3 |
| 15 | 10 | Anti-GITR NB-ratIgG2b chimera | 25 mg/kg | IP | Q1Dx1 |
|   |    | Anti-PD-1 | 10 mg/kg | IP | Q5Dx3 |
|   |    | 5-FU | 25 mg/kg | IV | Q7Dx3 |
| 16 | 10 | Anti-GITR NB-ratIgG2b chimera | 1 × 25 mg/kg loading dose | IP | Q2Dx10 |
|   |    |                                | 9 × 10 mg/kg maintenance dose |   |   |
|   |    | Anti-PD-1 | 10 mg/kg | IP | Q5Dx3 |
|   |    | 5-FU | 25 mg/kg | IV | Q7Dx3 |
| Total | 160 |   |   |   |   |

*TWx2: total of 4 injections with 2 injections per week: on Monday/Thursday or on Tuesday/Friday. Q5Dx3: 3 injections with 1 injection every 5 days; Q7Dx3: 3 injections with 1 injection every 7 days; Q2Dx10: 10 injections with 1 injection every 2 days, in case of combinations: DTA-1, anti-GITR NB, anti-GITR NB-ratIgG2b chimera or irrelevant NB is injected after the anti-PD-1. The anti-PD-1 is injected after 5-FU.

neously in 200 µL of RPMI 1640 into the left flank of animals from groups 2, 3, 4, 5, 7 and 9.

Only mice whose first CT26 tumour has been eliminated by the effect of the treatment are injected with the second CT26 tumour cells.

In addition, in order to demonstrate the CT26 tumour growth in absence of an immunological memory, $1 \times 10^6$ of CT26 cells will be injected subcutaneously in 200 µL of RPMI 1640 into the left flank of nine (9) naive mice.

The monitoring of animals is performed as described above.

Markedly delay in onset of tumour development or complete tumour rejection with GITR targeting Nanobody® or Nanobody®-ratIgG2b chimera is expected.

Example 14: Agonistic Anti-GITR Nanobodies® Alone or in Combination with an Anti-PD-1 Antibody Cause Tumor Regression and Increase Survival Time in a Syngeneic CT-26 Colon Carcinoma Mouse Model Anti-tumor efficacy of agonistic anti-GITR Nanobodies® (Nb) was demonstrated in a syngeneic CT-26 colon carcinoma model, in which BALB/c mice were inoculated with BALB/c-derived colorectal carcinoma cells (CT-26 cells). CT-26 cells were cultured in RPMI 1640 medium supplemented with 10% heat-inactivated fetal bovine serum and 2 mM L-glutamine. BALB/c mice were subcutaneously injected with $1 \times 10^6$ CT-26 cells in 200 µL volume of RPMI 1640 into the right flank. Tumor length and width was measured using calipers and tumor volume determined using the formula Tumor Volume $(mm^3) = 0.5 \times length \times width^2$, where length is the longer dimension. On day 8 after tumor challenge mice were randomized according to their individual tumor volume into 14 treatment groups with an equivalent mean tumor size of 89 $mm^3$ and dosing was started according to the treatment regimen presented in Table 8. Tumor volumes were recorded twice weekly. Survival was recorded every day. Mice were euthanized when tumors exceeded 10% of normal body weight.

Mice were treated with an anti-GITR Nanobody® or with anti-GITR Nanobody®-IgG chimeras of rat IgG2b or human IgG1 isotypes, either as a monotherapy or in combination with an anti-PD-1 monoclonal antibody (mAb; BioXCell clone RPM1-14). Mice treated with DTA-1 (BioXCell), an anti-GITR mAb, alone or in combination with anti-PD-1 mAb were included as positive reference control groups. One group of control mice (vehicle group 14) was left untreated. All treatments were administered via intraperitoneal injection (IP) starting on day 8 after tumor challenge. The groups of mice receiving DTA-1 were treated with a single dose of 25 mg/kg (groups 1 and 2). The groups of mice receiving anti-GITR Nanobody® were treated repeatedly with one IP injection every two days for 18 days, either at a dose level of 15 mg/kg single loading dose and 10 mg/kg maintenance dose (dose level 1; groups 3 and 7) or at a 30 mg/kg single loading dose and a 20 mg/kg maintenance dose (dose level 2; groups 5 and 8). Irrelevant control Nanobodies® were dosed at the respective dose level 1 (groups 4 and 9) and dose level 2 (groups 6 and 10) multiple dosing regimens. The anti-GITR NB-IgG chimera of the rat IgG2b and human IgG1 isotype were administered as a single dose of 5 mg/kg (group 11) and 25 mg/kg (groups 12 and 13), respectively. Groups of mice receiving a combination therapy were administered a total of three IP injections with anti-PD-1 mAb with one injection every five days at a dose level of 10 mg/kg (groups 2, 7, 8, 9, 10 and 13).

The anti-tumor efficacy of the anti-GITR Nanobody® and anti-GITR Nanobody®-IgG chimeras was evaluated and compared with respective control groups. Tumor growth inhibition, delay of tumor growth and tumor regression together with survival of animals served as read-outs for anti-tumor efficacy.

As depicted in FIG. 8, combination of anti-GITR Nanobody® with anti-PD-1 mAb (groups 7 and 8; FIGS. 8G and 8H) resulted in a synergistic efficacy with 7/10 and 8/10 animals showing a delayed tumor development for Nanobody® dose level 1 and 2, respectively, against 1/10 and 2/10 animals in the respective control groups (groups 9 and 10; FIGS. 8I and 8J) when compared with the vehicle group 14 (FIG. 8N).

Monotherapy with anti-GITR Nanobody® resulted in a delayed tumor development in 3/10 and in 4/10 animals at dose level 1 and 2, respectively, when compared to the respective control groups 5 and 6. Combination of anti-GITR Nanobody®-IgG chimera of the human IgG1 isotype with anti-PD-1 mAb resulted in a robust synergistic effect shown by a delay in tumor development in 8/10 animals and 50% complete regression (CR) (group 13). Monotherapy with the human IgG1 isotype chimera resulted in a delayed tumor growth in 6/10 animals with 1/10 animals showing complete tumor regression (group 12). Monotherapy with the rat IgG2b isotype chimera resulted in a delayed tumor growth in 6/10 animals (group 11) compared to the vehicle group. Treatment with the reference anti-GITR mAb, DTA-1, resulted in a delayed tumor development for 8/10 and 6/10 animals for monotherapy (group 1) and in combination with anti-PD-1 mAb (group 2), respectively, compared to their respective control groups. Both monotherapy and combination therapy resulted in a 20% complete regression.

In addition, as depicted in FIG. 9, the median survival time (start calculated from the day of tumor injection) of the vehicle group was 23 days (group 14). Median survival times for groups treated with the reference anti-GITR mAb, DTA-1, alone was 44.5 days with 40% of animals still alive on day 40 post treatment, whereas combination therapy with DTA-1 and anti-PD-1 mAb resulted in a median survival of 34 days with 30% of animals still alive on day 40 post treatment. The median survival for control groups receiving irrelevant Nanobody® in combination with anti-PD-1 mAb was 21.5 and 23 days at irrelevant Nanobody® dose levels 1 and 2, respectively. Monotherapy with anti-GITR Nanobody® corresponded to median survival times of 23 days for both dose levels (groups 3 and 5), whereas the respective control groups treated with irrelevant Nanobody® showed a median survival of 20 days for both dose levels (groups 4 and 6). Median survival of groups treated with the combination of anti-GITR Nanobody® and anti-PD-1 mAb was 30 days at Nanobody® dose level 1 (group 7), with 20% still alive on day 40 post treatment, and 28.5 days at Nanobody® dose level 2 (group 8). Animals receiving a monotherapy with anti-GITR Nanobody® chimera of the rat IgG2b isotype (group 11) presented with a median survival of 27 days, with 10% still alive on day 40 post treatment.

Animals treated with monotherapy of anti-GITR Nanobody® chimera of the human IgG1 isotype (group 12) had a median survival of 27 days, with 30% surviving on day 40 post treatment, whereas 60% of animals treated with the combination of the human IgG isotype chimera and anti-PD-1 mAb were still alive on day 40 post treatment (group 13). In sum, the agonistic anti-GITR Nanobodies® of the present invention show statistically significant effects in a relevant tumor model. These results were further confirmed by a separate and independent statistical analysis of the data obtained, which was an extended version of the so-called to bit regression model (Dagne & Huang, 2012).

TABLE 8

Treatment regimen

| Group | No. Animals | Treatment | Dose | Route | Treatment Schedule |
|---|---|---|---|---|---|
| 1 | 10 | DTA-1 | 25 mg/kg | IP | Q1Dx1 |
| 2 | 10 | DTA-1 | 25 mg/kg | IP | Q1Dx1 |
|   |   | anti-PD-1 Ab | 10 mg/kg | IP | Q5Dx3 |
| 3 | 10 | anti-GITR NB (A023100035) | 1 × 15 mg/kg loading dose, then 9 × 10 mg/kg maintenance dose | IP | Q2Dx10 |
| 4 | 10 | irrelevant NB | 1 × 15 mg/kg loading dose, then 9 × 10 mg/kg maintenance dose | IP | Q2Dx10 |
| 5 | 10 | anti-GITR NB (A023100035) | 1 × 30 mg/kg loading dose, then 9 × 20 mg/kg maintenance dose | IP | Q2Dx10 |
| 6 | 10 | irrelevant NB | 1 × 30 mg/kg loading dose, then 9 × 20 mg/kg maintenance dose | IP | Q2Dx10 |
| 7 | 10 | anti-GITR NB (A023100035) | 1 × 15 mg/kg loading dose, then 9 × 10 mg/kg maintenance dose | IP | Q2Dx10 |
|   |   | anti-PD-1 Ab | 10 mg/kg | IP | Q5Dx3 |
| 8 | 10 | anti-GITR NB (A023100035) | 1 × 30 mg/kg loading dose, then 9 × 20 mg/kg maintenance dose | IP | Q2Dx10 |
|   |   | anti-PD-1 Ab | 10 mg/kg | IP | Q5Dx3 |
| 9 | 10 | irrelevant NB | 1 × 15 mg/kg loading dose, then 9 × 10 mg/kg maintenance dose | IP | Q2Dx10 |
|   |   | anti-PD-1 | 10 mg/kg | IP | Q5Dx3 |
| 10 | 10 | irrelevant NB | 1 × 30 mg/kg loading dose, then 9 × 20 mg/kg maintenance dose | IP | Q2Dx10 |
|   |   | anti-PD-1 | 10 mg/kg | IP | Q5Dx3 |
| 11 | 10 | anti-GITR NB-rat IgG2b (A-0231-00_TP010) | 5 mg/kg | IP | Q1Dx1 |
| 12 | 10 | anti-GITR NB-human IgG1 (A-0231-00_TP008) | 25 mg/kg | IP | Q1Dx1 |
| 13 | 10 | anti-GITR NB-human IgG1 (A-0231-00_TP008) | 25 mg/kg | IP | Q1Dx1 |
|   |   | anti-PD-1 | 10 mg/kg | IP | Q5Dx3 |
| 14 | 10 | vehicle | — | IP | Q1Dx1 |

Q1Dx1: Single injection on the day of start of treatment; Q5Dx3: 3 injections with 1 injection every 5 days; Q2Dx10: 10 injections with 1 injection every 2 days. In case of combinations: DTA-1, anti-GITR NB, anti-GITR NB-ratIgG2b chimera, anti-GITR NB-human IgG1 chimera, or irrelevant NB is injected after the anti-PD-1.

Example 15: In Vitro Benchmarking of the Anti-GITR Nanobodies® in the T Cell Activation Assay The T cell experiments were performed as described in Example 10. Results are shown in FIGS. 10A-10C. These experiments show that the tested anti-GITR compounds have a similar potency (EC50) as the clinical stage 36E5 mAb. However, Nanobody® constructs A023100035 and A-0231-00_TP008 clearly show a higher maximal efficacy compared to 36E5. This is clinically very important as the effectiveness of a drug depends on its maximal efficacy. Nanobody® A023100014 shows an equal maximal efficacy compared to 36E5, which is maintained at higher concentrations, in contrast to 36E5.

Example 16: In Vivo Proof-of-Concept of A023100035 and A-0231-00_TP008 in an OVA Immunization Model The adjuvant effect of an anti-GITR multivalent Nanobody® (A023100035) and anti-GITR Nanobody®-huIgG1 chimera (A-0231-00_TP008) on the humoral immune response to OVA was demonstrated, reflecting the immune-enhancing effect of anti-GITR agonist Nanobodies® and an anti-GITR Nanobody®-huIgG1 chimera.

In the OVA immunization model, BALB/c mice were immunized on day zero (day 0) by subcutaneous (s.c.) administration of 100 µg OVA in saline or in a 1:1 mixture with Incomplete Freund's Adjuvant (IFA) followed by a boost with the same s.c. dose in saline or IFA on day 14.

To assess the effect of the anti-GITR Nanobody® on the humoral response to OVA, the anti-GITR Nanobody® was administered intraperitoneally at different dosing regimens, i.e. a single dosing regimen with administration on the day of primary (day 0) and of boost (day 14) immunization at 15 mg/kg (single dose level 1, SDL1) or 30 mg/kg (SDL2); a repeated dosing regimen with administration starting on day 0 and on day 14 with a loading dose level of 15 mg/kg and two maintenance dose levels of 10 mg/kg (Q2Dx3; repeated dosing regimen 1, RD1); a repeated dosing regimen with administration starting on day 0 with a loading dose level of 15 mg/kg and ten maintenance dose levels of 10 mg/kg (Q2Dx11; RD2). Irrelevant control Nanobody® was administered at dosing regimens corresponding to the respective dosing regimen of anti-GITR Nanobody®. Anti-GITR Nanobody®-huIgG1 chimera was administered as a single dose on day 0 and day 14 at a dose level of 20 mg/kg and compared to an irrelevant human IgG1 mAb (Synagis) given at the same dosing regimen and level. An anti-mouse GITR agonist mAb (DTA-1; BioXCell) was included as a positive reference control and compared to its respective isotype control (anti-KLH, clone LTF-2, BioXCell), both administered at a single dosing regimen on day 0 and on day 14 at a dose level of 20 mg/kg. On day 0 and day 14 treatments were given prior to OVA immunization. OVA mixed with IFA was included as a reference comparison. Anti-OVA total IgG serum titres were determined by ELISA on day 13 and day 21 after primary immunization. As depicted in FIG. 11, on day 13 OVA titres significantly increased in animals subjected to the continuous repeated dosing regimen RD2 with a mean log 10 titre of 4.273 (±0.284) versus its respective control (3.325±0.104; p<0.0001). On day 21 OVA titres further increased to 6.071 (±0.277), significantly different versus control (4.962±0.225; p<0.0001). In animals receiving anti-GITR Nanobody® at SDL1, SDL2 and RD1 the highest titres on day 21 were induced by RD1 (6.744±0.151) versus its respective control (5.090±0.206; p<0.0001) and SDL1 (6.628±0.125) versus its respective control (5.156±0.368; p<0.0001). Similarly to SDL1, anti-GITR Nanobody® at SDL2 resulted in increased OVA titres (6.225±0.473), significantly different compared to its respective control (4.799±0.081; p<0.0001). On day 21 anti-GITR Nanobody®-huIgG1 chimera resulted in an OVA titre increase of 5.903 (±0.249), significantly different compared to its isotype control (5.326±0.237). Similarly, the difference in titre of treated versus control animals was significant upon treatment with DTA-1 (5.530±0.343 versus 4.971±0.281, respectively; p=0.0002).

Example 17: Sequence Optimization of Anti-GITR Nanobodies®

17.1 Sequence Optimization: Sequence Analysis

Parental wild type Nanobody® sequences were mutated to yield Nanobody® sequences that are more identical to human VH3-JH germline consensus sequences. Specific amino acids in the framework regions that differ between the Nanobody® and the human VH3-JH germline consensus were altered to the human counterpart in such a way that the protein structure, activity and stability were kept intact. For Nanobody® A0231004B01, a variant (A023100061, SEQ ID NO: 269) including the 5 mutations L11V, A74S, K83R, V89L, K105Q was generated (numbering according to Kabat). For A0231005A03, a variant (A023100078, SEQ ID NO: 271) with the same 5 mutations (11V, A74S, K83R, V89L, K105Q) was generated. In addition, the methionine on position 100e was further substituted by a leucine (A023100090, SEQ ID NO: 272), a lysine (A023100091, SEQ ID NO: 273), an arginine (A023100092, SEQ ID NO: 274) or a glutamine (A023100093, SEQ ID NO: 275). For A0231034A08, a variant (A023100063, SEQ ID NO: 270) with the 5 mutations D10G, L11V, A74S, K83R, V89L was generated. And finally for Nanobody® A0231052E08, a variant (A023100050, SEQ ID NO: 268) carrying the 9 following mutations was generated: L11V, A14P, S60A, A74S, M78L, K83R, A87T, G88A, V89L.

17.2 Construction, Expression and Purification of Multivalent Sequence Optimized Anti-GITR Nanobody® Constructs For variants A023100061 and A023100090 different constructs were made as listed in Table A-11 (SEQ ID NOs: 285-290). All multivalent Nanobody® constructs had C-terminal Albumin binding Nb (Alb92) and were subsequently expressed in *Pichia pastoris* according to standard conditions. The constructs were purified via protein A binding.

Example 18: Activation of GITR by Sequence Optimized Anti-GITR Multivalent Nanobodies® Assessed in a NF-κB Luciferase Reporter Assay The functionality of the sequence optimized formatted Nanobodies® was determined in a NF-κB luciferase reporter assay as described in Example 9.

$EC_{50}$ values and efficacies are shown in Table 9. Illustrative activation curves are shown in FIG. 12A-D.

TABLE 9

$EC_{50}$ (M) and efficacy values (human GITR ligand = 100%) of anti-GITR sequence optimized multivalent Nanobodies ® and reference compound

| Construct ID | HEK293_NF-κB luc reporter $EC_{50}$ (M) | HEK293_NF-κB luc reporter Efficacy (%) |
| --- | --- | --- |
| A023100101<br>A023100090(E1D)-9GS-A023100090-9GS-<br>A023100090-35GS-Alb92-A | 2.00E−11 | 135.5 |
| A023100107<br>A023100090(E1D)-9GS-A023100090-9GS-<br>A023100090-9GS-A023100090-35GS-Alb92-A | 1.47E−11 | 147.3 |
| A023100118<br>A023100090(E1D)-9GS-A023100090-9GS-<br>A023100090-9GS-A023100090-9GS-<br>A023100090-35GS-Alb92-A | 1.28E−11 | 140.2 |
| A023100105<br>A023100061(E1D)-9GS-A023100061-9GS-<br>A023100061-35GS-Alb92-A | N.D. | N.D. |
| A023100127<br>A023100061(E1D)-9GS-A023100061-9GS-<br>A023100061-9GS-A023100061-35GS-Alb92-A | 1.57E−11 | 149.6 |
| A023100129<br>A023100061(E1D)-9GS-A023100061-9GS-<br>A023100061-9GS-A023100061-9GS-<br>A023100061-35GS-Alb92-A | 1.18E−11 | 145.8 |
| A-0231-00_TP011<br>Reference compound | 1.80E−11 | 66.6 |
| 36E5 | 2.56E−11 | 20.4 |

Example 19: Human T Cell Activation Capacity of Sequence Optimized Anti-GITR Nanobodies®

The functionality of the sequence optimized formatted Nanobodies® was also evaluated in a human T cell activation assay. The experiments were performed as described in Example 10.

Table 10 shows the effect on IFN-γ production of multivalent anti-GITR Nanobodies® and anti-GITR antibodies in comparison to the natural ligand. $EC_{50}$ values reflect the potency of the Nanobodies®. The maximal efficacy as percentage of the Emax (=maximal response induced by the natural ligand) is also presented. All Nanobody® constructs show an efficacy comparable to the natural ligand, which was set at 100%. Illustrative activation curves are shown in FIG. 13A-G.

TABLE 10

$EC_{50}$ values (M) and the maximal efficacy values (human GITR ligand = 100%) of anti-GITR sequence optimized multivalent Nanobody ® constructs and reference compounds (IFN-γ read-out).

| Construct ID | $EC_{50}$ (M) | Maximal Efficacy (%) |
|---|---|---|
| A023100101 A023100090(E1D)-9GS-A023100090-9GS-A023100090-35GS-Alb92-A | 6.42E−11 | 92.6 |
| A023100107 A023100090(E1D)-9GS-A023100090-9GS-A023100090-9GS-A023100090-35GS-Alb92-A | 6.46E−11 | 99.8 |
| A023100118 A023100090(E1D)-9GS-A023100090-9GS-A023100090- 9GS-A023100090-9GS-A023100090-35GS-Alb92-A | 4.26E−11 | 95.6 |
| A023100105 A023100061(E1D)-9GS-A023100061-9GS-A023100061-35GS-Alb92-A | 6.00E−11 | 97.0 |
| A023100127 A023100061(E1D)-9GS-A023100061-9GS-A023100061-9GS-A023100061-35GS-Alb92-A | 5.87E−11 | 86.8 |
| A023100129 A023100061(E1D)-9GS-A023100061-9GS-A023100061-9GS-A023100061-9GS-A023100061-35GS-Alb92-A | 5.15E−11 | 107.6 |
| A-0231-00_TP011 Reference compound | 4.62E−11 | 86.0 |
| 36E5 | 4.37E−11 | 82.3 |

Example 20: In Vivo Proof-of-Concept of Sequence Optimized Anti-GITR Multivalent Nanobodies® in an OVA Immunization Model The adjuvant effect of anti-GITR multivalent Nanobodies® (A023100101, A023100107, A023100118) on the humoral immune response to OVA is evaluated, reflecting the immune-enhancing effect of anti-GITR agonist Nanobodies®.

In the OVA immunization model, BALB/c mice are immunized on day zero (day 0) by subcutaneous (s.c.) administration of 100 μg OVA in saline or in a 1:1 mixture with Incomplete Freund's Adjuvant (IFA) followed by a boost with the same s.c. dose in saline or IFA on day 14.

To assess the effect of anti-GITR multivalent Nanobodies® on the humoral response to OVA, the anti-GITR Nanobodies® are administered intraperitoneally on the day of primary (day 0) and of boost (day 14) OVA immunization at a single dosing regimen with dose levels ranging from 0.5 to 20 mg/kg and prior to OVA immunization. Irrelevant control Nanobody® is administered at a similar single dosing regimen at a dose level of 15 mg/kg. An anti-mouse GITR agonist mAb (DTA-1; BioXCell) is included as a positive reference control and is compared to its respective isotype control (anti-KLH, clone LTF-2, BioXCell), both administered at a single dosing regimen on day 0 and on day 14 at a dose level of 20 mg/kg. OVA mixed with IFA is included as a reference comparison.

Anti-OVA total IgG serum titres are determined by ELISA on day 13 and day 21 after primary immunization. Significant increase of total anti-OVA IgG levels in anti-GITR Nanobody®-treated animals are expected compared to untreated and control animals.

Example 21: Anti-Tumor Efficacy of Agonistic Sequence Optimized Anti-GITR Multivalent Nanobodies® Alone or in Combination with an Anti-PD-1 Antibody in a Syngeneic CT-26 Colon Carcinoma Mouse Model Anti-tumor efficacy of anti-GITR agonistic multivalent Nanobodies® (Nb) and an anti-GITR Nanobody®-huIgG1 chimera was demonstrated in a syngeneic CT-26 colon carcinoma model, in which BALB/c mice were inoculated with BALB/c-derived colorectal carcinoma cells (CT-26 cells). CT-26 cells were cultured in RPMI 1640 medium supplemented with 10% heat-inactivated fetal bovine serum and 2 mM L-glutamine. BALB/c mice were subcutaneously injected with $1 \times 10^6$ CT-26 cells in 200 μL volume of RPMI 1640 into the right flank. Tumor length and width was measured using calipers and tumor volume determined using the formula Tumor Volume $(mm^3)=0.5 \times length \times width^2$ where length is the longer dimension. On day 7 after tumor challenge mice were randomized according to their individual tumor volume into 15 treatment groups of 10 animals each with a mean tumor volume of $55 \pm 19$ $mm^3$. Dosing was started according to the treatment regimen presented in Table 11. Tumor volumes were recorded twice weekly. Survival, behavior and body weight were recorded every day. Animals were monitored until day 42 after treatment start.

Mice were treated with anti-GITR multivalent Nanobodies® (A023100101, A023100107, A023100118) or with an anti-GITR Nanobody®-huIgG1 chimera (A-0231-00_TP011), either as a monotherapy or in combination therapy with an anti-PD-1 monoclonal antibody (mAb). Mice treated with the anti-GITR mAb DTA-1, alone or in combination with anti-PD-1 mAb were included as positive control groups. One group of control mice (group 1) was left untreated. All treatments were administered via intraperitoneal injection (IP) starting on day 7 after tumor challenge. The groups of mice receiving DTA-1 were treated with a single dose of 25 mg/kg (groups 2 and 3). The groups of mice receiving anti-GITR Nanobodies® were treated via a multiple dosing regimen with one IP injection every two days during 18 days, consisting of one loading dose and nine maintenance doses. Groups treated with anti-GITR Nanobody® A023100101 received a loading dose of 15 mg/kg and a maintenance dose of 10 mg/kg (groups 8 and 9). Anti-GITR Nanobody® A023100107 was dosed at 18.7 mg/kg loading dose and 12.5 mg/kg maintenance dose (groups 10 and 11). Anti-GITR Nanobody® A023100118 was dosed at 22.5 mg/kg loading dose and 14 mg/kg maintenance dose (groups 12 and 13). Dose levels of the latter two anti-GITR Nanobodies® A023100107 and A023100118 were set to be equimolar to anti-GITR Nanobody® A023100101. Irrelevant control Nanobody® was dosed similarly as anti-GITR Nanobody® A023100101. Anti-GITR Nanobody®-huIgG1 chimera was administered as a single dose of 25 mg/kg (groups 14 and 15), respectively. Groups of mice receiving combination therapy were administered a total of three IP injections with anti-PD-1 mAb, with one injection every five days at a dose level of 10 mg/kg (groups 3, 5, 7, 9, 11, 13, 15).

The anti-tumor efficacy of anti-GITR multivalent Nanobodies® and anti-GITR Nanobody®-huIgG1 chimera was evaluated and compared with respective control groups. Tumor growth and survival served as read-outs for anti-tumor efficacy. Animals were monitored until day 49 after tumour challenge, corresponding to day 42 after treatment start.

As shown in FIG. 14, anti-GITR Nanobodies® A023100101 (group 8) and A023100118 (group 12) showed a delayed trend in tumor growth for 1/10 animals compared to their respective control group (irrelevant Nanobody®, group 6), whereas anti-GITR Nanobody® A023100107 (group 10) significantly inhibited tumor growth development (p=0.323) compared to irrelevant Nanobody®. Anti-GITR Nanobody®-huIgG1 chimera (group 14) resulted in a significant inhibition of tumour growth (p<0.0001) compared to its respective control (huIgG1 isotype, group 4) with 5/10 and 3/10 animals showing delayed tumor growth development and a complete tumor regression, respectively. Similarly, anti-tumor efficacy was confirmed for DTA-1 mAb, showing significant inhibition of tumor growth development (p<0.0001), with 3/10 animals with complete regression. A synergistic tumor growth inhibition was observed with anti-GITR Nanobody® A023100101 (group 9; p<0.0022) and with A023100107 (group 11; p<0.0007) in combination with anti-PD-1 mAb, compared to the corresponding anti-PD-1 mAb control group (group 7). In group 9, in 1 out of 6 animals with delayed tumor growth a complete regression was observed, whereas in group 11 two animals out of 5 with delayed tumor growth showed a complete regression. The combination of anti-GITR Nanobody®-huIgG1 chimera with anti-PD-1 mAb (group 15) resulted in a significant tumor growth inhibition (p<0.0001) compared to huIgG1 isotype control (group 5). Similarly, DTA-1 mAb in combination with anti-PD-1 mAb showed a significant anti-tumor effect compared to group 7, as 5 animals showed a complete regression (p<0.0001).

As depicted in FIG. 15, the median survival time (from treatment start) of vehicle group 1 was 15 days, with 100% mortality from day 21. Median survival time upon treatment with DTA-1 alone was 34.5 days with 40% survival on day 42 post treatment (p<0.0001), whereas combination therapy with DTA-1 and anti-PD-1 mAb resulted in a median survival of 34 days with 60% of animals still alive on day 42 post treatment (p=0.0003). The median survival for anti-PD-1 mAb control groups 5 and 7 was 19.5 days. Survival analysis of anti-GITR Nanobody® monotherapy was significant for A023100107 (p<0.0391) with a median survival of 19.5 days and 20% survival on day 42. In combination with anti-PD-1 mAb survival analysis was significant for anti-GITR Nanobodies® A023100101 (group 9; p=0.0026) and A023100107 (group 10; p=0.0056) showing 50% and 30% survival on day 42, respectively. Anti-GITR Nanobody® A023100118 in combination with anti-PD-1 mAb (group 13) resulted in a median survival of 28 days. Monotherapy with anti-GITR Nanobody®-huIgG1 chimera (group 14) showed a median survival time of 34.5 days and 40% survival on day 42 (p<0.0001), whereas combination therapy with anti-PD-1 mAb (group 15) resulted in a median survival time of 29.5 days and 30% survival on day 42 post treatment.

TABLE 11

| Group | No. Animals | Treatment | Dose | Route | Treatment Schedule |
|---|---|---|---|---|---|
| 1 | 10 | vehicle | — | IP | Q1Dx1 |
| 2 | 10 | DTA-1 | 25 mg/kg | IP | Q1Dx1 |
| 3 | 10 | DTA-1 | 25 mg/kg | IP | Q1Dx1 |
|   |    | anti-PD-1 | 10 mg/kg | IP | Q5Dx3 |
| 4 | 10 | huIgG1 isotype control | 25 mg/kg | IP | Q1Dx1 |
| 5 | 10 | huIgG1 isotype control | 25 mg/kg | IP | Q1Dx1 |
|   |    | anti-PD-1 | 10 mg/kg | IP | Q5Dx3 |
| 6 | 10 | Irrelevant NB | 1 × 15 mg/kg, then 9 × 10 mg/kg | IP | Q2Dx10 |
| 7 | 10 | Irrelevant NB | 1 × 15 mg/kg, then 9 × 10 mg/kg | IP | Q2Dx10 |
|   |    | anti-PD-1 | 10 mg/kg | IP | Q5Dx3 |
| 8 | 10 | anti-GITR NB (A023100101) | 1 × 15 mg/kg, then 9 × 10 mg/kg | IP | Q2Dx10 |
| 9 | 10 | anti-GITR NB (A023100101) | 1 × 15 mg/kg, then 9 × 10 mg/kg | IP | Q2Dx10 |
|   |    | anti-PD-1 | 10 mg/kg | IP | Q5Dx3 |
| 10 | 10 | anti-GITR NB (A023100107) | 1 × 18.7 mg/kg, then 9 × 12.5 mg/kg | IP | Q2Dx10 |
| 11 | 10 | anti-GITR NB (A023100107) | 1 × 18.7 mg/kg, then 9 × 12.5 mg/kg | IP | Q2Dx10 |
|    |    | anti-PD-1 | 10 mg/kg | IP | Q5Dx3 |
| 12 | 10 | anti-GITR NB (A023100118) | 1 × 22.5 mg/kg, then 9 × 14 mg/kg | IP | Q2Dx10 |

TABLE 11-continued

Treatment regimen

| Group | No. Animals | Treatment | Dose | Route | Treatment Schedule |
|---|---|---|---|---|---|
| 13 | 10 | anti-GITR NB (A023100118) | 1 × 22.5 mg/kg, then 9 × 14 mg/kg | IP | Q2Dx10 |
|  |  | anti-PD-1 | 10 mg/kg | IP | Q5Dx3 |
| 14 | 10 | anti-GITR NB-huIgG1 chimera (A-0231-00-TP011) | 25 mg/kg | IP | Q1Dx1 |
| 15 | 10 | anti-GITR NB-huIgG1 chimera (A-0231-00-TP011) | 25 mg/kg | IP | Q1Dx1 |
|  |  | anti-PD-1 | 10 mg/kg | IP | Q5Dx3 |

Q1Dx1: Single injection on the day of start of treatment; Q5Dx3: 3 injections with 1 injection every 5 days; Q2Dx10: 10 injections with 1 injection every 2 days. In case of combinations: DTA-1, anti-GITR NB, anti-GITR NB-huIgG1 chimera, irrelevant NB or isotype control mAb is injected after anti-PD-1 mAb.

TABLE A-1

Sequence alignment of GITR Family 7 binders

```
PA0231PMP005A03.1:   evqlvesggglvgpggslrlscaasETIFSIDSMAwyrqapgkqrelvaAIT
                     GGGSPNyadsvkgrftissdvakrtvylgmnslkpedtavyycnaEGQAGWGTALMDYwgkgtlvtvss
                     (SEQ ID NO: 1)

PA0231PMP004A03.1:   .......................t...S.....A.G.h............
                     H.....RS.............g.s...........................
                     (SEQ ID NO: 2)

PA0231PMP004A12.1:   ...........................S.....A.G..h...........
                     T......T.............g.s........d..................
                     (SEQ ID NO: 3)

PA0231PMP004F05.1:   ..................s...............S.....A.G.......
                     T.....RR......m...s..g.n...........................q.....
                     (SEQ ID NO: 4)

PA0231PMP005A01.1:   ...........................S.....A.G.h............
                     H.....RS.............g.s...........................g.....
                     (SEQ ID NO: 5)

PA0231PMP005A02.1:   .......................t...S.....A.G.h............
                     H.....RS.............g.s..........r................
                     (SEQ ID NO: 6)

PA0231PMP005A10.1:   ............r...............S.....A.G.............
                     TM.....T...........................................g.....
                     (SEQ ID NO: 7)

PA0231PMP005B02.1:   .......................t...S.....A.G.h............
                     H.....GS.............g.s...........................q.....
                     (SEQ ID NO: 8)

PA0231PMP005B08.1:   ..........................................r......
                     ...................................................
                     (SEQ ID NO: 9)

PA0231PMP005C01.1:   ...................................................
                     ..........................a........................
                     (SEQ ID NO: 10)

PA0231PMP005G10.1:   ............r...............S.....A.G.............
                     TM.....T......r....................................q.....
                     (SEQ ID NO: 11)

PA0231PMP006E02.1:   .......................t...S.....A.G.h............
                     H.....RS..........a..g.s...........................q.....
                     (SEQ ID NO: 12)

PA0231PMP006E08.1:   ...........................S.....A.G..............
                     T......T.............g.s........d..................
                     (SEQ ID NO: 13)

PA0231PMP006G04.1:   ............r.......p.......S.....A.G..............
                     TM.....T............................................
                     (SEQ ID NO: 14)
```

TABLE A-1-continued

Sequence alignment of GITR Family 7 binders

```
PA0231PMP012E03.1:      .............s.........S.....NA.G.............
                        T.....RR......m...s..g.n.......................q.....
                        (SEQ ID NO: 15)

PA0231PMP012G07.1:      ........................S.....A.G.............
                        T....S.T.............g.n.......................g.....
                        (SEQ ID NO: 16)

PA0231PMP020B05.1:      ........................S.....A.G.............
                        T......T.............g.n...................a.........
                        (SEQ ID NO: 17)

PA0231PMP020D02.1:      ..................t...S.....A.G.h.............
                        H.....RS.............g.s................g............g.....
                        (SEQ ID NO: 18)

PA0231PMP020E12.1:      ........................S.....A.G.............
                        T......T.............g.n.......................q.....
                        (SEQ ID NO: 19)

PA0231PMP021B02.1:      ..................t...S.....A.G.h.............
                        H.....R..............g.s..............................
                        (SEQ ID NO: 20)

PA0231PMP023G01.1:      .....................g..S.....A.G.............
                        G.S...RT.............g.n..n...................P..N....
                        (SEQ ID NO: 21)
```

TABLE A-2

Sequence alignment of GITR Family 26 binders

```
PA0231PMP004B01.1: evqlvesggglvqpggelrlscaasGSIFSIDSMGwyrqapgkqrelvarelvaAITSSINy
                   adsvkgrftisrdnakntvylqmnslkpedtavyycnlEGQAGWGTALINYwgkgtlvtvss
                   (SEQ ID NO: 22)

PA0231PMP004B02.1:................t..........A.................S...T....e...
                  ........a...................vK..T......MD......q.....
                  (SEQ ID NO: 23)

PA0231PMP012F03.1:................t..........A.................S...T....e...
                  ........a.................svK..T......MD.............
                  (SEQ ID NO: 24)

PA0231PMP012D08.1:............................NA.................G.....a.
                  ........h.......................T......MD.............
                  (SEQ ID NO: 25)

PA0231PMP006C07.1:............................NA.................G.......
                  ........h.......................T......MD......q.....
                  (SEQ ID NO: 26)

PA0231PMP005G01.1:...................f........NA.................G.......
                  r.......h.......................T......MD......q.....
                  (SEQ ID NO: 27)

PA0231PMP005A08.1:............................NA.................G.......
                  ........h.......................T......MD.............
                  (SEQ ID NO: 28)

PA0231PMP004B03.1:...........................................R.I.....
                  ................................................MD...........
                  (SEQ ID NO: 29)

PA0231PMP004A05.1:............................A.................T...GK......
                  ..........a.....................MD......q.....
                  (SEQ ID NO: 30)

PA0231PMP004A01.1:.....................................................
                  ................t........................MD......q.....
                  (SEQ ID NO: 31)
```

TABLE A-2-continued

Sequence alignment of GITR Family 26 binders

```
PA0231PMP005B05.1:............................NA.............................
                  .......a.....................h..........LD.............
                  (SEQ ID NO: 32)
```

TABLE A-3

Sequence alignment of GITR Family 82 binders

```
PA0231PMP034A08.1: evqlvesggdlvqpggslrlscaasGSVFSINDMGwfrqapgkqrelvaDIISRGVTNyads
                   vkgrftisgdpakntvylqmnslkpedtavyycnaHISTGWGRPHNNYwgqgtqvtvss
                   (SEQ ID NO: 33)

PA0231PMP033B12.1:.........................I...DS...................AD.......
                  ..........h...................................................
                  (SEQ ID NO: 34)

PA0231PMP033F01.1:.........................I...DS...................AD.......
                  ..........h.q.................................................
                  (SEQ ID NO: 35)

PA0231PMP034B06.1:.........................I...DS...................A........
                  ..........h...................................................
                  (SEQ ID NO: 36)

PA0231PMP048A08.1:.........................I...D....................A........
                  ..........h..................................................l.....
                  (SEQ ID NO: 37)

PA0231PMP034A03.1:.........................I.....V............................
                  ...............................a..............................
                  (SEQ ID NO: 38)

PA0231PMP034A02.1:..............p..........NI...................................
                  ...............................................................
                  (SEQ ID NO: 39)

PA0231PMP034B09.1:..............p..........I....................................
                  ...............................................................
                  (SEQ ID NO: 40)

PA0231PMP034A01.1:.........................I....................................
                  ...............................................................
                  (SEQ ID NO: 41)

PA0231PMP034A09.1:.........................I.....T..............................
                  ...............................................................
                  (SEQ ID NO: 42)

PA0231PMP034A10.1:.........................I.......................A...........
                  ...............................................................
                  (SEQ ID NO: 43)

PA0231PMP034C06.1:.........................I.........................G.........
                  ...............................................................
                  (SEQ ID NO: 44)

PA0231PMP034D02.1:.........................I....................................
                  ...............a................................................
                  (SEQ ID NO: 45)

PA0231PMP034F01.1:................g........I....................................
                  ...............................................................
                  (SEQ ID NO: 46)

PA0231PMP048D06.1:.........r...............I....................................
                  ...............................................................
                  (SEQ ID NO: 47)

PA0231PMP048D12.1:.........................I..............................c...
                  ...............................................................
                  (SEQ ID NO: 48)
```

TABLE A-3-continued

Sequence alignment of GITR Family 82 binders

```
PA0231PMP048C07.1: ........................I.........l..............
                   ..................................................
                   (SEQ ID NO: 49)

PA0231PMP036C11.1: ........................I........................
                   ..r...............................................
                   (SEQ ID NO: 50)

PA0231PMP036A04.1: ........g...............I........................
                   ..................................................
                   (SEQ ID NO: 51)

PA0231PMP034F11.1: ........................I........................
                   ........v.........................................
                   (SEQ ID NO: 52)

PA0231PMP034E12.1: ........................I........................
                   ............h.....................................
                   (SEQ ID NO: 53)

PA0231PMP047G08.1: ........................I..................D.....
                   ............h.....................................
                   (SEQ ID NO: 54)

PA0231PMP034F10.1: ........................I........................
                   .............................M.............l.....
                   (SEQ ID NO: 55)
```

TABLE A-4

Sequence alignment of GITR Family 109 binders

```
PA0231PMP052E08.1: evqlvesggglvqaggslrlsctgsRSIFSTYAMAwhrqapgkqrelvgRIYWGGTTTysds
                   vkgrftisrdnakntmylqnnslkpedagvyycniYGSYALPwgqgtlvtvss
                   (SEQ ID NO: 56)

PA0231PMP052A03.1: ........................N...................S.v..
                   ..........................a........................
                   (SEQ ID NO: 57)

PA0231PMP052B05.1: ..................................................
                   ..............................q...................
                   (SEQ ID NO: 58)

PA0231PMP052C04.1: ........m...........N...................S.v..
                   ..........................a..............q.....
                   (SEQ ID NO: 59)

PA0231PMP052D06.1: ...................................................S.v..
                   ..........................a........................
                   (SEQ ID NO: 60)

PA0231PMP052F03.1: ..................................................
                   ..............s....................................
                   (SEQ ID NO: 61)
```

TABLE A-5

Sequence alignment of GITR Family 85 binders

```
PA0231PMP033B02.1: EVQLVESGGGLVQPGGSLRLSCAASGTIFSISTMGWYRQAPGKQREVVAVTSGFSTNYSSAV
                   KGRFTLSRDPAKNTVFLQMNSLQPEDTATYYCNAYLSLAWRDPDRSYWGQGTQVTTVSS
                   (SEQ ID NO: 62)
```

TABLE A-6

Sequence alignment of GITR Family 38 binders

PA0231PMP003D11.1: evqlvesggglvqageslrlscaasGSIFSIDAMGwyrqapgkqrelvaEISDHTTydgsvk
grftisrgnaentvalqmnslkpedtgvyycnvHHPRGWGTSITVTwgqgtqvtvss
(SEQ ID NO: 63)

PA0231PMP017E06.1: .....................................................A...........
...................................................................
(SEQ ID NO: 64)

PA0231PMP017G05.1: ..............................................................m.
...................................................................
(SEQ ID NO: 65)

PA0231PMP010C09.1: .........r..........................................G............
.........................................P.........................
(SEQ ID NO: 66)

PA0231PMP017C01.1: .........r.........................................................
.........................................P.........................
(SEQ ID NO: 67)

PA0231PMP017B08.1: ..............r...................................................
................................................l.....
(SEQ ID NO: 68)

TABLE A-7

Sequence alignment of GITR Family 110 binders

PA0231PMP052A08.1: evqlvesggglvqaggslrlscvasGSISSITAMGwhrqapgaqresvaVTSRSGATMlvds
vkgrftivqdnakntvylqmnslkvedtavygcsaITQGRTYwgqgtlvtvss
(SEQ ID NO: 69)

PA0231PMP052A01.1: ...............................................I.............
............................................q.....
(SEQ ID NO: 70)

PA0231PMP052A05.1: ...............................................A.......I.a..
..........................EQ.......q.....
(SEQ ID NO: 71)

TABLE A-8

Sequence alignment of GITR Family 108 binders

PA0231PMP051E01.1: EVQLVESGGGLVQAGGSLRLSCAASGSIFSFIVMGWYRQAPGEQRALVATVTSGGDTFYVDS
VKDRFTISRDNAKNTVYLQMNSLKPEDTAVYFCYFTKVSPYKETTWGQGTLVTSS
(SEQ ID NO: 72)

TABLE A-9

Amino acid sequences of monovalent anti-GTR Nanobodies ®
("ID" refers to the SEQ ID NO as used herein)

| Name | ID | Amino acid sequence |
|---|---|---|
| A0231PMP005A03 | 1 | EQLVESGGGLVQPGGSLRLSCAASETIFSIDSMAWYRQAPGKQRELVAAITGGGSPNYADSVKGRFTISSDVAKRTVYL QMNSLKPEDTAVYYCNAEGQAGWGTALMDYWGKGTLVTVSS |
| A0231PMP004A03 | 2 | EVQLVESGGGLVQPGGSLRLSCTASESIFSDAMGWHRQAPGKQRELVAHITGGGRSNYADSVKGRFTISGDSAKRTVYL QMNSLKPEDTAVYYCNAEGQAGWGTALMDYWGKGTLVTVSS |
| A0231PMP004A12 | 3 | EVQLVESGGGLVQPGGSLRLSCAASESIPSIDAMGWYHQAPGKQRELVATITGGGSTNYADSVKGRFTISGDSAKRTVYL QMDSLKPEDTAVYYCNAEGQAGWGTALMDYWGKGTLVTVSS |
| A0231PMP004F05 | 4 | EVQLVESGGGLVQSGGSLRLSCAASESIFSIDAMGWYRQAPGKQRELVATITGGGRRNYADSVVIGRFSISGDNAKRTVY LQMNSLKPEDTAVYYCNAEGQAGWGTALMDYWGKGTQVTVSS |

TABLE A-9-continued

Amino acid sequences of monovalent anti-GTR Nanobodies ®
("ID" refers to the SEQ ID NO as used herein)

| Name | ID | Amino acid sequence |
|---|---|---|
| A0231PMP005A01 | 5 | EVQLVESGGGLVQPGGSLRLSCAASESIFSDAMGWHRQAPGKQRELVAHITGGGRSNYADSVKGRFTISGDSAKRTVYLQMNSLKPEDTAVYYCNAEGQAGWGTALMDYWGKGTQVTVSS |
| A0231PMP005A02 | 6 | EVQLVESGGGLVQPGGSLRLSCTASESIFSIDAMGWHRQAMKQRELVAHITGGGRSNYADSVKGRFTISGDSAKRTVYLQMNSLRPEQTAVYYCNAEGQAGWGTALMDYWGKGTLVTVSS |
| A0231PMP005A10 | 7 | EVQLVESGGGLVRPGGSLRLSCAASESFSIDAMGWYRQAPGKQRELVATMTGGGSTNYADSVKGRFISSDVAKRTVYLQMNSLKPEDTAVYYCNAEGQAGWGTALMDYWGKGTQVTVSS |
| A0231PMP005B02 | 8 | EVQLVESGGGLVQPGGSLRLSCAASISIFSIDAMGWYRQAPGKQRELVATMTTGGGGSNYADSVKGRFTISGDSAKRTVYLQMNSLKPEDTAVYYCNAEGQAGWGTALMDYWGKGTQVTVSS |
| A0231PMP005B08 | 9 | EVQLVESGGGLVQPGGSLRLSCAASETIFSIDSMAWYRQAPGRQRELVAAITGGGSPNYADSVKGRFTISSDVAKRTVYLQMNSLKPEDTAVYYCNAEGQAGWGTALMDYWGKGTLVTVSS |
| A0231PMP005C01 | 10 | EVQLVESGGGLVQPGGSLRLSCAASETIFSIDSMAWYRQAPGKQRELVAAITGGGSPNYADSVKGRFTISSDVAKRTAYLQMNSLKPEDTAVYYCNAEGQAGWGTALMDYWGKGTLVTVSS |
| A0231PMP005G10 | 11 | EVQLVESGGGLVRPGGSLRLSCAASESFSIDAMGWYRQAPGKQRELVATMTGGGSTNYADSVRGRFTISSDVAKRTVYLQMNSLKPEDTAVYYCNAEGQAGWGTALMDYWGKGTQVIVSS |
| A0231PMP006E02 | 12 | EVQLVESGGGLVQPGGSLRLSCTASESIFSIDAMGWHRQAPGKQRELVAHITGGGRSNYADSVKGRFAISGDSAKRTVYLQMNSLKPEDTAVYYCNAEGQAGWGTALMDYWGKETQVTVSS |
| A0231PMP006E08 | 13 | EVQLVESGGGLVQPGGSLRLSCAASESIFSIDAMGWYRQAPGKQRELVATITGGGSTNYADSVKGRFTISGDSAKRTVYLQMDSLKPEDTAVYYCNAEGQAGWGTALMDYWGKGILVIVSS |
| A0231PMP006G04 | 14 | EVQLVESGGGLVRPGGSLRLPCAASESIFSIDAMGWYRQAPGKQRELVATMTGGGSTNYADSVKGRFTISSDVAKRTVYLQMNSLKPEDTAVYYCNAEGQAGWGTALMDYWGKGTLVTVSS |
| A0231PMP012E03 | 15 | EVQLVESGGGLVQSGGSLRLSCAASESIFSINAMGWYRQAPGKQRELVATITGGGRRNYADSVMGRFSISGDNAKRTVYLQMNSLKPEDTAVYYCNAEGQAGWGTALMDYVVGKGTQVTVSS |
| A0231PMP012G07 | 16 | EVQLVESGGGLVQPGGSLRLSCAASESIFSIDAMGWYRQAPGKQRELVATITGGSSTNYADSVKGRFTISGDNAKRTVYLQMNSLKPEDTAVYYCNAEGQAGWGTALMDYWGKGTQNTVSS |
| A0231PMP020B05 | 17 | EVQLVESGGGLVQPGGSLRLSCAASESIFSIDAMGWYRQAPGKQRELVATITGGGSTNYADSVKGRFTISGDNAKRTVYLQMNSLKPEDTAAYYCNAEGQAGWGTALMDYWGKGTLVTVSS |
| A0231PMP020D02 | 18 | EVQLVESGGGLVQPGGSLRLSCTASESIFSIDAMGWHRQAPGKQRELVAHITGGGRSNYADSVKGRETISGDSAKRTVYLQMNSLKPGDTAVYYCNAEGQAGWGTALMDYWGKGTQVTVSS |
| A0231PMP020E12 | 19 | EVQLVESGGGLVQPGGSLRLSCAASESIFSIDAMGWYRQAPGKQRELVATITGGGSTNYADSVKGRFTISGDNAKRTVYLQMNSLKPEDTAVYYCNAEGQAGWGTALMDYWGKGTQVTVSS |
| A0231PMP021B02 | 20 | EVQLVESGGGLVQPGGSLRLSCTASESIFSIDAMGWHRQAPGKQRELVAHITGGGRPNYADSVKGRFTISGDSAKRTVYLQMNSLKPEDTAVYYCNAEGQAGWGTALMDYWGKGTLVTVSS |
| A0231PMP023G01 | 21 | EVQLVESGGGLVQPGGSLRLSCAGSESIFSIDAMGWYRQAPGKQRELVAGISGGGRTNYADSVKGRFTISGDNAKNTVYLQMNSLKPEDTAVYYCNAEGQAGWGTPLMNYWGKGTLVTVSS |
| A0231PMP004B01 | 22 | EVQLVESGGGLVQPGGSLRLSCAASGSIFSIDSMGWYRQAPGKQRELVAAITSSTNYADSVKGRFTISRDNAKNTVYLQMNSLKPEDTAVYYCNLEGQAGWGTALINYWGKGTLVIVSS |
| A0231PMP004B02 | 23 | EVQLVESGGGLVQPGGSLRLTCAASGSIFSIDAMGWYRQAPGKQRELVASITSTTNYAESVKGRFTISRANAKNTVYLQMNSLKPEDTAVYYCNVKGQTGWGTALMDYWGKGTQVTVSS |
| A0231PMP012F03 | 24 | EVQLVESGGGLVQPGGSLRLTCAASGSIFSIDAMGWYRQAPGKQRELVASITSTTNYAESVKGRFTISRANAKNTVYLQMNSLKPEDTAVYYCSVKGQTGWGTALMDYWGKGTLVTVSS |
| A0231PMP012D08 | 25 | EVQLVESGGGLVQPGGSLRLSCAASGSIFSINAMGWYRQAPGKQRELVAAITSGTNYADSAKGRFTISRDHAKNTVYLQMNSLKPEDTAVYYCNLEGQTGWGTALMDYWGKGTLVTVSS |
| A0231PMP006C07 | 26 | EVQLVESGGGLVQPGGSLRLSCAASGSIFSINAMGWYRQAPGKQRELVAAITSGTNYADSVKGRFTISRDHAKNTVYLQMNSLKPEDTAVYYCNLEGQTGWGTALMDYWGKGTQVTVSS |
| A0231PMP005G01 | 27 | EVQLVESGGGLVQPGGSLRLFCAASGSIFSINAMGWYRQAPGKQRELVAAFFSGTNYADSVRGRFTISRDHAKNTVYLQMNSLKPEDTAVYYCNLEGQTGWGTALMDYWGKETQVTVSS |
| A0231PMP005A08 | 28 | EVQLVESGGGLVQPGGSLRLSCAASGSIFSINAMGWYRQAPGKQRELVAAITSGTNYADSVKGRFTISRDHAKNTVYLQMNSLKPEDTAVYYCNLEGQTGWGTALMDYWGKGTLVIVSS |
| A0231PMP004B03 | 29 | EVQLVESGGGLVQPGGSLRLSCAASGSIFSIDSMGWYRQAPGKQRELVAAITSRTIYADSVKGRFTISRDNAKNTVYLQMNSLKPEDTAVYYCNLEGQAGWGTALMDYWGKETLATTVSS |

TABLE A-9-continued

Amino acid sequences of monovalent anti-GTR Nanobodies ®
("ID" refers to the SEQ ID NO as used herein)

| Name | ID | Amino acid sequence |
|---|---|---|
| A0231PMP004A05 | 30 | EVQLVESGGGLVQPGGSLRLSCAASGSIFSIDAMGWYRQAPGKQRELVATITSGKNYADSVKGRFTISRDNAKNAVYLQ<br>MNSLKPEDTAVYYCNLEGQAGWGTALMDYWGKETQVTVSS |
| A0231PMP004A01 | 31 | EVQLVESGGGLVQPGGSLRLSCAASGSIFSIDSMGWYRQAPGKQRELVAAITSSTNYADSVKGRFTISRDNAKNTVYLQT<br>NSLKPEDTAVYYCNLEGQAGWGTALMDYWGKGTQVTVSS |
| A0231PMP005B05 | 32 | EVQLVESGGGLVQPGGSLRLSCAASGSIFSINAMGWYRQAPGKQRELVAAITSSTNYADSVKGRFTISRANAKNTVYLQ<br>MNSLKPEDTAVYYCHLEGQAGWGTALLDYWGKGTLVTVSS |
| A0231PMP034A08 | 33 | EVQLVESGGDLVQPGGSLRLSCAASGSVFSINDMGWFRQAPGKQRELVADIISRGVINYADSVKGRFTISGDPAKNTVYL<br>QMNSLKPEDTAWYCNAHISTGWGRPHNNYWGQGTQVTVSS |
| A0231PMP033B12 | 34 | EVQLVESGGDLVQPGGSLRLSCAASGSIFSIDSMGWFRQAPGKQRELVADIISADVTNYADSVKGRFTISGDHAKNTVYL<br>QMNSLKPEDTAVYYCNAHISTGWGRPHNNYWGQGTQVTVSS |
| A0231PMP033F01 | 35 | EVQLVESGGDLVQPGGSLRLSCAASGSIFSIDSMGWFRQAPGKQRELVADIISADVINYADSVKGRFTISGDHAQNTVYL<br>QMNSLKPEDTAVYYCNAHISTGWGRPHNNYWGQGTQVTVSS |
| A0231PMP034B06 | 36 | EVQLVESGGDLVQPGGSLRLSCAASGSIFSIDSMGWFRQAPGKQRELVADIISAGVTNYADSVKGRFTISGDHAKNTVYL<br>QMNSLKPEDTAVYYCNAHISTGWGRPHNNYWGQGTQVTVSS |
| A0231PMP048A08 | 37 | EVQLVESGGDLVQPGGSLRLSCAASGSIFSIDDMGWFRQAPGKQRELVADIISAGVINYADSVKGRFTISGDHAKNTVYL<br>QMNSLKPEDTAVYYCNAHISTGWGRPHNNYWGQGTLVTVSS |
| A0231PMP034A03 | 38 | EVQLVESGGDLVQPGGSLRLSCAASGSIFSINDVGWFRQAPGKQRELVADIISRGVTNYADSVKGRFTISGDPAKNTVYL<br>QMNSLKPEDTAAYYCNAHISTGWGRPHNNYWGQGTQVTVSS |
| A0231PMP034A02 | 39 | EVQLVESGGDLVQPGGPLRLSCAASGNIFSINDMGWFRQAPGKQRELVADIISRGVTNYADSVKGRFTISGDPAKNTVYL<br>QMNSLKPEDTAVYYCNAHISTGWGRPHNNYWGQGTQVTVSS |
| A0231PMP034B09 | 40 | EVQLVESGGDLVQPGGPLRLSCAASGSIFSINDMGWFRQAPGKQRELVADIISRGVTNYADSVKGRFTISGDPAKNTVYL<br>QMNSLKPEDTAVYYCNAHISTGWGRPHNNYWGQGTQVTVSS |
| A0231PMP034A01 | 41 | EVQLVESGGDLVQPGGSLRLSCAASGSIFSINDMGWFRQAPGKQRELVADIISRGVTNYADSVKGRFTISGDPAKNTVYL<br>QMNSLKPEDTAVYYCNAHISTGWGRPHNNYWGQGTQVTVSS |
| A0231PMP034A09 | 42 | EVQLVESGGDLVOPGGSLRLSCAASGSIFSINDTGWFRQAPGKQRELVADIISRGVTNYADSVKGRFTISGDPAKNTVYLQ<br>MNSLKPEDTAVYYCNAHISTGWGRPHNNYWGQGTQVTVSS |
| A0231PMP034A10 | 43 | EVQLVESGGDLVQPGGSLRLSCAASGSIFSINDMGWFRQAPGKQRELVADIISAGVTNYADSVKGRFTISGDPAKNTVYL<br>QMNSLKPEDTAWYCNAHISTGWGRPHNNYWGQGTQVTVSS |
| A0231PMP034C06 | 44 | EVQLVESGGDLNQPGGSLRLSCAASGSIFSINDMGWFRQAPGKQRELVAGIISRGVTNYADSVKGRFTISGDPAKNTVYL<br>QMNSLIKPEDTAVYYCNAHISTGWGRPHNNYWGQGTQVTVSS |
| A0231PMP034D02 | 45 | EVQLVESGGDLVQPGGSLRLSCAASGSIFSINDMGWFRQAPGKQRELVADIISRGVTNYADSVKGRFTISGDPAKNTAYL<br>QMNSLKPEDTAVYYCNAHISTGWGRPHNNYWGQGTQVTVSS |
| A0231PMP034F01 | 46 | EVQLVESGGDLVQPGGSLGLSCAASGSIFSINDMGWFRQAPGKQRELVADIISRGVTNYADSVKGRFTISGDPAKNTVYL<br>QMNSLKPEDTAVYYCNAHISTGWGRPHNNYWGQGTQVTVSS |
| A0231PMP048D06 | 47 | EVQLVESGGDLNRPGGSLRLSCAASGSIFSINDMGWFRQAPGKQRELVADIISRGVTNYADSVKGRFTISGDPAKNTVYL<br>QMNSLKPEDTAVYYCNAHISTGWGRPHNNYWGQGTQVTVSS |
| A0231PMP048D12 | 48 | EVQLVESGGDLVQPGGSLRLSCAASGSIFSINDMGWFRQAPGKQRELVADIISRGVTNCADSVKGRFTISGDPAKNTVYL<br>QMNSLKPEDTAVYYCNAHISTGWGRPHNNYWGQGTQVTVSS |
| A0231PMP048C07 | 49 | EVQLVESGGDLVQPGGSLRLSCAASGSIFSINDMGWLRQAPGKQRELVADIISRGVTNYADSVKGRFTISGDPAKNTVYL<br>QMNSLKPEDTAVYYCNAHISTGWGRPHNNYWGQGTQVTVSS |
| A0231PMP036C11 | 50 | EVQLVESGGDLVQPGGSLRLSCAASGSIFSINDMGWFRQAPGKQRELVADIISRGVTNYADSVRGRFTISGDPAKNTVYL<br>QMNSLKPEDTAVYYCNAHISTGWGRPHNNYWGQGTQVTVSS |
| A0231PMP036A04 | 51 | EVQLVESGGGLVQPGGSLRLSCAASGSIFSNDMGWFRQAPGKQRELVADIISRGVINYADSVKGRFTISGDPAKNTVYL<br>QMNSLKPEDTAVYYCNAHISTGWGRPHNNYWGQGTQVTVSS |
| A0231PMP034F11 | 52 | EVQLVESGGDLVOPGGSLRLSCAASGSIFSINDMGWERQAPGKQRELVADIISRGVTNYADSVKGRFTVSGDPAKNTVYL<br>QMNSLKPEDTAVYYCNAHISTGWGRPHNNYWGQGTQVTVSS |
| A0231PMP034E12 | 53 | EVQLVESGGDLVQPGGSLRLSCAASGSIFSINDMGWFRQAPGKQRELVADIISRGVINYADSVKGRFTISGDHAKIVIVYL<br>QMNSLKPEDTAVYYCNAHISTGWGRPHNNYWGQGTQVTVSS |
| A0231PMP047G08 | 54 | EVQLVESGGDLVQPGGSLRLSCAASGSIFSINDMGWFRQAPGKQRELVADIISRDVTNYADSVKGRFTISGDHAKNTVYL<br>QMNSLKPEDTAVYYCNAHISTGWGRPHNNYWGQGTQVTVSS |

TABLE A-9-continued

Amino acid sequences of monovalent anti-GTR Nanobodies ®
("ID" refers to the SEQ ID NO as used herein)

| Name | ID | Amino acid sequence |
|---|---|---|
| A0231PMP034F10 | 55 | EVQLVESGGDLVQPGGSLRLSCAASGSIFSINDMONFRQAPGKQRELVADIISRGVTNYADSVKGRFTISGDPAKNTVYL QMNSLKPEDTAVYYCNAHISMGWGRPHNNYWGQGTLVTVSS |
| A0231PMP052E08 | 56 | EVQLVESGGGLVQAGGSLRLSCTGSRSIFSTYAMAWHRQAPGKQRELVGFIYWGGTTTYSDSVKGRFTISRDNAKNTMY LQMNSLKPEDAGVYYCNIYGSYALPVVGQGTLVTVSS |
| A0231PMP052A03 | 57 | EVQLVESGGGLVQAGGSLRLSCTGSRNIFSTYAMAWHRQAPGKQRELVGFIYWGGTTSYVDSVKGRFTISRDNAKNTM YLQMNSLKPEDAAVYYCNIYGSYALPWGQGTLVTVSS |
| A0231PMP052B05 | 58 | EVQLVESGGGLVQAGGSLRLSCTGSRSIFSTYAMAWHRQAPGKQRELVGFIYWGGTTTYSDSVKGRFTISRDNAKNTMY LQMNSLKPEDAGVYYCNIYGSYALPQGQGTLVTVSS |
| A0231PMP052C04 | 59 | EVQLVESGGGMVQAGGSLRLSCTGSRNIFSTYAMAWHRQAPGKQRELVGFIYWGGTTSYVDSVKGRFTISRDNAKNT MYLWNSLKPEDAAVYYCNIYGSYALPWGQGTQVTVSS |
| A0231PMP052D06 | 60 | EVQLVESGGGLVQAGGSLRLSCTGSRSIFSTYAMAWHRQAPGKQRELVGFIYWGGTTSYVDSVKGRFTISRDNAKNTM YLQMNSLKPEDAAVYYCNIYGSYALPWGQGTLVTVSS |
| A0231PMP052F03 | 61 | EVQLVESGGGLVQAGGSLRLSCTGSRSIFSTYAMAWHROAPGKQRELVGFIYWGGTTTYSDSVKGRFTISRDNAKSTMY LQMNSLKPEDAGVYYCNIYGSYALPWGQGTLVTVSS |
| A0231PMP033B02 | 62 | EVQLVESGGGLVQPGGSLRLSCAASGTIFSISTMGWYRQAPGKQREVVAVTSGFSTNYSSAVKGRFTLSRDPAKNTVFLQ MNSLQPEDTATYYCNAYLSLAWRDPDRDYWGQGTQVTVSS |
| A0231PMP003D11 | 63 | EVQLVESGGGLVQAGESLRLSCAASGSIFSIDAMGWYRQAPGKQRELVAEISDHTTYGDSVKGRFTISRGNAENTVALQ MNSLKPEDTGVYYCNVHHQRGWGTSITVTWGQGTQVTVSS |
| A0231PMP017E06 | 64 | EVQLVESGGGLVQAGESLRLSCAASGSIFSIDAMGWYRQAPGKQRELVAEISDHTTYGDSVKGRFTISRGNAENTVALQ MNSLKPEDTGVYYCNVHHQRGWGTSITVAWGQGTQVTVSS |
| A0231PMP017G05 | 65 | EVQLVESGGGLVQAGESLRLSCAASGSIFSIDAMGWYRQAPGKQRELVAEISDHTTYGDSMKGRFTISRGNAENTVALQ MNSLKPEDTGVYYCNVHHQRGWGTSITVTWGQGTQVTVSS |
| A0231PMP010C09 | 66 | EVQLVESGGRLVQAGESLRLSCAASGSIFSIDAMGWYRQAPGKQRELVAEISGHTTYGDSVKGRFTISRGNAENTVALQ MNSLKPEDTGVYYCNVHHQRGWGTPITVTWGQGTQVTVSS |
| A0231PMP017C01 | 67 | EVQLVESGGRLVQAGESLRLSCAASGSIFSIDAMGWYRQAPGKQRELVAEISDHTTYGDSVKGRFTISRGNAENTVALQ MNSLKPEDTGVYYCNVHHQRGWGTPITVTWGQGTQVTVSS |
| A0231PMP017B08 | 68 | EVQLVESGGGLVRAGESLRLSCAASGSIFSIDAMGWYRQAPGKQRELVAEISDHTTYGDSVKGRFTISRGNAENTVALQ MNSLKPEDTGVYYCNVHHQRGWGTSITVIWGQGTLVTVSS |
| A0231PMP052A08 | 69 | EVQLVESGGGLVQAGGSLRLSCVASGSISSITAMGWHRQAPGAQREGVAVISRSGATMLVDSVKGRFTIVQDNAKNTV YLQMNSLKVEDTAVYGCSAITQGRTYWGQGTLVTVSS |
| A0231PMP052A01 | 70 | EVQLVESGGGLVQAGGSLRLSCVASGSISSTTAMGWHRQAPGAQREGVAIISRSGATMLVDSVKGRFTIVQDNAKNTVY LQMNSLKVEDTAVYGCSAITQGRTYWGQGTQVTVSS |
| A0231PMP052A05 | 71 | EVQLVESGGGLVQAGGSLRLSCVASGSISSITAMGWHRQAPGAQREGVAAISRSGATILADSVKGRETIVQDNAKNTVYL QMNSLKVEDTAVYGCSAITQEQTYWGQGTQVTVSS |
| A0231PMP051E01 | 72 | EVQLVESGGGLVQAGGSLRLSCAASGSIFSFIVMGWYRQAPGEQRALVATVTSGGDTFYVDSVKDRFTISRDNAKNTVYL QMNSLKPEDTAVYFCYFTKVSPYKETTWGQGTLVTVSS |
| A023100050 | 268 | EVQLVESGGGVVQPGGSLRLSCIGSRSIFSTYAMAWHRQAPGKQRELVGFIYWGGTITYADSVKGRFTISRDNSKNTLY LQMNSLRPEDTALYYCNIYGSYALPWGQGTLVTVSS |
| A023100061 | 269 | EVQLVESGGGVVQPGGSLRLSCAASGSIFSIDSMGWYRQAPGKQRELVAAITSSTNYADSVKGRFTISRDNSKNTVYLQ MNSLRPEDTALYYCNLEGQAGWGTALINYWGQGTLVTVSS |
| A023100063 | 270 | EVQLVESGGGVVQPGGSLRLSCAASGSVFSINDMGWFRQAPGKQRELVADIISRGVTNYADSVKGRFTISGDPSKNTVY LQMNSLRPEDTALYYCNAHISTGWGRPHNNYWGQGTLVTVSS |
| A023100078 | 271 | EVQLVESGGGVVQPGGSLRLSCAASETIFSIDSMAWYROAPGKQRELVAAITGGGSPNYADSVKGRFTISSDVSKRTVYL QMNSLRPEDTALYYCNAEGQAGVVGTALMDYWGQGTLVTVSS |
| A023100090 | 272 | EVQLVESGGGVVQPGGSLRLSCAASEMFSIDSMAWYRQAPGKQRELVAAITGGGSPNYADSVKGRFTLSSDVSKRTVYL QMNSLRPEDTALYYCNAEGQAGWGTALLDYWGQGTLVTVSS |
| A023100091 | 273 | EVOLVESGGGVVQPGGSLRLSCAASETIFSIDSMAWYRQAPGKORELVAAITGGGSPNYADSVKGRFTISSDVSKRTVYL QMNSLRPEDTALYYCNAEGQAGWGTALKDYWGQGTLVIVSS |
| A023100092 | 274 | EVQLVESGGGVVQPGGSLRLSCAASETIFSIDSMAWYRQAPGKQRELVAAITGGGSPNYADSVKGREYISSDVSKRTVYL QMNSLRPEDTALYYCNAEGQAGWGTALRDYWGQGTLVTVSS |

TABLE A-9-continued

Amino acid sequences of monovalent anti-GTR Nanobodies ®
("ID" refers to the SEQ ID NO as used herein)

| Name | ID | Amino acid sequence |
|---|---|---|
| A023100093 | 275 | EVQLVESGGGVVQPGGSLRLSCAASETIFSIDSMAWYRQAPGKQRELVAAITGGGSPNYADSVKGRFTSSDVSKRTVYLQMNSLRPEDTALYYCNAEGQAGWGTALQDYWGQGTLVTVSS |

TABLE A-10

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 1 | A0231PMP005A03 | 134 | EVQLVESGGGLV QPGGSLRLSCAAS | 73 | ETIFSIDS MA | 153 | WYRQAPGKQ RELVA | 90 | AITGGGS PN | 163 | YADSVKGRFTISSDVAKRTVY LQMNSLKPEDTAVYYCNA | 118 | EGQAGWGTAL MDY | 201 | WGKGTL VTVSS |
| 2 | A0231PMP004A03 | 135 | EVQLVESGGGLV QPGGSLRLSCTAS | 74 | ESIFSIDA MG | 154 | WHRQAPGKQ RELVA | 91 | HITGGG RSN | 164 | YADSVKGRFTISGDSAKRTVY LQMNSLKPEDTAVYYCNA | 118 | EGQAGWGTAL MDY | 201 | WGKGTL VTVSS |
| 3 | A0231PMP004A12 | 134 | EVQLVESGGGLV QPGGSLRLSCAAS | 74 | ESIFSIDA MG | 155 | WYRQAPGKQ RELVA | 92 | TITGGGS TN | 165 | YADSVKGRFTISGDSAKRTVY LQMNSLKPEDTAVYYCNA | 118 | EGQAGWGTAL MDY | 201 | WGKGTL VTVSS |
| 4 | A0231PMP004F05 | 136 | EVQLVESGGGLV QPGGSLRLSCAAS | 74 | ESIFSIDA MG | 153 | WYRQAPGKQ RELVA | 93 | TITGGG RN | 166 | YADSVMGRESISGDNAKRTVY YLQMNSLKPEDTAVYYCNA | 118 | EGQAGWGTAL MDY | 202 | WGKGTQ VTVSS |
| 5 | A0231PMP005A01 | 134 | EVQLVESGGGLV QPGGSLRLSCAAS | 74 | ESIFSIDA MG | 154 | WHRQAPGKQ RELVA | 91 | HITGGG RSN | 164 | YADSVKGRFTISGDSAKRTVY LQMNSLKPEDTAVYYCNA | 118 | EGQAGWGTAL MDY | 202 | WGKGTQ VTVSS |
| 6 | A0231PMP005A02 | 135 | EVQLVESGGGLV QPGGSLRLSCTAS | 74 | ESIFSIDA MG | 154 | WHRQAPGKQ RELVA | 91 | HITGGG RSN | 167 | YADSVKGRFTISGDSAKRTVY LQMNSLRPEDTAVYYCNA | 118 | EGQAGWGTAL MDY | 201 | WGKGTL VTVSS |
| 7 | A0231PMP005A10 | 137 | EVQLVESGGGLV RPGGSLRLSCAAS | 74 | ESIFSIDA MG | 153 | WYRQAPGKQ RELVA | 94 | TMTGGG STN | 163 | YADSVKGRFTISSDVAKRTVY LQMNSLKPEDTAVYYCNA | 118 | EGQAGWGTAL MDY | 202 | WGKGTQ VTVSS |
| 8 | A0231PMP005802 | 135 | EVQLVESGGGLV QPGGSLRLSCTAS | 74 | ESIFSIDA MG | 154 | WHRQAPGKQ RELVA | 95 | HITGGG GSN | 164 | YADSVKGRFTISGDSAKRTVY LQMNSLKPEDTAVYYCNA | 118 | EGQAGWGTAL MDY | 202 | WGKGTQ VTVSS |
| 9 | A0231PMP051308 | 134 | EVQLVESGGGLV QPGGSLRLSCAAS | 73 | ETIFSIDS MA | 156 | WYRQAPGRQ RELVA | 90 | AITGGGS PN | 163 | YADSVKGRFTISSDVAKRTVY LQMNSLKPEDTAVYYCNA | 118 | EGQAGWGTAL MDY | 201 | WGKGTL VTVSS |
| 10 | A0231PMP005C01 | 134 | EVQLVESGGGLV QPGGSLRLSCAAS | 73 | ETIFSIDS MA | 153 | WYRQAPGKQ RELVA | 90 | AITGGGS PN | 168 | YADSVPGRETISSDVAKRTAY LQMNSLKPEDTAVYYCNA | 118 | EGQAGWGTAL MDY | 201 | WGKGTL VTVSS |
| 11 | A0231PMP005G10 | 137 | EVQLVESGGGLV RPGGSLRLSCAAS | 74 | ESIFSIDA MG | 153 | WYRQAPGKQ RELVA | 94 | TMTGGG STN | 169 | YADSVPGRFTISSDVAKRTVY LQMNSLKPEDTAVYYCNA | 118 | EGQAGWGTAL MDY | 202 | WGKGTQ VTVSS |
| 12 | A0231PMP006E02 | 135 | EVQLVESGGGLV QPGGSLRLSCTAS | 74 | ESIFSIDA MG | 154 | WHRQAPGKQ RELVA | 91 | HITGGG RSN | 170 | YADSVKGRFAISGDSAKRTVY LQMNSLKPEDTAVYYCNA | 118 | EGQAGWGTAL MDY | 202 | WGKGTQ VTVSS |
| 13 | A0231PMP006E08 | 134 | EVQLVESGGGLV QPGGSLRLSCAAS | 74 | ESIFSIDA MG | 153 | WYRQAPGKQ RELVA | 92 | TITGGGS TN | 165 | YADSVKGRFTISGDSAKRTVY LQMNSLKPEDTAVYYCNA | 118 | EGQAGWGTAL MDY | 201 | WGKGTL VTVSS |
| 14 | A0231PMP006G04 | 138 | EVQLVESGGGLV RPGGSLRLPCAAS | 74 | ESIFSIDA MG | 153 | WYRQAPGKQ RELVA | 94 | TMTGGG STN | 163 | YADSVKGRFTISSDVAKRTVY LQMNSLKPEDTAVYYCNA | 118 | EGQAGWGTAL MDY | 201 | WGKGTL VTVSS |
| 15 | A0231PMP012E03 | 136 | EVQLVESGGGLV QSGGSLRLSCAAS | 75 | ESIFSINA MG | 153 | WYRQAPGKQ RELVA | 93 | TITGGGR RN | 166 | YADSVMGRESISGDNAKRTV YLQMNSLKPEDTAVYYCNA | 118 | EGQAGWGTAL MDY | 202 | WGKGTQ VTVSS |

TABLE A-10-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 16 | A0231PMP012G07 | 134 | EVQLVESGGGLV QPGGSLRLSCAAS | 74 | ESIFSIDA MG | 153 | WYRQAPGKQ RELVA | 96 | TITGGSS TN | 171 | YADSVKGRFTISGDNAKRTVY LQMNSLKPEDTAVYYCNA | 118 | EGQAGWGTAL MDY | 202 | WGKGTQ VTVSS |
| 17 | A0231PMP020805 | 134 | EVQLVESGGGLV QPGGSLRLSCAAS | 74 | ESIFSIDA MG | 153 | WYRQAPGKQ RELVA | 92 | TITGGGS TN | 172 | YADSVKGRFTISGDNAKRTVY LQMNSLKPEDTAAYYCNA | 118 | EGQAGWGTAL MDY | 201 | WGKGTL VTVSS |
| 18 | A0231PMP020D02 | 135 | EVQLVESGGGLV QPGGSLRLSCTAS | 74 | ESIFSIDA MG | 154 | WHRQAPGKQ RELVA | 91 | HITGGG RSN | 173 | YADSVKGRFTISGDSAKRTVY LQMNSLKPGDTAVYYCNA | 118 | EGQAGWGTAL MDY | 202 | WGKGTQ VTVSS |
| 19 | A0231PMP020E12 | 134 | EVQLVESGGGLV QPGGSLRLSCAAS | 74 | ESIFSIDA MG | 153 | WYRQAPGKQ RELVA | 92 | TITGGGS TN | 171 | YADSVKGRFTISGDNAKRTVY LQMNSLKPEDTAVYYCNA | 118 | EGQAGWGTAL MDY | 202 | WGKGTQ VTVSS |
| 20 | A0231PMP021B02 | 135 | EVQLVESGGGLV QPGGSLRLSCTAS | 74 | ESIFSIDA MG | 154 | WHRQAPGKQ RELVA | 97 | HITGGG RPN | 164 | YADSVKGRFTISGDSAKRTVY LQMNSLKPEDTAVYYCNA | 118 | EGQAGWGTAL MDY | 201 | WGKGTL VTVSS |
| 21 | A0231PMP023G01 | 139 | EVQLVESGGGLV QPGGSLRLSCAGS | 74 | ESIFSIDA MG | 153 | WYRQAPGKQ RELVA | 98 | GISGGGR TN | 174 | YADSVKGRFTISGDNAKNTV YLQMNSLKPEDTPANYCNA | 118 | EGQAGWGTPL MNY | 201 | WGKGTL VTVSS |
| 22 | A0231PMP004801 | 134 | EVQLVESGGGLV QPGGSLRLSCAAS | 76 | GSIFSIDS MG | 153 | WYRQAPGKQ RELVA | 99 | AITSSTN | 175 | YAESVKGRFTESRANAKNTV YLQMNSLKPEDTAVYYCNV | 119 | EGQAGWGTAL NY | 120 | WGKGTL VTVSS |
| 23 | A0231PMP004802 | 140 | EVQLVESGGGLV QPGGSLRLTCAAS | 77 | GSIFSIDA MG | 153 | WYRQAPGKQ RELVA | 100 | SITSTIN | 176 | YAESVKGRFTESRANAKNTV YLQMNSLKPEDTAVYYCNV | 120 | EGQAGWGTAL NY | 202 | WGKGTQ VTVSS |
| 24 | A0231PMP012F03 | 140 | EVQLVESGGGLV QPGGSLRLTCAAS | 77 | GSIFSIDA MG | 153 | WYRQAPGKQ RELVA | 100 | SITSTIN | 177 | YAESVKGRFTESRANAKNTV YLQMNSLKPEDTAVYYCSV | 121 | KGQTGWGTAL MDY | 201 | WGKGTL VTVSS |
| 25 | A0231PMP012008 | 134 | EVQLVESGGGLV QPGGSLRLSCAAS | 78 | GSIFSINA MG | 153 | WYRQAPGKQ RELVA | 101 | AITSGTN | 178 | YADSAKGRFTISRDHAKNTVY LQMNSLKPEDTAVYYCNL | 121 | KGQTGWGTAL MN | 201 | WGKGTL VTVSS |
| 26 | A0231PMP006C07 | 134 | EVQLVESGGGLV QPGGSLRLSCAAS | 78 | GSIFSINA MG | 153 | WYRQAPGKQ RELVA | 101 | AITSGTN | 179 | YADSVKGRFTISRDHAKNTVY LQMNSLKPEDTAVYYCNL | 122 | EGQTGWGTAL MDY | 202 | WGKGTQ VTVSS |
| 27 | A0231PMP005G01 | 141 | EVQLVESGGGLV QPGGSLRLFCAAS | 18 | GSIFSINA MG | 153 | WYRQAPGKQ RELVA | 101 | AITSGTN | 180 | YADSVKGRFTISRDHAKNTVY LQMNSLKPEDTAVYYCNL | 122 | EGQTGWGTAL MDY | 202 | WGKGTQ VTVSS |
| 28 | A0231PMP005A08 | 134 | EVQLVESGGGLV QPGGSLRLSCAAS | 78 | GSIFSINA MG | 153 | WYRQAPGKQ RELVA | 101 | AITSGTN | 179 | YADSVKGRFTISRDHAKNTVY LQMNSLKPEDTAVYYCNL | 122 | EGQTGWGTAL MN | 201 | WGKGTL VTVSS |
| 29 | A0231PMP004803 | 134 | EVQLVESGGGLV QPGGSLRLSCAAS | 76 | GSIFSIDS MG | 153 | WYRQAPGKQ RELVA | 102 | AITSRTI | 175 | YADSVKGRFTISRDHAKNTVY LQMNSLKPEDTAVYYCNL | 118 | EGQAGWGTAL MDY | 201 | WGKGTL VTVSS |
| 30 | A0231PMP004A05 | 134 | EVQLVESGGGLV QPGGSLRLSCAAS | 77 | GSIFSIDA MG | 153 | WYRQAPGKQ RELVA | 103 | TITSGKN | 181 | YADSVKGRFTISRDNAKNAV YLQMNSLKPEDTAVYYCNL | 118 | EGQAGWGTAL MDY | 202 | WGKGTQ VTVSS |
| 31 | A0231PMP004A01 | 134 | EVQLVESGGGLV QPGGSLRLSCAAS | 76 | GSIFSIDS MG | 153 | WYRQAPGKQ RELVA | 99 | AITSSTN | 182 | YADSVKGRFTISRDNAKNTVY LQTNSLKPEDTAVYYCNL | 118 | EGQAGWGTAL MDY | 202 | WGKGTQ VTVSS |

TABLE A-10-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | FR1 | ID | CDR1 | ID | FR2 | ID | CDR2 | ID | FR3 | ID | CDR3 | ID | FR4 |
|---|---|---|---|---|---|---|---|---|---|---|---|---|---|---|
| 32 | A0231PMP005805 | EVQLVESGGGLV QPGGSLRLSCAAS | 134 | GSIFSINA MG | 78 | WYRQAPGKQ RELVA | 153 | AITSSTN | 99 | YADSVKGRFTISRANAKINTVY LQMNSLKPEDTAVYYCHL | 183 | EGQAGWGTAL LDY | 123 | WGKGTL VTVSS | 201 |
| 33 | A0231PMP034A08 | EVQLVESGGGLV QPGGSLRLSCAAS | 142 | GSVFSIND MG | 79 | WFRQAPGKQ RELVA | 157 | DIISRGV TN | 104 | YADSVKGRFTISGDPAKNTVY LQMNSLKPEDTAVYYCNA | 184 | HISTGWGRPHN NY | 124 | WGQGTQ VTVSS | 203 |
| 34 | A0231PMP033812 | EVQLVESGGGLV QPGGSLRLSCAAS | 142 | GSIFSIDS MG | 76 | WFRQAPGKQ RELVA | 157 | DIISADV TN | 105 | YADSVKGRFTISGDHAKNTVY LQMNSLKPEDTAVYYCNA | 185 | HISTGWGRPHN NY | 124 | WGQGTQ VTVSS | 203 |
| 35 | A0231PMP033E01 | EVQLVESGGGLV QPGGSLRLSCAAS | 142 | GSIFSIDS MG | 76 | WFRQAPGKQ RELVA | 157 | DIISADV TN | 105 | YADSVKGRFTISGDHACINTV YLQMNSLKPEDTAVYYCNA | 186 | HISTGWGRPHN NY | 124 | WGQGTQ VTVSS | 203 |
| 36 | A0231PMP034806 | EVQLVESGGGLV QPGGSLRLSCAAS | 142 | GSIFSIDS MG | 76 | WFRQAPGKQ RELVA | 157 | DIESAGV TN | 106 | YADSVKGRFTISGDHAKNTVY LQMNSLKPEDTAVYYCNA | 185 | HISTGWGRPHN NY | 124 | WGQGTQ VTVSS | 203 |
| 37 | A0231PMP048A08 | EVQLVESGGGLV QPGGSLRLSCAAS | 142 | GSIFSIDD MG | 80 | WFRQAPGKQ RELVA | 157 | DIISAGV TN | 106 | YADSVKGRFTISGDHAKNIVY LQMNSLKPEDTAVYYCNA | 185 | HISTGWGRPHN NY | 124 | WGQGTL VTVSS | 204 |
| 38 | A0231PMP034A03 | EVQLVESGGIAV QPGGSLRLSCAAS | 142 | GSIESIND VG | 81 | WFRQAPGKG RELVA | 157 | DIISRGV TN | 104 | YADSVKGRFTISGDPAKNTVY LQMNSLKPEDTAAYYCNA | 187 | HISTGWGRPHN NY | 124 | WGQGTQ VTVSS | 203 |
| 39 | A0231PMP034A02 | EVQLVESGGIAV QPGGPLRLSCAAS | 143 | GNIFSIND MG | 82 | WFRQAPGKQ RELVA | 157 | DIISRGV TN | 104 | YADSVKGRFTISGDPAKNTVY LQMNSLKPEDTAVYYCNA | 184 | HISTGWGRPHN NY | 124 | WGQGTQ VTVSS | 203 |
| 40 | A0231PMP034809 | EVQLVESGGGLV QPGPGLRLSCAAS | 143 | GSIMND MG | 83 | WFRQAPGKQ RELVA | 157 | DILSRGV TN | 104 | YADSVKGRFTISGDPAKNTVY LQMNSLKPEDTAVYYCNA | 184 | HISTGWGRPHN NY | 124 | WGQGTQ VTVSS | 203 |
| 41 | A0231PMP034A01 | EVQLVESGGGLV QPGGSLRLSCAAS | 142 | GSIFSIND MG | 83 | WFRQAPGKQ RELVA | 157 | DIISRGV TN | 104 | YADSVKGRFTISGDPAKNTVY LQMNSLKPEDTAVYYCNA | 184 | HISTGWGRPHN NY | 124 | WGQGTQ VTVSS | 203 |
| 42 | A0231P1VT034A09 | EVQLVESGGGLV QPGGSLRLSCAAS | 142 | GSIFSINDT G | 84 | WFRQAPGKQ RELVA | 157 | DIISRGV TN | 104 | YADSVKGRFTISGDPAKNTVY LQMNSLKPEDTAVYYCNA | 184 | HISTGWGRPHN NY | 124 | WGQGTQ VTVSS | 203 |
| 43 | A0231PMP034A10 | EVQLVESGGGLV QPGGSLRLSCAAS | 142 | GSIFSIND MG | 83 | WFRQAPGKQ RELVA | 157 | DIISAGV TN | 106 | YADSVKGRFTISGDPAKNTVY LQMNSLKPEDTAVYYCNA | 184 | HISTGWGRPHN NY | 124 | WGQGTQ VTVSS | 203 |
| 44 | A0231PMP034C06 | EVQLVESGGGLV QPGGSLRLSCAAS | 142 | GSIFSIND MG | 83 | WFRQAPGKQ RELVA | 157 | GIISRGV TN | 107 | YADSVKGRFTISGDPAKNTVY LQMNSLKPEDTAVYYCNA | 184 | HISTGWGRPHN NY | 124 | WGQGTQ VTVSS | 203 |
| 45 | A0231PMP034D02 | EVQLVESGGGLV QPGGSLRLSCAAS | 142 | GSIFSIND MG | 83 | WFRQAPGKQ RELVA | 157 | DIISRGV TN | 104 | YADSVKGRFTISGDPAKNTAY LQMNSLKPEDTAVYYCNA | 188 | HISTGWGRPHN NY | 124 | WGQGTQ VTVSS | 203 |
| 46 | A0231PMP034E01 | EVQLVESGGGLV QPGGSLGLSCAAS | 144 | GSIFSIND MG | 83 | WFRQAPGKQ RELVA | 157 | DIISRGV TN | 104 | YADSVKGRFTISGDPAKNTVY LQMNSLKPEDTAVYYCNA | 184 | HISTGWGRPHN NY | 124 | WGQGTQ VTVSS | 203 |
| 47 | A0231PMP048006 | EVQLVESGGGLV QPGGSLRLSCAAS | 145 | GSIFSIND MG | 83 | WFRQAPGKQ RELVA | 157 | DIISRGV TN | 104 | YADSVKGRFTISGDPAKNTVY LQMNSLKPEDTAVYYCNA | 184 | HISTGWGRPHN NY | 124 | WGQGTQ VTVSS | 203 |

TABLE A-10-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 48 | A0231PMP048012 | 142 | EVQLVESGGGLV QPGGSLRLSCAAS | 83 | GSIFSIND MG | 157 | WFRQAPGKQ RELVA | 104 | DIISRGV TN | 189 | CADSVKGRFTISGPAKNTVY LQMNSLKPEDTAVYYCNA | 124 | HISTGWGRPHN NY | 203 | WGQGTQ VTVSS |
| 49 | A0231PMP048C07 | 142 | EVQLVESGGDLV QPGGSLRLSCAAS | 83 | GSIESIND MG | 158 | WLRQAPGKQ RELVA | 104 | DIISRGV TN | 184 | YADSVKGRFTISGDPAKNTVY LQMNSLKPEDTAVYYCNA | 124 | HISTGWGRPHN NY | 203 | WGQGTQ VTVSS |
| 50 | A0231PMP036C11 | 142 | EVQLVESGGDLV QPGGSLRLSCAAS | 83 | GSIFSIND MG | 157 | WFRQAPGKQ RELVA | 104 | DIISRGV TN | 190 | YADSVKGRFTISGDPAKNTVY LQMNSLKPEDTAVYYCNA | 124 | HISTGWGRPHN NY | 203 | WGQGTQ VTVSS |
| 51 | A0231PMP036A04 | 134 | EVQLVESGGDLV QPGGSLRLSCAAS | 83 | GSIFSIND MG | 157 | WFRQAPGKQ RELVA | 104 | DIISRGV TN | 184 | YADSVKGRFTISGDPAKNTVY LQMNSLKPEDTAVYYCNA | 124 | HISTGWGRPHN NY | 203 | WGQGTQ VTVSS |
| 52 | A0231PMP034E11 | 142 | EVQLVESGGDLV QPGGSLRLSCAAS | 83 | GSIFSIND MG | 157 | WFRQAPGKQ RELVA | 104 | DIISRGV TN | 191 | YADSVKGRFTVSGDPAKNTVY YLQMNSLKPEDTAVYYCNA | 124 | HISTGWGRNIN NY | 203 | WGQGTQ VTVSS |
| 53 | A0231PMP034E12 | 142 | EVQLVESGGDLV QPGGSLRLSCAAS | 83 | GSIFSIND MG | 157 | WFRQAPGKQ RELVA | 104 | DIISRGV TN | 185 | YADSVKGRFTISGDHAKNTVY LQMNSLKPEDTAVYYCNA | 124 | HISTGWGRNIN NY | 203 | WGQGTQ VTVSS |
| 54 | A0231PMP047G08 | 142 | EVQLVESGGDLV QPGGSLRLSCAAS | 83 | GSIFSIND MG | 157 | WFRQAPGKQ RELVA | 108 | DIISRDVT N | 185 | YADSVKGRFTISGDHAKNTVY LQMNSLKPEDTAVYYCNA | 124 | HISTGWGRPHN NY | 203 | WGQGTQ VTVSS |
| 55 | A0231PMP034E10 | 142 | EVQLVESGGDLV QPGGSLRLSCAAS | 83 | GSIFS1ND MG | 157 | WFRQAPGKQ RELVA | 104 | DIISRGV TN | 184 | YADSVKGRFTISGDPAKNTVY LQMNSLKPEDTAVYYCNA | 125 | HISMGWGRPH NNY | 204 | WGQGTL VTVSS |
| 56 | A0231PMP052E08 | 146 | EVQLVESGGGLV QAGGSLRLSCTGS | 85 | RSIESTYA MA | 159 | NFIRQAPGKQ RELVG | 109 | FIYWGG TTT | 192 | YSDSVKGRETISRDNAKNTM YLQMNSLKPEDAGVYYCNI | 126 | YGSYALP | 204 | WGQGTL VTVSS |
| 57 | A0231PMP052A03 | 146 | EVQLVESGGGLV QAGGSLRLSCTGS | 86 | RNIFSTYA MA | 159 | WHRQAPGKQ RELVG | 110 | FIYWGG TTS | 193 | YVDSVKGRETISRDNAKNTM YLQMNSLKPEDAAVYYCNI | 126 | YGSYALP | 204 | WGQGTL VTVSS |
| 58 | A0231PMP052805 | 146 | EVQLVESGGGLV QAGGSLRLSCTGS | 85 | RSIESTYA MA | 159 | WHRQAPGKQ RELVG | 109 | FIYWGG TTT | 192 | YSDSVKGRETISRDNAKNTM YLQMNSLKPEDAGVYYCNI | 126 | YGSYALP | 205 | QGQGTLV TVSS |
| 59 | A0231PMP052C04 | 146 | EVQLVESGGGLV QAGGSLRLSCTGS | 86 | RNIFSTYA MA | 159 | WHRQAPGKQ RELVG | 110 | FIYWGG TTS | 193 | YVDSVKGRETISRDNAKNTM YLQMNSLKPEDAAVYYCNI | 126 | YGSYALP | 203 | WGQGTQ VTVSS |
| 60 | A0231PMP052D06 | 146 | EVQLVESGGGLV QAGGSLRLSCTCGS | 85 | RSIESTYA MA | 159 | WHRQAPGKQ RELVG | 110 | FIYWGG TTS | 193 | YVDSVKGRETISRDNAKNTM YLQMNSLKPEDAAVYYCNI | 126 | YGSYALP | 204 | WGQGTL VTVSS |
| 61 | A0231PMP052F03 | 146 | EVQLVESGGGLV QAGGSLRLSCTGS | 85 | RSIESTYA MA | 159 | WHRQAPGKQ RELVG | 109 | FIYWGG TTT | 194 | YSDSVKGRFTISRDNAKSIMY LQMNSLKPEDAGWYYCNI | 126 | YGSYALP | 204 | WGQGTL VTVSS |
| 62 | A0231PMP033802 | 134 | EVQLVESGGGLV QPGGSLRLSCAAS | 87 | GTIFSIST MG | 160 | WYRQAPGKQ REVVA | 111 | VTSGEST N | 195 | YSSAVKGRETISRDPAKNTVF LQMNSLQPEDTATYYCNA | 127 | YLSLAWRDPDR DY | 203 | WGQGTQ VTVSS |
| 63 | A0231PMP003D11 | 148 | EVQLVESGGGLV QAGESLRLSCASS | 77 | GSIFSIDA MG | 153 | WYRQAPGKQ RELVA | 112 | EISDHTT | 196 | YGDSVKGRFISRGNAENTV ALQMNSLKPEDTGVYYCNV | 128 | HHQRGWGTSIT VT | 203 | WGQGTQ VTVSS |

TABLE A-10-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 64 | A0231PMP017E06 | 148 | EVQLVESGGGLV QAGESLRLSCAAS | 77 | GSIFSIDA MG | 153 | WRQAPGKQ RELVA | 112 | EISDHTT | 196 | YGDSVKGRFTISRGNAENTV ALQMNSLKPEDTGVYYCNV | 129 | HHQRGWGTSIT VA | 203 | WGQGTQ VTVSS |
| 65 | A0231PMP017G05 | 148 | EVQLVESGGGLV QAGESLRLSCAAS | 77 | GSIFSIDA MG | 153 | WYRQAPGKQ RELVA | 112 | EISDHTT | 197 | YGDSMKGRFTISRGNAENTV ALQMNSLKPEDTGVYYCNV | 128 | HHQRGWGTSIT VT | 203 | WGQGTQ VTVSS |
| 66 | A0231PMP010C09 | 149 | EVQLVESGGRLV QAGESLRLSCAAS | 77 | GSIFSIDA MG | 153 | WYRQAPGKQ RELVA | 113 | EISGHTT | 196 | YGDSVKGRFTISRDNAKNIVY ALQMNSLKPEDTGVYYCNV | 130 | HHQRGWGTPI TVT | 203 | WGQGTQ VTVSS |
| 67 | A0231PMP017C01 | 149 | EVQLVESGGRLV QAGELRLSCAAS | 77 | GSIFSIDA MG | 153 | WYRQAPGKQ RELVA | 112 | EISGHTT | 196 | YGDSVKGRFTESRANAKNTVY ALQMNSLKPEDTAVYYCNV | 130 | HHQRGWGTPI TVT | 203 | WGQGTQ VTVSS |
| 68 | A0231PMP017B08 | 150 | EVQLVESGGGLV RAGESLRLSCAAS | 77 | GSIFSIDA MG | 153 | WYRQAPGKQ RELVA | 112 | EISGHTT | 196 | YGDSVKGRFTESRANAKNTVY ALQMNSLKPEDTAVYYCNV | 128 | HHQRGWGTSIT VT | 204 | WGKGTL VTVSS |
| 69 | A0231PMP052A08 | 151 | EVQLVESGGGLV QAGGSLRLSCVAS | 88 | GSIFSITA MG | 161 | WYRQAPGAQ REGVA | 114 | VISRSGA TM | 198 | LVDSVKGRFTIVQDNAKNTV YLQMNSLKVEDTAVYGCSA | 131 | ITQGRTY | 204 | WGKGTL VTVSS |
| 70 | A0231PMP052A01 | 151 | EVQLVESGGGLV QAGGSLRLSCVAS | 88 | GSISSITA MG | 161 | WHRQAPGAQ RELVA | 115 | IISRSGAT M | 198 | LVDSVKGRFTIVQDNAKNTV YLQMNSLKVEDTAVYGCSA | 131 | ITQGRTY | 203 | WGQGTQ VTVSS |
| 71 | A0231PMP052A05 | 151 | EVQLVESGGGLV QAGGSLRLFCVAS | 88 | GSISSITA MG | 161 | WHRQAPGKQ RELVA | 116 | AISRSGA TI | 199 | LADSVKGRFTIVQDNAKNTV YLQMNSLKVEDTAVYGCSA | 132 | ITQEQTV | 203 | WGQGTQ VTVSS |
| 72 | A0231PMP051E01 | 152 | EVQLVESGGGLV QAGGSLRLSCAAS | 89 | GSIFSFIV MG | 162 | WYRQAPGEQ RELVA | 117 | TVTSGG DTF | 200 | YVDSVKGRFTISRDHAKNTVY LQMNSLKPEDTAVYFCYF | 133 | TKVSPYKETT | 204 | WGKGTL VTVSS |

TABLE A-10-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 268 | A023100050 | 276 | EVQLVESGGGVV QPGGSLRLSCTGS | 85 | RSIFSTYA MA | 159 | WHRQAPGKQ RELVA | 109 | FIYWGG TTT | 277 | YADSVKGRTISRDNSKNTLY LQMNSLRPEDTALYYCNI | 126 | YGSYALP | 204 | WGQGTL VTVSS |
| 269 | A023100061 | 278 | EVQLVESGGGVV QPGGSLRLSCAAS | 76 | GSIFSIDS MG | 153 | WYRQAPGKQ RELVA | 99 | AITSSTN | 279 | YADSVKGRFTISRDNAKNTVY LQMNSLRPEDTALYYCNL | 120 | EGQAGWGTALI MDY | 202 | WGQGTQ VTVSS |
| 270 | A023100063 | 278 | EVQLVESGGGVV QPGGSLRLSCAAS | 79 | GSIFSIND MG | 157 | WFRQAPGKQ RELVA | 104 | DIISRGV TN | 280 | YADSVKGRFTISRDNAKNTVY LQTNSLKPEDTAVYYCNA | 124 | HISTGWGRPHN NY | 204 | WGQGTQ VTVSS |
| 271 | A023100078 | 278 | EVQLVESGGGVV QPGGSLRLSCAAS | 73 | ETIFSIDS MA | 153 | WYRQAPGKQ RELVA | 90 | AITGGGS PN | 281 | YADVKGRFTISSDVSKRTVYL QMNSLRPEDTALYYCNA | 118 | EGQAGWGTAL MDY | 204 | WGQGTL VTVSS |
| 272 | A023100000 | 278 | EVQLVESGGGVV QPGGSLRLSCASS | 73 | ETIFSIDS MA | 153 | WYRQAPGKQ RELVA | 90 | AITGG SPN | 281 | YADSVKGRFTISSDVSKRTVYL QMNSLRPEDTALYYCNA | 123 | EGQAGWGTAL LDY | 204 | WGQGTL VTVSS |
| 273 | A023100091 | 278 | WVQLVESGGGV VQPGGSLRLSC AAS | 73 | ETIFSIDS MA | 153 | QYRQAPGK QRELVA | 90 | AITGGG SPN | 281 | YADSVKGRFTISSDVSKRT VYLQMNSLRPEDTALYYC NA | 282 | EGQAGWGTAL KDY | 204 | WGQGTL VTVSS |
| 274 | A023100092 | 278 | EVQLVESGGGV VQPGGSLRLSC AAS | 73 | ETIFSIDS MA | 153 | WYRQAPGK QRELVA | 90 | AITGGG SPN | 281 | YADSVKGRFTISSDVSKRT VYLQMNSLRPEDTALYYC NA | 283 | EGQAGWGTAL QDY | 204 | WGQGTL VTVSS |
| 275 | A023100093 | 278 | EVQLVESGGGV VQPGGSLRLSC ASS | 73 | ETIFSIDS MA | 153 | WYRQAPGK QRELVA | 90 | AITGGG SPN | 281 | YADSVKGRFTISSDVSKRT VYQMNSLRPEDTALYYC NA | 284 | EGQAGWGTAL QDY | 204 | WGQGTL VTVSS |

TABLE A-11

Amino acid sequences of selected multivalent anti-GITR Nanobodies®

| Name | ID | Amino acid sequence |
|------|-----|---------------------|
| A023100001 | 206 | EVQLVESGGGLVQPGGSLRLSCAASGSIFSIDSMGWYRQAPGKQRELVAAITSSTNYADSVKGRFTISRDNAKN TVYLQMNSLKPEDTAVYYCNLEGQAGWGTALINYWGKGTLVTVSSGGGGSGGGGSGGGGSGGGGSGGGGS GGGGSGGGGSEVQLVESGGGLVQPGGSLRLSCAASGSIFSIDSMGWYRQAPGKQRELVAAITSSTNYADSVKG RFTISRDNAKNTVYLQMNSLKPEDTAVYYCNLEGQAGWGTALINYWGKGTLVTVSSGGGGSGGGGSGGGGS GGGGSGGGGSGGGGSGGGGSEVQLVESGGGLVQPGNSLRLSCAASGFTFSSFGMSWVRQAPGKGLEWVSSI SGSGSDTLYADSVKGRFTISRDNAKTTLYLQMNSLRPEDTAVYYCTIGGSLSRSSQGTLVTVSS |
| A023100003 | 207 | EVQLVESGGGLVQPGGSLRLSCAASETIFSIDSMAWYRQAPGKQRELVAAITGGGSPNYADSVKGRFTISSDVA KRTVYLQMNSLKPEDTAVYYCNAEGQAGWGTALMDYWGKGTLVTVSSGGGGSGGGGSGGGGSGGGGSGG GGSGGGGSGGGGSEVQLVESGGGLVQPGGSLRLSCAASETIFSIDSMAWYRQAPGKQRELVAAITGGGSPNY ADSVKGRFTISSDVAKRTVYLQMNSLKPEDTAVYYCNAEGQAGWGTALMDYWGKGTLVTVSSGGGGSGGG GSGGGGSGGGGSGGGGSGGGGSEVQLVESGGGLVQPGNSLRLSCAASGFTFSSFGMSWVRQAPGK GLEWVSSISGSGSDTLYADSVKGRFTISRDNAKTTLYLQMNSLRPEDTAVYYCTIGGSLSRSSQGTLVTVSS |
| PA023100013 | 208 | EVQLVESGGGLVQAGGSLRLSCVASGSISSITAMGWHRQAPGAQREGVAVISRSGATMLVDSVKGRFTIVQDN AKNIVYLQMNSLKVEDTAVYGCSAITQGRTYWGQGTLVTVSSGGGGSGGGGSGGGGSGGGGSGGGGSGGG GSGGGGSEVQLVESGGGLVQAGGSLRLSCVASGSISSITAMGWHRQAPGAQREGVAVISRSGATMLVDSVKG RFTIVQDNAKNTVYLQMNSLKVEDTAVYGCSAITQGRTYWGQGTLVTVSSGGGGSGGGGSGGGGSGGGGSG GGGSGGGGSGGGGSEVQLVESGGGLVQPGNSLRLSCAASGFTFSSFGMSWVRQAPGKGLEWVSSISGSGSD TLYADSVKGRFTISRDNAKTTLYLQMNSLRPEDTAVYYCTIGGSLSRSSQGTLVTVSS |
| A023100014 | 209 | EVQLVESGGGLVQPGGSLRLSCAASGSIFSIDSMGWYRQAPGKQRELVAAITSSTNYADSVKGRFTISRDNAKN TVYLQMNSLKPEDTAVYYCNLEGQAGWGTALINYWGKGTLVTVSSGGGGSGGGGSGGGGSGGGGSGGGGS GGGGSGGGGSEVQLVESGGGLVQPGGSLRLSCAASGSIFSIDSMGWYRQAPGKQRELVAAITSSTNYADSVKG RFTISRDNAKNTVYLQMNSLKPEDTAVYYCNLEGQAGWGTALINYWGKGTLVTVSSGGGGSGGGGSGGGGS GGGGSGGGGSGGGGSGGGGSEVQLVESGGGLVQPGGSLRLSCAASGSIFSIDSMGWYRQAPGKQRELVAAIT SSTNYADSVKGRFTISRDNAKNTVYLQMNSLKPEDTAVYYCNLEGQAGWGTALINYWGKGTLVTVSSGGGGS GGGGSGGGGSGGGGSGGGGSGGGGSGGGGSEVQLVESGGGLVQPGNSLRLSCAASGFTFSSFGMSWVRQ APGKGLEWVSSISGSGSDTLYADSVKGRFTISRDNAKTTLYLQMNSLRPEDTAVYYC- TIGGSLSRSSQGTLVTVSS |
| A023100015 | 210 | EVQLVESGGGLVQAGGSLRLSCVASGSISSITAMGWHRQAPGAQREGVAVISRSGATMLVDSVKGRFTIVQDN AKNTVYLQMNSLKVEDTAVYGCSAITQGRTYWGQGTLVTVSSGGGGSGGGGSGGGGSGGGGSGGGGSGGG GSGGGGSEVQLVESGGGLVQAGGSLRLSCVASGSISSITAMGWHRQAPGAQREGVAVISRSGATMLVDSVKG RFTIVQDNAKNTVYLQMNSLKVEDTAVYGCSAITQGRTYWGQGTLVTVSSGGGGSGGGGSGGGGSGGGGSG GGGSGGGGSGGGGSEVQLVESGGGLVQAGGSLRLSCVASGSISSITAMGWHRQAPGAQREGVAVISRSGAT MLVDSVKGRFTIVQDNAKNTVYLQMNSLKVEDTAVYGCSAITQGRTYWGQGTLVTVSSGGGGSGGGGSGGG GSGGGGSGGGGSGGGGSGGGGSEVQLVESGGGLVQPGNSLRLSCAASGFTFSSFGMSWVRQAPGKGLEWV SSISGSGSDTLYADSVKGRFTISRDNAKTTLYLQMNSLRPEDTAVYYCTIGGSLSRSSQGTLVTVSS |
| A023100021 | 211 | EVQLVESGGGLVQAGESLRLSCAASGSIFSIDAMGWYRQAPGKQRELVAEISDHTTYGDSVKGRFTISRGNAEN TVALQMNSLKPEDTGVYYCNVHHQRGWGTSITVTWGQGTLVTVSSGGGGSGGGGSGGGGSGGGGSGGGG SGGGGSGGGGSEVQLVESGGGLVQAGESLRLSCAASGSIFSIDAMGWYRQAPGKQRELVAEISDHTTYGDSVK GRFTISRGNAENTVALQMNSLKPEDTGVYYCNVHHQRGWGTSITVTWGQGTLVTVSSGGGGSGGGGSGGG GSGGGGSGGGGSGGGGSGGGGSEVQVESGGGLVQAGESLRLSCAASGSIFSIDAMGWYRQAPGKQRELVA EISDHTTYGDSVKGRFTISRGNAENTVALQMNSLKPEDTGVYYCNVHHQRGWGTSITVTWGQGTLVTVSSGG VGGSGGGGSGGGGSGGGGSGGGGSGGGGSGGGGSEVQLVESGGGLVQPGNSLRLSCAASGFTFSSFGMSWV RQAPGKGLEWVSSISGSGSDTLYADSVKGRFTISRDNAKTTLYLQMNSLRPEDTAVYYCTIGGSLSRSSQGTLVT VSS |
| A023100022 | 212 | EVQLVESGGGLVQPGGSLRLSCAASETIFSIDSMAWYRQAPGKQRELVAAITGGGSPNYADSVKGRFTISSDVA KRTVYLQMNSLKPEDIAVYYCNAEGQAGWGTALMDYWGKGTLVTVSSGGGGSGGGGSGGGGSGGGGSGG GGSGGGGSEVQLVESGGGLVQPGGSLRLSCAASETIFSIDSMAWYRQAPGKQRELVAAITGGGSPNY ADSVKGRFTISSDVAKRTVYLQMNSLKPEDTAVYYCNAEGQAGWGTALMDYWGKGTLVTVSSGGGGSGGG GSGGGGSGGGGSGGGGSGGGGSEVQLVESGGGLVQPGGSLRLSCAASETIFSIDSMAWYRQAPGKQ RELVAAITGGGSPNYADSVKGRFTISSDVAKRTVYLQMNSLKPEDTAVYYCNAEGQAGWGTALMDYWGKGTL VTVSSGGGGSGGGGSGGGGSGGGGSGGGGSGGGGSGGGGSEVQLVESGGGLVQPGNSLRLSCAASGFTFSS FGMSWVRQAPGKGLEWVSSISGSGSDTLYADSVKGRFTISRDNAKTILYLQMNSLRPEDTAVYYCTIGGSLSRS SQGTLVTVSS |
| A023100025 | 213 | EVQLVESGGGLVQAGGSLRLSCTGSRSIFSTYAMAWHRQAPGKQRELVGFIYWGGTTTYSDSVKGRFTISRDN AKNTMYLQMNSLKPEDAGVYYCNIYGSYALPWGQGTLVTVSSGGGGSGGGGSGGGGSGGGGSGGGGSGGG GSGGGGSEVQLVESGGGLVQAGGSLRLSCTGSRSIFSTYAMAWHRQAPGKQRELVGFIYWGGTTTYSDSVK GRFTISRDNAKNTMYLQMNSLKPEDAGVYYCNIYGSYALPWGQGTLVTVSSGGGGSGGGGSGGGGSGGGGS GGGGSGGGGSGGGGSEVQLVESGGGLVQAGGSLRLSCTGSRSIFSTYAMAWHRQAPGKQRELVGFIYWGGT TTYSDSVKGRFTISRDNAKNIMYLQMNSLKPEDAGVYYCNIYGSYALPWGQGTLVTVSSGGGGSGGGGSGGG GSGGGGSGGGGSGGGGSGGGGSEVQLVESGGGLVQPGNSLRLSCAASGFTFSSFGMSWVRQAPGKGLEWV SSISGSGSDTLYADSVKGRFTISRDNAKTTLYLQMNSLRPEDTAVYYCTIGGSLSRSSQGTLVTVSS |
| A023100029 | 214 | EVQLVESGGDLVQPGGSLRLSCAASGSVFSINDMGWFRQAPGKQRELVADIISRGVTNYADSVKGRFTISGDPA KNTVYLQMNSLKPEDTAVYYCNAHISTGWGRPHNNYWGQGTLVTVSSGGGGSGGGGSGGGGSGGGGSGG GGSGGGGSGGGGSEVQLVESGGDLVQPGGSLRLSCAASGSVFSINDMGWFRQAPGKQRELVADIISRGVTNY ADSVKGRFTISGDPAKNTVYLQMNSLKPEDTAVYYCNAHISTGWGRPHNNYWGQGTLVTVSSGGGGSGGGG SGGGGSGGGGSGGGGSGGGGSGGGGSEVQLVESGGDLVQPGGSLRLSCAASGSVFSINDMGWFRQAPGKQ RELVADIISRGVTNYADSVKGRFTISGDPAKNTVYLQMNSLKPEDTAVYYCNAHISTGWGRPHNNYWGQGTLV TVSSGGGGSGGGGSGGGGSGGGGSGGGGSGGGGSGGGGSEVQLVESGGGLVQPGNSLRLSCAASGFTFSSF |

TABLE A-11-continued

Amino acid sequences of selected multivalent anti-GITR Nanobodies®

| Name | ID | Amino acid sequence |
|---|---|---|
| | | GMSWVRQAPGKGLEWVSSISGSGSDTLYADSVKGRFTISRDNAKTTLYLQMNSLRPEDTAVYYCTIGGSLSRSS QGTLVTVSS |
| A023100030 | 215 | EVQLVESGGGLVQPGGSLRLSCAASGTIFSISTMGWYRQAPGKQREVVAVTSGFSTNYSSAVKGRFTLSRDPAK NIVFLQMNSLQPEDTATYYCNAYLSLAWRDPDRDYWGQGTLVTVSSGGGGSGGGGSGGGGSGGGGSGGG GSGGGGSGGGGSEVQLVESGGGLVQPGGSLRLSCAASGTIFSISTMGWYRQAPGKQREVVAVTSGFSTNYSSA VKGRFTLSRDPAKNTVFLQMNSLQPEDTATYYCNAYLSLAWRDPDRDYWGQGTLVTVSSGGGGSGGGGSGG GGSGGGGSGGGGSGGGGSGGGGSEVQLVESGGGLVQPGGSLRLSCAASGTIFSISTMGWYRQAPGKQREVV AVTSGFSTNYSSAVKGRFTLSRDPAKNTVFLQMNSLQPEDTATYYCNAYLSLAWRDPDRDYWGQGTLVTVSSG GGGSGGGGSGGGGSGGGGSGGGGSGGGGSGGGGSEVQLVESGGGLVQPGNSLRLSCAASGFTFSSFGMS WVRQAPGKGLEWVSSISGSGSDTLYADSVKGRFTISRDNAKTILYLQMNSLRPEDTAVYYCTIGGSLSRSSQGTL VTVSS |
| A023100032 | 216 | EVQLVESGGGLVQPGGSLRLSCAASETIFSIDSMAWYRQAPGKQRELVAAITGGGSPNYADSVKGRFTISSDVA KRIVYLQMNSLKPEDTAVYYCNAEGQAGWGTALMDYWKGTLVTVSSGGGGSGGGSEVQLVESGGGLVQP GGSLRLSCAASETIFSIDSMAWYRQAPGKQRELVAAITGGGSPNYADSVKGRFTISSDVAKRTVYLQMNSLKPE DTAVYYCNAEGQAGWGTALMDYWKGTLVFVSSGGGGSGGGSEVQLVESGGGLVQPGNSLRLSCAASGFTF SSFGMSWVRQAPGKGLEWVSSISGSGSDTLYADSVKGRFTISRDNAKTTLYLQMNSLRPEDTAVYYCTIGGSLS RSSQGTLVTVSS |
| A023100034 | 217 | EVQLVESGGGLVQPGGSLRLSCAASETIFSIDSMAWYRQAPGKQRELVAAITGGGSPNYADSVKGRFTISSDVA KRTVYLQMNSLKPEDTAVYYCNAEGQAGWGTALMDYWKGTLVTVSSGGGGSGGGGSGGGGSGGGGSGG GGSGGGGSGGGGSEVQLVESGGGLVQPGGSLRLSCAASETIFSIDSMAWYRQAPGKQRELVAAITGGGSPNY ADSVKGRFTISSDVAKRTVYLQMNSLIKPEDTAVYYCNAEGQAGVVGTALMMANGKGTLVTVSSGGGGSGGG GSGGGGESGGGGSGGGGSGGGGSGGGESEVQLVESGGGLVQPGNSLRLSCAASGFTFSSFGMSWVRQAPGK GLEMSSISGSGSDTLYADSVKGRFTISRDNAKTILYLQMNSLRPEDTAVYYCTIGGSLSRSSQGTLVTVSS |
| A023100035 | 218 | EVQLVESGGGLVQPGGSLRLSCAASETIFSIDSMAWYRQAPGKQRELVAAITGGGSPNYADSVKGRFTISSDVA KRTVYLQMNSLKPEDTAVYYCNAEGQAGWGTALMDYWKGTLVTVSSGGGGSGGGSEVQLVESGGGLVQP GGSLRLSCAASETIFSIDSMAWYRQAPGKQRELVAAITGGGSPNYADSVKGRFTISSDVAKRIVYLQMNSLKPE DTAVYYCNAEGQAGWGTALMDYWKGTLVFVSSGGGGSGGGSEVQLVESGGGLVQPGGSLRLSCAASETIF SIDSMAWYRQAPGKQRELVAAITGGGSPNYADSVKGRFTISSDVAKRTVYLQMNSLKPEDTAVYYCNAEGQA GWGTALMDYWKGTLVTVSSGGGGSGGGSEVQLVESGGGLVQPGNSLRLSCAASGFTFSSFGMSWVRQAP GKGLEWVSSISGSGSDTLYADSVKGRFTISRDNAKTTLYLQMNSLRPEDTAVYYCTIGGSLSRSSQGTLVTVSS |
| A023100045 | 219 | EVQLVESGGGLVQPGGSLRLSCAASGSIFSIDSMGWYRQAPGKQRELVAAITSSTNYADSVKGRFTISRDNAKN TVYLQMNSLKPEDTAVYYCNLEGQAGWGTALINYWGKGTLVTVSSAAAEVQLVESGGGLVQPGGSLRLSCAA SGSIFSIDSMGWYRQAPGKQRELVAAITSSTNYADSVKGRFTISRDNAKNTVYLQMNSLKPEDTAVYYCNLEGQ AGWGTALINYWGKGTLVTVSSGGGGSGGGSEVQLVESGGGLVQPGNSLRLSCAASGFTFSSFGMSWVRQAP GKGLEWVSSISGSGSDTLYADSVKGRFTISRDNAKTTLYLQMNSLRPEDTAVYYCTIGGSLSRSSQGTLVTVSS |
| A023100082 | 220 | EVQLVESGGGLVQPGGSLRLSCAASGSIFSIDSMGWYRQAPGKQRELVAAITSSTNYADSVKGRFTISRDNAKN TVYLQMNSLKPEDTAVYYCNLEGQAGWGTALINYWGKGTLVTVSSAAAEVQLVESGGGLVQPGGSLRLSCAA SGSIFSIDSMGWYRQAPGKQRELVAAITSSTNYADSVKGRFTISRDNAKNTVYLQMNSLKPEDTAVYYCNLEGQ AGWGTALINYWGKGTLVTVSSAAAEVQLVESGGGLVQPGNSLRLSCAASGFTFSSFGMSWVRQAPGKGLEW VSSISGSGSDTLYADSVKGRFTISRDNAKTTLYLQMNSLRPEDTAVYYCTIGGSLSRSSQGTLVTVSS |
| A023100083 | 221 | EVQLVESGGGLVQPGGSLRLSCAASGSIFSIDSMGWYRQAPGKQRELVAAITSSTNYADSVKGRFTISRDNAKN TVYLQMNSLKPEDTAVVYCNLEGQAGWGTALINYVVGKGTLVTVSSGGGGSGGGSEVQLVESGGGLVQPGGS LRLSCAASGSIFSIDSMGWYRQAPGKQRELVAAITSSTNYADSVKGRIMSRDNAKNTVYLQMNSLKPEDTAVYY CNLEGQAGWGTALINYWGKGTLVTVSSGGGGSGGGSEVQLVESGGGLVQPGNSLRLSCAASGFTFSSFGMS WVRQAPGKGLEWVSSISGSGSDTLYADSVKGRFTISRDNAKTTLYLQMNSLRPEDTAVYYCTIGGSLSRSSQGTL VTVSS |
| A023100084 | 222 | EVQLVESGGGLVQPGGSLRLSCAASGSIFSIDSMGWYRQAPGKQRELVAAITSSTNYADSVKGRFTISRDNAKN TVYLQMNSLKPEDTAVYYCNLEGQAGWGTALINYWGKGTLVTVSSGGGGSGGGSEVQLVESGGGLVQPGGS LRLSCAASGSIFSIDSMGWYRQAPGKQRELVAAITSSTNYADSVKGRFTISRDNAKNTVYLQMNSLKPEDTAVYY CNLEGQAGWGTALINYWGKGTLVIVSSGGGGSGGGSEVQLVESGGGLVQPGGSLRLSCAASGSIFSIDSMGW YRQAPGKQRELVAAITSSTNYADSVKGRFTISRDNAKNTVYLQMNSLKPEDTAVYYCNLEGQAGWGTALINYW GKGTLVTVSSGGGGSGGGSEVQLVESGGGLVQPGNSLRLSCAASGFTFSFGMSWVRQAPGKGLEWVSSISG SGSDTLYADSVKGRFTISRDNAKTILYLQMNSLRPEDTAVYYCTIGGSLSRSSQGTLVTVSS |
| A023100085 | 223 | EVQLVESGGGLVQPGGSLRLSCAASGSIFSIDSMGWYRQAPGKQRELVAAITSSTNYADSVKGRFTISRDNAKN TVYLQMNSLKPEDTAVYYCNLEGQAGWGTALINYWGKGTLVTVSSAAAEVQLVESGGGLVQPGGSLRLSCAA SGSIFSIDSMGWYRQAPGKQRELVAAITSSTNYADSVKGRFTISRDNAKNTVYLQMNSLKPEDTAVYYCNLEGQ AGWGTALINYWGKGTLVTVSSAAAEVQLVESGGGLVQPGGSLRLSCAASGSIFSIDSMGWYRQAPGKQRELV AAITSSTNYADSVKGRFTISRDNAKNTVYLQMNSLKPEDTAVYYCNLEGQAGWGTALINYWGKGILVTVSSAA AEVQLVESGGGLVQPGNSLRLSCAASGFTFSSFGMSWVRQAPGKGLEMSSISGSGSDTLYADSVKGRFTISRD NAKTTLYLQMNSLRPEDTAVYYCTIGGSLSRSSQGTLVTVSS |
| A023100012 | 224 | EVQLVESGGGLVQAGGSLRLSCAASGSIFSFIVMGWYRQAPGEQRALVATVTSGGDIFYVDSVKDRFTISRDNA KNTVYLQMNSLKPEDTAVYFCYFTKVSPYKETTWGQGTLVTVSSGGGGSGGGGSGGGGSGGGGSGGGGSGG GGSGGGGSEVQLVESGGGLVQAGGSLRLSCAASGSIFSFIVMGWYRQAPGEQRALVATVTSGGDTFYVDSVK DRFTISRDNAKNTVYLQMNSLKPEDTAVYFCYFTKVSPYKETTWGQGTLVTVSSGGGGSGGGGSGGGGSGGG GSGGGGSGGGGSGGGGSEVCILVESGGGLVQPGNSLRLSCAASGFTFSSFGMSWVRQAPGKGLEWVSSISGS GSDTLYADSVKGRFTISRDNAKTTLYLQMNSLRPEDTAVYYCTIGGSLSRSSQGTLVTVSS |

TABLE A-11-continued

Amino acid sequences of selected multivalent anti-GITR Nanobodies®

| Name | ID | Amino acid sequence |
|---|---|---|
| A023100020 | 225 | EVQLVESGGGLVQAGGSLRLSCAASGSIFSFIVMGWYRQAPGEQRALVATVTSGGDTFYVDSVKDRFTISRDNA KNTVYLQMNSLKPEDTAVYFCYFTKVSPYKETTWGQGTLVTVSSGGGGSGGGGSGGGGSGGGGSGGGGSGG GGSGGGGSEVQLVESGGGLVQAGGSLRLSCAASGSIFSFIVMGWYRQAPGEQRALVATVTSGGDTFYVDSVK DRFTISRDNAKNIVYLQMNSLKPEDTAVYFCYFIKVSPYKETTWGQGTLVIVSSGGGGSGGGGSGGGGSGGG GSGGGGSGGGGSGGGGSGGGGSGGGGSEVQLVESGGGLVQAGGSLRLSCAASGSIFSFIVMGWYRQAPGEQRALVATVISG GDTFYVDSVKDRFTISRDNAKNTVYLQMNSLKPEDTAVYFCYFTKVSPYKETTWGQGTLVTVSSGGGGSGGGG SGGGGSGGGGSGGGGSGGGGSGGGGSEVQLVESGGGLVQPGNSLRLSCAASGFTFSSFGMSWVRQAPGKG LEWVSSISGSGSDTLYADSVKGRFTISRDNAKTTLYLQMNSLRPEDTAVYYCTIGGSLSRSSQGTLVTVSS |
| A023100031 | 226 | EVQLVESGGGLVQAGGSLRLSCAASGSIFSFIVMGWYRQAPGEQRALVATVTSGGDTFYVDSVKDRFTISRDNA KNTVYLQMNSLKPEDTAVYFCYFTKVSPIKETTWGQGTLVTVSSGGGGSGGGSEVQLVESGGGLVQAGGSLRL SCAASGSIFSFNMGWYRQAPGEQRALVATVTSGGDTFYVDSVKDRFTISRDNAKNTVYLQMNSLKPEDTAVYF CYFTKVSPYKETTWGQGTLVTVSSGGGGSGGGSEVQLVESGGGLVQPGNSLRLSCAASGFTFSSFGIVISWVRQ APGKGLEWVSSISGSGSDTLYADSVKGRTISRDNAKTTLYLQMNSLRPEDTAVYYCTIGGSLSRSSQGTLVTVSS |
| A023100036 | 227 | EVQLVESGGGLVQAGGSLRLSCAASGSIFSFIVMGWYRQAPGEQRALVATVTSGGDTFYVDSVICRFTISRDNA KNTVYLQMNSLKPEDTAVYFCYFTKVSPYKETTWGQGTLVIVSSGGGGSGGGSEVQLVESGGGLVQAGGSLRL SCAASGSIFSFIVMGWYRQAPGEQRALVATVTSGGDTFYVDSVKDRFTISRDNAKNIVYLQMNSLKPEDTAVYF CYFTKVSPYKETTWGQGTLVTVSSGGGGSGGGSEVQLVESGGGLVQAGGSLRLSCAASGSIFSFIVMGWYRQA PGEQRALVATVTSGGDTFYVDSVKDRFTISRDNAKNTVYLQMNSLKPEDTAVYFCYFTKVSPYKETTWGQGTLV TVSSGGGGSGGGSEVQLVESGGGLVQPGNSLRLSCAASGFTFSSFGMSWVRQAPGKGLENVSSISGSGSDTLY ADSVKGRFTISRDNAKTTLYLQMNSLRPEDTAVYYCTIGGSLSRSSQGTLVTVSS |
| A023100101 | 285 | DVQLVESGGGVVQPGGSLRLSCAASETIFSIDSMAWYRQAPGKQRELVAAITGGGSPNYADSVKGRFTISSDVS KRTVYLQMNSLRPEDTALYYCNAEGQAGWGTALLDYWGQGTLVTVSSGGGGSGGGSEVQLVESGGGVVQP GGSLRLSCAASETIFSIDSMAWYRQAPGKQRELVAAITGGGSPNYADSVKGRFTISSMKRTVYLQMNSLRPE DTALYYCNAEGQAGWGTALLDYWGQGTLVTVSSGGGGSGGGSEVQLVESGGGVVQPGGSLRLSCAASETIFS IDSMAWYRQAPGKQRELVAAITGGGSPNYADSVKGRFTISSDVSKRTVYLQMNSLRPEDTALYYCNAEGQAG WGTALLDYWGQGTLVTVSSGGGGSGGGSGGGGSGGGGSGGGGSGGGGSEVQLVESGGGVVQP GGSLRLSCAASGFTFRSFGMSWVRQAPGKGPEWVSSISGSGSDTLYADSVKGRFTISRDNSKNTLYLQMNSLRP EDTALYYCTIGGSLSRSSQGTLVTVSSA |
| A023100105 | 286 | DVQLVESGGGVVQPGGSLRLSCAASGSIFSIDSMGWYRQAPGKQRELVAAITSSTNYADSVKGRFTISRDNSKN TVYLQMNSLRPEDTALYYCNLEGQAGWGTALINYWGQGTLVTVSSGGGGSGGGSEVQLVESGGGVVQPGGS LRLSCAASGSIFSIDSMGWYRQAPGQRELVAAITSSTNYADSVKGRFTISRDNSKNTVYLQMNSLRPEDTALYY CNLEGQAGWGTALINYWGQGTLVTVSSGGGGSGGGSEVQLVESGGGVVQPGGSLRLSCAASGSIFSIDSMG WYRQAPGKQRELVAAITSSTNYADSVKGRFTISRDNSKNTVYLQMNSLRPEDTALYYCNLEGQAGWGTALINY WGQGTLVTVSSGGGGSGGGSGGGGSGGGGSGGGGSGGGGSEVQLVESGGGVVQPGGSLRLSCA ASGFTFRSFGMSWVRQAPGKGPEWVSSISGSGSDTLYADSVKGRFTISRDNSKNTLYLQMNSLRPEDTALYYCT IGGSLSRSSQGTLVTVSSA |
| A023100107 | 287 | DVQLVESGGGVVQPGGSLRLSCAASETIFSIDSMAWYRQAPGKQRELVAAITGGGSPNYADSVKGRFTISSDVS KRTVYLQMNSLRPEDTALYYCNAEGQAGWGTALLDYWGQGTLVTVSSGGGGSGGGSEVQLVESGGGVVQP GGSLRLSCAASETIFSIDSMAWYRQAPGKQRELVAAITGGGSPNYADSVKGRFTISSDVSKRTVYLQMNSLRPE DTALYYCNAEGQAGWGTALLDYWGQGTLVIVSSGGGGSGGGSEVQLVESGGGVVQPGGSLRLSCAASETIFS IDSMAWYRQAPGKQRELVAAITGGGSPNYADSVKGRTISSDVSKRTVYLQMNSLRPEDTALYYCNAEGQAG WGTALLDYWGQGTLVTVSSGGGGSGGGSEVQLVESGGGVVQPGGSLRLSCAASETIFSIDSMAWYRQAPGK QRELVAAITGGGSPNYADSVKGRFTISSDVSKRTVYLQMNSLRPEDTALYYCNAEGQAGWGTALLDYWGQGT LVTVSSGGGGSGGGGSGGGGSGGGGSGGGGSGGGGSEVQLVESGGGVVQPGGSLRLSCAASGFTF RSFGMSWVRQAPGKGPEWVSSISGSGSDTLYADSVKGRFTISRDNSKNTLYLQMNSLRPEDTALYYCTIGGSLS RSSQGTLVTVSSA |
| A023100118 | 288 | DVQLVESGGGVVQPGGSLRLSCAASETIFSIDSMAWYRQAPGKQRELVAAITGGGSPNYADSVKGRFTISSDVS KRTVYLQMNSLRPEDTALYYCNAEGQAGWGTALLDYWGQGTLVTVSSGGGGSGGGSEVQLVESGGGVVQP GGSLRLSCAASETIFSIDSMAWYRQAPGKQRELVAAITGGGSPNYADSVKGRFTISSDVSKRTVYLQMNSLRPE DTALYYCNAEGQAGWGTALLDYWGQGTLVTVSSGGGGSGGGSEVQLVESGGGVVQPGGSLRLSCAASETIFS IDSMAWYRQAPGKQRELVAAITGGGSPNYADSVKGRFTISSDVSKRTVYLQMNSLRPEDTALYYCNAEGQAG WGTALLDYWGQGTLVTVSSGGGGSGGGSEVQLVESGGGVVQPGGSLRLSCAASETIFSIDSMAWYRQAPGK QRELVAAITGGGSPNYADSVKGRMSSDVSKRTVYLQMNSLRPEDTALYYCNAEGQAGWGTALLDYWGQGTLVTVSSGGGGSGGGG SGGGGSGGGGSGGGGSGGGGSEVQLVESGGGVVQPGGSLRLSCAASGFTFRSFGMSWVRQAPGK GPEWVSSISGSGSDTLYADSVKGRFTISRDNSKNTLYLQMNSLRPEDTALYYCTIGGSLSRSSQGTLVTVSSA |
| A023100127 | 289 | DVQLVESGGGVVQPGGSLRLSCAASGSIFSIDSMGWYRQAPGKQRELVAAITSSTNYADSVKGRFTISRDNSKN TVYLQMNSLRPEDTALYYCNLEGQAGWGTALINYWGQGTLVTVSSGGGGSGGGSEVQLVESGGGVVQPGGS LRLSCAASGSIFSIDSMGWYRQAPGKQRELVAAITSSTNYADSVKGRFTISRDNSKNTVYLQMNSLRPEDTALYY CNLEGQAGWGTALINYWGQGTLVTVSSGGGGSGGGSEVQLVESGGGVVQPGGSLRLSCAASGSIFSIDSMG WYRQAPGKQRELVAAITSSTNYADSVKGRFTISRDNSKNTVYLQMNSLRPEDTALYYCNLEGQAGWGTALINY WGQGTLVTVSSGGGGSGGGSGGGGSEVQLVESGGGVVQPGGSLRLSCAASGSIFSIDSMGWYRQAPGKQRELVAAIT SSTNYADSVKGRFTISRDNSKNTVYLQMNSLRPEDTALYYCNLEGQAGWGTALINYWGQGTLVTVSSGGGGS GGGGSGGGGSGGGGSGGGGSGGGGSGGGGSEVQLVESGGGVVQPGGSLRLSCAASGFTFRSFGMSWVRQ APGKGPEWVSSISGSGSDTLYADSVKGRFTISRDNSKNTLYLQMNSLRPEDTALYYCTIGGSLSRSSQGTLVTV SSA |

TABLE A-11-continued

Amino acid sequences of selected multivalent anti-GITR Nanobodies®

| Name | ID | Amino acid sequence |
|---|---|---|
| A023100129 | 290 | DVQLVESGGGVVQPGGSLRLSCAASGSIFSIDSMGWYRQAPGKQRELVAAITSSTNYADSVKGRFTISRDNSKN<br>TVYLQMNSLRPEDTALYYCNLEGQAGWGTALINYINGQGTLVTVSSGGGGSGGGGSEVQLVESGGGVVQPGGS<br>LRLSCAASGSIFSIDSMGWYRQAPGKQRELVAAITSSTNYADSVKGRFTISRDNSKNTVYLQMNSLRPEDTALYY<br>CNLEGQAGWGTALINYWGQGTLVTVSSGGGGSGGGGSEVQLVESGGGVVQPGGSLRLSCAASGSIFSIDSMG<br>WYRQAPGKQRELVAAITSSINYADSVKGRFTISRDNSKNTVYLQMNSLRPEDTALYYCNLEGQAGWGTALINY<br>WGQGTLVTVSSGGGGSGGGGSEVQLVESGGGVVQPGGSLRLSCAASGSIFSIDSMGWYRQAPGKQRELVAAIT<br>SSTNYADSVKGRFTISRDNSKNTVYLQMNSLRPEDTALYYCNLEGQAGWGTALINYWGQGTLVTVSSGGGGS<br>GGGGSEVQLVESGGGVVQPGGSLRLSCAASGSIFSIDSMGWYRQAPGKQRELVAAITSSTNYADSVKGRFTISRD<br>NSKNTVYLQMNSLRPEDTALYYCNLEGQAGWGTALINYWGQGTLVTVSSGGGGSGGGGSGGGGSGGGGSG<br>GGGSGGGGSGGGGSEVQLVESGGGVVQPGGSLRLSCAASGFTFRSFGMSWVRQAPGKPEWVSSISGSGSD<br>TLYADSVKGRFTISRDNSKNTLYLQMNSLRPEDTALYYCTIGGSLSRSSQGTLVTVSSA |

TABLE A-12

Various amino acid sequences

| Name | ID | Amino acid sequence |
|---|---|---|
| IRR00077 | 228 | EVQLVESGGGSVQAGGSLRLSCAASGYTIGPYCMGWFRQAPGKEREGVAAINMGGGITYYADSVKGRFTISQ<br>DNAKNTVYLLMNSLEPEDTAIYCAADSTIYASYYECGHGLSTGGYGYDSWGQGTLVTVSSGGGGSGGGGSGG<br>GGSGGGGSGGGGSGGGGSGGGGSEVQLVESGGGSVQAGGSLRLSCAASGYTIGPYCMGWFRQAPGKEREG<br>VAAINMGGGITYYADSVKGRFTISQDNAKNTVYLLMNSLEPEDTAIYYCAADSTIYASYYECGHGLSTGGYGYDS<br>WGQGTLVTVSSGGGGSGGGGSGGGGSGGGGSGGGGSGGGGSEVQLVESGGGSVQAGGSLRLSCA<br>ASGYTIGPYCMGWERQAPGKEREGVAAINMGGGITYYADSVKGRFTISQDNAKNTVYLLMNSLEPEDTAIYYC<br>AADSTIYASYYECGHGLSTGGYGYDSWGQGTLVTVSSGGGGSGGGGSGGGGSGGGGSGGGGSGGGGSGGG<br>GSEVQLVESGGGLVQPGNSLRLSCAASGFTFSSFGMSWVRQAPGKGLEWVSSISGSGSDTLYADSVKGRFTISR<br>DNAKTTLYLQMNSLRPEDTAVYYCTIGGSLSRSSQGTLVTVSS |
| 5A03-human CL<br>(kappa) (light<br>chain of construct<br>A-0231-00_TP008) | 229 | MSVPTQVLGLLLLWLTDARCEVQLVESGGGLVQPGGSLRLSCAASETIFSIDSMAWYRQAPGKQRELVAAITG<br>GGSPNYADSVKGRFTISSDVAKRTVYLQMNSLKPEDTAVYYCNAEGQAGWGTALMDYWGKGTLVTVSSRTV<br>AAPSVFIFPPSDEQLKSGTASVVCLLNNFYPREAKVQWKVDNALQSGNSQESVFEQDSKDSTYSLSSTLTLSKAD<br>YEKHKVYACEVTHQGLSSPVTKSFNRGEC |
| 5A03-human CHI-3<br>(IgG1) (heavy<br>chain of construct<br>A-0231-00_TP008) | 230 | MEWSWVFLFFLSVTTGVHSEVQLVESGGGLVQPGGSLRLSCAASETIFSIDSMAWYRQAPGKQRELVAAITGG<br>GSPNYADSVKGRFTISSDVAKRTVYLQMNSLKPEDTAVYYCNAEGQAGWGTALMDYWGKGTLVTVSSASTKG<br>PSVFPLAPSSKSTSGGTAALGCLVKDYFPEPVTVSWNSGALTSGVHTFPAVLQSSGLYSLSSVVTVPSSSLGTQ<br>TYICNVNHKPSNTKVDKKVEPICSCDKTHTCPPCPAPELLGGPSVFLFPPKPKDTLMISRTPEVTCVVVDVSHE<br>DPEVKFNWYVDGVEVHNAKIKPREEQYNSTYRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTIPPVLDSDGSFFLYSKLTVDKSRWQ<br>QGNVFSCSVMHEALHNHYTQKSLSLSPGK |
| 5A03-rat CL<br>(lambda) | 266 | MSVPTQVLGIILLWLTDARCEVQLVESGGGLVQPGGSLRLSCAASETIFSIDSMAWYRCIAPGKQRELVAAITGG<br>GSPNYADSVKGRFTISSDVAKRTVYLQMNSLKPEDTAVYYCNAEGQAGWGTALNADYWGKGTLVTVSSQPK<br>STPQLTVFPRSTEELQGNKATLVCLISDPIPSDVEVAWKANGAPISQGVDTANFIKQGNKYIASSFLRLTAEQW<br>RSRNSFTCQVTHEGNTVEKSLSPAECV |
| 5A03-rat CH1-3<br>(IgG2b) | 267 | MEWSWVFLFFLSVTTGVHSEVQLVESGGGLVQPGGSLRLSCAASETIFSIDSMAWYRQAPGKQRELVAAITGG<br>GSPNYADSVKGRFTISSDVAKRTVYLQMNSLKPEDTAVYYCNAEGQAGWGTALMDYWGKGTLVTVSSAQTT<br>APSVYPLAPGCGDTTSSTVTLGCLVKGYFPEPVTVTWNSGALSSDVHTFPAVLQSGLYTLTSSVTSSTWPSQTVT<br>CNVAHPASSTKVTDKKVERRNGGIGHKCPTCPTCHKCPVPELLGGPSVFIFPPKPKDILLISQNAKVICVVVDV<br>SEEEPDVQFSWFVNNVEVHTAQTQPREEQYNSTFRVVSALPIQHQDWMSGKEFKCKVNNKALPSPIEKTISKP<br>KGLVRKPQVYVMGPPTEQLTEQTVSLTCLTSGFLPNDIGVEWTSNGHIEKNYKNTEPVMDSGSFFMYSKLNV<br>ERSRWDSRAPFVCSVVHEGLHNHHVEKSISRPPGK |
| A023100090-human<br>CL (kappa) | 291 | MSVPTQVLGLLIIWLTDARCEVQLVESGGGVVQPGGSLRLSCAASETIFSIDSMAWYRQAPGKQRELVAAITGG<br>GSPNYADSVKGRFTISSDVSKRTVYLQMNSLRPEDTALYYCNAEGQAGWGTALLDYWGQGTLVIVSSRTVA<br>APSVFIFPPSDEQLKSGTASVVCLLNNFYPREAKVQWKVDNALQSGNSQESVTEQDSKDSTYSLSSTLTLSKADY<br>EKHKVYACEVTHQGLSSPVTKSFNRGEC |
| A023100090-human<br>CH1-3 (IgG1) | 292 | MEWSWVFLFFLSVITGVHSEVQLVESGGGVVQPGGSLRLSCAASETIFSIDSMAWYRQAPGKQRELVAAITGG<br>GSPNYADSVKGRFTISSDVSKRTVYLQMNSLRPEDTALYKNAEGQAGWGTALLDYWGQGTLVTVSSASTKGP<br>SVFPLAPSSKSTSGGTAALGCLVKDYFPEPVTVSWNSGALTSGVHTFPAVLQSSGLYSLSSWTVPSSSLGTQTYIC<br>NVNHKPSNTKVDKKVEPKSCDKTHTCPPCPAPELLGGPSVFLFPPKPKDTLMISRTPEVTCVVVDVSHEDPEVKF<br>NWYVDGVEVHNAKTKPREEQYNSTYRWSVLTVLHQDWLNGKEYKCKVSNKALPAPIEKTISKAKGQPREPQV<br>YTLPPSRDELTKNQVSLTCLVKGFYPSDIAVEWESNGQPENNYKTTPPVLDSDGSFFLYSKLTVDKSRWQQGNV<br>FSCSVMHEALHNHYTQKSLSLSPGK |

TABLE A-13

GITR sequences from various species ("ID" refers to the SEQ ID NO as used herein)

| Prot ID | Species | ID | Sequence |
|---|---|---|---|
| Q9Y5U5 | Homo sapiens | 231 | MAQHGAMGAFRALCGLALLCALSLGQRPTGGPCGPGRLLLGTGTDARCCRVHTTRCCRDYPGEECCSE WDCMCVQPEFHCGDPCCTTCRHHPCPPGQGVQSQGKFSFGFQCIDCASGTFSGGHEGHCKPWTDCTQ FGFLTVFPGNKTHNAVCVPGSPPAEPLGWLTVVLLAVAACVLLLTSAQLGLHIWQLRSQCMWPRETQLLL EVPPSTEDARSCQFPEEERGERSAEEKGRLGDLWV |
| O35714 | Mus musculus | 232 | MGAWAMLYGVSMLCVLDLGQPSVVEEPGCGPGKVQNGSGNNTRCCSLYAPGKEDCPKERCICVTPEYH CGDPQCKICKHYPCQPGQRVESQGDIVFGFRCVACAMGTFSAGRDGHCRLWTNCSQFGFLTMFPGNKT HNAVCIPEPLPTEQYGHLTVIFLVMAACIFFLTTVQLGLHIWQLRRQHMCPRETQPFAEVQLSAEDACSFQ FPEEERGEQTEEKCHLGGRWP |
| XP_005545180 | Macaca fascicularis | 233 | MCACGTLCCLALLCAASLGQRPTGGPCGPGRLLLGTGKDARCCRVHPTRCCRDYQSEECCSEWDCVCV QPEFHCGNPCCTTCQHHPCPSGQGVQPQGKFSFGFRCVDCALGTFSRGHDGHCKPWTDCTQFGFLTVF PGNKTHNAVCVPGSPPAEPPGWLTIVLLAVAACVLLLTSAQLGLHIWQLGSQPTGPRETQLLLEVPPSTED ASSCQFPEEERGERLAEEKGRLGDLWV |

TABLE A-14

Serum albumin binding ISVD sequences ("ID" refers to the SEQ ID NO as used herein)

| Name | ID | Amino acid sequence |
|---|---|---|
| Alb8 | 234 | EVQLVESGGGLVQPGNSLRLSCAASGFTFSSFGMSWVRQAPGKGLEWVSSISGSGSDTLYADS VKGRFTISRDNAKTTLYLQMNSLRPEDTAVYYCTIGGSLSRSSQGTLVTVSS |
| Alb23 | 235 | EVQLLESGGGLVQPGGSLRLSCAASGFTFRSFGMSWVRQAPGKGPEWVSSISGSGSDTLYADS VKGRFTISRDNSKNTLYLQMNSLRPEDTAVYYCTIGGSLSRSSQGTLVTVSS |
| Alb129 | 236 | EVQLVESGGGVVQPGNSLRLSCAASGFTFSSFGMSWVRQAPGKGLEWVSSISGSGSDTLYADS VKGRFTISRDNAKTTLYLQMNSLRPEDTATYYCTIGGSLSRSSQGTLVTVSSA |
| Alb132 | 237 | EVQLVESGGGVVQPGGSLRLSCAASGFTFRSFGMSWVRQAPGKGPEWVSSISGSGSDRYAD SVKGRFTISRDNSKNTLYLQMNSLRPEDTATYYCTIGGSLSRSSQGTLVTVSSA |
| Alb11 | 238 | EVQLVESGGGLVQPGNSLRLSCAASGFTFSSFGMSWVRQAPGKGLEWVSSISGSGSDTLYADS VKGRFTISRDNAKTTLYLQMNSLRPEDTAVYYCTIGGSLSRSSQGTLVTVSS |
| Alb11 (S112K)-A | 239 | EVQLVESGGGLVQPGNSLRLSCAASGFTFSSFGMSWVRQAPGKGLEWVSSISGSGSDTLYADS VKGRFTISRDNAKTTLYLQMNSLRPEDTAVYYCTIGGSLSRSSQGTLVKVSSA |
| Alb82 | 240 | EVQLVESGGGVVQPGNSLRLSCAASGFTFSSFGMSWVRQAPGKGLEWVSSISGSGSDTLYADS VKGRFTSRDNAKTTLYLQMNSLRPEDTALYYCTIGGSLSRSSQGTLVTVSS |
| Alb82-A | 241 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSSA |
| Alb82-AA | 242 | EVQLVESGGGVVQPGNSLRLSCAASGFTESSFGMSWVRQAPGKGLEWVSSISGSGSDTLYADS VKGRFTISRDNAKTTLYLQMNSLRPEDTALYYCTIGGSLSRSSQGTLVTVSSAA |
| Alb82-AAA | 243 | EVQLVESGGGVVQPGNSLRLSCAASGFTFSSFGMSWVRQAPGKGLEWVSSISGSGSDTLYADS VKGRFITSRDNAKTTLYLQMNSLRPEDTALYYCTIGGSLSRSSQGTLVTVSSAAA |
| Alb82-G | 244 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSSG |
| Alb82-GG | 245 | EVQLVESGGGVVQPGNSLRLSCAASGFTFSSFGMSWVRQAPGKGLEWVSSISGSGSDTLYADS VKGRFTISRDNAKTTLYLQIVINSLRPEDTALYYCTIGGSLSRSSQGTLVTVSSGG |
| Alb82-GGG | 246 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSSGGG |
| Alb92 | 264 | EVQLVESGGGVVQPGGSLRLSCAASGFTFRSFGIVISWVRQAPGKGPEWVSSISGSGSDTLYAD SVKGRFTISRDNSKNTLYLQMNSLRPEDTAYYYCTIGGSLSRSSQGTLVTVSS |
| Alb223 | 265 | EVQLVESGGGVVQPGGSLRLSCAASGFTFRSFGMSWVRQAPGKGPEWVSSISGSGSDRYAD SVKGRFTISRDNSKNTLYLQMNSLRPEDTATYYCTIGGSLSRSSQGTLVTVSSA |

TABLE A-15

Linker sequences ("ID" refers to the SEQ ID NO as used herein)

| Name | ID | Amino acid sequence |
|---|---|---|
| 3A linker | 247 | AAA |
| 5G5 linker | 248 | GGGGS |
| 7GS linker | 249 | SGGSGGS |
| 8GS linker | 250 | GGGGCGGGS |
| 9GS linker | 251 | GGGGSGGGS |
| 10GS linker | 252 | GGGGSGGGGS |
| 15GS linker | 253 | GGGGSGGGGSGGGGS |
| 18GS linker | 254 | GGGGSGGGGSGGGGGGS |
| 20GS linker | 255 | GGGGSGGGGSGGGGSGGGGS |
| 25G5 linker | 256 | GGGGSGGGGSGGGGSGGGGSGGGGS |
| 30GS linker | 257 | GGGGSGGGGSGGGGSGGGGSGGGGSGGGGS |
| 35GS linker | 258 | GGGGSGGGGSGGGGSGGGGSGGGGSGGGGSGGGGS |
| 40GS linker | 259 | GGGGSGGGGSGGGGSGGGGSGGGGSGGGGSGGGGSGGGGS |
| G1 hinge | 260 | EPKSCDKTHTCPPCP |
| 9GS-G1 hinge | 261 | GGGGSGGGSEPKSCDKTHTCPPCP |
| Llama upper long hinge region | 262 | EPKTPKPQPAAA |
| G3 hinge | 263 | ELKTPLGDTTHTCPRCPEPKSCDTPPPCPRCPEPKSCDTPPPCPRCPEPKSCDTPPPCPRCP |

EQUIVALENTS

The foregoing written specification is considered to be sufficient to enable one skilled in the art to practice the invention. The present invention is not to be limited in scope by examples provided, since the examples are intended as an illustration of certain aspects and embodiments of the invention. Other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The invention claimed is:

1. A method for inhibiting tumor growth, wherein said method comprises administering a pharmaceutically active amount of at least one polypeptide, wherein the polypeptide comprises at least one immunoglobulin single variable domain (ISVD) that specifically binds glucocorticoid-induced TNFR family-related receptor (GITR) with an $EC_{50}$ value of less than 200 pM, wherein the binding of said ISVD to said GITR enhances an immune response, and wherein said at least one immunoglobulin single variable domain essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 73-88; and
    (b) amino acid sequences that have 4, 3, 2, or 1 amino acid(s) difference with the amino acid sequences of SEQ ID NOs: 73-88; and/or
  (ii) CDR2 is chosen from the group consisting of:
    (c) SEQ ID NOs: 90-116; and
    (d) amino acid sequences that have 4, 3, 2, or 1 amino acid(s) difference with the amino acid sequences of SEQ ID NOs: 90-116; and/or
  (iii) CDR3 is chosen from the group consisting of:
    (e) SEQ ID NOs: 118-132 and 282-284; and
    (f) amino acid sequences that have 4, 3, 2, or 1 amino acid(s) difference with the amino acid sequences of SEQ ID NOs: 118-132 and 282-284.

2. The method according to claim 1, wherein said at least one immunoglobulin single variable domain essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 73-75; and
    (b) amino acid sequences that have 4, 3, 2, or 1 amino acid(s) difference with the amino acid sequence of SEQ ID NO: 73; and/or
  (ii) CDR2 is chosen from the group consisting of:
    (c) SEQ ID NOs: 90-98; and
    (d) amino acid sequences that have 4, 3, 2, or 1 amino acid(s) difference with the amino acid sequence of SEQ ID NO: 90; and/or
  (iii) CDR3 is chosen from the group consisting of:
    (e) SEQ ID NOs: 118-119, 123 and 282-284; and
    (f) amino acid sequences that have 2, or 1 amino acid(s) difference with the amino acid sequence of SEQ ID NO: 118.

3. The method according to claim 2, in which said at least one immunoglobulin single variable domain essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NO: 73; and
    (b) amino acid sequences that have 4, 3, 2, or 1 amino acid difference(s) with SEQ ID NO: 73, wherein
      at position 2 the T has been changed into S;
      at position 7 the D has been changed into N;
      at position 8 the S has been changed into A; and/or
      at position 10 the A has been changed into G;
  and/or
  (ii) CDR2 is chosen from the group consisting of:
    (c) SEQ ID NO: 90; and
    (d) amino acid sequences that have 4, 3, 2, or 1 amino acid difference(s) with SEQ ID NO: 90, wherein
      at position 1 the A has been changed into H, T, or G;
      at position 2 the I has been changed into M;
      at position 3 the T has been changed into S;
      at position 6 the G has been changed into S;
      at position 7 the S has been changed into R, or G; and/or
      at position 8 the P has been changed into S, T, or R;
  and/or
  (iii) CDR3 is chosen from the group consisting of:
    (e) SEQ ID NO: 118; and
    (f) amino acid sequences that have 2, or 1 amino acid difference(s) with SEQ ID NO: 118, wherein
      at position 9 the A has been changed into P;
      at position 11 the M has been changed into L, K, R, or Q; and/or
      at position 12 the D has been changed into N.

4. The method according to claim 3, in which said at least one immunoglobulin single variable domain essentially consists of 4 framework regions (FR1 to FR4, respectively) and 3 complementarity determining regions (CDR1 to CDR3, respectively), in which:
  i) CDR1 is SEQ ID NO: 73, CDR2 is SEQ ID NO: 90, and CDR3 is SEQ ID NO: 118; or ii) CDR1 is SEQ ID NO: 73, CDR2 is SEQ ID NO: 90, and CDR3 is SEQ ID NO: 123.

5. The method according to claim 1, wherein said at least one immunoglobulin single variable domain essentially consists of 4 framework regions (FR1 to FR4, respectively) and 3 complementarity determining regions (CDR1 to CDR3, respectively), in which:
CDR1 is SEQ ID NO: 73, CDR2 is SEQ ID NO: 90; and CDR3 is SEQ ID NO: 123;
CDR1 is SEQ ID NO: 73, CDR2 is SEQ ID NO: 90; and CDR3 is SEQ ID NO: 118;
CDR1 is SEQ ID NO: 74, CDR2 is SEQ ID NO: 91; and CDR3 is SEQ ID NO: 118;
CDR1 is SEQ ID NO: 74, CDR2 is SEQ ID NO: 92; and CDR3 is SEQ ID NO: 118;
CDR1 is SEQ ID NO: 74, CDR2 is SEQ ID NO: 93; and CDR3 is SEQ ID NO: 118;
CDR1 is SEQ ID NO: 74, CDR2 is SEQ ID NO: 94; and CDR3 is SEQ ID NO: 118;
CDR1 is SEQ ID NO: 74, CDR2 is SEQ ID NO: 95; and CDR3 is SEQ ID NO: 118;
CDR1 is SEQ ID NO: 75, CDR2 is SEQ ID NO: 93; and CDR3 is SEQ ID NO: 118;
CDR1 is SEQ ID NO: 74, CDR2 is SEQ ID NO: 96; and CDR3 is SEQ ID NO: 118;
CDR1 is SEQ ID NO: 74, CDR2 is SEQ ID NO: 97; and CDR3 is SEQ ID NO: 118;
CDR1 is SEQ ID NO: 74, CDR2 is SEQ ID NO: 98; and CDR3 is SEQ ID NO: 119;
CDR1 is SEQ ID NO: 73, CDR2 is SEQ ID NO: 90; and CDR3 is SEQ ID NO: 282;
CDR1 is SEQ ID NO: 73, CDR2 is SEQ ID NO: 90; and CDR3 is SEQ ID NO: 283;
CDR1 is SEQ ID NO: 73, CDR2 is SEQ ID NO: 90; and CDR3 is SEQ ID NO: 284;
CDR1 is SEQ ID NO: 76, CDR2 is SEQ ID NO: 99; and CDR3 is SEQ ID NO: 120;
CDR1 is SEQ ID NO: 77, CDR2 is SEQ ID NO: 100; and CDR3 is SEQ ID NO: 121;
CDR1 is SEQ ID NO: 78, CDR2 is SEQ ID NO: 101; and CDR3 is SEQ ID NO: 122;
CDR1 is SEQ ID NO: 76, CDR2 is SEQ ID NO: 102; and CDR3 is SEQ ID NO: 118;
CDR1 is SEQ ID NO: 77, CDR2 is SEQ ID NO: 103; and CDR3 is SEQ ID NO: 118;
CDR1 is SEQ ID NO: 76, CDR2 is SEQ ID NO: 99; and CDR3 is SEQ ID NO: 118;
CDR1 is SEQ ID NO: 78, CDR2 is SEQ ID NO: 99; and CDR3 is SEQ ID NO: 123;
CDR1 is SEQ ID NO: 79, CDR2 is SEQ ID NO: 104; and CDR3 is SEQ ID NO: 124;
CDR1 is SEQ ID NO: 76, CDR2 is SEQ ID NO: 105; and CDR3 is SEQ ID NO: 124;
CDR1 is SEQ ID NO: 76, CDR2 is SEQ ID NO: 106; and CDR3 is SEQ ID NO: 124;
CDR1 is SEQ ID NO: 80, CDR2 is SEQ ID NO: 106; and CDR3 is SEQ ID NO: 124;
CDR1 is SEQ ID NO: 81, CDR2 is SEQ ID NO: 104; and CDR3 is SEQ ID NO: 124;
CDR1 is SEQ ID NO: 82, CDR2 is SEQ ID NO: 104; and CDR3 is SEQ ID NO: 124;
CDR1 is SEQ ID NO: 83, CDR2 is SEQ ID NO: 104; and CDR3 is SEQ ID NO: 124;
CDR1 is SEQ ID NO: 84, CDR2 is SEQ ID NO: 104; and CDR3 is SEQ ID NO: 124;
CDR1 is SEQ ID NO: 83, CDR2 is SEQ ID NO: 106; and CDR3 is SEQ ID NO: 124;
CDR1 is SEQ ID NO: 83, CDR2 is SEQ ID NO: 107; and CDR3 is SEQ ID NO: 124;
CDR1 is SEQ ID NO: 83, CDR2 is SEQ ID NO: 108; and CDR3 is SEQ ID NO: 124;
CDR1 is SEQ ID NO: 83, CDR2 is SEQ ID NO: 104; and CDR3 is SEQ ID NO: 125;
CDR1 is SEQ ID NO: 85, CDR2 is SEQ ID NO: 109; and CDR3 is SEQ ID NO: 126;
CDR1 is SEQ ID NO: 86, CDR2 is SEQ ID NO: 110; and CDR3 is SEQ ID NO: 126;
CDR1 is SEQ ID NO: 85, CDR2 is SEQ ID NO: 110; and CDR3 is SEQ ID NO: 126;
CDR1 is SEQ ID NO: 87, CDR2 is SEQ ID NO: 111; and CDR3 is SEQ ID NO: 127;
CDR1 is SEQ ID NO: 77, CDR2 is SEQ ID NO: 112; and CDR3 is SEQ ID NO: 128;
CDR1 is SEQ ID NO: 77, CDR2 is SEQ ID NO: 112; and CDR3 is SEQ ID NO: 129;
CDR1 is SEQ ID NO: 77, CDR2 is SEQ ID NO: 113; and CDR3 is SEQ ID NO: 130;
CDR1 is SEQ ID NO: 77, CDR2 is SEQ ID NO: 112; and CDR3 is SEQ ID NO: 130;
CDR1 is SEQ ID NO: 88, CDR2 is SEQ ID NO: 114; and CDR3 is SEQ ID NO: 131;
CDR1 is SEQ ID NO: 88, CDR2 is SEQ ID NO: 115; and CDR3 is SEQ ID NO: 131; or
CDR1 is SEQ ID NO: 88, CDR2 is SEQ ID NO: 116; and CDR3 is SEQ ID NO: 132.

6. The method according to claim 1, wherein said at least one immunoglobulin single variable domain essentially consists of a dAb, an immunoglobulin that is suitable for use as a dAb, a VHH sequence, a humanized VHH sequence, a camelized VH sequence, or a VHH sequence that has been obtained by affinity maturation; and wherein said at least one immunoglobulin single variable domain is chosen from the group consisting of ISVDs with SEQ ID NOs: 1-71 and 268-275 and ISVDs that have a sequence identity of more than 80% with SEQ ID NOs: 1-71 and 268-275.

7. The method according to claim 1, wherein said at least one polypeptide comprises at least two, at least three, at least four or at least five immunoglobulin single variable domains that can bind GITR, wherein said at least two, said at least three, said at least four or said at least five ISVDs can be the same or different.

8. The method according to claim 1, wherein said at least one polypeptide further comprises one or more other groups, residues, moieties or binding units.

9. The method according to claim 8, in which said one or more other groups, residues, moieties or binding units provide the polypeptide with increased half-life, compared to the corresponding polypeptide without said one or more other groups, residues, moieties or binding units.

10. The method according to claim 9, in which said one or more other binding units that provide the polypeptide with increased half-life are chosen from the group consisting of domain antibodies, amino acids that are suitable for use as a domain antibody, single domain antibodies, amino acids that are suitable for use as a single domain antibody, "dAb" 's, amino acids that are suitable for use as a dAb, VHH sequences, humanized VHH sequences, and camelized VH sequences that can bind to serum albumin or a serum immunoglobulin.

11. The method according to claim 10, wherein said polypeptide is chosen from the group consisting of SEQ ID NOs: 206-223 and 285-290 and polypeptides that have a sequence identity of more than 80% with SEQ ID NOs: 206-223 and 285-290.

12. The method according to claim 1, wherein said pharmaceutically active amount of the polypeptide is administered as a pharmaceutical composition, which comprises at least one pharmaceutically acceptable carrier, diluent or excipient and/or adjuvant.

13. The method of claim 8, wherein the one or more other groups, residues, moieties or binding units are linked via one or more peptidic linkers.

14. The method of claim 12, wherein the pharmaceutical composition comprises one or more further pharmaceutically active polypeptides and/or compounds.

15. A method for treatment of cancer, wherein said method comprises administering, to a subject in need thereof, a pharmaceutically active amount of at least one polypeptide, wherein the polypeptide comprises at least one immunoglobulin single variable domain (ISVD) that specifically binds glucocorticoid-induced TNFR family-related receptor (GITR) with an $EC_{50}$ value of less than 200 pM, wherein the binding of said ISVD to said GITR enhances an immune response, and wherein said at least one immunoglobulin single variable domain essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 73-88; and
    (b) amino acid sequences that have 4, 3, 2, or 1 amino acid(s) difference with the amino acid sequences of SEQ ID NOs: 73-88; and/or
  (ii) CDR2 is chosen from the group consisting of:
    (c) SEQ ID NOs: 90-116; and
    (d) amino acid sequences that have 4, 3, 2, or 1 amino acid(s) difference with the amino acid sequences of SEQ ID NOs: 90-116; and/or
  (iii) CDR3 is chosen from the group consisting of:
    (e) SEQ ID NOs: 118-132 and 282-284; and
    (f) amino acid sequences that have 4, 3, 2, or 1 amino acid(s) difference with the amino acid sequences of SEQ ID NOs: 118-132 and 282-284.

16. The method according to claim 15, wherein said at least one immunoglobulin single variable domain essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NOs: 73-75; and
    (b) amino acid sequences that have 4, 3, 2, or 1 amino acid(s) difference with the amino acid sequence of SEQ ID NO: 73; and/or
  (ii) CDR2 is chosen from the group consisting of:
    (c) SEQ ID NOs: 90-98; and
    (d) amino acid sequences that have 4, 3, 2, or 1 amino acid(s) difference with the amino acid sequence of SEQ ID NO: 90; and/or
  (iii) CDR3 is chosen from the group consisting of:
    (e) SEQ ID NOs: 118-119, 123 and 282-284; and
    (f) amino acid sequences that have 2, or 1 amino acid(s) difference with the amino acid sequence of SEQ ID NO: 118.

17. The method according to claim 16, in which said at least one immunoglobulin single variable domain essentially consists of 4 framework regions (FR1 to FR4, respectively) and 3 complementarity determining regions (CDR1 to CDR3, respectively), in which:
  (i) CDR1 is chosen from the group consisting of:
    (a) SEQ ID NO: 73; and
    (b) amino acid sequences that have 4, 3, 2, or 1 amino acid difference(s) with SEQ ID NO: 73, wherein
      at position 2 the T has been changed into S;
      at position 7 the D has been changed into N;
      at position 8 the S has been changed into A; and/or
      at position 10 the A has been changed into G;
    and/or
  (ii) CDR2 is chosen from the group consisting of:
    (c) SEQ ID NO: 90; and
    (d) amino acid sequences that have 4, 3, 2, or 1 amino acid difference(s) with SEQ ID NO: 90, wherein
      at position 1 the A has been changed into H, T, or G;
      at position 2 the I has been changed into M;
      at position 3 the T has been changed into S;
      at position 6 the G has been changed into S;
      at position 7 the S has been changed into R, or G; and/or
      at position 8 the P has been changed into S, T, or R;
    and/or
  (iii) CDR3 is chosen from the group consisting of:
    (e) SEQ ID NO: 118; and
    (f) amino acid sequences that have 2, or 1 amino acid difference(s) with SEQ ID NO: 118, wherein
      at position 9 the A has been changed into P;
      at position 11 the M has been changed into L, K, R, or Q; and/or
      at position 12 the D has been changed into N.

18. A method for treatment of cancer, wherein said method comprises administering, to a subject in need thereof, a pharmaceutically active amount of at least one polypeptide, wherein the polypeptide comprises at least one immunoglobulin single variable domain (ISVD) that specifically binds glucocorticoid-induced TNFR family-related receptor (GITR) with an $EC_{50}$ value of less than 200 pM, wherein the binding of said ISVD to said GITR enhances an immune response, and wherein the cancer is selected from squamous cell cancer, small-cell lung cancer, non-small cell lung cancer, melanoma, kidney cancer such as renal cell carcinoma and Wilms' tumors, glioblastoma, glioma, prostate cancer, testicular cancer, gastrointestinal cancer, pancreatic cancer, biliary tract cancer, cervical cancer, ovarian cancer, liver cancer, bladder cancer, breast cancer, colon cancer, colorectal cancer, small bowel or appendix cancer, uterine or endometrial cancer, multiple myeloma, salivary gland carcinoma, adrenal gland cancer, osteosarcoma, chondrosarcoma, nasopharyngeal carcinoma, basal cell carcinoma, vulval cancer, thyroid cancer, testicular cancer, esophageal cancer, head and neck cancer, leukemia, lymphomas, merkel cell cancer and other hematologic malignancies.

19. The method according to claim 18, wherein the method further comprises one or more of the following:
  a) administering chemotherapy;
  b) administering radiation therapy;
  c) administering cancer vaccines; and/or
  d) administering one or more additional therapeutic agents.

20. The method according to claim 19, wherein the one or more additional therapeutic agents is chosen from the list of PD-1, PD-L1, PD-L2, CTLA-4, 4-1 BB (CD137), 4-1BB ligand, OX40, OX40 ligand, CD27, TNFRSF25, TL1A, CD40, CD40 ligand, LIGHT, LTA, HVEM, BTLA, CD160, CEACAM-1, CEACAM-5, LAIR1, 2B4, TGFR, LAG-3, TIM-3, Siglecs, ICOS (CD278), ICOS ligand, B7-H3, B7-H4, B7-1, B7-2, VISTA, HHLA2, TMIGD2, BTNL2, CD244, CD48, CD2, CDS, TIGIT, PVR family members, KIRs, ILTs, LIRs, NKG2D, NKG2A, MICA, MICB, CSF1R, IDO, TGFβ, adenosine, ICAM-1, ICAM-2, ICAM-3, LFA-1 (CD11a/CD18), LFA-2, LFA-3, BAFFR, NKG2C, SLAMF7, NKp80, CD83 ligand, CD24, CD39, CD30, CD70, CD73, CD7, CXCR4, CXCL12, phosphatidylserine, SIRPA, CD47, VEGF and Neuropilin.

* * * * *